(12) United States Patent
Czabaniuk et al.

(10) Patent No.: US 12,319,691 B2
(45) Date of Patent: *Jun. 3, 2025

(54) HETEROCYCLIC COMPOUNDS AS TRIGGERING RECEPTOR EXPRESSED ON MYELOID CELLS 2 AGONISTS AND METHODS OF USE

(71) Applicants: AMGEN INC., Thousand Oaks, CA (US); Vigil Neuroscience, Inc., Watertown, MA (US)

(72) Inventors: Lara C. Czabaniuk, Thousand Oaks, CA (US); Timothy Hopper, Thousand Oaks, CA (US); Jonathan B. Houze, Cambridge, MA (US); Gwenaella Rescourio, Thousand Oaks, CA (US); Vincent Santora, Thousand Oaks, CA (US); Haoxuan Wang, Thousand Oaks, CA (US); Ryan D. White, Thousand Oaks, CA (US); Alice R. Wong, Thousand Oaks, CA (US); Yongwei Wu, Thousand Oaks, CA (US)

(73) Assignees: Amgen Inc., Thousand Oaks, CA (US); Vigil Neuroscience, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/309,281

(22) Filed: Apr. 28, 2023

(65) Prior Publication Data
US 2024/0124446 A1 Apr. 18, 2024

Related U.S. Application Data

(63) Continuation of application No. 18/072,497, filed on Nov. 30, 2022, now Pat. No. 11,718,617, which is a continuation of application No. 17/923,160, filed as application No. PCT/US2021/030719 on May 4, 2021.

(60) Provisional application No. 63/019,768, filed on May 4, 2020.

(51) Int. Cl.
| | |
|---|---|
| C07D 471/04 | (2006.01) |
| A61K 31/519 | (2006.01) |
| A61K 31/5377 | (2006.01) |
| C07D 413/14 | (2006.01) |
| C07D 519/00 | (2006.01) |

(52) U.S. Cl.
CPC .......... C07D 471/04 (2013.01); A61K 31/519 (2013.01); A61K 31/5377 (2013.01); C07D 413/14 (2013.01); C07D 519/00 (2013.01)

(58) Field of Classification Search
CPC .................................................. C07D 471/04
USPC .................................................... 514/234.2
See application file for complete search history.

(56) References Cited

U.S. PATENT DOCUMENTS

| | | | |
|---|---|---|---|
| 2,940,972 | A | 6/1960 | Roch |
| 2,963,481 | A | 12/1960 | Grannells et al. |
| 3,712,892 | A | 1/1973 | Inaba et al. |
| 5,620,978 | A | 4/1997 | Cai et al. |
| 7,521,455 | B2 | 4/2009 | Nagase et al. |
| 7,582,366 | B2 | 9/2009 | Hwang et al. |
| 7,635,683 | B2 | 12/2009 | Gai et al. |
| 8,084,459 | B2 | 12/2011 | Kok et al. |
| 8,298,825 | B1 | 10/2012 | Hochedlinger et al. |
| 8,722,692 | B2 | 5/2014 | Che et al. |
| 9,905,773 | B2 | 2/2018 | Park et al. |
| 10,403,826 | B2 | 9/2019 | Dyatkin et al. |
| 10,573,692 | B2 | 2/2020 | Lim et al. |
| 11,608,344 | B2 | 3/2023 | Czabaniuk et al. |

(Continued)

FOREIGN PATENT DOCUMENTS

| | | |
|---|---|---|
| CN | 103374021 B | 10/2015 |
| CN | 102887895 B | 8/2016 |

(Continued)

OTHER PUBLICATIONS

"SID 378004572 Substance Record: 1265848-98-3," PubChem. Available Jan. 17, 2019: https://pubchem.ncbi.nlm.nih.gov/substance/378004572.

(Continued)

*Primary Examiner* — Niloofar Rahmani
(74) *Attorney, Agent, or Firm* — Sterne, Kessler, Goldstein & Fox P.L.L.C.

(57) ABSTRACT

The present disclosure provides compounds of Formula I, useful for the activation of Triggering Receptor Expressed on Myeloid Cells 2 ("TREM2").

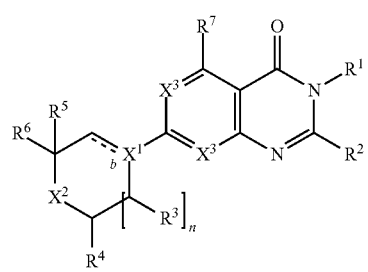

This disclosure also provides pharmaceutical compositions comprising the compounds, uses of the compounds, and compositions for treatment of, for example, a neurodegenerative disorder. Further, the disclosure provides intermediates useful in the synthesis of compounds of Formula I.

20 Claims, No Drawings

(56) References Cited

U.S. PATENT DOCUMENTS

| | | | |
|---|---|---|---|
| 11,718,617 B2* | 8/2023 | Czabaniuk | A61P 25/16 514/234.2 |
| 11,884,675 B2 | 1/2024 | Czabaniuk et al. | |
| 11,912,711 B2 | 2/2024 | Czabaniuk et al. | |
| 2002/0161014 A1 | 10/2002 | Sadhu et al. | |
| 2005/0096327 A1 | 5/2005 | Caprathe et al. | |
| 2007/0225271 A1 | 9/2007 | Binggeli et al. | |
| 2009/0099174 A1 | 4/2009 | Smith et al. | |
| 2011/0124638 A1 | 5/2011 | Duggan et al. | |
| 2013/0012489 A1 | 1/2013 | Mederski et al. | |
| 2016/0272632 A1 | 9/2016 | Childers et al. | |
| 2019/0343838 A1 | 11/2019 | Allen et al. | |
| 2020/0048207 A1 | 2/2020 | Parham et al. | |
| 2020/0075870 A1 | 3/2020 | Boudreault et al. | |
| 2020/0275661 A1 | 9/2020 | Tamai et al. | |
| 2021/0070792 A1 | 3/2021 | Shih et al. | |
| 2023/0002390 A1 | 1/2023 | Czabaniuk et al. | |
| 2023/0144581 A1 | 5/2023 | Czabaniuk et al. | |
| 2023/0295169 A1 | 9/2023 | Czabaniuk et al. | |
| 2023/0295170 A1 | 9/2023 | Czabaniuk et al. | |
| 2024/0182477 A1 | 6/2024 | Czabaniuk et al. | |
| 2024/0190863 A1 | 6/2024 | Czabaniuk et al. | |

FOREIGN PATENT DOCUMENTS

| | | |
|---|---|---|
| CN | 109265457 A | 1/2019 |
| CN | 110283171 A | 9/2019 |
| CN | 111454265 A | 7/2020 |
| CN | 108484680 B | 12/2020 |
| EP | 3229290 A1 | 10/2017 |
| IN | 2009MU01140 A | 11/2010 |
| JP | H-05170744 A | 7/1993 |
| JP | 2003005355 A | 1/2003 |
| KR | 2015080966 A | 7/2015 |
| KR | 2016060572 A | 5/2016 |
| KR | 2018107604 A | 10/2018 |
| KR | 2018116822 A | 10/2018 |
| WO | WO-1999021840 A1 | 5/1999 |
| WO | WO-2002058695 A1 | 8/2002 |
| WO | WO-2004031161 A1 | 4/2004 |
| WO | WO-2004055013 A1 | 7/2004 |
| WO | WO-2005007099 A2 | 1/2005 |
| WO | WO-2005039587 A1 | 5/2005 |
| WO | WO-2005087742 A1 | 9/2005 |
| WO | WO-2006039718 A2 | 4/2006 |
| WO | WO-2006128129 A2 | 11/2006 |
| WO | WO-2006128172 A2 | 11/2006 |
| WO | WO-2007038331 A2 | 4/2007 |
| WO | WO-2007103759 A2 | 9/2007 |
| WO | WO-2008003149 A2 | 1/2008 |
| WO | WO-2008130600 A2 | 10/2008 |
| WO | WO-2009100406 A2 | 8/2009 |
| WO | WO-2010033906 A2 | 3/2010 |
| WO | WO-2010042925 A2 | 4/2010 |
| WO | WO-2010107768 A1 | 9/2010 |
| WO | WO-2011014039 A1 | 2/2011 |
| WO | WO-2011037731 A1 | 3/2011 |
| WO | WO-2011053861 A1 | 5/2011 |
| WO | WO-2011119565 A1 | 9/2011 |
| WO | WO-2011156889 A1 | 12/2011 |
| WO | WO-2013117615 A1 | 8/2013 |
| WO | WO-2015002729 A2 | 1/2015 |
| WO | WO-2015017335 A1 | 2/2015 |
| WO | WO-2015086523 A1 | 6/2015 |
| WO | WO-2015112806 A2 | 7/2015 |
| WO | WO-2016166078 A1 | 10/2016 |
| WO | WO-2017025164 A1 | 2/2017 |
| WO | WO-2017031427 A1 | 2/2017 |
| WO | WO-2017181177 A1 | 10/2017 |
| WO | WO-2018066812 A1 | 4/2018 |
| WO | WO-2018067704 A1 | 4/2018 |
| WO | WO-2018108110 A1 | 6/2018 |
| WO | WO-2018169352 A1 | 9/2018 |
| WO | WO-2018183923 A1 | 10/2018 |
| WO | WO-2018195450 A1 | 10/2018 |
| WO | WO-2018204764 A1 | 11/2018 |
| WO | WO-2018204765 A1 | 11/2018 |
| WO | WO-2018227228 A1 | 12/2018 |
| WO | WO-2019079596 A1 | 4/2019 |
| WO | WO-2019079607 A1 | 4/2019 |
| WO | WO-2020231739 A2 | 11/2020 |
| WO | WO-2021224802 A1 | 11/2021 |
| WO | WO-2021225968 A1 | 11/2021 |
| WO | WO-2021226629 A1 | 11/2021 |
| WO | WO-2023137265 A1 | 7/2023 |

OTHER PUBLICATIONS

"SID 396338721 Substance Record," PubChem. Available Dec. 6, 2019: https://pubchem.ncbi.nlm.nih.gov/substance/396338721.

Bergner, et al., "Microglia damage precedes major myelin breakdown in X-linked adrenoleukodystrophy and metachromatic leukodystrophy," Glia. Jun. 2019;67(6):1196-1209.

Bianchin, et al., "Nasu-Hakola disease (polycystic lipomembranous osteodysplasia with sclerosing leukoencephalopathy—PLOSL): a dementia associated with bone cystic lesions. From clinical to genetic and molecular aspects," Cell Mol Neurobiol. Feb. 2004;24(1):1-24.

Bianchin, et al., "Nasu-Hakola disease and primary microglial dysfunction," Nat Rev Neurol. Sep. 2010;6(9):2 p following 523.

Cantoni, et al., "TREM2 regulates microglial cell activation in response to demyelination in vivo," Acta Neuropathol. Mar. 2015;129(3):429-47.

Colonna and Butovsky, "Microglia Function in the Central Nervous System During Health and Neurodegeneration" Annu Rev Immunol. Apr. 26, 2017;35:441-468.

Condello, et al., "Microglia constitute a barrier that prevents neurotoxic protofibrillar A(beta)42 hotspots around plaques," Nat Commun. Jan. 29, 2015;6:6176.

Cserép, et al., "Microglia monitor and protect neuronal function through specialized somatic purinergic junctions," Science. Jan. 31, 2020;367(6477):528-537.

Dardiotis, et al., "A novel mutation in TREM2 gene causing Nasu-Hakola disease and review of the literature," Neurobiol Aging. May 2017;53:194.e13-194.e22.

Deming, et al., "The MS4A gene cluster is a key modulator of soluble TREM2 and Alzheimer's disease risk," Sci Transl Med. Aug. 14, 2019;11(505):eaau2291.

Doens and Fernández, "Microglia receptors and their implications in the response to amyloid beta for Alzheimer's disease pathogenesis," J Neuroinflammation. Mar. 13, 2014;11:48.

Domingues, et al., "Oligodendrocyte, Astrocyte, and Microglia Crosstalk in Myelin Development, Damage, and Repair," Front Cell Dev Biol. Jun. 28, 2016;4:71.

Ewers, et al., "Increased soluble TREM2 in cerebrospinal fluid is associated with reduced cognitive and clinical decline in Alzheimer's disease," Sci Transl Med. Aug. 2, 20198;11(507):eaav6221.

Filipello, et al., "The Microglial Innate Immune Receptor TREM2 Is Required for Synapse Elimination and Normal Brain Connectivity," Immunity. May 15, 2018;48(5):979-991.e8.

Golde, et al., "Alzheimer's disease risk alleles in TREM2 illuminate innate immunity in Alzheimer's disease," Alzheimers Res Ther. May 21, 2013;5(3):24.

Gong, et al., "Microglial dysfunction as a key pathological change in adrenomyeloneuropathy," Ann Neurol. Nov. 2017;82(5):813-27.

Guerreiro, et al., "TREM2 variants in Alzheimer's disease," N Engl J Med. Jan. 10, 2013;368(2):117-27.

Guerreiro, et al., "Using exome sequencing to reveal mutations in TREM2 presenting as a frontotemporal dementia-like syndrome without bone involvement," JAMA Neurol. Jan. 2013;70(1):78-84.

Guo, et al., "TREM2 deficiency aggravates—synuclein-induced neurodegeneration and neuroinflammation in Parkinson's disease models," FASEB J. Nov. 2019;33(11):12164-12174.

Hickman and El Khoury, "Analysis of the Microglial Sensome," Methods Mol Biol. 2019;2034:305-323.

Hickman, et al., "Microglia in neurodegeneration," Nat Neurosci. Oct. 2018;21(10):1359-1369.

(56) References Cited

OTHER PUBLICATIONS

Hickman, et al., "Microglia in neurodegeneration," Nat Neurosci. 2018;21(10):1359-1369.
Hickman, et al., "The microglial sensome revealed by direct RNA sequencing," Nat Neurosci. Oct. 27, 2013;16(12):1896-1905.
Hollingworth, et al., "Common variants at ABCA7, MS4A6A/MS4A4E, EPHA1, CD33 and CD2AP are associated with Alzheimer's disease," Nat Genet. May 2011;43(5):429-35.
Hong, et al., "New insights on the role of microglia in synaptic pruning in health and disease," Curr Opin Neurobiol. Feb. 2016;36:128-34.
Hori, et al., "Novel 4-phenoxy-2-(1-piperazinyl)quinazolines as potent anticonvulsive and antihypoxic agents," Chem Pharm Bull (Tokyo). Mar. 1990;38(3):681-7.
Huang and Pope, "The role of toll-like receptors in rheumatoid arthritis," Curr Rheumatol Rep. Oct. 2009;11(5):357-64.
Ikegami, et al., "Microglia: Lifelong modulator of neural circuits," Neuropathology. Jun. 2019;39(3):173-180.
Jaitin, et al., "Lipid-Associated Macrophages Control Metabolic Homeostasis in a Trem2-Dependent Manner," Cell. Jul. 25, 2019;178(3):686-698.e14.
Jay, et al., "TREM2 deficiency eliminates TREM2+ inflammatory macrophages and ameliorates pathology in Alzheimer's disease mouse models," J Exp Med. Mar. 9, 2015;212(3):287-95.
Jay, et al., "TREM2 in Neurodegenerative Diseases," Mol Neurodegener. Aug. 2, 2017;12(1):56.
Jonsson, et al., "Variant of TREM2 associated with the risk of Alzheimer's disease," N Engl J Med. Jan. 10, 2013;368(2):107-16.
Kang, et al., "Behavioral and transcriptomic analysis of Trem2-null mice: not all knockout mice are created equal," Hum Mol Genet. Jan. 15, 2018;27(2):211-223.
Keren-Shaul, et al., "A Unique Microglia Type Associated with Restricting Development of Alzheimer's Disease," Cell. Jun. 15, 2017;169(7):1276-1290.e17.
Kim, et al., "Deficient autophagy in microglia impairs synaptic pruning and causes social behavioral defects," Mol Psychiatry. Nov. 2017;22(11):1576-1584.
Kleinberger, et al., "TREM2 mutations implicated in neurodegeneration impair cell surface transport and phagocytosis," Sci Transl Med. Jul. 2, 2014;6(243):243ra86.
Kobayashi, et al., "TREM2/DAP12 Signal Elicits Proinflammatory Response in Microglia and Exacerbates Neuropathic Pain," J Neurosci. Oct. 26, 2016;36(43):11138-11150.
Kober and Brett, "TREM2-Ligand Interactions in Health and Disease," J Mol Biol. Jun. 2, 2017;429(11):1607-1629.
Konno, et al., "CSF1R-related leukoencephalopathy: A major player in primary microgliopathies", Neurology, Dec. 11, 2018;91(24):1092-1104.
Lee, et al., "Elevated TREM2 Gene Dosage Reprograms Microglia Responsivity and Ameliorates Pathological Phenotypes in Alzheimer's Disease Models," Neuron. Mar. 7, 2018;97(5):1032-1048.e5.
Leyns, et al., "TREM2 function impedes tau seeding in neuritic plaques," Nat Neurosci. Aug. 2019;22(8):1217-1222.
Li and Barres, "Microglia and macrophages in brain homeostasis and disease," Nat Rev Immunol. Apr. 2018;18(4):225-242.
Liddelow, et al., "Neurotoxic reactive astrocytes are induced by activated microglia," Nature. Jan. 26, 2017;541(7638):481-487.
Madry and Attwell, "Receptors, ion channels, and signaling mechanisms underlying microglial dynamics," J Biol Chem. May 15, 2015;290(20):12443-50.
Madry, et al., "Nasu-Hakola disease (PLOSL): report of five cases and review of the literature," Clin Orthop Relat Res. Jan. 2007;454:262-9.
Oosterhof, et al., "Colony-Stimulating Factor 1 Receptor (CSF1R) Regulates Microglia Density and Distribution, but Not Microglia Differentiation In Vivo," Cell Rep. Jul. 3, 2018;24(5):1203-1217.
Otero, et al., "TREM2 and beta-catenin regulate bone homeostasis by controlling the rate of osteoclastogenesis," J Immunol. Mar. 15, 2012;188(6):2612-21.
Paloneva, et al., "DAP12/TREM2 deficiency results in impaired osteoclast differentiation and osteoporotic features," J Exp Med. Aug. 18, 2003;198(4):669-75.
Paolicelli, et al., "Synaptic pruning by microglia is necessary for normal brain development," Science. Sep. 9, 2011;333(6048):1456-8.
Parhizkar, et al., "Loss of TREM2 function increases amyloid seeding but reduces plaque-associated ApoE," Nat Neurosci. Feb. 2019;22(2):191-204.
PCT International Search Report and Written Opinion from PCT/US2021/030719, dated Aug. 20, 2021.
PCT International Search Report and Written Opinion from PCT/US2021/070507 dated Jun. 30, 2021.
PCT International Search Report and Written Opinion from PCT/US2022/072095, dated Aug. 25, 2022.
Peng, et al., "TREM2- and DAP12-dependent activation of PI3K requires DAP10 and is inhibited by SHIP1," Sci Signal. May 18, 2010;3(122):ra38.
Rademakers, et al, "Mutations in the colony stimulating factor 1 receptor (CSF1R) gene cause hereditary diffuse leukoencephalopathy with spheroids," Nat Genet. 2012;44(2):200-5.
Schlepckow, et al. "Enhancing Protective Microglial Activities With a Dual Function TREM2 Antibody to the Stalk Region," EMBO Mol Med. Apr. 7, 2020;12(4):e11227.
Sellgren, et al., "Increased synapse elimination by microglia in schizophrenia patient-derived models of synaptic pruning," Nat Neurosci. Mar. 2019;22(3):374-385.
Shinozaki, et al., "Transformation of Astrocytes to a Neuroprotective Phenotype by Microglia via P2Y1 Receptor Downregulation," Cell Rep. May 9, 2017;19(6):1151-1164.
Shirotani, et al., "Aminophospholipids are signal-transducing TREM2 ligands on apoptotic cells," Sci Rep. May 17, 2019;9(1):7508.
Sims, et al., "Rare coding variants in PLCG2, ABI3, and TREM2 implicate microglial-mediated innate immunity in Alzheimer's disease," Nat Genet. Sep. 2017;49(9):1373-1384.
Spangenberg, et al., "Sustained microglial depletion with CSF1R inhibitor impairs parenchymal plaque development in an Alzheimer's disease model," Nat Commun. 2019;10:3758.
Suárez-Calvet, et al., "Early increase of CSF sTREM2 in Alzheimer's disease is associated with tau related-neurodegeneration but not with amyloid-beta pathology," Mol Neurodegener. Jan. 10, 2019;14(1):1.
Tang, et al., "Loss of mTOR-dependent macroautophagy causes autistic-like synaptic pruning deficits," Neuron. Sep. 3, 2014;83(5):1131-43.
Ulland, et al., "TREM2 Maintains Microglial Metabolic Fitness in Alzheimer's Disease," Cell. Aug. 10, 2017;170(4):649-663.e13.
Ulrich and Holtzman, "TREM2 Function in Alzheimer's Disease and Neurodegeneration," ACS Chem Neurosci. Apr. 20, 2016;7(4):420-7.
Ulrich et al., "Elucidating the Role of TREM2 in Alzheimer's Disease," Neuron. Apr. 19, 2017;94(2):237-248.
Wang, et al., "TREM2 lipid sensing sustains the microglial response in an Alzheimer's disease model," Cell. Mar. 12, 2015;160(6):1061-71.
Wang, et al., "Anti-human TREM2 induces microglia proliferation and reduces pathology in an Alzheimer's disease model", J Exp Med. Sep. 7, 2020;217(9):e20200785.
Weinhofer, et al., "Impaired plasticity of macrophages in X-linked adrenoleukodystrophy," Brain. Aug. 1, 2018;141(8):2329-2342.
Wu, et al., "TREM2 protects against cerebral ischemia/reperfusion injury," Mol Brain. Jun. 7, 2017;10(1):20.
Yeh, et al., "TREM2 Binds to Apolipoproteins, Including APOE and CLU/APOJ, and Thereby Facilitates Uptake of Amyloid-Beta by Microglia," Neuron. Jul. 20, 2016;91(2):328-40.
Yuan, et al., "TREM2 Haplodeficiency in Mice and Humans Impairs the Microglia Barrier Function Leading to Decreased Amyloid Compaction and Severe Axonal Dystrophy," Neuron. May 18, 2016;90(4):724-39.
Co-pending Application, U.S. Appl. No. 17/923,160, inventors Czabaniuk, L., et al., filed on Nov. 3, 2022 (Not yet Published).
Co-pending Application, U.S. Appl. No. 18/472,147, inventors Czabaniuk, L., et al., filed Sep. 21, 2023 (Not yet Published).

(56) References Cited

OTHER PUBLICATIONS

Wilen, et al., "Strategies in optical resolutions," Tetrahedron May 3, 1977; 33(21): 2725-2736.
Berge, et al., "Pharmaceutical Salts," J. Pharm. Sci. Jan. 1977; 66(1): 1-19.
Hayes, S., Remington: *The Science and Practice of Pharmacy*, vol. I and vol. II, twenty-second edition, Loyd V. Allen Jr. ed., Pharmaceutical Press, Philadelphia, PA, 2012.
Lieberman, H. A., et al., eds., *Pharmaceutical Dosage Forms*, vol. 1-3, Marcel Dekker, New York, NY, 1992.
Kibbe, A. H., ed., *Handbook of Pharmaceutical Excipients*, 3rd Ed., American Pharmaceutical Association, Washington, 2000.
Tovey, G. D., ed., *Pharmaceutical Formulation: The Science and Technology of Dosage Forms*, Drug Discovery Series No. 64, The Royal Society of Chemistry, 2018.
Sorrell, T. N., *Organic Chemistry*, $2^{nd}$ edition, University Science Books, Sausalito, CA, 2006.
Smith, M. B., and March, J., *March's Advanced Organic Chemistry: Reactions, Mechanisms, and Structure*, $8^{th}$ Ed., John Wiley & Sons, Inc., Hoboken, NJ, 2020.
Jacques, J., et al., "Resolution of alcohols," in *Enantiomers, racemates and resolutions*, pp. 263-266, Wiley, New York, NY, 1981.
Eliel, E. L., *Stereochemistry of Carbon Compounds*, McGraw-Hill, New York, 1962.
Wilen, S. H., *Tables of Resolving Agents and Optical Resolutions*, University of Notre Dame Press: Notre Dame, IN, 1972.
Stahl, P. H., and Wermuth, C. G., eds., Pharmaceutical Salts: Properties, Selection, and Use, 2nd revised edition, Wiley-VCH, Weinheim, Germany, 2011.
Miller, M., et al. "Identification of ML204, a Novel Potent Antagonist That Selectively Modulates Native TRPC4/C5 Ion Channels," J Biol Chem 286(38):33436-33446, Elsevier, Netherlands (Sep. 2011).
Zhao, H., and Jin, J., "Visible Light-Promoted Aliphatic C-H Arylation Using Selectfluor as a Hydrogen Atom Transfer Reagent," Org Lett 21(16):6179-6184, American Chemical Society, United States (Aug. 2019).
Wuyts, B., et al., "Biopharmaceutical profiling of a pyrido[4,3-d] pyrimidine compound library," Int J Pharm 455(1-2):19-30, Elsevier, Netherlands (Oct. 2013).
Xu, T., "The role of myeloid cell-triggered receptor 2 in neurodegenerative diseases," Journal of Apolexy and Neurological Diseases 36(11):1053-1056, Jilin Dayijingcheng Media Co., China (Nov. 2019).

\* cited by examiner

HETEROCYCLIC COMPOUNDS AS TRIGGERING RECEPTOR EXPRESSED ON MYELOID CELLS 2 AGONISTS AND METHODS OF USE

CROSS REFERENCE TO RELATED APPLICATION

This application is a continuation application of U.S. patent application Ser. No. 17/923,160, filed Nov. 3, 2022, which is a 371 of International Patent Application No. PCT/US2021/030719, filed May 4, 2021, which claims the benefit under 35 U.S.C. § 119(e) to U.S. Provisional Application No. 63/019,768, filed May 4, 2020, the entire contents of each of which are incorporated herein by reference.

FIELD

The present disclosure provides compounds useful for the activation of Triggering Receptor Expressed on Myeloid Cells 2 ("TREM2"). This disclosure also provides pharmaceutical compositions comprising the compounds, uses of the compounds, and compositions for treatment of, for example, a neurodegenerative disorder. Further, the disclosure provides intermediates useful in the synthesis of compounds of Formula I.

BACKGROUND

Microglia are resident innate immune cells in the brain and are important for the maintenance of homeostatic conditions in the central nervous system. Hickman et al. 2018, Li and Barres 2018. These resident macrophages express a variety of receptors that allow them to sense changes in their microenvironment and alter their phenotypes to mediate responses to invading pathogens, proteotoxic stress, cellular injury, and other infarcts that can occur in health and disease. Id. Microglia reside in the parenchyma of the brain and spinal cord where they interact with neuronal cell bodies (Cserep et al. 2019), neuronal processes (Paolicelli et al. 2011, Ikegami et al. 2019) in addition to other types of glial cells (Domingues et al. 2016, Liddelow et al. 2017, Shinozaki et al. 2017), playing roles in a multitude of physiological processes. With the ability to rapidly proliferate in response to stimuli, microglia characteristically exhibit myeloid cell functions such as phagocytosis, cytokine/chemokine release, antigen presentation, and migration. Colonna and Butovsky 2017. More specialized functions of microglia include the ability to prune synapses from neurons and directly communicate with their highly arborized cellular processes that survey the area surrounding the neuronal cell bodies. Hong et al. 2016, Sellgren et al. 2019.

The plasticity of microglia and their diverse states as described through single-cells RNASeq profiling are thought to arise through the integration of signaling from a diverse array of cell surface receptors. Hickman et al. 2013. Collectively known as the microglial "sensome," these receptors are responsible for transducing activating or activation-suppressing intracellular signaling and include protein families such as Sialic acid-binding immunoglobulin-type lectins ("SIGLEC"), Toll-like receptors ("TLR"), Fc receptors, nucleotide-binding oligomerization domain ("NOD") and purinergic G protein-coupled receptors. Doens and Fernandez 2014, Madry and Attwell 2015, Hickman and El Khoury 2019. Similar to other cells of the myeloid lineage, the composition of microglial sensomes is dynamically regulated and acts to recognize molecular pattern that direct phenotypic responses to homeostatic changes in the central nervous system ("CNS"). Id. One of the receptors selectively expressed by brain microglia is TREM2, composed of a single-pass transmembrane domain, an extracellular stalk region, and extracellular immunoglobulin variable ("IgV")-like domain responsible for ligand interaction. Kleinberger et al. 2014. As TREM2 does not possess intracellular signal transduction-mediating domains, biochemical analysis has illustrated that interaction with adaptor proteins DAP10 and DAP12 mediate downstream signal transduction following ligand recognition. Peng et al. 2010, Jay et al. 2017. TREM2/DAP12 complexes in particular act as a signaling unit that can be characterized as pro-activation on microglial phenotypes in addition to peripheral macrophages and osteoclasts. Otero et al. 2012, Kobayashi et al. 2016, Jaitin et al. 2019. In the CNS, signaling through TREM2 has been studied in the context of ligands such as phospholipids, cellular debris, apolipoproteins, and myelin. Wang et al. 2015, Kober and Brett 2017, Shirotani et al. 2019). In mice lacking functional TREM2 expression or expressing a mutated form of the receptor, a core observation is blunted microglial responses to insults such as oligodendrocyte demyelination, stroke-induced tissue damage in the brain, and proteotoxic inclusions in vivo. Cantoni et al. 2015, Wu et al. 2017.

Coding variants in the TREM12 locus has been associated with late onset Alzheimer's disease ("LOAD") in human genome-wide association studies, linking a loss-of-receptor function to a gain in disease risk. Jonsson et al. 2013, Sims et al. 2017. Genetic variation of other genes selectively expressed by microglia in the CNS, for example, CD33, PLCg2 and MS4A4A/6A have reached genome-wide significance for their association with LOAD risk. Hollingworth et al. 2011, Sims et al. 2017, Deming et al. 2019. Together, these genetic findings link together in a putative biochemical circuit that highlights the importance of microglial innate immune function in LOAD. Additionally, increase or elevation in the soluble form of TREM2 ("sTREM2") in the cerebrospinal fluid (CSF) of human subjects is associated with disease progression and emergence of pathological hallmarks of LOAD including phosphorylated Tau. Suarez-Calvet et al. 2019. Furthermore, natural history and human biology studies indicate that baseline sTREM2 levels in the CSF can stratify the rate of temporal lobe volume loss and episodic memory decline in longitudinally monitored cohorts. Ewers et al. 2019.

In addition to human genetic evidence supporting a role of TREM2 in LOAD, homozygous loss-of-function mutations in TREM12 are causal for an early onset dementia syndrome known as Polycystic lipomembranous osteodysplasia with sclerosing leukoencephalopathy ("PLOSL") or Nasu-Hakola disease ("NHD"). Golde et al. 2013, Dardiotis et al. 2017. This progressive neurodegenerative disease typically manifests in the 3rd decade of life and is pathologically characterized by loss of myelin in the brain concomitant with gliosis, unresolved neuroinflammation, and cerebral atrophy. Typical neuropsychiatric presentations are often preceded by osseous abnormalities, such as bone cysts and loss of peripheral bone density. Bianchin et al. 2004, Madry et al. 2007, Bianchin et al. 2010). Given that osteoclasts of the myeloid lineage are also known to express TREM2, the PLOSL-related symptoms of wrist and ankle pain, swelling, and fractures indicate that TREM2 may act to regulate bone homeostasis through defined signaling pathways that parallel the microglia in the CNS. Paloneva et al. 2003, Otero et al. 2012. The link between TREM2 function and PLOSL has illustrated the importance of the receptor in sustaining key physiological aspects of myeloid cell function in the human body.

Efforts have been made to model the biology of TREM2 in mice prompting the creation of TREM2 knock out ("KO") mice in addition to the LOAD-relevant TREM2 R47H loss-of-function mutant transgenic mice. Ulland et al. 2017, Kang et al. 2018. Although unable to recapitulate the neurological manifestations of PLOSL, TREM2 KO mice show abnormalities in bone ultrastructure. Otero et al. 2012. When the TREM2 KO or mutant mice have been crossed onto familial Alzheimer's disease transgenic mouse background such as the 5XFAD amyloidogenic mutation lines, marked phenotypes have been observed. Ulrich et al. 2017. These in vivo phenotypes of TREM2 loss-of-function in the CNS include elevated the plaque burden and lower levels of secreted microglial factors SPP1 and Osteopontin that are characteristic of the microglial response to amyloid pathology. Ulland, et al. 2017. Other rodent studies have demonstrated that loss of TREM2 leads to decreased microglial clustering around plaques and emergence of less compact plaque morphology in familial AD amyloid models. Parhizkar et al. 2019. With regards to the Tau protein pathology that is observed in LOAD, familial tauopathy models in mice demonstrated an enhanced spreading of pathological human Tau aggregates from point of injection into mouse brain in TREM2 KO mice. Leyns et al. 2019. Furthermore, single-cell RNASeq studies with the TREM2 KO mice in aged scenarios, 5XFAD familial Alzheimer's disease model mice, and Amyotrophic Lateral Sclerosis SOD1 mutant mouse backgrounds indicate that TREM2 receptor function is critical for a conserved set of phenotypic transformations within microglial populations in response to CNS pathology. Keren-Shaul et al. 2017.

In rodent models where TREM2 expression levels are elevated, brain amyloid pathology in the 5XFAD transgenic mice displayed reduced plaque volume and altered morphology. Lee et al. 2018). The changes in immunohistological markers relating to brain amyloid pathology were also accompanied by an attenuated presence of dystrophic neurites when TREM2 was overexpressed. Id. Therefore, the pharmacological activation of TREM2 is a target of interest for treating or preventing neurological, neurodegenerative and other diseases. Despite many attempts to alter disease progression by targeting the pathological hallmarks of LOAD through anti-amyloid and anti-Tau therapeutics, there is a need for activators of TREM2 to address the genetics-implicated neuroimmune aspects of, for example, LOAD. Such TREM2 activators may be suitable for use as therapeutic agents and remain in view of the significant continuing societal burden that remains unmitigated for diseases, such as Alzheimer's disease.

SUMMARY

First, provided herein is a compound of Formula I

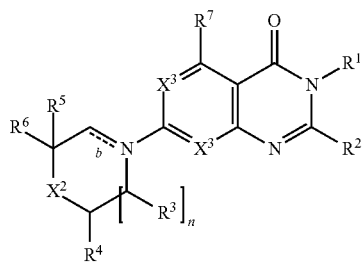

I or a tautomer thereof, or a pharmaceutically acceptable salt of said compound or said tautomer, wherein $X^1$ is (1) CH or N and b is a single bond; or (2) C and b is a double bond;

$X^2$ is $CH_2$, CHF, $CF_2$, O, or NH;

wherein, optionally, $R^3$ is absent and the $X^2CR^6$ group forms a 5- or 6-membered heteroaryl, wherein the 5-membered heteroaryl contains only one ring atom selected from N, O, and S and optionally only one further N ring atom and wherein the 6 membered heteroaryl contains only one or only two N ring atoms, and wherein said 5- or 6-membered heteroaryl is optionally substituted with halogen, $C_{1-3}$alkyl, or $C_{1-3}$alkoxy;

$X^3$ at each occurrence independently is CH or N;

$R^1$ is H, $C_{1-6}$alkyl, $C_{1-6}$haloalkyl, or $C_{3-6}$cycloalkyl;

$R^2$ is H, $C_{1-3}$alkyl, $C_{1-3}$haloalkyl, or $C_{3-6}$cycloalkyl;

$R^3$ is H or $C_{1-3}$alkyl;

$R^4$ is H or $C_{1-3}$alkyl;

$R^5$ is H or $C_{1-3}$alkyl;

$R^6$ is $C_{2-6}$alkyl, $C_{1-6}$haloalkyl, $diC_{1-3}$alkylamino, —C(=O)O($C_{1-6}$alkyl), $C_{3-6}$cycloalkyl, $C_{3-6}$heterocycloalkyl, phenyl, 5-membered heteroaryl, or 6-membered heteroaryl; wherein (1) $C_{3-6}$cycloalkyl or $C_{3-6}$heterocycloalkyl is optionally substituted with C=O, (2) the phenyl, 5-membered heteroaryl, or 6-membered heteroaryl group is optionally substituted with 1 to 3 substituents independently selected from halogen, $C_{1-6}$alkyl, $C_{1-6}$haloalkyl, $C_{1-6}$alkoxy, $C_{1-6}$haloalkoxy, —($C_{1-3}$alkyl)O($C_{1-3}$alkyl), —($C_{1-3}$alkyl)$NH_2$, —($C_{1-3}$alkyl)NH($C_{1-3}$alkyl), —($C_{1-3}$alkyl)N[($C_{1-3}$alkyl)($C_{1-3}$alkyl)], —CN, $C_{2-4}$alkenyl, $C_{3-6}$cycloalkyl, phenyl, and $C_{3-6}$heterocycloalkyl; wherein the $C_{1-6}$alkyl and $C_{1-6}$haloalkyl of subsection (2) are optionally substituted with OH; and wherein the $C_{3-6}$heterocycloalkyl of subsection (2) is optionally substituted with 1 to 3 substituents selected from halogen, $C_{1-3}$alkyl, and —C(=O)O($C_{1-6}$alkyl);

$R^7$ is $C_{5-6}$cycloalkyl, $C_{5-8}$spiroalkyl, $C_{5-8}$tricycloalkyl, phenyl, or 6-membered heteroaryl; wherein $R^7$ is further optionally substituted with 1 to 4 substituents independently selected from halogen, $C_{1-3}$alkyl, and $C_{1-3}$haloalkyl; and n is 0 or 1; provided that when $X^1$ is N and n is 0, $X^2$ is not NH or O.

Second, provided herein is a pharmaceutical composition comprising a compound of Formula I, or a tautomer thereof, or a pharmaceutically acceptable salt of said compound or said tautomer, and a pharmaceutically acceptable excipient.

Third, provided herein is a compound of Formula I, or a tautomer thereof, or a pharmaceutically acceptable salt of said compound or said tautomer, or a pharmaceutical composition as described hereinabove, for use in treating or preventing a condition associated with a loss of function of human TREM2.

Fourth, provided herein is a compound of Formula I, or a tautomer thereof, or a pharmaceutically acceptable salt of said compound or said tautomer, or a pharmaceutical composition described hereinabove, for use in treating or preventing Parkinson's disease, rheumatoid arthritis, Alzheimer's disease, Nasu-Hakola disease, frontotemporal dementia, multiple sclerosis, prion disease, or stroke.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as Embodiment 1 is a compound of Formula I

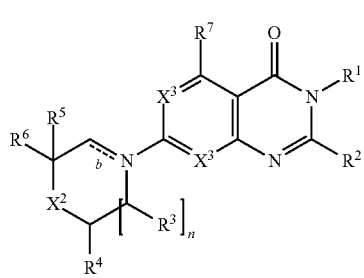

I or a tautomer thereof, or a pharmaceutically acceptable salt of said compound or said tautomer, wherein $X^1$ is (1) CH or N and b is a single bond; or (2) C and b is a double bond;

$X^2$ is $CH_2$, CHF, $CF_2$, O, or NH;

wherein, optionally, $R^5$ is absent and the $X^2CR^6$ group forms a 5- or 6-membered heteroaryl, wherein the 5-membered heteroaryl contains only one ring atom selected from N, O, and S and optionally only one further N ring atom and wherein the 6 membered heteroaryl contains only one or only two N ring atoms, and wherein said 5- or 6-membered heteroaryl is optionally substituted with halogen, $C_{1-3}$alkyl, or $C_{1-3}$alkoxy;

$X^3$ at each occurrence independently is CH or N;

$R^1$ is H, $C_{1-6}$alkyl, $C_{1-6}$haloalkyl, or $C_{3-6}$cycloalkyl;

$R^2$ is H, $C_{1-3}$alkyl, $C_{1-3}$haloalkyl, or $C_{3-6}$cycloalkyl;

$R^3$ is H or $C_{1-3}$alkyl;

$R^4$ is H or $C_{1-3}$alkyl;

$R^5$ is H or $C_{1-3}$alkyl;

$R^6$ is $C_{2-6}$alkyl, $C_{1-6}$haloalkyl, di$C_{1-3}$alkylamino, —C(=O)O($C_{1-6}$alkyl), $C_{3-6}$cycloalkyl, $C_{3-6}$heterocycloalkyl, phenyl, 5-membered heteroaryl, or 6-membered heteroaryl; wherein (1) $C_{3-6}$cycloalkyl or $C_{3-6}$heterocycloalkyl is optionally substituted with C=O, (2) the phenyl, 5-membered heteroaryl, or 6-membered heteroaryl group is optionally substituted with 1 to 3 substituents independently selected from halogen, $C_{1-6}$alkyl, $C_{1-6}$haloalkyl, $C_{1-6}$alkoxy, $C_{1-6}$haloalkoxy, —($C_{1-3}$alkyl)O($C_{1-3}$alkyl), —($C_{1-3}$alkyl)$NH_2$, —($C_{1-3}$alkyl)NH($C_{1-3}$alkyl), —($C_{1-3}$alkyl)N[($C_{1-3}$alkyl)($C_{1-3}$alkyl)], —CN, $C_{2-4}$alkenyl, $C_{3-6}$cycloalkyl, phenyl, and $C_{3-6}$heterocycloalkyl; wherein the $C_{1-6}$alkyl and $C_{1-6}$haloalkyl of subsection (2) are optionally substituted with OH; and wherein the $C_{3-6}$heterocycloalkyl of subsection (2) is optionally substituted with 1 to 3 substituents selected from halogen, $C_{1-3}$alkyl, and —C(=O)O($C_{1-6}$alkyl);

$R^7$ is $C_{5-6}$cycloalkyl, $C_{5-8}$spiroalkyl, $C_{5-8}$tricycloalkyl, phenyl, or 6-membered heteroaryl; wherein $R^7$ is further optionally substituted with 1 to 4 substituents independently selected from halogen, $C_{1-3}$alkyl, and $C_{1-3}$haloalkyl; and n is 0 or 1; provided that when $X^1$ is N and n is 0, $X^2$ is not NH or O.

Provided herein as Embodiment 2 is the compound according to Embodiment 1, or a tautomer thereof, or a pharmaceutically acceptable salt of said compound or said tautomer, wherein the compound is not 5-(5-chloro-3-methyl-2-pyridinyl)-2,3-dimethyl-7-(2-(1-methyl-1H-pyrazol-4-yl)-4-morpholinyl)pyrido[4,3-d]pyrimidin-4(3H)-one;

5-(4-chloro-2-fluorophenyl)-2,3-dimethyl-7-(3-methyl-3-phenyl-1-piperidinyl)pyrido[4,3-d]pyrimidin-4(3H)-one; or 5-(4-chloro-2-fluorophenyl)-2,3-dimethyl-7-(3-(1-methyl-1H-imidazol-2-yl)-1-pyrrolidinyl)pyrido[4,3-d]pyrimidin-4(3H)-one.

Provided herein as Embodiment 3 is the compound according to Embodiment 1 or Embodiment 2, or a tautomer thereof, or a pharmaceutically acceptable salt of said compound or said tautomer, wherein the compound is a compound of Formula II

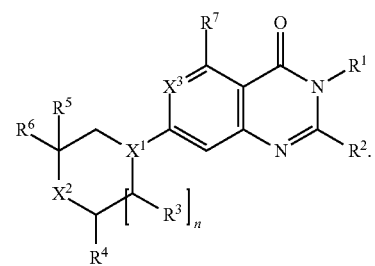

II

Provided herein as Embodiment 4 is the compound according to Embodiment 1 or Embodiment 2, or a tautomer thereof, or a pharmaceutically acceptable salt of said compound or said tautomer, wherein the compound is a compound of Formula IIA

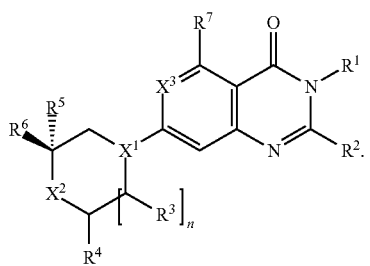

IIA

Provided herein as Embodiment 5 is the compound according to Embodiment 1 or Embodiment 2, or a tautomer thereof, or a pharmaceutically acceptable salt of said compound or said tautomer, wherein the compound is a compound of Formula IIB

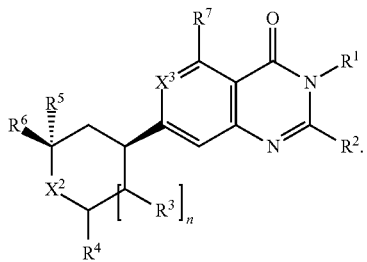

IIB

Provided herein as Embodiment 6 is the compound according to Embodiment 1 or Embodiment 2, or a tautomer thereof, or a pharmaceutically acceptable salt of said compound or said tautomer, wherein the compound is a compound of Formula IIC

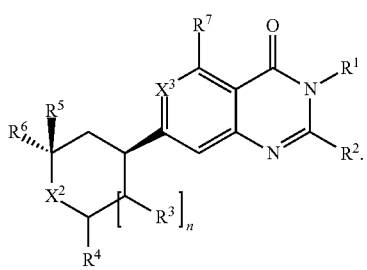

IIC

Provided herein as Embodiment 7 is the compound according to Embodiment 1 or Embodiment 2, or a tautomer thereof, or a pharmaceutically acceptable salt of said compound or said tautomer, wherein the compound is a compound of Formula IID

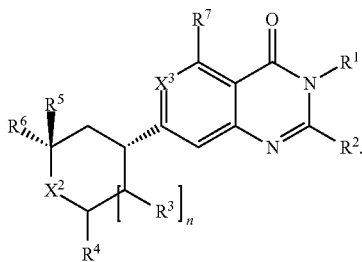

IID

Provided herein as Embodiment 8 is the compound according to Embodiment 1 or Embodiment 2, or a tautomer thereof, or a pharmaceutically acceptable salt of said compound or said tautomer, wherein the compound is a compound of Formula IIE

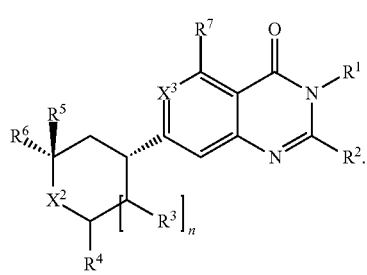

IIE

Provided herein as Embodiment 9 is the compound according to any one of Embodiments 1-4, or a tautomer thereof, or a pharmaceutically acceptable salt of said compound or said tautomer, wherein $X^1$ is CH.

Provided herein as Embodiment 10 is the compound according to any one of Embodiments 1-4, or a tautomer thereof, or a pharmaceutically acceptable salt of said compound or said tautomer, wherein $X^1$ is N.

Provided herein as Embodiment 11 is the compound according to any one of Embodiments 1-10, or a tautomer thereof, or a pharmaceutically acceptable salt of said compound or said tautomer, wherein $X^2$ is $CH_2$, $CF_2$, or O.

Provided herein as Embodiment 12 is the compound according to any one of Embodiments 1-10, or a tautomer thereof, or a pharmaceutically acceptable salt of said compound or said tautomer, wherein $X^2$ is O.

Provided herein as Embodiment 13 is the compound according to Embodiment 1, or a tautomer thereof, or a pharmaceutically acceptable salt of said compound or said tautomer, wherein the

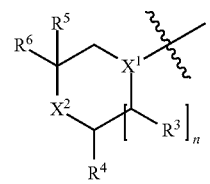

portion of Formula I is

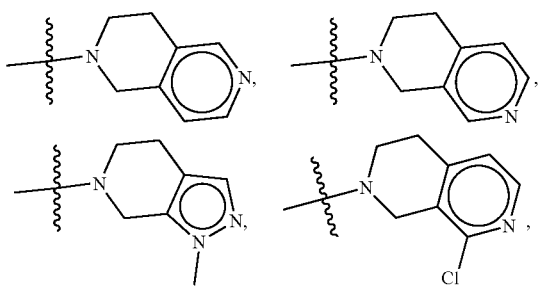

-continued

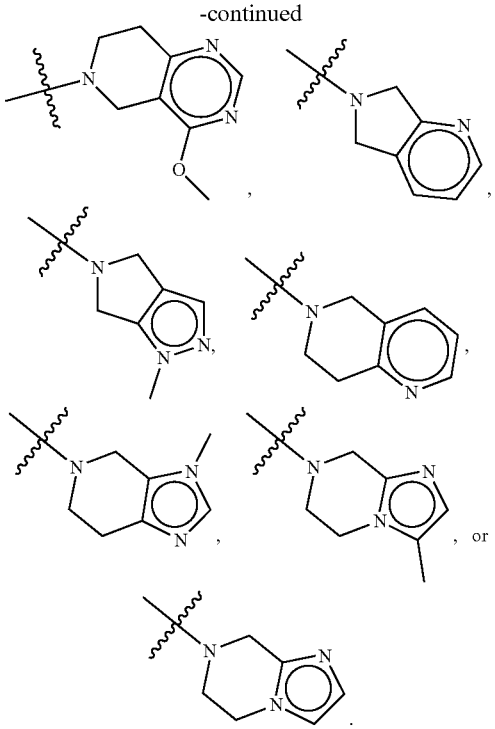

Provided herein as Embodiment 14 is the compound according to Embodiment 1, or a tautomer thereof, or a pharmaceutically acceptable salt of said compound or said tautomer, wherein the

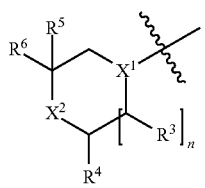

portion of Formula I is

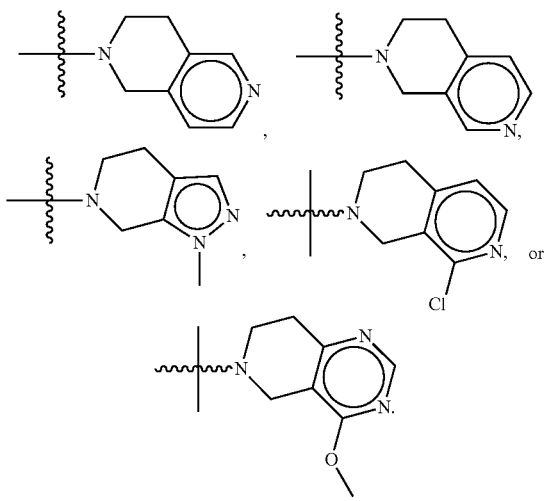

Provided herein as Embodiment 15 is the compound according to any one of Embodiments 1-14, or a tautomer thereof, or a pharmaceutically acceptable salt of said compound or said tautomer, wherein
$X^3$ is CH.

Provided herein as Embodiment 16 is the compound according to any one of Embodiments 1-14, or a tautomer thereof, or a pharmaceutically acceptable salt of said compound or said tautomer, wherein
$X^3$ is N.

Provided herein as Embodiment 17 is the compound according to any one of Embodiments 1-16, or a tautomer thereof, or a pharmaceutically acceptable salt of said compound or said tautomer, wherein
$R^1$ is methyl, ethyl, propyl, —CH$_2$CF$_3$, cyclopropyl, or cyclohexyl.

Provided herein as Embodiment 18 is the compound according to any one of Embodiments 1-16, or a tautomer thereof, or a pharmaceutically acceptable salt of said compound or said tautomer, wherein
$R^1$ is methyl.

Provided herein as Embodiment 19 is the compound according to any one of Embodiments 1-18, or a tautomer thereof, or a pharmaceutically acceptable salt of said compound or said tautomer, wherein
$R^2$ is H, methyl, trifluoromethyl, or cyclopropyl.

Provided herein as Embodiment 20 is the compound according to any one of Embodiments 1-18, or a tautomer thereof, or a pharmaceutically acceptable salt of said compound or said tautomer, wherein
$R^2$ is methyl.

Provided herein as Embodiment 21 is the compound according to any one of Embodiments 1-20, or a tautomer thereof, or a pharmaceutically acceptable salt of said compound or said tautomer, wherein
$R^3$ is H or methyl.

Provided herein as Embodiment 22 is the compound according to any one of Embodiments 1-20, or a tautomer thereof, or a pharmaceutically acceptable salt of said compound or said tautomer, wherein
$R^3$ is H.

Provided herein as Embodiment 23 is the compound according to any one of Embodiments 1-22, or a tautomer thereof, or a pharmaceutically acceptable salt of said compound or said tautomer, wherein
$R^4$ is H or methyl.

Provided herein as Embodiment 24 is the compound according to any one of Embodiments 1-22, or a tautomer thereof, or a pharmaceutically acceptable salt of said compound or said tautomer, wherein
$R^4$ is H.

Provided herein as Embodiment 25 is the compound according to any one of Embodiments 1-22, or a tautomer thereof, or a pharmaceutically acceptable salt of said compound or said tautomer, wherein
$R^4$ is methyl.

Provided herein as Embodiment 26 is the compound according to any one of Embodiments 1-25, or a tautomer thereof, or a pharmaceutically acceptable salt of said compound or said tautomer, wherein
$R^5$ is H or methyl.

Provided herein as Embodiment 27 is the compound according to any one of Embodiments 1-25, or a tautomer thereof, or a pharmaceutically acceptable salt of said compound or said tautomer, wherein
$R^5$ is H.

Provided herein as Embodiment 28 is the compound according to any one of Embodiments 1-27, or a tautomer thereof, or a pharmaceutically acceptable salt of said compound or said tautomer, wherein $R^6$ is difluoromethyl, trifluoromethyl, —$CH_2CF_3$, dimethylamino, —C(=O)OCH$_2$CH$_3$, optionally substituted cyclopropyl, optionally substituted cyclobutyl, optionally substituted oxetanyl, optionally substituted azetidinyl, optionally substituted tetrahydrofuranyl, optionally substituted pyrrolidinyl, optionally substituted phenyl, optionally substituted pyrazolyl, optionally substituted imidazolyl, optionally substituted 1,3-oxazolyl, optionally substituted 1,2,4-oxadiazolyl, optionally substituted 1,3,4-oxadiazolyl, optionally substituted thiophenyl, optionally substituted thiazolyl, optionally substituted pyridinyl, optionally substituted pyridazinyl, or optionally substituted pyrimidinyl.

In some embodiments, $R^6$ is difluoromethyl. In some embodiments, $R^6$ is trifluoromethyl. In some embodiments, $R^6$ is —$CH_2CF_3$. In some embodiments, $R^6$ is dimethylamino. In some embodiments, $R^6$ is —C(=O)OCH$_2$CH$_3$. In some embodiments, $R^6$ is optionally substituted cyclopropyl. In some embodiments, $R^6$ is optionally substituted cyclobutyl. In some embodiments, $R^6$ is optionally substituted oxetanyl. In some embodiments, $R^6$ is optionally substituted azetidinyl. In some embodiments, $R^6$ is optionally substituted tetrahydrofuranyl. In some embodiments, $R^6$ is optionally substituted pyrrolidinyl. In some embodiments, $R^6$ is optionally substituted phenyl. In some embodiments, $R^6$ is optionally substituted pyrazolyl. In some embodiments, $R^6$ is optionally substituted imidazolyl. In some embodiments, R6 is optionally substituted 1,3-oxazolyl. In some embodiments, R6 is optionally substituted 1,2,4-oxadiazolyl. In some embodiments, R6 is optionally substituted 1,3,4-oxadiazolyl. In some embodiments, $R^6$ is optionally substituted thiophenyl. In some embodiments, $R^6$ is optionally substituted thiazolyl. In some embodiments, R6 is optionally substituted pyridinyl. In some embodiments, $R^6$ is optionally substituted pyridazinyl. In some embodiments, $R^6$ is optionally substituted pyrimidinyl Provided herein as Embodiment 29 is the compound according to any one of Embodiments 1-27, or a tautomer thereof, or a pharmaceutically acceptable salt of said compound or said tautomer, wherein $R^6$ is difluoromethyl, trifluoromethyl, —$CH_2CF_3$, dimethylamino, —C(=O)OCH$_2$CH$_3$, cyclopropyl, cyclobutyl, oxetan-2-yl, azetidine-1-yl, tetrahydrofuran-3-yl,

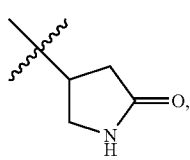 [SMILES: *C1CNC(=O)C1]

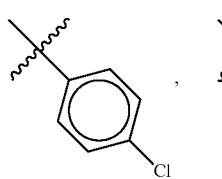, 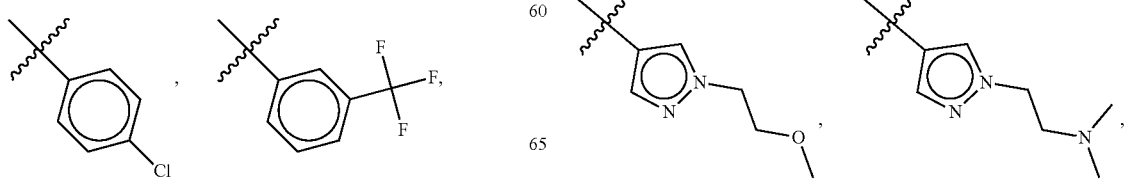

-continued

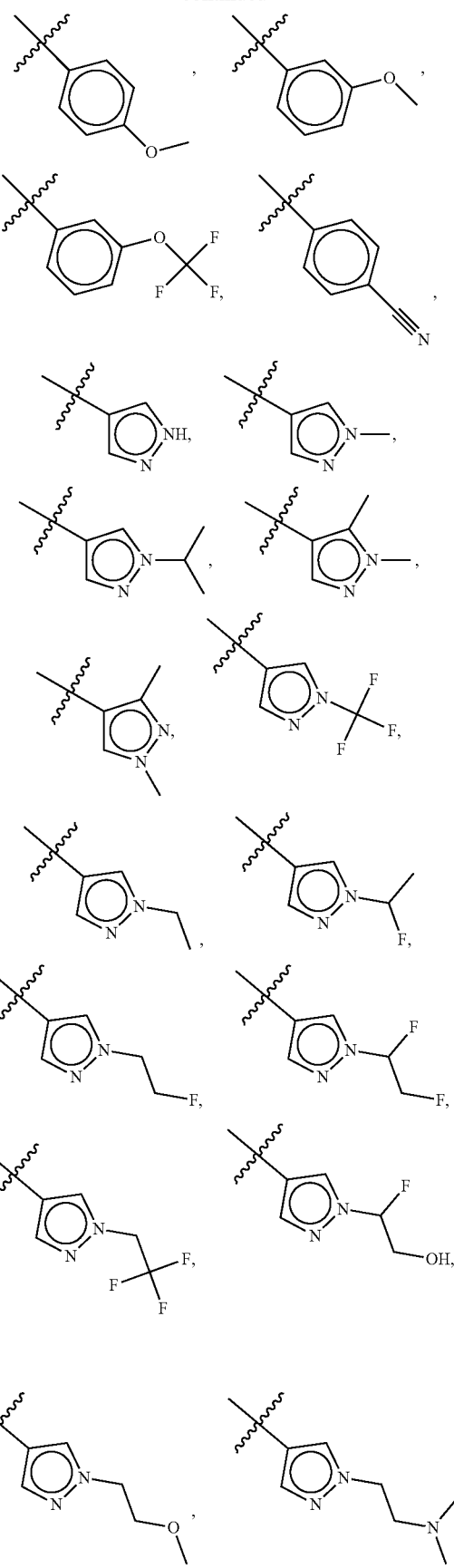

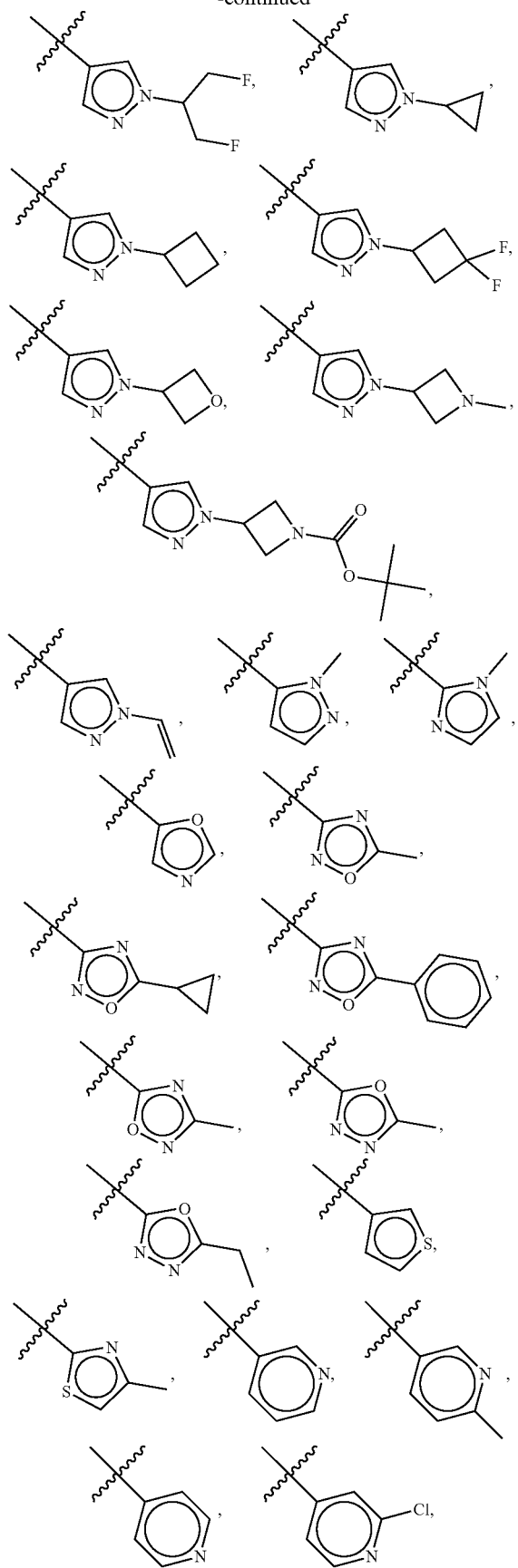

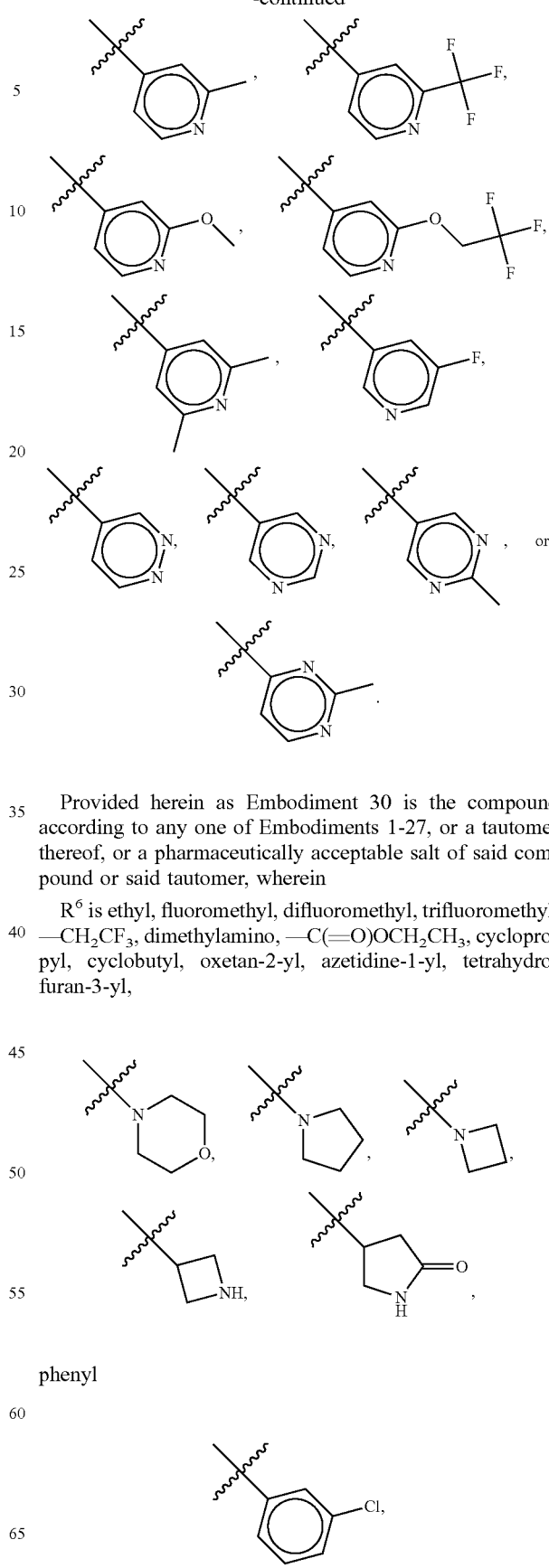

Provided herein as Embodiment 30 is the compound according to any one of Embodiments 1-27, or a tautomer thereof, or a pharmaceutically acceptable salt of said compound or said tautomer, wherein $R^6$ is ethyl, fluoromethyl, difluoromethyl, trifluoromethyl, —$CH_2CF_3$, dimethylamino, —C(=O)OCH$_2$CH$_3$, cyclopropyl, cyclobutyl, oxetan-2-yl, azetidine-1-yl, tetrahydrofuran-3-yl,

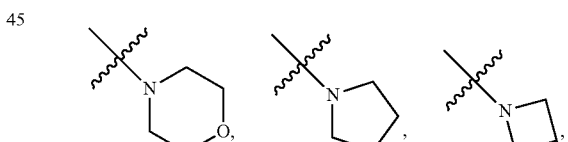

phenyl

-continued
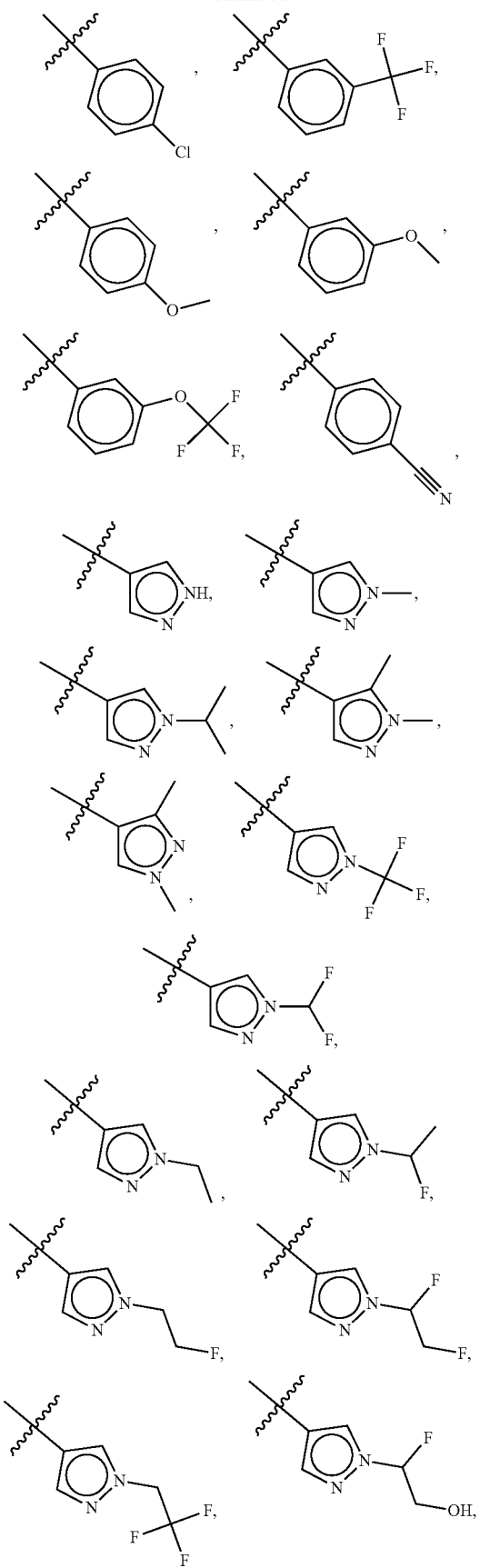
-continued
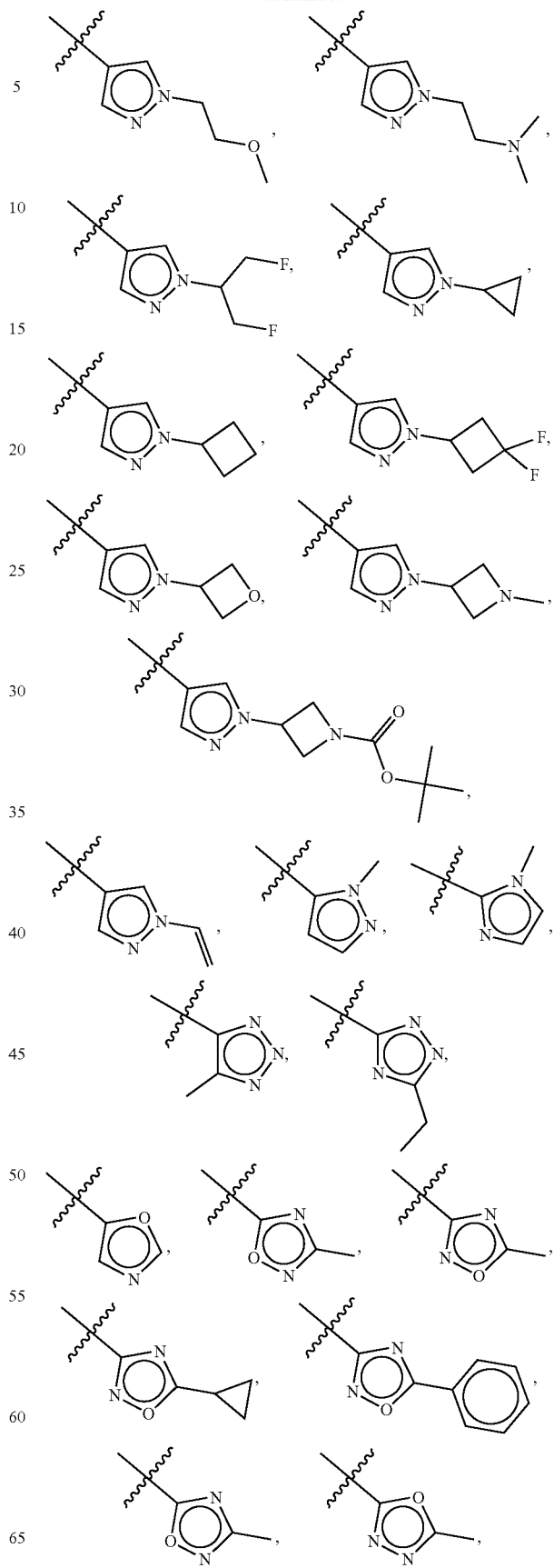

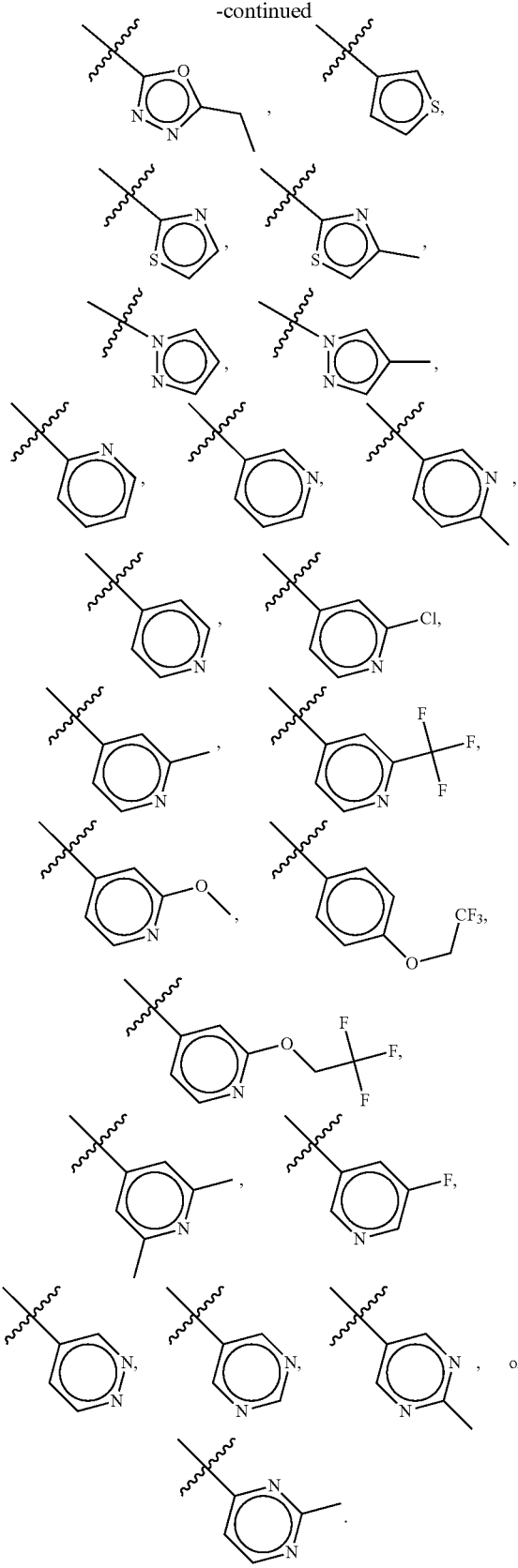

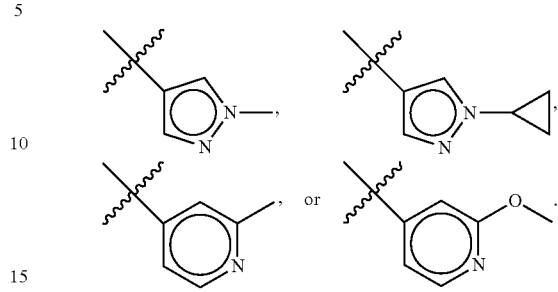

Provided herein as Embodiment 31 is the compound according to any one of Embodiments 1-27, or a tautomer thereof, or a pharmaceutically acceptable salt of said compound or said tautomer, wherein $R^6$ is Provided herein as Embodiment 32 is the compound according to any one of Embodiments 1-31, or a tautomer thereof, or a pharmaceutically acceptable salt of said compound or said tautomer, wherein $R^7$ is optionally substituted $C_{5-6}$cycloalkyl, optionally substituted phenyl, or optionally substituted 6-membered heteroaryl.

Provided herein as Embodiment 33 is the compound according to any one of Embodiments 1-31, or a tautomer thereof, or a pharmaceutically acceptable salt of said compound or said tautomer, wherein $R^7$ is optionally substituted $C_{5-6}$cycloalkyl, optionally substituted phenyl, or optionally substituted pyridinyl.

Provided herein as Embodiment 34 is the compound according to any one of Embodiments 1-31, or a tautomer thereof, or a pharmaceutically acceptable salt of said compound or said tautomer, wherein $R^7$ is optionally substituted phenyl.

Provided herein as Embodiment 35 is the compound according to any one of Embodiments 1-31, or a tautomer thereof, or a pharmaceutically acceptable salt of said compound or said tautomer, wherein $R^7$ is optionally substituted pyridinyl.

Provided herein as Embodiment 36 is the compound according to any one of Embodiments 1-31, or a tautomer thereof, or a pharmaceutically acceptable salt of said compound or said tautomer, wherein $R^7$ is optionally substituted $C_{5-6}$cycloalkyl.

Provided herein as Embodiment 37 is the compound according to any one of Embodiments 1-31, or a tautomer thereof, or a pharmaceutically acceptable salt of said compound or said tautomer, wherein

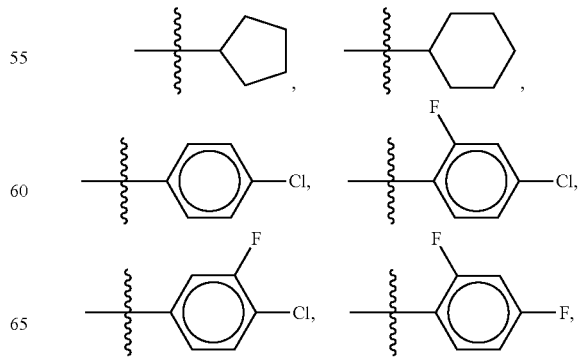

-continued

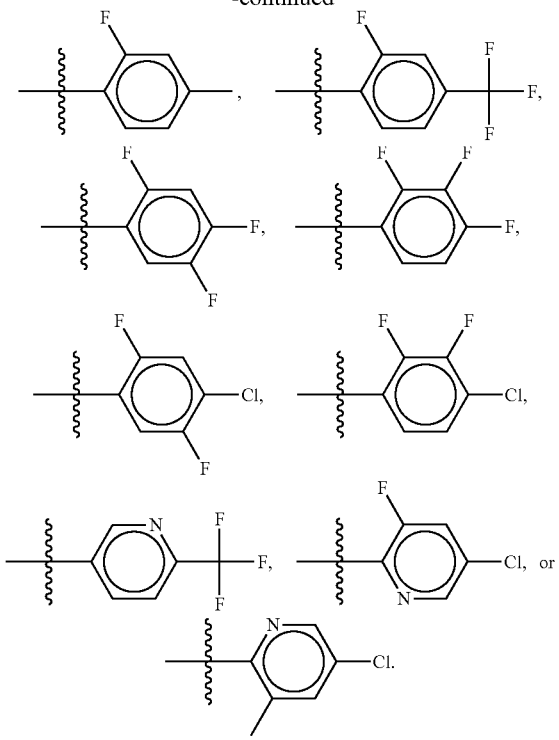

Provided herein as Embodiment 38 is the compound according to any one of Embodiments 1-31, or a tautomer thereof, or a pharmaceutically acceptable salt of said compound or said tautomer, wherein

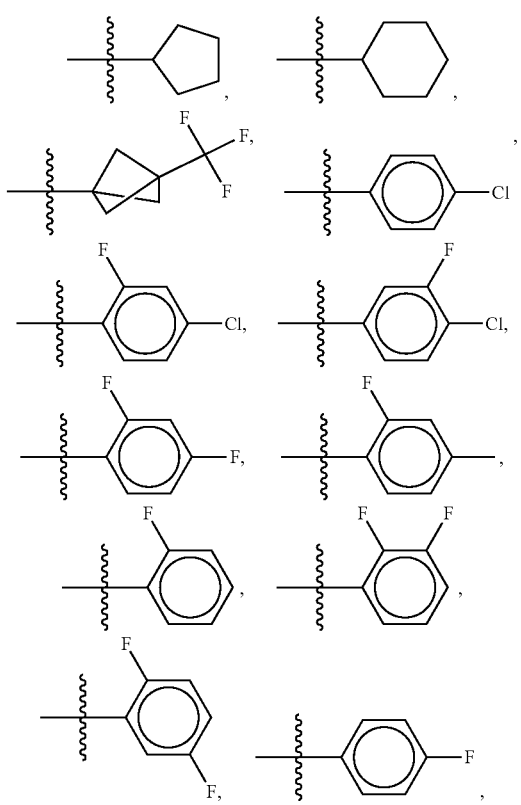

-continued

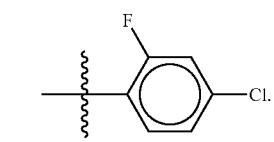

Provided herein as Embodiment 39 is the compound according to any one of Embodiments 1-31, or a tautomer thereof, or a pharmaceutically acceptable salt of said compound or said tautomer, wherein
$R^7$ is Provided herein as Embodiment 40 is the compound according to any one of Embodiments 1-12 and 15-39, or a tautomer thereof, or a pharmaceutically acceptable salt of said compound or said tautomer, wherein
n is 0.

Provided herein as Embodiment 41 is the compound according to any one of Embodiments 1-39, or a tautomer thereof, or a pharmaceutically acceptable salt of said compound or said tautomer, wherein
n is 1.

Provided herein as Embodiment 42 is the compound according to Embodiment 1, or a tautomer thereof, or a pharmaceutically acceptable salt of said compound or said tautomer, wherein the compound is
5-(4-chloro-2-fluorophenyl)-2,3-dimethyl-7-((2S)-2-(1-methyl-1H-pyrazol-4-yl)-4-morpholinyl)pyrido[4,3-d]pyrimidin-4(3H)-one;
5-(4-chloro-2-fluorophenyl)-2,3-dimethyl-7-((2R)-2-(1-methyl-1H-pyrazol-4-yl)-4-morpholinyl)pyrido[4,3-d]pyrimidin-4(3H)-one;
5-(4-chloro-2-fluorophenyl)-2,3-dimethyl-7-((2S)-2-(1-methyl-1H-pyrazol-4-yl)-4-morpholinyl)-4(3H)-quinazolinone;

5-(4-chloro-2-fluorophenyl)-2,3-dimethyl-7-((2R)-2-(1-methyl-1H-pyrazol-4-yl)-4-morpholinyl)-4(3H)-quinazolinone;

5-(4-chlorophenyl)-2,3-dimethyl-7-((2S)-2-(1-methyl-1H-pyrazol-4-yl)-4-morpholinyl)pyrido[4,3-d]pyrimidin-4(3H)-one;

5-(4-chlorophenyl)-2,3-dimethyl-7-((2R)-2-(1-methyl-1H-pyrazol-4-yl)-4-morpholinyl)pyrido[4,3-d]pyrimidin-4(3H)-one;

5-(4-chloro-3-fluorophenyl)-2,3-dimethyl-7-((2S)-2-(1-methyl-1H-pyrazol-4-yl)-4-morpholinyl)pyrido[4,3-d]pyrimidin-4(3H)-one;

5-(2,4-difluorophenyl)-2,3-dimethyl-7-((2S)-2-(1-methyl-1H-pyrazol-4-yl)-4-morpholinyl)pyrido[4,3-d]pyrimidin-4(3H)-one;

2,3-dimethyl-7-((2S)-2-(1-methyl-1H-pyrazol-4-yl)-4-morpholinyl)-5-(2,3,4-trifluorophenyl)pyrido[4,3-d]pyrimidin-4(3H)-one;

2,3-dimethyl-7-((2S)-2-(1-methyl-1H-pyrazol-4-yl)-4-morpholinyl)-5-(2,4,5-trifluorophenyl)pyrido[4,3-d]pyrimidin-4(3H)-one;

5-(4-chloro-2,5-difluorophenyl)-2,3-dimethyl-7-((2S)-2-(1-methyl-1H-pyrazol-4-yl)-4-morpholinyl)pyrido[4,3-d]pyrimidin-4(3H)-one;

5-(2-fluoro-4-methylphenyl)-2,3-dimethyl-7-((2S)-2-(1-methyl-1H-pyrazol-4-yl)-4-morpholinyl)pyrido[4,3-d]pyrimidin-4(3H)-one;

5-(2-fluoro-4-(trifluoromethyl)phenyl)-2,3-dimethyl-7-((2S)-2-(1-methyl-1H-pyrazol-4-yl)-4-morpholinyl)pyrido[4,3-d]pyrimidin-4(3H)-one;

5-(4-chloro-2,3-difluorophenyl)-2,3-dimethyl-7-((2S)-2-(1-methyl-1H-pyrazol-4-yl)-4-morpholinyl)pyrido[4,3-d]pyrimidin-4(3H)-one;

5-(5-chloro-3-fluoro-2-pyridinyl)-2,3-dimethyl-7-(2-(1-methyl-1H-pyrazol-4-yl)-4-morpholinyl)-4(3H)-quinazolinone;

2,3-dimethyl-7-((2S)-2-(1-methyl-1H-pyrazol-4-yl)-4-morpholinyl)-5-(6-(trifluoromethyl)-3-pyridinyl)pyrido[4,3-d]pyrimidin-4(3H)-one;

5-(4-chloro-2-fluorophenyl)-3-cyclohexyl-2-methyl-7-((2S)-2-(1-methyl-1H-pyrazol-4-yl)-4-morpholinyl)pyrido[4,3-d]pyrimidin-4(3H)-one;

5-(4-chloro-2-fluorophenyl)-2-methyl-7-((2S)-2-(1-methyl-1H-pyrazol-4-yl)-4-morpholinyl)-3-(2,2,2-trifluoroethyl)pyrido[4,3-d]pyrimidin-4(3H)-one;

5-(4-chloro-2-fluorophenyl)-3-cyclopropyl-2-methyl-7-((2S)-2-(1-methyl-1H-pyrazol-4-yl)-4-morpholinyl)pyrido[4,3-d]pyrimidin-4(3H)-one;

±5-(5-chloro-3-fluoro-2-pyridinyl)-2-methyl-7-(2-(1-methyl-1H-pyrazol-4-yl)-4-morpholinyl)-3-propylpyrido-[4,3-d]pyrimidin-4(3H)-one;

5-(4-chloro-2-fluorophenyl)-2,3-dimethyl-7-((2S)-2-(1H-pyrazol-4-yl)-4-morpholinyl)pyrido[4,3-d]pyrimidin-4(3H)-one;

5-(4-chloro-2-fluorophenyl)-7-((2S)-2-(1-ethyl-1H-pyrazol-4-yl)-4-morpholinyl)-2,3-dimethylpyrido[4,3-d]pyrimidin-4(3H)-one;

5-(4-chloro-2-fluorophenyl)-7-((2R)-2-(1-ethyl-1H-pyrazol-4-yl)-4-morpholinyl)-2,3-dimethylpyrido[4,3-d]pyrimidin-4(3H)-one;

5-(4-chloro-2-fluorophenyl)-2,3-dimethyl-7-((2S,5R)-5-methyl-2-(1-methyl-1H-pyrazol-4-yl)-4-morpholinyl)pyrido[4,3-d]pyrimidin-4(3H)-one;

5-(4-chloro-2-fluorophenyl)-2,3-dimethyl-7-((2R,5R)-5-methyl-2-(1-methyl-1H-pyrazol-4-yl)-4-morpholinyl)pyrido[4,3-d]pyrimidin-4(3H)-one;

5-(4-chloro-2-fluorophenyl)-2,3-dimethyl-7-((2R,6R)-2-methyl-6-(1-methyl-1H-pyrazol-4-yl)-4-morpholinyl)pyrido[4,3-d]pyrimidin-4(3H)-one;

5-(4-chloro-2-fluorophenyl)-2,3-dimethyl-7-((2R,6S)-2-methyl-6-(1-methyl-1H-pyrazol-4-yl)-4-morpholinyl)pyrido[4,3-d]pyrimidin-4(3H)-one;

5-(4-chloro-2-fluorophenyl)-2,3-dimethyl-7-((2S,6R)-2-methyl-6-(1-methyl-1H-pyrazol-4-yl)-4-morpholinyl)pyrido[4,3-d]pyrimidin-4(3H)-one;

5-(4-chloro-2-fluorophenyl)-2,3-dimethyl-7-((2S,6S)-2-methyl-6-(1-methyl-1H-pyrazol-4-yl)-4-morpholinyl)pyrido[4,3-d]pyrimidin-4(3H)-one;

5-(4-chloro-2-fluorophenyl)-2,3-dimethyl-7-(2-methyl-2-(1-methyl-1H-pyrazol-4-yl)-4-morpholinyl)pyrido[4,3-d]pyrimidin-4(3H)-one;

5-(4-chloro-2-fluorophenyl)-7-((2S)-2-cyclopropyl-4-morpholinyl)-2,3-dimethylpyrido[4,3-d]pyrimidin-4(3H)-one;

5-(4-chloro-2-fluorophenyl)-7-(2-cyclobutyl-4-morpholinyl)-2,3-dimethylpyrido[4,3-d]pyrimidin-4(3H)-one;

5-(4-chloro-2-fluorophenyl)-7-((2S,6R)-2-cyclopropyl-6-methyl-4-morpholinyl)-2,3-dimethylpyrido[4,3-d]pyrimidin-4(3H)-one;

5-(4-chloro-2-fluorophenyl)-7-((2S,6S)-2-cyclopropyl-6-methyl-4-morpholinyl)-2,3-dimethylpyrido[4,3-d]pyrimidin-4(3H)-one;

5-(4-chloro-2-fluorophenyl)-7-((2R,6R)-2-cyclopropyl-6-methyl-4-morpholinyl)-2,3-dimethylpyrido[4,3-d]pyrimidin-4(3H)-one;

5-(4-chloro-2-fluorophenyl)-7-((2R,6S)-2-cyclopropyl-6-methyl-4-morpholinyl)-2,3-dimethylpyrido[4,3-d]pyrimidin-4(3H)-one;

5-(4-chloro-2-fluorophenyl)-2,3-dimethyl-7-((2R)-2-((2R)-2-oxetanyl)-4-morpholinyl)pyrido[4,3-d]pyrimidin-4(3H)-one;

5-(4-chloro-2-fluorophenyl)-2,3-dimethyl-7-((2R)-2-((2S)-2-oxetanyl)-4-morpholinyl)pyrido[4,3-d]pyrimidin-4(3H)-one;

5-(4-chloro-2-fluorophenyl)-2,3-dimethyl-7-((2S)-2-((2S)-2-oxetanyl)-4-morpholinyl)pyrido[4,3-d]pyrimidin-4(3H)-one;

5-(4-chloro-2-fluorophenyl)-2,3-dimethyl-7-((2S)-2-((2R)-2-oxetanyl)-4-morpholinyl)pyrido[4,3-d]pyrimidin-4(3H)-one;

5-(4-chloro-2-fluorophenyl)-2,3-dimethyl-7-((2S)-2-((3S)-tetrahydro-3-furanyl)-4-morpholinyl)pyrido[4,3-d]pyrimidin-4(3H)-one;

5-(4-chloro-2-fluorophenyl)-2,3-dimethyl-7-((2R)-2-((3S)-tetrahydro-3-furanyl)-4-morpholinyl)pyrido[4,3-d]pyrimidin-4(3H)-one;

5-(4-chloro-2-fluorophenyl)-2,3-dimethyl-7-((2S)-2-((3R)-tetrahydro-3-furanyl)-4-morpholinyl)pyrido[4,3-d]pyrimidin-4(3H)-one;

5-(4-chloro-2-fluorophenyl)-2,3-dimethyl-7-((2R)-2-((3R)-tetrahydro-3-furanyl)-4-morpholinyl)pyrido[4,3-d]pyrimidin-4(3H)-one;

5-(4-chloro-2-fluorophenyl)-2,3-dimethyl-7-((2S)-2-(3-pyridinyl)-4-morpholinyl)pyrido[4,3-d]pyrimidin-4(3H)-one;

5-(4-chloro-2-fluorophenyl)-2,3-dimethyl-7-((2R)-2-(3-pyridinyl)-4-morpholinyl)pyrido[4,3-d]pyrimidin-4(3H)-one;

5-(4-chloro-2-fluorophenyl)-2,3-dimethyl-7-((2R)-2-(4-pyridinyl)-4-morpholinyl)pyrido[4,3-d]pyrimidin-4(3H)-one;

5-(4-chloro-2-fluorophenyl)-2,3-dimethyl-7-((2S)-2-(4-pyridinyl)-4-morpholinyl)pyrido[4,3-d]pyrimidin-4(3H)-one;

5-(4-chloro-2-fluorophenyl)-2,3-dimethyl-7-(2-(4-pyridazinyl)-4-morpholinyl)pyrido[4,3-d]pyrimidin-4(3H)-one;

5-(4-chloro-2-fluorophenyl)-2,3-dimethyl-7-(2-(5-pyrimidinyl)-4-morpholinyl)pyrido[4,3-d]pyrimidin-4(3H)-one;

5-(4-chloro-2-fluorophenyl)-2,3-dimethyl-7-(2-(1-methyl-1H-pyrazol-5-yl)-4-morpholinyl)pyrido[4,3-d]pyrimidin-4(3H)-one;

5-(4-chloro-2-fluorophenyl)-2,3-dimethyl-7-(2-(2,2,2-trifluoroethyl)-4-morpholinyl)pyrido[4,3-d]pyrimidin-4(3H)-one;

5-(4-chloro-2-fluorophenyl)-2,3-dimethyl-7-((2R)-2-(thiophen-3-yl)morpholino)pyrido[4,3-d]pyrimidin-4(3H)-one;

5-(4-chloro-2-fluorophenyl)-2,3-dimethyl-7-((2S)-2-(3-thiophenyl)-4-morpholinyl)pyrido[4,3-d]pyrimidin-4(3H)-one;

5-(4-chloro-2-fluorophenyl)-2,3-dimethyl-7-((2R)-2-(5-methyl-1,2,4-oxadiazol-3-yl)-4-morpholinyl)pyrido[4,3-d]pyrimidin-4(3H)-one;

5-(4-chloro-2-fluorophenyl)-2,3-dimethyl-7-((2S)-2-(5-methyl-1,2,4-oxadiazol-3-yl)-4-morpholinyl)pyrido[4,3-d]pyrimidin-4(3H)-one;

5-(4-chloro-2-fluorophenyl)-2,3-dimethyl-7-((2S)-2-(5-methyl-1,3,4-oxadiazol-2-yl)-4-morpholinyl)pyrido[4,3-d]pyrimidin-4(3H)-one;

5-(4-chloro-2-fluorophenyl)-2,3-dimethyl-7-((2R)-2-(5-methyl-1,3,4-oxadiazol-2-yl)-4-morpholinyl)pyrido[4,3-d]pyrimidin-4(3H)-one;

5-(4-chloro-2-fluorophenyl)-2,3-dimethyl-7-(2-(6-methyl-3-pyridinyl)-4-morpholinyl)pyrido[4,3-d]pyrimidin-4(3H)-one;

5-(4-chloro-2-fluorophenyl)-2,3-dimethyl-7-((2S)-2-(2-methyl-4-pyridinyl)-4-morpholinyl)pyrido[4,3-d]pyrimidin-4(3H)-one;

5-(4-chloro-2-fluorophenyl)-2,3-dimethyl-7-((2R)-2-(2-methyl-4-pyridinyl)-4-morpholinyl)pyrido[4,3-d]pyrimidin-4(3H)-one;

5-(4-chloro-2-fluorophenyl)-2,3-dimethyl-7-(2-(2-methyl-4-pyrimidinyl)-4-morpholinyl)pyrido[4,3-d]pyrimidin-4(3H)-one;

5-(4-chloro-2-fluorophenyl)-2,3-dimethyl-7-((2R)-2-(2-methyl-5-pyrimidinyl)-4-morpholinyl)pyrido[4,3-d]pyrimidin-4(3H)-one;

5-(4-chloro-2-fluorophenyl)-2,3-dimethyl-7-((2S)-2-(2-methyl-5-pyrimidinyl)-4-morpholinyl)pyrido[4,3-d]pyrimidin-4(3H)-one;

5-(4-chloro-2-fluorophenyl)-7-((2R)-2-(1,5-dimethyl-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1,5-dimethyl-1H-pyrazol-4-yl)-4-morpholinyl)-2,3-dimethylpyrido[4,3-d]pyrimidin-4(3H)-one;

5-(4-chloro-2-fluorophenyl)-7-(2-(1,3-dimethyl-1H-pyrazol-4-yl)-4-morpholinyl)-2,3-dimethylpyrido[4,3-d]pyrimidin-4(3H)-one;

5-(4-chloro-2-fluorophenyl)-7-(2-(5-fluoro-3-pyridinyl)-4-morpholinyl)-2,3-dimethylpyrido[4,3-d]pyrimidin-4(3H)-one;

5-(4-chloro-2-fluorophenyl)-7-(2-(5-ethyl-1,3,4-oxadiazol-2-yl)-4-morpholinyl)-2,3-dimethylpyrido[4,3-d]pyrimidin-4(3H)-one;

5-(4-chloro-2-fluorophenyl)-2,3-dimethyl-7-((2S,6S)-2-methyl-6-(3-thiophenyl)-4-morpholinyl)pyrido[4,3-d]pyrimidin-4(3H)-one;

5-(4-chloro-2-fluorophenyl)-2,3-dimethyl-7-((2S,6R)-2-methyl-6-(3-thiophenyl)-4-morpholinyl)pyrido[4,3-d]pyrimidin-4(3H)-one;

5-(4-chloro-2-fluorophenyl)-2,3-dimethyl-7-((2R,6S)-2-methyl-6-(3-thiophenyl)-4-morpholinyl)pyrido[4,3-d]pyrimidin-4(3H)-one;

5-(4-chloro-2-fluorophenyl)-2,3-dimethyl-7-((2R,6R)-2-methyl-6-(3-thiophenyl)-4-morpholinyl)pyrido[4,3-d]pyrimidin-4(3H)-one;

5-(4-chloro-2-fluorophenyl)-2,3-dimethyl-7-(2-(4-methyl-1,3-thiazol-2-yl)-4-morpholinyl)pyrido[4,3-d]pyrimidin-4(3H)-one;

5-(4-chloro-2-fluorophenyl)-7-((2R)-2-(2,6-dimethyl-4-pyridinyl)-4-morpholinyl)-2,3-dimethylpyrido[4,3-d]pyrimidin-4(3H)-one;

5-(4-chloro-2-fluorophenyl)-7-((2S)-2-(2,6-dimethyl-4-pyridinyl)-4-morpholinyl)-2,3-dimethylpyrido[4,3-d]pyrimidin-4(3H)-one;

5-(4-chloro-2-fluorophenyl)-7-((2S)-2-(4-methoxyphenyl)-4-morpholinyl)-2,3-dimethylpyrido[4,3-d]pyrimidin-4(3H)-one;

5-(4-chloro-2-fluorophenyl)-7-((2R)-2-(4-methoxyphenyl)-4-morpholinyl)-2,3-dimethylpyrido[4,3-d]pyrimidin-4(3H)-one;

5-(4-chloro-2-fluorophenyl)-7-((2S)-2-(3-methoxyphenyl)-4-morpholinyl)-2,3-dimethylpyrido[4,3-d]pyrimidin-4(3H)-one;

5-(4-chloro-2-fluorophenyl)-7-((2R)-2-(3-methoxyphenyl)-4-morpholinyl)-2,3-dimethylpyrido[4,3-d]pyrimidin-4(3H)-one;

5-(4-chloro-2-fluorophenyl)-7-((2S)-2-(2-methoxy-4-pyridinyl)-4-morpholinyl)-2,3-dimethylpyrido[4,3-d]pyrimidin-4(3H)-one;

5-(4-chloro-2-fluorophenyl)-7-((2R)-2-(2-methoxy-4-pyridinyl)-4-morpholinyl)-2,3-dimethylpyrido[4,3-d]pyrimidin-4(3H)-one;

5-(4-chloro-2-fluorophenyl)-7-((2R)-2-(5-cyclopropyl-1,2,4-oxadiazol-3-yl)-4-morpholinyl)-2,3-dimethylpyrido[4,3-d]pyrimidin-4(3H)-one;

5-(4-chloro-2-fluorophenyl)-7-((2S)-2-(5-cyclopropyl-1,2,4-oxadiazol-3-yl)-4-morpholinyl)-2,3-dimethylpyrido[4,3-d]pyrimidin-4(3H)-one;

5-(4-chloro-2-fluorophenyl)-7-((2R)-2-(4-chlorophenyl)-4-morpholinyl)-2,3-dimethylpyrido[4,3-d]pyrimidin-4(3H)-one;

5-(4-chloro-2-fluorophenyl)-7-((2S)-2-(4-chlorophenyl)-4-morpholinyl)-2,3-dimethylpyrido[4,3-d]pyrimidin-4(3H)-one;

5-(4-chloro-2-fluorophenyl)-7-((2R)-2-(2-chloro-4-pyridinyl)-4-morpholinyl)-2,3-dimethylpyrido[4,3-d]pyrimidin-4(3H)-one;

5-(4-chloro-2-fluorophenyl)-7-((2S)-2-(2-chloro-4-pyridinyl)-4-morpholinyl)-2,3-dimethylpyrido[4,3-d]pyrimidin-4(3H)-one;

4-(4-(5-(4-chloro-2-fluorophenyl)-2,3-dimethyl-4-oxo-3,4-dihydropyrido[4,3-d]pyrimidin-7-yl)-2-morpholinyl)benzonitrile;

5-(4-chloro-2-fluorophenyl)-2,3-dimethyl-7-((2S)-2-(3-(trifluoromethyl)phenyl)-4-morpholinyl)pyrido[4,3-d]pyrimidin-4(3H)-one;

5-(4-chloro-2-fluorophenyl)-2,3-dimethyl-7-((2R)-2-(3-(trifluoromethyl)phenyl)-4-morpholinyl)pyrido[4,3-d]pyrimidin-4(3H)-one;

5-(4-chloro-2-fluorophenyl)-2,3-dimethyl-7-(2-(5-phenyl-1,2,4-oxadiazol-3-yl)-4-morpholinyl)pyrido[4,3-d]pyrimidin-4(3H)-one;

5-(4-chloro-2-fluorophenyl)-2,3-dimethyl-7-(2-(2-(trifluoromethyl)-4-pyridinyl)-4-morpholinyl)pyrido[4,3-d]pyrimidin-4(3H)-one;

5-(4-chloro-2-fluorophenyl)-2,3-dimethyl-7-((2R)-2-(2-(2,2,2-trifluoroethoxy)-4-pyridinyl)-4-morpholinyl)pyrido[4,3-d]pyrimidin-4(3H)-one;

5-(4-chloro-2-fluorophenyl)-2,3-dimethyl-7-((2S)-2-(2-(2,2,2-trifluoroethoxy)-4-pyridinyl)-4-morpholinyl)pyrido[4,3-d]pyrimidin-4(3H)-one;

5-(4-chloro-2-fluorophenyl)-2,3-dimethyl-7-((2R)-2-(3-(trifluoromethoxy)phenyl)-4-morpholinyl)pyrido[4,3-d]pyrimidin-4(3H)-one;

5-(4-chloro-2-fluorophenyl)-2,3-dimethyl-7-((2S)-2-(3-(trifluoromethoxy)phenyl)-4-morpholinyl)pyrido[4,3-d]pyrimidin-4(3H)-one;

5-(4-chloro-2-fluorophenyl)-2,3-dimethyl-7-((3S)-3-(1-methyl-1H-pyrazol-4-yl)-1-piperidinyl)pyrido[4,3-d]pyrimidin-4(3H)-one;

5-(4-chloro-2-fluorophenyl)-2,3-dimethyl-7-((3R)-3-(1-methyl-1H-pyrazol-4-yl)-1-piperidinyl)pyrido[4,3-d]pyrimidin-4(3H)-one;

5-(4-chloro-2-fluorophenyl)-7-(3,4-dihydro-2,6-naphthyridin-2(1H)-yl)-2,3-dimethylpyrido[4,3-d]pyrimidin-4(3H)-one;

5-(4-chloro-2-fluorophenyl)-7-(3,4-dihydro-2,7-naphthyridin-2(1H)-yl)-2,3-dimethylpyrido[4,3-d]pyrimidin-4(3H)-one;

5-(4-chloro-2-fluorophenyl)-2,3-dimethyl-7-(1-methyl-1,4,5,7-tetrahydro-6H-pyrazolo[3,4-c]pyridin-6-yl)pyrido[4,3-d]pyrimidin-4(3H)-one;

5-(4-chloro-2-fluorophenyl)-2,3-dimethyl-7-(3-(1,3-oxazol-5-yl)-1-piperidinyl)pyrido[4,3-d]pyrimidin-4(3H)-one;

5-(4-chloro-2-fluorophenyl)-2,3-dimethyl-7-(3-(5-oxo-3-pyrrolidinyl)-1-piperidinyl)pyrido[4,3-d]pyrimidin-4(3H)-one;

5-(4-chloro-2-fluorophenyl)-2,3-dimethyl-7-((3S)-3-(1H-pyrazol-4-yl)-1-piperidinyl)pyrido[4,3-d]pyrimidin-4(3H)-one;

5-(4-chloro-2-fluorophenyl)-2,3-dimethyl-7-((3R)-3-(1H-pyrazol-4-yl)-1-piperidinyl)pyrido[4,3-d]pyrimidin-4(3H)-one;

5-(4-chloro-2-fluorophenyl)-7-(3-(dimethylamino)-1-piperidinyl)-2,3-dimethylpyrido[4,3-d]pyrimidin-4(3H)-one;

7-(3-(1-azetidinyl)-1-piperidinyl)-5-(4-chloro-2-fluorophenyl)-2,3-dimethylpyrido[4,3-d]pyrimidin-4(3H)-one;

5-(4-chloro-2-fluorophenyl)-2,3-dimethyl-7-((3R)-3-(3-methyl-1,2,4-oxadiazol-5-yl)-1-piperidinyl)pyrido[4,3-d]pyrimidin-4(3H)-one;

5-(4-chloro-2-fluorophenyl)-2,3-dimethyl-7-((3S)-3-(3-methyl-1,2,4-oxadiazol-5-yl)-1-piperidinyl)pyrido[4,3-d]pyrimidin-4(3H)-one;

5-(4-chloro-2-fluorophenyl)-2,3-dimethyl-7-((3S)-3-(4-pyridinyl)-1-piperidinyl)pyrido[4,3-d]pyrimidin-4(3H)-one;

5-(4-chloro-2-fluorophenyl)-2,3-dimethyl-7-((3R)-3-(4-pyridinyl)-1-piperidinyl)pyrido[4,3-d]pyrimidin-4(3H)-one;

7-(8-chloro-3,4-dihydro-2,7-naphthyridin-2(1H)-yl)-5-(4-chloro-2-fluorophenyl)-2,3-dimethylpyrido[4,3-d]pyrimidin-4(3H)-one;

5'-(4-chloro-2-fluorophenyl)-4-methoxy-2',3'-dimethyl-7,8-dihydro-5H-[6,7'-bipyrido[4,3-d]pyrimidin]-4'(3'H)-one;

5-(4-chloro-2-fluorophenyl)-7-((3R)-4,4-difluoro-3-(1-methyl-1H-pyrazol-4-yl)-1-piperidinyl)-2,3-dimethylpyrido[4,3-d]pyrimidin-4(3H)-one;

5-(4-chloro-2-fluorophenyl)-7-((3S)-4,4-difluoro-3-(1-methyl-1H-pyrazol-4-yl)-1-piperidinyl)-2,3-dimethylpyrido[4,3-d]pyrimidin-4(3H)-one;

5-(4-chloro-2-fluorophenyl)-2,3-dimethyl-7-(3-(trifluoromethyl)-1-pyrrolidinyl)pyrido[4,3-d]pyrimidin-4(3H)-one;

5-(4-chloro-2-fluorophenyl)-7-(3-(difluoromethyl)-1-pyrrolidinyl)-2,3-dimethylpyrido[4,3-d]pyrimidin-4(3H)-one;

5-(4-chloro-2-fluorophenyl)-2,3-dimethyl-7-(3-(3-pyridinyl)-1-pyrrolidinyl)pyrido[4,3-d]pyrimidin-4(3H)-one;

5-(4-chloro-2-fluorophenyl)-2,3-dimethyl-7-((2S)-2-(1-(2-propanyl)-1H-pyrazol-4-yl)-4-morpholinyl)pyrido[4,3-d]pyrimidin-4(3H)-one;

5-(4-chloro-2-fluorophenyl)-7-((2S)-2-(1-cyclobutyl-1H-pyrazol-4-yl)-4-morpholinyl)-2,3-dimethylpyrido[4,3-d]pyrimidin-4(3H)-one;

5-(4-chloro-2-fluorophenyl)-2,3-dimethyl-7-((2S)-2-(1-(3-oxetanyl)-1H-pyrazol-4-yl)-4-morpholinyl)pyrido[4,3-d]pyrimidin-4(3H)-one;

5-(4-chloro-2-fluorophenyl)-2,3-dimethyl-7-((2S)-2-(1-(2,2,2-trifluoroethyl)-1H-pyrazol-4-yl)-4-morpholinyl)pyrido[4,3-d]pyrimidin-4(3H)-one;

5-(4-chloro-2-fluorophenyl)-7-((2S)-2-(1-(2-methoxyethyl)-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1-(2-fluoroethyl)-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1-(1-fluoroethyl)-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1-(1-fluoro-2-hydroxyethyl)-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1-(3,3-difluorocyclobutyl)-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1-(2-(dimethylamino)ethyl)-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1-(1,3-difluoro-2-propanyl)-1H-pyrazol-4-yl)-4-morpholinyl)-2,3-dimethylpyrido[4,3-d]pyrimidin-4(3H)-one;

2-methyl-2-propanyl 3-(4-((2S)-4-(5-(4-chloro-2-fluorophenyl)-2,3-dimethyl-4-oxo-3,4-dihydropyrido[4,3-d]pyrimidin-7-yl)-2-morpholinyl)-1H-pyrazol-1-yl)-1-azetidinecarboxylate;

5-(4-chloro-2-fluorophenyl)-7-((2S)-2-(1-(1,2-difluoroethyl)-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1-cyclopropyl-1H-pyrazol-4-yl)-4-morpholinyl)-2,3-dimethylpyrido[4,3-d]pyrimidin-4(3H)-one;

5-(4-chloro-2-fluorophenyl)-7-((2S)-2-(1-ethenyl-1H-pyrazol-4-yl)-4-morpholinyl)-2,3-dimethylpyrido[4,3-d]pyrimidin-4(3H)-one;

5-(4-chloro-2-fluorophenyl)-2,3-dimethyl-7-((2S)-2-(1-(1-methyl-3-azetidinyl)-1H-pyrazol-4-yl)-4-morpholinyl)pyrido[4,3-d]pyrimidin-4(3H)-one;

5-(4-chloro-2-fluorophenyl)-2,3-dimethyl-7-((2S)-2-(6-methyl-3-pyridinyl)-4-morpholinyl)pyrido[4,3-d]pyrimidin-4(3H)-one;

5-(4-chloro-2-fluorophenyl)-2,3-dimethyl-7-((2R)-2-(6-methyl-3-pyridinyl)-4-morpholinyl)pyrido[4,3-d]pyrimidin-4(3H)-one;

5-(4-chloro-2-fluorophenyl)-2,3-dimethyl-7-((2S)-2-(1-(trifluoromethyl)-1H-pyrazol-4-yl)-4-morpholinyl)pyrido[4,3-d]pyrimidin-4(3H)-one;

5-(4-chloro-2-fluorophenyl)-2-cyclopropyl-3-methyl-7-((2S)-2-(1-methyl-1H-pyrazol-4-yl)-4-morpholinyl)pyrido[4,3-d]pyrimidin-4(3H)-one;

5-(4-chloro-2-fluorophenyl)-3-methyl-7-((2S)-2-(1-methyl-1H-pyrazol-4-yl)-4-morpholinyl)-2-(trifluoromethyl)pyrido[4,3-d]pyrimidin-4(3H)-one;

5-(4-chloro-2-fluorophenyl)-3-ethyl-7-((2S)-2-(1-methyl-1H-pyrazol-4-yl)-4-morpholinyl)-2-(trifluoromethyl)pyrido[4,3-d]pyrimidin-4(3H)-one;

5-(4-chloro-2-fluorophenyl)-2-methyl-7-((2S)-2-(1-methyl-1H-pyrazol-4-yl)-4-morpholinyl)pyrido[4,3-d]pyrimidin-4(3H)-one;

5-(4-chloro-2-fluorophenyl)-3-ethyl-2-methyl-7-((2S)-2-(1-methyl-1H-pyrazol-4-yl)-4-morpholinyl)pyrido[4,3-d]pyrimidin-4(3H)-one;

5-(4-chloro-2-fluorophenyl)-3-ethyl-2-methyl-7-((2S)-2-(5-methyl-1,2,4-oxadiazol-3-yl)-4-morpholinyl)pyrido[4,3-d]pyrimidin-4(3H)-one;

5-(4-chloro-2-fluorophenyl)-3-ethyl-2-methyl-7-((2R)-2-(5-methyl-1,2,4-oxadiazol-3-yl)-4-morpholinyl)pyrido[4,3-d]pyrimidin-4(3H)-one;

5-(4-chloro-2-fluorophenyl)-3-ethyl-2-methyl-7-((2S)-2-(2-methyl-4-pyridinyl)-4-morpholinyl)pyrido[4,3-d]pyrimidin-4(3H)-one;

5-(2,4-difluorophenyl)-3-ethyl-2-methyl-7-((2S)-2-(2-methyl-4-pyridinyl)-4-morpholinyl)pyrido[4,3-d]pyrimidin-4(3H)-one;

7-((2S)-2-(1-cyclopropyl-1H-pyrazol-4-yl)-4-morpholinyl)-5-(2,4-difluorophenyl)-3-ethyl-2-methylpyrido[4,3-d]pyrimidin-4(3H)-one;

5-(4-chloro-2-fluorophenyl)-2-methyl-7-((2S)-2-(1-methyl-1H-pyrazol-4-yl)-4-morpholinyl)-3-propylpyrido[4,3-d]pyrimidin-4(3H)-one;

5-(5-chloro-3-fluoro-2-pyridinyl)-2-methyl-7-((2S)-2-(1-methyl-1H-pyrazol-4-yl)-4-morpholinyl)-3-propylpyrido[4,3-d]pyrimidin-4(3H)-one;

5-(4-chloro-2-fluorophenyl)-2-methyl-7-((2S)-2-(1-methyl-1H-pyrazol-5-yl)-4-morpholinyl)-3-propylpyrido[4,3-d]pyrimidin-4(3H)-one;

5-(4-chloro-2-fluorophenyl)-2-methyl-7-((2R)-2-(1-methyl-1H-pyrazol-5-yl)-4-morpholinyl)-3-propylpyrido[4,3-d]pyrimidin-4(3H)-one;

5-(4-chloro-2-fluorophenyl)-7-((2R)-2-(difluoromethyl)-4-morpholinyl)-2-methyl-3-propylpyrido[4,3-d]pyrimidin-4(3H)-one;

5-(4-chloro-2-fluorophenyl)-2-methyl-7-((2S)-2-phenyl-4-morpholinyl)-3-propylpyrido[4,3-d]pyrimidin-4(3H)-one;

5-(4-chloro-2-fluorophenyl)-3-methyl-7-((2S)-2-(1-methyl-1H-pyrazol-4-yl)-4-morpholinyl)pyrido[4,3-d]pyrimidin-4(3H)-one;

5-cyclohexyl-2,3-dimethyl-7-((2S)-2-(1-methyl-1H-pyrazol-4-yl)-4-morpholinyl)pyrido[4,3-d]pyrimidin-4(3H)-one;

5-cyclopentyl-2,3-dimethyl-7-((2S)-2-(1-methyl-1H-pyrazol-4-yl)-4-morpholinyl)pyrido[4,3-d]pyrimidin-4(3H)-one;

5-(4-chloro-2-fluorophenyl)-2,3-dimethyl-7-((2R,4R)-2-(1-methyl-1H-pyrazol-4-yl)tetrahydro-2H-pyran-4-yl)pyrido[4,3-d]pyrimidin-4(3H)-one and 5-(4-chloro-2-fluorophenyl)-2,3-dimethyl-7-((2S,4S)-2-(1-methyl-1H-pyrazol-4-yl)tetrahydro-2H-pyran-4-yl)pyrido[4,3-d]pyrimidin-4(3H)-one;

5-(4-chloro-2-fluorophenyl)-2,3-dimethyl-7-((2R,4S)-2-(1-methyl-1H-pyrazol-4-yl)tetrahydro-2H-pyran-4-yl)pyrido[4,3-d]pyrimidin-4(3H)-one;

5-(4-chloro-2-fluorophenyl)-2,3-dimethyl-7-((2S,4R)-2-(1-methyl-1H-pyrazol-4-yl)tetrahydro-2H-pyran-4-yl)pyrido[4,3-d]pyrimidin-4(3H)-one;

5-(4-chloro-2-fluorophenyl)-2,3-dimethyl-7-(6-(1-methyl-1H-pyrazol-4-yl)-3,6-dihydro-2H-pyran-4-yl)pyrido[4,3-d]pyrimidin-4(3H)-one;

5-(4-chloro-2-fluorophenyl)-7-((2R,4S)-2-(1-cyclopropyl-1H-pyrazol-4-yl)tetrahydro-2H-pyran-4-yl)-2,3-dimethylpyrido[4,3-d]pyrimidin-4(3H)-one;

5-(4-chloro-2-fluorophenyl)-7-((2S,4R)-2-(1-cyclopropyl-1H-pyrazol-4-yl)tetrahydro-2H-pyran-4-yl)-2,3-dimethylpyrido[4,3-d]pyrimidin-4(3H)-one;

ethyl (2R,4S)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate and ethyl (2S,4R)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate;

ethyl (2S,4S)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate and ethyl (2R,4R)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate;

5-(4-chloro-2-fluorophenyl)-2,3-dimethyl-7-((2R,4S)-2-(2-methyl-4-pyridinyl)tetrahydro-2H-pyran-4-yl)pyrido[4,3-d]pyrimidin-4(3H)-one;

5-(4-chloro-2-fluorophenyl)-2,3-dimethyl-7-((2S,4R)-2-(2-methyl-4-pyridinyl)tetrahydro-2H-pyran-4-yl)pyrido[4,3-d]pyrimidin-4(3H)-one;

5-(4-chloro-2-fluorophenyl)-2,3-dimethyl-7-(2-(6-methylpyridin-3-yl)tetrahydro-2H-pyran-4-yl)pyrido[4,3-d]pyrimidin-4(3H)-one;

5-(4-chloro-2-fluorophenyl)-7-((2R,4S)-2-(2-methoxy-4-pyridinyl)tetrahydro-2H-pyran-4-yl)-2,3-dimethylpyrido[4,3-d]pyrimidin-4(3H)-one;

5-(4-chloro-2-fluorophenyl)-7-((2S,4R)-2-(2-methoxy-4-pyridinyl)tetrahydro-2H-pyran-4-yl)-2,3-dimethylpyrido[4,3-d]pyrimidin-4(3H)-one;

5-(4-chloro-2-fluorophenyl)-7-((2R,4R)-2-(2-methoxy-4-pyridinyl)tetrahydro-2H-pyran-4-yl)-2,3-dimethylpyrido[4,3-d]pyrimidin-4(3H)-one;

5-(4-chloro-2-fluorophenyl)-7-((2S,4S)-2-(2-methoxy-4-pyridinyl)tetrahydro-2H-pyran-4-yl)-2,3-dimethylpyrido[4,3-d]pyrimidin-4(3H)-one;

5-(4-chloro-2-fluorophenyl)-2,3-dimethyl-7-((2R,4R)-2-(3-pyridinyl)tetrahydro-2H-pyran-4-yl)pyrido[4,3-d]pyrimidin-4(3H)-one and 5-(4-chloro-2-fluorophenyl)-2,3-dimethyl-7-((2S,4S)-2-(3-pyridinyl)tetrahydro-2H-pyran-4-yl)pyrido[4,3-d]pyrimidin-4(3H)-one;

5-(4-chloro-2-fluorophenyl)-2,3-dimethyl-7-((2R,4S)-2-(3-pyridinyl)tetrahydro-2H-pyran-4-yl)pyrido[4,3-d]pyrimidin-4(3H)-one; or 5-(4-chloro-2-fluorophenyl)-2,3-dimethyl-7-((2S,4R)-2-(3-pyridinyl)tetrahydro-2H-pyran-4-yl)pyrido[4,3-d]pyrimidin-4(3H)-one.

Provided herein as Embodiment 43 is the compound according to Embodiment 1, or a tautomer thereof, or a pharmaceutically acceptable salt of said compound or said tautomer, wherein the compound is a compound of Table A.

Provided herein as Embodiment 44 is the compound according to Embodiment 1, or a tautomer thereof, or a pharmaceutically acceptable salt of said compound or said tautomer, wherein the compound is not 5-(2,4-difluorophenyl)-2,3-dimethyl-7-(2-(2-methylpyridin-4-yl)morpholino)pyrido[4,3-d]pyrimidin-4(3H)-one; 2,3- dimethyl-7-(2-(2-methylpyridin-4-yl)tetrahydro-2H-pyran-4-yl)-5-(6-(trifluoromethyl)pyridin-3-yl)pyrido[4,3-d]pyrimidin-4(3H)-one;
5-(2,4-difluorophenyl)-2,3-dimethyl-7-(2-(2-methylpyridin-4-yl)tetrahydro-2H-pyran-4-yl)pyrido[4,3-d]pyrimidin-4(3H)-one;
5-(2,4-difluorophenyl)-7-(2-(2-methoxypyridin-4-yl)morpholino)-2,3-dimethylpyrido[4,3-d]pyrimidin-4(3H)-one;
2,3-dimethyl-7-(2-(2-methylpyridin-4-yl)morpholino)-5-(6-(trifluoromethyl)pyridin-3-yl)pyrido[4,3-d]pyrimidin-4(3H)-one;
2,3-dimethyl-7-(2-(2-methylpyridin-4-yl)tetrahydro-2H-pyran-4-yl)-5-(3-(trifluoromethyl)bicyclo[1.1.1]pentan-1-yl)pyrido[4,3-d]pyrimidin-4(3H)-one;
2,3-dimethyl-7-(2-(2-methylpyridin-4-yl)morpholino)-5-(3-(trifluoromethyl)bicyclo[1.1.1]pentan-1-yl)pyrido[4,3-d]pyrimidin-4(3H)-one; or
7-(2-(2-methoxypyridin-4-yl)morpholino)-2,3-dimethyl-5-(3-(trifluoromethyl)bicyclo[1.1.1]pentan-1-yl)pyrido[4,3-d]pyrimidin-4(3H)-one.

Provided herein as Embodiment 45 is the compound according to Embodiment 1, or a tautomer thereof, or a pharmaceutically acceptable salt of said compound or said tautomer, wherein the compound is a compound of Formula II

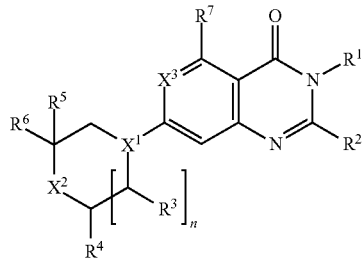

wherein
n is 1;
$X^1$ is CH or N;
$X^2$ is O;
$X^3$ is N;
$R^1$ and $R^2$ are both methyl;
$R^3$, $R^4$, and $R^5$ are each H;
$R^6$ is

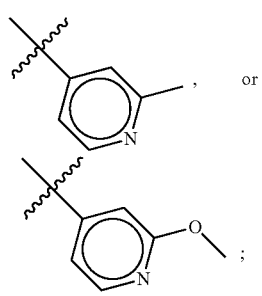

and
$R^7$ is $C_{5-6}$cycloalkyl, $C_{5-8}$spiroalkyl, $C_{5-8}$tricycloalkyl, phenyl, or 6-membered heteroaryl; wherein $R^7$ is further optionally substituted with 1 to 4 substituents independently selected from halogen, $C_{1-3}$alkyl, and $C_{1-3}$haloalkyl;

provided that $R^7$ is not

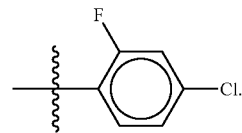

Provided herein as Embodiment 46 is the compound according to Embodiment 1, or a tautomer thereof, or a pharmaceutically acceptable salt of said compound or said tautomer, wherein the compound is a compound of Formula II

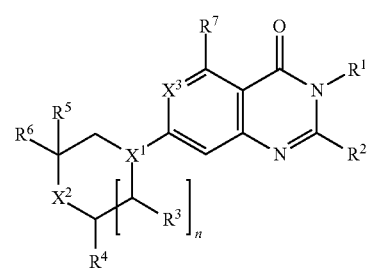

wherein
n is 1;
$X^1$ is CH or N;
$X^2$ is O;
$X^3$ is N;
$R^1$ and $R^2$ are both methyl;
$R^3$, $R^4$, and $R^5$ are each H;
$R^6$ is

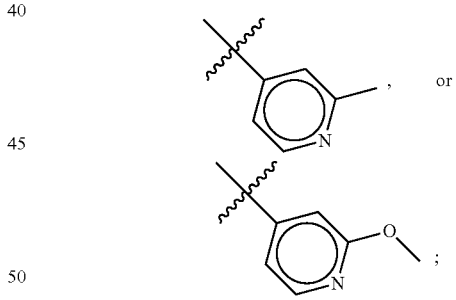

and
$R^7$ is

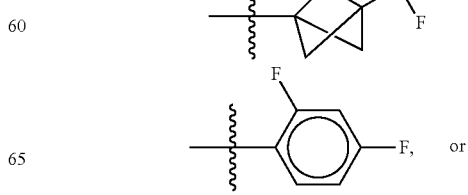

-continued

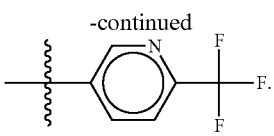

Provided herein as Embodiment 47 is the compound according to Embodiment 1, or a pharmaceutically acceptable salt thereof, wherein the compound is

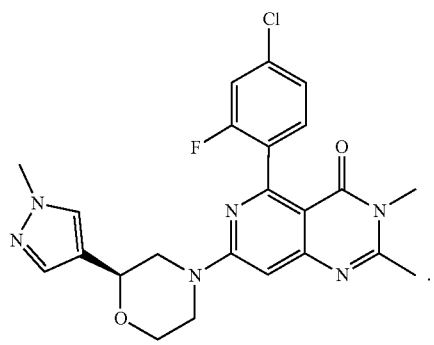 [SMILES: Cc1nc2cc(N3CCO[C@@H](c4cnn(C)c4)C3)nc(-c3ccc(Cl)cc3F)c2c(=O)n1C]

Provided herein as Embodiment 48 is the compound according to Embodiment 1, or a pharmaceutically acceptable salt thereof, wherein the compound is

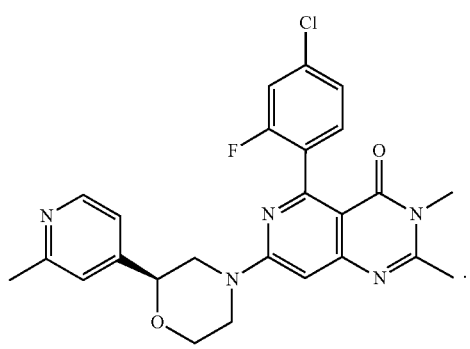

Provided herein as Embodiment 49 is the compound according to Embodiment 1, or a pharmaceutically acceptable salt thereof, wherein the compound is

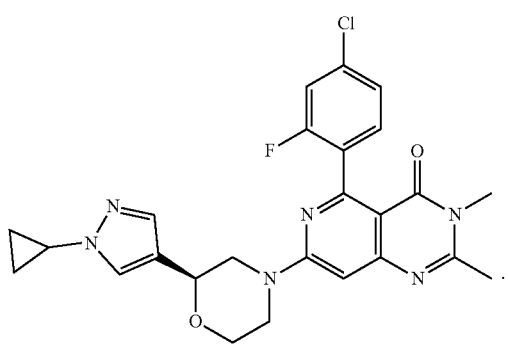 [SMILES: Cc1nc2cc(N3CCO[C@@H](c4cnn(C5CC5)c4)C3)nc(-c3ccc(Cl)cc3F)c2c(=O)n1C]

Provided herein as Embodiment 50 is the compound according to Embodiment 1, or a pharmaceutically acceptable salt thereof, wherein the compound is

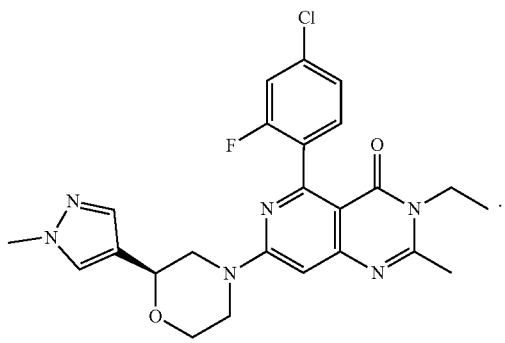 [SMILES: CCn1c(C)nc2cc(N3CCO[C@@H](c4cnn(C)c4)C3)nc(-c3ccc(Cl)cc3F)c2c1=O]

Provided herein as Embodiment 51 is the compound according to Embodiment 1, or a pharmaceutically acceptable salt thereof, wherein the compound is

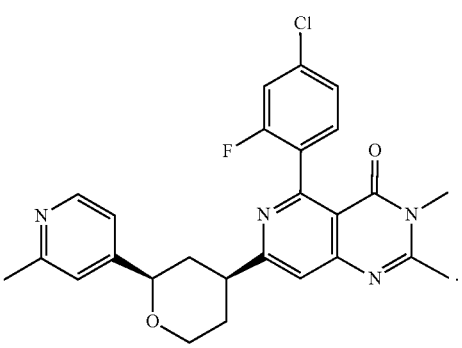

Provided herein as Embodiment 52 is the compound according to Embodiment 1, or a pharmaceutically acceptable salt thereof, wherein the compound is

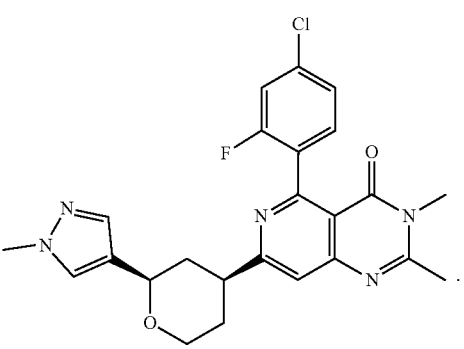

Provided herein as Embodiment 53 is the compound according to Embodiment 1, or a pharmaceutically acceptable salt thereof, wherein the compound is

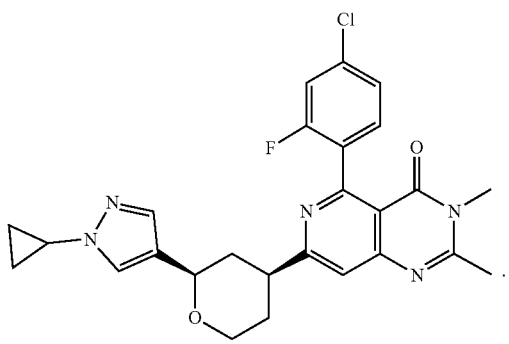 [SMILES: Cc1nc2cc([C@H]3CCO[C@@H](c4cnn(C5CC5)c4)C3)nc(-c3ccc(Cl)cc3F)c2c(=O)n1C]

Provided herein as Embodiment 54 is the compound according to Embodiment 1, or

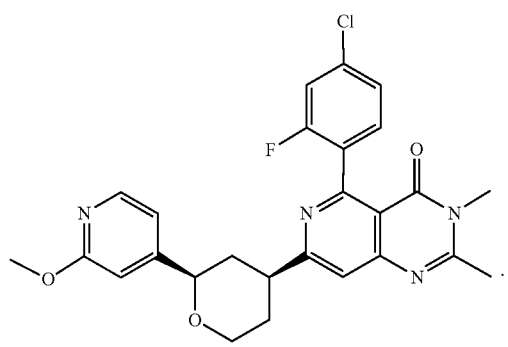

Exemplary compounds of the invention are set forth in Table A, below. In some embodiments, the compound of Formula I is a compound set forth in Table A. In some embodiments, the present invention provides a compound as depicted in Table A or a pharmaceutically acceptable salt thereof.

TABLE A

| Exemplary Compounds | |
|---|---|
| I # | Structure |
| I-1 | |
| I-2 | |
| I-3 | |
| I-4 | |
| I-5 | |

TABLE A-continued

Exemplary Compounds

| I # | Structure |
|---|---|
| I-6 | 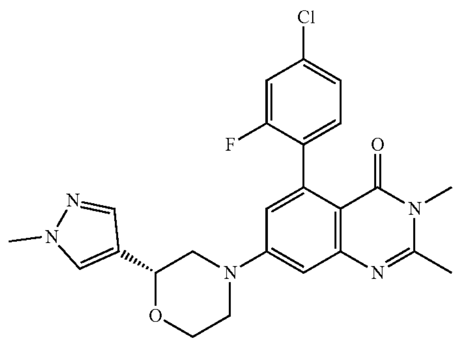 |
| I-7 | 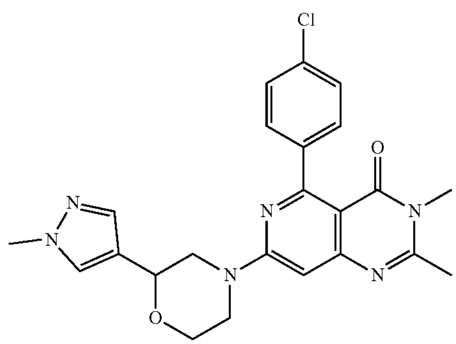 |
| I-8 | 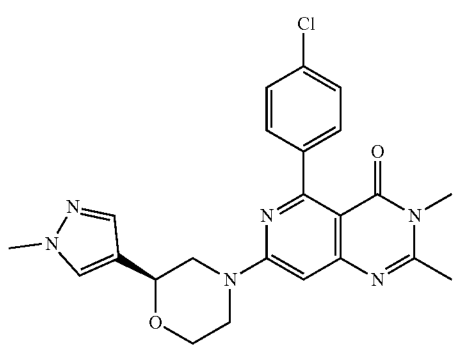 |
| I-9 | 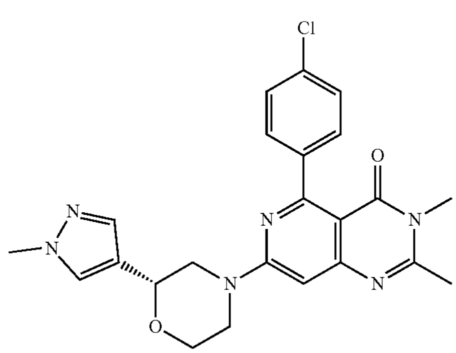 |
| I-10 | |
| I-11 | |
| I-12 | |
| I-13 | |

TABLE A-continued

Exemplary Compounds

| I # | Structure |
|---|---|
| I-14 | 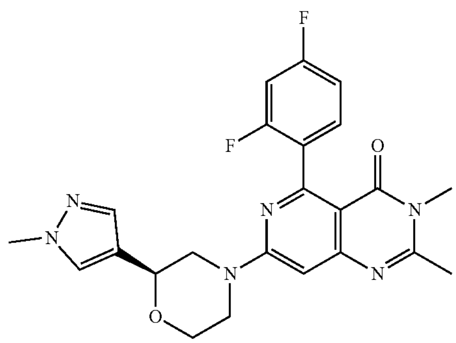 |
| I-15 | 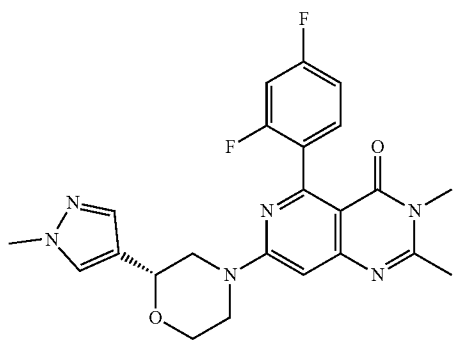 |
| I-16 | 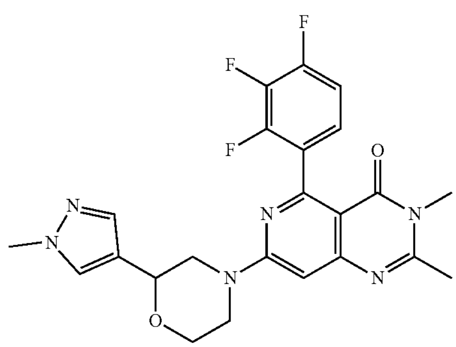 |
| I-17 | 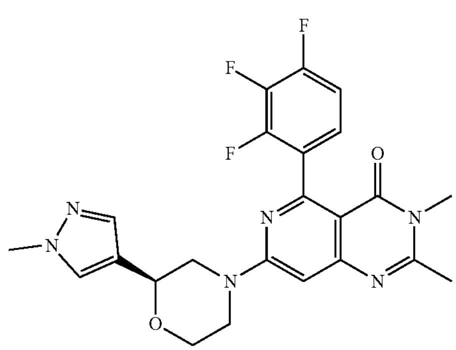 |
| I-18 | |
| I-19 | |
| I-20 | |
| I-21 | |

TABLE A-continued

Exemplary Compounds

| I # | Structure |
|---|---|
| I-22 | (structure) |
| I-23 | (structure) |
| I-24 | (structure) |
| I-25 | (structure) |
| I-26 | (structure) |
| I-27 | (structure) |
| I-28 | (structure) |
| I-29 | (structure) |

TABLE A-continued

Exemplary Compounds

| I # | Structure |
|---|---|
| I-30 | 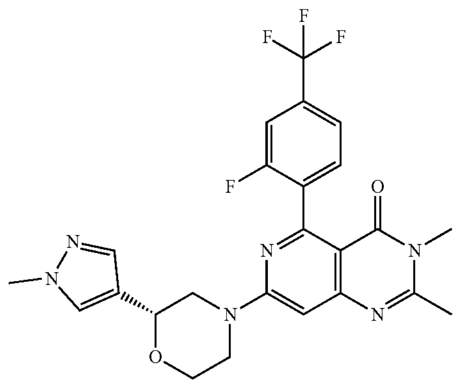 |
| I-31 | 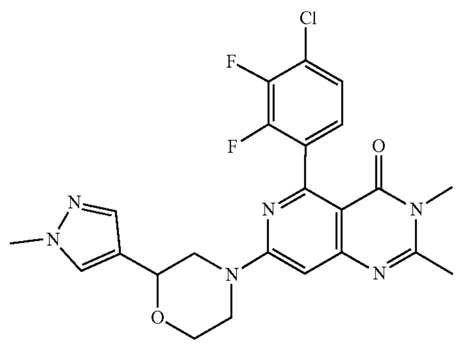 |
| I-32 | 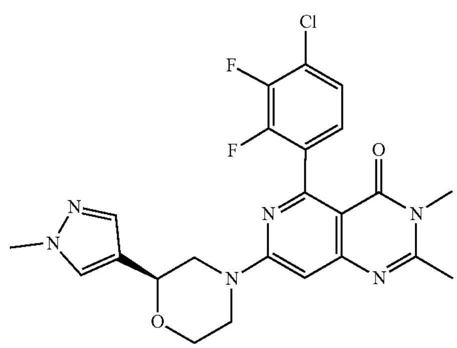 |
| I-33 | 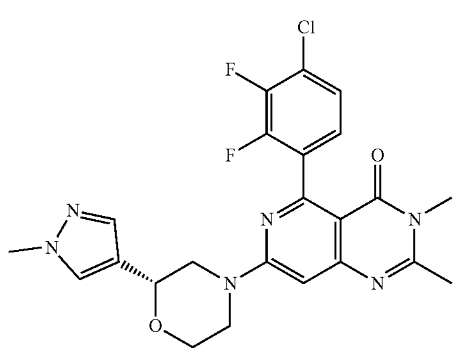 |
| I-34 | |
| I-35 | |
| I-36 | |
| I-37 | |

TABLE A-continued

Exemplary Compounds

| I # | Structure |
|---|---|
| I-38 | (structure) |
| I-39 | (structure) |
| I-40 | (structure) |
| I-41 | (structure) |
| I-42 | (structure) |
| I-43 | (structure) |
| I-44 | (structure) |
| I-45 | (structure) |

TABLE A-continued

Exemplary Compounds

| I # | Structure |
|---|---|
| I-46 | (structure) |
| I-47 | (structure) |
| I-48 | (structure) |
| I-49 | (structure) |
| I-50 | (structure) |
| I-51 | (structure) |
| I-52 | (structure) |
| I-53 | (structure) |

TABLE A-continued

Exemplary Compounds

| I # | Structure |
|---|---|
| I-54 | (structure) |
| I-55 | (structure) |
| I-56 | (structure) |
| I-57 | (structure) |
| I-58 | (structure) |
| I-59 | (structure) |
| I-60 | (structure) |
| I-61 | (structure) |

TABLE A-continued

Exemplary Compounds

| I # | Structure |
|---|---|
| I-62 | (structure) |
| I-63 | (structure) |
| I-64 | (structure) |
| I-65 | (structure) |
| I-66 | (structure) |
| I-67 | (structure) |
| I-68 | (structure) |
| I-69 | (structure) |

TABLE A-continued
Exemplary Compounds
| I # | Structure |
|---|---|
| I-70 | 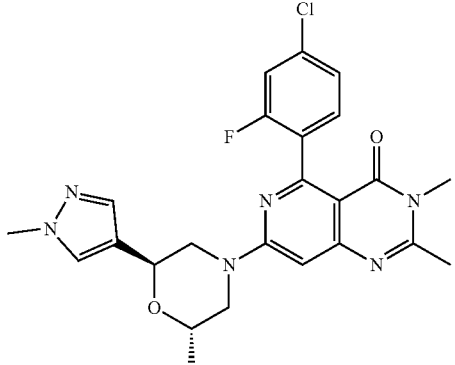 |
| I-71 | 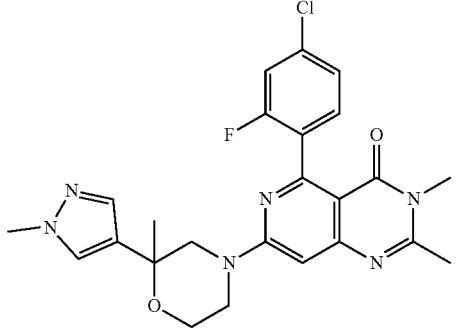 |
| I-72 | 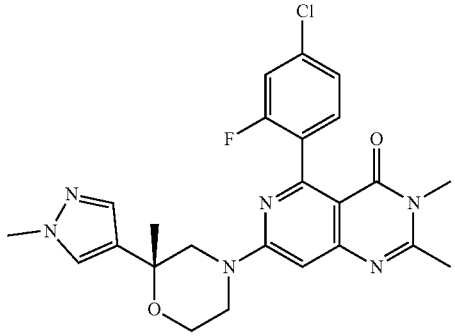 |
| I-73 | 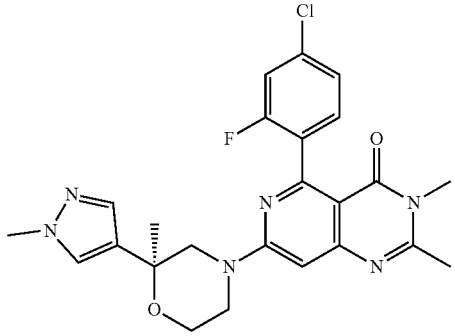 |
| I-74 | 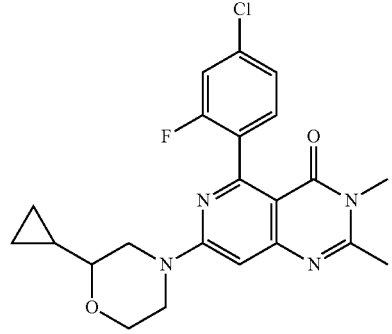 [SMILES: Cc1nc2cc(N3CCOC(C4CC4)C3)nc(-c3ccc(Cl)cc3F)c2c(=O)n1C] |
| I-75 | 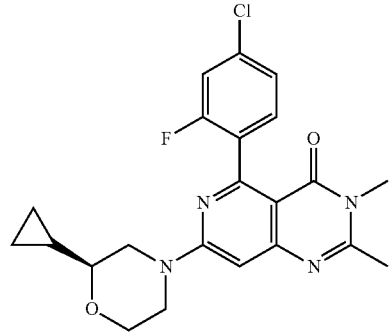 [SMILES: Cc1nc2cc(N3CCO[C@@H](C4CC4)C3)nc(-c3ccc(Cl)cc3F)c2c(=O)n1C] |
| I-76 | 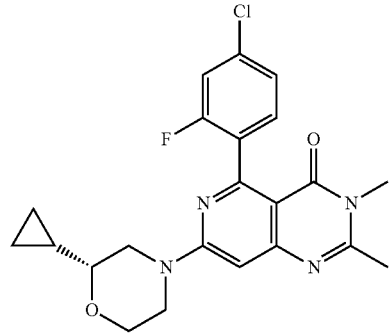 [SMILES: Cc1nc2cc(N3CCO[C@H](C4CC4)C3)nc(-c3ccc(Cl)cc3F)c2c(=O)n1C] |
| I-77 | 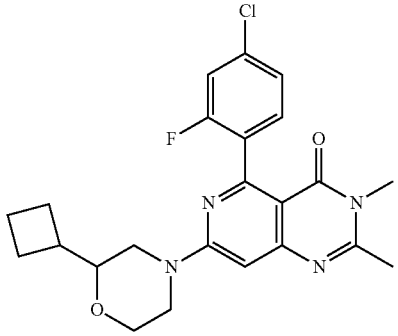 |

TABLE A-continued
Exemplary Compounds
| I # | Structure |
|---|---|
| I-78 | 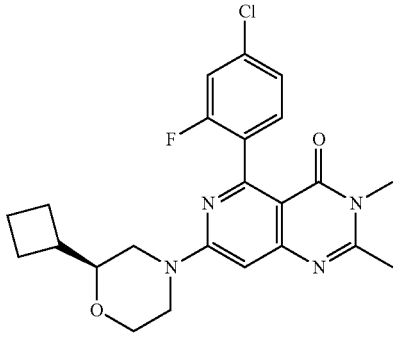 [SMILES: Cc1nc2cc(N3CCO[C@@H](C4CCC4)C3)nc(-c3ccc(Cl)cc3F)c2c(=O)n1C] |
| I-79 | 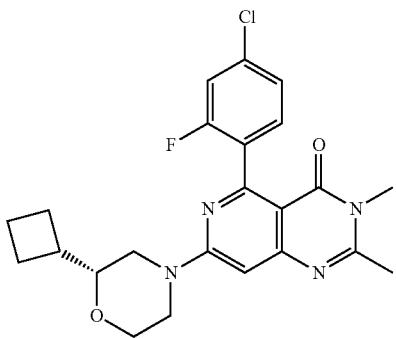 |
| I-80 | 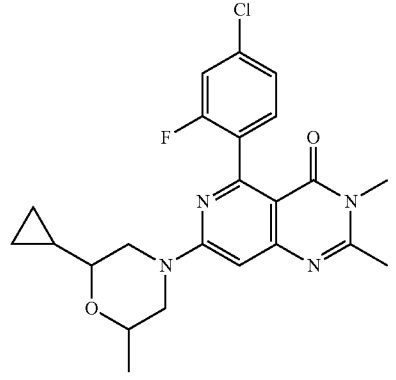 [SMILES: Cc1nc2cc(N3CC(C)OC(C4CC4)C3)nc(-c3ccc(Cl)cc3F)c2c(=O)n1C] |
| I-81 | 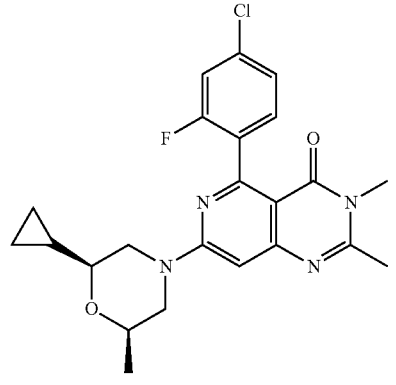 [SMILES: Cc1nc2cc(N3C[C@@H](C)O[C@@H](C4CC4)C3)nc(-c3ccc(Cl)cc3F)c2c(=O)n1C] |
| I-82 | 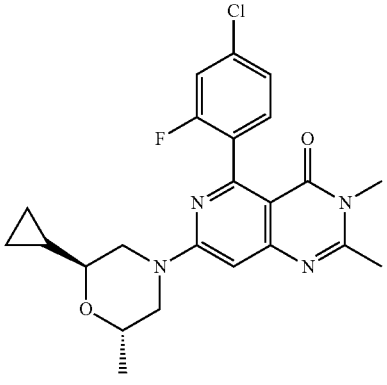 [SMILES: Cc1nc2cc(N3C[C@H](C)O[C@@H](C4CC4)C3)nc(-c3ccc(Cl)cc3F)c2c(=O)n1C] |
| I-83 | 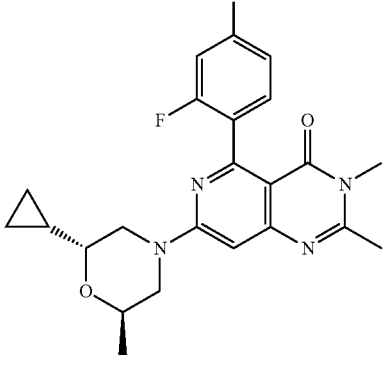 |
| I-84 | 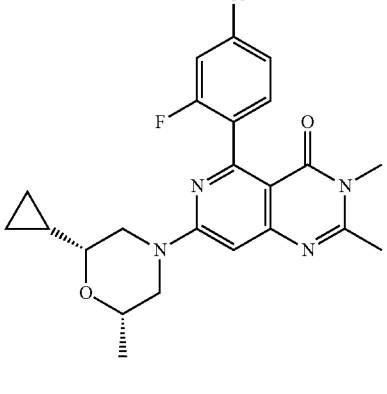 |
| I-85 | 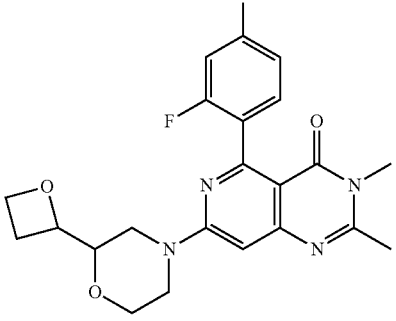 |

TABLE A-continued

Exemplary Compounds

| I # | Structure |
|---|---|
| I-86 | (structure) |
| I-87 | (structure) |
| I-88 | (structure) |
| I-89 | (structure) |
| I-90 | (structure) |
| I-91 | (structure) |
| I-92 | (structure) |
| I-93 | (structure) |

TABLE A-continued

Exemplary Compounds

| I # | Structure |
|---|---|
| I-94 | 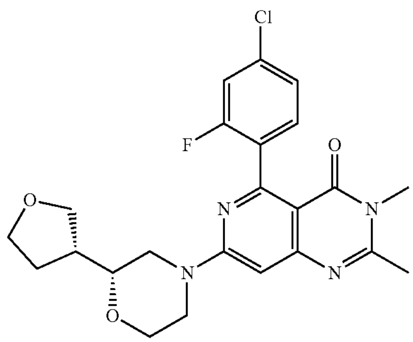 [SMILES: Cc1nc2cc(N3CCO[C@H]([C@@H]4CCOC4)C3)nc(-c3ccc(Cl)cc3F)c2c(=O)n1C] |
| I-95 | 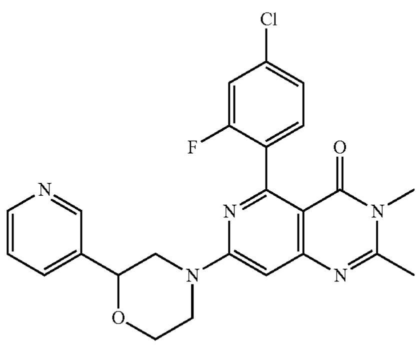 [SMILES: Cc1nc2cc(N3CCOC(c4cccnc4)C3)nc(-c3ccc(Cl)cc3F)c2c(=O)n1C] |
| I-96 | 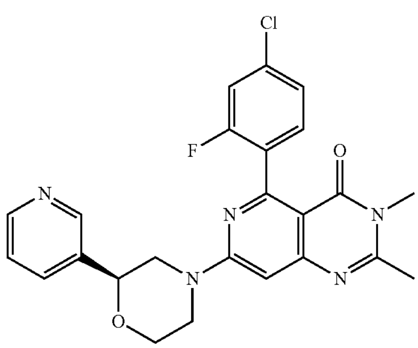 [SMILES: Cc1nc2cc(N3CCO[C@@H](c4cccnc4)C3)nc(-c3ccc(Cl)cc3F)c2c(=O)n1C] |
| I-97 | 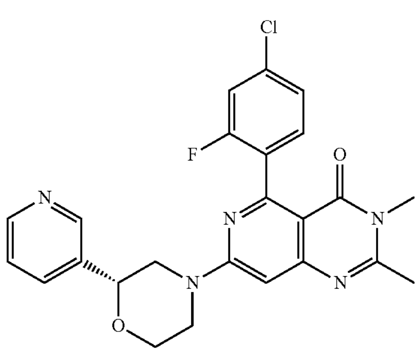 [SMILES: Cc1nc2cc(N3CCO[C@H](c4cccnc4)C3)nc(-c3ccc(Cl)cc3F)c2c(=O)n1C] |
| I-98 | |
| I-99 | |
| I-100 | |
| I-101 | |

TABLE A-continued

Exemplary Compounds

| I # | Structure |
|---|---|
| I-102 | (structure) |
| I-103 | (structure) |
| I-104 | (structure) |
| I-105 | (structure) |
| I-106 | (structure) |
| I-107 | (structure) |
| I-108 | (structure) |
| I-109 | (structure) |

TABLE A-continued

Exemplary Compounds

| I # | Structure |
|---|---|
| I-110 | 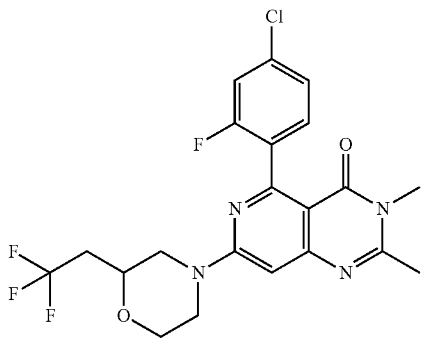 [SMILES: Cc1nc2cc(N3CCOC(CC(F)(F)F)C3)nc(-c3ccc(Cl)cc3F)c2c(=O)n1C] |
| I-111 | 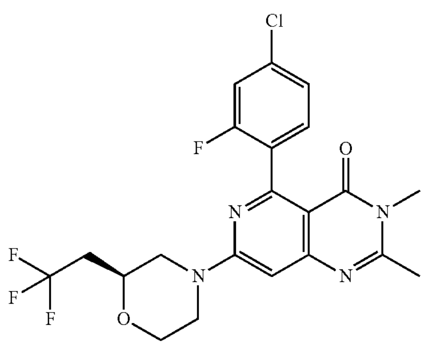 [SMILES: Cc1nc2cc(N3CCO[C@@H](CC(F)(F)F)C3)nc(-c3ccc(Cl)cc3F)c2c(=O)n1C] |
| I-112 | 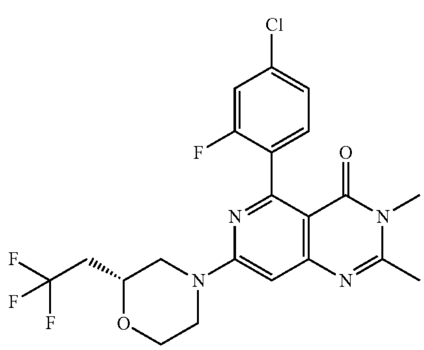 [SMILES: Cc1nc2cc(N3CCO[C@H](CC(F)(F)F)C3)nc(-c3ccc(Cl)cc3F)c2c(=O)n1C] |
| I-113 | 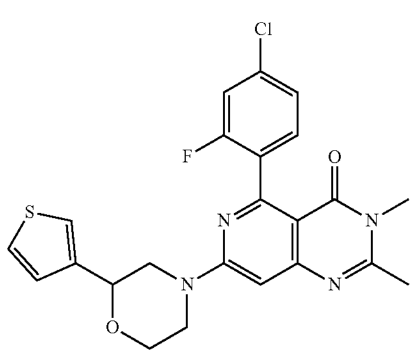 |
| I-114 | |
| I-115 | |
| I-116 | |
| I-117 | |

TABLE A-continued
Exemplary Compounds
| I # | Structure |
|---|---|
| I-118 | 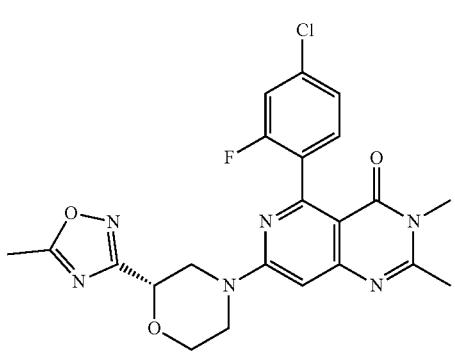 |
| I-119 | 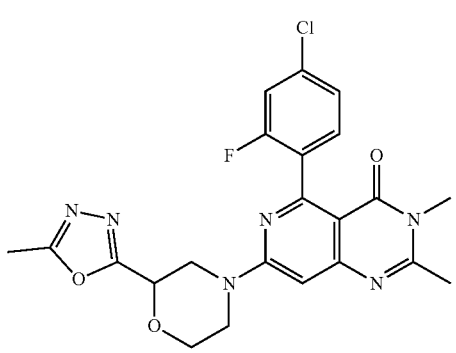 |
| I-120 | 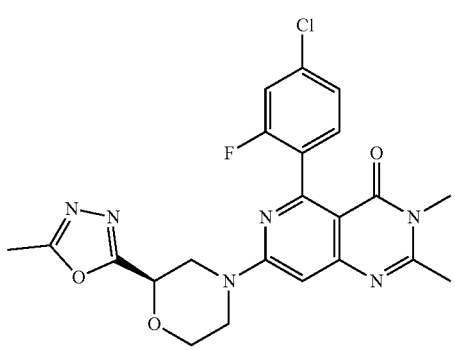 |
| I-121 | 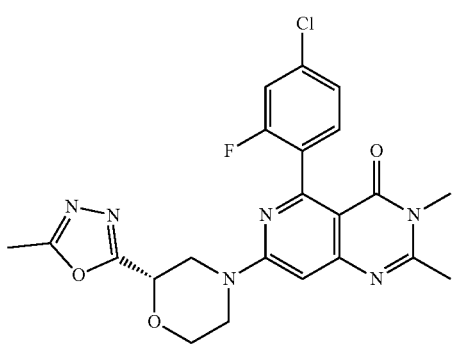 |
| I-122 | 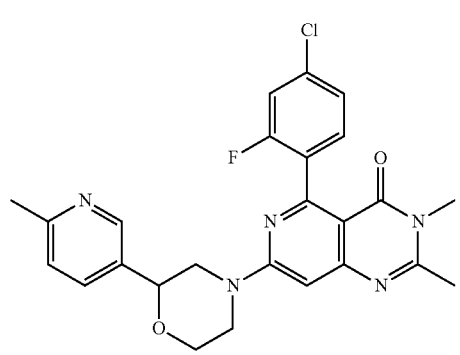 |
| I-123 | 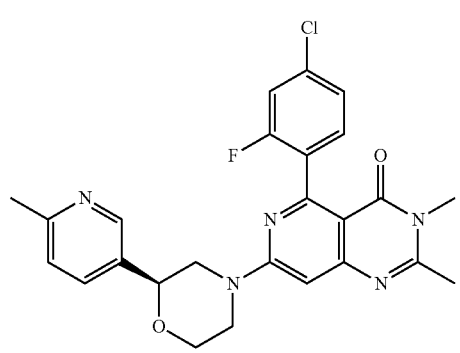 |
| I-124 | 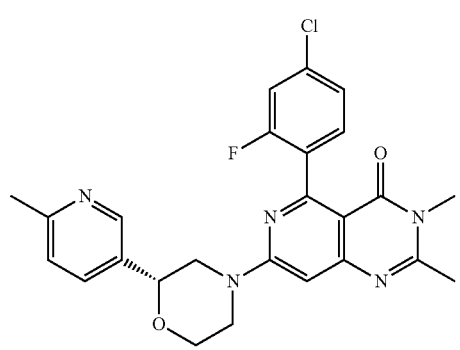 |
| I-125 | 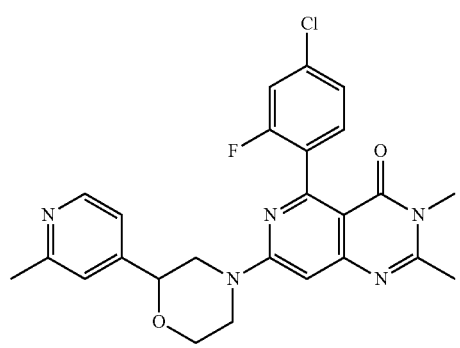 |

TABLE A-continued

Exemplary Compounds

| I # | Structure |
|---|---|
| I-126 | 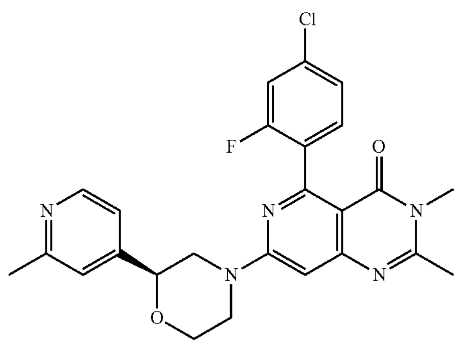 |
| I-127 | 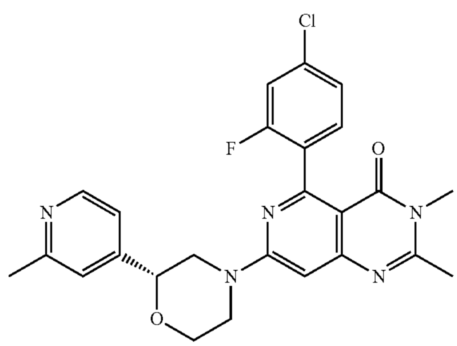 |
| I-128 | 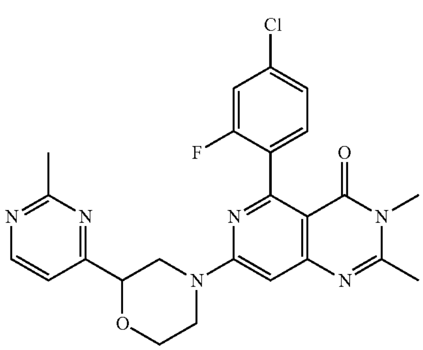 |
| I-129 | 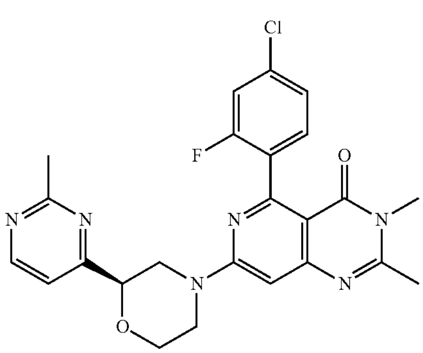 [SMILES: Cc1nccc([C@H]2CN(c3cc4nc(C)n(C)c(=O)c4c(-c4ccc(Cl)cc4F)n3)CCO2)n1] |
| I-130 | 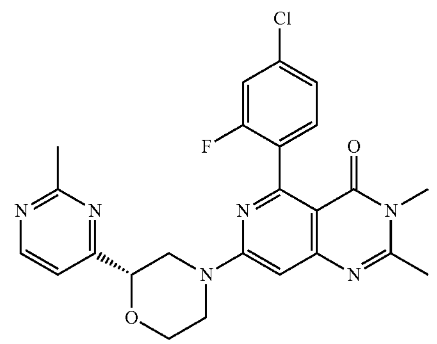 [SMILES: Cc1nccc([C@@H]2CN(c3cc4nc(C)n(C)c(=O)c4c(-c4ccc(Cl)cc4F)n3)CCO2)n1] |
| I-131 | 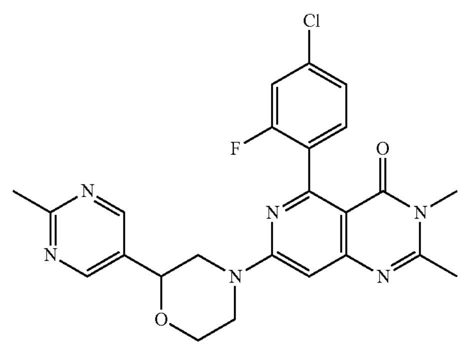 |
| I-132 | 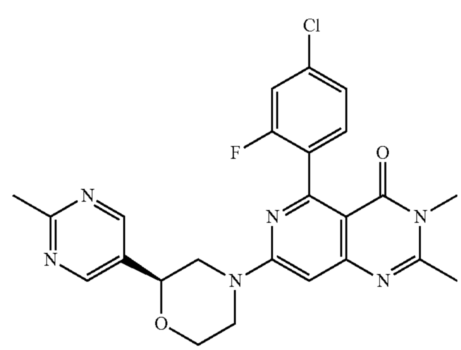 |
| I-133 | 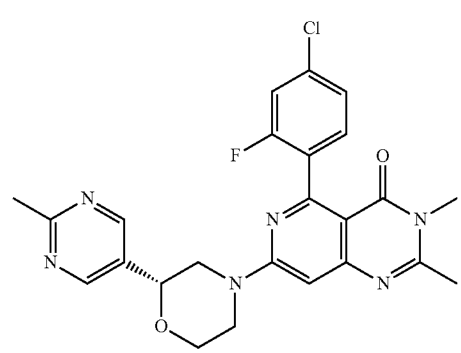 |

TABLE A-continued

Exemplary Compounds

| I # | Structure |
|---|---|
| I-134 | 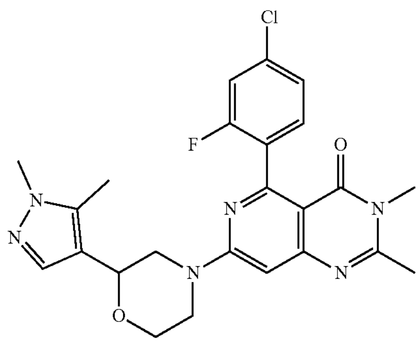 [SMILES: Cc1c(C2CN(c3cc4nc(C)n(C)c(=O)c4c(-c4ccc(Cl)cc4F)n3)CCO2)cnn1C] |
| I-135 | 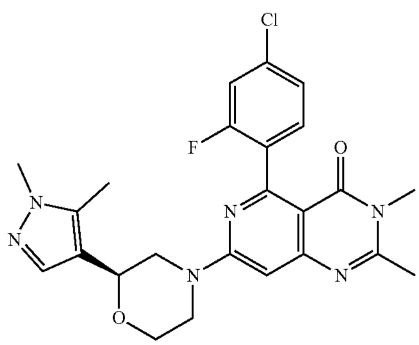 [SMILES: Cc1c([C@H]2CN(c3cc4nc(C)n(C)c(=O)c4c(-c4ccc(Cl)cc4F)n3)CCO2)cnn1C] |
| I-136 | 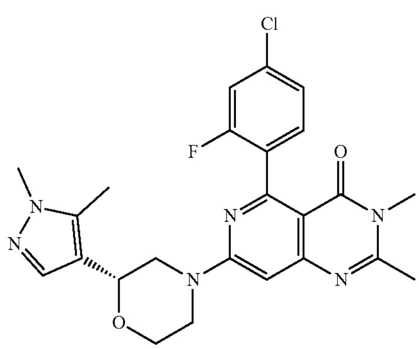 [SMILES: Cc1c([C@@H]2CN(c3cc4nc(C)n(C)c(=O)c4c(-c4ccc(Cl)cc4F)n3)CCO2)cnn1C] |
| I-137 | 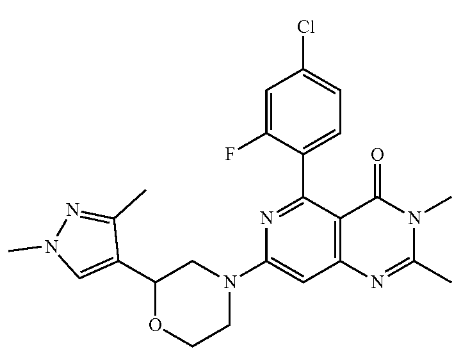 |
| I-138 | |
| I-139 | |
| I-140 | |
| I-141 | |

TABLE A-continued

Exemplary Compounds

| I # | Structure |
|---|---|
| I-142 | 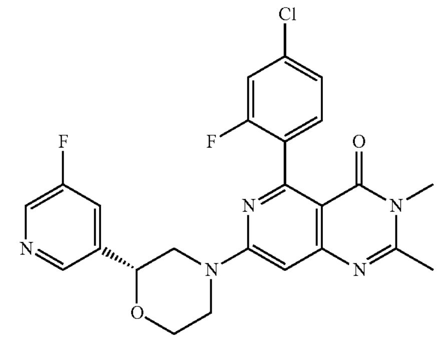 [SMILES: Cc1nc2cc(N3CCO[C@H](c4cncc(F)c4)C3)nc(-c3ccc(Cl)cc3F)c2c(=O)n1C] |
| I-143 | 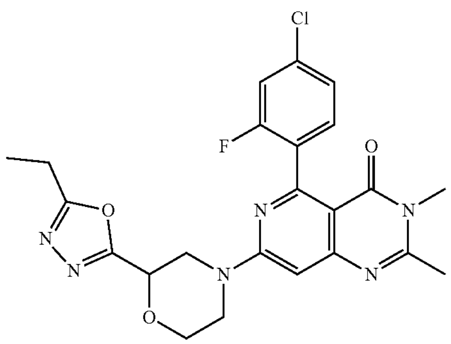 [SMILES: CCc1nnc(C2CN(c3cc4nc(C)n(C)c(=O)c4c(-c4ccc(Cl)cc4F)n3)CCO2)o1] |
| I-144 | 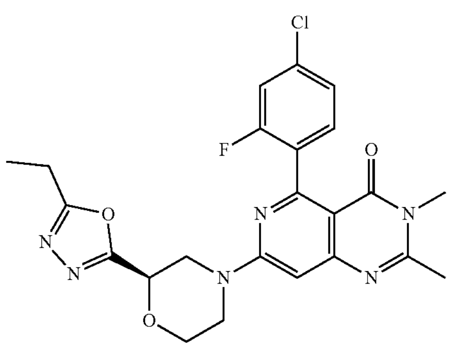 [SMILES: CCc1nnc([C@H]2CN(c3cc4nc(C)n(C)c(=O)c4c(-c4ccc(Cl)cc4F)n3)CCO2)o1] |
| I-145 | 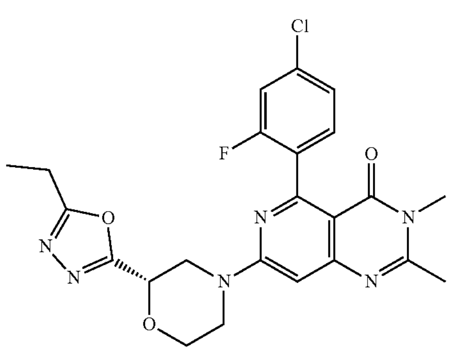 [SMILES: CCc1nnc([C@@H]2CN(c3cc4nc(C)n(C)c(=O)c4c(-c4ccc(Cl)cc4F)n3)CCO2)o1] |
| I-146 | |
| I-147 | |
| I-148 | |
| I-149 | |

TABLE A-continued

Exemplary Compounds

| I # | Structure |
|---|---|
| I-150 | 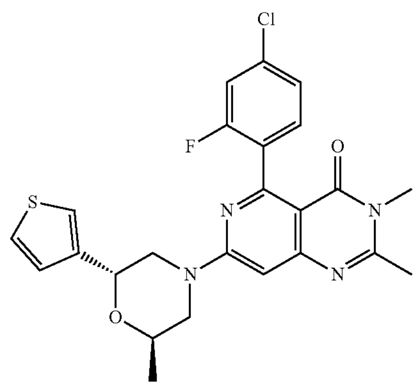 [SMILES: Cc1nc2cc(N3C[C@@H](C)O[C@H](c4ccsc4)C3)nc(-c3ccc(Cl)cc3F)c2c(=O)n1C] |
| I-151 | 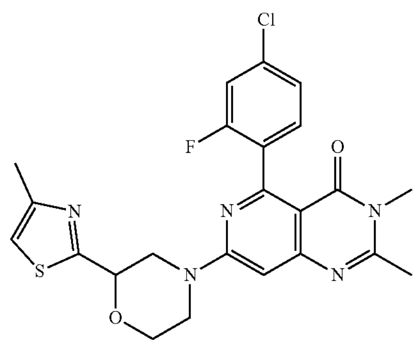 [SMILES: Cc1csc(C2CN(c3cc4nc(C)n(C)c(=O)c4c(-c4ccc(Cl)cc4F)n3)CCO2)n1] |
| I-152 | 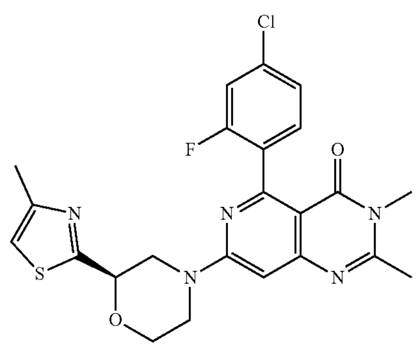 [SMILES: Cc1csc([C@H]2CN(c3cc4nc(C)n(C)c(=O)c4c(-c4ccc(Cl)cc4F)n3)CCO2)n1] |
| I-153 | 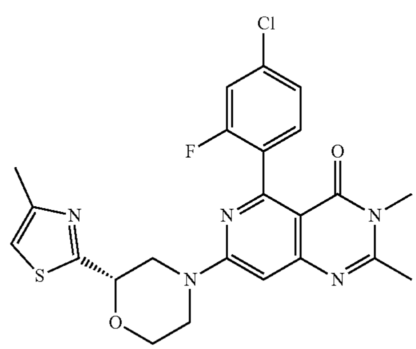 [SMILES: Cc1csc([C@@H]2CN(c3cc4nc(C)n(C)c(=O)c4c(-c4ccc(Cl)cc4F)n3)CCO2)n1] |
| I-154 | |
| I-155 | |
| I-156 | |
| I-157 | |

TABLE A-continued
Exemplary Compounds
| I # | Structure |
|---|---|
| I-158 | 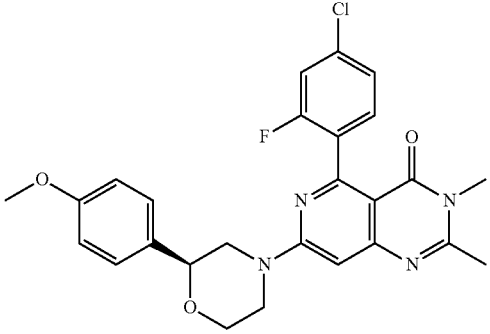 |
| I-159 | 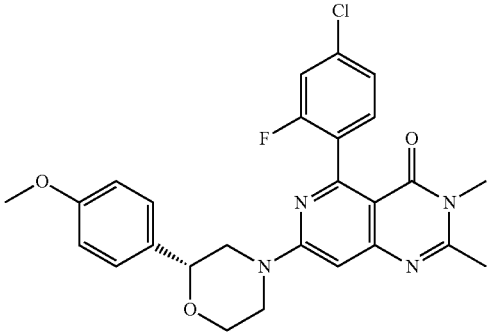 |
| I-160 | 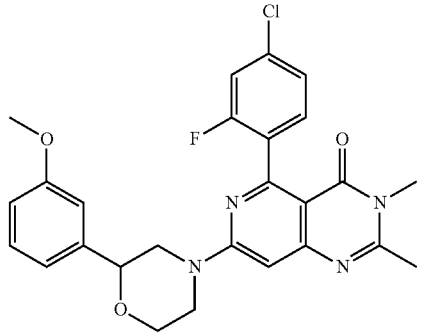 |
| I-161 | 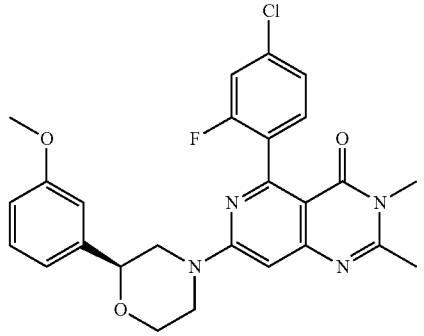 |
| I-162 | 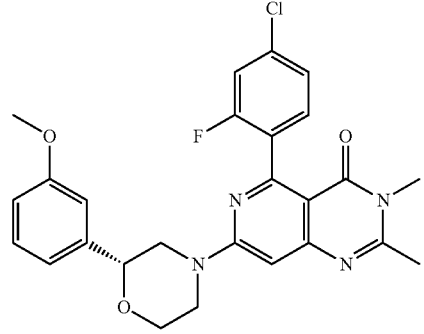 |
| I-163 | 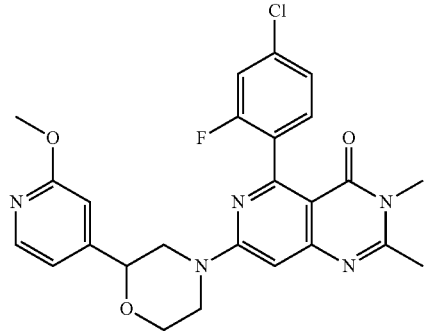 |
| I-164 | 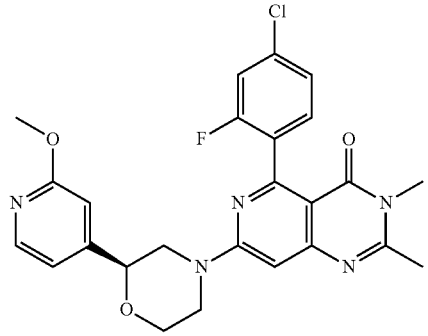 |
| I-165 | 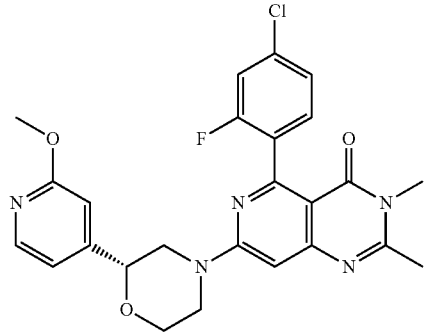 |

TABLE A-continued
Exemplary Compounds
| I # | Structure |
|---|---|
| I-166 | 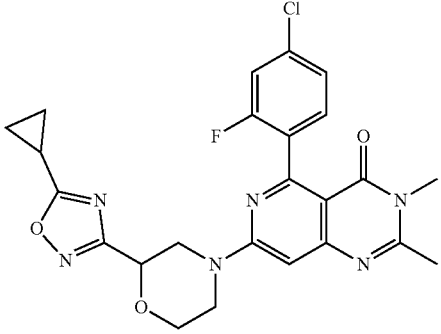 [SMILES: Cc1nc2cc(N3CCOC(c4noc(C5CC5)n4)C3)nc(-c3ccc(Cl)cc3F)c2c(=O)n1C] |
| I-167 | 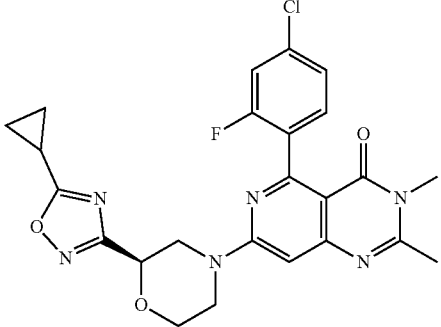 [SMILES: Cc1nc2cc(N3CCO[C@@H](c4noc(C5CC5)n4)C3)nc(-c3ccc(Cl)cc3F)c2c(=O)n1C] |
| I-168 | 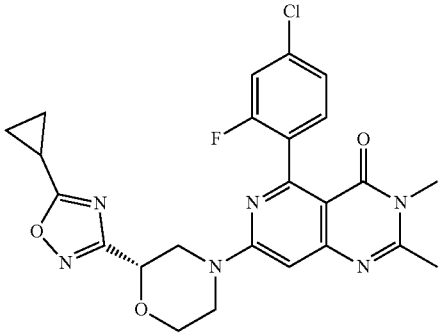 [SMILES: Cc1nc2cc(N3CCO[C@H](c4noc(C5CC5)n4)C3)nc(-c3ccc(Cl)cc3F)c2c(=O)n1C] |
| I-169 | 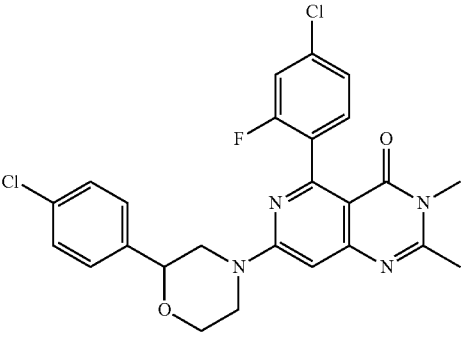 [SMILES: Cc1nc2cc(N3CCOC(c4ccc(Cl)cc4)C3)nc(-c3ccc(Cl)cc3F)c2c(=O)n1C] |
| I-170 | 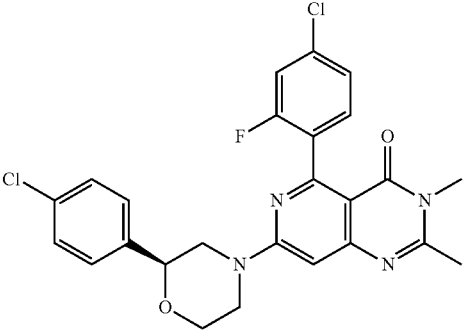 [SMILES: Cc1nc2cc(N3CCO[C@@H](c4ccc(Cl)cc4)C3)nc(-c3ccc(Cl)cc3F)c2c(=O)n1C] |
| I-171 | 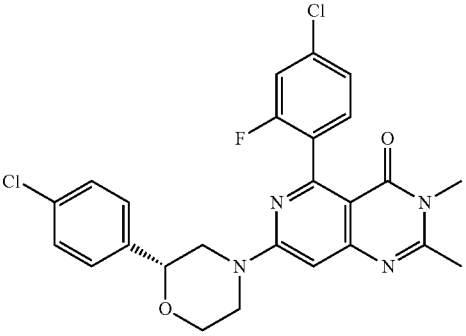 [SMILES: Cc1nc2cc(N3CCO[C@H](c4ccc(Cl)cc4)C3)nc(-c3ccc(Cl)cc3F)c2c(=O)n1C] |
| I-172 | 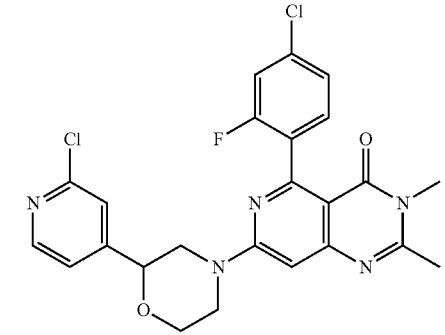 [SMILES: Cc1nc2cc(N3CCOC(c4ccnc(Cl)c4)C3)nc(-c3ccc(Cl)cc3F)c2c(=O)n1C] |
| I-173 | 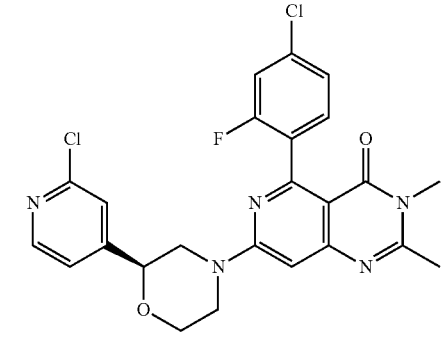 [SMILES: Cc1nc2cc(N3CCO[C@@H](c4ccnc(Cl)c4)C3)nc(-c3ccc(Cl)cc3F)c2c(=O)n1C] |

TABLE A-continued

Exemplary Compounds

| I # | Structure |
|---|---|
| I-174 | 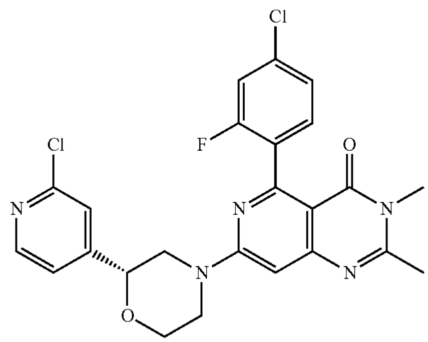 [SMILES: Cc1nc2cc(N3CCO[C@H](c4ccnc(Cl)c4)C3)nc(-c3ccc(Cl)cc3F)c2c(=O)n1C] |
| I-175 | 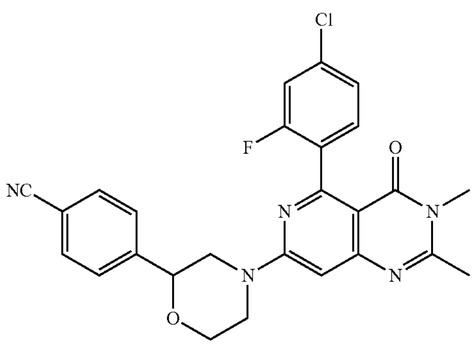 [SMILES: Cc1nc2cc(N3CCOC(c4ccc(C#N)cc4)C3)nc(-c3ccc(Cl)cc3F)c2c(=O)n1C] |
| I-176 | 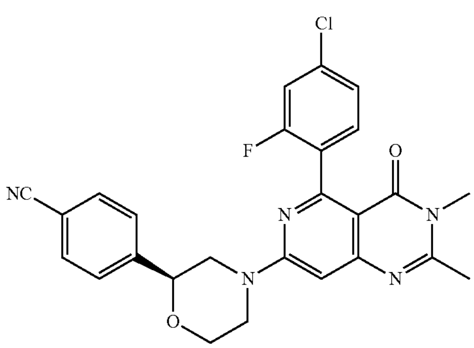 [SMILES: Cc1nc2cc(N3CCO[C@@H](c4ccc(C#N)cc4)C3)nc(-c3ccc(Cl)cc3F)c2c(=O)n1C] |
| I-177 | 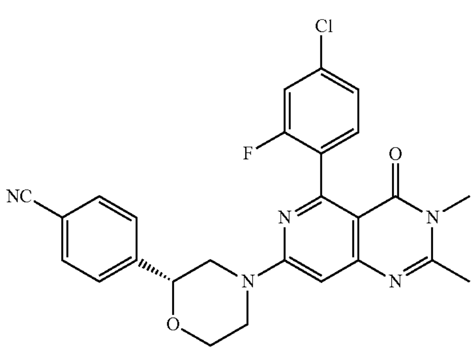 |
| I-178 | |
| I-179 | |
| I-180 | |
| I-181 | |

TABLE A-continued
Exemplary Compounds
| I # | Structure |
|---|---|
| I-182 | 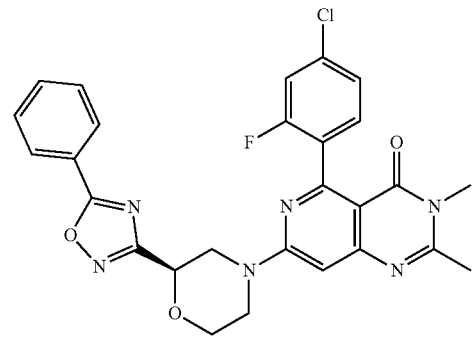 [SMILES: Cc1nc2cc(N3CCO[C@@H](c4noc(-c5ccccc5)n4)C3)nc(-c3ccc(Cl)cc3F)c2c(=O)n1C] |
| I-183 | 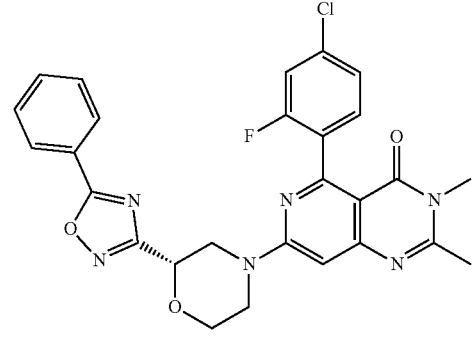 [SMILES: Cc1nc2cc(N3CCO[C@H](c4noc(-c5ccccc5)n4)C3)nc(-c3ccc(Cl)cc3F)c2c(=O)n1C] |
| I-184 | 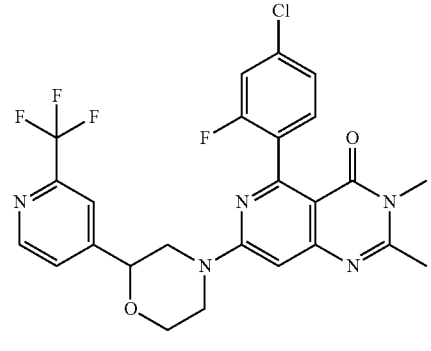 [SMILES: Cc1nc2cc(N3CCOC(c4ccnc(C(F)(F)F)c4)C3)nc(-c3ccc(Cl)cc3F)c2c(=O)n1C] |
| I-185 | 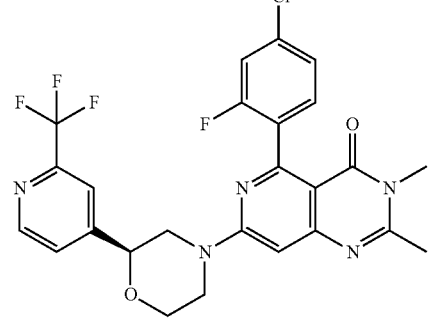 |
| I-186 | 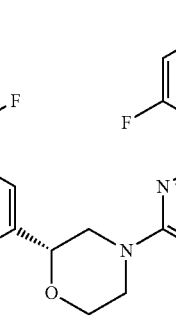 |
| I-187 | 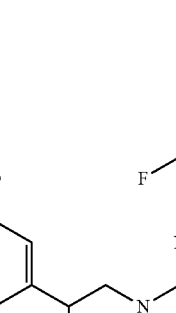 |
| I-188 | 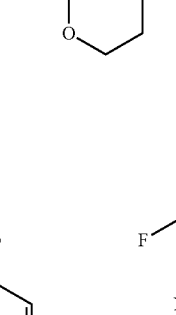 |
| I-189 | 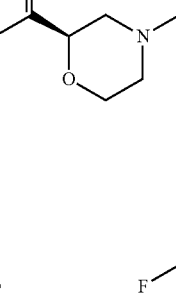 |

TABLE A-continued

Exemplary Compounds

| I # | Structure |
|-----|-----------|
| I-190 | (structure) |
| I-191 | (structure) |
| I-192 | (structure) |
| I-193 | (structure) |
| I-194 | (structure) |
| I-195 | (structure) |
| I-196 | (structure) |
| I-197 | (structure) |

TABLE A-continued

Exemplary Compounds

| I # | Structure |
|---|---|
| I-198 | (structure) |
| I-199 | (structure) |
| I-200 | (structure) |
| I-201 | (structure) |
| I-202 | (structure) |
| I-203 | (structure) |
| I-204 | (structure) |
| I-205 | (structure) |

TABLE A-continued

Exemplary Compounds

| I # | Structure |
|---|---|
| I-206 | 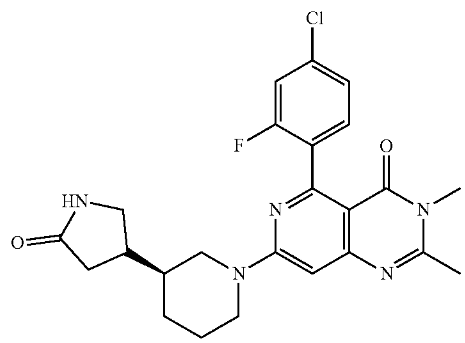 [SMILES: Cc1nc2cc(N3CCC[C@@H](C4CNC(=O)C4)C3)nc(-c3ccc(Cl)cc3F)c2c(=O)n1C] |
| I-207 | 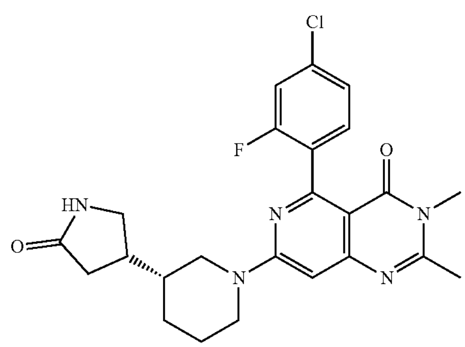 [SMILES: Cc1nc2cc(N3CCC[C@H](C4CNC(=O)C4)C3)nc(-c3ccc(Cl)cc3F)c2c(=O)n1C] |
| I-208 | 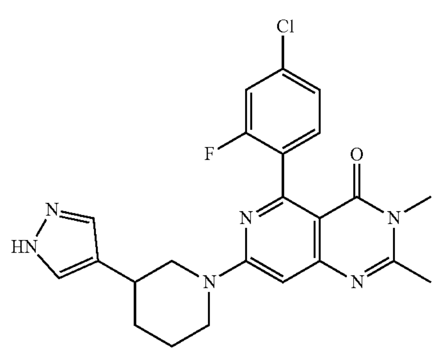 [SMILES: Cc1nc2cc(N3CCCC(c4cn[nH]c4)C3)nc(-c3ccc(Cl)cc3F)c2c(=O)n1C] |
| I-209 | 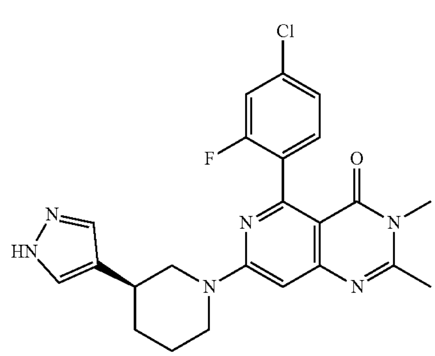 [SMILES: Cc1nc2cc(N3CCC[C@@H](c4cn[nH]c4)C3)nc(-c3ccc(Cl)cc3F)c2c(=O)n1C] |
| I-210 | |
| I-211 | |
| I-212 | |
| I-213 | |

TABLE A-continued

Exemplary Compounds

| I # | Structure |
|---|---|
| I-214 | 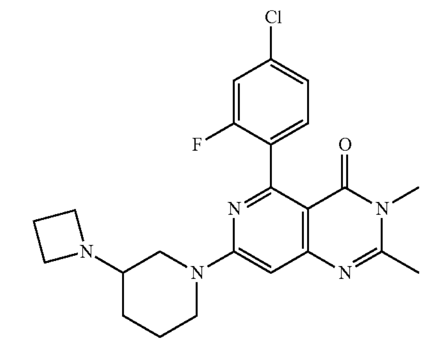 [SMILES: Cc1nc2cc(N3CCCC(N4CCC4)C3)nc(-c3ccc(Cl)cc3F)c2c(=O)n1C] |
| I-215 | 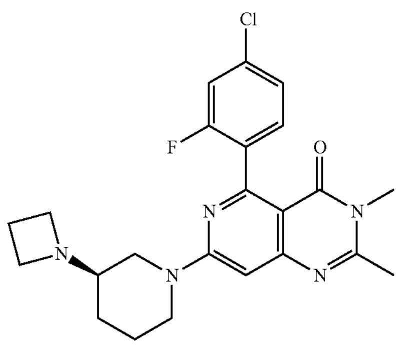 [SMILES: Cc1nc2cc(N3CCC[C@@H](N4CCC4)C3)nc(-c3ccc(Cl)cc3F)c2c(=O)n1C] |
| I-216 | 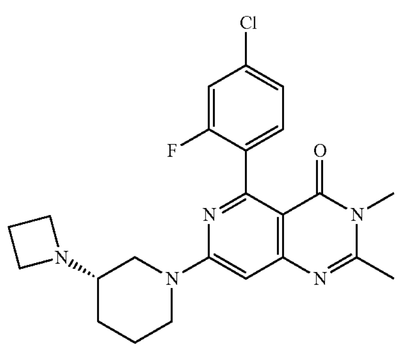 [SMILES: Cc1nc2cc(N3CCC[C@H](N4CCC4)C3)nc(-c3ccc(Cl)cc3F)c2c(=O)n1C] |
| I-217 | 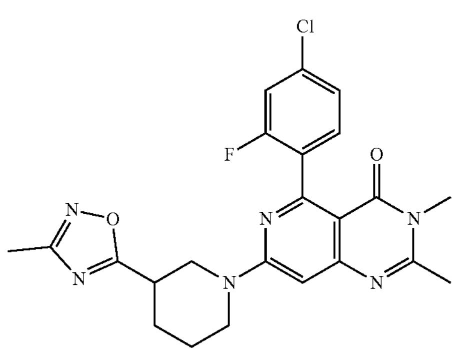 |
| I-218 | |
| I-219 | |
| I-220 | |
| I-221 | |

TABLE A-continued
Exemplary Compounds
| I # | Structure |
|---|---|
| I-222 | 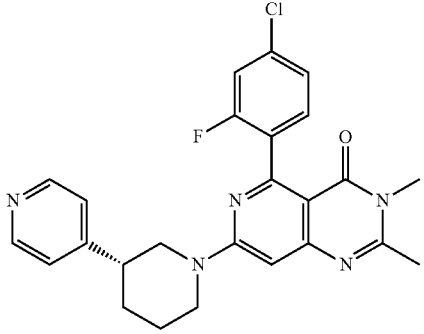 |
| I-223 | 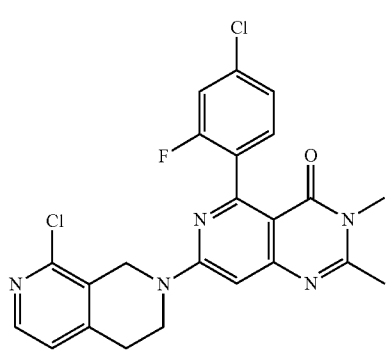 [SMILES: Cc1nc2cc(N3CCc4ccnc(Cl)c4C3)nc(-c3ccc(Cl)cc3F)c2c(=O)n1C] |
| I-224 | 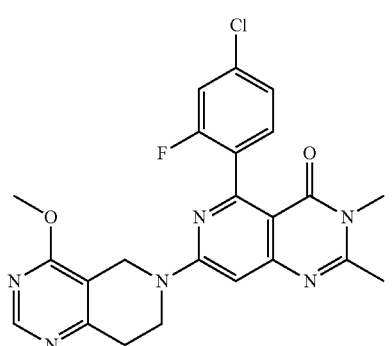 |
| I-225 | 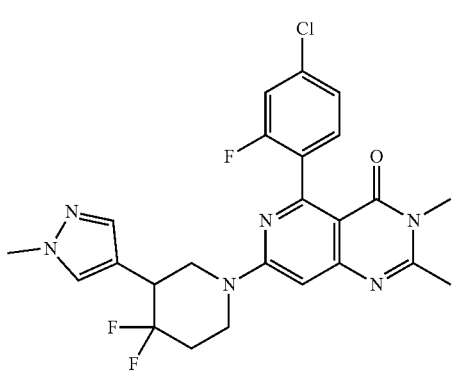 |
| I-226 | 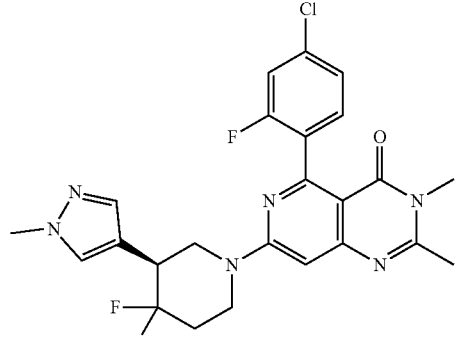 |
| I-227 | 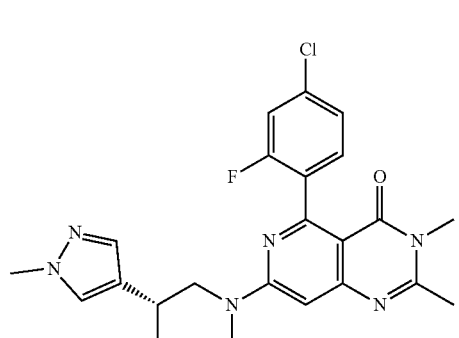 |
| I-228 | 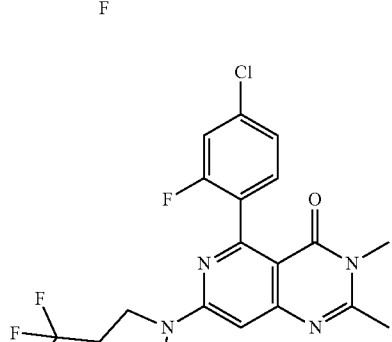 |
| I-229 | 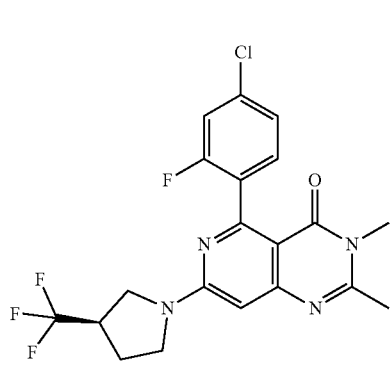 |

TABLE A-continued
Exemplary Compounds
| I # | Structure |
|---|---|
| I-230 | 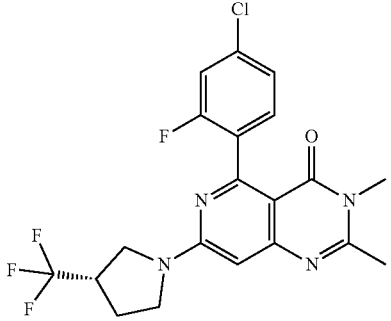 [SMILES: Cc1nc2cc(N3CCC(C(F)(F)F)C3)nc(-c3ccc(Cl)cc3F)c2c(=O)n1C] |
| I-231 | 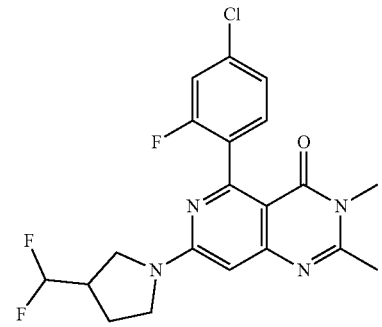 [SMILES: Cc1nc2cc(N3CCC(C(F)F)C3)nc(-c3ccc(Cl)cc3F)c2c(=O)n1C] |
| I-232 | 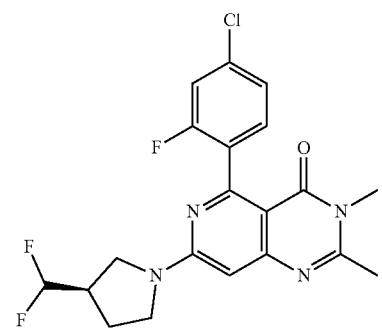 [SMILES: Cc1nc2cc(N3CC[C@@H](C(F)F)C3)nc(-c3ccc(Cl)cc3F)c2c(=O)n1C] |
| I-233 | 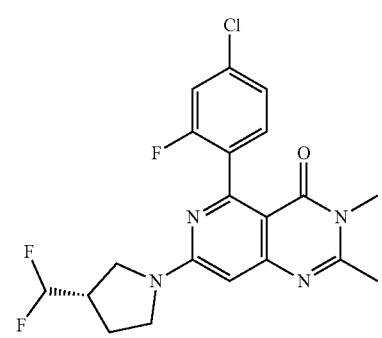 |
| I-234 | 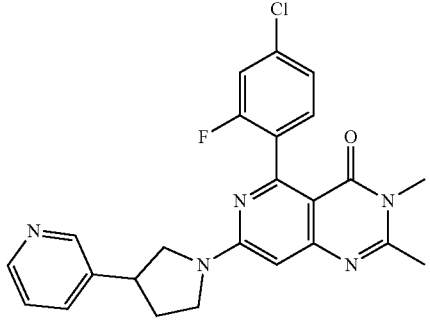 [SMILES: Cc1nc2cc(N3CCC(c4cccnc4)C3)nc(-c3ccc(Cl)cc3F)c2c(=O)n1C] |
| I-235 | 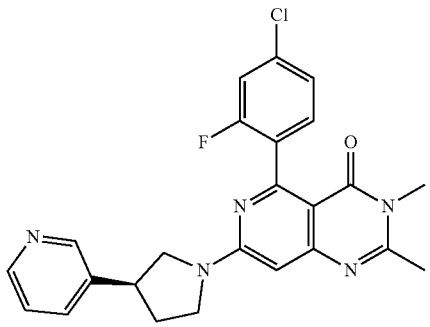 [SMILES: Cc1nc2cc(N3CC[C@@H](c4cccnc4)C3)nc(-c3ccc(Cl)cc3F)c2c(=O)n1C] |
| I-236 | 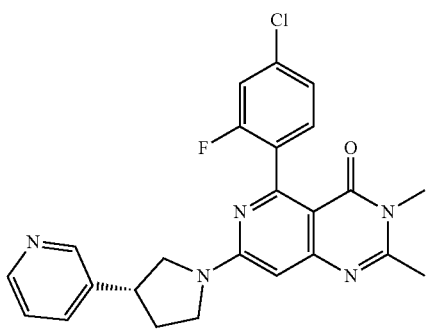 [SMILES: Cc1nc2cc(N3CC[C@H](c4cccnc4)C3)nc(-c3ccc(Cl)cc3F)c2c(=O)n1C] |
| I-237 | 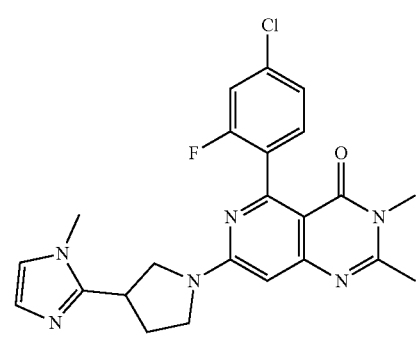 [SMILES: Cc1nc2cc(N3CCC(c4nccn4C)C3)nc(-c3ccc(Cl)cc3F)c2c(=O)n1C] |

TABLE A-continued

Exemplary Compounds

| I # | Structure |
|---|---|
| I-238 | 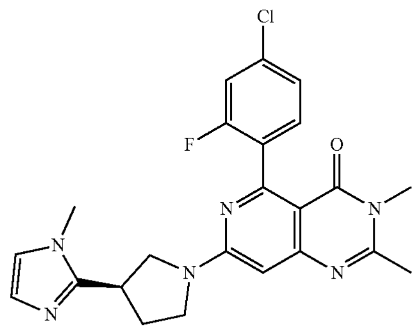 [SMILES: Cc1nc2cc(N3CC[C@@H](c4nccn4C)C3)nc(-c3ccc(Cl)cc3F)c2c(=O)n1C] |
| I-239 | 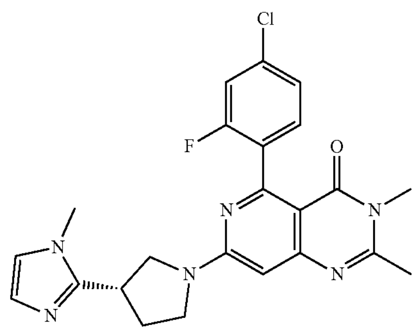 [SMILES: Cc1nc2cc(N3CC[C@H](c4nccn4C)C3)nc(-c3ccc(Cl)cc3F)c2c(=O)n1C] |
| I-240 | 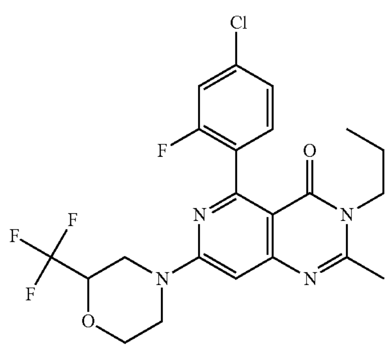 [SMILES: CCCn1c(C)nc2cc(N3CCOC(C(F)(F)F)C3)nc(-c3ccc(Cl)cc3F)c2c1=O] |
| I-241 | 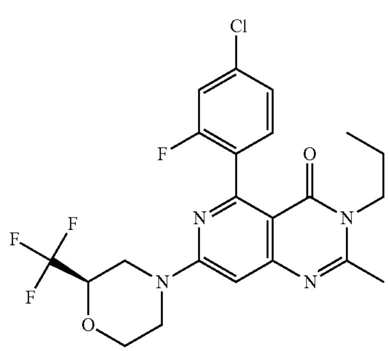 [SMILES: CCCn1c(C)nc2cc(N3CCO[C@@H](C(F)(F)F)C3)nc(-c3ccc(Cl)cc3F)c2c1=O] |
| I-242 | |
| I-243 | |
| I-244 | |
| I-245 | |

TABLE A-continued
Exemplary Compounds
| I # | Structure |
|---|---|
| I-246 | 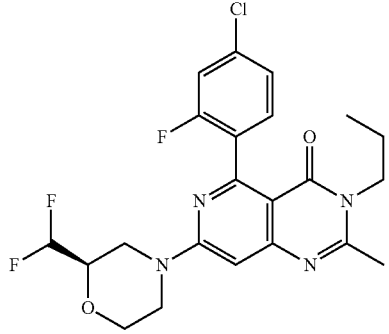 [SMILES: CCCn1c(C)nc2cc(N3CCO[C@@H](C(F)F)C3)nc(-c3ccc(Cl)cc3F)c2c1=O] |
| I-247 | 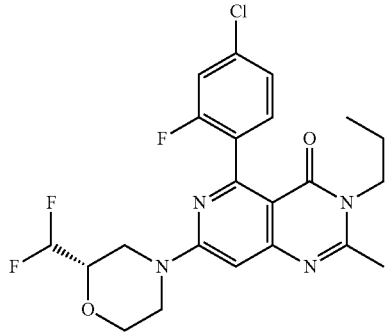 |
| I-248 | 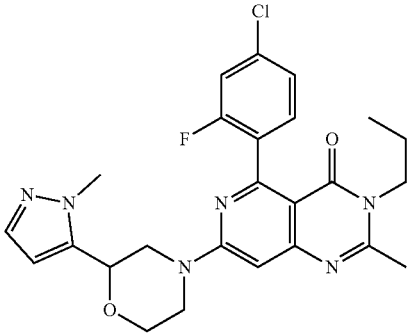 |
| I-249 | 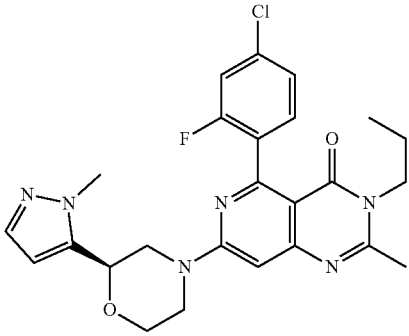 [SMILES: CCCn1c(C)nc2cc(N3CCO[C@@H](c4ccnn4C)C3)nc(-c3ccc(Cl)cc3F)c2c1=O] |
| I-250 | 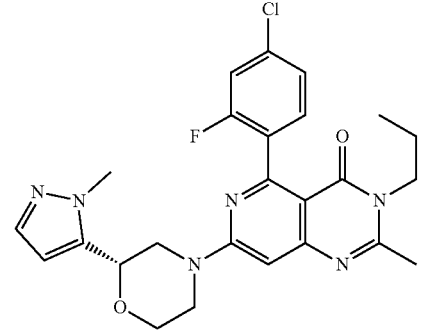 [SMILES: CCCn1c(C)nc2cc(N3CCO[C@H](c4ccnn4C)C3)nc(-c3ccc(Cl)cc3F)c2c1=O] |
| I-251 | 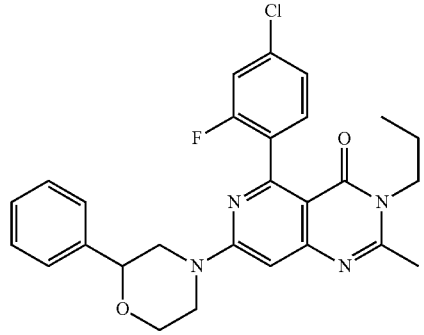 |
| I-252 | 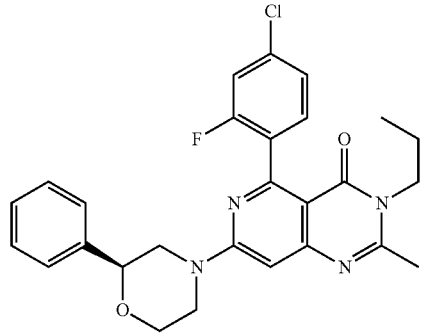 |
| I-253 | 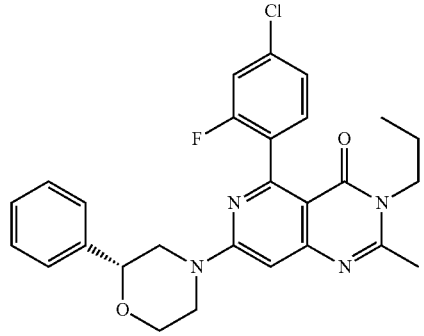 |

TABLE A-continued

Exemplary Compounds

| I # | Structure |
|---|---|
| I-254 | (structure) |
| I-255 | (structure) |
| I-256 | (structure) |
| I-257 | (structure) |
| I-258 | (structure) |
| I-259 | (structure) |
| I-260 | (structure) |
| I-261 | (structure) |

TABLE A-continued
Exemplary Compounds
| I # | Structure |
|---|---|
| I-262 | 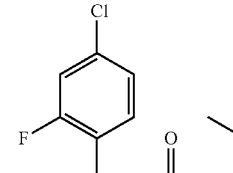 |
| I-263 | 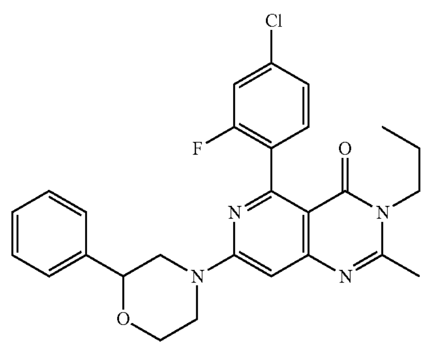 |
| I-264 | 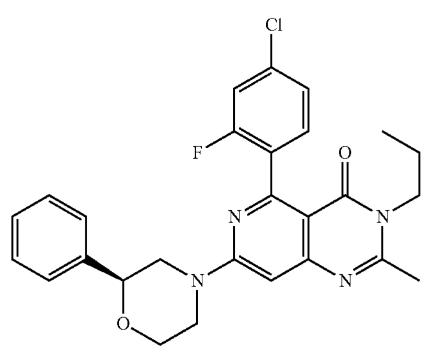 [SMILES: CCCn1c(C)nc2cc(N3CCO[C@@H](c4ccccc4)C3)nc(-c3ccc(Cl)cc3F)c2c1=O] |
| I-265 | 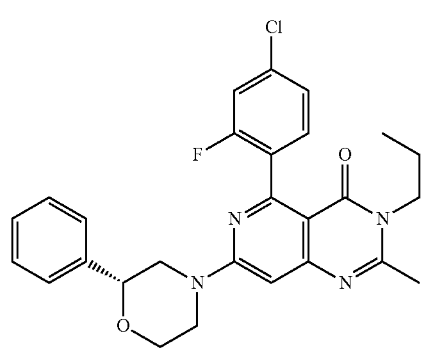 [SMILES: CCCn1c(C)nc2cc(N3CCO[C@H](c4ccccc4)C3)nc(-c3ccc(Cl)cc3F)c2c1=O] |
| I-266 | 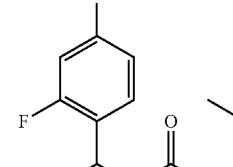 |
| I-267 | |
| I-268 | |
| I-269 | |

TABLE A-continued
Exemplary Compounds
| I # | Structure |
|---|---|
| I-270 | 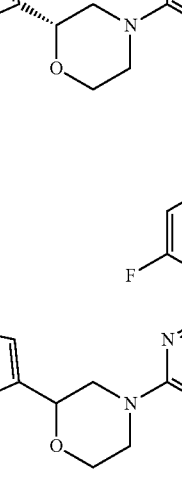 |
| I-271 | 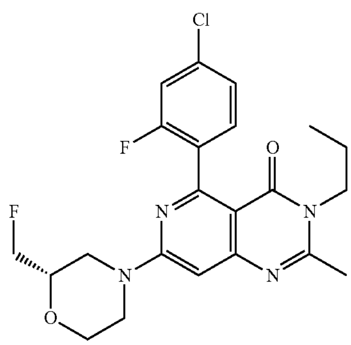 |
| I-272 | 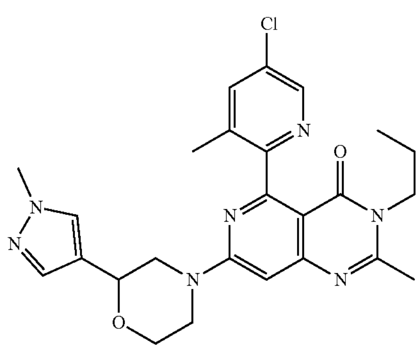 [SMILES: CCCn1c(C)nc2cc(N3CCOC(c4cnn(C)c4)C3)nc(-c3ncc(Cl)cc3C)c2c1=O] |
| I-273 | 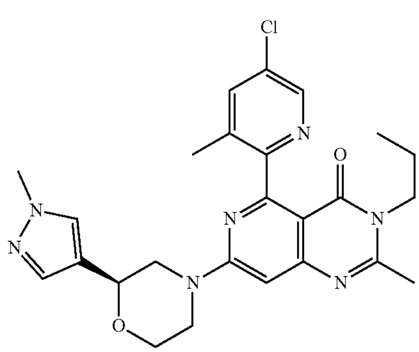 [SMILES: CCCn1c(C)nc2cc(N3CCO[C@@H](c4cnn(C)c4)C3)nc(-c3ncc(Cl)cc3C)c2c1=O] |
| I-274 | 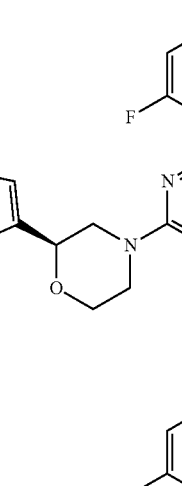 |
| I-275 | |
| I-276 | |
| I-277 | |

TABLE A-continued
Exemplary Compounds
| I # | Structure |
|---|---|
| I-278 | 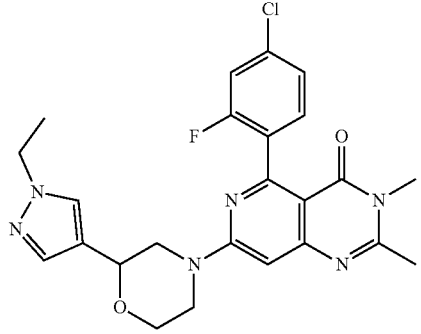 [SMILES: CCn1cc(C2CN(c3cc4nc(C)n(C)c(=O)c4c(-c4ccc(Cl)cc4F)n3)CCO2)cn1] |
| I-279 | 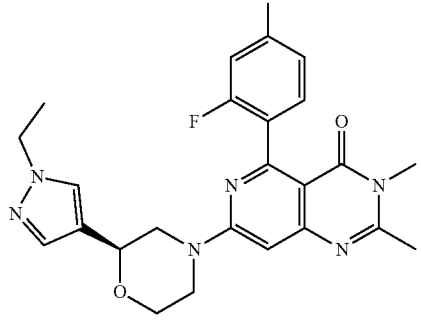 |
| I-280 | 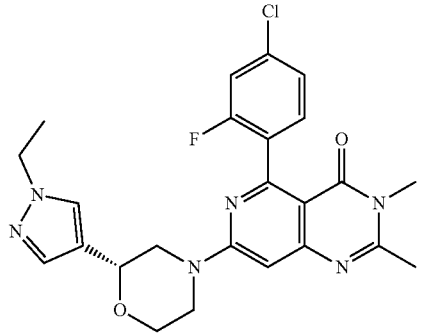 [SMILES: CCn1cc([C@@H]2CN(c3cc4nc(C)n(C)c(=O)c4c(-c4ccc(Cl)cc4F)n3)CCO2)cn1] |
| I-281 | 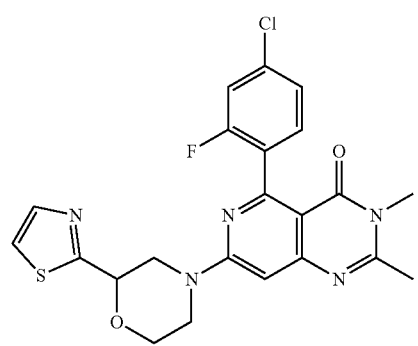 |
| I-282 | 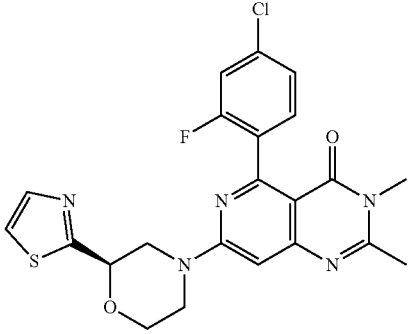 [SMILES: Cc1nc2cc(N3CCO[C@@H](c4nccs4)C3)nc(-c3ccc(Cl)cc3F)c2c(=O)n1C] |
| I-283 | 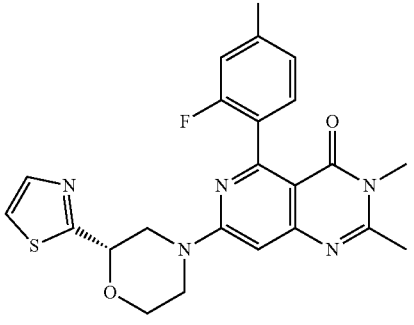 |
| I-284 | 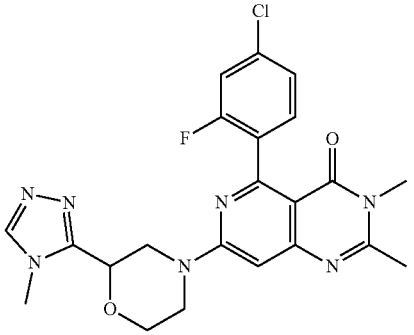 [SMILES: Cc1nc2cc(N3CCOC(c4nncn4C)C3)nc(-c3ccc(Cl)cc3F)c2c(=O)n1C] |
| I-285 | 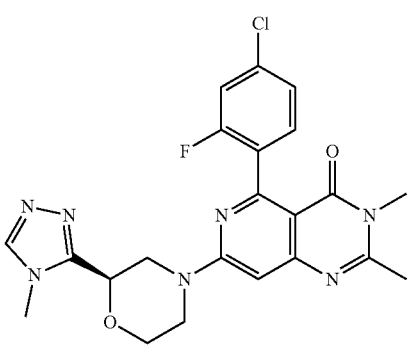 [SMILES: Cc1nc2cc(N3CCO[C@@H](c4nncn4C)C3)nc(-c3ccc(Cl)cc3F)c2c(=O)n1C] |

TABLE A-continued

Exemplary Compounds

| I # | Structure |
|---|---|
| I-286 | (structure) |
| I-287 | (structure) |
| I-288 | (structure) |
| I-289 | (structure) |
| I-290 | (structure) |
| I-291 | (structure) |
| I-292 | (structure) |
| I-293 | (structure) |

TABLE A-continued

Exemplary Compounds

| I # | Structure |
|---|---|
| I-294 | 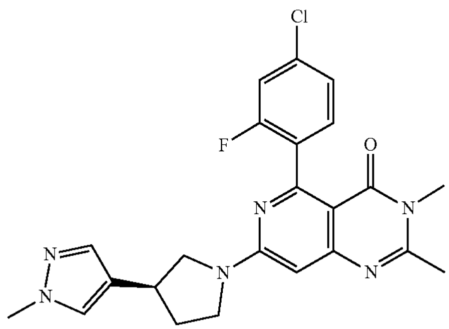 |
| I-295 | 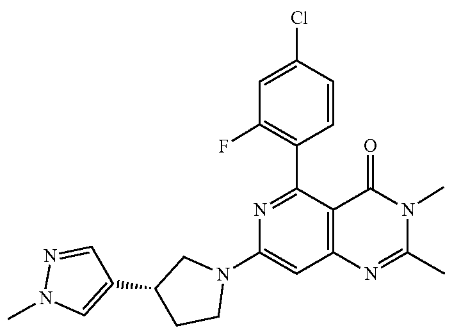 |
| I-296 | 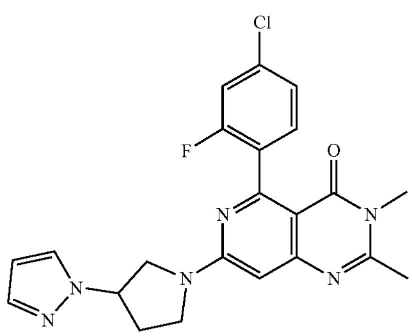 [SMILES: Cc1nc2cc(N3CCC(n4cccn4)C3)nc(-c3ccc(Cl)cc3F)c2c(=O)n1C] |
| I-297 | 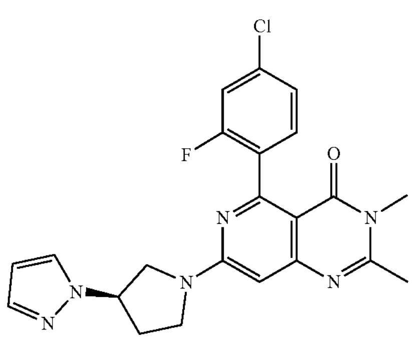 [SMILES: Cc1nc2cc(N3CC[C@@H](n4cccn4)C3)nc(-c3ccc(Cl)cc3F)c2c(=O)n1C] |
| I-298 | 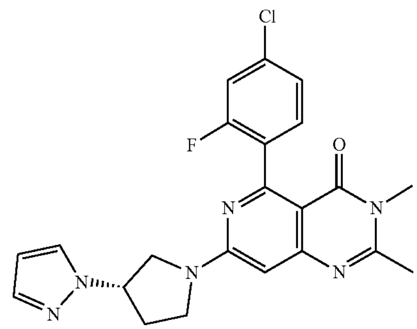 [SMILES: Cc1nc2cc(N3CC[C@H](n4cccn4)C3)nc(-c3ccc(Cl)cc3F)c2c(=O)n1C] |
| I-299 | 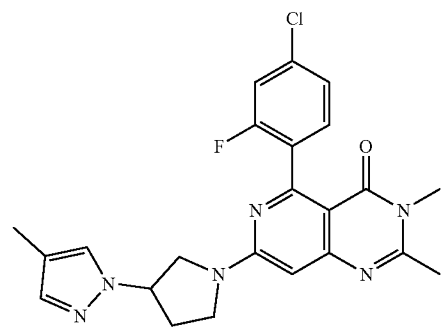 |
| I-300 | 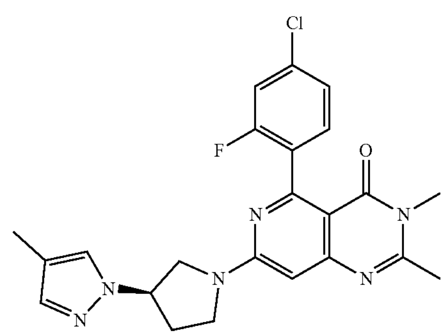 |
| I-301 | 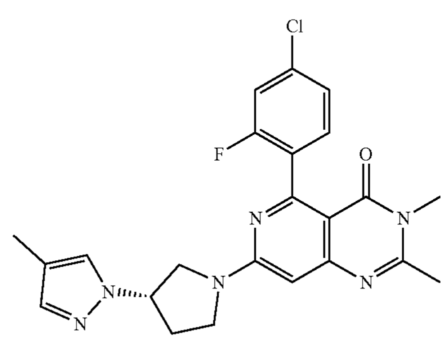 |

TABLE A-continued
Exemplary Compounds
| I # | Structure |
|---|---|
| I-302 | 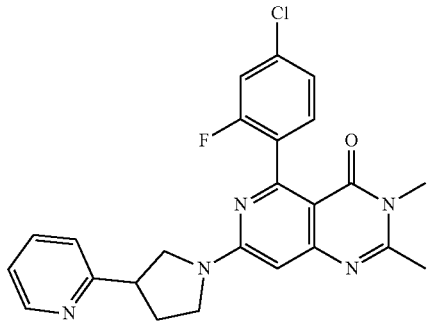 [SMILES: Cc1nc2cc(N3CCC(c4ccccn4)C3)nc(-c3ccc(Cl)cc3F)c2c(=O)n1C] |
| I-303 | 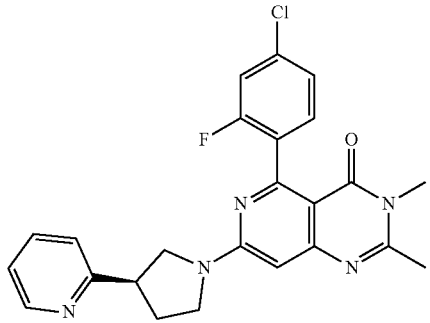 [SMILES: Cc1nc2cc(N3CC[C@@H](c4ccccn4)C3)nc(-c3ccc(Cl)cc3F)c2c(=O)n1C] |
| I-304 | 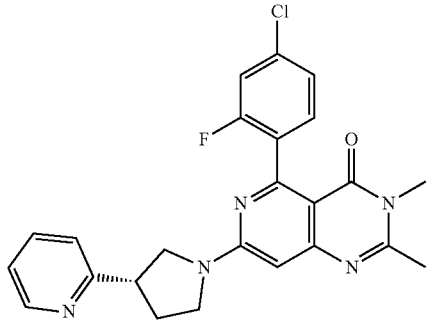 |
| I-305 | 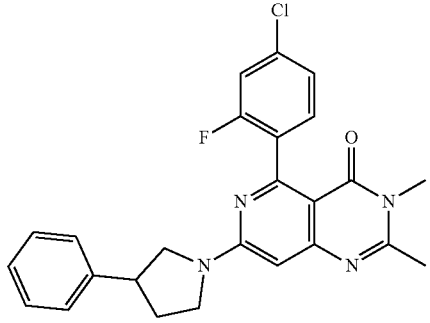 [SMILES: Cc1nc2cc(N3CCC(c4ccccc4)C3)nc(-c3ccc(Cl)cc3F)c2c(=O)n1C] |
| I-306 | 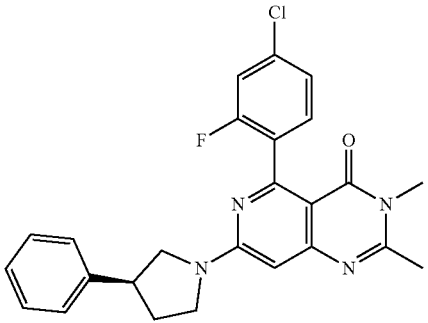 |
| I-307 | 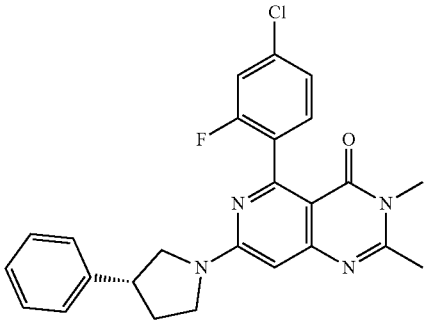 [SMILES: Cc1nc2cc(N3CC[C@H](c4ccccc4)C3)nc(-c3ccc(Cl)cc3F)c2c(=O)n1C] |
| I-308 | 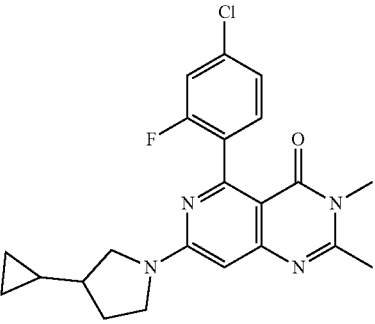 [SMILES: Cc1nc2cc(N3CCC(C4CC4)C3)nc(-c3ccc(Cl)cc3F)c2c(=O)n1C] |
| I-309 | 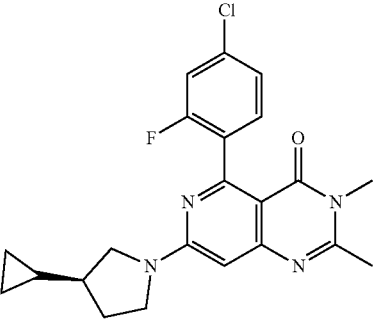 [SMILES: Cc1nc2cc(N3CC[C@@H](C4CC4)C3)nc(-c3ccc(Cl)cc3F)c2c(=O)n1C] |

TABLE A-continued

Exemplary Compounds

| I # | Structure |
|---|---|
| I-310 | (structure) |
| I-311 | (structure) |
| I-312 | (structure) |
| I-313 | (structure) |
| I-314 | (structure) |
| I-315 | (structure) |
| I-316 | (structure) |
| I-317 | (structure) |

TABLE A-continued

Exemplary Compounds

| I # | Structure |
|---|---|
| I-318 | (structure) |
| I-319 | (structure) |
| I-320 | (structure) |
| I-321 | (structure) |
| I-322 | (structure) |
| I-323 | (structure) |
| I-324 | (structure) |
| I-325 | (structure) |

TABLE A-continued

Exemplary Compounds

| I # | Structure |
|---|---|
| I-326 | (structure) |
| I-327 | (structure) |
| I-328 | (structure) |
| I-329 | (structure) |
| I-330 | (structure) |
| I-331 | (structure) |
| I-332 | (structure) |
| I-333 | (structure) |

TABLE A-continued
Exemplary Compounds
| I # | Structure |
|---|---|
| I-334 |  |
| I-335 | |
| I-336 | |
| I-337 | |
| I-338 | 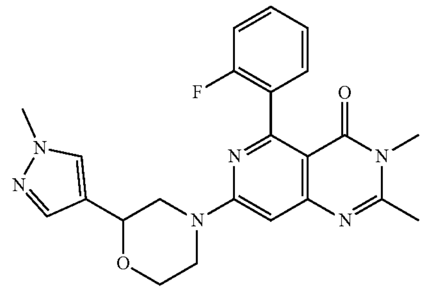 [SMILES: Cc1nc2cc(N3CCOC(c4cnn(C)c4)C3)nc(-c3ccccc3F)c2c(=O)n1C] |
| I-339 | 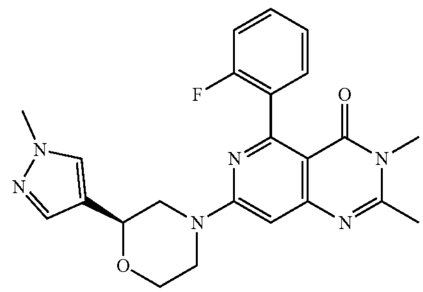 [SMILES: Cc1nc2cc(N3CCO[C@@H](c4cnn(C)c4)C3)nc(-c3ccccc3F)c2c(=O)n1C] |
| I-340 | 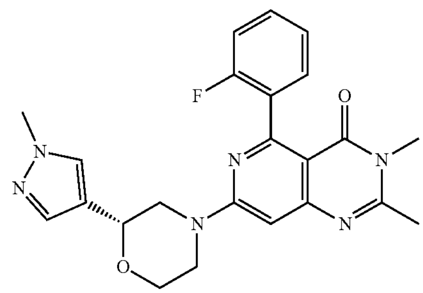 [SMILES: Cc1nc2cc(N3CCO[C@H](c4cnn(C)c4)C3)nc(-c3ccccc3F)c2c(=O)n1C] |
| I-341 | 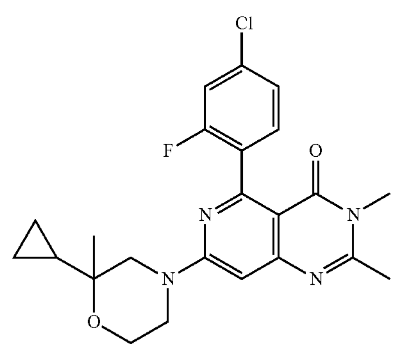 [SMILES: Cc1nc2cc(N3CCOC(C)(C4CC4)C3)nc(-c3ccc(Cl)cc3F)c2c(=O)n1C] |
| I-342 | 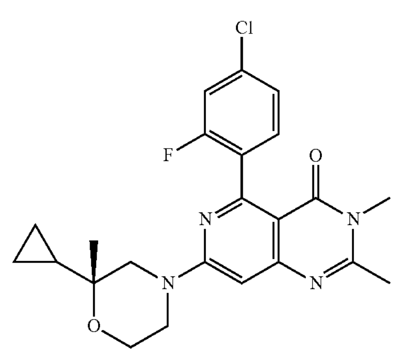 [SMILES: Cc1nc2cc(N3CCO[C@](C)(C4CC4)C3)nc(-c3ccc(Cl)cc3F)c2c(=O)n1C] |

TABLE A-continued
Exemplary Compounds
| I # | Structure |
|---|---|
| I-343 | 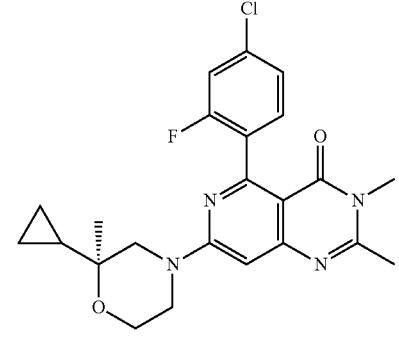 [SMILES: Cc1nc2cc(N3CCO[C@@](C)(C4CC4)C3)nc(-c3ccc(Cl)cc3F)c2c(=O)n1C] |
| I-344 | 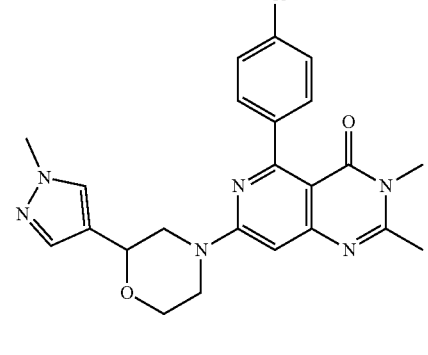 |
| I-345 | 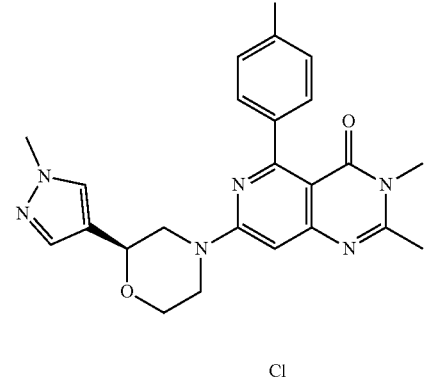 |
| I-346 | 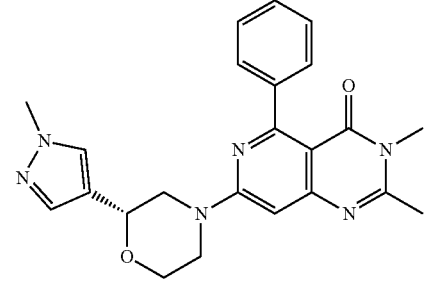 |
| I-347 | 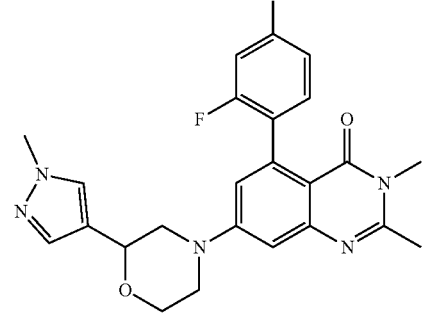 |
| I-348 | 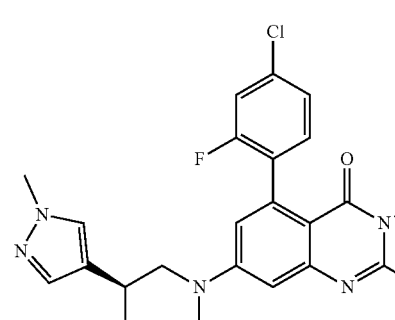 |
| I-349 | 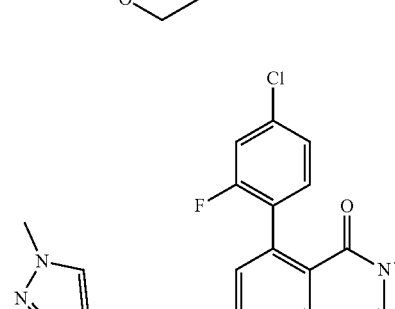 |
| I-350 | 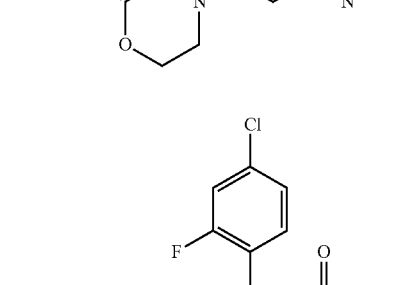 |

TABLE A-continued

Exemplary Compounds

| I # | Structure |
|---|---|
| I-351 | 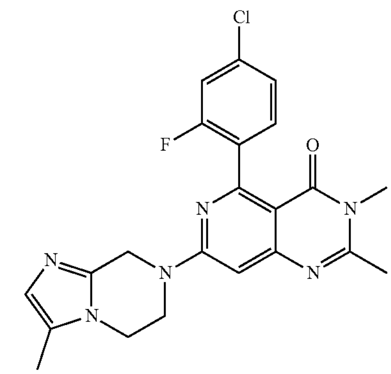 [SMILES: Cc1cnc2n1CCN(c1cc3nc(C)n(C)c(=O)c3c(-c3ccc(Cl)cc3F)n1)C2] |
| I-352 | 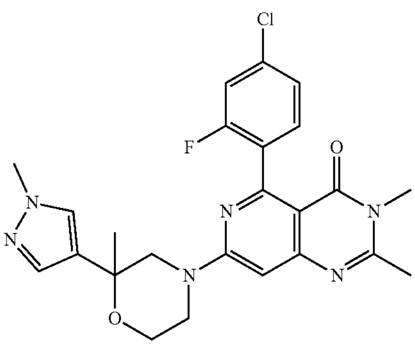 [SMILES: Cc1nc2cc(N3CCOC(C)(c4cnn(C)c4)C3)nc(-c3ccc(Cl)cc3F)c2c(=O)n1C] |
| I-353 | 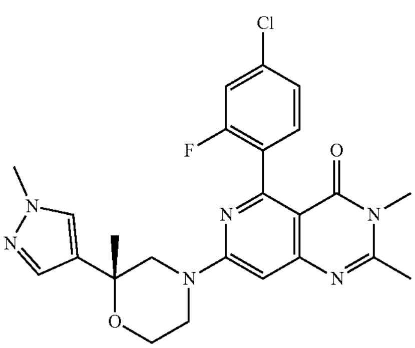 [SMILES: Cc1nc2cc(N3CCO[C@](C)(c4cnn(C)c4)C3)nc(-c3ccc(Cl)cc3F)c2c(=O)n1C] |
| I-354 | 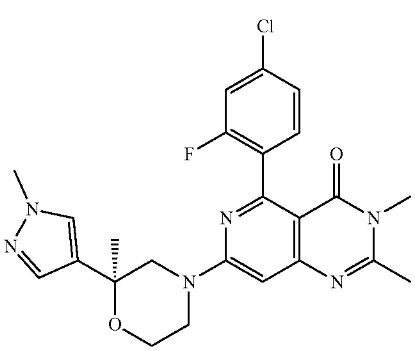 [SMILES: Cc1nc2cc(N3CCO[C@@](C)(c4cnn(C)c4)C3)nc(-c3ccc(Cl)cc3F)c2c(=O)n1C] |
| I-355 | |
| I-356 | |
| I-357 | |
| I-358 | |

TABLE A-continued
Exemplary Compounds
| I # | Structure |
|---|---|
| I-359 | 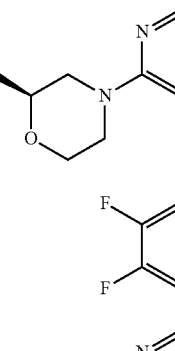 |
| I-360 | 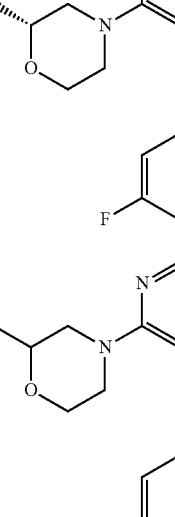 |
| I-361 | 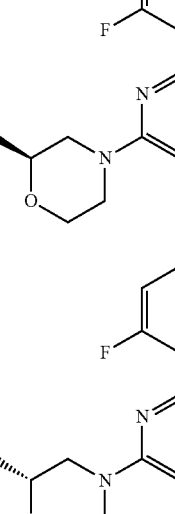 |
| I-362 | 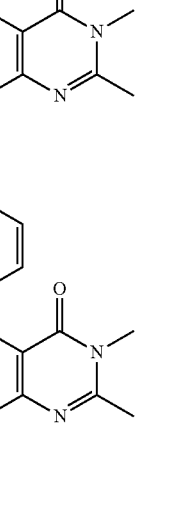 |
| I-363 | 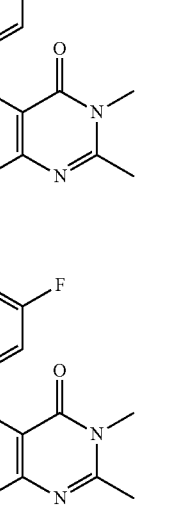 |
| I-364 | 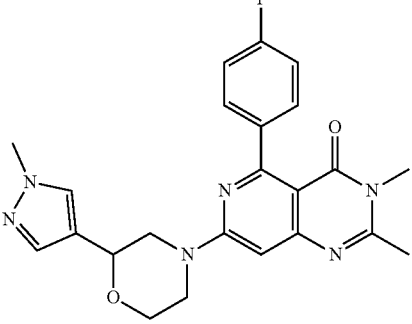 |
| I-365 | 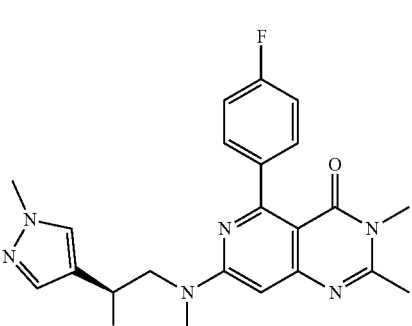 |
| I-366 | 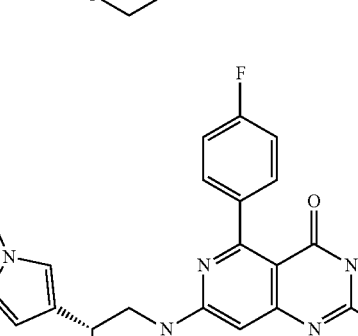 |
| I-367 | 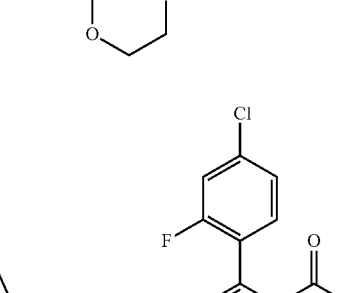 |

TABLE A-continued

Exemplary Compounds

| I # | Structure |
|---|---|
| I-368 | 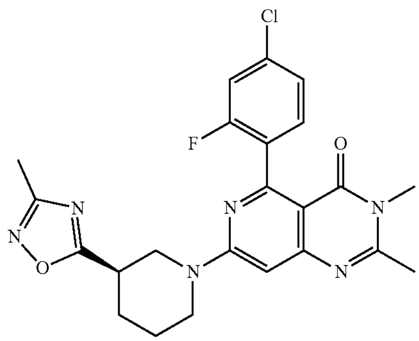 [SMILES: Cc1noc([C@@H]2CCCN(c3cc4nc(C)n(C)c(=O)c4c(-c4ccc(Cl)cc4F)n3)C2)n1] |
| I-369 | 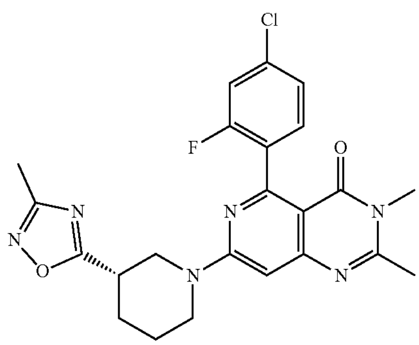 [SMILES: Cc1noc([C@H]2CCCN(c3cc4nc(C)n(C)c(=O)c4c(-c4ccc(Cl)cc4F)n3)C2)n1] |
| I-370 | 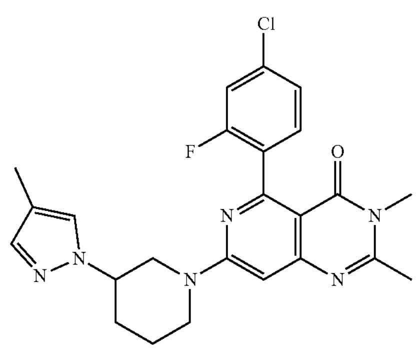 [SMILES: Cc1cnn(C2CCCN(c3cc4nc(C)n(C)c(=O)c4c(-c4ccc(Cl)cc4F)n3)C2)c1] |
| I-371 | 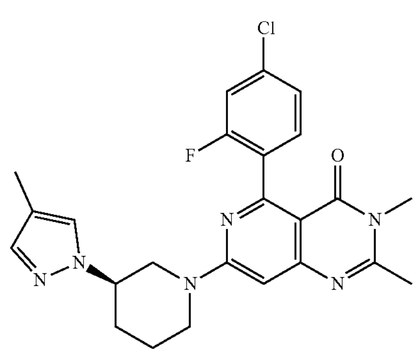 [SMILES: Cc1cnn([C@@H]2CCCN(c3cc4nc(C)n(C)c(=O)c4c(-c4ccc(Cl)cc4F)n3)C2)c1] |
| I-372 | |
| I-373 | |
| I-374 | |
| I-375 | |

TABLE A-continued
Exemplary Compounds
| I # | Structure |
|---|---|
| I-376 | 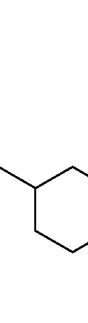 |
| I-377 | 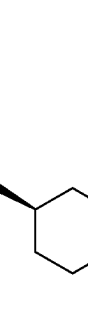 |
| I-378 | 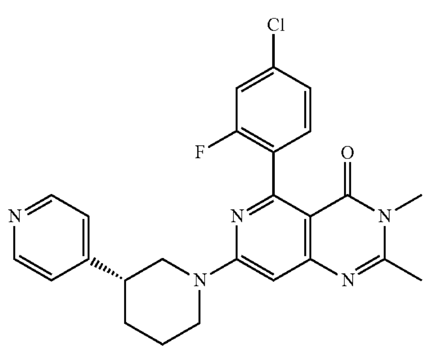 |
| I-379 | 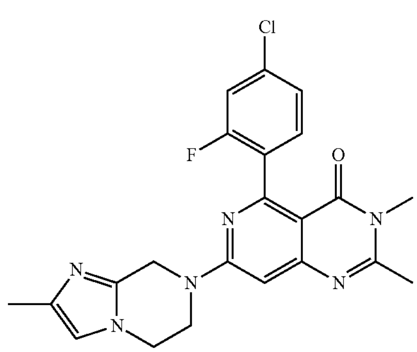 |
| I-380 | 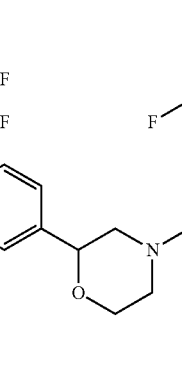 |
| I-381 | 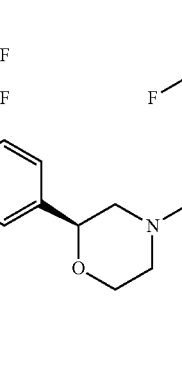 |
| I-382 | 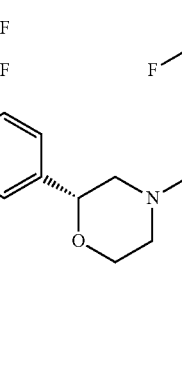 |
| I-383 | 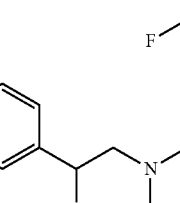 |

TABLE A-continued

Exemplary Compounds

| I # | Structure |
|---|---|
| I-384 | (structure) |
| I-385 | (structure) |
| I-386 | (structure) |
| I-387 | (structure) |
| I-388 | (structure) |
| I-389 | (structure) |
| I-390 | (structure) |
| I-391 | (structure) |

TABLE A-continued
Exemplary Compounds
| I # | Structure |
|---|---|
| I-392 | 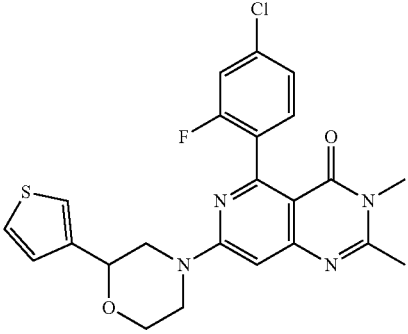 |
| I-393 | 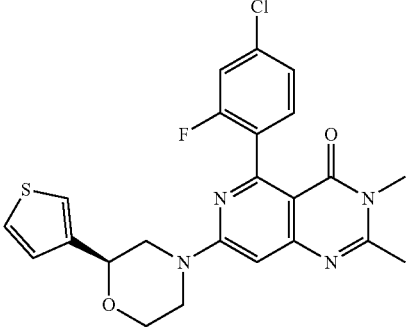 |
| I-394 | 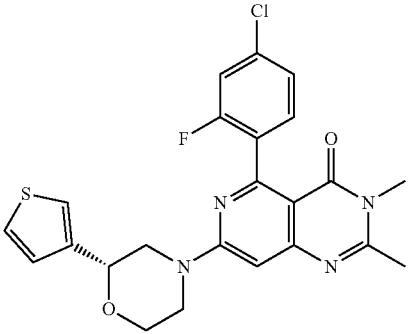 [SMILES: Cc1nc2cc(N3CCO[C@H](c4ccsc4)C3)nc(-c3ccc(Cl)cc3F)c2c(=O)n1C] |
| I-395 | 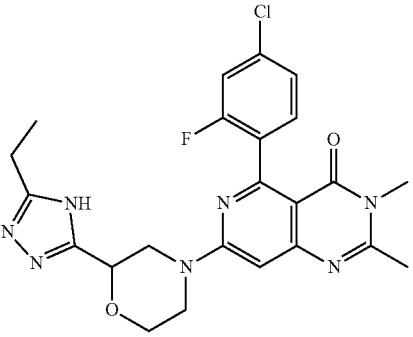 [SMILES: CCc1nnc(C2CN(c3cc4nc(C)n(C)c(=O)c4c(-c4ccc(Cl)cc4F)n3)CCO2)[nH]1] |
| I-396 | 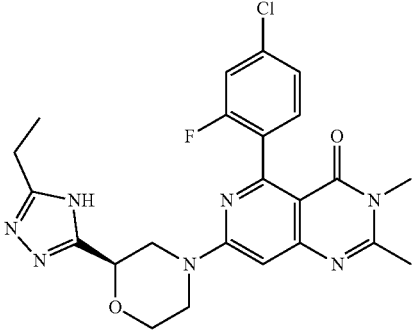 [SMILES: CCc1nnc([C@H]2CN(c3cc4nc(C)n(C)c(=O)c4c(-c4ccc(Cl)cc4F)n3)CCO2)[nH]1] |
| I-397 | 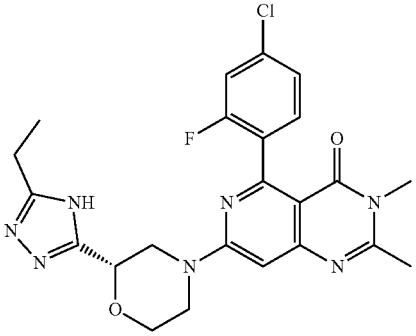 [SMILES: CCc1nnc([C@@H]2CN(c3cc4nc(C)n(C)c(=O)c4c(-c4ccc(Cl)cc4F)n3)CCO2)[nH]1] |
| I-398 | 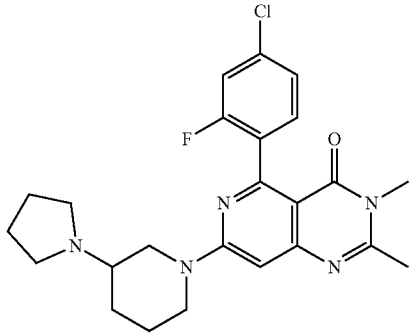 |
| I-399 | 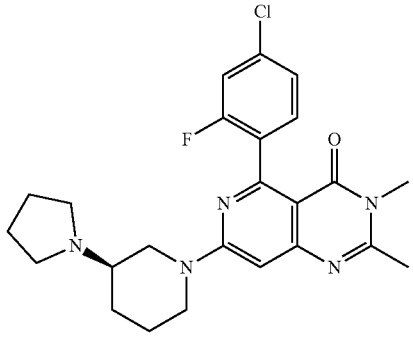 [SMILES: Cc1nc2cc(N3CCC[C@@H](N4CCCC4)C3)nc(-c3ccc(Cl)cc3F)c2c(=O)n1C] |

TABLE A-continued

Exemplary Compounds

| I # | Structure |
|---|---|
| I-400 | (structure) |
| I-401 | (structure) |
| I-402 | (structure) |
| I-403 | (structure) |
| I-404 | (structure) |
| I-405 | (structure) |
| I-406 | (structure) |
| I-407 | (structure) |

TABLE A-continued

Exemplary Compounds

| I # | Structure |
|---|---|
| I-408 | (structure) |
| I-409 | (structure) |
| I-410 | (structure) |
| I-411 | (structure) |
| I-412 | (structure) |
| I-413 | (structure) |
| I-414 | (structure) |
| I-415 | (structure) |

TABLE A-continued

Exemplary Compounds

| I # | Structure |
|---|---|
| I-416 | 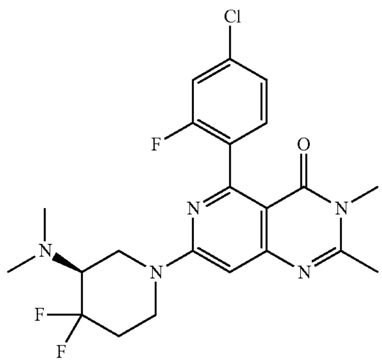 |
| I-417 | 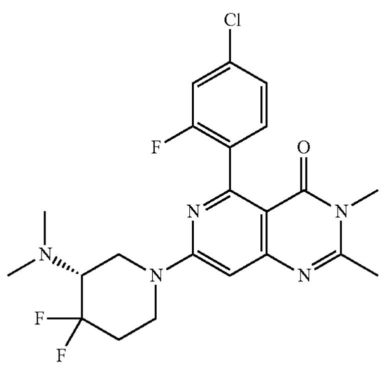 |
| I-418 | 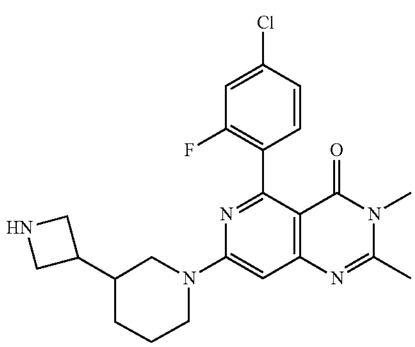 [SMILES: Cc1nc2cc(N3CCCC(C4CNC4)C3)nc(-c3ccc(Cl)cc3F)c2c(=O)n1C] |
| I-419 | 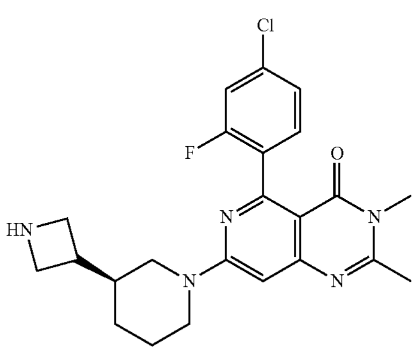 [SMILES: Cc1nc2cc(N3CCC[C@@H](C4CNC4)C3)nc(-c3ccc(Cl)cc3F)c2c(=O)n1C] |
| I-420 | |
| I-421 | |
| I-422 | |
| I-423 | |

TABLE A-continued
Exemplary Compounds
| I # | Structure |
|---|---|
| I-424 | 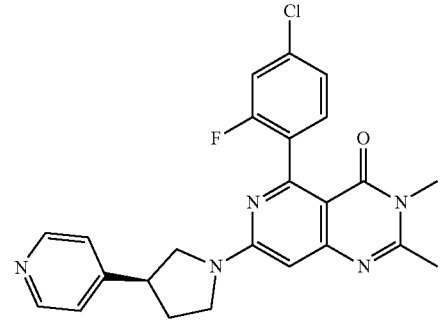 |
| I-425 | 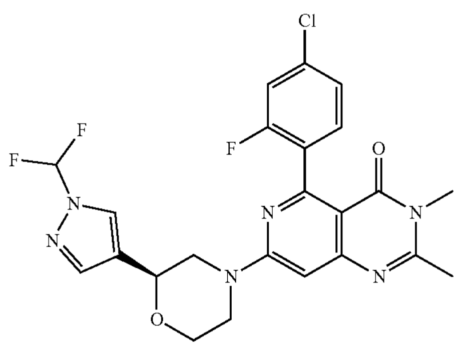 |
| I-426 | 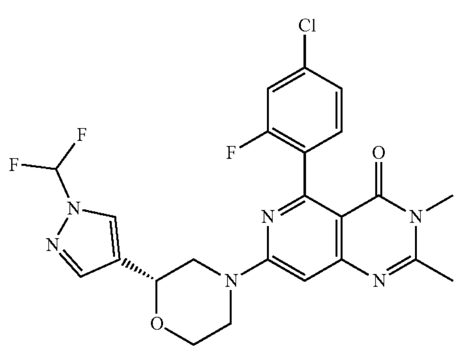 [SMILES: Cc1nc2cc(N3CCOC(c4cnn(C(F)F)c4)C3)nc(-c3ccc(Cl)cc3F)c2c(=O)n1C] |
| I-427 | 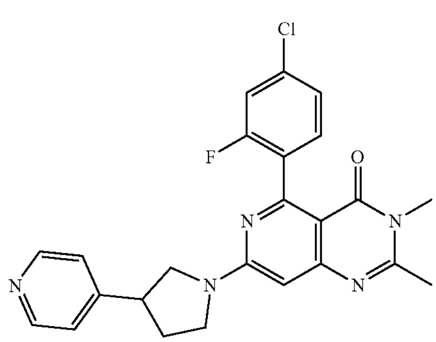 [SMILES: Cc1nc2cc(N3CCC(c4ccncc4)C3)nc(-c3ccc(Cl)cc3F)c2c(=O)n1C] |
| I-428 | 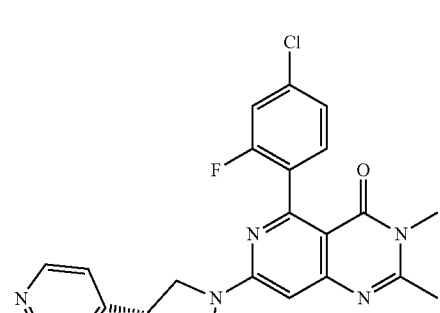 |
| I-429 | |
| I-430 | |
| I-431 | |

TABLE A-continued
Exemplary Compounds
| I # | Structure |
|---|---|
| I-432 | 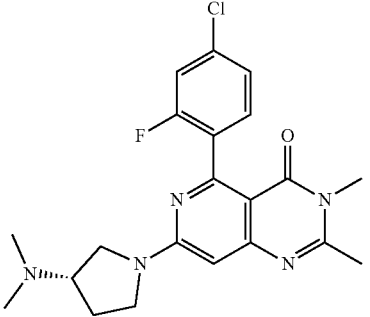 |
| I-433 | 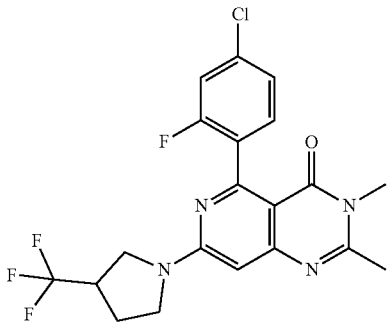 [SMILES: Cc1nc2cc(N3CCC(C(F)(F)F)C3)nc(-c3ccc(Cl)cc3F)c2c(=O)n1C] |
| I-434 | 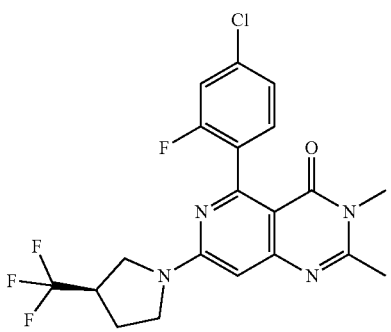 [SMILES: Cc1nc2cc(N3CC[C@@H](C(F)(F)F)C3)nc(-c3ccc(Cl)cc3F)c2c(=O)n1C] |
| I-435 | 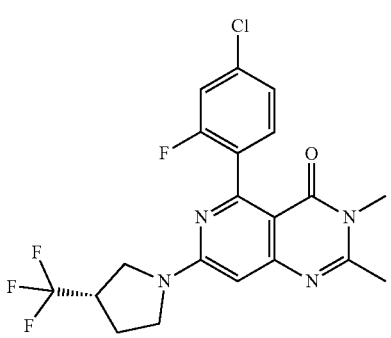 [SMILES: Cc1nc2cc(N3CC[C@H](C(F)(F)F)C3)nc(-c3ccc(Cl)cc3F)c2c(=O)n1C] |
| I-436 | 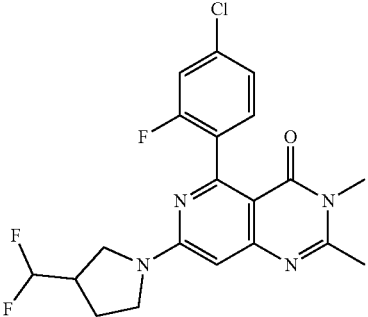 [SMILES: Cc1nc2cc(N3CCC(C(F)F)C3)nc(-c3ccc(Cl)cc3F)c2c(=O)n1C] |
| I-437 | 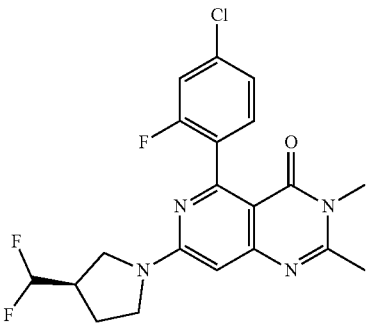 [SMILES: Cc1nc2cc(N3CC[C@@H](C(F)F)C3)nc(-c3ccc(Cl)cc3F)c2c(=O)n1C] |
| I-438 | 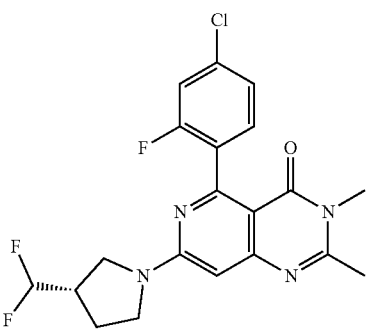 [SMILES: Cc1nc2cc(N3CC[C@H](C(F)F)C3)nc(-c3ccc(Cl)cc3F)c2c(=O)n1C] |
| I-439 | 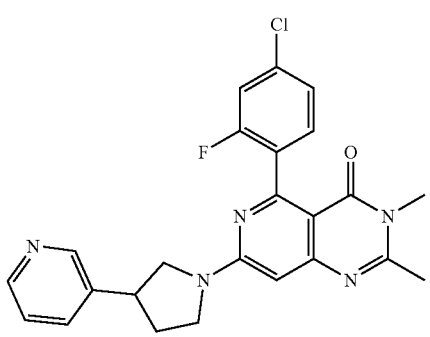 [SMILES: Cc1nc2cc(N3CCC(c4cccnc4)C3)nc(-c3ccc(Cl)cc3F)c2c(=O)n1C] |

TABLE A-continued
Exemplary Compounds
| I # | Structure |
|---|---|
| I-440 | 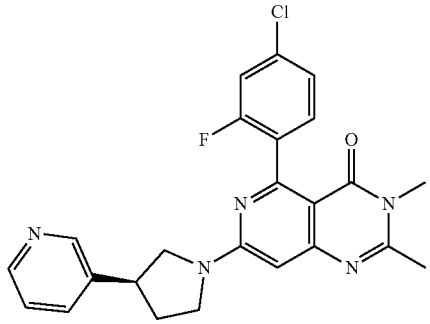 [SMILES: Cc1nc2cc(N3CC[C@@H](c4cccnc4)C3)nc(-c3ccc(Cl)cc3F)c2c(=O)n1C] |
| I-441 | 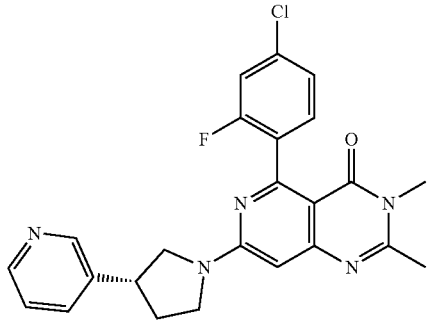 [SMILES: Cc1nc2cc(N3CC[C@H](c4cccnc4)C3)nc(-c3ccc(Cl)cc3F)c2c(=O)n1C] |
| I-442 | 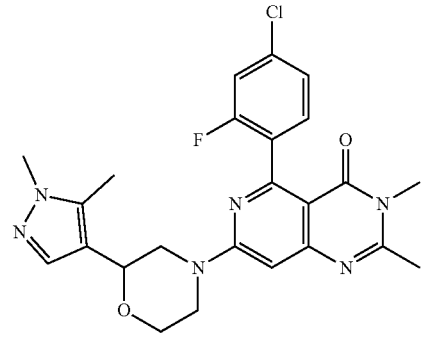 |
| I-443 | 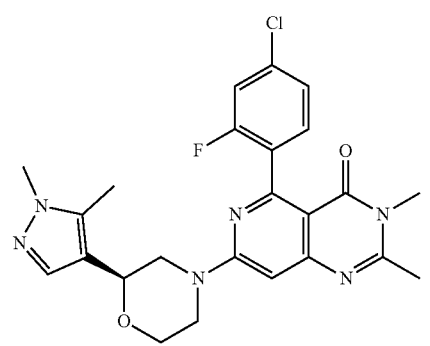 [SMILES: Cc1c([C@H]2CN(c3cc4nc(C)n(C)c(=O)c4c(-c4ccc(Cl)cc4F)n3)CCO2)cnn1C] |
| I-444 | 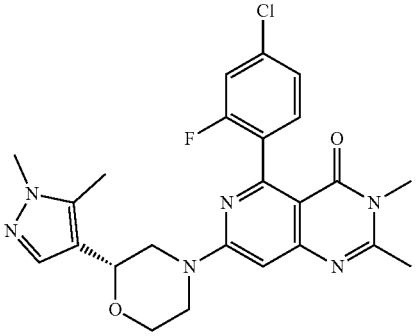 [SMILES: Cc1c([C@@H]2CN(c3cc4nc(C)n(C)c(=O)c4c(-c4ccc(Cl)cc4F)n3)CCO2)cnn1C] |
| I-445 | 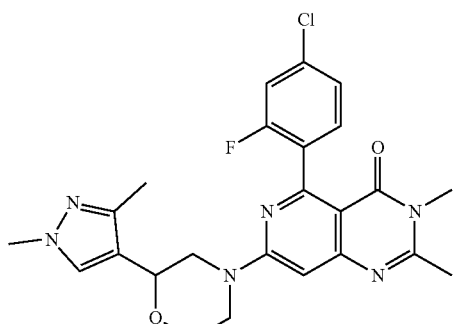 |
| I-446 | 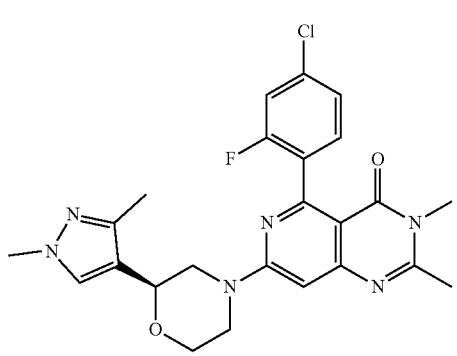 |
| I-447 | 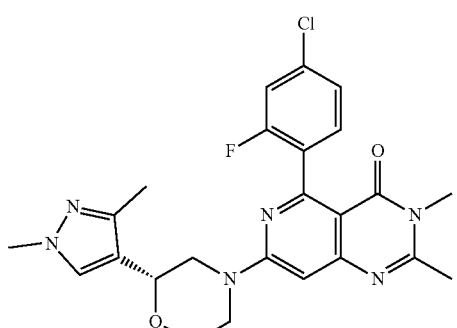 |

TABLE A-continued

Exemplary Compounds

| I # | Structure |
|---|---|
| I-448 | 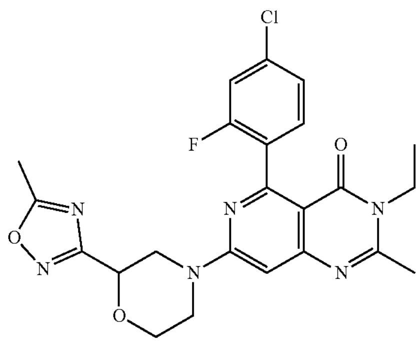 [SMILES: CCn1c(C)nc2cc(N3CCOC(c4noc(C)n4)C3)nc(-c3ccc(Cl)cc3F)c2c1=O] |
| I-449 | 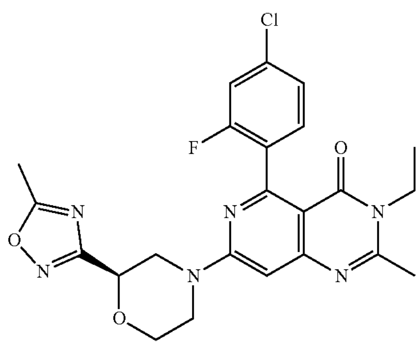 [SMILES: CCn1c(C)nc2cc(N3CCO[C@@H](c4noc(C)n4)C3)nc(-c3ccc(Cl)cc3F)c2c1=O] |
| I-450 | 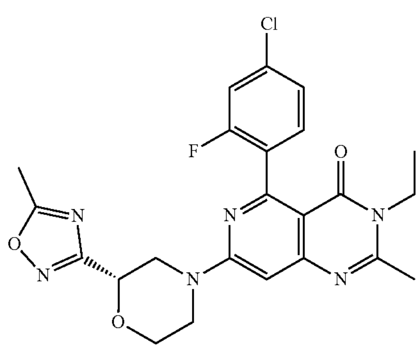 [SMILES: CCn1c(C)nc2cc(N3CCO[C@H](c4noc(C)n4)C3)nc(-c3ccc(Cl)cc3F)c2c1=O] |
| I-451 | 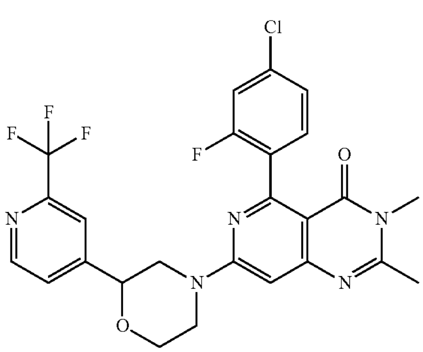 [SMILES: Cc1nc2cc(N3CCOC(c4ccnc(C(F)(F)F)c4)C3)nc(-c3ccc(Cl)cc3F)c2c(=O)n1C] |
| I-452 | |
| I-453 | |
| I-454 | |
| I-455 | |

TABLE A-continued

Exemplary Compounds

| I # | Structure |
| --- | --- |
| I-456 | 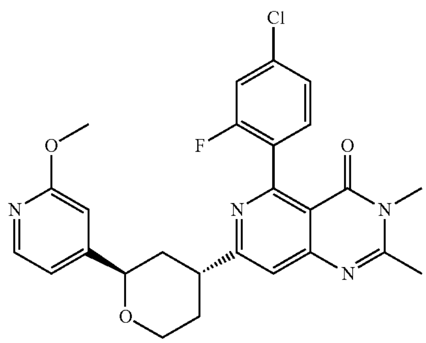 |
| I-457 | 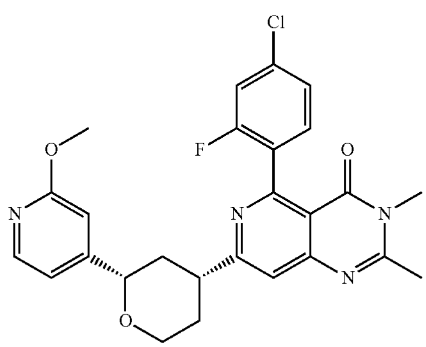 [SMILES: COc1cc(C2CC(c3cc4nc(C)n(C)c(=O)c4c(-c4ccc(Cl)cc4F)n3)CCO2)ccn1] |
| I-458 | 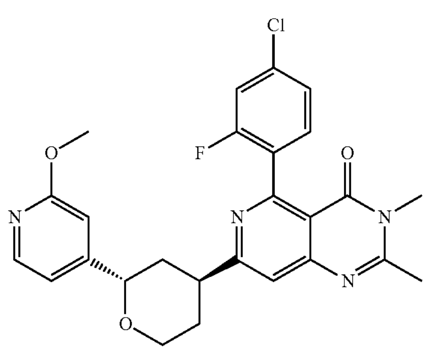 [SMILES: COc1cc([C@@H]2C[C@@H](c3cc4nc(C)n(C)c(=O)c4c(-c4ccc(Cl)cc4F)n3)CCO2)ccn1] |
| I-459 | 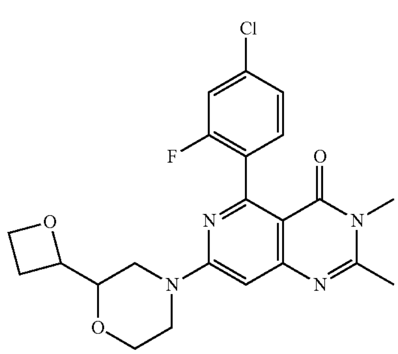 |
| I-460 | 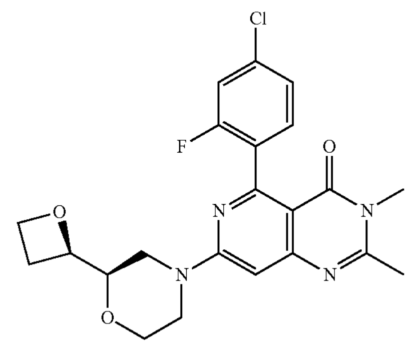 [SMILES: Cc1nc2cc(N3CCO[C@@H]([C@H]4CCO4)C3)nc(-c3ccc(Cl)cc3F)c2c(=O)n1C] |
| I-461 | 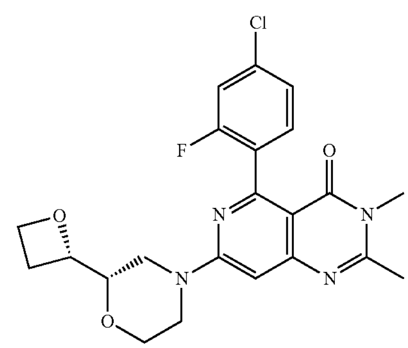 |
| I-462 | 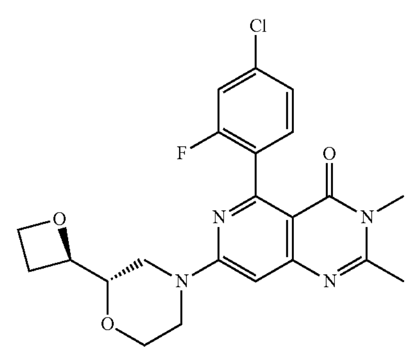 [SMILES: Cc1nc2cc(N3CCO[C@H]([C@H]4CCO4)C3)nc(-c3ccc(Cl)cc3F)c2c(=O)n1C] |
| I-463 | 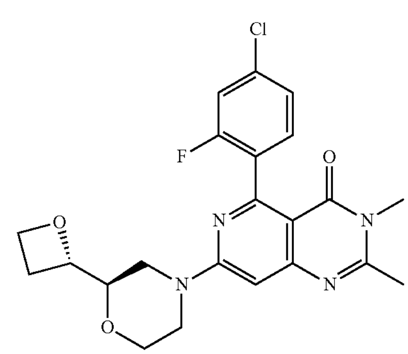 [SMILES: Cc1nc2cc(N3CCO[C@@H]([C@@H]4CCO4)C3)nc(-c3ccc(Cl)cc3F)c2c(=O)n1C] |

TABLE A-continued

Exemplary Compounds

| I # | Structure |
|---|---|
| I-464 | 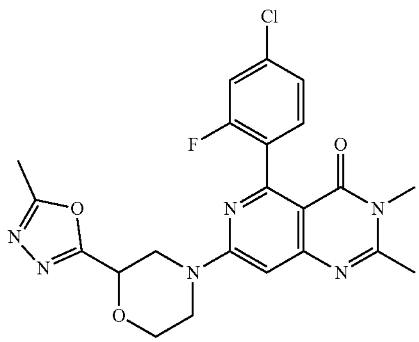 [SMILES: Cc1nnc(C2CN(c3cc4nc(C)n(C)c(=O)c4c(-c4ccc(Cl)cc4F)n3)CCO2)o1] |
| I-465 | 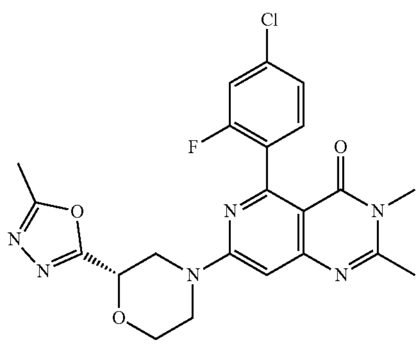 [SMILES: Cc1nnc([C@@H]2CN(c3cc4nc(C)n(C)c(=O)c4c(-c4ccc(Cl)cc4F)n3)CCO2)o1] |
| I-466 | 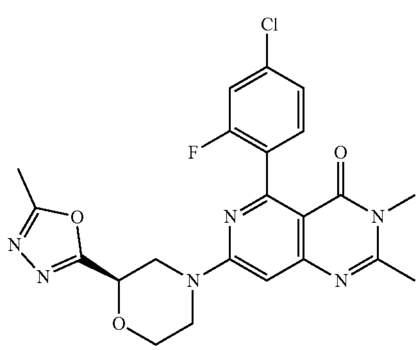 [SMILES: Cc1nnc([C@H]2CN(c3cc4nc(C)n(C)c(=O)c4c(-c4ccc(Cl)cc4F)n3)CCO2)o1] |
| I-467 | 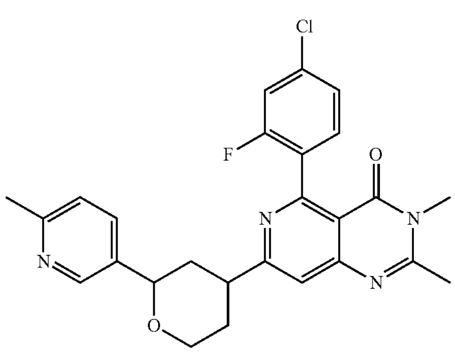 |
| I-468 | |
| I-469 | |
| I-470 | |
| I-471 | |

TABLE A-continued
Exemplary Compounds
| I # | Structure |
|---|---|
| I-472 | 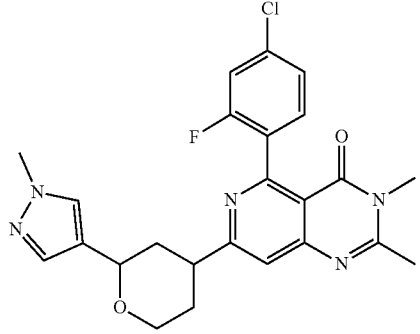 |
| I-473 | 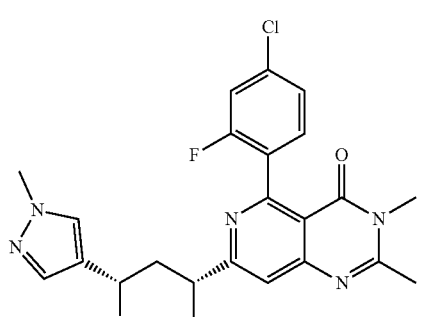 |
| I-474 | 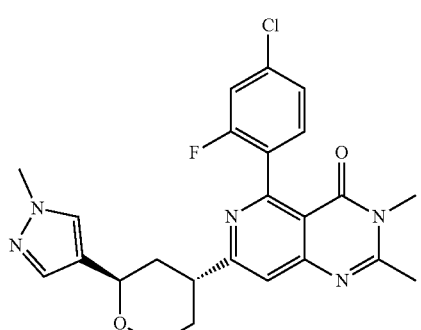 |
| I-475 | 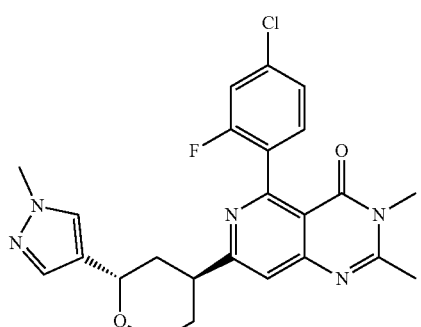 |
| I-476 | 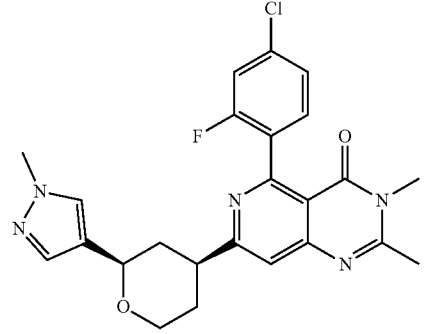 [SMILES: Cc1nc2cc([C@H]3CCO[C@@H](c4cnn(C)c4)C3)nc(-c3ccc(Cl)cc3F)c2c(=O)n1C] |
| I-477 | 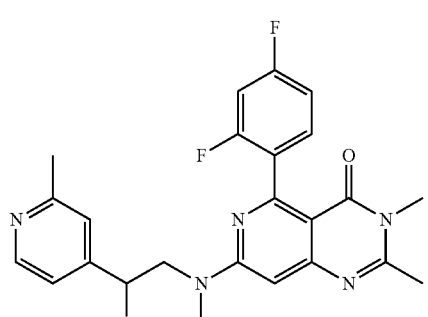 |
| I-478 | 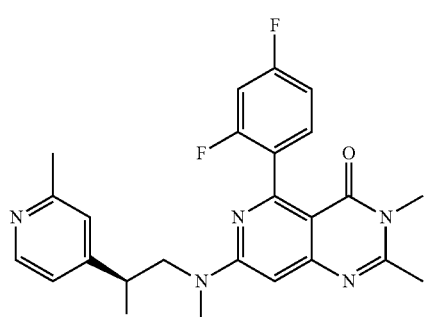 |
| I-479 | 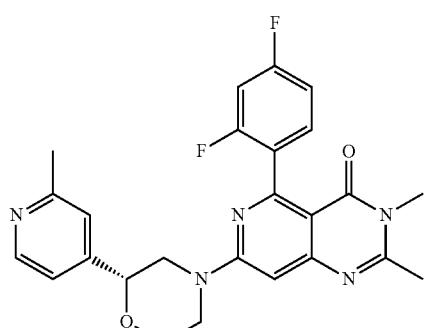 |

TABLE A-continued

Exemplary Compounds

| I # | Structure |
|---|---|
| I-480 | 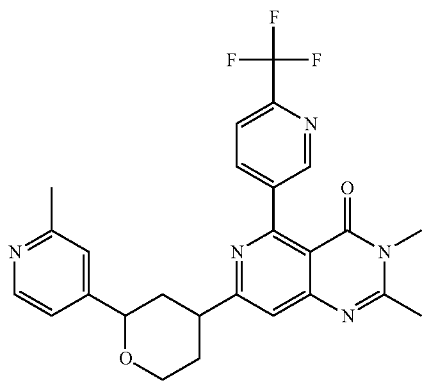 [SMILES: Cc1cc(C2CC(c3cc4nc(C)n(C)c(=O)c4c(-c4ccc(C(F)(F)F)nc4)n3)CCO2)ccn1] |
| I-481 | 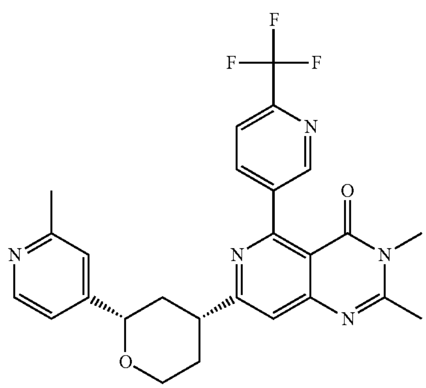 [SMILES: Cc1cc([C@@H]2C[C@H](c3cc4nc(C)n(C)c(=O)c4c(-c4ccc(C(F)(F)F)nc4)n3)CCO2)ccn1] |
| I-482 | 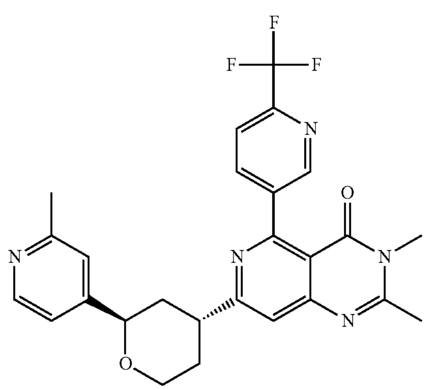 [SMILES: Cc1cc([C@H]2C[C@H](c3cc4nc(C)n(C)c(=O)c4c(-c4ccc(C(F)(F)F)nc4)n3)CCO2)ccn1] |
| I-483 | 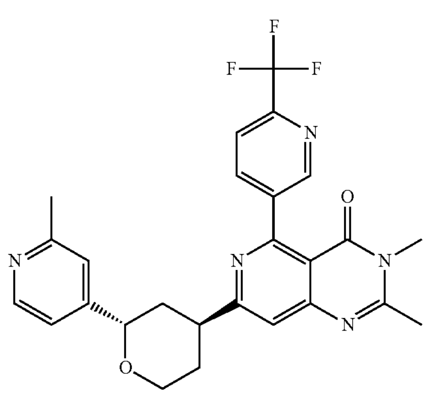 [SMILES: Cc1cc([C@@H]2C[C@@H](c3cc4nc(C)n(C)c(=O)c4c(-c4ccc(C(F)(F)F)nc4)n3)CCO2)ccn1] |
| I-484 | |
| I-485 | |
| I-486 | |
| I-487 | |

TABLE A-continued
Exemplary Compounds
| I # | Structure |
|---|---|
| I-488 | 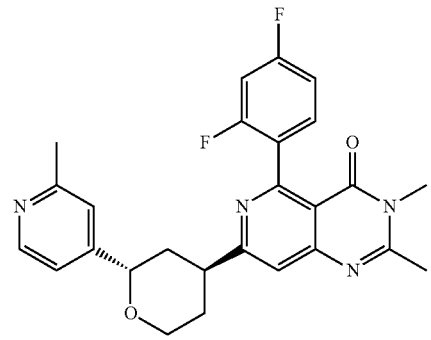 [SMILES: Cc1cc([C@@H]2C[C@@H](c3cc4nc(C)n(C)c(=O)c4c(-c4ccc(F)cc4F)n3)CCO2)ccn1] |
| I-489 | 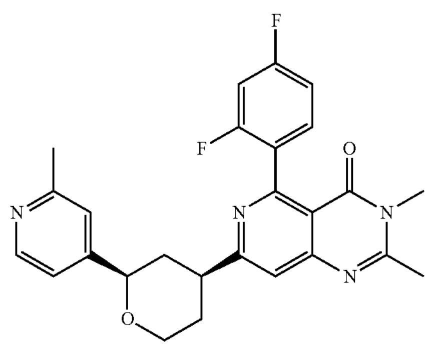 [SMILES: Cc1cc([C@H]2C[C@@H](c3cc4nc(C)n(C)c(=O)c4c(-c4ccc(F)cc4F)n3)CCO2)ccn1] |
| I-490 | 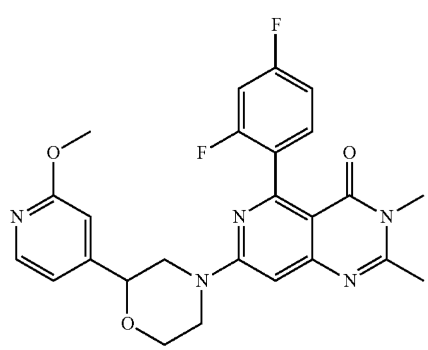 [SMILES: COc1cc(C2CN(c3cc4nc(C)n(C)c(=O)c4c(-c4ccc(F)cc4F)n3)CCO2)ccn1] |
| I-491 | 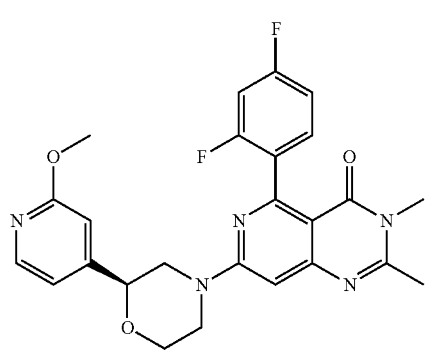 [SMILES: COc1cc([C@H]2CN(c3cc4nc(C)n(C)c(=O)c4c(-c4ccc(F)cc4F)n3)CCO2)ccn1] |
| I-492 | 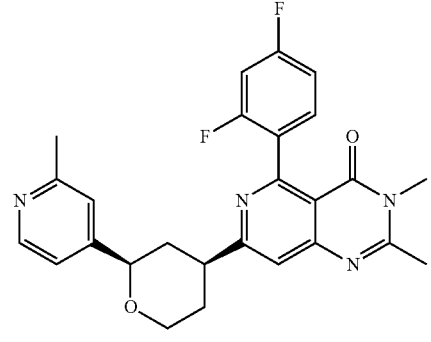 |
| I-493 | |
| I-494 | |
| I-495 | |

TABLE A-continued

Exemplary Compounds

| I # | Structure |
|---|---|
| I-496 | 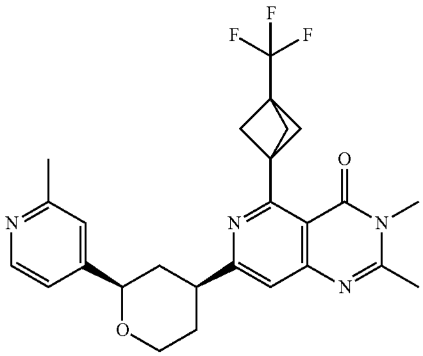 [SMILES: Cc1cc([C@H]2C[C@@H](c3cc4nc(C)n(C)c(=O)c4c(C45CC(C(F)(F)F)(C4)C5)n3)CCO2)ccn1] |
| I-497 | 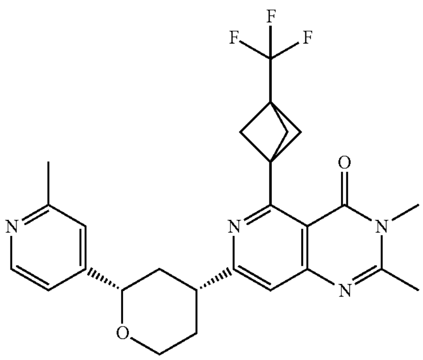 [SMILES: Cc1cc([C@@H]2C[C@H](c3cc4nc(C)n(C)c(=O)c4c(C45CC(C(F)(F)F)(C4)C5)n3)CCO2)ccn1] |
| I-498 | 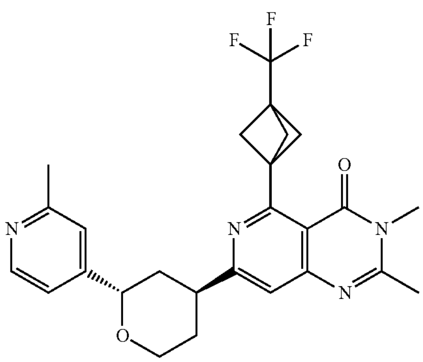 [SMILES: Cc1cc([C@@H]2C[C@@H](c3cc4nc(C)n(C)c(=O)c4c(C45CC(C(F)(F)F)(C4)C5)n3)CCO2)ccn1] |
| I-499 | 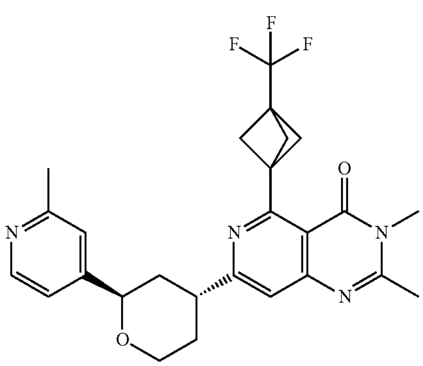 [SMILES: Cc1cc([C@H]2C[C@H](c3cc4nc(C)n(C)c(=O)c4c(C45CC(C(F)(F)F)(C4)C5)n3)CCO2)ccn1] |
| I-500 | |
| I-501 | |
| I-502 | |
| I-503 | |

TABLE A-continued

Exemplary Compounds

| I # | Structure |
|---|---|
| I-504 | 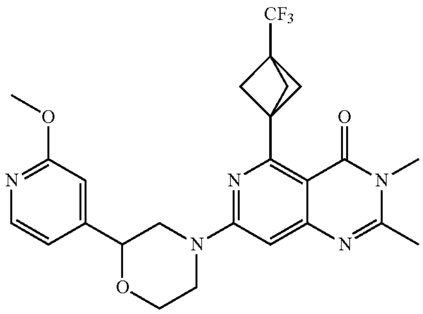 [SMILES: COc1cc(C2CN(c3cc4nc(C)n(C)c(=O)c4c(C45CC(C(F)(F)F)(C4)C5)n3)CCO2)ccn1] |
| I-505 | 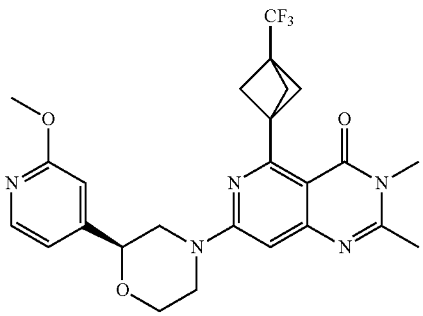 [SMILES: COc1cc([C@H]2CN(c3cc4nc(C)n(C)c(=O)c4c(C45CC(C(F)(F)F)(C4)C5)n3)CCO2)ccn1] |
| I-506 | 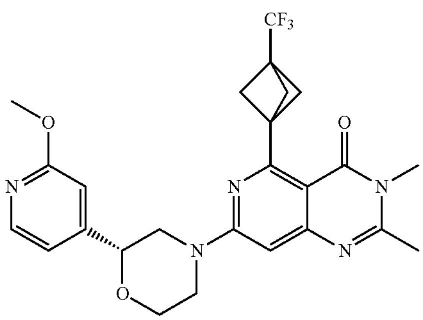 [SMILES: COc1cc([C@@H]2CN(c3cc4nc(C)n(C)c(=O)c4c(C45CC(C(F)(F)F)(C4)C5)n3)CCO2)ccn1] |

The foregoing merely summarizes certain aspects of this disclosure and is not intended, nor should it be construed, as limiting the disclosure in any way.

Formulation and Route of Administration

While it may be possible to administer a compound disclosed herein alone in the uses described, the compound administered normally will be present as an active ingredient in a pharmaceutical composition. Thus, in one embodiment, provided herein is a pharmaceutical composition comprising a compound disclosed herein in combination with one or more pharmaceutically acceptable excipients, such as diluents, carriers, adjuvants and the like, and, if desired, other active ingredients. See, e.g., Remington: The Science and Practice of Pharmacy, Volume I and Volume II, twenty-second edition, edited by Loyd V. Allen Jr., Philadelphia, PA, Pharmaceutical Press, 2012; Pharmaceutical Dosage Forms (Vol. 1-3), Liberman et al., Eds., Marcel Dekker, New York, NY, 1992; Handbook of Pharmaceutical Excipients (3rd Ed.), edited by Arthur H. Kibbe, American Pharmaceutical Association, Washington, 2000; Pharmaceutical Formulation: The Science and Technology of Dosage Forms (Drug Discovery), first edition, edited by GD Tovey, Royal Society of Chemistry, 2018. In one embodiment, a pharmaceutical composition comprises a therapeutically effective amount of a compound disclosed herein.

The compound(s) disclosed herein may be administered by any suitable route in the form of a pharmaceutical composition adapted to such a route and in a dose effective for the treatment intended. The compounds and compositions presented herein may, for example, be administered orally, mucosally, topically, transdermally, rectally, pulmonarily, parentally, intranasally, intravascularly, intravenously, intraarterial, intraperitoneally, intrathecally, subcutaneously, sublingually, intramuscularly, intrasternally, vaginally or by infusion techniques, in dosage unit formulations containing conventional pharmaceutically acceptable excipients.

The pharmaceutical composition may be in the form of, for example, a tablet, chewable tablet, minitablet, caplet, pill, bead, hard capsule, soft capsule, gelatin capsule, granule, powder, lozenge, patch, cream, gel, sachet, microneedle array, syrup, flavored syrup, juice, drop, injectable solution, emulsion, microemulsion, ointment, aerosol, aqueous suspension, or oily suspension. The pharmaceutical composition is typically made in the form of a dosage unit containing a particular amount of the active ingredient.

Provided herein as Embodiment 55 is a pharmaceutical composition comprising the compound according to any one of Embodiments 1-54, or a tautomer thereof, or a pharmaceutically acceptable salt of said compound or said tautomer, and a pharmaceutically acceptable excipient.

Provided herein as Embodiment 56 is a compound according to any one of Embodiments 1-54, or a tautomer thereof, or a pharmaceutically acceptable salt of said compound or said tautomer, or the pharmaceutical composition according to Embodiment 55 for use as a medicament.

Pharmaceutically Acceptable Compositions

According to some embodiments, the present disclosure provides a composition comprising a compound of this disclosure or a pharmaceutically acceptable derivative thereof and a pharmaceutically acceptable carrier, adjuvant, or vehicle. The amount of compound in compositions of this disclosure is such that it is effective to measurably activate a TREM2 protein, or a mutant thereof, in a biological sample or in a patient. In certain embodiments, the amount of compound in compositions of this disclosure is such that it is effective to measurably activate a TREM2 protein, or a mutant thereof, in a biological sample or in a patient. In certain embodiments, a composition of this disclosure is formulated for administration to a patient in need of such composition. In some embodiments, a composition of this disclosure is formulated for oral administration to a patient.

Compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of compounds of the present disclosure that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

Methods of Use

As discussed herein (see, section entitled "Definitions"), the compounds described herein are to be understood to include all stereoisomers, tautomers, or pharmaceutically acceptable salts of any of the foregoing or solvates of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals and farm animals, including mammals, rodents, and the like. For example, animals including horses, dogs, and cats may be treated with compounds provided herein.

Without wishing to be bound by any particular theory, the following is noted: TREM2 has been implicated in several myeloid cell processes, including phagocytosis, proliferation, survival, and regulation of inflammatory cytokine production. Ulrich and Holtzman 2016. In the last few years, TREM2 has been linked to several diseases. For instance, mutations in both TREM2 and DAP12 have been linked to the autosomal recessive disorder Nasu-Hakola Disease, which is characterized by bone cysts, muscle wasting and demyelination phenotypes. Guerreiro et al. 2013. More recently, variants in the TREM2 gene have been linked to increased risk for Alzheimer's disease (AD) and other forms of dementia including frontotemporal dementia. Jonsson et al. 2013, Guerreiro, Lohmann et al. 2013, and Jay, Miller et al. 2015. In particular, the R47H variant has been identified in genome-wide studies as being associated with increased risk for late-onset AD with an overall adjusted odds ratio (for populations of all ages) of 2.3, second only to the strong genetic association of ApoE to Alzheimer's. The R47H mutation resides on the extracellular lg V-set domain of the TREM2 protein and has been shown to impact lipid binding and uptake of apoptotic cells and Abeta (Wang et al. 2015; Yeh et al. 2016), suggestive of a loss-of-function linked to disease. Further, postmortem comparison of AD patients' brains with and without the R47H mutation are supportive of a novel loss-of-microglial barrier function for the carriers of the mutation, with the R47H carrier microglia putatively demonstrating a reduced ability to compact plaques and limit their spread. Yuan et al. 2016. Impairment in microgliosis has been reported in animal models of prion disease, multiple sclerosis, and stroke, suggesting that TREM2 may play an important role in supporting microgliosis in response to pathology or damage in the central nervous system. Ulrich and Holtzman 2016. In addition, knockdown of TREM2 has been shown to aggravate α-syn-induced inflammatory responses in vitro and exacerbate dopaminergic neuron loss in response to AAV-SYN in vivo (a model of Parkinson's disease), suggesting that impaired microglial TREM2 signaling exacerbates neurodegeneration by modulating microglial activation states. Guo et. al. 2019. A variety of animal models also suggest that Toll-Like Receptor (TLR) signaling is important in the pathogenesis of Rheumatoid Arthritis (RA) via persistent expression of pro-inflammatory cytokines by macrophages. Signaling through TREM2/DAP12 inhibits TLR responses by reducing MAPK (Erk1/2) activation, suggesting that TREM2 activation may act as a negative regulator of TLR driven RA pathogenesis. Huang and Pope 2009.

In view of the data indicating that deficits in TREM2 activity affect macrophage and microglia function, the compounds disclosed herein are of particular use in disorders, such as those described above and in the embodiments that follow and in neurodegenerative disorders more generally.

Provided herein as Embodiment 57 is a compound according to any one of embodiments 1-54, or a tautomer thereof, or a pharmaceutically acceptable salt of said compound or said tautomer, or the pharmaceutical composition according to Embodiment 55 for use in treating or preventing a condition associated with a loss of function of human TREM2.

Provided herein as Embodiment 58 is a compound according to any one of embodiments 1-54, or a tautomer thereof, or a pharmaceutically acceptable salt of said compound or said tautomer, or the pharmaceutical composition according to Embodiment 55 for use in treating or preventing Parkinson's disease, rheumatoid arthritis, Alzheimer's disease, Nasu-Hakola disease, frontotemporal dementia, multiple sclerosis, prion disease, or stroke.

Provided herein as Embodiment 59 is a use of the compound according to any one of embodiments 1-54, or a tautomer thereof, or a pharmaceutically acceptable salt of said compound or said tautomer, or the pharmaceutical composition according to Embodiment 55 in the preparation of a medicament for treating or preventing a condition associated with a loss of function of human TREM2.

Provided herein as Embodiment 60 is a use of the compound according to any one of embodiments 1-54, or a tautomer thereof, or a pharmaceutically acceptable salt of said compound or said tautomer, or the pharmaceutical composition according to Embodiment 55 in the preparation of a medicament for treating or preventing Parkinson's disease, rheumatoid arthritis, Alzheimer's disease, Nasu-Hakola disease, frontotemporal dementia, multiple sclerosis, prion disease, or stroke.

Provided herein as Embodiment 61 is a method of treating or preventing a condition associated with a loss of function of human TREM2 in a subject in need thereof, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55.

Provided herein as Embodiment 62 is a method of treating or preventing Parkinson's disease, rheumatoid arthritis, Alzheimer's disease, Nasu-Hakola disease, frontotemporal dementia, multiple sclerosis, prion disease, or stroke in a subject in need thereof, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55.

In some embodiments, the condition associated with a loss of function of human TREM2 is Parkinson's disease. In some embodiments, the condition associated with a loss of function of human TREM2 is rheumatoid arthritis. In some embodiments, the condition associated with a loss of function of human TREM2 is Alzheimer's disease. In some embodiments, the condition associated with a loss of function of human TREM2 is Nasu-Hakola disease. In some embodiments, the condition associated with a loss of function of human TREM2 is frontotemporal dementia. In some embodiments, the condition associated with a loss of function of human TREM2 is multiple sclerosis. In some embodiments, the condition associated with a loss of function of human TREM2 is prion disease. In some embodiments, the condition associated with a loss of function of human TREM2 is stroke.

CSF1R

CSF1R is a cell-surface receptor primarily for the cytokine colony stimulating factor 1 (CSF-1), also known until recently as macrophage colony-stimulating factor (M-CSF), which regulates the survival, proliferation, differentiation and function of mononuclear phagocytic cells, including microglia of the central nervous system. CSF1R is composed of a highly glycosylated extracellular ligand-binding domain, a trans-membrane domain and an intracellular tyrosine-kinase domain. Binding of CSF-1 to CSF1R results in the formation of receptor homodimers and subsequent autophosphorylation of several tyrosine residues in the cytoplasmic domain, notably Syk. In the brain, CSF1R is predominantly expressed in microglial cells. It has been found that microglia in CSF1R+/− patients are depleted and show increased apoptosis (Oosterhof et al., 2018).

The present invention relates to the unexpected discovery that administration of a TREM2 agonist can rescue the loss of microglia in cells having mutations in CSF1R. It has been previously shown that TREM2 agonist antibody 4D9 increases ATP luminescence (a measure of cell number and activity) in a dose dependent manner when the levels of M-CSF in media are reduced to 5 ng/mL (Schlepckow et al, EMBO Mol Med., 2020) and that TREM2 agonist AL002c increases ATP luminescence when M-CSF is completely removed from the media (Wang et al, J. Exp. Med.; 2020, 217(9): e20200785). This finding suggests that TREM2 agonism can compensate for deficiency in CSF1R signaling caused by a decrease in the concentration of its ligand. In a 5×FAD murine Alzheimer's disease model of amyloid pathology, doses of a CSF1R inhibitor that almost completely eliminate microglia in the brains of wild-type animals show surviving microglia clustered around the amyloid plaques (Spangenberg et al, Nature Communications 2019). Plaque amyloid has been demonstrated in the past to be a ligand for TREM2, and it has been shown that microglial engagement with amyloid is dependent on TREM2 (Condello et al, Nat Comm., 2015). The present invention relates to the unexpected discovery that it is activation of TREM2 that rescued the microglia in the presence of the CSF1R inhibitor, and that this effect is also observed in patients suffering from loss of microglia due to CSF1R mutation. This discovery has not been previously taught or suggested in the available art.

To date, no prior study has shown that TREM2 agonism can rescue the loss of microglia in cells where mutations in the CSF1R kinase domain reduce CSF1R activity, rather than the presence of a CSF1R inhibitor or a deficiency in CSF1R ligand. Furthermore, no prior study has taught or suggested that reversal of the loss of microglia due to a CSF1R mutation through TREM2 agonism can be used to treat a disease or disorder caused by and/or associated with a CSF1R mutation.

Adult-onset leukoencephalopathy with axonal spheroids and pigmented glia (ALSP), previously recognized as hereditary diffuse leukoencephalopathy with axonal spheroids (HDLS) or pigmentary orthochromatic leukodystrophy (POLD), is an autosomal-dominant central nervous system disease that manifests in the form of variable behavioral, cognitive and motor function changes in patients suffering from the disease. ALSP is characterized by patchy cerebral white matter abnormalities visible by magnetic resonance imaging. However, the clinical symptoms and MRI changes are not specific to ALSP and are common for other neurological conditions, including Nasu-Hakola disease (NHD) and AD, making diagnosis and treatment of ALSP very difficult.

Recent studies have discovered that ALSP is a Mendelian disorder in which patients carry a heterozygous loss of function mutation in the kinase domain of CSF1R, suggesting a reduced level of signaling on the macrophage colony-stimulating factor (M-CSF)/CSF1R axis (Rademakers et al, Nat Genet 2012; Konno et al, Neurology 2018). In one aspect, the present invention relates to the surprising discovery that activation of the TREM2 pathway can rescue the loss of microglia in CSF1R+/− ALSP patients, preventing microglia apoptosis, thereby treating the ALSP condition.

Provided herein as Embodiment 63 is a compound according to any one of embodiments 1-54, or a tautomer thereof, or a pharmaceutically acceptable salt of said compound or said tautomer, or the pharmaceutical composition according to Embodiment 55 for use in treating or preventing a condition associated with dysfunction of Colony stimulating factor 1 receptor (CSF1R, also known as macrophage colony-stimulating factor receptor/M-CSFR, or cluster of differentiation 115/CD 115).

Provided herein as Embodiment 64 is a compound according to any one of embodiments 1-54, or a tautomer thereof, or a pharmaceutically acceptable salt of said compound or said tautomer, or the pharmaceutical composition according to Embodiment 55 for use in treating or preventing adult-onset leukoencephalopathy with axonal spheroids and pigmented glia (ALSP), hereditary diffuse leukoencephalopathy with axonal spheroids (HDLS), pigmentary orthochromatic leukodystrophy (POLD), pediatric-onset leukoencephalopathy, congenital absence of microglia, or brain abnormalities neurodegeneration and dysosteosclerosis (BANDDOS).

Provided herein as Embodiment 65 is a use of the compound according to any one of embodiments 1-54, or a tautomer thereof, or a pharmaceutically acceptable salt of said compound or said tautomer, or the pharmaceutical composition according to Embodiment 55 in the preparation of a medicament for treating or preventing a condition associated with dysfunction of CSF1R.

Provided herein as Embodiment 66 is a use of the compound according to any one of embodiments 1-54, or a tautomer thereof, or a pharmaceutically acceptable salt of said compound or said tautomer, or the pharmaceutical composition according to Embodiment 55 in the preparation of a medicament for treating or preventing adult-onset leukoencephalopathy with axonal spheroids and pigmented glia (ALSP), hereditary diffuse leukoencephalopathy with axonal spheroids (HDLS), pigmentary orthochromatic leukodystrophy (POLD), pediatric-onset leukoencephalopathy, congenital absence of microglia, or brain abnormalities neurodegeneration and dysosteosclerosis (BANDDOS).

Provided herein as Embodiment 67 is a method of treating or preventing a disease or disorder associated with dysfunction of CSF1R in a subject in need thereof, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55. In some embodiments, the subject is selected for treatment based on a diagnosis that includes the presence of a mutation in a CSF1R gene affecting the function of CSF1R. In some embodiments, the mutation in the CSF1R gene is a mutation that causes a decrease in CSF1R activity or a cessation of CSF1R activity. In some embodiments, the disease or disorder is caused by a heterozygous CSF1R mutation. In some embodiments, the disease or disorder is caused by a homozygous CSF1R mutation. In some embodiments, the disease or disorder is caused by a splice mutation in the csflr gene. In some embodiments, the disease or disorder is caused by a missense mutation in the csflr gene. In some embodiments, the disease or disorder is caused by a mutation in the catalytic kinase domain of CSF1R. In some embodiments, the disease or disorder is caused by a mutation in an immunoglobulin domain of CSF1R. In some embodiments, the disease or disorder is caused by a mutation in the ectodomain of CSF1R. In some embodiments, the disease or disorder is a disease or disorder resulting from a change (e.g. increase, decrease or cessation) in the activity of CSF1R. In some embodiments, the disease or disorder is a disease or disorder resulting from a decrease or cessation in the activity of CSF1R. CSF1R related activities that are changed in the disease or disorder include, but are not limited to: decrease or loss of microglia function; increased microglia apoptosis; decrease in Src signaling; decrease in Syk signaling; decreased microglial proliferation; decreased microglial response to cellular debris; decreased phagocytosis; and decreased release of cytokines in response to stimuli. In some embodiments, the disease or disorder is caused by a loss-of-function mutation in CSF1R. In some embodiments, the loss-of-function mutation results in a complete cessation of CSF1R function. In some embodiments, the loss-of-function mutation results in a partial loss of CSF1R function, or a decrease in CSF1R activity.

Provided herein as Embodiment 68 is a method of treating or preventing adult-onset leukoencephalopathy with axonal spheroids and pigmented glia (ALSP), hereditary diffuse leukoencephalopathy with axonal spheroids (HDLS), pigmentary orthochromatic leukodystrophy (POLD), pediatric-onset leukoencephalopathy, congenital absence of microglia, or brain abnormalities neurodegeneration and dysosteosclerosis (BANDDOS) in a subject in need thereof, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55. In some embodiments, the method treats or prevents ALSP, which is an encompassing and superseding name for both HDLS and POLD. In some embodiments, the disease or disorder is a homozygous mutation in CSF1R. In some embodiments, the method treats or prevents pediatric-onset leukoencephalopathy. In some embodiments, the method treats or prevents congenital absence of microglia. In some embodiments, the method treats or prevents brain abnormalities neurodegeneration and dysosteosclerosis (BANDDOS).

Provided herein as Embodiment 69 is a method of treating or preventing Nasu-Hakola disease, Alzheimer's disease, frontotemporal dementia, multiple sclerosis, Guillain-Barre syndrome, amyotrophic lateral sclerosis (ALS), Parkinson's disease, traumatic brain injury, spinal cord injury, systemic lupus erythematosus, rheumatoid arthritis, prion disease, stroke, osteoporosis, osteopetrosis, osteosclerosis, skeletal dysplasia, dysosteoplasia, Pyle disease, cerebral autosomal dominant arteriopathy with subcortical infarcts and leukoencephalopathy, cerebral autosomal recessive arteriopathy with subcortical infarcts and leukoencephalopathy, cerebroretinal vasculopathy, or metachromatic leukodystrophy wherein any of the aforementioned diseases or disorders are present in a patient exhibiting CSF1R dysfunction, or having a mutation in a gene affecting the function of CSF1R, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55.

ABCD1

The ABCD1 gene provides instructions for producing the adrenoleukodystrophy protein (ALDP). ABCD1 (ALDP) maps to Xq28. ABCD1 is a member of the ATP-binding cassette (ABC) transporter superfamily. The superfamily contains membrane proteins that translocate a wide variety of substrates across extra- and intracellular membranes, including metabolic products, lipids and sterols, and drugs. ALDP is located in the membranes of cell structures called peroxisomes. Peroxisomes are small sacs within cells that process many types of molecules. ALDP brings a group of fats called very long-chain fatty acids (VLCFAs) into peroxisomes, where they are broken down. As ABCD1 is highly expressed in microglia, it is possible that microglial dysfunction and their close interaction with other cell types actively participates in neurodegenerative processes (Gong et al., Annals of Neurology. 2017; 82(5):813-827.). It has been shown that severe microglia loss and damage is an early feature in patients with cerebral form of x-linked ALD (cALD) carrying ABCD1 mutations (Bergner et al., Glia. 2019; 67: 1196-1209). It has also been shown that ABCD1-deficiency leads to an impaired plasticity of myeloid lineage cells that is reflected in incomplete establishment of anti-inflammatory responses, thus possibly contributing to the devastating rapidly progressive demyelination in cerebral adrenoleukodystrophy (Weinhor et al., BRAIN 2018: 141; 2329-2342). These findings emphasize microglia/monocytes/macrophages as crucial therapeutic targets for preventing or stopping myelin destruction in patients with X-linked adrenoleukodystrophy.

The present invention relates to the unexpected discovery that administration of a TREM2 agonist can rescue the loss of microglia in cells having mutations in the ABCD1 gene. It has been previously shown that TREM2 agonist antibody 4D9 increases ATP luminescence (a measure of cell number and activity) in a dose dependent manner when the levels of M-CSF in media are reduced to 5 ng/mL (Schlepckow et al, EMBO Mol Med., 2020) and that TREM2 agonist AL002c increases ATP luminescence when M-CSF is completely removed from the media (Wang et al, J. Exp. Med.; 2020, 217(9): e20200785). This finding suggests that TREM2 agonism can compensate for deficiency in ABCD1 function leading to sustained activation, proliferation, chemotaxis of microglia, maintenance of anti-inflammatory environment and reduced astrocytosis caused by a decrease in ABCD1 and accumulation of VLCFAs. The present invention relates to the unexpected discovery that activation of TREM2 can rescue the microglia in the presence of the ABCD1 mutation and an increase in VLCFA, and that this effect may be also observed in patients suffering from loss of microglia due to ABCD1 mutation. This discovery has not been previously taught or suggested in the available art.

To date, no prior study has shown that TREM2 agonism can rescue the loss of microglia in cells where mutations in the ABCD1 and a VLCFA increase is present. No prior study has taught or suggested that reversal of the loss of microglia due to an ABCD1 mutation through TREM2 agonism can be used to treat a disease or disorder caused by and/or associated with an ABCD1 mutation.

Provided herein as Embodiment 70 is a compound according to any one of embodiments 1-54, or a tautomer thereof, or a pharmaceutically acceptable salt of said compound or said tautomer, or the pharmaceutical composition according to Embodiment 55 for use in treating or preventing a condition associated with dysfunction of ATP-binding cassette transporter 1 (ABCD1).

Provided herein as Embodiment 71 is a compound according to any one of embodiments 1-54, or a tautomer thereof, or a pharmaceutically acceptable salt of said compound or said tautomer, or the pharmaceutical composition according to Embodiment 55 for use in treating or preventing X-linked adrenoleukodystrophy (x-ALD), Globoid cell leukodystrophy (also known as Krabbe disease), Metachromatic leukodystrophy (MLD), Cerebral autosomal dominant arteriopathy with subcortical infarcts and leukoencephalopathy (CADASIL), Vanishing white matter disease (VWM), Alexander disease, fragile X-associated tremor ataxia syndrome (FXTAS), adult-onset autosomal dominant leukodystrophy (ADLD), and X-linked Charcot-Marie-Tooth disease (CMTX).

Provided herein as Embodiment 72 is a use of the compound according to any one of embodiments 1-54, or a tautomer thereof, or a pharmaceutically acceptable salt of said compound or said tautomer, or the pharmaceutical composition according to Embodiment 55 in the preparation of a medicament for treating or preventing a condition associated with dysfunction of ABCD1.

Provided herein as Embodiment 73 is a use of the compound according to any one of embodiments 1-54, or a tautomer thereof, or a pharmaceutically acceptable salt of said compound or said tautomer, or the pharmaceutical composition according to Embodiment 55 in the preparation of a medicament for treating or preventing X-linked adrenoleukodystrophy (x-ALD), Globoid cell leukodystrophy (also known as Krabbe disease), Metachromatic leukodystrophy (MLD), Cerebral autosomal dominant arteriopathy with subcortical infarcts and leukoencephalopathy (CADASIL), Vanishing white matter disease (VWM), Alexander disease, fragile X-associated tremor ataxia syndrome (FXTAS), adult-onset autosomal dominant leukodystrophy (ADLD), and X-linked Charcot-Marie-Tooth disease (CMTX).

Provided herein as Embodiment 74 is a method of treating or preventing a disease or disorder associated with dysfunction of ABCD1 in a subject in need thereof, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55. In some embodiments, the patient is selected for treatment based on a diagnosis that includes the presence of a mutation in an ABCD1 gene affecting the function of ABCD1. In some embodiments, the mutation in the ABCD1 gene is a mutation that causes a decrease in ABCD1 activity or a cessation of ABCD1 activity. In some embodiments, the disease or disorder is caused by a heterozygous ABCD1 mutation. In some embodiments, the disease or disorder is caused by a homozygous ABCD1 mutation. In some embodiments, the disease or disorder is caused by a splice mutation in the ABCD1 gene. In some embodiments, the disease or disorder is caused by a missense mutation in the ABCD1 gene. In some embodiments, the disease or disorder is a disease or disorder resulting from a change (e.g. increase, decrease or cessation) in the activity of ABCD1. In some embodiments, the disease or disorder is a disease or disorder resulting from a decrease or cessation in the activity of ABCD1. ABCD1 related activities that are changed in the disease or disorder include, but are not limited to peroxisomal import of fatty acids and/or fatty acyl-CoAs and production of adrenoleukodystrophy protein (ALDP). In some embodiments, the disease or disorder is caused by a loss-of-function mutation in ABCD1. In some embodiments, the loss-of-function mutation results in a complete cessation of ABCD1 function. In some embodiments, the loss-of-function mutation results in a partial loss of ABCD1 function, or a decrease in ABCD1 activity. In some embodiments, the disease or disorder is caused by a homozygous mutation in ABCD1. In some embodiments, the disease or disorder is a neurodegenerative disorder. In some embodiments, the disease or disorder is a neurodegenerative disorder caused by and/or associated with an ABCD1 dysfunction. In some embodiments, the disease or disorder is an immunological disorder. In some embodiments, the disease or disorder is an immunological disorder caused by and/or associated with an ABCD1 dysfunction.

Provided herein as Embodiment 75 is a method of treating or preventing X-linked adrenoleukodystrophy (x-ALD), Globoid cell leukodystrophy (also known as Krabbe disease), Metachromatic leukodystrophy (MLD), Cerebral autosomal dominant arteriopathy with subcortical infarcts and leukoencephalopathy (CADASIL), Vanishing white matter disease (VWM), Alexander disease, fragile X-associated tremor ataxia syndrome (FXTAS), adult-onset autosomal dominant leukodystrophy (ADLD), and X-linked Charcot-Marie-Tooth disease (CMTX) in a subject in need thereof, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55. In some embodiments, any of the aforementioned diseases are present in a patient exhibiting ABCD1 dysfunction or having a mutation in a gene affecting the function of ABCD1. In some embodiments, the method treats or prevents X-linked adrenoleukodystrophy (x-ALD). In some embodiments, the x-ALD is a cerebral form of x-linked ALD (cALD). In some embodiments, the method treats or prevents Addison disease wherein the patient has been found to have a mutation in one or more ABCD1 genes affecting ABCD1 function. In some embodiments, the method treats or prevents Addison disease, wherein the patient has a loss-of-function mutation in ABCD1.

Provided herein as Embodiment 76 is a method of treating or preventing Nasu-Hakola disease, Alzheimer's disease, frontotemporal dementia, multiple sclerosis, Guillain-Barre syndrome, amyotrophic lateral sclerosis (ALS), or Parkinson's disease, wherein any of the aforementioned diseases or disorders are present in a patient exhibiting ABCD1 dysfunction, or having a mutation in a gene affecting the function of ABCD1, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55.

Autism Spectrum Disorders

It has been found that TREM2 deficient mice exhibit symptoms reminiscent of autism spectrum disorders (ASDs) (Filipello et al., Immunity, 2018, 48, 979-991). It has also been found that microglia depletion of the autophagy Aatg7 gene results in defective synaptic pruning and results in increased dendritic spine density, and abnormal social interaction and repetitive behaviors indicative of ASDs (Kim, et al., Molecular Psychiatry, 2017, 22, 1576-1584.). Further studies have shown that increased dendritic spin density detected in postmortem ASD brains, likely caused by defective synaptic pruning, results in circuit hypoconnectivity and behavioral defects and are a potential origin of a number of neurodevelopmental diseases (Tang, et al., Neuron, 2014, 83, 1131-1143). Without intending to be limited to any particular theory, these findings suggest that TREM2 activation can reverse microglia depletion, and therefore correct the defective synaptic pruning that is central to neurodevelopmental diseases such as ASDs. The present invention relates to the unexpected discovery that activation of TREM2, using a compound of the present invention, can rescue microglia in subjects suffering from an ASD. This discovery has not been previously taught or suggested in the available art.

Provided herein as Embodiment 77 is a compound according to any one of embodiments 1-54, or a tautomer thereof, or a pharmaceutically acceptable salt of said compound or said tautomer, or the pharmaceutical composition according to Embodiment 55 for use in treating autism or autism spectrum disorders.

Provided herein as Embodiment 78 is a use of the compound according to any one of embodiments 1-54, or a tautomer thereof, or a pharmaceutically acceptable salt of said compound or said tautomer, or the pharmaceutical composition according to Embodiment 55 in the preparation of a medicament for treating autism or autism spectrum disorders.

Provided herein as Embodiment 79 is a method of treating autism or autism spectrum disorders in a subject in need thereof, the method comprising administering to the subject a therapeutically effective amount of the compound according to any one of embodiments 1-54, or a tautomer thereof, or a pharmaceutically acceptable salt of said compound or said tautomer, or the pharmaceutical composition according to Embodiment 55. In some embodiments, the method treats autism. In some embodiments, the method treats Asperger syndrome.

In some embodiments, the disclosure provides a method of increasing the activity of TREM2, the method comprising contacting a compound of the present disclosure, or a pharmaceutically acceptable salt thereof with the TREM2. In some embodiments, the contacting takes place in vitro. In some embodiments, the contacting takes place in vivo. In some embodiments, the TREM2 is human TREM2.

Combination Therapies

Depending upon the particular condition, or disease, to be treated, additional therapeutic agents, which are normally administered to treat that condition, may be administered in combination with compounds and compositions of this disclosure. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this disclosure may also be combined with include, without limitation: treatments for Parkinson's disease, rheumatoid arthritis, Alzheimer's disease, Nasu-Hakola disease, frontotemporal dementia, multiple sclerosis, prion disease, or stroke.

As used herein, the term "combination," "combined," and related terms refers to the simultaneous or sequential administration of therapeutic agents in accordance with this disclosure. For example, a combination of the present disclosure may be administered with another therapeutic agent simultaneously or sequentially in separate unit dosage forms or together in a single unit dosage form.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the present disclosure, as part of a multiple dosage regimen. Alternatively, one or more other therapeutic agents may be part of a single dosage form, mixed together with a compound of this disclosure in a single composition. If administered as a multiple dosage regime, one or more other therapeutic agent and a compound or composition of the present disclosure may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the present disclosure are administered as a multiple dosage regimen within greater than 24 hours a parts.

In one embodiment, the present disclosure provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

Definitions

The following definitions are provided to assist in understanding the scope of this disclosure.

Unless otherwise indicated, all numbers expressing quantities of ingredients, reaction conditions, and so forth used in the specification or claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

As used herein, the following definitions shall apply unless otherwise indicated. For purposes of this disclosure, the chemical elements are identified in accordance with the Periodic Table of the Elements, CAS version, Handbook of Chemistry and Physics, 101$^{st}$ Ed. Additionally, general principles of organic chemistry are described in "Organic Chemistry", Thomas Sorrell, University Science Books, Sausalito: 2005, and "March's Advanced Organic Chemistry: Reactions Mechanisms and Structure", 8$^{th}$ Ed., Ed.: Smith, M. B., John Wiley & Sons, New York: 2019, the entire contents of which are hereby incorporated by reference.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, and atropoisomers. Accordingly, the scope of the instant disclosure is to be understood to encompass all possible stereoisomers of the illustrated compounds, including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers, or mixture of any of the foregoing) of any chemical structures disclosed herein (in whole or in part), unless the stereochemistry is specifically identified.

If the stereochemistry of a structure or a portion of a structure is not indicated with, for example, bold or dashed lines, the structure or portion of the structure is to be interpreted as encompassing all stereoisomers of it. If the stereochemistry of a structure or a portion of a structure is indicated with, for example, bold or dashed lines, the structure or portion of the structure is to be interpreted as encompassing only the stereoisomer indicated. For example, 5-(4-chloro-2-fluorophenyl)-7-((2S)-2-(1-(1-fluoroethyl)-1H-pyrazol-4-yl)-4-morpholinyl)-2,3-dimethylpyrido[4,3-d]pyrimidin-4(3H)-one (Example 129) is meant to encompass 5-(4-chloro-2-fluorophenyl)-7-((2S)-2-(1-((S)-1-fluoroethyl)-1H-pyrazol-4-yl)-4-morpholinyl)-2,3-dimethylpyrido[4,3-d]pyrimidin-4(3H)-one and 5-(4-chloro-2-fluorophenyl)-7-((2S)-2-(1-((R)-1-fluoroethyl)-1H-pyrazol-4-yl)-4-morpholinyl)-2,3-dimethylpyrido[4,3-d]pyrimidin-4(3H)-one. A bond drawn with a wavy line indicates that both stereoisomers are encompassed. This is not to be confused with a wavy line drawn perpendicular to a bond which indicates the point of attachment of a group to the rest of the molecule.

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of the other enantiomer and diastereomers of the compound. A typical stereoisomerically pure compound comprises greater than about 80% by weight of one stereoisomer of the compound and equal or less than about 20% by weight of other stereoisomers of the compound, greater than about 90% by weight of one stereoisomer of the compound and equal or less than about 10% by weight of the other stereoisomers of the compound, greater than about 95% by weight of one stereoisomer of the compound and equal or less than about 5% by weight of the other stereoisomers of the compound, or greater than about 97% by weight of one stereoisomer of the compound and equal or less than about 3% by weight of the other stereoisomers of the compound.

This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., Tetrahedron 33:2725; Eliel, Stereochemistry of Carbon Compounds (McGraw-Hill, N Y, 1962); and Wilen, Tables of Resolving Agents and Optical Resolutions, page 268 (Eliel, Ed., Univ. of Notre Dame Press, Notre Dame, I N, 1972).

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example, the following is illustrative of tautomers of the compounds of Formula I, wherein $R^1$ is H:

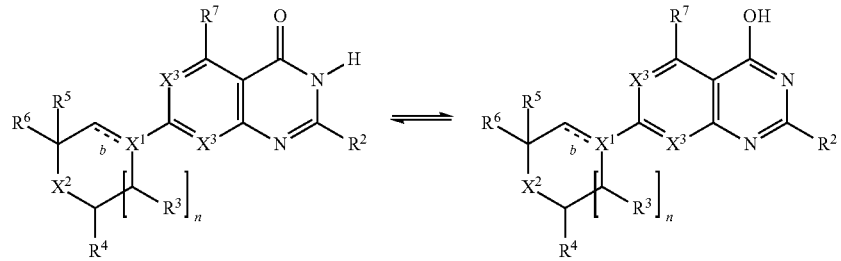

Accordingly, the scope of the instant disclosure is to be understood to encompass all tautomeric forms of the compounds disclosed herein.

Isotopically-Labelled Compounds

Further, the scope of the present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of Formula I, for example, those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with isotopes such as deuterium ($^2H$ or D) may afford certain therapeutic advantages resulting from greater metabolic stability, for example, increased in vivo half-life or reduced dosage requirements, and hence may be advantageous in some circumstances. Substitution with positron emitting isotopes, such as $^{11}C$, $^{18}F$, $^{15}O$ and $^{13}N$, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Schemes and Examples using an appropriate isotopically-labelled reagent in place of the non-labelled reagent previously employed.

Solvates

As discussed above, the compounds disclosed herein and the stereoisomers, tautomers, and isotopically-labelled forms thereof or a pharmaceutically acceptable salt of any of the foregoing may exist in solvated or unsolvated forms.

The term "solvate" as used herein refers to a molecular complex comprising a compound or a pharmaceutically acceptable salt thereof as described herein and a stoichiometric or non-stoichiometric amount of one or more pharmaceutically acceptable solvent molecules. If the solvent is water, the solvate is referred to as a "hydrate."

Accordingly, the scope of the instant disclosure is to be understood to encompass all solvents of the compounds disclosed herein and the stereoisomers, tautomers and isotopically-labelled forms thereof or a pharmaceutically acceptable salt of any of the foregoing.

Miscellaneous Definitions

This section will define additional terms used to describe the scope of the compounds, compositions and uses disclosed herein.

The terms "$C_{1-3}$alkyl," "$C_{1-5}$alkyl," and "$C_{1-6}$alkyl" as used herein refer to a straight or branched chain hydrocarbon containing from 1 to 3, 1 to 5, and 1 to 6 carbon atoms, respectively. Representative examples of $C_{1-3}$alkyl, $C_{1-5}$alky, or $C_{1-6}$alkyl include, but are not limited to, methyl, ethyl, n-propyl, iso-propyl, n-butyl, sec-butyl, iso-butyl, tert-butyl, pentyl and hexyl.

The term "$C_{2-4}$alkenyl" as used herein refers to a saturated hydrocarbon containing 2 to 4 carbon atoms having at least one carbon-carbon double bond. Alkenyl groups include both straight and branched moieties. Representative examples of $C_{2-4}$alkenyl include, but are not limited to, 1-propenyl, 2-propenyl, 2-methyl-2-propenyl, and butenyl.

The term "$C_{3-6}$cycloalkyl" as used herein refers to a saturated carbocyclic molecule wherein the cyclic framework has 3 to 6 carbon atoms. Representative examples of $C_{3-5}$cycloalkyl include, but are not limited to, cyclopropyl, cyclobutyl, cyclopentyl, and cyclohexyl.

The terms "di$C_{1-3}$alkylamino" as used herein refer to —NR*R**, wherein R* and R** independently represent a $C_{1-3}$alkyl as defined herein. Representative examples of di$C_{1-3}$alkylamino include, but are not limited to, —N(CH$_3$)$_2$, —N(CH$_2$CH$_3$)$_2$, —N(CH$_3$)(CH$_2$CH$_3$), —N(CH$_2$CH$_2$CH$_3$)$_2$, and —N(CH(CH$_3$)$_2$)$_2$.

The term "$C_{1-3}$alkoxy" and "$C_{1-6}$alkoxy" as used herein refer to —OR$^\#$, wherein R$^\#$ represents a $C_{1-3}$alkyl and $C_{1-6}$alkyl group, respectively, as defined herein. Representative examples of $C_{1-3}$alkoxy or $C_{1-6}$alkoxy include, but are not limited to, methoxy, ethoxy, propoxy, iso-propoxy, and butoxy.

The term "halogen" as used herein refers to —F, —Cl, —Br, or —I.

The term "halo" as used herein as a prefix to another term for a chemical group refers to a modification of the chemical group, wherein one or more hydrogen atoms are substituted with a halogen as defined herein. The halogen is independently selected at each occurrence. For example, the term "$C_{1-6}$haloalkyl" refers to a $C_{1-6}$alkyl as defined herein, wherein one or more hydrogen atoms are substituted with a halogen. Representative examples of $C_{1-6}$haloalkyl include, but are not limited to, —CH$_2$F, —CHF$_2$, —CF$_3$, —CHFCl, —CH$_2$CF$_3$, —CFHCF$_3$, —CF$_2$CF$_3$, —CH(CF$_3$)$_2$, —CF(CHF$_2$)$_2$, and —CH(CH$_2$F)(CF$_3$). Further, the term "$C_{1-6}$haloalkoxy" for example refers to a $C_{1-6}$alkoxy as defined herein, wherein one or more hydrogen atoms are substituted with a halogen. Representative examples of $C_{1-6}$haloalkoxy include, but are not limited to, —OCH$_2$F, —OCHF$_2$, —OCF$_3$, —OCHFCl, —OCH$_2$CF$_3$, —OCFHCF$_3$, —OCF$_2$CF$_3$, —OCH(CF$_3$)$_2$, —OCF(CHF$_2$)$_2$, and —OCH(CH$_2$F)(CF$_3$).

The term "5-membered heteroaryl" or "6-membered heteroaryl" as used herein refers to a 5 or 6-membered carbon ring with two or three double bonds containing one ring heteroatom selected from N, S, and O and optionally one or two further ring N atoms instead of the one or more ring carbon atom(s). Representative examples of a 5-membered heteroaryl include, but are not limited to, furyl, imidazolyl, pyrazolyl, isoxazolyl, isothiazolyl, oxadiazolyl, and oxazolyl. Representative examples of a 6-membered heteroaryl include, but are not limited to, pyridyl, pyrimidyl, pyrazyl, and pyridazyl.

The term "$C_{3-6}$heterocycloalkyl" as used herein refers to a saturated carbocyclic molecule wherein the cyclic framework has 3 to 6 carbons and wherein one carbon atom is substituted with a heteroatom selected from N, O, and S. If the $C_{3-6}$heterocycloalkyl group is a $C_6$heterocycloalkyl, one or two carbon atoms are substituted with a heteroatom independently selected from N, O, and S. Representative examples of $C_{3-6}$heterocycloalkyl include, but are not limited to, aziridinyl, azetidinyl, oxetanyl, pyrrolidinyl, piperazinyl, morpholinyl, and thiomorpholinyl.

The term "$C_{5-8}$spiroalkyl" as used herein refers a bicyclic ring system, wherein the two rings are connected through a single common carbon atom. Representative examples of $C_{5-8}$spiroalkyl include, but are not limited to, spiro[2.2]pentanyl, spiro[3.2]hexanyl, spiro[3.3]heptanyl, spiro[3.4]octanyl, and spiro[2.5]octanyl.

The term "$C_{5-8}$tricycloalkyl" as used herein refers a tricyclic ring system, wherein all three cycloalkyl rings share the same two ring atoms. Representative examples of $C_{5-8}$tricycloalkyl include, but are not limited to, tricyclo[1.1.1.0$^{1,3}$]pentanyl,

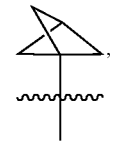 [SMILES: *C12CC(C1)C2]

tricyclo[2.1.1.0$^{1,4}$]hexanyl, tricyclo[3.1.1.0$^{1,5}$]hexanyl, and tricyclo[3.2.1.0$^{1,5}$]octanyl.

The term "aryl" used alone or as part of a larger moiety as in "aralkyl," "aralkoxy," or "aryloxyalkyl," refers to monocyclic or bicyclic ring systems having a total of 4 to 14 ring members, wherein at least one ring in the system is aromatic and wherein each ring in the system contains three to seven ring members. The term "aryl" may be used interchangeably with the term "aryl ring". In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" in the context of "heteroaryl" particularly includes, but is not limited to, nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. A heteroaryl ring may include one or more oxo (=O) or thioxo (=S) substituent. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As described herein, compounds of the present disclosure may contain "substituted" moieties. In general, the term "substituted" means that one or more hydrogens of the designated moiety are replaced with a suitable substituent. Unless otherwise indicated, an "optionally substituted" group may have a suitable substituent at one or more substitutable position of the group, and when more than one position in any given structure is substituted with more than one substituent selected from a specified group, the substituent may be either the same or different at every position. Combinations of substituents envisioned by the present disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1):1-19 (1977). See also Stahl et al., Pharmaceutical Salts: Properties, Selection, and Use, 2$^{nd}$ Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "therapeutically effective amount" as used herein refers to that amount of a compound disclosed herein that will elicit the biological or medical response of a tissue, a system, or subject that is being sought by a researcher, veterinarian, medical doctor or other clinician.

General Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following scheme. Any variables used in the following scheme are the variables as defined for Formula I, unless otherwise noted. All starting materials are either commercially available, for example, from Merck Sigma-Aldrich Inc. and Enamine Ltd. or known in the art and may be synthesized by employing known procedures using ordinary skill. Starting material may also be synthesized via the procedures disclosed herein. Suitable reaction conditions, such as, solvent, reaction temperature, and reagents, for the Schemes discussed in this section, may be found in the examples provided herein.

Scheme 1

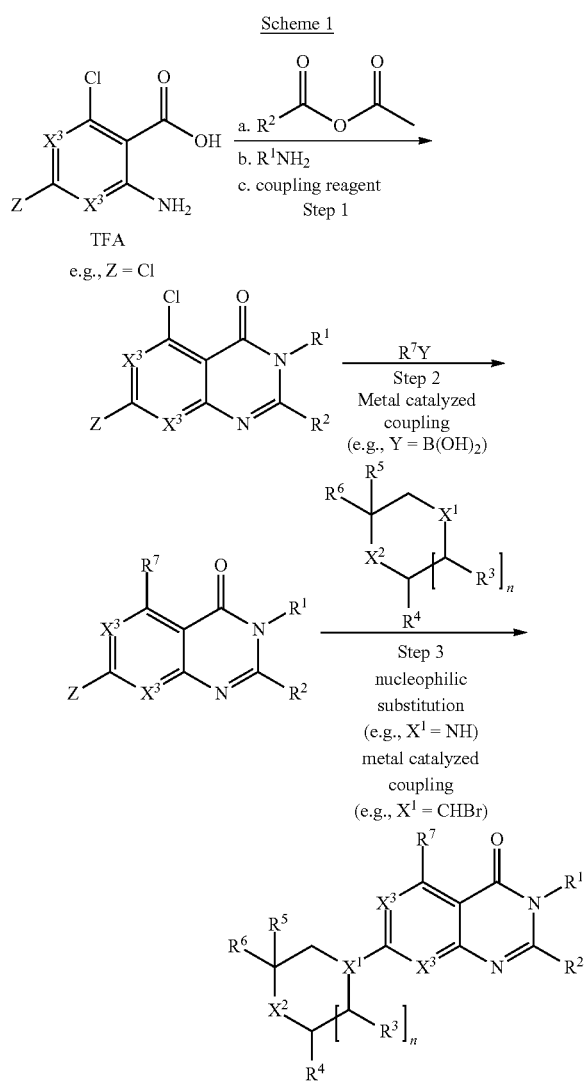

As can be appreciated by the skilled artisan, the above synthetic scheme and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Purification methods for the compounds described herein are known in the art and include, for example, crystallization, chromatography (for example, liquid and gas phase), extraction, distillation, trituration, and reverse phase HPLC.

The disclosure further encompasses "intermediate" compounds, including structures produced from the synthetic procedures described, whether isolated or generated in-situ and not isolated, prior to obtaining the finally desired compound. These intermediates are included in the scope of this disclosure. Exemplary embodiments of such intermediate compounds are set forth in the Examples below.

EXAMPLES

This section provides specific examples of compounds of Formula I and methods of making the same.

| List of Abbreviations | |
|---|---|
| AcOH | acetic acid |
| aq or aq. | aqueous |
| BOC or Boc | tert-butyloxycarbonyl |
| DCM | dichloromethane |
| DIPEA or Hunig's Base | N,N-diisopropylethylamine |
| DMAP | 4-dimethylaminopyridine |
| DME | 1,2-dimethoxyethane |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | equivalent |
| ESI or ES | electrospray ionization |
| Et | ethyl |
| $Et_2O$ | diethyl ether |
| EtOAc | ethyl acetate |
| g | gram(s) |
| h or hr | hour(s) |
| HPLC | high pressure liquid chromatography |
| iPr | isopropyl |
| $iPr_2NEt$ or DIPEA | N-ethyl diisopropylamine (Hunig's base) |
| KHMDS | potassium hexamethyldisilazide |
| KOAc | potassium acetate |
| LC MS, LCMS, LC-MS or LC/MS | liquid chromatography mass spectroscopy |
| LHMDS or LiHMDS | lithium hexamethyldisilazide |
| m/z | mass divided by charge |
| Me | methyl |
| $CH_3CN$ | acetonitrile |
| MeOH | methanol |
| mg | milligrams |
| min | minutes |
| mL | milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| $Pd_2(dba)_3$ | tris(dibenzylideneacetone)dipalladium(0) |
| $Pd(dppf)Cl_2$•DCM, $Pd(dppf)Cl_2$ | [1,1'-bis(diphenylphosphino)ferrocene] dichloropalladium(II), complex with dichloromethane |
| $Pd(PPh_3)_4$ | tetrakis(triphenylphosphine)palladium(O) |
| Ph | phenyl |
| rbf | round-bottom flask |
| RP-HPLC | reverse phase high pressure liquid chromatography |
| RT or rt or r.t. | room temperature |
| sat. | saturated |
| SFC | supercritical fluid chromatography |
| TBAF | tetra-n-butylammonium fluoride |
| TEA or Et3N | triethylamine |
| TFA | trifluoroacetic acid |
| THF | tetrahydrofuran |
| UV | ultraviolet |

General Analytical and Purification Methods

Provided in this section are descriptions of the general analytical and purification methods used to prepare the specific compounds provided herein.

Chromatography:

Unless otherwise indicated, crude product-containing residues were purified by passing the crude material or concentrate through either a Biotage brand silica gel column pre-packed with flash silica ($SiO_2$) or reverse phase flash silica (C18) and eluting the product off the column with a solvent gradient as indicated. For example, a description of silica gel (0-40% EtOAc/hexane) means the product was obtained by elution from the column packed with silica using a solvent gradient of 0% to 40% EtOAc in hexanes.

Preparative HPLC Method:

Where so indicated, the compounds described herein were purified via reverse phase HPLC using Waters Fractionlynx semi-preparative HPLC-MS system utilizing one of the following two HPLC columns: (a) Phenominex Gemini column (5 micron, C18, 150×30 mm) or (b) Waters X-select CSH column (5 micron, C18, 100×30 mm).

A typical run through the instrument included: eluting at 45 mL/min with a linear gradient of 10% (v/v) to 100% MeCN (0.1% v/v formic acid) in water (0.1% formic acid) over 10 minutes; conditions can be varied to achieve optimal separations.

Proton NMR Spectra:

Unless otherwise indicated, all $^1$H NMR spectra were collected on a Bruker NMR Instrument at 300, 400 or 500 Mhz. Where so characterized, all observed protons are reported as parts-per-million (ppm) downfield from tetramethylsilane (TMS) using the internal solvent peak as reference.

Mass Spectra (MS)

Unless otherwise indicated, all mass spectral data for starting materials, intermediates and/or exemplary compounds are reported as mass/charge (m/z), having an [M+H]$^+$ molecular ion. The molecular ion reported was obtained by electrospray detection method (commonly referred to as an ESI MS) utilizing a Waters Acquity UPLC/MS system. Compounds having an isotopic atom, such as bromine and the like, are generally reported according to the detected isotopic pattern, as appreciated by those skilled in the art.

Compound Names

The compounds disclosed and described herein have been named using the IUPAC naming function provided with Biovia Pipeline Pilot.

SPECIFIC EXAMPLES

Provided in this section are the procedures to synthesize specific examples of the compounds provided herein. All starting materials are either commercially available from Merck Sigma-Aldrich Inc., unless otherwise noted, or known in the art and may be synthesized by employing known procedures using ordinary skill.

SYNTHESIS OF EXAMPLES

Method 1

Example 1: 5-(4-chloro-2-fluorophenyl)-2,3-dimethyl-7-((2S)-2-(1-methyl-1H-pyrazol-4-yl)-4-morpholinyl)pyrido[4,3-d]pyrimidin-4(3H)-one

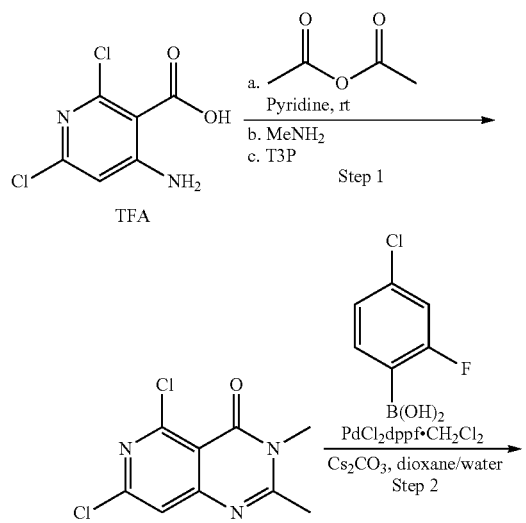

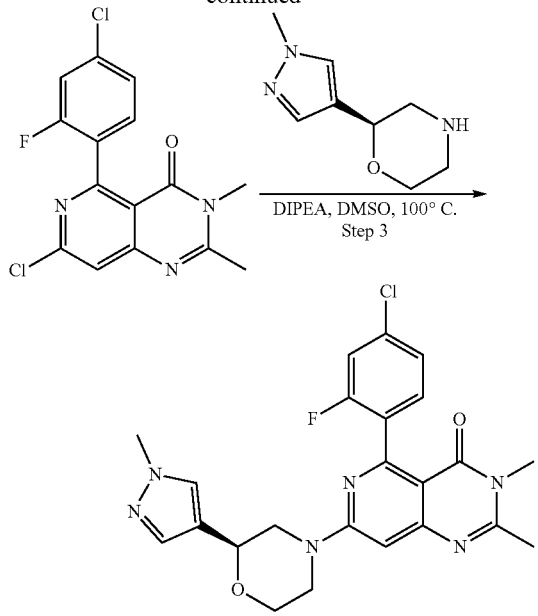

Step 1: 5,7-dichloro-2,3-dimethylpyrido[4,3-d]pyrimidin-4(3H)-one. To a 10-L four necked round-bottomed flask was added 4-amino-2,6-dichloronicotinic acid 2,2,2-trifluoroacetic acid salt (110 g, 343 mmol) and acetic anhydride (129 mL, 1371 mmol) in pyridine (1100 mL). The reaction was stirred at room temperature for 1 hour. The reaction mixture was cooled to 0° C., and methaneamine (2 M in THF, 1028 mL, 2056 mmol) was added dropwise. The cold bath was removed, and the reaction was stirred for 30 min. The mixture was cooled to 0° C. and 2,4,6-tripropyl-1,3,5,2,4,6-trioxatriphosphinane 2,4,6-trioxide (50% in EtOAc solution) (550 mL, 685 mmol) was added. The cold bath was removed, and the reaction was stirred for 1 hour and the mixture was quenched with water (2.5 L) and extracted with EtOAc (2 L). The organic layer was washed with water (2 L) and brine solution (2.5 L). The organic phase was dried over Na$_2$SO$_4$, filtered, and concentrated under reduced pressure. The crude material was purified via silica gel chromatography (0-40% EtOAc in hexane) to provide a yellow solid which was dissolved in DCM (500 mL) and precipitated with petroleum ether. The obtained solid was filtered and dried to provide 5,7-dichloro-2,3-dimethylpyrido[4,3-d]pyrimidin-4(3H)-one (60 g, 246 mmol, 71.7% yield) as yellow solid. $^1$H NMR (400 MHz, DMSO-d6) δ ppm 7.63 (s, 1H), 3.49 (s, 3H), 2.60 (s, 3H). m/z (ESI, +ive ion): 244.0 (M+H).

Step 2: 7-chloro-5-(4-chloro-2-fluorophenyl)-2,3-dimethylpyrido[4,3-d]pyrimidin-4(3H)-one. To a 10-L four necked round-bottomed flask was added 5,7-dichloro-2,3-dimethylpyrido-[4,3-d]pyrimidin-4(3H)-one (100 g, 410 mmol) and (4-chloro-2-fluorophenyl)boronic acid (71.4 g, 410 mmol), 1,4-dioxane (3000 mL), and water (1000 mL). To this mixture was added cesium carbonate (400 g, 1229 mmol) and the reaction mass was purged with nitrogen gas for 10 min. PdCl$_2$(dppf)-CH$_2$Cl adduct (16.73 g, 20.49 mmol) was added, and the reaction mass was stirred at room temperature for 0.5 h. The reaction mixture was quenched with water (4 L) and extracted with DCM (2×3500 mL). The combined organics were washed with brine solution (4000 mL), dried over Na$_2$SO$_4$, filtered, and concentrated under reduced pressure. The crude material was absorbed onto a plug of 100-200 mesh silica gel and purified by chromatography through a 100-200 mesh silica gel column, eluting with a gradient of 0% to 40% EtOAc in hexane. The obtained solid was triturated in EtOAc (150 mL), filtered, and washed with dry n-Hexane, to obtain 7-chloro-5-(4-chloro-2-fluorophenyl)-2,3-dimethylpyrido[4,3-d]pyrimidin-4(3H)-one (62.5 g, 185 mmol, 45.1% yield) as a white solid. $^1$H NMR (400 MHz, DMSO-d6) δ ppm 7.48-7.71 (m, 1H), 7.45-7.51 (m, 2H), 7.37-7.41 (m, 1H), 3.42 (s, 3H), 2.62 (s, 3H). m/z (ESI, +ive ion): 338.0 (M+H).

Step 3: (S)-5-(4-chloro-2-fluoropheny)-2,3-dimethyl-7-(2-(1-methyl-1H-pyrazol-4-yl)morpholino)pyrido[4,3-d]pyrimidin-4(3H)-one. A 250 mL flask was charged with (S)-2-(1-methyl-1H-pyrazol-4-yl)morpholine (Intermediate 3, 5.93 g, 35.5 mmol), 7-chloro-5-(4-chloro-2-fluorophenyl)-2,3-dimethylpyrido[4,3-d]pyrimidin-4(3H)-one (10 g, 29.6 mmol), DMSO (74 mL) and 1,1'-dimethyltriethylamine (11.47 g, 89 mmol). The reaction was heated to 100° C. for 16 h. The reaction was quenched with water and filtered to provide the crude material. The crude material was purified using silica gel column, eluting with 0 to 100% EtOH/EtOAc (1:3) in heptane. The collected fractions were concentrated and triturated with hot isopropanol to yield (S)-5-(4-chloro-2-fluoropheny)-2,3-dimethyl-7-(2-(1-methyl-1H-pyrazol-4-yl)morpholino)pyrido[4,3-d]pyrimidin-4(3H)-one (9.91 g, 71.50 yield) as a white solid. Absolute stereochemistry assigned by x-ray crystallography. H NMR (500 MHz, DMSO-d6) δ ppm 7.70-7.73 (m, 1H), 7.44-7.46 (m, 1H), 7.36-7.41 (m, 2H), 7.30-7.34 (m, 1H), 6.81-6.83 (m, 1H), 4.50-4.54 (m, 1H), 4.36-4.40 (m, 1H), 4.19-4.24 (m, 1H), 3.96-4.02 (m, 1H), 3.78-3.82 (m, 3H), 3.63-3.70 (m, 1H), 3.34-3.37 (m, 3H), 3.04-3.11 (m, 1H), 2.97-3.02 (m, 1H), 2.52-2.55 (m, 3H). m/z (ESI, +ive ion): 469.0 (M+H)$^+$.

TABLE 1

Compounds 2 to 122 were prepared following the procedure described in Method 1, steps 1-3, as follows:

| Ex. # | Structure | Name | Reagents/Conditions |
|---|---|---|---|
| 2 | 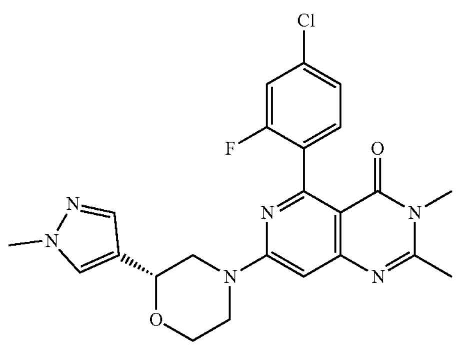 | 5-(4-chloro-2-fluorophenyl)-2,3-dimethyl-7-((2R)-2-(1-methyl-1H-pyrazol-4-yl)-4-morpholinyl)pyrido[4,3-d]pyrimidin-4(3H)-one | Step 3: (R)-2-(1-methyl-1H-pyrazol-4-yl)morpholine (Intermediate 4) |
| 3 | 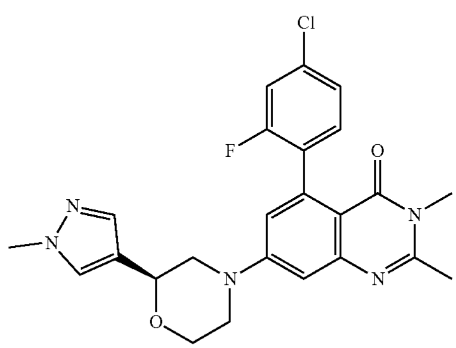 | 5-(4-chloro-2-fluorophenyl)-2,3-dimethyl-7-((2S)-2-(1-methyl-1H-pyrazol-4-yl)-4-morpholinyl)-4(3H)-quinazolinone | Step 1: Starting material 2-amino-4,6-dichlorobenzoic acid<br>Step 3: (S)-2-(1-methyl-1H-pyrazol-4-yl)morpholine (Intermediate 3), (RuPhosG3) (2-dicyclohexylphosphino-2',6'-diisopropoxy-1,1'-biphenyl)[2-(2'-amino-1,1'-biphenyl)]palladium(ii) methanesulfonate, 2-dicyclohexylphosphino-2,6-di-i-propoxy-1,1-biphenyl, Cs$_2$CO$_3$, Dioxane, 80° C. |
| 4 | 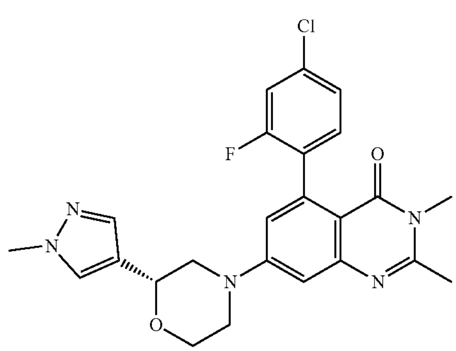 | 5-(4-chloro-2-fluorophenyl)-2,3-dimethyl-7-((2R)-2-(1-methyl-1H-pyrazol-4-yl)-4-morpholinyl)-4(3H)-quinazolinone | Step 1: 2-amino-4,6-dichlorobenzoic acid<br>Step 3: (R)-2-(1-methyl-1H-pyrazol-4-yl)morpholine (Intermediate 4), (RuPhosG3) (2-dicyclohexylphosphino-2',6'-diisopropoxy-1,1'-biphenyl)[2-(2'-amino-1,1'-biphenyl)]palladium(ii) methanesulfonate, 2-dicyclohexylphosphino-2,6-di-i-propoxy-1,1-biphenyl, Cs$_2$CO$_3$, Dioxane, 80° C. |

TABLE 1-continued

Compounds 2 to 122 were prepared following the procedure described in Method 1, steps 1-3, as follows:

| Ex. # | Structure | Name | Reagents/Conditions |
|---|---|---|---|
| 5 | 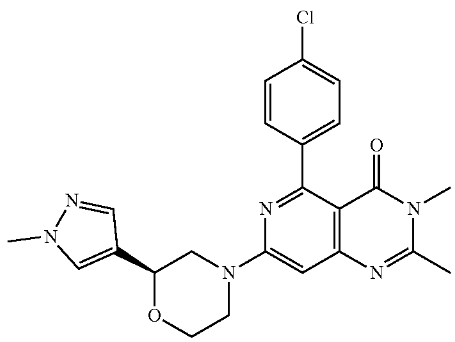 | 5-(4-chlorophenyl)-2,3-dimethyl-7-((2S)-2-(1-methyl-1H-pyrazol-4-yl)-4-morpholinyl)pyrido[4,3-d]pyrimidin-4(3H)-one | Step 2: 4-Chlorophenylboronic acid |
| 6 | 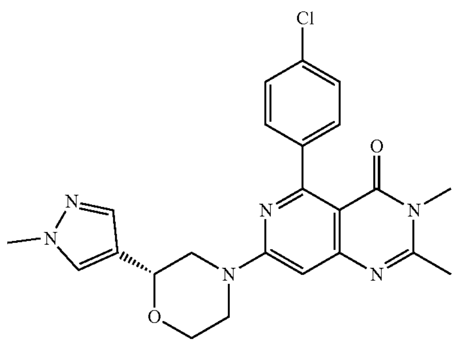 | 5-(4-chlorophenyl)-2,3-dimethyl-7-((2R)-2-(1-methyl-1H-pyrazol-4-yl)-4-morpholinyl)pyrido[4,3-d]pyrimidin-4(3H)-one | Step 2: 4-Chlorophenyl-boronic acid<br>Step 3: (R)-2-(1-methyl-1H-pyrazol-4-yl)morpholine (Intermediate 4) |
| 7 | 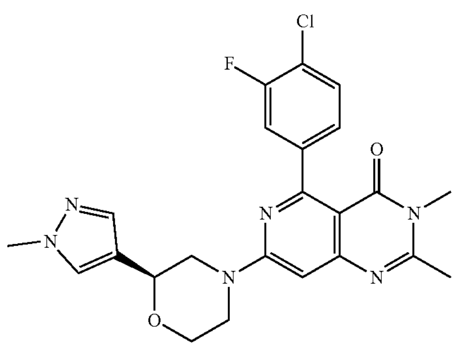 | 5-(4-chloro-3-fluorophenyl)-2,3-dimethyl-7-((2S)-2-(1-methyl-1H-pyrazol-4-yl)-4-morpholinyl)pyrido[4,3-d]pyrimidin-4(3H)-one | Step 2: 3-Fluoro-4-Chlorophenylboronic acid |
| 8 | 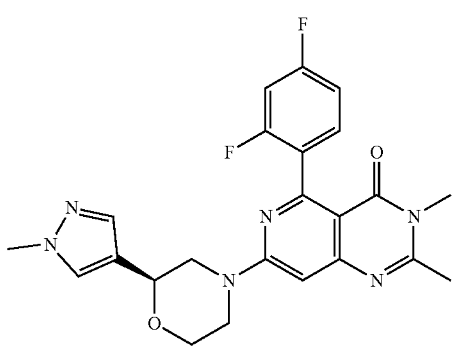 | 5-(2,4-difluorophenyl)-2,3-dimethyl-7-((2S)-2-(1-methyl-1H-pyrazol-4-yl)-4-morpholinyl)pyrido[4,3-d]pyrimidin-4(3H)-one | Step 2: 2,4 Difluorophenyl-boronic acid |

TABLE 1-continued

Compounds 2 to 122 were prepared following the procedure described in Method 1, steps 1-3, as follows:

| Ex. # | Structure | Name | Reagents/Conditions |
|---|---|---|---|
| 9 | 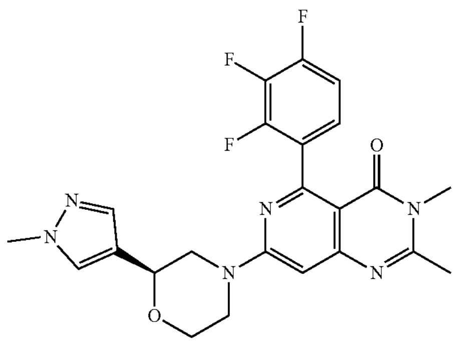 | 2,3-dimethyl-7-((2S)-2-(1-methyl-1H-pyrazol-4-yl)-4-morpholinyl)-5-(2,3,4-trifluorophenyl)pyrido[4,3-d]pyrimidin-4(3H)-one | Step 2: 2,3,4-trifluorophenyl-boronic acid |
| 10 | 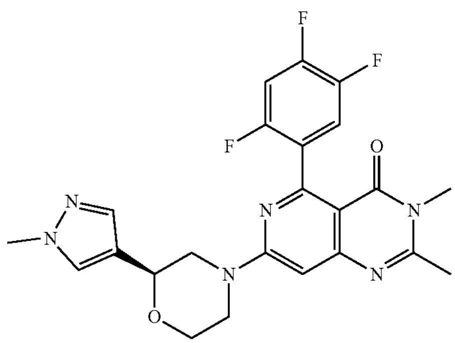 | 2,3-dimethyl-7-((2S)-2-(1-methyl-1H-pyrazol-4-yl)-4-morpholinyl)-5-(2,4,5-trifluorophenyl)pyrido[4,3-d]pyrimidin-4(3H)-one | Step 2: 2,4,5-trifluorophenyl-boronic acid |
| 11 | 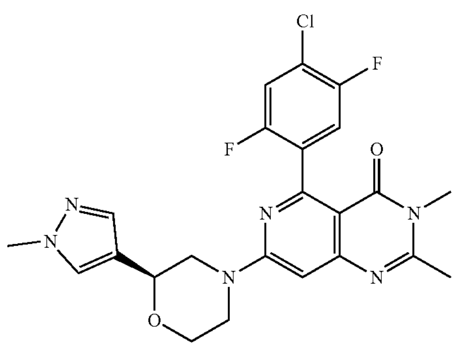 | 5-(4-chloro-2,5-difluorophenyl)-2,3-dimethyl-7-((2S)-2-(1-methyl-1H-pyrazol-4-yl)-4-morpholinyl)pyrido[4,3-d]pyrimidin-4(3H)-one | Step 2: 4-chloro-2,5-difluorophenylboronic acid |
| 12 | 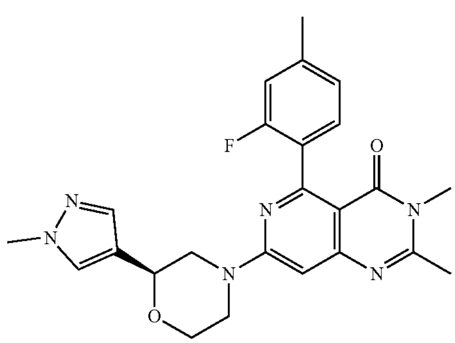 | 5-(2-fluoro-4-methylphenyl)-2,3-dimethyl-7-((2S)-2-(1-methyl-1H-pyrazol-4-yl)-4-morpholinyl)pyrido[4,3-d]pyrimidin-4(3H)-one | Step 2: (2-fluoro-4-methylphenylboronic acid |

TABLE 1-continued

Compounds 2 to 122 were prepared following the procedure described in Method 1, steps 1-3, as follows:

| Ex. # | Structure | Name | Reagents/Conditions |
|---|---|---|---|
| 13 | 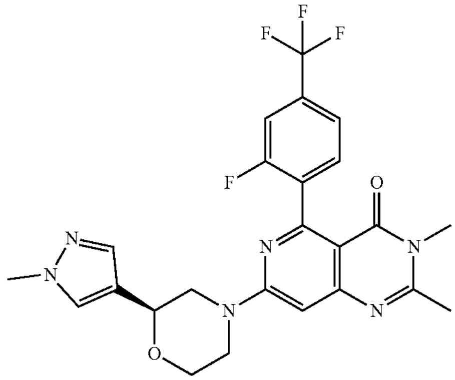 | 5-(2-fluoro-4-(trifluoromethyl)phenyl)-2,3-dimethyl-7-((2S)-2-(1-methyl-1H-pyrazol-4-yl)-4-morpholinyl)pyrido[4,3-d]pyrimidin-4(3H)-one | Step 2: 2-fluoro-4-(trifluoromethyl)phenyl-boronic acid |
| 14 | 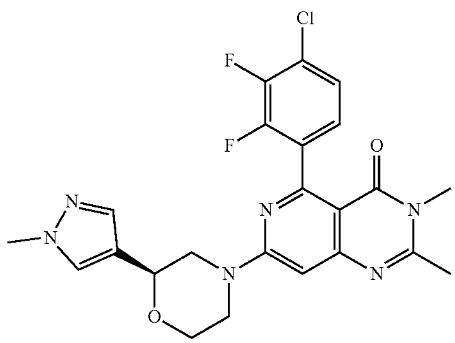 | 5-(4-chloro-2,3-difluorophenyl)-2,3-dimethyl-7-((2S)-2-(1-methyl-1H-pyrazol-4-yl)-4-morpholinyl)pyrido[4,3-d]pyrimidin-4(3H)-one | Step 2: 4-chloro-2,3-difluorophenylboronic acid |
| 15 | 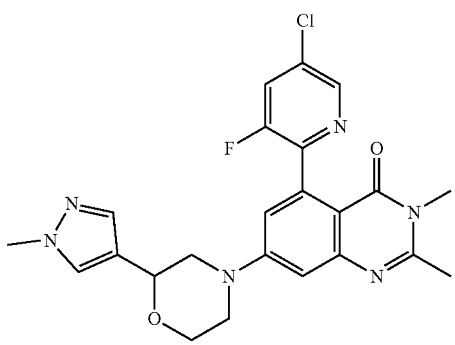 | 5-(5-chloro-3-fluoro-2-pyridinyl)-2,3-dimethyl-7-(2-(1-methyl-1H-pyrazol-4-yl)-4-morpholinyl)-4(3H)-quinazolinone | Step 1: Skip
Step 2: 5,7-dibromo-2,3-dimethylquinazolin-4(3H)-one, Pd(Ph$_3$)$_4$, (5-chloropyridin-2-yl)zinc(II) bromide, THF, 70° C.
Step 3: 2-(1-methyl-1H-pyrazol-4-yl)morpholine (Enamine Inc., Monmouth Jct., NJ, USA), (RuPhosG3) (2-dicyclohexyl-phosphino-2',6'-diisopropoxy-1,1'-biphenyl)[2-(2'-amino-1,1'-biphenyl)]palladium(ii) methanesulfonate, 2-dicyclohexylphosphino-2,6-di-i-propoxy-1,1-biphenyl, Cs$_2$CO$_3$, Dioxane, 80° C. |
| 16 | | 5-(5-chloro-3-methyl-2-pyridinyl)-2,3-dimethyl-7-(2-(1-methyl-1H-pyrazol-4-yl)-4-morpholinyl)pyrido[4,3-d]pyrimidin-4(3H)-one | Step 2: (5-chloro-3-fluoropyridin-2-yl)zinc(II) bromide, Pd(Ph$_3$)$_4$, THF, 70° C.
Step 3: 2-(1-methyl-1H-pyrazol-4-yl)morpholine |

TABLE 1-continued

Compounds 2 to 122 were prepared following the procedure described in Method 1, steps 1-3, as follows:

| Ex. # | Structure | Name | Reagents/Conditions |
|---|---|---|---|
| 17 | 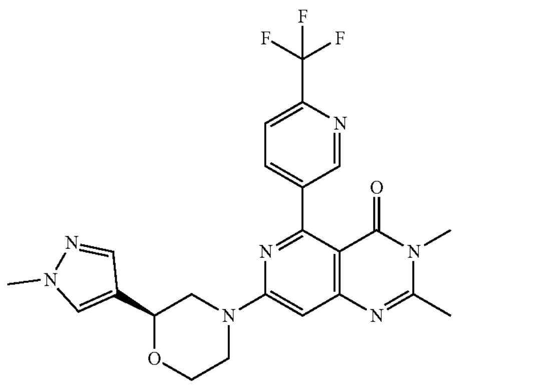 | 2,3-dimethyl-7-((2S)-2-(1-methyl-1H-pyrazol-4-yl)-4-morpholinyl)-5-(6-(trifluoromethyl)-3-pyridinyl)pyrido[4,3-d]pyrimidin-4(3H)-one | Step 2: (6-(trifluoromethyl)-3-pyridinylboronic acid<br>Step 3: 2-(1-methyl-1H-pyrazol-4-yl)morpholine |
| 18 | 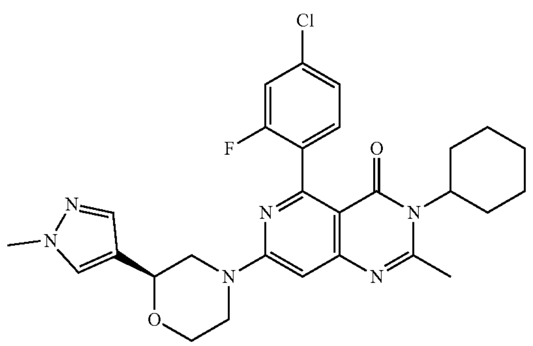 [SMILES: Cc1nc2cc(N3CCO[C@@H](c4cnn(C)c4)C3)nc(-c3ccc(Cl)cc3F)c2c(=O)n1C1CCCCC1] | 5-(4-chloro-2-fluorophenyl)-3-cyclohexyl-2-methyl-7-((2S)-2-(1-methyl-1H-pyrazol-4-yl)-4-morpholinyl)pyrido[4,3-d]pyrimidin-4(3H)-one | Step 1b: cyclohexylamine |
| 19 | 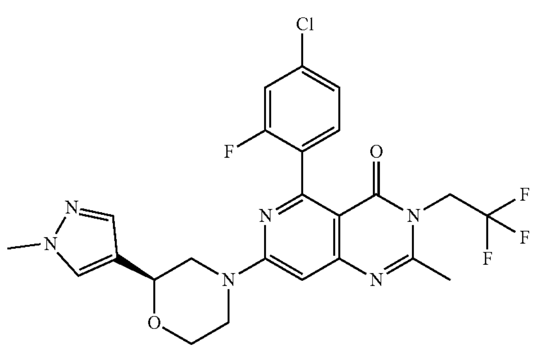 [SMILES: Cc1nc2cc(N3CCO[C@@H](c4cnn(C)c4)C3)nc(-c3ccc(Cl)cc3F)c2c(=O)n1CC(F)(F)F] | 5-(4-chloro-2-fluorophenyl)-2-methyl-7-((2S)-2-(1-methyl-1H-pyrazol-4-yl)-4-morpholinyl)-3-(2,2,2-trifluoroethyl)pyrido[4,3-d]pyrimidin-4(3H)-one | Step 1b: 2,2,2-trifluoroethyl-amine |
| 20 | 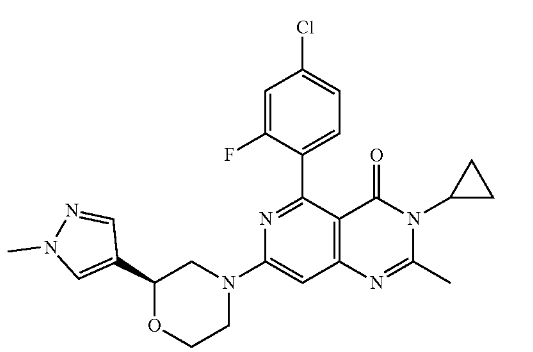 [SMILES: Cc1nc2cc(N3CCO[C@@H](c4cnn(C)c4)C3)nc(-c3ccc(Cl)cc3F)c2c(=O)n1C1CC1] | 5-(4-chloro-2-fluorophenyl)-3-cyclopropyl-2-methyl-7-((2S)-2-(1-methyl-1H-pyrazol-4-yl)-4-morpholinyl)pyrido[4,3-d]pyrimidin-4(3H)-one | Step 1b: cyclopropylamine |

TABLE 1-continued

Compounds 2 to 122 were prepared following the procedure described in Method 1, steps 1-3, as follows:

| Ex. # | Structure | Name | Reagents/Conditions |
|---|---|---|---|
| 21 | 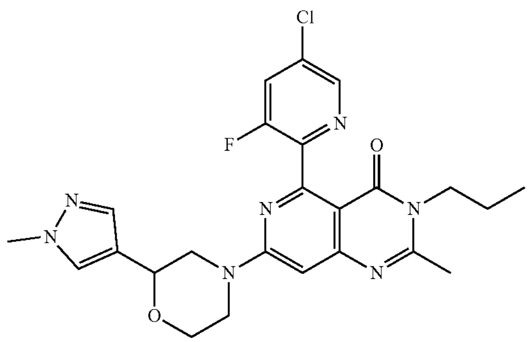 [SMILES: CCCn1c(C)nc2cc(N3CCOC(c4cnn(C)c4)C3)nc(-c3ncc(Cl)cc3F)c2c1=O] | 5-(5-chloro-3-fluoro-2-pyridinyl)-2-methyl-7-(2-(1-methyl-1H-pyrazol-4-yl)-4-morpholinyl)-3-propylpyrido-[4,3-d]pyrimidin-4(3H)-one | Step 1b: N-propylamine<br>Step 2: Pd(Ph$_3$)$_4$, (5-chloropyridin-2-yl)zinc(II) bromide, THF, 70° C.<br>Step 3: 2-(1-methyl-1H-pyrazol-4-yl)morpholine |
| 22 | 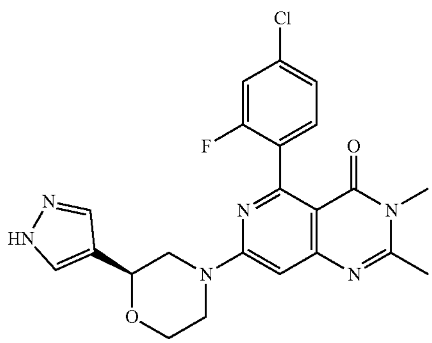 | 5-(4-chloro-2-fluorophenyl)-2,3-dimethyl-7-((2S)-2-(1H-pyrazol-4-yl)-4-morpholinyl)pyrido[4,3-d]pyrimidin-4(3H)-one | Step 3: (S)-2-(1H-pyrazol-4-yl)morpholine (Intermediate 1) |
| 23 | 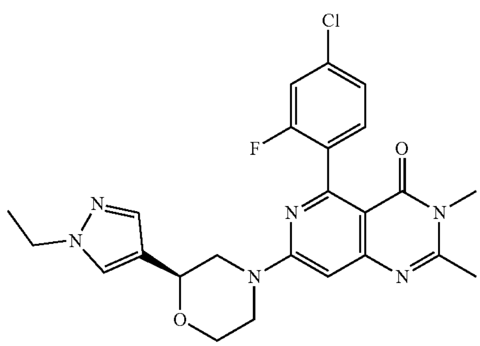 [SMILES: CCn1cc([C@H]2CN(c3cc4nc(C)n(C)c(=O)c4c(-c4ccc(Cl)cc4F)n3)CCO2)cn1] | 5-(4-chloro-2-fluorophenyl)-7-((2S)-2-(1-ethyl-1H-pyrazol-4-yl)-4-morpholinyl)-2,3-dimethylpyrido[4,3-d]pyrimidin-4(3H)-one. Stereochemistry arbitrarily assigned | Step 3: (1-ethyl-1H-pyrazol-4-yl)-4-morpholine<br>Step 4: Purification by chiral SFC, Chiralpak AD-H 2 × 15 cm, 5 um column, 40% methanol, F = 80 mL/min. |
| 24 | 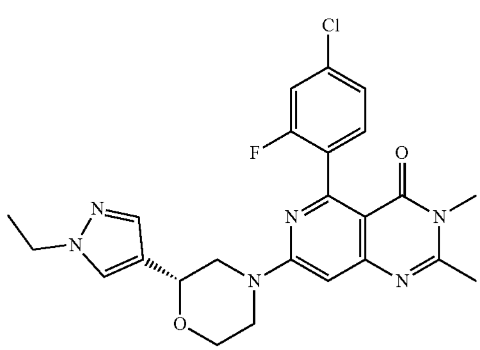 [SMILES: CCn1cc([C@@H]2CN(c3cc4nc(C)n(C)c(=O)c4c(-c4ccc(Cl)cc4F)n3)CCO2)cn1] | 5-(4-chloro-2-fluorophenyl)-7-((2R)-2-(1-ethyl-1H-pyrazol-4-yl)-4-morpholinyl)-2,3-dimethylpyrido[4,3-d]pyrimidin-4(3H)-one. Stereochemistry arbitrarily assigned | Step 3: (1-ethyl-1H-pyrazol-4-yl)-4-morpholine<br>Step 4: Purification by chiral SFC, Chiralpak AD-H 2 × 15 cm, 5 um column, 40% methanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 25 | 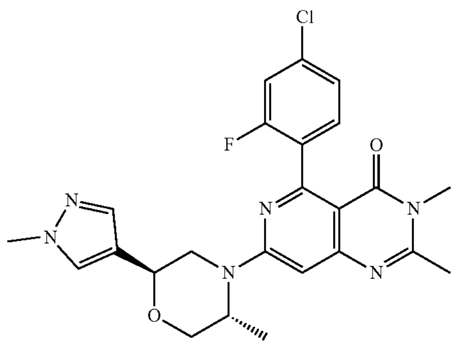 | 5-(4-chloro-2-fluorophenyl)-2,3-dimethyl-7-((2S,5R)-5-methyl-2-(1-methyl-1H-pyrazol-4-yl)-4-morpholinyl)pyrido[4,3-d]pyrimidin-4(3H)-one. Absolute stereochemistry arbitrarily assigned. Relative stereochemistry (cis/trans) determined by NMR. | Step 3: 5-methyl-2-(1-methyl-1H-pyrazol-4-yl)morpholine (Intermediate 5) Step 4: Purification by chiral SFC, Chiralpak AD-H 2 × 15 cm, 5 um column, 40% methanol, F = 80 mL/min. |
| 26 | 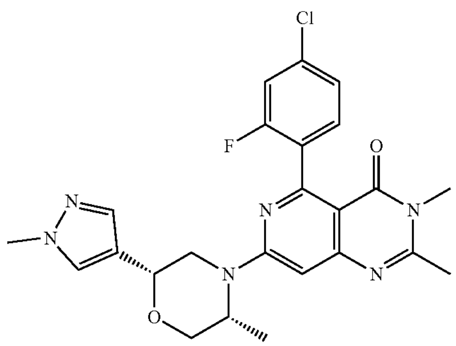 | 5-(4-chloro-2-fluorophenyl)-2,3-dimethyl-7-((2R,5R)-5-methyl-2-(1-methyl-1H-pyrazol-4-yl)-4-morpholinyl)pyrido[4,3-d]pyrimidin-4(3H)-one. Absolute stereochemistry arbitrarily assigned. Relative stereochemistry (cis/trans) determined by NMR. | Step 3: 5-methyl-2-(1-methyl-1H-pyrazol-4-yl)morpholine (Intermediate 5) Step 4: Purification by chiral SFC, Chiralpak AD-H 2 × 15 cm, 5 um column, 40% methanol F = 80 mL/min. |
| 27 | 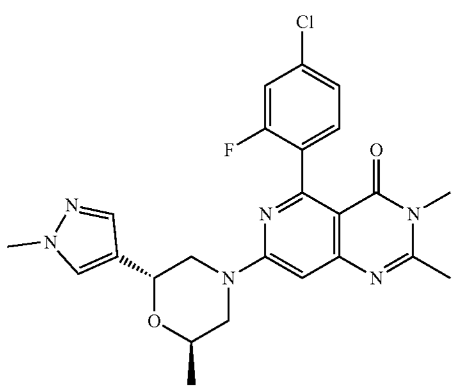 | 5-(4-chloro-2-fluorophenyl)-2,3-dimethyl-7-((2R,6R)-2-methyl-6-(1-methyl-1H-pyrazol-4-yl)-4-morpholinyl)pyrido[4,3-d]pyrimidin-4(3H)-one. Absolute stereochemistry arbitrarily assigned. Relative stereochemistiy (cis/trans) determined by NMR. | Step 3: 2-methyl-6-(1-methyl-1H-pyrazol-4-yl)morpholine (Intermediate 5)6 Step 4: Purification by chiral Step 4: Purification by chiral SFC, Chiralpak AD-H 2 × 15 cm, 5 um column, 40% methanol, F = 70 mL/min. |
| 28 | 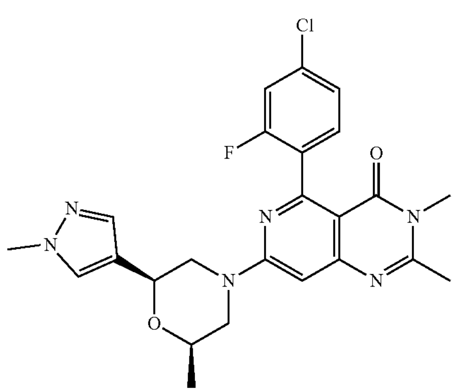 | 5-(4-chloro-2-fluorophenyl)-2,3-dimethyl-7-((2R,6S)-2-methyl-6-(1-methyl-1H-pyrazol-4-yl)-4-morpholinyl)pyrido[4,3-d]pyrimidin-4(3H)-one. Absolute stereochemistry arbitrarily assigned. Relative stereochemistry (cis/trans) determined by NMR. | Step 3: 2-methyl-6-(1-methyl-1H-pyrazol-4-yl)morpholine (Intermediate 6) Step 4: Purification by chiral Step 4: Purification by chiral SFC, Chiralpak AD-H 2 × 15 cm, 5 um column, 40% methanol, F = 70 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 29 | 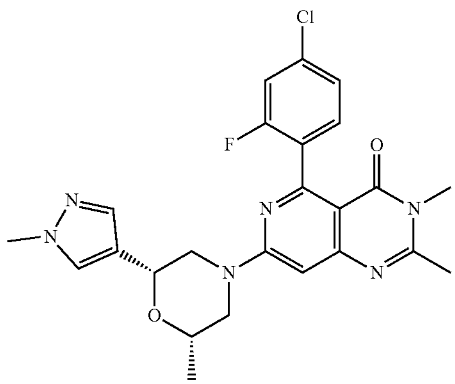 | 5-(4-chloro-2-fluorophenyl)-2,3-dimethyl-7-((2S,6R)-2-methyl-6-(1-methyl-1H-pyrazol-4-yl)-4-morpholinyl)pyrido[4,3-d]pyrimidin-4(3H)-one. Absolute stereochemistry arbitrarily assigned. Relative stereochemistry (cis/trans) determined by NMR. | Step 3: 2-methyl-6-(1-methyl-1H-pyrazol-4-yl)morpholine (Intermediate 6) Step 4: Purification by chiral SFC, Chiralpak AD-H 2 × 15 cm, 5 um column, 40% methanol, F = 70 mL/min. |
| 30 | 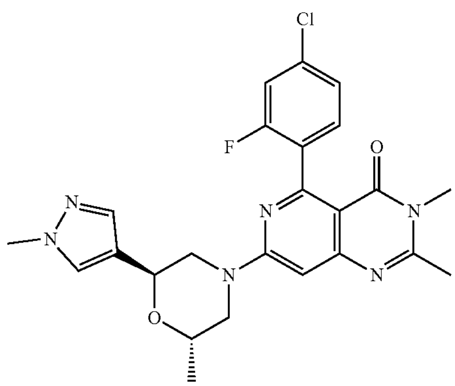 | 5-(4-chloro-2-fluorophenyl)-2,3-dimethyl-7-((2S,6S)-2-methyl-6-(1-methyl-1H-pyrazol-4-yl)-4-morpholinyl)pyrido[4,3-d]pyrimidin-4(3H)-one. Absolute stereochemistry arbitrarily assigned. Relative stereochemistry (cis/trans) determined by NMR. | Step 3: 2-methyl-6-(1-methyl-1H-pyrazol-4-yl)morpholine (Intermediate 6) Step 4: Purification by chiral SFC, Chiralpak AD-H 2 × 15 cm, 5 um column, 40% methanol, F = 70 mL/min. |
| 31 | 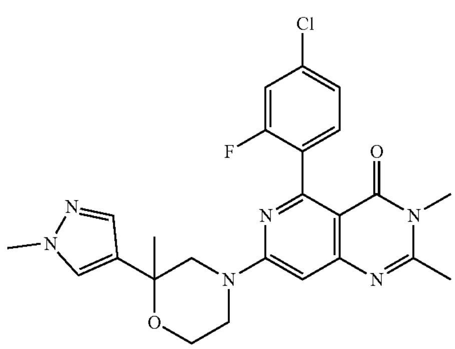 | 5-(4-chloro-2-fluorophenyl)-2,3-dimethyl-7-(2-methyl-2-(1-methyl-1H-pyrazol-4-yl)-4-morpholinyl)pyrido[4,3-d]pyrimidin-4(3H)-one | Step 3: 2-methyl-2-(1-methyl-1H-pyrazol-4-yl)morpholine (Enamine Inc., Monmouth Jct., NJ, USA) |
| 32 | 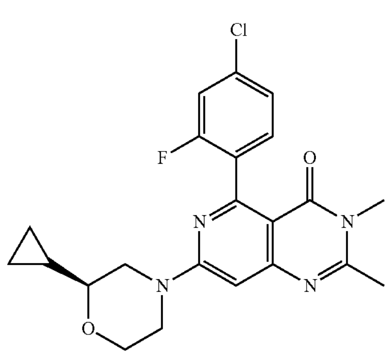 [SMILES: Cc1nc2cc(N3CCO[C@@H](C4CC4)C3)nc(-c3ccc(Cl)cc3F)c2c(=O)n1C] | 5-(4-chloro-2-fluorophenyl)-7-((2S)-2-cyclopropyl-4-morpholinyl)-2,3-dimethylpyrido[4,3-d]pyrimidin-4(3H)-one | Step 3: (S)-2-cyclopropyl-4-morpholine (Enamine Inc., Monmouth Jct., NJ, USA) |

TABLE 1-continued

Compounds 2 to 122 were prepared following the procedure described in Method 1, steps 1-3, as follows:

| Ex. # | Structure | Name | Reagents/Conditions |
|---|---|---|---|
| 33 | 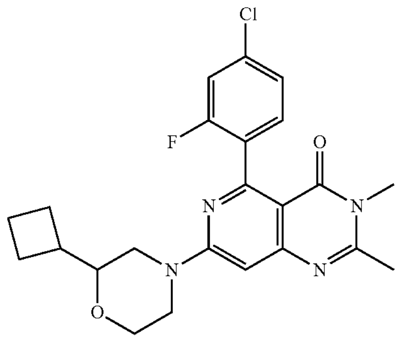 | 5-(4-chloro-2-fluorophenyl)-7-(2-cyclobutyl-4-morpholinyl)-2,3-dimethyl-pyrido[4,3-d]pyrimidin-4(3H)-one | Step 3: 2-cyclobutyl-4-morpholine (Enamine Inc., Monmouth Jct., NJ, USA) |
| 34 | 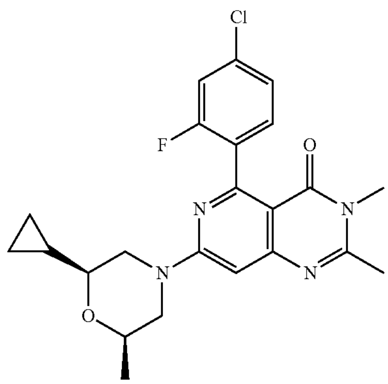 [SMILES: Cc1nc2cc(N3C[C@@H](C)O[C@@H](C4CC4)C3)nc(-c3ccc(Cl)cc3F)c2c(=O)n1C] | 5-(4-chloro-2-fluorophenyl)-7-((2S,6R)-2-cyclopropyl-6-methyl-4-morpholinyl)-2,3-dimethylpyrido[4,3-d]pyrimidin-4(3H)-one. Absolute stereochemistry arbitrarily assigned. Relative stereochemistry (cis/trans) determined by NMR. | Step 3: 2-cyclopropyl-6-methyl-4-morpholine (Enamine Inc., Monmouth Jct., NJ, USA) Step 4: Purification by chiral SFC, Chiralpak AD-H 2 × 15 cm, 5 um column, 40% methanol, F = 70 mL/min. |
| 35 | 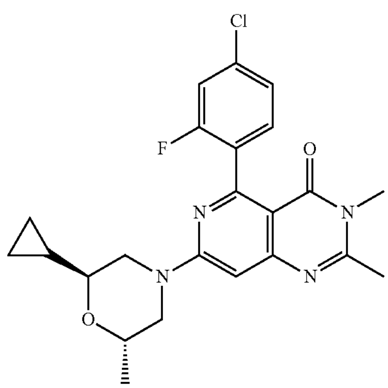 [SMILES: Cc1nc2cc(N3C[C@H](C)O[C@@H](C4CC4)C3)nc(-c3ccc(Cl)cc3F)c2c(=O)n1C] | 5-(4-chloro-2-fluorophenyl)-7-((2S,6S)-2-cyclopropyl-6-methyl-4-morpholinyl)-2,3-dimethylpyrido[4,3-d]pyrimidin-4(3H)-one. Absolute stereochemistry arbitrarily assigned. Relative stereochemistry (cis/trans) determined by NMR. | Step 3: 2-cyclopropyl-6-methyl-4-morpholine (Enamine Inc., Monmouth Jct., NJ, USA) Step 4: Purification by chiral SFC, Chiralpak AD-H 2 × 15 cm, 5 um column, 40% methanol, F = 70 mL/min. |
| 36 | 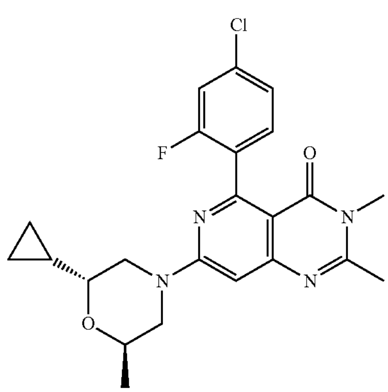 [SMILES: Cc1nc2cc(N3C[C@@H](C)O[C@H](C4CC4)C3)nc(-c3ccc(Cl)cc3F)c2c(=O)n1C] | 5-(4-chloro-2-fluorophenyl)-7-((2R,6R)-2-cyclopropyl-6-methyl-4-morpholinyl)-2,3-dimethylpyrido[4,3-d]pyrimidin-4(3H)-one. Absolute stereochemistry arbitrarily assigned. Relative stereochemistiy (cis/trans) determined by NMR. | Step 3: 2-cyclopropyl-6-methyl-4-morpholine (Enamine Inc., Monmouth Jct., NJ, USA) Step 4: Purification by chiral SFC, Chiralpak AD-H 2 × 15 cm, 5 um column, 40% methanol, F = 70 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 37 | 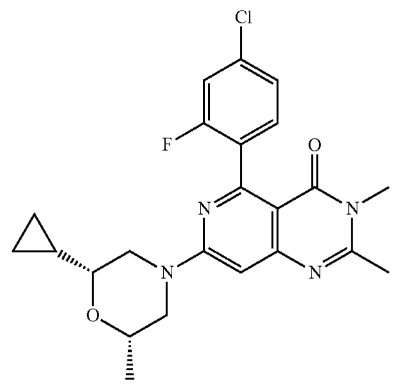 | 5-(4-chloro-2-fluorophenyl)-7-((2R,6S)-2-cyclopropyl-6-methyl-4-morpholinyl)-2,3-dimethylpyrido[4,3-d]pyrimidin-4(3H)-one. Absolute stereochemistry arbitrarily assigned. Relative stereochemistry (cis/trans) determined by NMR. | Step 3: 2-cyclopropyl-6-methyl-4-morpholine (Enamine Inc., Monmouth Jct., NJ, USA) Step 4: Purification by chiral SFC, Chiralpak AD-H 2 × 15 cm, 5 um column, 40% methanol, F = 70 mL/min. |
| 38 | 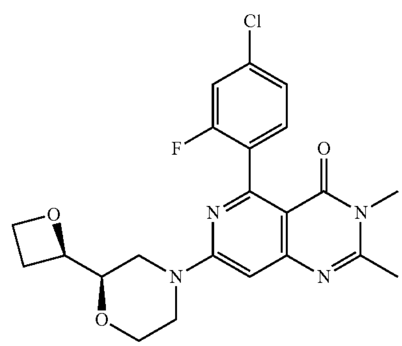 [SMILES: Cc1nc2cc(N3CCO[C@@H]([C@H]4CCO4)C3)nc(-c3ccc(Cl)cc3F)c2c(=O)n1C] | 5-(4-chloro-2-fluorophenyl)-2,3-dimethyl-7-((2R)-2-((2R)-2-oxetanyl)-4-morpholinyl)pyrido[4,3-d]pyrimidin-4(3H)-one. Absolute stereochemistry arbitrarily assigned. Relative stereochemistry determined by NMR. | Step 3: 2-(oxetan-2-yl)morpholine (Enamine Inc., Monmouth Jct., NJ, USA) Step 4: Purification by chiral SFC, Chiralpak AD-H 2 × 15 cm, 5 um column, 40% methanol, F = 70 mL/min. |
| 39 | 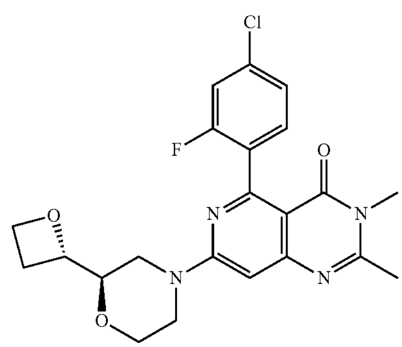 [SMILES: Cc1nc2cc(N3CCO[C@@H]([C@@H]4CCO4)C3)nc(-c3ccc(Cl)cc3F)c2c(=O)n1C] | 5-(4-chloro-2-fluorophenyl)-2,3-dimethyl-7-((2R)-2-((2S)-2-oxetanyl)-4-morpholinyl)pyrido[4,3-d]pyrimidin-4(3H)-one. Absolute stereochemistry arbitrarily assigned. Relative stereochemistry determined by NMR. | Step 3: 2-(oxetan-2-yl)morpholine (Enamine Inc., Monmouth Jct., NJ, USA) Step 4: Purification by chiral SFC, Chiralpak AD-H 2 × 15 cm, 5 um column, 40% methanol, F = 70 mL/min. |
| 40 | 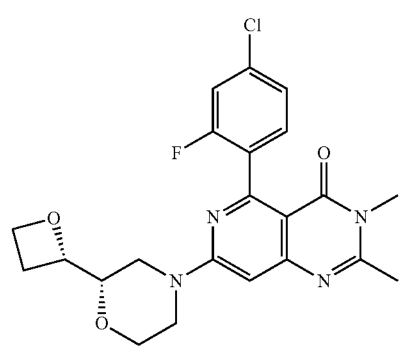 [SMILES: Cc1nc2cc(N3CCO[C@H]([C@@H]4CCO4)C3)nc(-c3ccc(Cl)cc3F)c2c(=O)n1C] | 5-(4-chloro-2-fluorophenyl)-2,3-dimethyl-7-((2S)-2-((2S)-2-oxetanyl)-4-morpholinyl)pyrido[4,3-d]pyrimidin-4(3H)-one. Absolute stereochemistry arbitrarily assigned. Relative stereochemistry determined by NMR. | Step 3: 2-(oxetan-2-yl)morpholine (Enamine Inc., Monmouth Jct., NJ, USA) Step 4: Purification by chiral SFC, Chiralpak AD-H 2 × 15 cm, 5 um column, 40% methanol, F = 70 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 41 | 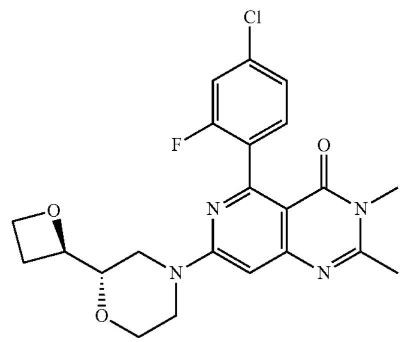 [SMILES: Cc1nc2cc(N3CCO[C@H]([C@H]4CCO4)C3)nc(-c3ccc(Cl)cc3F)c2c(=O)n1C] | 5-(4-chloro-2-fluorophenyl)-2,3-dimethyl-7-((2S)-2-((2R)-2-oxetanyl)-4-morpholinyl)pyrido[4,3-d]pyrimidin-4(3H)-one. Absolute stereochemistry arbitrarily assigned. Relative stereochemistry determined by NMR. | Step 3: 2-(oxetan-2-yl)morpholine (Enamine Inc., Monmouth Jct., NJ, USA) Step 4: Purification by chiral SFC, Chiralpak AD-H 2 × 15 cm, 5 um column, 40% methanol, F = 70 mL/min. |
| 42 | 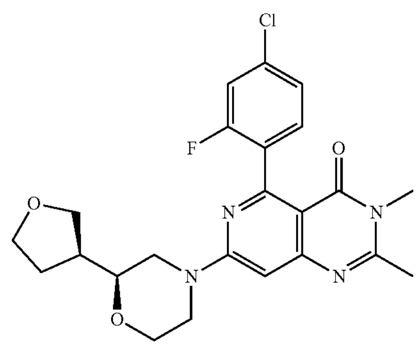 [SMILES: Cc1nc2cc(N3CCO[C@@H]([C@H]4CCOC4)C3)nc(-c3ccc(Cl)cc3F)c2c(=O)n1C] | 5-(4-chloro-2-fluorophenyl)-2,3-dimethyl-7-((2S)-2-((3S)-tetrahydro-3-furanyl)-4-morpholinyl)pyrido[4,3-d]pyrimidin-4(3H)-one. Absolute stereochemistry arbitrarily assigned. Relative stereochemistry determined by NMR. | Step 3: 2-(tetrahydrofuran-3-yl)morpholine (Enamine Inc., Monmouth Jct., NJ, USA) Step 4: Purification by chiral SFC, Chiralpak AD-H 2 × 15 cm, 5 um column, 60% methanol, F = 70 mL/min. |
| 43 | 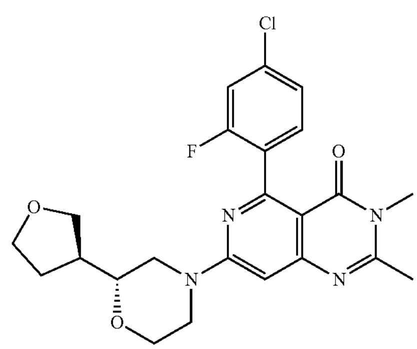 [SMILES: Cc1nc2cc(N3CCO[C@H]([C@H]4CCOC4)C3)nc(-c3ccc(Cl)cc3F)c2c(=O)n1C] | 5-(4-chloro-2-fluorophenyl)-2,3-dimethyl-7-((2R)-2-((3S)-tetrahydro-3-furanyl)-4-morpholinyl)pyrido[4,3-d]pyrimidin-4(3H)-one. Absolute stereochemistry arbitrarily assigned. Relative stereochemistiy determined by NMR. | Step 3: 2-(tetrahydrofuran-3-yl)morpholine (Enamine Inc., Monmouth Jct., NJ, USA) Step 4: Purification by chiral SFC, Chiralpak AD-H 2 × 15 cm, 5 um column, 60% methanol, F = 70 mL/min. |
| 44 | 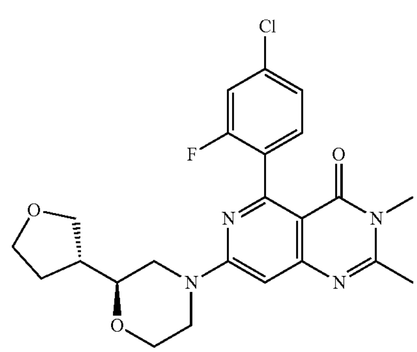 [SMILES: Cc1nc2cc(N3CCO[C@@H]([C@@H]4CCOC4)C3)nc(-c3ccc(Cl)cc3F)c2c(=O)n1C] | 5-(4-chloro-2-fluorophenyl)-2,3-dimethyl-7-((2S)-2-((3R)-tetrahydro-3-furanyl)-4-morpholinyl)pyrido[4,3-d]pyrimidin-4(3H)-one. Absolute stereochemistry arbitrarily assigned. Relative stereochemistry determined by NMR. | Step 3: 2-(tetrahydrofuran-3-yl)morpholine (Enamine Inc., Monmouth Jct., NJ, USA) Step 4: Purification by chiral SFC, Chiralpak AD-H 2 × 15 cm, 5 um column, 60% methanol, F = 70 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 45 | 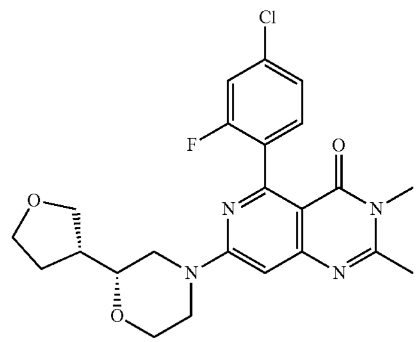 [SMILES: Cc1nc2cc(N3CCO[C@H]([C@@H]4CCOC4)C3)nc(-c3ccc(Cl)cc3F)c2c(=O)n1C] | 5-(4-chloro-2-fluorophenyl)-2,3-dimethyl-7-((2R)-2-((3R)-tetrahydro-3-furanyl)-4-morpholinyl)pyrido[4,3-d]pyrimidin-4(3H)-one. Absolute stereochemistry arbitrarily assigned. Relative stereochemistry determined by NMR. | Step 3: 2-(tetrahydrofuran-3-yl)morpholine (Enamine Inc., Monmouth Jct., NJ, USA) Step 4: Purification by chiral SFC, Chiralpak AD-H 2 × 15 cm, 5 um column, 60% methanol, F = 70 mL/min. |
| 46 | 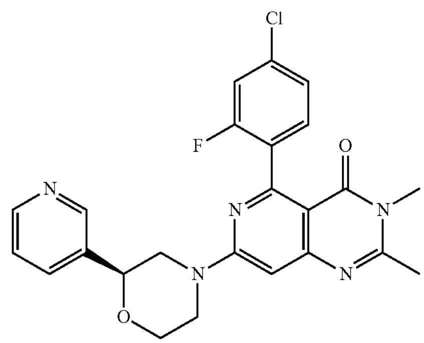 [SMILES: Cc1nc2cc(N3CCO[C@@H](c4cccnc4)C3)nc(-c3ccc(Cl)cc3F)c2c(=O)n1C] | 5-(4-chloro-2-fluorophenyl)-2,3-dimethyl-7-((2S)-2-(3-pyridinyl)-4-morpholinyl)pyrido[4,3-d]pyrimidin-4(3H)-one. Absolute stereochemistry arbitrarily assigned. | Step 3: 2-(pyridin-3-yl)morpholine (Enamine Inc., Monmouth Jct., NJ, USA) Step 4: Purification by chiral SFC, Chiralpak AD-H 2 × 15 cm, 5 um column, 45% methanol, F = 70 mL/min. |
| 47 | 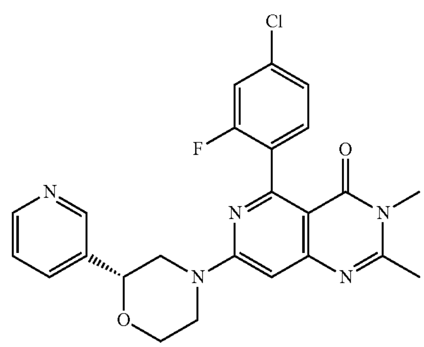 [SMILES: Cc1nc2cc(N3CCO[C@H](c4cccnc4)C3)nc(-c3ccc(Cl)cc3F)c2c(=O)n1C] | 5-(4-chloro-2-fluorophenyl)-2,3-dimethyl-7-((2R)-2-(3-pyridinyl)-4-morpholinyl)pyrido[4,3-d]pyrimidin-4(3H)-one. Absolute stereochemistry arbitrarily assigned. | Step 3: 2-(pyridin-3-yl)morpholine (Enamine Inc., Monmouth Jct., NJ, USA) Step 4: Purification by chiral SFC, Chiralpak AD-H 2 × 15 cm, 5 um column, 45% methanol, F = 70 mL/min. |
| 48 | 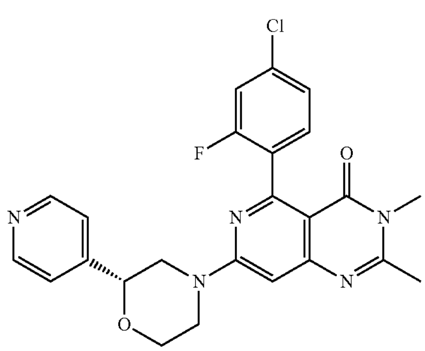 | 5-(4-chloro-2-fluorophenyl)-2,3-dimethyl-7-((2R)-2-(4-pyridinyl)-4-morpholinyl)pyrido[4,3-d]pyrimidin-4(3H)-one. Absolute stereochemistry arbitrarily assigned. | Step 3: 2-(pyridin-4-yl)morpholine (Enamine Inc., Monmouth Jct., NJ, USA) Step 4: Purification by chiral SFC, Chiralpak AD-H 2 × 15 cm, 5 um column, 45% methanol, F = 70 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 49 | 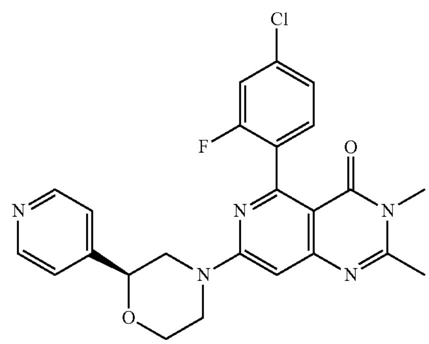 [SMILES: Cc1nc2cc(N3CCO[C@@H](c4ccncc4)C3)nc(-c3ccc(Cl)cc3F)c2c(=O)n1C] | 5-(4-chloro-2-fluorophenyl)-2,3-dimethyl-7-((2S)-2-(4-pyridinyl)-4-morpholinyl)pyrido[4,3-d]pyrimidin-4(3H)-one. Absolute stereochemistry arbitrarily assigned. | Step 3: 2-(pyridin-4-yl)morpholine (Enamine Inc., Monmouth Jct., NJ, USA) Step 4: Purification by chiral SFC, Chiralpak AD-H 2 × 15 cm, 5 um column, 45% methanol, F = 70 mL/min. |
| 50 | 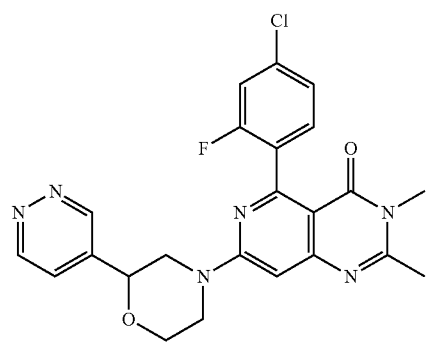 [SMILES: Cc1nc2cc(N3CCOC(c4ccnnc4)C3)nc(-c3ccc(Cl)cc3F)c2c(=O)n1C] | 5-(4-chloro-2-fluorophenyl)-2,3-dimethyl-7-(2-(4-pyridazinyl)-4-morpholinyl)pyrido[4,3-d]pyrimidin-4(3H)-one | Step 3: 2-(pyridazin-4-yl)morpholine (FCH Group, Chernigiv, Ukraine) |
| 51 | 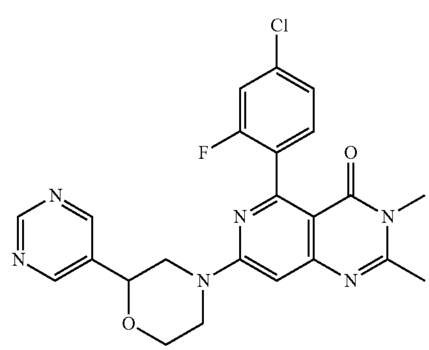 [SMILES: Cc1nc2cc(N3CCOC(c4cncnc4)C3)nc(-c3ccc(Cl)cc3F)c2c(=O)n1C] | 5-(4-chloro-2-fluorophenyl)-2,3-dimethyl-7-(2-(5-pyrimidinyl)-4-morpholinyl)pyrido[4,3-d]pyrimidin-4(3H)-one | Step 3: 2-(pyrimidin-5-yl)morpholine (Enamine Inc., Monmouth Jct., NJ, USA) |
| 52 | 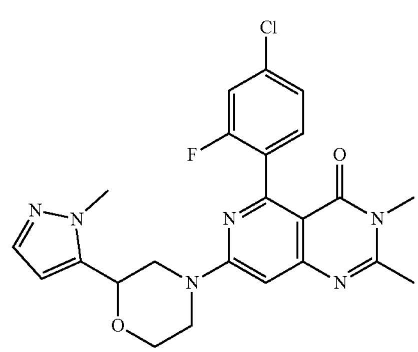 [SMILES: Cc1nc2cc(N3CCOC(c4ccnn4C)C3)nc(-c3ccc(Cl)cc3F)c2c(=O)n1C] | 5-(4-chloro-2-fluorophenyl)-2,3-dimethyl-7-(2-(1-methyl-1H-pyrazol-5-yl)-4-morpholinyl)pyrido[4,3-d]pyrimidin-4(3H)-one | Step 3: 2-(1-methyl-1H-pyrazol-5-yl)morpholine (Enamine Inc., Monmouth Jct., NJ, USA) |

TABLE 1-continued

Compounds 2 to 122 were prepared following the procedure described in Method 1, steps 1-3, as follows:

| Ex. # | Structure | Name | Reagents/Conditions |
|---|---|---|---|
| 53 | 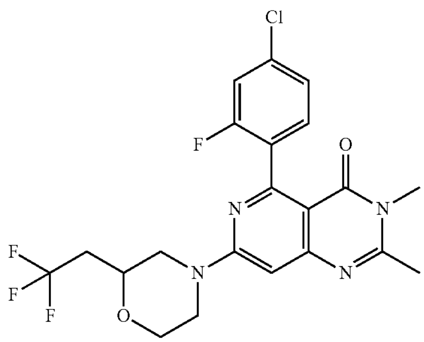 | 5-(4-chloro-2-fluorophenyl)-2,3-dimethyl-7-(2-(2,2,2-trifluoroethyl)-4-morpholinyl)pyrido[4,3-d]pyrimidin-4(3H)-one | Step 3: 2-(2,2,2-trifluoro-ethyl)morpholine (Enamine Inc., Monmouth Jct., NJ, USA) |
| 54 | 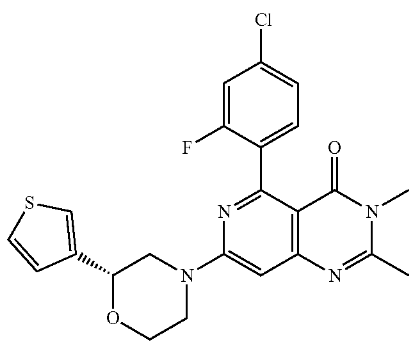 [SMILES: Cc1nc2cc(N3CCO[C@H](c4ccsc4)C3)nc(-c3ccc(Cl)cc3F)c2c(=O)n1C] | 5-(4-chloro-2-fluorophenyl)-2,3-dimethyl-7-((2R)-2-(thiophen-3-yl)morpholino)pyrido[4,3-d]pyrimidin-4(3H)-one. Absolute stereochemistry arbitrarily assigned. | Step 3: 2-(thiophen-3-yl)morpholine (Enamine Inc., Monmouth Jct., NJ, USA) Step 4: Purification by chiral SFC, Chiralpak AD-H 2 × 15 cm, 5 um column, 45% isopropanol, F = 80 mL/min. |
| 55 | 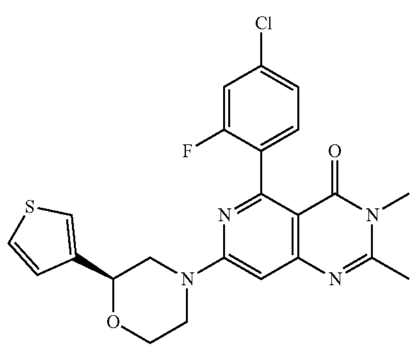 [SMILES: Cc1nc2cc(N3CCO[C@@H](c4ccsc4)C3)nc(-c3ccc(Cl)cc3F)c2c(=O)n1C] | 5-(4-chloro-2-fluorophenyl)-2,3-dimethyl-7-((2S)-2-(3-thiophenyl)-4-morpholinyl)pyrido[4,3-d]pyrimidin-4(3H)-one. Absolute stereochemistry arbitrarily assigned. | Step 3: 2-(thiophen-3-yl)morpholine (Enamine Inc., Monmouth Jct., NJ, USA) Step 4: Purification by chiral SFC, Chiralpak AD-H 2 × 15 cm, 5 um column, 45% isopropanol, F = 80 mL/min. |
| 56 | 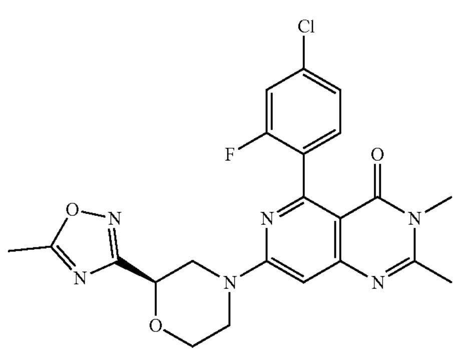 | 5-(4-chloro-2-fluorophenyl)-2,3-dimethyl-7-((2R)-2-(5-methyl-1,2,4-oxadiazol-3-yl)-4-morpholinyl)pyrido[4,3-d]pyrimidin-4(3H)-one. Absolute stereochemistry arbitrarily assigned. | Step 3: 2-(5-methyl-1,2,4-oxadiazol-3-yl)morpholine (Enamine Inc., Monmouth Jct., NJ, USA) Step 4: Purification by chiral SFC, Chiralpak AD-H 2 × 15 cm, 5 um column, 40% methanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 57 | 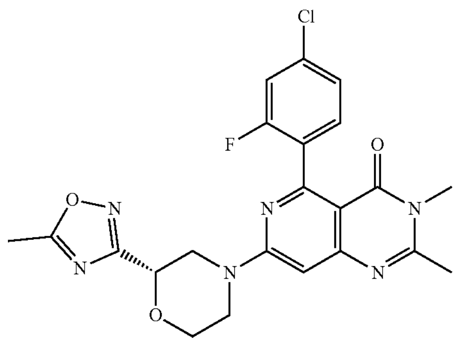 | 5-(4-chloro-2-fluorophenyl)-2,3-dimethyl-7-((2S)-2-(5-methyl-1,2,4-oxadiazol-3-yl)-4-morpholinyl)pyrido[4,3-d]pyrimidin-4(3H)-one. Absolute stereochemistry arbitrarily assigned. | Step 3: 2-(5-methyl-1,2,4-oxadiazol-3-yl)morpholine (Enamine Inc., Monmouth Jct., NJ, USA) Step 4: Purification by chiral SFC, Chiralpak AD-H 2 × 15 cm, 5 um column, 40% methanol, F = 80 mL/min. |
| 58 | 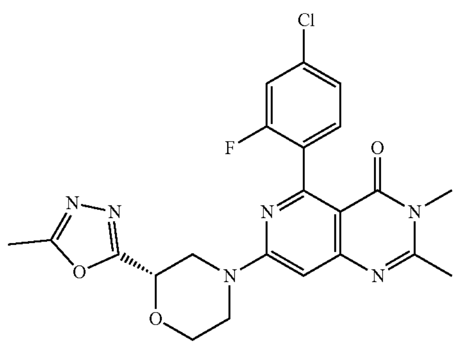 | 5-(4-chloro-2-fluorophenyl)-2,3-dimethyl-7-((2S)-2-(5-methyl-1,3,4-oxadiazol-2-yl)-4-morpholinyl)pyrido[4,3-d]pyrimidin-4(3H)-one. Absolute stereochemistry arbitrarily assigned. | Step 3: 2-(5-methyl-1,3,4-oxadiazol-2-yl)morpholine (Enamine Inc., Monmouth Jct., NJ, USA) Step 4: Purification by chiral SFC, Chiralpak AD-H 2 × 15 cm, 5 um column, 40% methanol, F = 80 mL/min. |
| 59 | 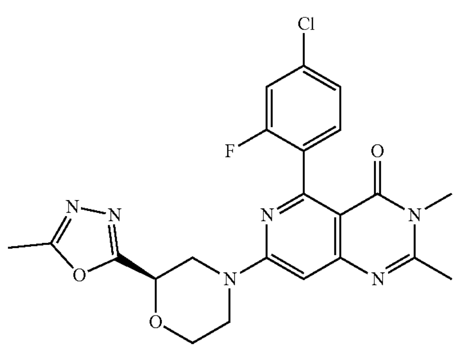 | 5-(4-chloro-2-fluorophenyl)-2,3-dimethyl-7-((2R)-2-(5-methyl-1,3,4-oxadiazol-2-yl)-4-morpholinyl)pyrido[4,3-d]pyrimidin-4(3H)-one. Absolute stereochemistry arbitrarily assigned. | Step 3: 2-(5-methyl-1,3,4-oxadiazol-2-yl)morpholine (Enamine Inc., Monmouth Jct., NJ, USA) (Enamine Inc., Monmouth Jct., NJ, USA) Step 4: Purification by chiral SFC, Chiralpak AD-H 2 ×15 cm, 5 um column, 40% methanol, F = 80 mL/min. |
| 60 | 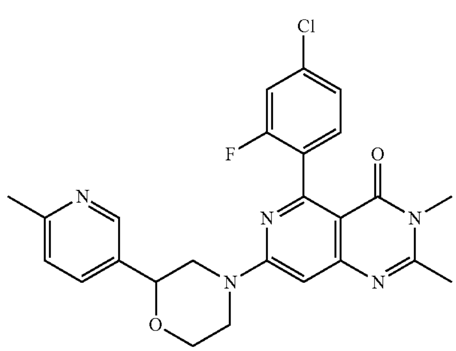 | 5-(4-chloro-2-fluorophenyl)-2,3-dimethyl-7-(2-(6-methyl-3-pyridinyl)-4-morpholinyl)pyrido[4,3-d]pyrimidin-4(3H)-one | Step 3: (2-(6-methyl-3-pyridinyl)-4-morpholine (Enamine Inc., Monmouth Jct., NJ, USA). |

TABLE 1-continued

Compounds 2 to 122 were prepared following the procedure described in Method 1, steps 1-3, as follows:

| Ex. # | Structure | Name | Reagents/Conditions |
|---|---|---|---|
| 61 | 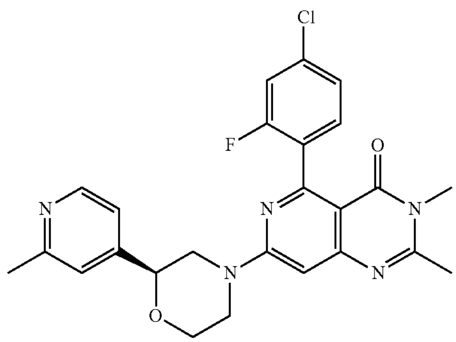 | 5-(4-chloro-2-fluorophenyl)-2,3-dimethyl-7-((2S)-2-(2-methyl-4-pyridinyl)-4-morpholinyl)pyrido[4,3-d]pyrimidin-4(3H)-one | Step 3: (S)-2-(2-methylpyridin-4-yl)morpholine (Enamine Inc., Monmouth Jct., NJ, USA). |
| 62 | 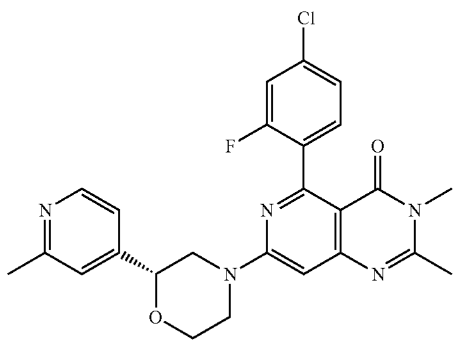 | 5-(4-chloro-2-fluorophenyl)-2,3-dimethyl-7-((2R)-2-(2-methyl-4-pyridinyl)-4-morpholinyl)pyrido[4,3-d]pyrimidin-4(3H)-one | Step 3: (R)-2-(2-methylpyridin-4-yl)morpholine (Enamine Inc., Monmouth Jct., NJ, USA). |
| 63 | 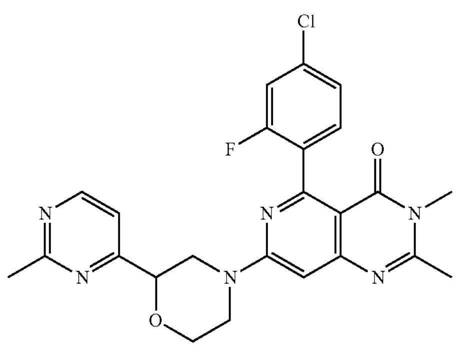 | 5-(4-chloro-2-fluorophenyl)-2,3-dimethyl-7-(2-(2-methyl-4-pyrimidinyl)-4-morpholinyl)pyrido[4,3-d]pyrimidin-4(3H)-one | Step 3: 2-(2-methylpyrimidin-4-yl)morpholine (Intermediate 7) |
| 64 | 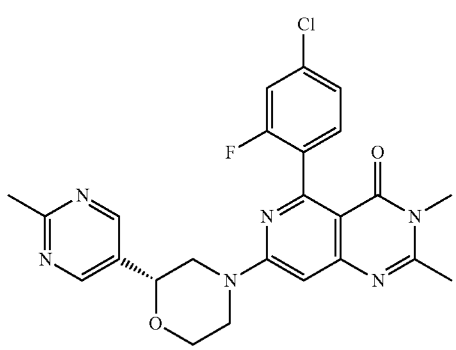 | 5-(4-chloro-2-fluorophenyl)-2,3-dimethyl-7-((2R)-2-(2-methyl-5-pyrimidinyl)-4-morpholinyl)pyrido[4,3-d]pyrimidin-4(3H)-one. Absolute stereochemistry arbitrarily assigned. | Step 3: 2-(2-methylpyrimidin-5-yl)morpholine (Intermediate 8) Step 4: Purification by chiral SFC, Chiralpak AD-H 2 × 15 cm, 5 um column, 15% methanol, F = 120 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 65 | 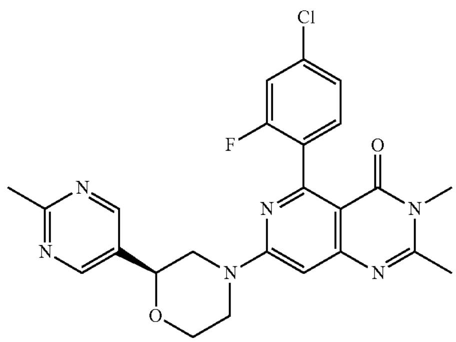 | 5-(4-chloro-2-fluorophenyl)-2,3-dimethyl-7-((2S)-2-(2-methyl-5-pyrimidinyl)-4-morpholinyl)pyrido[4,3-d]pyrimidin-4(3H)-one. Absolute stereochemistry arbitrarily assigned. | Step 3: 2-(2-methylpyrimidin-5-yl)morpholine (Intermediate 8) Step 4: Purification by chiral SFC, Chiralpak AD-H 2 ×15 cm, 5 um column, 15% methanol, F = 120 mL/min. |
| 66 | 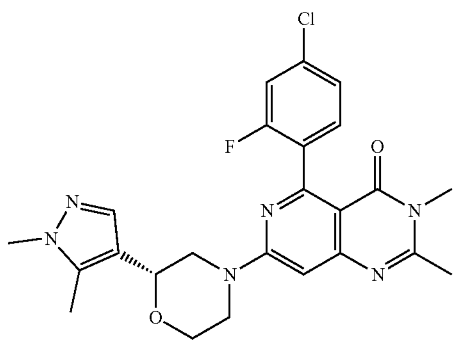 | 5-(4-chloro-2-fluorophenyl)-7-((2R)-2-(1,5-dimethyl-1H-pyrazol-4-yl)-4-morpholinyl)-2,3-dimethylpyrido[4,3-d]pyrimidin-4(3H)-one. Absolute stereochemistry arbitrarily assigned. | Step 3: 2-(1,5-dimethyl-1H-pyrazol-4-yl)morpholine (Intermediate 9) Step 4: Purification by chiral SFC, Chiralpak AD-H 2 × 15 cm, 5 um column, 40% methanol, F = 80 mL/min. |
| 67 | 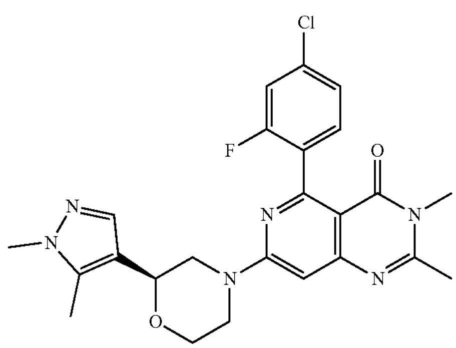 | 5-(4-chloro-2-fluorophenyl)-7-((2S)-2-(1,5-dimethyl-1H-pyrazol-4-yl)-4-morpholinyl)-2,3-dimethylpyrido[4,3-d]pyrimidin-4(3H)-one. Absolute stereochemistry arbitrarily assigned. | Step 3: 2-(1,5-dimethyl-1H-pyrazol-4-yl)morpholine (Intermediate 9) Step 4: Purification by chiral SFC, Chiralpak AD-H 2 × 15 cm, 5 um column, 40% methanol, F = 80 mL/min. |
| 68 | 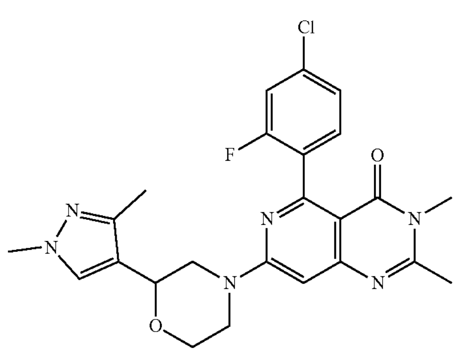 | 5-(4-chloro-2-fluorophenyl)-7-(2-(1,3-dimethyl-1H-pyrazol-4-yl)-4-morpholinyl)-2,3-dimethylpyrido[4,3-d]pyrimidin-4(3H)-one | Step 3: 2-(1,3-dimethyl-1H-pyrazol-4-yl)morpholine (Intermediate 10) |

TABLE 1-continued

Compounds 2 to 122 were prepared following the procedure described in Method 1, steps 1-3, as follows:

| Ex. # | Structure | Name | Reagents/Conditions |
|---|---|---|---|
| 69 | 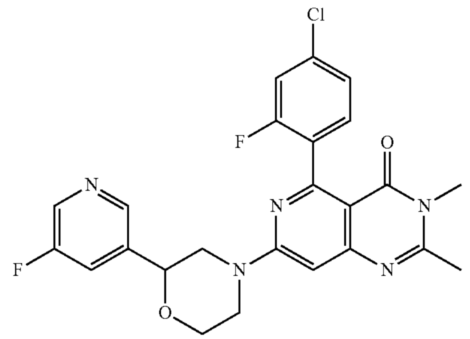 [SMILES: Cc1nc2cc(N3CCOC(c4cncc(F)c4)C3)nc(-c3ccc(Cl)cc3F)c2c(=O)n1C] | 5-(4-chloro-2-fluorophenyl)-7-(2-(5-fluoro-3-pyridinyl)-4-morpholinyl)-2,3-dimethylpyrido[4,3-d]pyrimidin-4(3H)-one | Step 3: 2-(5-fluoropyridin-3-yl)morpholine (Enamine Inc., Monmouth Jct., NJ, USA) |
| 70 | 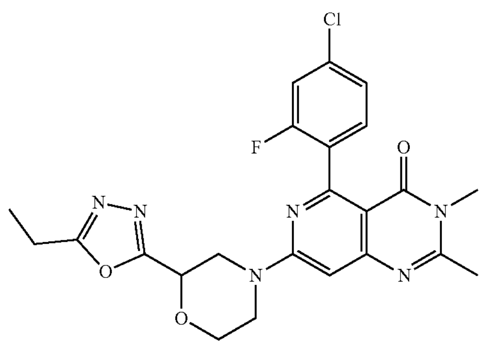 [SMILES: CCc1nnc(C2CN(c3cc4nc(C)n(C)c(=O)c4c(-c4ccc(Cl)cc4F)n3)CCO2)o1] | 5-(4-chloro-2-fluorophenyl)-7-(2-(5-ethyl-1,3,4-oxadiazol-2-yl)-4-morpholinyl)-2,3-dimethylpyrido[4,3-d]pyrimidin-4(3H)-one | Step 3: 2-(5-ethyl-1,3,4-oxadiazol-2-yl)morpholine (Enamine Inc., Monmouth Jct., NJ, USA) |
| 71 | 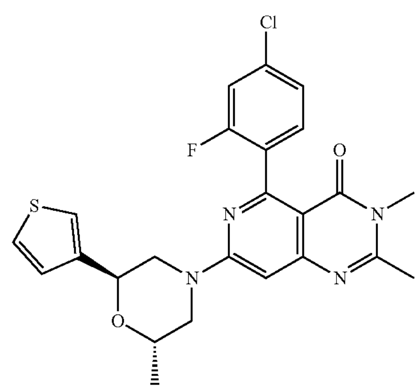 [SMILES: Cc1nc2cc(N3C[C@H](C)O[C@@H](c4ccsc4)C3)nc(-c3ccc(Cl)cc3F)c2c(=O)n1C] | 5-(4-chloro-2-fluorophenyl)-2,3-dimethyl-7-((2S,6S)-2-methyl-6-(3-thiophenyl)-4-morpholinyl)pyrido[4,3-d]pyrimidin-4(3H)-one. Absolute stereochemistry arbitrarily assigned. Relative stereochemistry determined by NMR. | Step 3: 2-methyl-6-(thiophen-3-yl)morpholine (Enamine Inc., Monmouth Jct., NJ, USA) Step 4: Purification by chiral SFC, Chiralpak AD-H 2 × 15 cm, 5 um column, 45% isopropanol, F = 80 mL/min. |
| 72 | 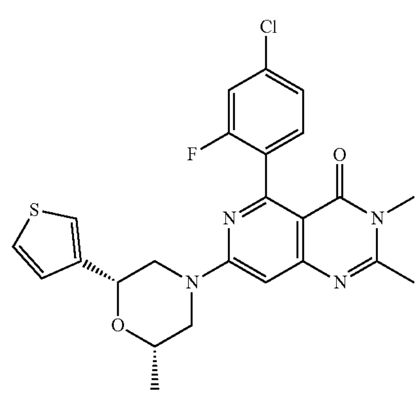 [SMILES: Cc1nc2cc(N3C[C@@H](c4ccsc4)O[C@@H](C)C3)nc(-c3ccc(Cl)cc3F)c2c(=O)n1C] | 5-(4-chloro-2-fluorophenyl)-2,3-dimethyl-7-((2S,6R)-2-methyl-6-(3-thiophenyl)-4-morpholinyl)pyrido[4,3-d]pyrimidin-4(3H)-one. Absolute stereochemistry arbitrarily assigned. Relative stereochemistry determined by NMR | Step 3: 2-methyl-6-(thiophen-3-yl)morpholine (Enamine Inc., Monmouth Jct., NJ, USA) Step 4: Purification by chiral SFC, Chiralpak AD-H 2 × 15 cm, 5 um column, 45% isopropanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 73 | 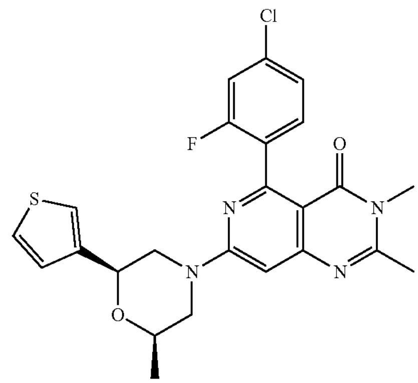 [SMILES: Cc1nc2cc(N3C[C@@H](C)O[C@@H](c4ccsc4)C3)nc(-c3ccc(Cl)cc3F)c2c(=O)n1C] | 5-(4-chloro-2-fluorophenyl)-2,3-dimethyl-7-((2R,6S)-2-methyl-6-(3-thiophenyl)-4-morpholinyl)pyrido[4,3-d]pyrimidin-4(3H)-one. Absolute stereochemistry arbitrarily assigned. Relative stereochemistry determined by NMR | Step 3: 2-methyl-6-(thiophen-3-yl)morpholine (Enamine Inc., Monmouth Jct., NJ, USA) Step 4: Purification by chiral SFC, Chiralpak AD-H 2 × 15 cm, 5 um column, 45% isopropanol, F = 80 mL/min. |
| 74 | 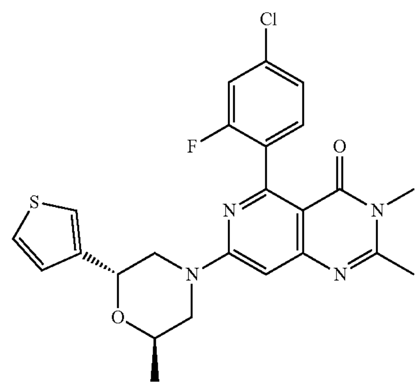 [SMILES: Cc1nc2cc(N3C[C@@H](C)O[C@H](c4ccsc4)C3)nc(-c3ccc(Cl)cc3F)c2c(=O)n1C] | 5-(4-chloro-2-fluorophenyl)-2,3-dimethyl-7-((2R,6R)-2-methyl-6-(3-thiophenyl)-4-morpholinyl)pyrido[4,3-d]pyrimidin-4(3H)-one. Absolute stereochemistry arbitrarily assigned. Relative stereochemistry determined by NMR | Step 3: 2-methyl-6-(thiophen-3-yl)morpholine (Enamine Inc., Monmouth Jct., NJ, USA) Step 4: Purification by chiral SFC, Chiralpak AD-H 2 × 15 cm, 5 um column, 45% isopropanol, F = 80 mL/min. |
| 75 | 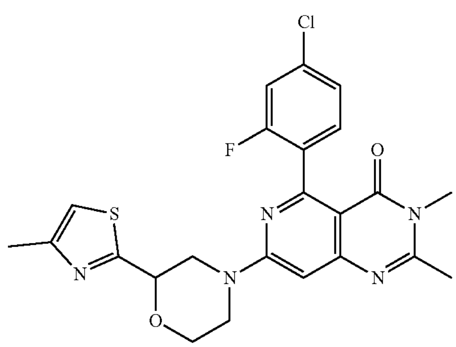 | 5-(4-chloro-2-fluorophenyl)-2,3-dimethyl-7-(2-(4-methyl-1,3-thiazol-2-yl)-4-morpholinyl)pyrido[4,3-d]pyrimidin-4(3H)-one | Step 3: 2-(4-methylthiazol-2-yl)morpholine (Enamine Inc., Monmouth Jct., NJ, USA) |
| 76 | 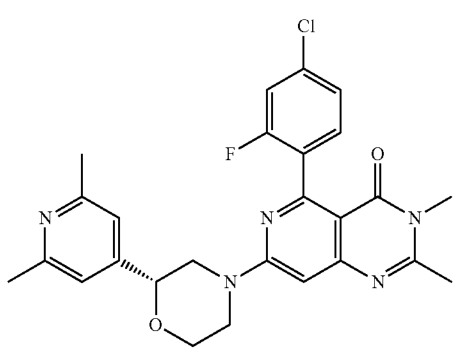 | 5-(4-chloro-2-fluorophenyl)-7-((2R)-2-(2,6-dimethyl-4-pyridinyl)-4-morpholinyl)-2,3-dimethylpyrido[4,3-d]pyrimidin-4(3H)-one. Absolute stereochemistry arbitrarily assigned. | Step 3: 2-(2,6-dimethyl-pyridin-4-yl)morpholine (Intermediate 13). |

TABLE 1-continued

Compounds 2 to 122 were prepared following the procedure described in Method 1, steps 1-3, as follows:

| Ex. # | Structure | Name | Reagents/Conditions |
|---|---|---|---|
| 77 | 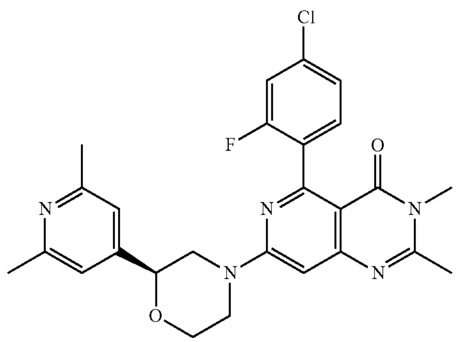 | 5-(4-chloro-2-fluorophenyl)-7-((2S)-2-(2,6-dimethyl-4-pyridinyl)-4-morpholinyl)-2,3-dimethylpyrido[4,3-d]pyrimidin-4(3H)-one. Absolute stereochemistry arbitrarily assigned. | Step 3: 2-(2,6-dimethylpyridin-4-yl)morpholine (Intermediate 12). |
| 78 | 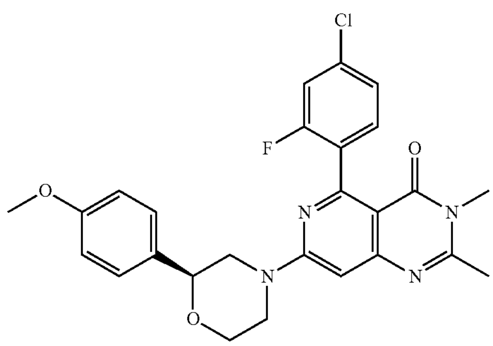 | 5-(4-chloro-2-fluorophenyl)-7-((2S)-2-(4-methoxyphenyl)-4-morpholinyl)-2,3-dimethylpyrido[4,3-d]pyrimidin-4(3H)-one. Absolute stereochemistry arbitrarily assigned. | Step 3: 2-(4-methoxyphenyl)-4-morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 79 | 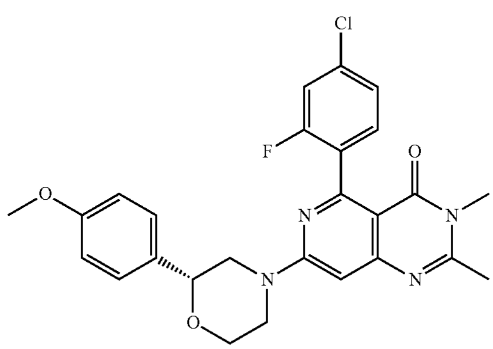 | 5-(4-chloro-2-fluorophenyl)-7-((2R)-2-(4-methoxyphenyl)-4-morpholinyl)-2,3-dimethylpyrido[4,3-d]pyrimidin-4(3H)-one. Absolute stereochemistry arbitrarily assigned. | Step 3: 2-(4-methoxyphenyl)-4-morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 80 | 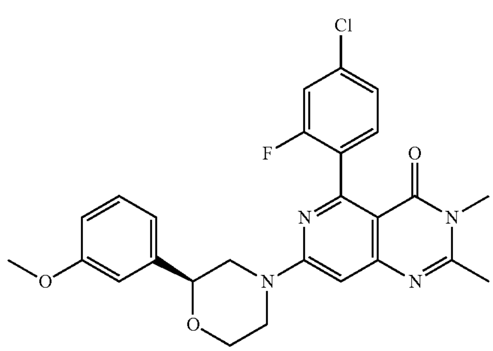 | 5-(4-chloro-2-fluorophenyl)-7-((2S)-2-(3-methoxyphenyl)-4-morpholinyl)-2,3-dimethylpyrido[4,3-d]pyrimidin-4(3H)-one. Absolute stereochemistiy arbitrarily assigned. | Step 3: 2-(3-methoxyphenyl)-4-morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 81 | 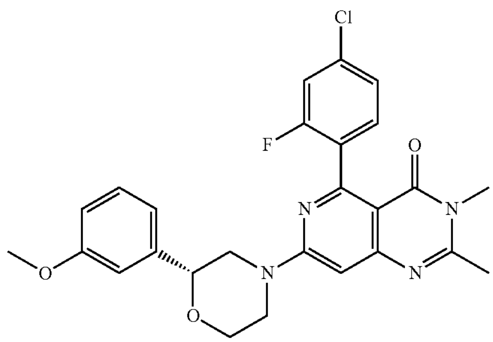 | 5-(4-chloro-2-fluorophenyl)-7-((2R)-2-(3-methoxyphenyl)-4-morpholinyl)-2,3-dimethylpyrido[4,3-d]pyrimidin-4(3H)-one. Absolute stereochemistry arbitrarily assigned. | Step 3: 2-(3-methoxyphenyl)-4-morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 82 | 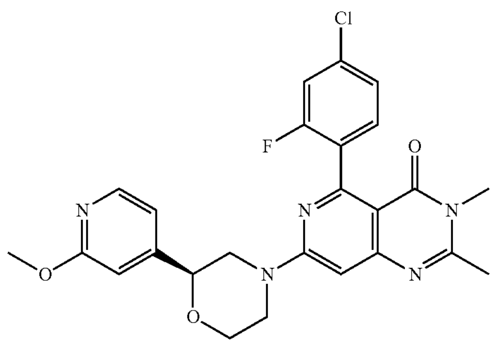 | 5-(4-chloro-2-fluorophenyl)-7-((2S)-2-(2-methoxy-4-pyridinyl)-4-morpholinyl)-2,3-dimethylpyrido[4,3-d]pyrimidin-4(3H)-one. Absolute stereochemistry arbitrarily assigned. | Step 3: 2-(2-methoxypyridin-4-yl)morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 83 | 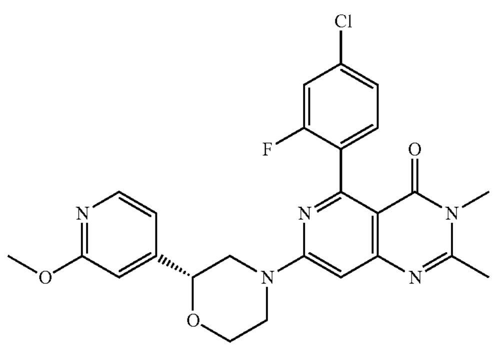 | 5-(4-chloro-2-fluorophenyl)-7-((2R)-2-(2-methoxy-4-pyridinyl)-4-morpholinyl)-2,3-dimethylpyrido[4,3-d]pyrimidin-4(3H)-one. Absolute stereochemistry arbitrarily assigned. | Step 3: 2-(2-methoxypyridin-4-yl)morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 84 | 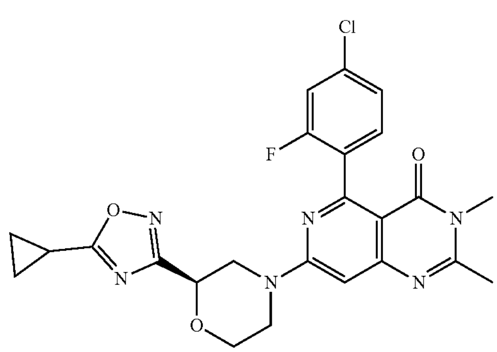 [SMILES: Cc1nc2cc(N3CCO[C@@H](c4noc(C5CC5)n4)C3)nc(-c3ccc(Cl)cc3F)c2c(=O)n1C] | 5-(4-chloro-2-fluorophenyl)-7-((2R)-2-(5-cyclopropyl-1,2,4-oxadiazol-3-yl)-4-morpholinyl)-2,3-dimethylpyrido[4,3-d]pyrimidin-4(3H)-one. Absolute stereochemistry arbitrarily assigned. | Step 3: 2-(5-cyclopropyl-1,2,4-oxadiazol-3-yl)morpholine (Intermediate 14) Step 4: Purification by chiral SFC, Chiralpak AD-H 2 × 15 cm, 5 um column, 40% isopropanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 85 | 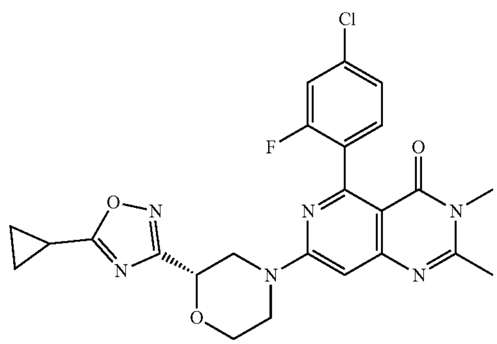 [SMILES: Cc1nc2cc(N3CCO[C@H](c4noc(C5CC5)n4)C3)nc(-c3ccc(Cl)cc3F)c2c(=O)n1C] | 5-(4-chloro-2-fluorophenyl)-7-((2S)-2-(5-cyclopropyl-1,2,4-oxadiazol-3-yl)-4-morpholinyl)-2,3-dimethylpyrido[4,3-d]pyrimidin-4(3H)-one. Absolute stereochemistry arbitrarily assigned. | Step 3: 2-(5-cyclopropyl-1,2,4-oxadiazol-3-yl)morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 86 | 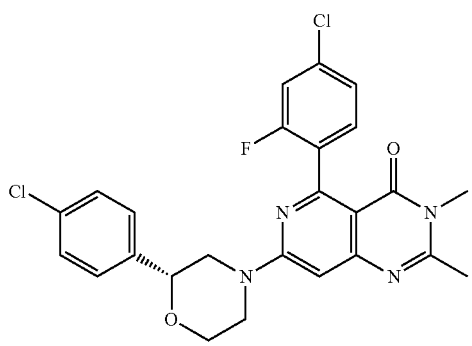 | 5-(4-chloro-2-fluorophenyl)-7-((2R)-2-(4-chlorophenyl)-4-morpholinyl)-2,3-dimethylpyrido[4,3-d]pyrimidin-4(3H)-one. Absolute stereochemistry arbitrarily assigned. | Step 3: 2-(4-chlorophenyl)-morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 87 | 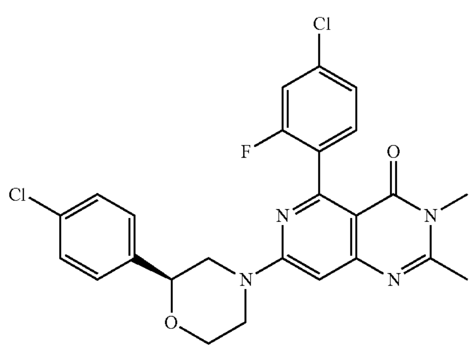 [SMILES: Cc1nc2cc(N3CCO[C@@H](c4ccc(Cl)cc4)C3)nc(-c3ccc(Cl)cc3F)c2c(=O)n1C] | 5-(4-chloro-2-fluorophenyl)-7-((2S)-2-(4-chlorophenyl)-4-morpholinyl)-2,3-dimethylpyrido[4,3-d]pyrimidin-4(3H)-one. Absolute stereochemistiy arbitrarily assigned. | Step 3: 2-(4-chlorophenyl)-morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 88 | 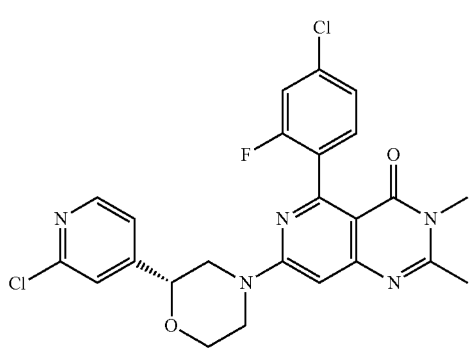 [SMILES: Cc1nc2cc(N3CCO[C@H](c4ccnc(Cl)c4)C3)nc(-c3ccc(Cl)cc3F)c2c(=O)n1C] | 5-(4-chloro-2-fluorophenyl)-7-((2R)-2-(2-chloro-4-pyridinyl)-4-morpholinyl)-2,3-dimethylpyrido[4,3-d]pyrimidin-4(3H)-one. Absolute stereochemistry arbitrarily assigned. | Step 3: 2-(2-chloropyridin-4-yl)morpholine (Enamine Inc., Monmouth Jct., NJ, USA) Step 4: Purification by chiral SFC, Chiralpak AD-H 2 × 15 cm, 5 um column, 40% isopropanol, F = 80 mL/min, |

TABLE 1-continued

Compounds 2 to 122 were prepared following the procedure described in Method 1, steps 1-3, as follows:

| Ex. # | Structure | Name | Reagents/Conditions |
|---|---|---|---|
| 89 | 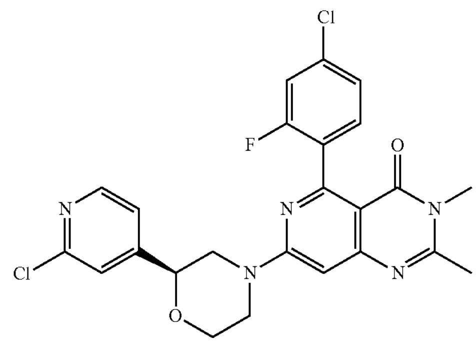 [SMILES: Cc1nc2cc(N3CCO[C@@H](c4ccnc(Cl)c4)C3)nc(-c3ccc(Cl)cc3F)c2c(=O)n1C] | 5-(4-chloro-2-fluorophenyl)-7-((2S)-2-(2-chloro-4-pyridinyl)-4-morpholinyl)-2,3-dimethylpyrido[4,3-d]pyrimidin-4(3H)-one. Absolute stereochemistry arbitrarily assigned. | Step 3: 2-(2-chloropyridin-4-yl)morpholine (Enamine Inc., Monmouth Jct., NJ, USA) Step 4: Purification by chiral SFC, Chiralpak AD-H 2 × 15 cm, 5 um column, 40% isopropanol, F = 80 mL/min, |
| 90 | 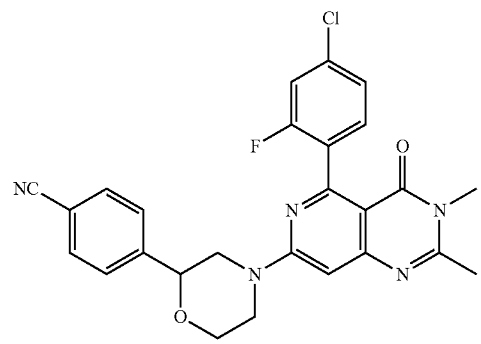 [SMILES: Cc1nc2cc(N3CCOC(c4ccc(C#N)cc4)C3)nc(-c3ccc(Cl)cc3F)c2c(=O)n1C] | 4-(4-(5-(4-chloro-2-fluoro-phenyl)-2,3-dimethyl-4-oxo-3,4-dihydropyrido[4,3-d]pyrimidin-7-yl)-2-morpholinyl)benzonitrile | Step 3: 4-(morpholin-2-yl)benzonitrile (Enamine Inc., Monmouth Jct., NJ, USA) |
| 91 | 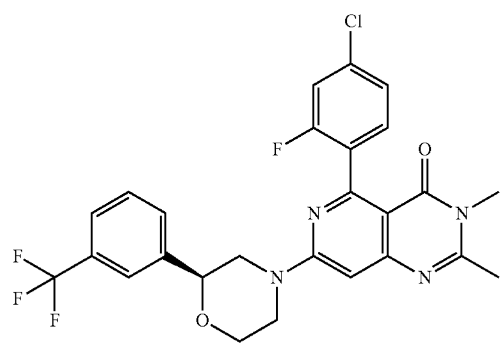 [SMILES: Cc1nc2cc(N3CCO[C@@H](c4cccc(C(F)(F)F)c4)C3)nc(-c3ccc(Cl)cc3F)c2c(=O)n1C] | 5-(4-chloro-2-fluorophenyl)-2,3-dimethyl-7-((2S)-2-(3-(trifluoromethyl)phenyl)-4-morpholinyl)pyrido[4,3-d]pyrimidin-4(3H)-one. Absolute stereochemistry arbitrarily assigned. | Step 3: 2-(3-(trifluoromethyl)-phenyl)morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 92 | 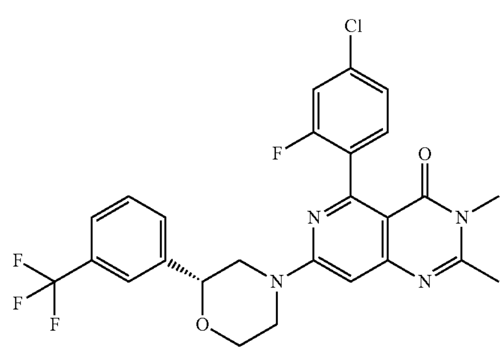 [SMILES: Cc1nc2cc(N3CCO[C@H](c4cccc(C(F)(F)F)c4)C3)nc(-c3ccc(Cl)cc3F)c2c(=O)n1C] | 5-(4-chloro-2-fluorophenyl)-2,3-dimethyl-7-((2R)-2-(3-(trifluoromethyl)phenyl)-4-morpholinyl)pyrido[4,3-d]pyrimidin-4(3H)-one. Absolute stereochemistry arbitrarily assigned. | Step 3: 2-(3-(trifluoromethyl)-phenyl)morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 93 | 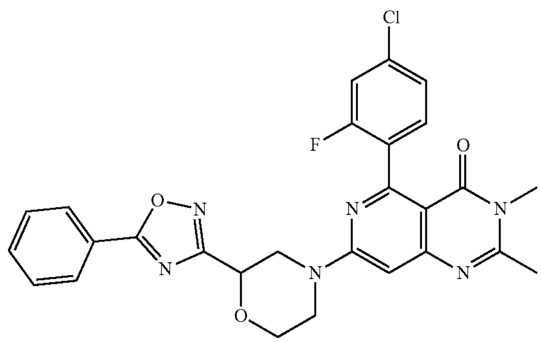 [SMILES: Cc1nc2cc(N3CCOC(c4noc(-c5ccccc5)n4)C3)nc(-c3ccc(Cl)cc3F)c2c(=O)n1C] | 5-(4-chloro-2-fluorophenyl)-2,3-dimethyl-7-(2-(5-phenyl-1,2,4-oxadiazol-3-yl)-4-morpholinyl)pyrido[4,3-d]pyrimidin-4(3H)-one | Step 3: 2-(5-phenyl-1,2,4-oxadiazol-3-yl)morpholine (Enamine Inc., Monmouth Jct., NJ, USA) |
| 94 | 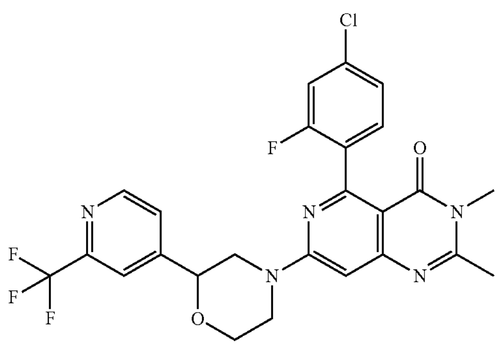 [SMILES: Cc1nc2cc(N3CCOC(c4ccnc(C(F)(F)F)c4)C3)nc(-c3ccc(Cl)cc3F)c2c(=O)n1C] | 5-(4-chloro-2-fluorophenyl)-2,3-dimethyl-7-(2-(2-(trifluoromethyl)-4-pyridinyl)-4-morpholinyl)pyrido[4,3-d]pyrimidin-4(3H)-one | Step 3: 2-(2-(trifluoromethyl)-pyridin-4-yl)morpholine (Intermediate 11) |
| 95 | 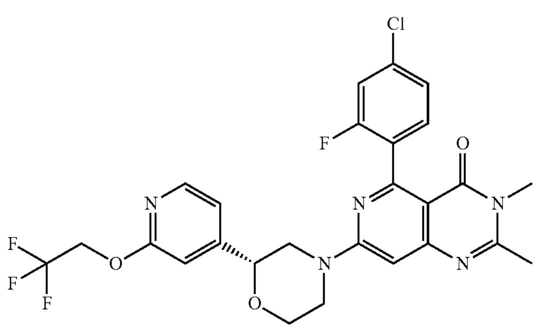 [SMILES: Cc1nc2cc(N3CCO[C@H](c4ccnc(OCC(F)(F)F)c4)C3)nc(-c3ccc(Cl)cc3F)c2c(=O)n1C] | 5-(4-chloro-2-fluorophenyl)-2,3-dimethyl-7-((2R)-2-(2-(2,2,2-trifluoroethoxy)-4-pyridinyl)-4-morpholinyl)pyrido[4,3-d]pyrimidin-4(3H)-one. Absolute stereochemistry arbitrarily assigned. | Step 3: 2-(2-(2,2,2-trifluoroethoxy)pyridin-4-yl)morpholine (Intermediate 15) Step 4: Purification by chiral SFC, Chiralpak AD-H 2 × 15 cm, 5 um column, 40% isopropanol, F = 80 mL/min. |
| 96 | 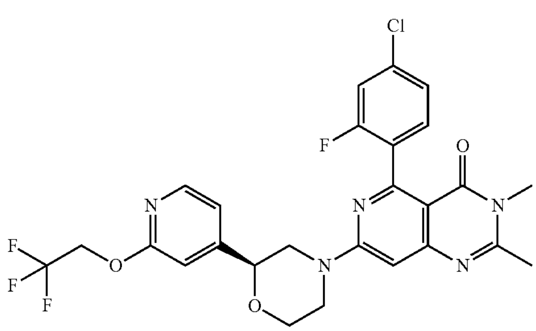 [SMILES: Cc1nc2cc(N3CCO[C@@H](c4ccnc(OCC(F)(F)F)c4)C3)nc(-c3ccc(Cl)cc3F)c2c(=O)n1C] | 5-(4-chloro-2-fluorophenyl)-2,3-dimethyl-7-((2S)-2-(2-(2,2,2-trifluoroethoxy)-4-pyridinyl)-4-morpholinyl)pyrido[4,3-d]pyrimidin-4(3H)-one. Absolute stereochemistry arbitrarily assigned. | Step 3: 2-(2-(2,2,2-trifluoroethoxy)pyridin-4-yl)morpholine (Intermediate 15) Step 4: Purification by chiral SFC, Chiralpak AD-H 2 × 15 cm, 5 um column, 40% isopropanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 97 | 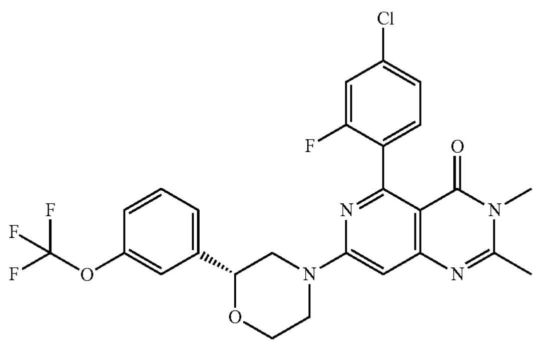 [SMILES: Cc1nc2cc(N3CCO[C@H](c4cccc(OC(F)(F)F)c4)C3)nc(-c3ccc(Cl)cc3F)c2c(=O)n1C] | 5-(4-chloro-2-fluorophenyl)-2,3-dimethyl-7-((2R)-2-(3-(trifluoromethoxy)phenyl)-4-morpholinyl)pyrido[4,3-d]pyrimidin-4(3H)-one. Absolute stereochemistry arbitrarily assigned. | Step 3: 2-(3-(trifluoromethoxy)phenyl)morpholine (Enamine Inc., Monmouth Jct., NJ, USA). Step 4: Purification by chiral SFC, Chiralpak AD-H 2 × 15 cm, 5 um column, 40% isopropanol, F = 80 mL/min. |
| 98 | 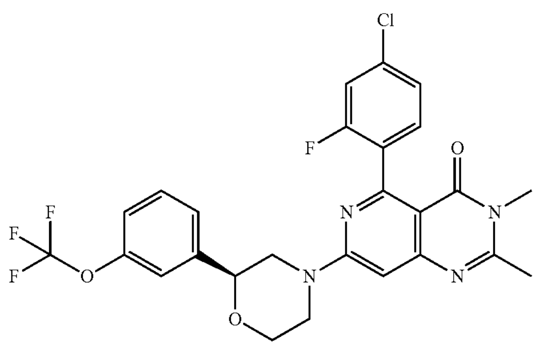 [SMILES: Cc1nc2cc(N3CCO[C@@H](c4cccc(OC(F)(F)F)c4)C3)nc(-c3ccc(Cl)cc3F)c2c(=O)n1C] | 5-(4-chloro-2-fluorophenyl)-2,3-dimethyl-7-((2S)-2-(3-(trifluoromethoxy)phenyl)-4-morpholinyl)pyrido[4,3-d]pyrimidin-4(3H)-one. Absolute stereochemistry arbitrarily assigned. | Step 3: 2-(3-(trifluoromethoxy)phenyl)morpholine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 99 | 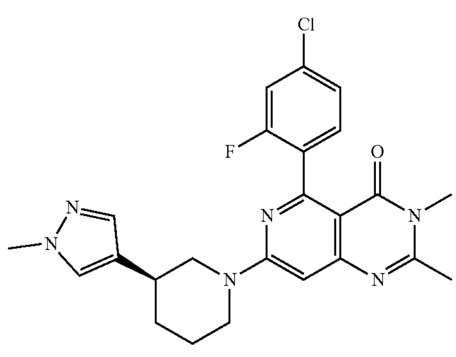 | 5-(4-chloro-2-fluorophenyl)-2,3-dimethyl-7-((3S)-3-(1-methyl-1H-pyrazol-4-yl)-1-piperidinyl)pyrido[4,3-d]pyrimidin-4(3H)-one. Absolute stereochemistry arbitrarily assigned. | Step 3: 3-(1-methyl-1H-pyrazol-4-yl)piperidine (Enamine Inc., Monmouth Jct., NJ, USA) Step 4: Purification by chiral SFC, Chiralpak AD-H 2 × 15 cm, 5 um column, 35% isopropanol, F = 80 mL/min. |
| 100 | 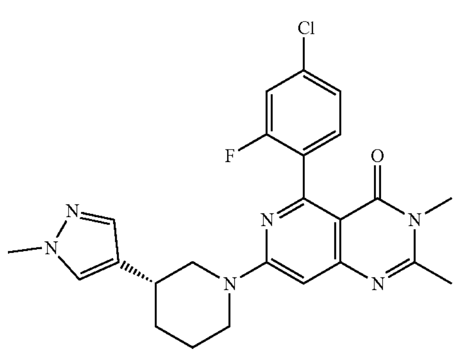 | 5-(4-chloro-2-fluorophenyl)-2,3-dimethyl-7-((3R)-3-(1-methyl-1H-pyrazol-4-yl)-1-piperidinyl)pyrido[4,3-d]pyrimidin-4(3H)-one. Absolute stereochemistry arbitrarily assigned. | Step 3: 3-(1-methyl-1H-pyrazol-4-yl)piperidine (Enamine Inc., Monmouth Jct., NJ, USA) Step 4: Purification by chiral SFC, Chiralpak AD-H 2 × 15 cm, 5 um column, 35% isopropanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 101 | 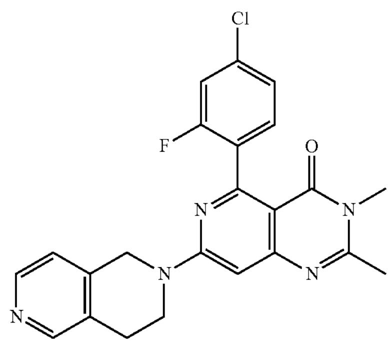 [SMILES: Cc1nc2cc(N3CCc4cnccc4C3)nc(-c3ccc(Cl)cc3F)c2c(=O)n1C] | 5-(4-chloro-2-fluorophenyl)-7-(3,4-dihydro-2,6-naphthyridin-2(1H)-yl)-2,3-dimethylpyrido[4,3-d]pyrimidin-4(3H)-one | Step 3: 1,2,3,4-tetrahydro-2,6-naphthyridine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 102 | 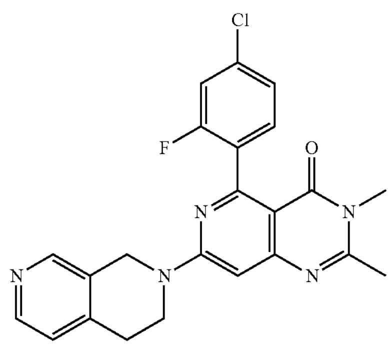 [SMILES: Cc1nc2cc(N3CCc4ccncc4C3)nc(-c3ccc(Cl)cc3F)c2c(=O)n1C] | 5-(4-chloro-2-fluorophenyl)-7-(3,4-dihydro-2,7-naphthyridin-2(1H)-yl)-2,3-dimethylpyrido[4,3-d]pyrimidin-4(3H)-one | Step 3: 1,2,3,4-tetrahydro-2,7-naphthyridine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 103 | 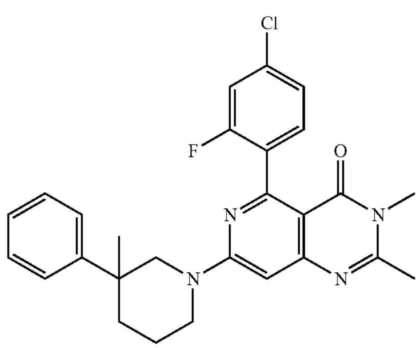 [SMILES: Cc1nc2cc(N3CCCC(C)(c4ccccc4)C3)nc(-c3ccc(Cl)cc3F)c2c(=O)n1C] | 5-(4-chloro-2-fluorophenyl)-2,3-dimethyl-7-(3-methyl-3-phenyl-1-piperidinyl)pyrido[4,3-d]pyrimidin-4(3H)-one | Step 3: 3-methyl-3-phenylpiperidine (Enamine Inc., Monmouth Jct., NJ, USA) |
| 104 | 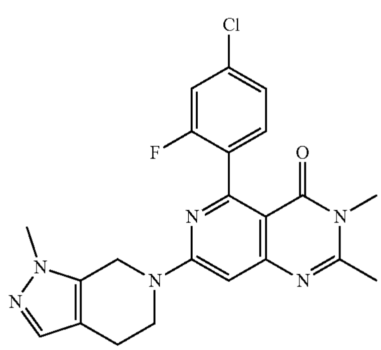 [SMILES: Cc1nc2cc(N3CCc4cnn(C)c4C3)nc(-c3ccc(Cl)cc3F)c2c(=O)n1C] | 5-(4-chloro-2-fluorophenyl)-2,3-dimethyl-7-(1-methyl-1,4,5,7-tetrahydro-6H-pyrazolo[3,4-c]pyridin-6-yl)pyrido[4,3-d]pyrimidin-4(3H)-one | Step 3: 1-methyl-4,5,6,7-tetrahydro-1H-pyrazolo[3,4-c]pyridine (Enamine Inc., Monmouth Jct., NJ, USA) Step 4: Purification by chiral SFC, Chiralpak AD-H 2 × 15 cm, 5 um column, 40% isopropanol, F = 80 mL/min |

TABLE 1-continued

Compounds 2 to 122 were prepared following the procedure described in Method 1, steps 1-3, as follows:

| Ex. # | Structure | Name | Reagents/Conditions |
|---|---|---|---|
| 105 | 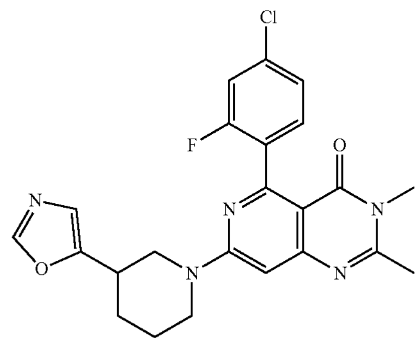 [SMILES: Cc1nc2cc(N3CCCC(c4cnco4)C3)nc(-c3ccc(Cl)cc3F)c2c(=O)n1C] | 5-(4-chloro-2-fluorophenyl)-2,3-dimethyl-7-(3-(1,3-oxazol-5-yl)-1-piperidinyl)pyrido[4,3-d]pyrimidin-4(3H)-one | Step 3: 5-(piperidin-3-yl)oxazole (Enamine Inc., Monmouth Jct., NJ, USA) |
| 106 | 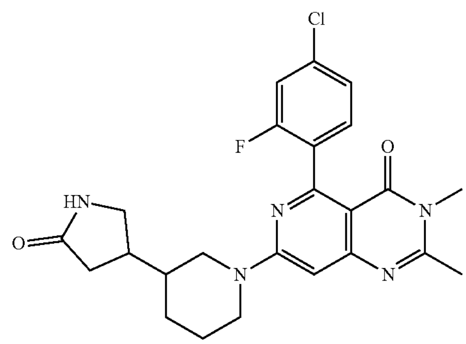 | 5-(4-chloro-2-fluorophenyl)-2,3-dimethyl-7-(3-(5-oxo-3-pyrrolidinyl)-1-piperidinyl)pyrido[4,3-d]pyrimidin-4(3H)-one | Step 3: 4-(piperidin-3-yl)pyrrolidin-2-one (Enamine Inc., Monmouth Jct., NJ, USA) |
| 107 | 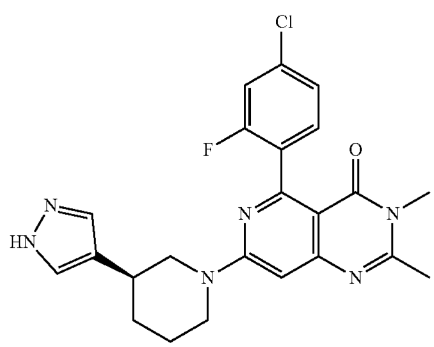 | 5-(4-chloro-2-fluorophenyl)-2,3-dimethyl-7-((3S)-3-(1H-pyrazol-4-yl)-1-piperidinyl)pyrido[4,3-d]pyrimidin-4(3H)-one. Absolute stereochemistry arbitrarily assigned. | Step 3: 3-(1H-pyrazol-4-yl)piperidine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 108 | 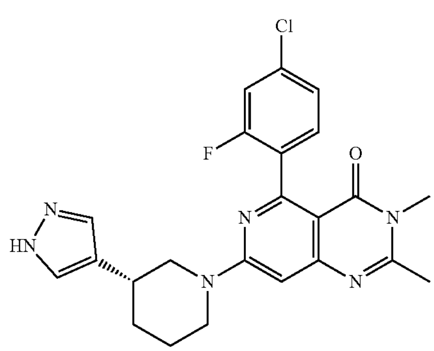 | 5-(4-chloro-2-fluorophenyl)-2,3-dimethyl-7-((3R)-3-(1H-pyrazol-4-yl)-1-piperidinyl)pyrido[4,3-d]pyrimidin-4(3H)-one. Absolute stereochemistry arbitrarily assigned. | Step 3: 3-(1H-pyrazol-4-yl)piperidine (Enamine Inc., Monmouth Jct., NJ, USA) Step 4: Purification by chiral SFC, Chiralpak AD-H 2 × 15 cm, 5 um column, 40% isopropanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 109 | 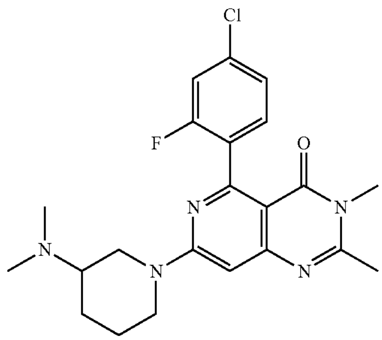 | 5-(4-chloro-2-fluorophenyl)-7-(3-(dimethylamino)-1-piperidinyl)-2,3-dimethylpyrido[4,3-d]pyrimidin-4(3H)-one | Step 3: N,N-dimethyl-piperidin-3-amine (Enamine Inc., Monmouth Jct., NJ, USA) |
| 110 | 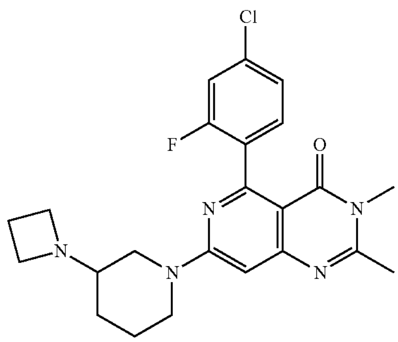 | 7-(3-(1-azetidinyl)-1-piperidinyl)-5-(4-chloro-2-fluorophenyl)-2,3-dimethylpyrido[4,3-d]pyrimidin-4(3H)-one | Step 3: 3-(azetidin-1-yl)piperidine (Enamine Inc., Monmouth Jct., NJ, USA) |
| 111 | 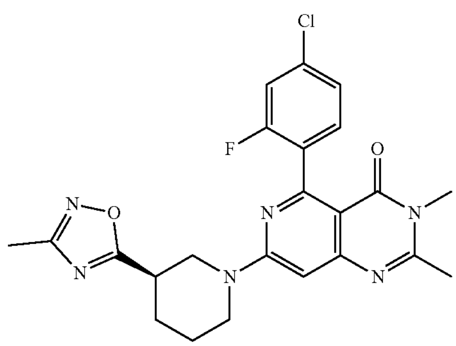 | 5-(4-chloro-2-fluorophenyl)-2,3-dimethyl-7-((3R)-3-(3-methyl-1,2,4-oxadiazol-5-yl)-1-piperidinyl)pyrido[4,3-d]pyrimidin-4(3H)-one. Absolute stereochemistry arbitrarily assigned. | Step 3: 3-methyl-5-(piperidin-3-yl)-1,2,4-oxadiazole (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 112 | 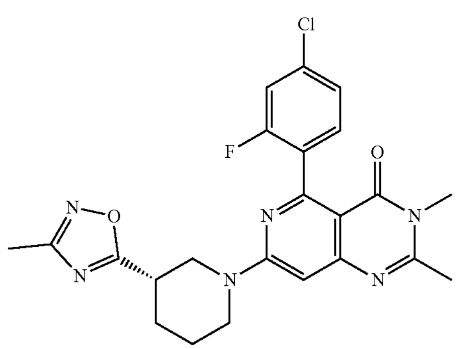 | 5-(4-chloro-2-fluorophenyl)-2,3-dimethyl-7-((3S)-3-(3-methyl-1,2,4-oxadiazol-5-yl)-1-piperidinyl)pyrido[4,3-d]pyrimidin-4(3H)-one. Absolute stereochemistry arbitrarily assigned. | Step 3: 3-methyl-5-(piperidin-3-yl)-1,2,4-oxadiazole (Enamine Inc., Monmouth Jct., NJ, USA) Step 4: Purification by chiral SFC, Chiralpak AD-H 2 × 15 cm, 5 um column, 40% isopropanol, F = 80 mL/min. |

TABLE 1-continued

Compounds 2 to 122 were prepared following the procedure described in Method 1, steps 1-3, as follows:

| Ex. # | Structure | Name | Reagents/Conditions |
|---|---|---|---|
| 113 | 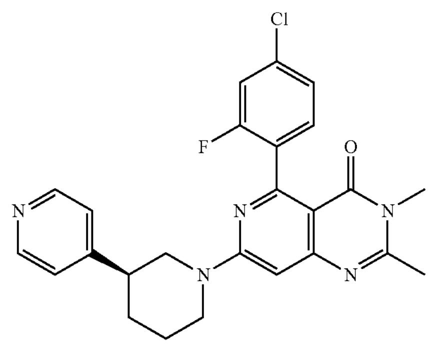 | 5-(4-chloro-2-fluorophenyl)-2,3-dimethyl-7-((3S)-3-(4-pyridinyl)-1-piperidinyl)pyrido[4,3-d]pyrimidin-4(3H)-one. Absolute stereochemistry arbitrarily assigned. | Step 3: 4-(piperidin-3-yl)pyridine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 114 | 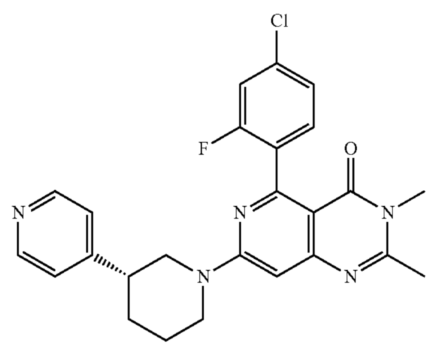 | 5-(4-chloro-2-fluorophenyl)-2,3-dimethyl-7-((3R)-3-(4-pyridinyl)-1-piperidinyl)pyrido[4,3-d]pyrimidin-4(3H)-one. Absolute stereochemistry arbitrarily assigned. | Step 3: 4-(piperidin-3-yl)pyridine (Enamine Inc., Monmouth Jct., NJ, USA) Step 4: Purification by chiral SFC, Chiralpak AD-H 2 × 15 cm, 5 um column, 40% isopropanol, F = 80 mL/min. |
| 115 | 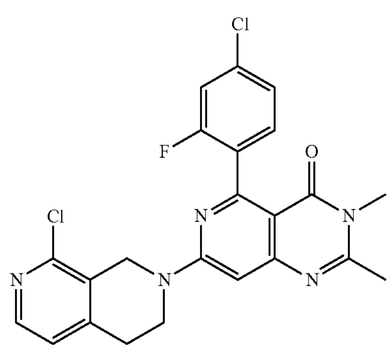 [SMILES: Cc1nc2cc(N3CCc4ccnc(Cl)c4C3)nc(-c3ccc(Cl)cc3F)c2c(=O)n1C] | 7-(8-chloro-3,4-dihydro-2,7-naphthyridin-2(1H)-yl)-5-(4-chloro-2-fluorophenyl)-2,3-dimethylpyrido[4,3-d]pyrimidin-4(3H)-one | Step 3: 8-chloro-1,2,3,4-tetrahydro-2,7-naphthyridine (Enamine Inc., Monmouth Jct., NJ, USA) |
| 116 | 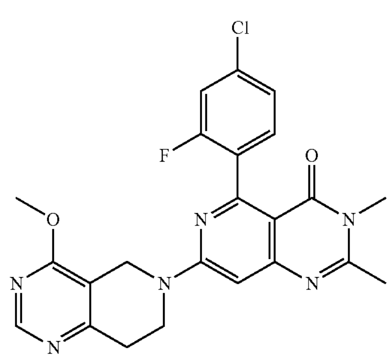 [SMILES: COc1ncnc2c1CN(c1cc3nc(C)n(C)c(=O)c3c(-c3ccc(Cl)cc3F)n1)CC2] | 5'-(4-chloro-2-fluorophenyl)-4-methoxy-2',3'-dimethyl-7,8-dihydro-5H-[6,7'-bipyrido[4,3-d]pyrimidin]-4'(3'H)-one | Step 3: 4-methoxy-5,6,7,8-tetrahydropyrido[4,3-d]pyrimidine (Enamine Inc., Monmouth Jct., NJ, USA) |

TABLE 1-continued

Compounds 2 to 122 were prepared following the procedure described in Method 1, steps 1-3, as follows:

| Ex. # | Structure | Name | Reagents/Conditions |
|---|---|---|---|
| 117 | 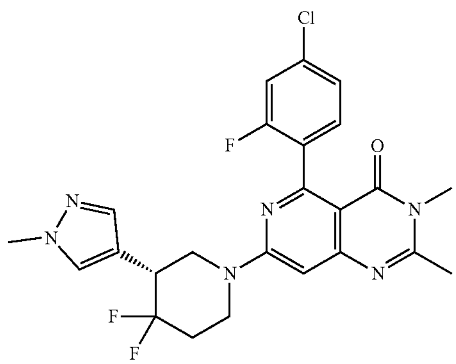 | 5-(4-chloro-2-fluorophenyl)-7-((3R)-4,4-difluoro-3-(1-methyl-1H-pyrazol-4-yl)-1-piperidinyl)-2,3-dimethylpyrido[4,3-d]pyrimidin-4(3H)-one. Absolute stereochemistry arbitrarily assigned. | Step 3: 4,4-difluoro-3-(1-methyl-1H-pyrazol-4-yl)piperidine (Intermediate 17) Step 4: Purification by chiral SFC, Chiralpak AD-H 2 × 15 cm, 5 um column, 40% isopropanol, F = 80 mL/min. |
| 118 | 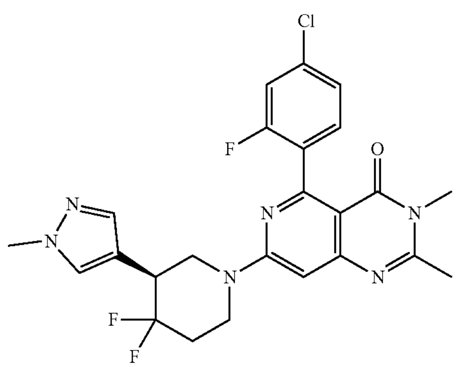 | 5-(4-chloro-2-fluorophenyl)-7-((3S)-4,4-difluoro-3-(1-methyl-1H-pyrazol-4-yl)-1-piperidinyl)-2,3-dimethylpyrido[4,3-d]pyrimidin-4(3H)-one. Absolute stereochemistry arbitrarily assigned. | Step 3: 4,4-difluoro-3-(1-methyl-1H-pyrazol-4-yl)piperidine (Intermediate 17) Step 4: Purification by chiral SFC, Chiralpak AD-H 2 × 15 cm, 5 um column, 40% isopropanol, F = 80 mL/min. |
| 119 | 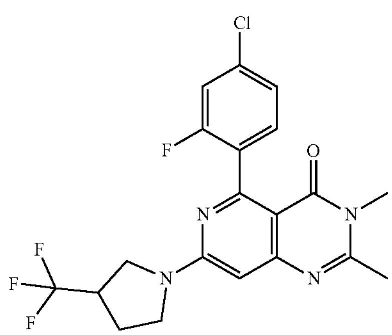 | 5-(4-chloro-2-fluorophenyl)-2,3-dimethyl-7-(3-(trifluoromethyl)-1-pyrrolidinyl)pyrido[4,3-d]pyrimidin-4(3H)-one | Step 3: 3-(trifluoromethyl)pyrrolidine (Combi-Blocks Inc., San Diego, CA, USA) |
| 120 | 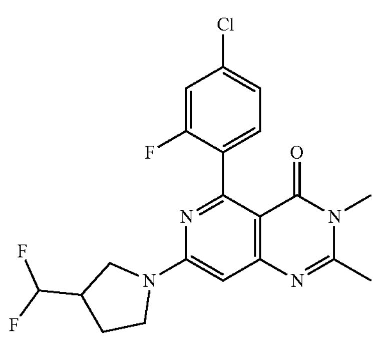 [SMILES: Cc1nc2cc(N3CCC(C(F)F)C3)nc(-c3ccc(Cl)cc3F)c2c(=O)n1C] | 5-(4-chloro-2-fluorophenyl)-7-(3-(difluoromethyl)-1-pyrrolidinyl)-2,3-dimethylpyrido[4,3-d]pyrimidin-4(3H)-one | Step 3: 3-(difluoromethyl)pyrrolidine (Enamine Inc., Monmouth Jct., NJ, USA) |

TABLE 1-continued

Compounds 2 to 122 were prepared following the procedure described in Method 1, steps 1-3, as follows:

| Ex. # | Structure | Name | Reagents/Conditions |
|---|---|---|---|
| 121 | 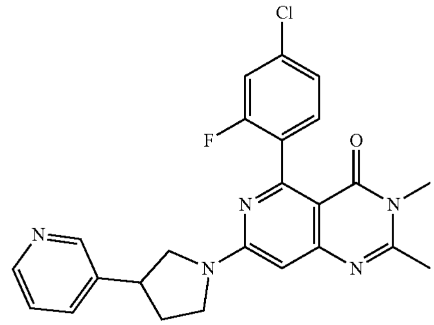 | 5-(4-chloro-2-fluorophenyl)-2,3-dimethyl-7-(3-(3-pyridinyl)-1-pyrrolidinyl)pyrido[4,3-d]pyrimidin-4(3H)-one | Step 3: 3-(pyrrolidin-3-yl)pyridine (Combi-Blocks Inc., San Diego, CA, USA) |
| 122 | 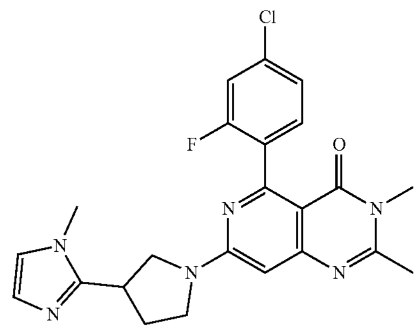 [SMILES: Cc1nc2cc(N3CCC(c4nccn4C)C3)nc(-c3ccc(Cl)cc3F)c2c(=O)n1C] | 5-(4-chloro-2-fluorophenyl)-2,3-dimethyl-7-(3-(1-methyl-1H-imidazol-2-yl)-1-pyrrolidinyl)pyrido[4,3-d]pyrimidin-4(3H)-one | Step 3: 1-methyl-2-(pyrrolidin-3-yl)-1H-imidazole (Enamine Inc., Monmouth Jct., NJ, USA) |

Method 2

Example 123: 5-(4-chloro-2-fluorophenyl)-2,3-dimethyl-7-((2S)-2-(1-(2-propanyl)-1H-pyrazol-4-yl)-4-morpholinyl)pyrido[4,3-d]pyrimidin-4(3H)-one

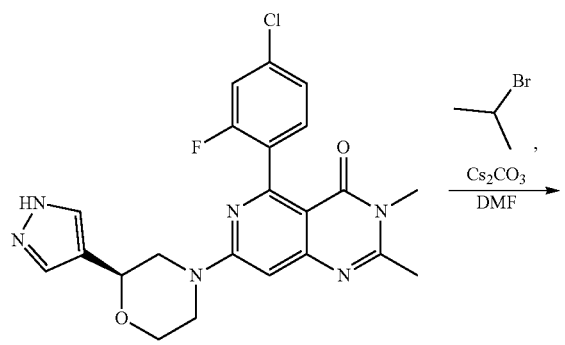

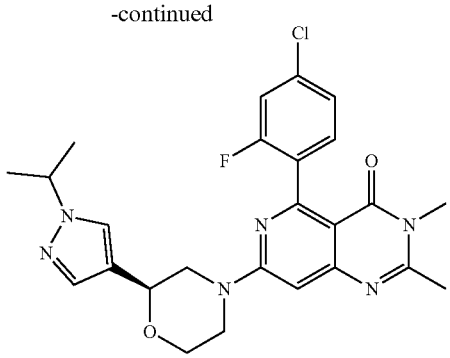

To a solution of (S)-7-(2-(1H-pyrazol-4-yl)morpholino)-5-(4-chloro-2-fluorophenyl)-2,3-dimethylpyrido[4,3-d]pyrimidin-4(3H)-one (Example 1-22, 0.065 g, 0.143 mmol) in DMF (0.572 mL) was added cesium carbonate (0.093 g, 0.286 mmol) and 2-bromopropane (0.053 g, 0.040 mL, 0.429 mmol). The reaction mixture was stirred at 60° C. overnight then cooled to room temperature. The reaction mixture was diluted with 20 mL DCM, washed with water 2×15 mL and the organic phase was separated and concentrated under vacuum. The crude product was purified by column chromatography eluting with a gradient of 0-10% MeOH (+0.1% NH$_3$) in DCM to afford 5-(4-chloro-2-fluorophenyl)-2,3-dimethyl-7-((2S)-2-(1-(2-propanyl)-1H- pyrazol-4-yl)-4-morpholinyl)pyrido[4,3-d]pyrimidin-4 (3H)-one (0.048 g, 0.097 mmol, 67.6% yield) as an off-white solid. ¹H NMR (500 MHz, DMSO-d6) δ 7.80 (s, 1H), 7.46 (s, 1H), 7.36-7.41 (m, 2H), 7.31 (dd, J=2.01, 8.24 Hz, 1H), 6.84 (s, 1H), 4.50 (dd, J=2.53, 10.44 Hz, 1H), 4.45 (td, J=6.63, 13.33 Hz, 1H), 4.39 (br d, J=12.20 Hz, 1H), 4.25 (br d, J=12.07 Hz, 1H), 3.97 (dd, J=2.01, 11.61 Hz, 1H), 3.66 (dt, J=2.47, 11.55 Hz, 1H), 3.34 (s, 3H), 2.97-3.08 (m, 2H), 2.52 (s, 3H), 1.40 (s, 3H), 1.38 (s, 3H). m/z (ESI, +ive ion): 497.0 (M+Na).

TABLE 2

Compounds 124 to 134 were prepared following the procedure described in Method 2, as follows:

| Ex. # | Structure | Name | Reagents/Conditions |
|---|---|---|---|
| 124 | 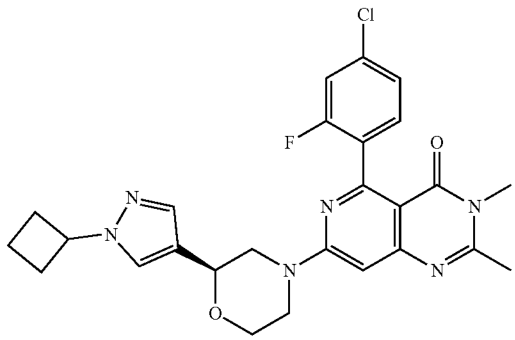 [SMILES: Cc1nc2cc(N3CCO[C@@H](c4cnn(C5CCC5)c4)C3)nc(-c3ccc(Cl)cc3F)c2c(=O)n1C] | 5-(4-chloro-2-fluorophenyl)-7-((2S)-2-(1-cyclobutyl-1H-pyrazol-4-yl)-4-morpholinyl)-2,3-dimethylpyrido[4,3-d]pyrimidin-4(3H)-one | Step 1: bromocyclobutane |
| 125 | 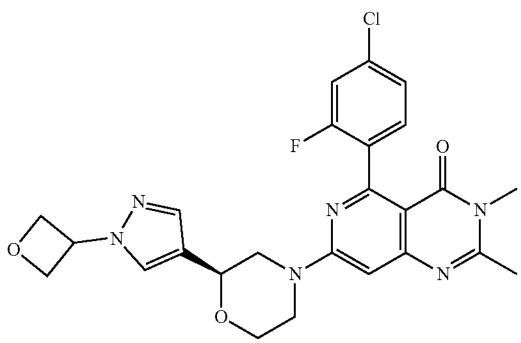 [SMILES: Cc1nc2cc(N3CCO[C@@H](c4cnn(C5COC5)c4)C3)nc(-c3ccc(Cl)cc3F)c2c(=O)n1C] | 5-(4-chloro-2-fluorophenyl)-2,3-dimethyl-7-((2S)-2-(1-(3-oxetanyl)-1H-pyrazol-4-yl)-4-morpholinyl)pyrido[4,3-d]pyrimidin-4(3H)-one | Step 1: 3-iodooxetane |
| 126 | 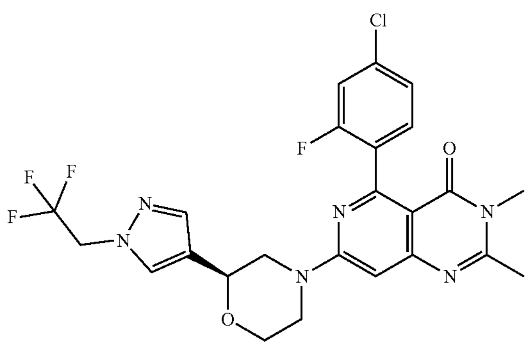 [SMILES: Cc1nc2cc(N3CCO[C@@H](c4cnn(CC(F)(F)F)c4)C3)nc(-c3ccc(Cl)cc3F)c2c(=O)n1C] | 5-(4-chloro-2-fluorophenyl)-2,3-dimethyl-7-((2S)-2-(1-(2,2,2-trifluoroethyl)-1H-pyrazol-4-yl)-4-morpholinyl)pyrido[4,3-d]pyrimidin-4(3H)-one | Step 1: 2,2,2-trifluoroethyl trifluoromethanesulfonate |
| 127 | 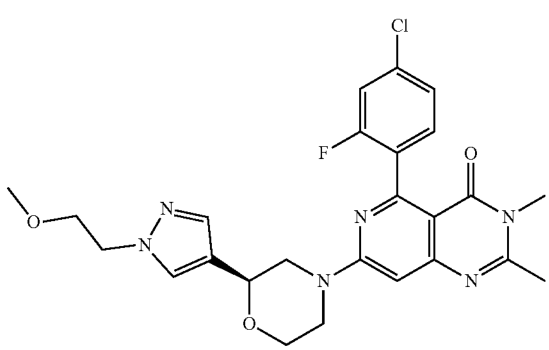 | 5-(4-chloro-2-fluorophenyl)-7-((2S)-2-(1-(2-methoxyethyl)-1H-pyrazol-4-yl)-4-morpholinyl)-2,3-dimethylpyrido[4,3-d]pyrimidin-4(3H)-one | Step 1: 1-bromo-2-methoxyethane |

TABLE 2-continued

Compounds 124 to 134 were prepared following the procedure described in Method 2, as follows:

| Ex. # | Structure | Name | Reagents/Conditions |
|---|---|---|---|
| 128 | 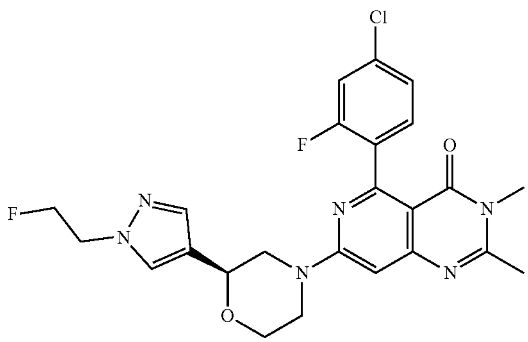 [SMILES: Cc1nc2cc(N3CCO[C@@H](c4cnn(CCF)c4)C3)nc(-c3ccc(Cl)cc3F)c2c(=O)n1C] | 5-(4-chloro-2-fluorophenyl)-7-((2S)-2-(1-(2-fluoroethyl)-1H-pyrazol-4-yl)-4-morpholinyl)-2,3-dimethylpyrido[4,3-d]pyrimidin-4(3H)-one | Step 1: 1-bromo-2-fluoroethane |
| 129 | 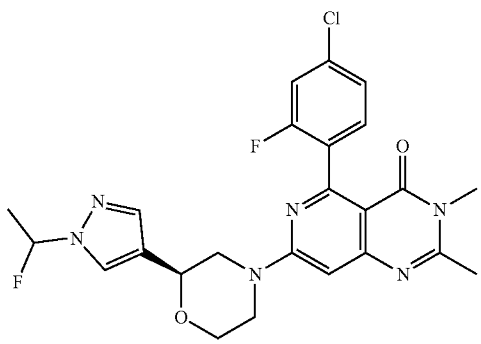 [SMILES: Cc1nc2cc(N3CCO[C@@H](c4cnn(C(C)F)c4)C3)nc(-c3ccc(Cl)cc3F)c2c(=O)n1C] | 5-(4-chloro-2-fluorophenyl)-7-((2S)-2-(1-(1-fluoroethyl)-1H-pyrazol-4-yl)-4-morpholinyl)-2,3-dimethylpyrido[4,3-d]pyrimidin-4(3H)-one | Step 1: 1-bromo-1-fluoroethane |
| 130 | 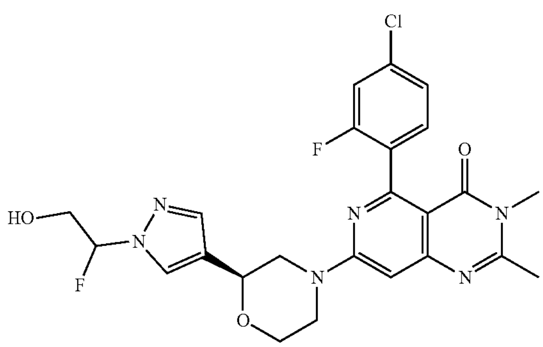 [SMILES: Cc1nc2cc(N3CCO[C@@H](c4cnn(C(F)CO)c4)C3)nc(-c3ccc(Cl)cc3F)c2c(=O)n1C] | 5-(4-chloro-2-fluorophenyl)-7-((2S)-2-(1-(1-fluoro-2-hydroxyethyl)-1H-pyrazol-4-yl)-4-morpholinyl)-2,3-dimethylpyrido[4,3-d]pyrimidin-4(3H)-one | Step 1: 2-bromo-2-fluoroethan-1-ol |
| 131 | 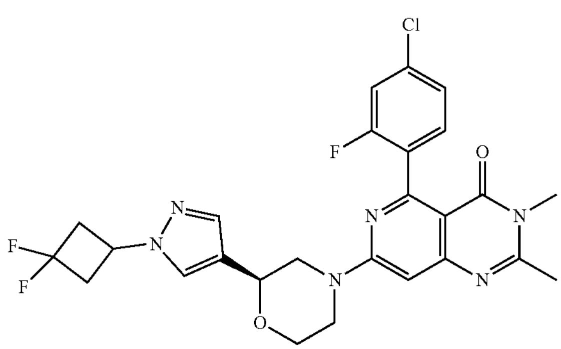 [SMILES: Cc1nc2cc(N3CCO[C@@H](c4cnn(C5CC(F)(F)C5)c4)C3)nc(-c3ccc(Cl)cc3F)c2c(=O)n1C] | 5-(4-chloro-2-fluorophenyl)-7-((2S)-2-(1-(3,3-difluorocyclobutyl)-1H-pyrazol-4-yl)-4-morpholinyl)-2,3-dimethylpyrido[4,3-d]pyrimidin-4(3H)-one | Step 1: 3,3-difluorocyclobutyl trifluoromethanesulfonate |

TABLE 2-continued

Compounds 124 to 134 were prepared following the procedure described in Method 2, as follows:

| Ex. # | Structure | Name | Reagents/Conditions |
|---|---|---|---|
| 132 | 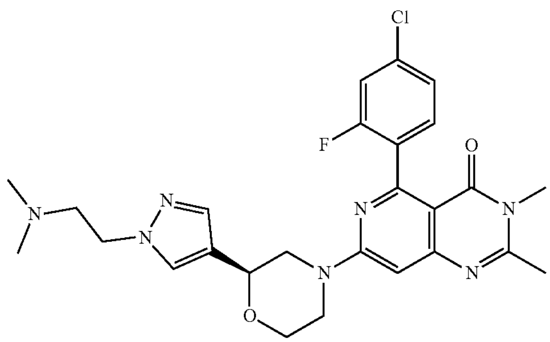 | 5-(4-chloro-2-fluorophenyl)-7-((2S)-2-(1-(2-(dimethylamino)ethyl)-1H-pyrazol-4-yl)-4-morpholinyl)-2,3-dimethylpyrido[4,3-d]pyrimidin-4(3H)-one | Step 1: 2-bromo-N,N-dimethylethan-1-amine hydrobromide |
| 133 | 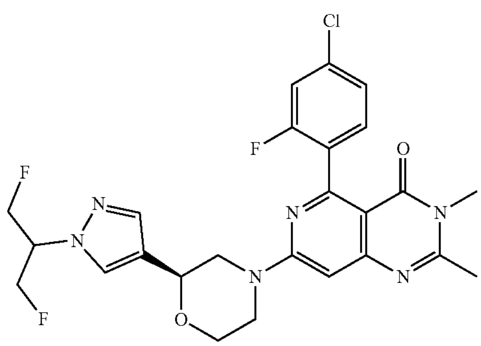 [SMILES: Cc1nc2cc(N3CCO[C@@H](c4cnn(C(CF)CF)c4)C3)nc(-c3ccc(Cl)cc3F)c2c(=O)n1C] | 5-(4-chloro-2-fluorophenyl)-7-((2S)-2-(1-(1,3-difluoro-2-propanyl)-1H-pyrazol-4-yl)-4-morpholinyl)-2,3-dimethylpyrido[4,3-d]pyrimidin-4(3H)-one | Step 1: 1,3-difluoropropan-2-yl trifluoromethanesulfonate |
| 134 | 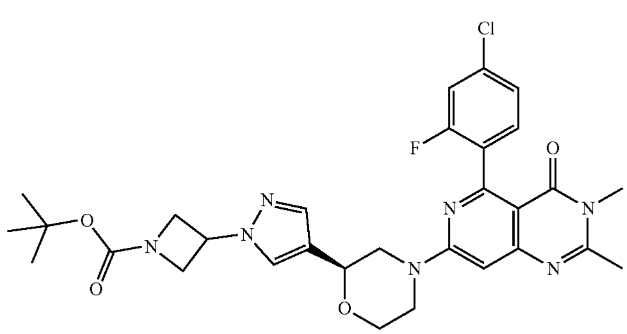 [SMILES: Cc1nc2cc(N3CCO[C@@H](c4cnn(C5CN(C(=O)OC(C)(C)C)C5)c4)C3)nc(-c3ccc(Cl)cc3F)c2c(=O)n1C] | 2-methyl-2-propanyl 3-(4-((2S)-4-(5-(4-chloro-2-fluorophenyl)-2,3-dimethyl-4-oxo-3,4-dihydropyrido[4,3-d]pyrimidin-7-yl)-2-morpholinyl)-1H-pyrazol-1-yl)-1-azetidinecarboxylate | Step 1: tert-butyl 3-iodoazetidine-1-carboxylate |

Method 3

Example 135: 5-(4-chloro-2-fluorophenyl)-7-((2S)-2-(1-(1,2-difluoroethyl)-1H-pyrazol-4-yl)-4-morpholinyl)-2,3-dimethylpyrido[4,3-d]pyrimidin-4(3H)-one

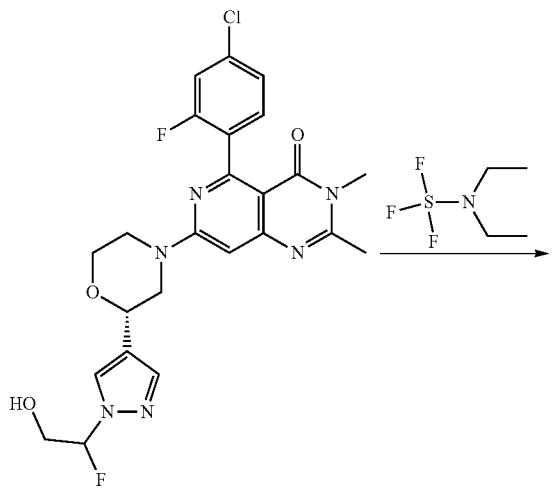

To a solution of 5-(4-chloro-2-fluorophenyl)-7-((2S)-2-(1-(1-fluoro-2-hydroxyethyl)-1H-pyrazol-4-yl)morpholino)-2,3-dimethylpyrido[4,3-d]pyrimidin-4(3H)-one (0.0485 g, 0.094 mmol, 125604-46-1) in DCM (0.938 mL) at −78° C. was slowly added a solution of DAST (1M in DCM) (0.117 mL, 0.117 mmol). The reaction mixture was allowed to warm to room temperature and stirred for 4 h. The reaction was quenched with saturated NaHCO₃ solution and the phases were separated. The organic phase was concentrated under vacuum and the crude was purified by column chromatography eluting with a gradient of 0-10% MeOH(+1% NH₃) in DCM to afford 5-(4-chloro-2-fluorophenyl)-7-((2S)-2-(1-(1,2-difluoroethyl)-1H-pyrazol-4-yl)-4-morpholinyl)-2,3-dimethylpyrido[4,3-d]pyrimidin-4(3H)-one (0.029 g, 0.056 mmol, 59.6% yield) as a white solid. ¹H NMR (500 MHz, DMSO-d6) δ ppm 8.15-8.18 (m, 1H), 7.78-7.81 (m, 1H), 7.37-7.41 (m, 2H), 7.29-7.33 (m, 1H), 6.86-6.88 (m, 1H), 6.80-6.84 (m, 1H), 4.86-4.93 (m, 2H), 4.56-4.59 (m, 1H), 4.41-4.45 (m, 1H), 4.22-4.27 (m, 1H), 3.98-4.02 (m, 1H), 3.66-3.71 (m, 1H), 3.33-3.35 (m, 3H), 3.03-3.09 (m, 1H), 2.96-3.02 (m, 1H), 2.51-2.53 (m, 3H). m/z (ESI, +ive ion): 541 (M+H).

Method 4

Example 136: 5-(4-chloro-2-fluorophenyl)-7-((2S)-2-(1-cyclopropyl-1H-pyrazol-4-yl)-4-morpholinyl)-2,3-dimethylpyrido[4,3-d]pyrimidin-4(3H)-one

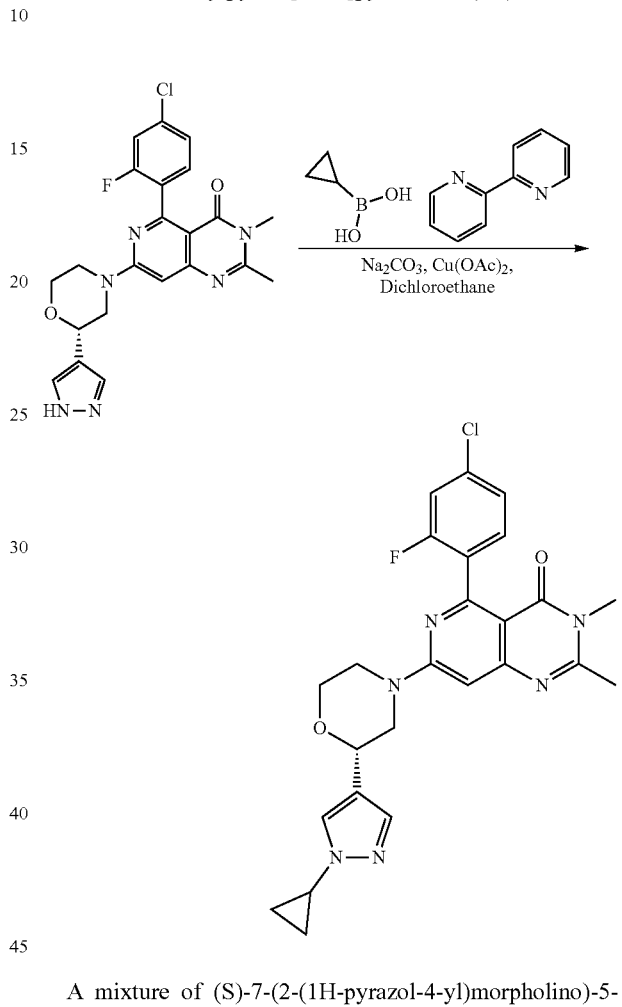

A mixture of (S)-7-(2-(1H-pyrazol-4-yl)morpholino)-5-(4-chloro-2-fluorophenyl)-2,3-dimethylpyrido[4,3-d]pyrimidin-4(3H)-one (Example 22, 0.2 g, 0.440 mmol), cyclopropyl-boronic acid (0.084 g, 0.980 mmol), 2,2'-bipyridine (0.072 g, 0.464 mmol) and sodium carbonate (0.104 g, 0.980 mmol, fisher) in 1,2-dichloroethane (1.912 mL) was stirred at 50° C. for 18 h (septum of vial was perforated with 2 needles to allow air to enter). After cooling to room temperature, the mixture was filtered over celite. The filtrate was washed with NH4Cl, dried over MgSO₄, filtered and concentrated. The crude was purified by column chromatography eluting with 0-10% DCM/MeOH to afford 5-(4-chloro-2-fluorophenyl)-7-((2S)-2-(1-cyclopropyl-1H-pyrazol-4-yl)-4-morpholinyl)-2,3-dimethylpyrido[4,3-d]pyrimidin-4(3H)-one (0.113 g, 0.228 mmol, 51.9% yield). ¹H NMR (500 MHz, DMSO-d6) δ 8.13 (s, 1H), 7.69 (s, 1H), 7.37-7.44 (m, 2H), 7.32 (dd, J=2.01, 8.11 Hz, 1H), 7.20 (dd, J=8.89, 15.64 Hz, 1H), 6.86 (s, 1H), 5.55 (d, J=15.57 Hz, 1H), 4.84 (d, J=8.43 Hz, 1H), 4.58 (dd, J=2.66, 10.32 Hz, 1H), 4.43 (br d, J=12.20 Hz, 1H), 4.27 (br d, J=12.46 Hz, 1H), 3.98-4.04 (m, 1H), 3.70 (dt, J=2.59, 11.55 Hz, 1H), 3.35 (s, 3H), 2.99-3.11 (m, 2H), 2.53 (s, 3H). m/z (ESI, +ive ion): 481.0 (M+H).

TABLE 3

Compound 137 was prepared following the procedure described in Method 4 as follows:

| Ex. # | Structure | Name | Reagents/Conditions |
|---|---|---|---|
| 137 | 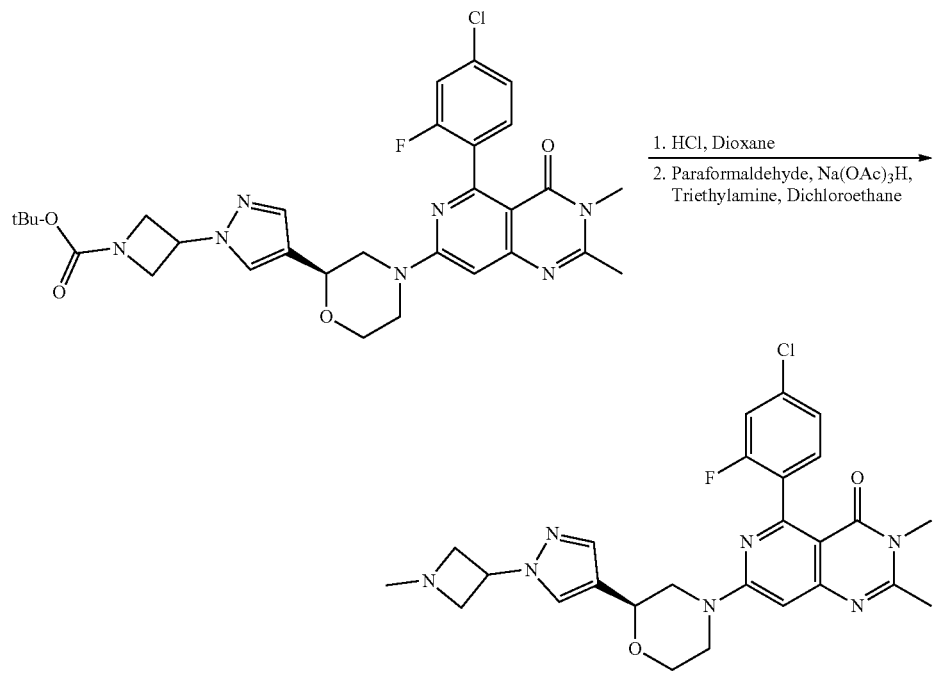 | 5-(4-chloro-2-fluorophenyl)-7-((2S)-2-(1-ethenyl-1H-pyrazol-4-yl)-4-morpholinyl)-2,3-dimethylpyrido[4,3-d]pyrimidin-4(3H)-one | Step 1: Potassium vinyltrifluoroborate |

Method 5

Example 138: 5-(4-chloro-2-fluorophenyl)-2,3-dimethyl-7-((2S)-2-(1-(1-methyl-3-azetidinyl)-1H-pyrazol-4-yl)-4-morpholinyl)pyrido[4,3-d]pyrimidin-4(3H)-one In a vial containing tert-butyl (S)-3-(4-(4-(5-(4-chloro-2-fluorophenyl)-2,3-dimethyl-4-oxo-3,4-dihydropyrido[4,3-d]pyrimidin-7-yl)morpholin-2-yl)-1H-pyrazol-1-yl)azetidine-1-carboxylate (Example 134, 0.02 g, 0.033 mmol) was added hydrogen chloride 4N in dioxane (0.3 mL, 1.2 mmol). The reaction mixture was stirred at room temperature for 1 h. The solvent was removed under vacuo. The solid residue was partitioned between sat NaHCO₃ and DCM. The organic phase was separated (phase separator) and concentrated under vacuo to provide the crude intermediate, which was used in the next step without further purification. To a solution of the intermediate, paraformaldehyde (4.92 mg, 0.164 mmol) and triethylamine (3.32 mg, 4.57 μl, 0.033 mmol) in 1,2-dichloroethane (0.131 mL) was added sodium triacetoxyhydroborate (10.4 mg, 0.049 mmol). The reaction mixture was stirred at room temperature for 4 h. The reaction mixture was quenched with NaHCO₃ solution. DCM was added and the organic phase was separated. The solvent was concentrated under vacuo. The crude was purified by column chromatography eluting with a gradient of 0-10% MeOH(+1% NH3) in DCM to afford 5-(4-chloro-2-fluorophenyl)-2,3-dimethyl-7-((2S)-2-(1-(1-methyl-3-azetidinyl)-

1H-pyrazol-4-yl)-4-morpholinyl)pyrido[4,3-d]pyrimidin-4 (3H)-one (0.007 g, 0.013 mmol, 38.4% yield). $^1$H NMR (500 MHz, CDCl$_3$) δ ppm 7.59-7.63 (m, 2H), 7.34-7.38 (m, 1H), 7.22-7.25 (m, 1H), 7.14-7.18 (m, 1H), 6.62-6.64 (m, 1H), 4.90-4.97 (m, 1H), 4.60-4.65 (m, 1H), 4.40-4.49 (m, 1H), 4.18-4.25 (m, 1H), 4.07-4.13 (m, 1H), 3.77-3.93 (m, 3H), 3.52-3.59 (m, 2H), 3.46-3.49 (m, 3H), 3.19-3.26 (m, 1H), 3.11-3.19 (m, 1H), 2.56-2.60 (m, 3H), 2.46-2.53 (m, 3H). m/z (ESI, +ive ion): 524.0 (M+H)

Method 6

Example 139: 5-(4-chloro-2-fluorophenyl)-2,3-dimethyl-7-((2S)-2-(6-methyl-3-pyridinyl)-4-morpholinyl)pyrido[4,3-d]pyrimidin-4(3H)-one Example 140: 5-(4-chloro-2-fluorophenyl)-2,3-dimethyl-7-((2R)-2-(6-methyl-3-pyridinyl)-4-morpholinyl)pyrido[4,3-d]pyrimidin-4(3H)-one

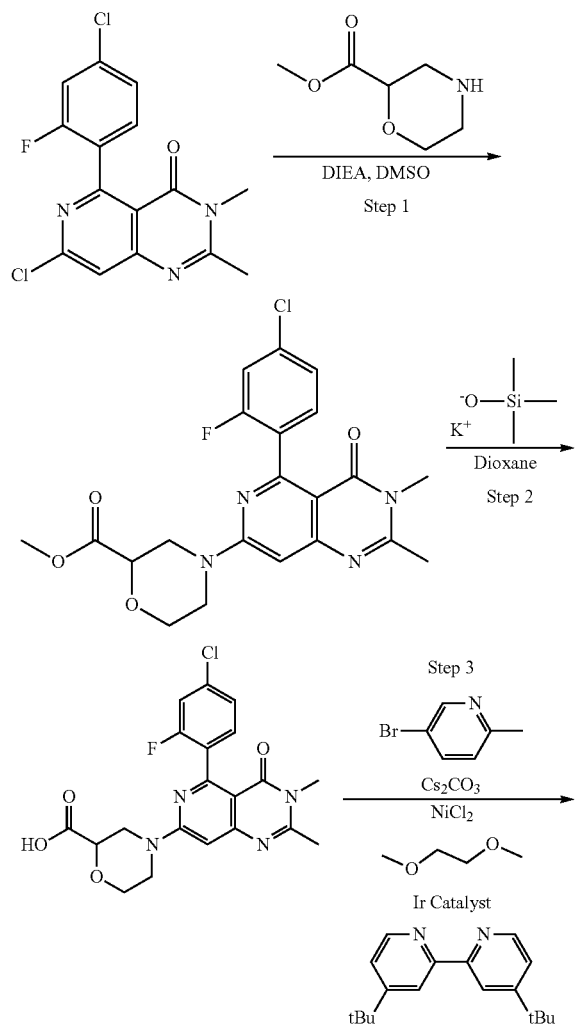

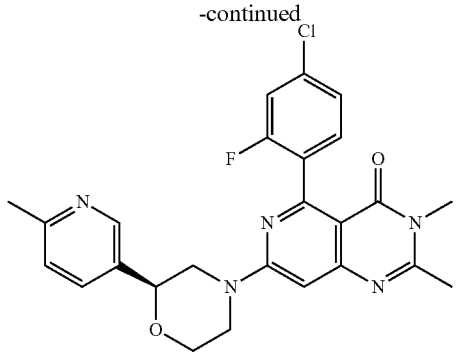

Ex. 139

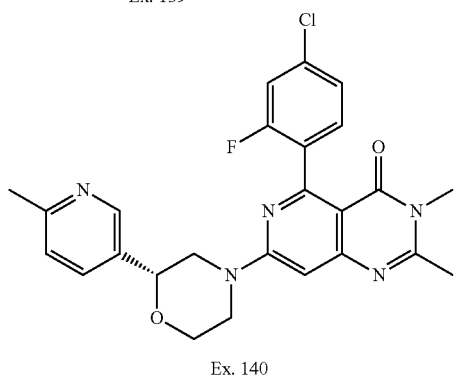

Ex. 140

Step 1: Methyl 4-(5-(4-chloro-2-fluorophenyl)-2,3-dimethyl-4-oxo-3,4-dihydropyrido[4,3-d]pyrimidin-7-yl)morpholine-2-carboxylate. To a 10 mL vial were added 7-chloro-5-(4-chloro-2-fluorophenyl)-2,3-dimethylpyrido[4,3-d]pyrimidin-4(3H)-one (1.014 g, 3 mmol), methyl morpholine-2-carboxylate and n,n-diisopropylethylamine (1.939 g, 15.00 mmol) in dimethyl sulfoxide (5 mL). The reaction was stirred at 100° C. for 24 h. The reaction mixture was partitioned between DCM and water and the organic phase was concentrated to provide methyl 4-(5-(4-chloro-2-fluorophenyl)-2,3-dimethyl-4-oxo-3,4-dihydropyrido[4,3-d]pyrimidin-7-yl)morpholine-2-carboxylate, which was used in the next step without further purification.

Step 2: 4-(5-(4-chloro-2-fluorophenyl)-2,3-dimethyl-4-oxo-3,4-dihydropyrido[4,3-d]pyrimidin-7-yl)morpholine-2-carboxylic acid. Methyl 4-(5-(4-chloro-2-fluorophenyl)-2,3-dimethyl-4-oxo-3,4-dihydropyrido[4,3-d]pyrimidin-7-yl)morpholine-2-carboxylate (4.92 g, 11 mmol, 125373-9) and potassium trimethyl(oxido)-silane (1.693 g, 13.20 mmol) were combined in 1,4-dioxane (11 mL) and the reaction was stirred at 80° C. for 30 min. The reaction mixture was cooled to room temperature, diluted with sat. NaHCO$_3$ solution and extracted with EtOAc. The aqueous phase was acidified to pH=3 and extracted 2× with EtOAc. The combined organics dried and concentrated to yield 1.9 g of crude product which was further purified via reverse phase chromatography to provide 4-(5-(4-chloro-2-fluorophenyl)-2,3-dimethyl-4-oxo-3,4-dihydropyrido[4,3-d]pyrimidin-7-yl)morpholine-2-carboxylic acid (1.85 g, 38.5%). m/z (ESI, +ive ion): 433.0 (M+H).

Step 3: 5-(4-chloro-2-fluorophenyl)-2,3-dimethyl-7-((2S)-2-(6-methyl-3-pyridinyl)-4-morpholinyl)pyrido[4,3-d]pyrimidin-4(3H)-one and 5-(4-chloro-2-fluorophenyl)-2,3-dimethyl-7-((2R)-2-(6-methyl-3-pyridinyl)-4-morpholinyl)pyrido[4,3-d]pyrimidin-4(3H)-one. A small vial was charged with, 4-(5-(4-chloro-2-fluorophenyl)-2,3- dimethyl-4-oxo-3,4-dihydropyrido[4,3-d]pyrimidin-7-yl) morpholine-2-carboxylic acid (130 mg, 0.3 mmol, 125373-25), 5-bromo-2-methylpyridine (6.6 mg, 0.3 mmol), nickel (II) chloride ethylene glycol dimethyl ether complex (6.59 mg, 0.030 mmol), 4,4'-di-tert-butyl-2,2'-dipyridyl (12.08 mg, 0.045 mmol), cesium carbonate (293 mg, 0.900 mmol) and 4,4'-di-tert-butyl-2,2'-bipyridine, bis(3,5-difluoro-2-(5-(trifluoromethyl)pyridin-2-yl)phenyl)iridium(III) hexafluorophosphate (Ir catalyst, 3.37 mg, 3.00 µmol). The vial was evacuated and filled with nitrogen 3×. N, N-dimethylformamide (5000 µl) was added, and the reaction vial was irradiated with 450 nm using an integrated photoreactor for 3 hr (Fan: 1500 rpm; Stir: 500 rpm; LED power: 100%). The reaction mixture was partitioned between EtOAc and water. The organic phase was dried, concentrated, and purified via reverse phase chromatography to yield 18 mg crude product. Chiral Purification via SFC stacked Chiralcel OJ-H 2×25 cm and Chiralcel OJ-H 2×15 cm, 5 um columns, mobile phase of 25% methanol, F=70 mL/min provided 5-(4-chloro-2-fluorophenyl)-2,3-dimethyl-7-((2S)-2-(6-methyl-3-pyridinyl)-4-morpholinyl)pyrido[4,3-d]pyrimidin-4(3H)-one (Example 139) and 5-(4-chloro-2-fluorophenyl)-2,3-dimethyl-7-((2R)-2-(6-methyl-3-pyridinyl)-4-morpholinyl)-pyrido[4,3-d]pyrimidin-4(3H)-one (Example 140) as off-white solids. The absolute stereochemistry was arbitrarily assigned. $^1$H NMR (500 MHz, CDCl$_3$) δ ppm 8.56-8.58 (m, 1H), 7.64-7.69 (m, 1H), 7.34-7.39 (m, 1H), 7.22-7.25 (m, 1H), 7.18-7.21 (m, 1H), 7.14-7.17 (m, 1H), 6.62-6.64 (m, 1H), 4.60-4.65 (m, 1H), 4.46-4.52 (m, 1H), 4.24-4.31 (m, 1H), 4.16-4.21 (m, 1H), 3.85-3.91 (m, 1H), 3.48 (s, 3H), 3.21-3.27 (m, 1H), 2.97-3.03 (m, 1H), 2.60 (s, 3H), 2.57-2.58 (m, 3H). m/z (ESI, +ive ion): 480.0 (M+H).

Method 7

Example 141: 5-(4-chloro-2-fluorophenyl)-2,3-dimethyl-7-((2S)-2-(1-(trifluoromethyl)-1H-pyrazol-4-yl)-4-morpholinyl)pyrido[4,3-d]pyrimidin-4(3H)-one

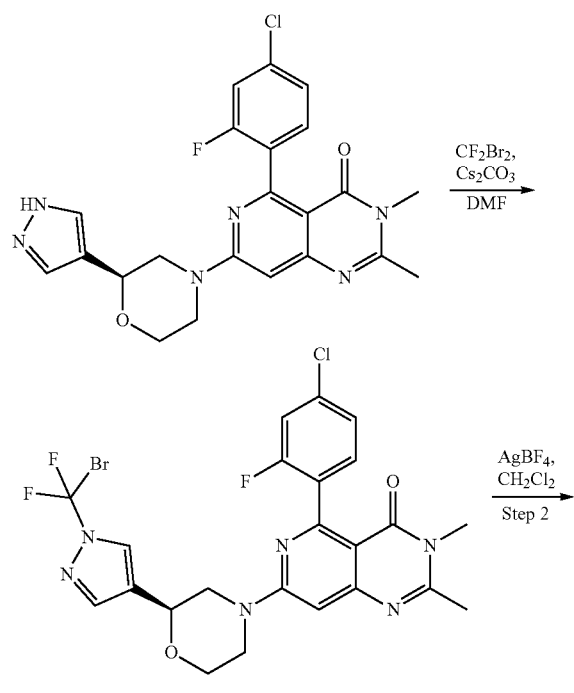

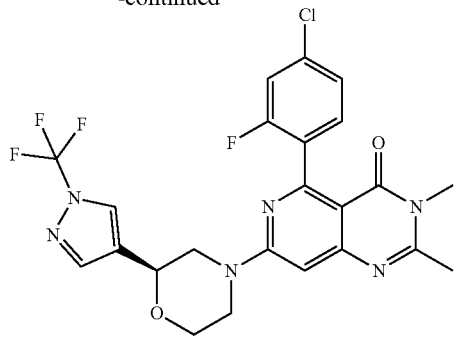

Step 1: (S)-7-(2-(1-(bromodifluoromethyl)-1H-pyrazol-4-yl)morpholino)-5-(4-chloro-2-fluorophenyl)-2,3-dimethylpyrido[4,3-d]pyrimidin-4(3H)-one. To a solution of (S)-7-(2-(1H-pyrazol-4-yl)morpholino)-5-(4-chloro-2-fluorophenyl)-2,3-dimethylpyrido[4,3-d]pyrimidin-4(3H)-one (Example 22, 0.065 g, 0.143 mmol, 124947-40-1) in DMF (0.572 mL) was added cesium carbonate (0.093 g, 0.286 mmol) and dibromo difluoromethane (0.039 mL, 0.09 g, 0.429 mmol). The reaction mixture was stirred at room temperature overnight, diluted with 10 mL DCM and washed with water. The organic phase was separated and concentrated under vacuo and the crude product was purified by column chromatography eluting with a gradient of 0-30% EtOAc-EtOH (3:1) in heptane to afford ((S)-7-(2-(1-(bromodifluoromethyl)-1H-pyrazol-4-yl)morpholino)-5-(4-chloro-2-fluorophenyl)-2,3-dimethylpyrido[4,3-d]pyrimidin-4(3H)-one (0.025 g, 0.043 mmol, 30% yield) as an off-white solid. m/z (ESI, +ive ion): 583.0 (M+H)$^+$.

Step 2: 5-(4-chloro-2-fluorophenyl)-2,3-dimethyl-7-((2S)-2-(1-(trifluoromethyl)-1H-pyrazol-4-yl)-4-morpholinyl)pyrido[4,3-d]pyrimidin-4(3H)-one. To a stirred solution of (S)-7-(2-(1-(bromodifluoromethyl)-1H-pyrazol-4-yl) morpholino)-5-(4-chloro-2-fluorophenyl)-2,3-dimethyl-pyrido[4,3-d]pyrimidin-4(3H)-one (0.025 g, 0.043 mmol, 124947-42-10) in DCM (0.428 mL) was added silver(I) tetrafluoroborate (0.017 g, 0.086 mmol) at −78° C. Then the solution was stirred at room temperature overnight. The mixture was diluted with DCM containing 5% MeOH, sonicated for 2-3 min, filtered and concentrated. The crude was purified by flash column eluting with a gradient of 0-10% MeOH (+0.1% Ammonia) in DCM to afford 5-(4-chloro-2-fluorophenyl)-2,3-dimethyl-7-((2S)-2-(1-(trifluoromethyl)-1H-pyrazol-4-yl)-4-morpholinyl)pyrido[4,3-d] pyrimidin-4(3H)-one (0.0169 g, 0.032 mmol, 75% yield). $^1$H NMR (500 MHz, DMSO-d6) δ 8.55 (s, 1H), 8.04 (s, 1H), 7.36-7.43 (m, 2H), 7.29-7.34 (m, 1H), 6.91 (s, 1H), 4.61-4.65 (m, 1H), 4.46 (br d, J=12.20 Hz, 1H), 4.32 (br d, J=13.10 Hz, 1H), 3.99-4.06 (m, 1H), 3.67-3.75 (m, 1H), 3.34 (s, 3H), 3.00-3.09 (m, 2H), 2.52 (s, 3H). m/z (ESI, +ive ion): 523.0 (M+H)$^+$.

Method 8

Example 142: 5-(4-chloro-2-fluorophenyl)-2-cyclopropyl-3-methyl-7-((2S)-2-(1-methyl-1H-pyrazol-4-yl)-4-morpholinyl)pyrido[4,3-d]pyrimidin-4(3H)-one

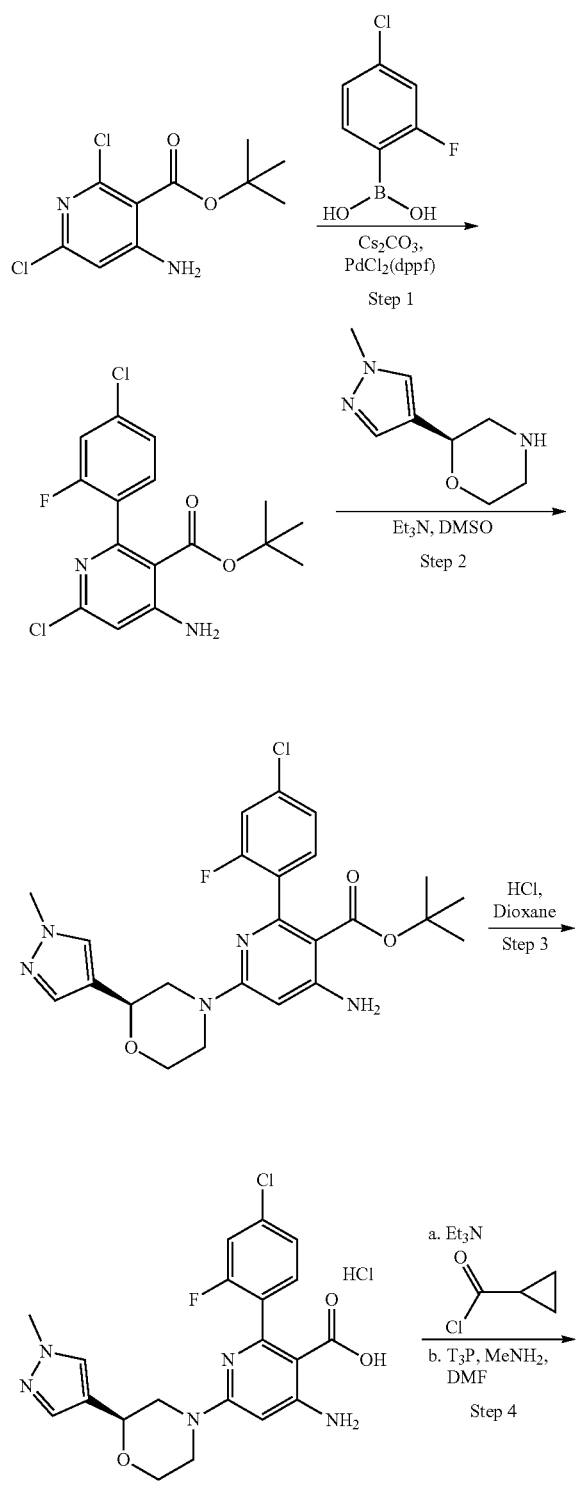

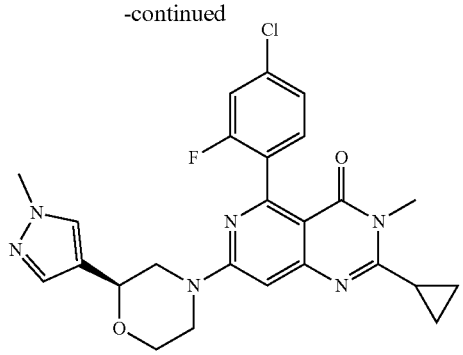

Step 1: Tert-butyl 4-amino-6-chloro-2-(4-chloro-2-fluorophenyl)nicotinate. To a 100 mL vial were added tert-butyl 4-amino-2,6-dichloronicotinate (2.5 g, 9.50 mmol, 125370-12), (4-chloro-2-fluorophenyl)boronic acid (2.319 g, 13.30 mmol,), $Cs_2CO_3$ (7.74 g, 23.75 mmol) and $PdCl_2$(dtbpf) (0.310 g, 0.475 mmol,). 1,4-dioxane (25.3 mL) and water (6.33 mL) were added and the mixture flushed with $N_2$ and stirred at 80° C. for 4 h. The resulting mixture was diluted with water and EtOAc and extracted 2× with EtOAc. The organic layer was dried over $MgSO_4$, filtered, and concentrated. Purification on silica, 0-20% EtOAc in heptane yielded tert-butyl 4-amino-6-chloro-2-(4-chloro-2-fluorophenyl)nicotinate as a pale orange solid. m/z (ESI, +ive ion): 356.9 $(M+H)^+$.

Step 2: Tert-butyl (S)-4-amino-2-(4-chloro-2-fluorophenyl)-6-(2-(1-methyl-1H-pyrazol-4-yl)morpholino)nicotinate. To a solution oftert-butyl 4-amino-6-chloro-2-(4-chloro-2-fluorophenyl)nicotinate (500 mg, 1.400 mmol, 125370-40) in dimethyl sulfoxide (4666 µl) was added (S)-2-(1-methyl-1H-pyrazol-4-yl)morpholine (Intermediate 3, 234 mg, 1.400 mmol) and triethylamine (425 mg, 585 µl, 4.20 mmol). The mixture was stirred at 125° C. for 72 h and subsequently diluted with EtOAc and washed with water. The organic layer was dried over $MgSO_4$, filtered, and concentrated. Purification on silica gel (0-100% EtOAc in heptane) provided tert-butyl (S)-4-amino-2-(4-chloro-2-fluorophenyl)-6-(2-(1-methyl-1H-pyrazol-4-yl)morpholino) nicotinate as a yellow solid. m/z (ESI, +ive ion): 488.0 $(M+H)^+$.

Step 3: (S)-4-amino-2-(4-chloro-2-fluorophenyl)-6-(2-(1-methyl-1H-pyrazol-4-yl)morpholino)nicotinic acid hydrochloride. In a 20 mL vial were combined tert-butyl (S)-4-amino-2-(4-chloro-2-fluorophenyl)-6-(2-(1-methyl-1H-pyrazol-4-yl)morpholino)nicotinate (342 mg, 0.701 mmol, 125520-8) and 4M HCl in dioxane (511 mg, 426 µl, 14.02 mmol). The mixture was heated at 60° C. for 90 min., allowed to cool to room temperature and concentrated to dryness to provide crude (S)-4-amino-2-(4-chloro-2-fluorophenyl)-6-(2-(1-methyl-1H-pyrazol-4-yl)morpholino)nicotinic acid hydrochloride, which was used in the next step without purification. m/z (ESI, +ive ion): 467.8 $(M+H)^+$.

Step 4: 5-(4-chloro-2-fluorophenyl)-2-cyclopropyl-3-methyl-7-((2S)-2-(1-methyl-1H-pyrazol-4-yl)-4-morpholinyl)pyrido[4,3-d]pyrimidin-4(3H)-one. To a solution of (S)-4-amino-2-(4-chloro-2-fluorophenyl)-6-(2-(1-methyl-1H-pyrazol-4-yl)morpholino)nicotinic acid (25 mg, 0.058 mmol, 125520-12) in DCM (193 µl) was added cyclopropane-carboxylic acid chloride (30.3 mg, 0.289 mmol) and triethylamine (17.57 mg, 24.21 µl, 0.174 mmol) and the mixture was stirred at room temperature for 30 min. The reaction mixture was concentrated to dryness and dissolved in 0.2 mL of pyridine. Aminomethane (57.9 µl, 0.116 mmol)

and T₃P in DMF (36.8 mg, 33.8 µl, 0.058 mmol) were added and the mixture stirred at 70° C. for 72 h. The reaction mixture was concentrated and purified using silica gel column, eluting with 0 to 100% EtOH/EtOAc (1:3) in heptane to provide 5-(4-chloro-2-fluorophenyl)-2-cyclopropyl-3-methyl-7-((2S)-2-(1-methyl-HH-pyrazol-4-yl)-4-morpholinyl)pyrido[4,3-d]pyrimidin-4(3H)-one as a light brown solid. ¹H NMR (500 MHz, DMSO-d6) δ ppm 7.72 (s, 1H), 7.45 (s, 1H), 7.36-7.41 (m, 2H), 7.29-7.33 (m, 1H), 6.72 (s, 1H), 4.50 (dd, J=10.32, 2.53 Hz, 1H), 4.36 (br d, J=12.07 Hz, 1H), 4.22 (br d, I=12.07 Hz, 1H), 3.94-4.00 (m, 1H), 3.81 (s, 3H), 3.62-3.70 (m, 1H), 3.52 (s, 3H), 2.95-3.08 (m, 2H), 2.21-2.26 (m, 1H), 1.15 (br s, 2H), 1.08 (br dd, 1=8.04, 3.24 Hz, 2H). m/z (ESI, +ive ion): 495.0 (M+H)⁺.

TABLE 4

Compounds 143 to 157 were prepared following the procedure described in Method 8, steps 1-4, as follows:

| Ex. # | Structure | Name | Reagents/Conditions |
|---|---|---|---|
| 143 | 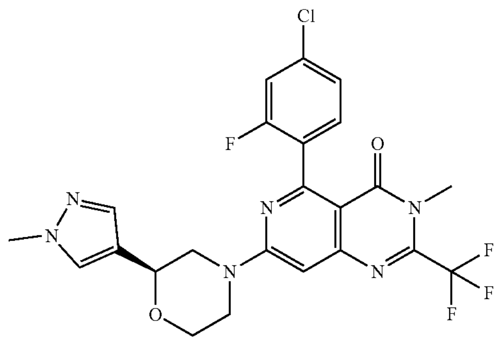 [SMILES: Cn1cc([C@H]2CN(c3cc4nc(C(F)(F)F)n(C)c(=O)c4c(-c4ccc(Cl)cc4F)n3)CCO2)cn1] | 5-(4-chloro-2-fluorophenyl)-3-methyl-7-((2S)-2-(1-methyl-1H-pyrazol-4-yl)-4-morpholinyl)-2-(trifluoromethyl)pyrido[4,3-d]pyrimidin-4(3H)-one | Step 4: Trifluoracetic acid chloride |
| 144 | 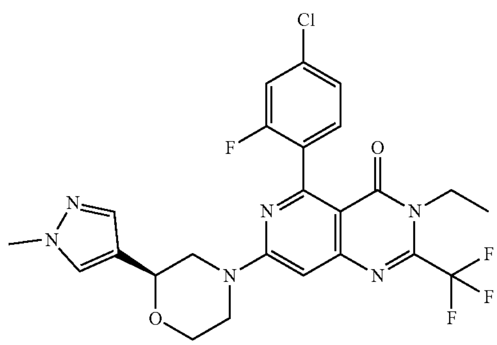 [SMILES: CCn1c(C(F)(F)F)nc2cc(N3CCO[C@@H](c4cnn(C)c4)C3)nc(-c3ccc(Cl)cc3F)c2c1=O] | 5-(4-chloro-2-fluorophenyl)-3-ethyl-7-((2S)-2-(1-methyl-1H-pyrazol-4-yl)-4-morpholinyl)-2-(trifluoromethyl)pyrido[4,3-d]pyrimidin-4(3H)-one | Step 4a: Trifluoracetic acid chloride Step 4b: N-ethylamine |
| 145 | 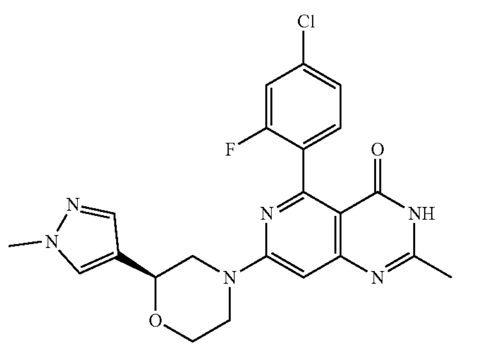 | 5-(4-chloro-2-fluorophenyl)-2-methyl-7-((2S)-2-(1-methyl-1H-pyrazol-4-yl)-4-morpholinyl)pyrido[4,3-d]pyrimidin-4(3H)-one | Step 4a: Acetyl chloride step 4b: Ammonia |
| 146 | 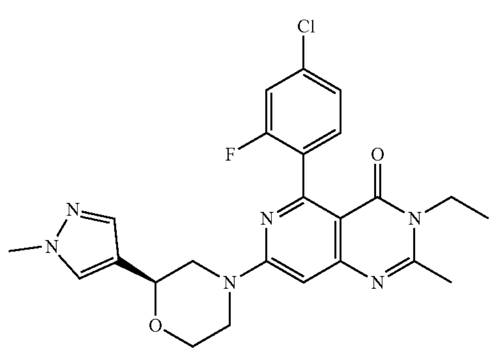 [SMILES: CCn1c(C)nc2cc(N3CCO[C@@H](c4cnn(C)c4)C3)nc(-c3ccc(Cl)cc3F)c2c1=O] | 5-(4-chloro-2-fluorophenyl)-3-ethyl-2-methyl-7-((2S)-2-(1-methyl-1H-pyrazol-4-yl)-4-morpholinyl)pyrido[4,3-d]pyrimidin-4(3H)-one | Step 4a: Acetyl chloride Step 4b: N-ethylamine |

TABLE 4-continued

Compounds 143 to 157 were prepared following the procedure described in Method 8, steps 1-4, as follows:

| Ex. # | Structure | Name | Reagents/Conditions |
|---|---|---|---|
| 147 | 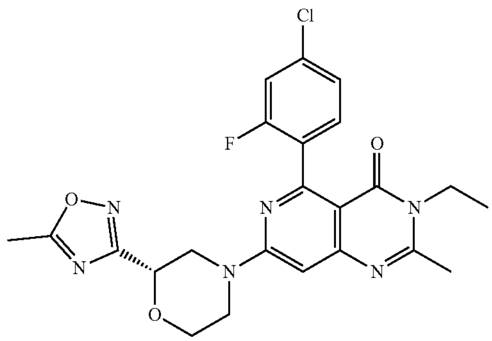 [SMILES: CCn1c(C)nc2cc(N3CCO[C@H](c4noc(C)n4)C3)nc(-c3ccc(Cl)cc3F)c2c1=O] | 5-(4-chloro-2-fluorophenyl)-3-ethyl-2-methyl-7-((2S)-2-(5-methyl-1,2,4-oxadiazol-3-yl)-4-morpholinyl)pyrido[4,3-d]pyrimidin-4(3H)-one | Step 2: (S)-2-(5-methyl-1,2,4-oxadiazol-3-yl)morpholine (Enamine Inc., Monmouth Jct., NJ, USA) Step 4a: Acetyl chloride Step 4b: N-ethylamine |
| 148 | 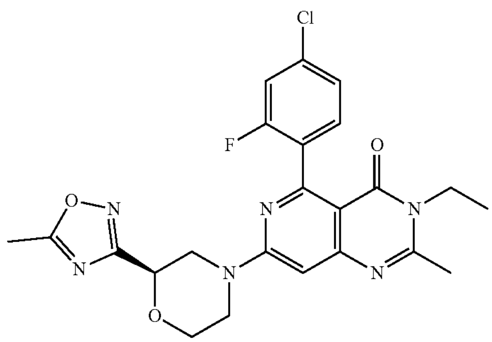 [SMILES: CCn1c(C)nc2cc(N3CCO[C@@H](c4noc(C)n4)C3)nc(-c3ccc(Cl)cc3F)c2c1=O] | 5-(4-chloro-2-fluorophenyl)-3-ethyl-2-methyl-7-((2R)-2-(5-methyl-1,2,4-oxadiazol-3-yl)-4-morpholinyl)pyrido[4,3-d]pyrimidin-4(3H)-one | Step 2: (R)-2-(5-methyl-1,2,4-oxadiazol-3-yl)morpholine (Enamine Inc., Monmouth Jct., NJ, USA) Step 4a: Acetyl chloride Step 4b: N-ethylamine |
| 149 | 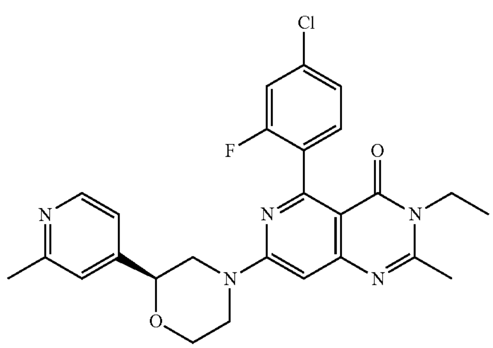 | 5-(4-chloro-2-fluorophenyl)-3-ethyl-2-methyl-7-((2S)-2-(2-methyl-4-pyridinyl)-4-morpholinyl)pyrido[4,3-d]pyrimidin-4(3H)-one | Step 2: (S)-2-(2-methylpyridin-4-yl)morpholine (Enamine Inc., Monmouth Jct., NJ, USA) Step 4a: Acetyl chloride Step 4b: N-ethylamine |
| 150 | 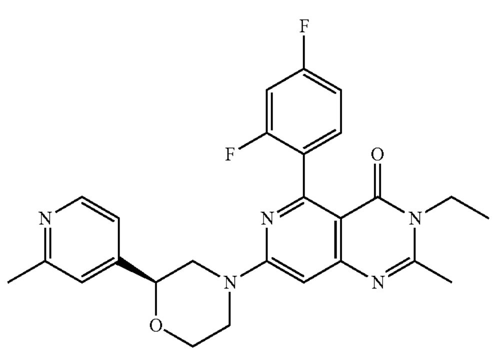 [SMILES: CCn1c(C)nc2cc(N3CCO[C@@H](c4ccnc(C)c4)C3)nc(-c3ccc(F)cc3F)c2c1=O] | 5-(2,4-difluorophenyl)-3-ethyl-2-methyl-7-((2S)-2-(2-methyl-4-pyridinyl)-4-morpholinyl)pyrido[4,3-d]pyrimidin-4(3H)-one | Step 2: (R)-2-(2-methylpyridin-4-yl)morpholine (Enamine Inc., Monmouth Jct., NJ, USA) Step 4a: Acetyl chloride Step 4b: N-ethylamine |

TABLE 4-continued

Compounds 143 to 157 were prepared following the procedure described in Method 8, steps 1-4, as follows:

| Ex. # | Structure | Name | Reagents/Conditions |
|---|---|---|---|
| 151 | 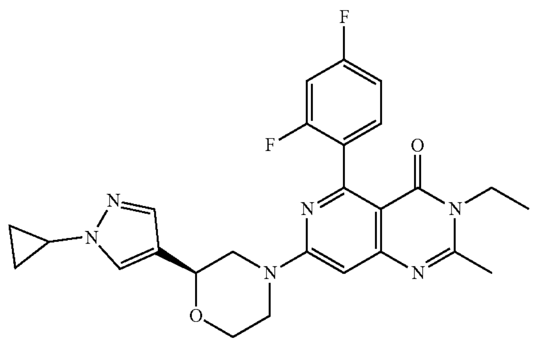 [SMILES: CCn1c(C)nc2cc(N3CCO[C@@H](c4cnn(C5CC5)c4)C3)nc(-c3ccc(F)cc3F)c2c1=O] | 7-((2S)-2-(1-cyclopropyl-1H-pyrazol-4-yl)-4-morpholinyl)-5-(2,4-difluorophenyl)-3-ethyl-2-methylpyrido[4,3-d]pyrimidin-4(3H)-one | Step 1: 2,4-difluorophenyl boronic acid<br>Step 2: (S)-2-(1-cyclopropyl-1H-pyrazol-4-yl)morpholine (Enamine Inc., Monmouth Jct., NJ, USA)<br>Step 4a: Acetyl chloride<br>Step 4b: N-Ethylamine |
| 152 | 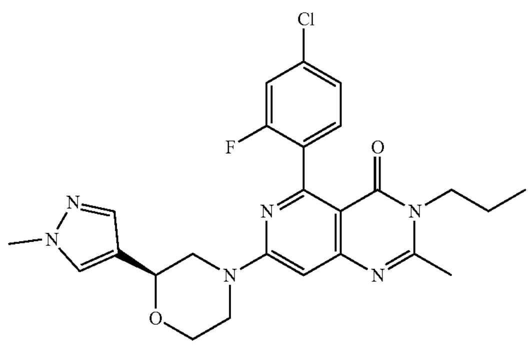 [SMILES: CCCn1c(C)nc2cc(N3CCO[C@@H](c4cnn(C)c4)C3)nc(-c3ccc(Cl)cc3F)c2c1=O] | 5-(4-chloro-2-fluorophenyl)-2-methyl-7-((2S)-2-(1-methyl-1H-pyrazol-4-yl)-4-morpholinyl)-3-propylpyrido[4,3-d]pyrimidin-4(3H)-one | Step 4a: Acetyl chloride Step 4b: N-propylamine |
| 153 | 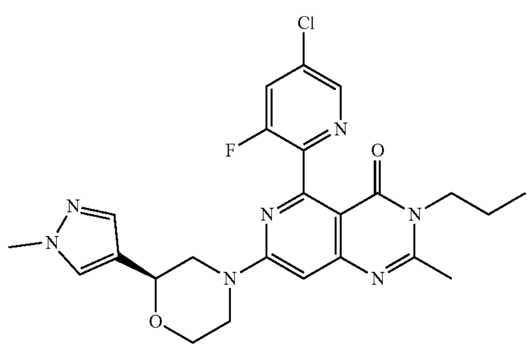 [SMILES: CCCn1c(C)nc2cc(N3CCO[C@@H](c4cnn(C)c4)C3)nc(-c3ncc(Cl)cc3F)c2c1=O] | 5-(5-chloro-3-fluoro-2-pyridinyl)-2-methyl-7-((2S)-2-(1-methyl-1H-pyrazol-4-yl)-4-morpholinyl)-3-propylpyrido[4,3-d]pyrimidin-4(3H)-one | Step 1: Pd(Ph$_3$)$_4$, (5-chloropyridin-2-yl)zinc(II) bromide, THF, 70° C.<br>Step 4a: Acetyl chloride Step 4b: N-propylamine |
| 154 | 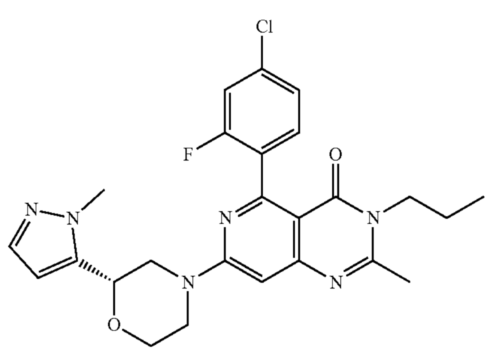 [SMILES: CCCn1c(C)nc2cc(N3CCO[C@H](c4ccnn4C)C3)nc(-c3ccc(Cl)cc3F)c2c1=O] | 5-(4-chloro-2-fluorophenyl)-2-methyl-7-((2S)-2-(1-methyl-1H-pyrazol-5-yl)-4-morpholinyl)-3-propylpyrido[4,3-d]pyrimidin-4(3H)-one | Step 2: (S)-2-(1-methyl-1H-pyrazol-5-yl)morpholine (Combi-Blocks Inc., San Diego, CA, USA)<br>Step 4a: Acetyl chloride<br>Step 4b: N-propylamine |

US 12,319,691 B2

267 268

TABLE 4-continued

Compounds 143 to 157 were prepared following the procedure described in Method 8, steps 1-4, as follows:

| Ex. # | Structure | Name | Reagents/Conditions |
|---|---|---|---|
| 155 | 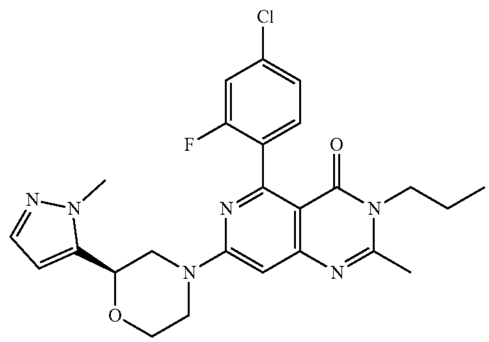 [SMILES: CCCn1c(C)nc2cc(N3CCO[C@@H](c4ccnn4C)C3)nc(-c3ccc(Cl)cc3F)c2c1=O] | 5-(4-chloro-2-fluorophenyl)-2-methyl-7-((2R)-2-(1-methyl-1H-pyrazol-5-yl)-4-morpholinyl)-3-propylpyrido[4,3-d]pyrimidin-4(3H)-one | Step 1: (R)-2-(1-methyl-1H-pyrazol-5-yl)morpholine (Combi-Blocks Inc., San Diego, CA, USA)<br>Step 4a: Acetyl chloride<br>Step 4b: N-Propylamine |
| 156 | 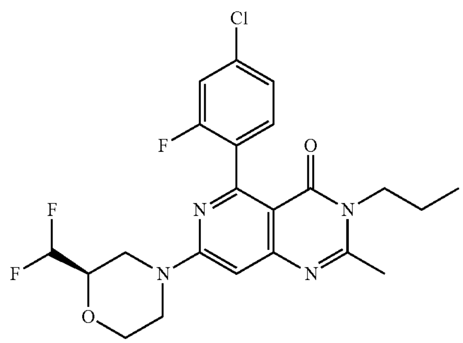 [SMILES: CCCn1c(C)nc2cc(N3CCO[C@@H](C(F)F)C3)nc(-c3ccc(Cl)cc3F)c2c1=O] | 5-(4-chloro-2-fluorophenyl)-7-((2R)-2-(difluoromethyl)-4-morpholinyl)-2-methyl-3-propylpyrido[4,3-d]pyrimidin-4(3H)-one | Step 2: (R)-2-(difluoromethyl)morpholine (FCH Group, Chernigiv, Ukraine)<br>Step 4a: Acetyl chloride<br>Step 4b: N-propylamine |
| 157 | 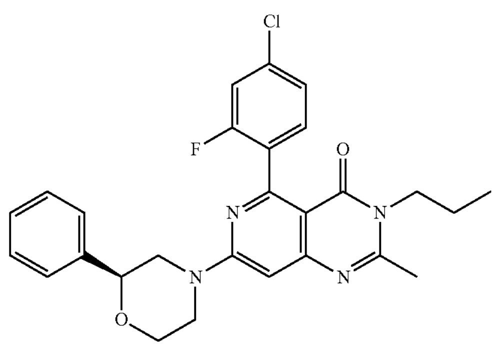 [SMILES: CCCn1c(C)nc2cc(N3CCO[C@@H](c4ccccc4)C3)nc(-c3ccc(Cl)cc3F)c2c1=O] | 5-(4-chloro-2-fluorophenyl)-2-methyl-7-((2S)-2-phenyl-4-morpholinyl)-3-propylpyrido[4,3-d]pyrimidin-4(3H)-one | Step 2: (S)-2-phenyl-4-morpholine (Combi-Blocks Inc., San Diego, CA, USA)<br>Step 4a: Acetyl chloride Step 4b: N-propylamine |

Method 9

Example 158: 5-(4-chloro-2-fluorophenyl)-3-methyl-7-((2S)-2-(1-methyl-1H-pyrazol-4-yl)-4-morpholinyl)pyrido[4,3-d]pyrimidin-4(3H)-one

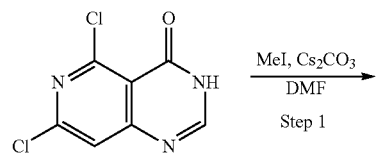

MeI, Cs$_2$CO$_3$
DMF
Step 1

-continued

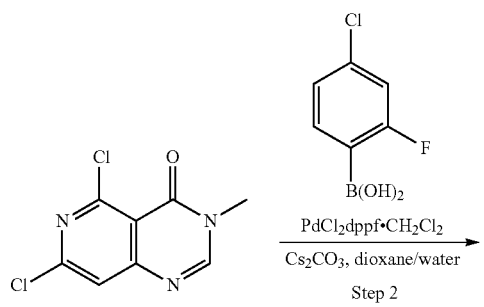

PdCl$_2$dppf·CH$_2$Cl$_2$
Cs$_2$CO$_3$, dioxane/water
Step 2

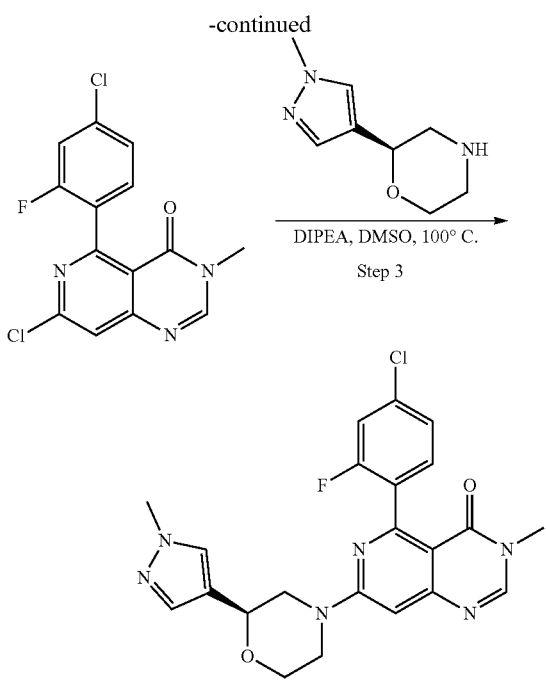

Step 1: 5,7-dichloro-3-methylpyrido[4,3-d]pyrimidin-4(3H)-one. 5,7-dichloropyrido[4,3-d]pyrimidin-4(3H)-one (0.086 g, 0.4 mmol), cesium carbonate (0.261 g, 0.8 mmol), and iodomethane (0.170 g, 1.2 mmol) were combined in DMF (2 mL). The reaction mixture was stirred at room temperature for 24 h then partitioned between EtOAc and water. The organic phase separated and dried with MgSO$_4$. The resulting solution was concentrated to provide crude 5,7-dichloro-3-methylpyrido[4,3-d]pyrimidin-4(3H)-one, which was used in the next step without further purification.

Step 2: 7-chloro-5-(4-chloro-2-fluorophenyl)-3-methylpyrido[4,3-d]pyrimidin-4(3H)-one. 5,7-dichloro-3-methylpyrido[4,3-d]pyrimidin-4(3H)-one (0.092 g, 0.4 mmol), (1,1'-bis(diphenylphosphino) ferrocene) dichloropalladium (0.015 g, 0.020 mmol), (4-chloro-2-fluorophenyl)boranediol (0.070 g, 0.400 mmol) and cesium carbonate (0.391 g, 1.200 mmol) were combined in a vial. 1,4-Dioxane (1.5 mL) and water (0.5 mL) were added and the reaction was stirred at 60° C. for 30 min. The reaction mixture was cooled to room temperature and partitioned between DCM and water. The mixture was passed through a phase separation cartridge, concentrated to obtain crude 7-chloro-5-(4-chloro-2-fluorophenyl)-3-methylpyrido[4,3-d]pyrimidin-4(3H)-one, which was used in the next step without further purification. m/z (ESI, +ive ion): 324.0 (M+H)$^+$.

Step 3: 5-(4-chloro-2-fluorophenyl)-3-methyl-7-((2S)-2-(1-methyl-1H-pyrazol-4-yl)-4-morpholinyl)pyrido[4,3-d]pyrimidin-4(3H)-one. 7-chloro-5-(4-chloro-2-fluorophenyl)-3-methylpyrido[4,3-d]pyrimidin-4(3H)-one (130 mg, 0.4 mmol), (S)-2-(1-methyl-1H-pyrazol-4-yl)morpholine (Intermediate 3)(80 mg, 0.480 mmol), and n,n-diisopropylethylamine (258 mg, 0.349 mL, 2.000 mmol) were combined in dimethyl sulfoxide (0.8 mL) and the reaction was stirred at 100° C. for 3 h. After cooling to room temperature, the mixture was concentrated and the crude product was purified on silica gel, eluting with 0-100% EtOH/EtOAc (1:3) in heptane to yield 5-(4-chloro-2-fluorophenyl)-3-methyl-7-((2S)-2-(1-methyl-1H-pyrazol-4-yl)-4-morpholinyl)pyrido[4,3-d]pyrimidin-4(3H)-one as a pale yellow solid (0.091 g, 0.2 mmol, 50% yield). $^1$H NMR (600 MHz, DMSO-d6) δ ppm 8.31-8.35 (m, 1H), 7.69-7.74 (m, 1H), 7.42-7.47 (m, 1H), 7.38-7.41 (m, 2H), 7.29-7.35 (m, 1H), 6.88-6.94 (m, 1H), 4.49-4.54 (m, 1H), 4.34-4.40 (m, 1H), 4.20-4.26 (m, 1H), 3.95-4.00 (m, 1H), 3.79-3.81 (m, 3H), 3.63-3.69 (m, 1H), 3.28-3.30 (m, 3H), 2.97-3.13 (m, 2H). m/z (ESI, +ive ion): 455.0 (M+H)$^+$.

Method 10

Example 159: 5-cyclohexyl-2,3-dimethyl-7-((2S)-2-(1-methyl-1H-pyrazol-4-yl)-4-morpholinyl)pyrido[4,3-d]pyrimidin-4(3H)-one

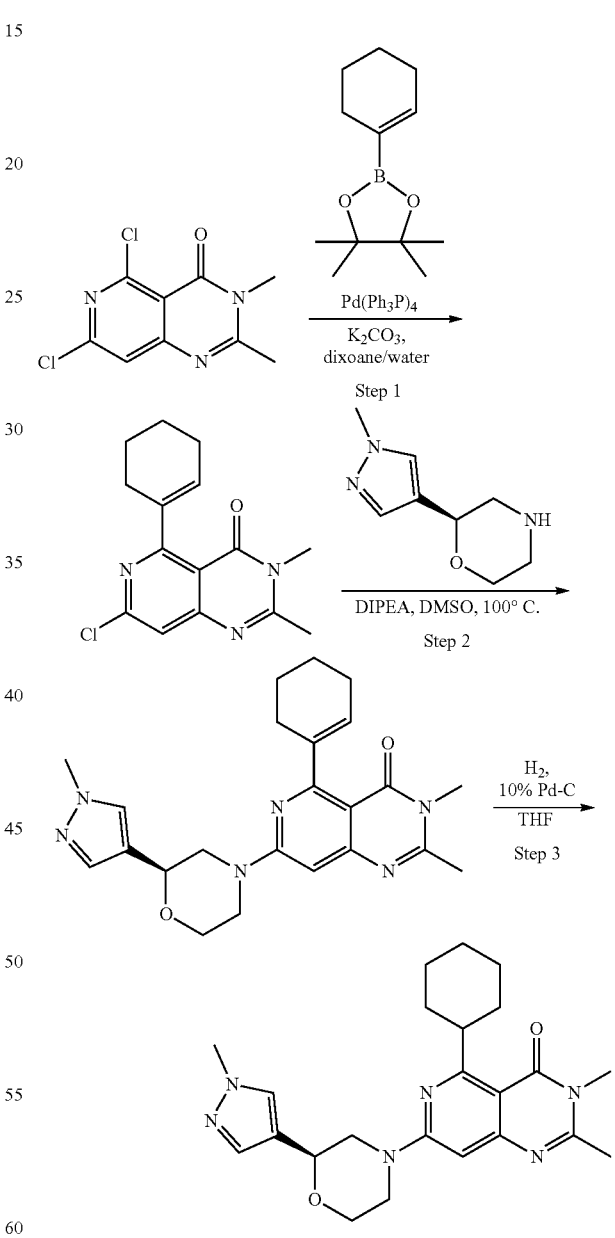

Step 1: 7-chloro-5-(cyclohex-1-en-1-yl)-2,3-dimethylpyrido[4,3-d]pyrimidin-4(3H)-one. A glass microwave reaction vessel was charged with 5,7-dichloro-2,3-dimethylpyrido[4,3-d]pyrimidin-4(3H)-one (Method 1—step 1, 0.30 g, 1.229 mmol) and 2-(cyclohex-1-en-1-yl)-4,4,5,5-tetramethyl-1,3,2-dioxaborolane (0.256 g, 1.229 mmol) in 1,4-dioxane (2.5 mL) and water (0.5 mL) followed by potassium carbonate (0.255 g, 1.844 mmol). The reaction mixture was degassed with nitrogen for 10 min, then added Pd(Ph₃P)₄ (0.142 g, 0.123 mmol) and the reaction mixture was heated in a microwave at 100° C. for 3 h. After cooling to room temperature, the reaction mixture was diluted with water (10 mL), extracted with EtOAc (2×10 mL) and the organic extracts were dried over Na₂SO₄. The solution was filtered and concentrated in vacuo to give the crude material was purified by silica gel chromatography eluting with a 5-80% EtOAc in hexane, to provide 7-chloro-5-(cyclohex-1-en-1-yl)-2,3-dimethylpyrido[4,3-d]pyrimidin-4(3H)-one (0.360 g, 1.24 mmol, 101% yield, ~75% pure) as a yellow solid. m/z (ESI, +ive ion): 290.0 (M+H)⁺.

Step 2: (S)-5-(cyclohex-1-en-1-yl)-2,3-dimethyl-7-(2-(1-methyl-1H-pyrazol-4-yl)morpholino)pyrido[4,3-d]pyrimidin-4(3H)-one. To a 25-mL round bottom flask were added (S)-2-(1-methyl-1H-pyrazol-4-yl)morpholine (Intermediate 3)(0.270 g, 1.615 mmol), 7-chloro-5-(cyclohex-1-en-1-yl)-2,3-dimethylpyrido[4,3-d]pyrimidin-4(3H)-one (0.360 g, 1.242 mmol) in 1,4-dioxane (6 mL) followed by DIPEA (0.434 mL, 2.485 mmol). The reaction mixture was heated at 100° C. for 16 h, then cooled to room temperature and concentrated under vacuum. The crude product was purified by reverse-phase preparative HPLC to provide (S)-5-(cyclohex-1-en-1-yl)-2,3-dimethyl-7-(2-(1-methyl-1H-pyrazol-4-yl)morpholino)pyrido[4,3-d]pyrimidin-4(3H)-one (0.21 g, 0.499 mmol, 40.2% yield) as an off-white solid. m/z (ESI, +ive ion): 421.1 (M+H)⁺.

Step 3: 5-cyclohexyl-2,3-dimethyl-7-((2S)-2-(1-methyl-1H-pyrazol-4-yl)-4-morpholinyl)pyrido[4,3-d]pyrimidin-4(3H)-one. To a 25 mL round-bottomed flask was added (S)-5-(cyclohex-1-en-1-yl)-2,3-dimethyl-7-(2-(1-methyl-1H-pyrazol-4-yl)morpholino)pyrido[4,3-d]pyrimidin-4(3H)-one (200 mg, 0.476 mmol) in THF (5 mL) followed by addition of 10% Pd—C (405 mg, 1.9 mmol) at room temperature. The mixture was stirred under hydrogen gas atmosphere at room temperature for 8 h then filtered through a celite bed and concentrated in vacuo. The crude product was purified by HPLC to provide 5-cyclohexyl-2,3-dimethyl-7-((2S)-2-(1-methyl-1H-pyrazol-4-yl)-4-morpholinyl)pyrido[4,3-d]pyrimidin-4(3H)-one (56.6 mg, 0.134 mmol, 28.2% yield) as an off-white solid. ¹H NMR (400 MHz, CDCl₃) δ ppm 7.53 (s, 1H), 7.44 (s, 1H), 4.59 (dd, J=11.4, 2.1 Hz, 1H), 4.28 (dt, J=11.2, 3.2 Hz, 1H), 4.18 (t, J=11.7 Hz, 1H), 3.90 (s, 3H), 3.83 (ddd, J=11.5, 8.2, 5.3 Hz, 1H), 3.41-3.52 (m, 1H), 2.84 (s, 3H), 2.80 (s, 3H), 2.42 (d, J=13.5 Hz, 1H), 2.32 (d, J=8.2 Hz, 2H), 2.12-2.23 (m, 5H), 1.96-2.12 (m, 4H). m/z (ESI, +ive ion): 443.2 (M+H)⁺.

Method 11

Examples 161-163: 5-(4-chloro-2-fluorophenyl)-2,3-dimethyl-7-((2R,4R)-2-(1-methyl-1H-pyrazol-4-yl)tetrahydro-2H-pyran-4-yl)pyrido[4,3-d]pyrimidin-4(3H)-one and 5-(4-chloro-2-fluorophenyl)-2,3-dimethyl-7-((2S,4S)-2-(1-methyl-1H-pyrazol-4-yl)tetrahydro-2H-pyran-4-yl)pyrido[4,3-d]pyrimidin-4(3H)-one; 5-(4-chloro-2-fluorophenyl)-2,3-dimethyl-7-((2R,4S)-2-(1-methyl-1H-pyrazol-4-yl)tetrahydro-2H-pyran-4-yl)pyrido[4,3-d]pyrimidin-4(3H)-one; and 5-(4-chloro-2-fluorophenyl)-2,3-dimethyl-7-((2S,4R)-2-(1-methyl-1H-pyrazol-4-yl)tetrahydro-2H-pyran-4-yl)pyrido[4,3-d]pyrimidin-4(3H)-one

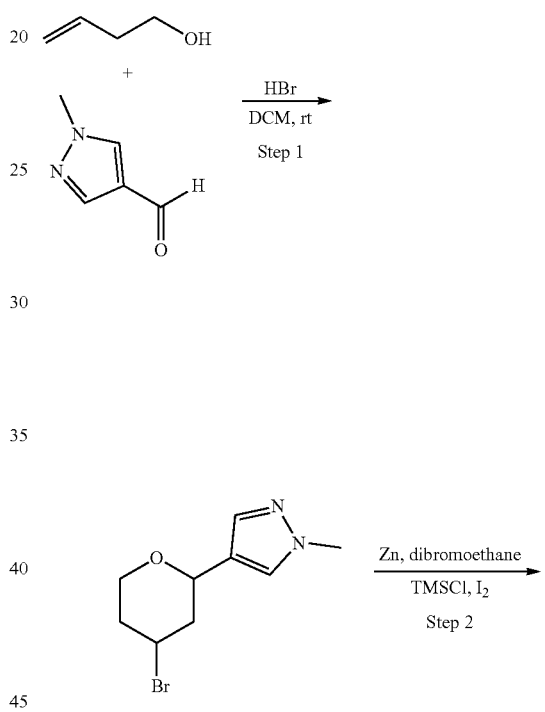

TABLE 5

Example 160 was prepared following the procedure described in Method 10, steps 1-3, as follows:

| Ex. # | Structure | Name | Reagents/Conditions |
|---|---|---|---|
| 160 | 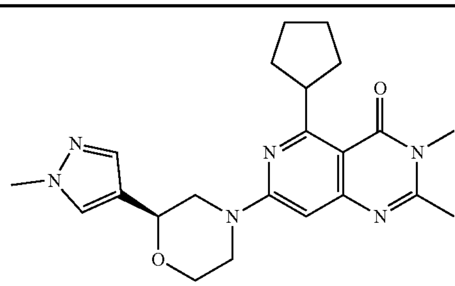 | 5-cyclopentyl-2,3-dimethyl-7-((2S)-2-(1-methyl-1H-pyrazol-4-yl)-4-morpholinyl)pyrido[4,3-d]pyrimidin-4(3H)-one | Step 1: Cyclopentenyl boronate |

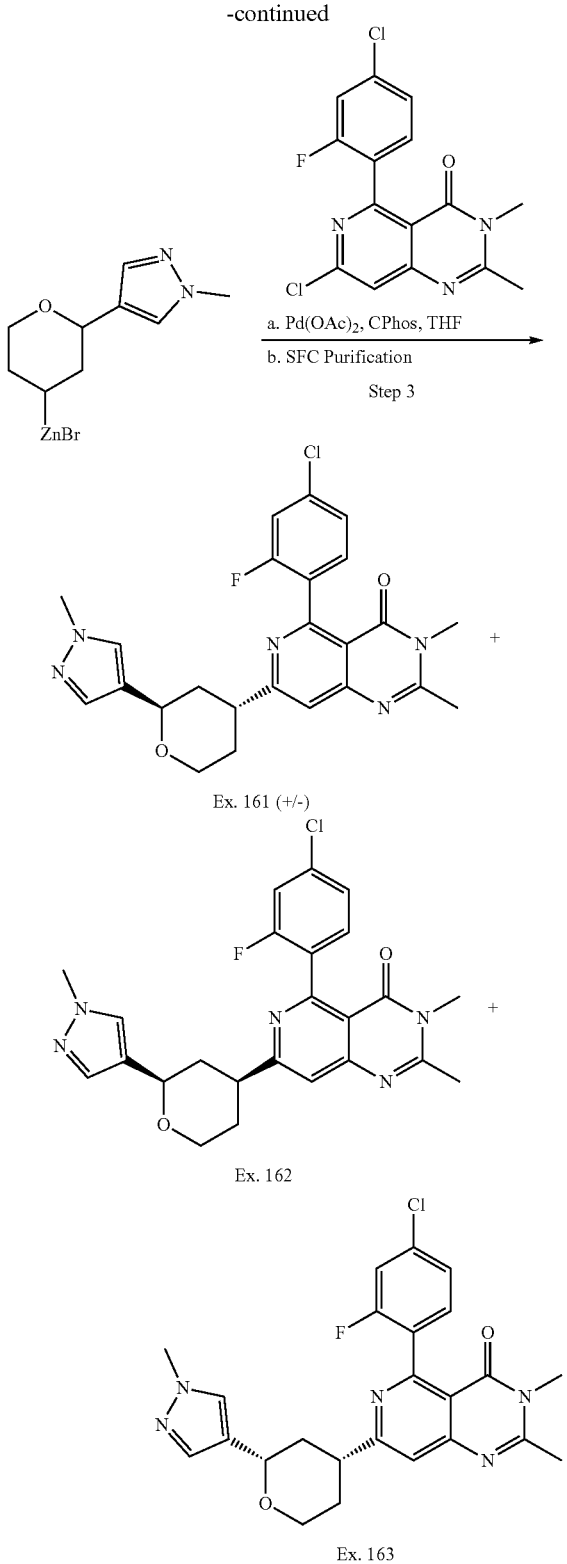

Step 1: 4-(4-bromotetrahydro-2H-pyran-2-yl)-1-methyl-1H-pyrazole. To a 100 mL flask was charged with 1-methyl-1H-pyrazole-4-carbaldehyde (1.03 g, 9.35 mmol), 3-buten-1-ol (0.708 g, 0.842 mL, 9.82 mmol) and DCM (18.71 mL). The vial was added hydrogen bromide-acetic acid (6.88 g, 5.08 mL, 28.1 mmol) in one portion. After 1 hour, the crude reaction was carefully quenched with saturated sodium bicarbonate solution and washed with EtOAc. The combined organic layers were dried over sodium sulfate, filtered and concentrated. The resulting crude material was purified by silica gel chromatography eluting with 0% to 40% EtOAc/EtOH (3:1) in heptane, to provide 4-(4-bromotetrahydro-2H-pyran-2-yl)-1-methyl-1H-pyrazole (1.307 g, 5.33 mmol, 57% yield) as a yellow oil (3.3:1 cis/trans mixture of diastereomers).

Major diastereomer (cis isomers): $^1$H NMR (500 MHz, CDCl$_3$) δ ppm 7.46 (s, 1H), 7.36 (s, 1H), 4.36 (dd, J=11.3, 2.1 Hz, 1H), 4.25 (tt, J=11.9, 4.5 Hz, 1H), 4.08 (ddd, J=12.0, 4.8, 1.8 Hz, 1H), 3.89 (s, 3H), 3.58 (td, J=12.1, 2.3 Hz, 1H), 2.52 (ddt, J=12.9, 4.3, 2.1, 2.1 Hz, 1H), 2.12-2.26 (m, 3H). m/z (ESI, +ive ion): 245.0 (M+H)$^+$.

Minor diastereomer (trans isomers): $^1$H NMR (500 MHz, CDCl$_3$) δ ppm 7.46 (s, 1H), 7.35 (s, 1H), 4.93 (dd, J=10.0, 2.9 Hz, 1H), 4.79 (quin, J=3.1 Hz, 1H), 4.12 (td, J=11.6, 2.1 Hz, 1H), 3.92-3.99 (m, 1H), 3.89 (s, 3H), 2.16-2.29 (m, 3H), 1.93-2.02 (m, 1H). m/z (ESI, +ive ion): 245.0 (M+H)$^+$.

Step 2: (2-(1-methyl-1H-pyrazol-4-yl)tetrahydro-2H-pyran-4-yl)zinc(II) bromide. To an oven-dried 50 mL flask was added Zn (0.320 g, 4.90 mmol), which was evacuated and backfilled with nitrogen 3 times. The flask was capped with a rubber septum and a thermocouple probe was inserted. Lithium chloride solution 0.5 M in anhydrous tetrahydrofuran (3.26 mL, 1.632 mmol) was added followed by 1,2-dibromoethane (0.015 g, 7.03 µL, 0.082 mmol) and the mixture was heated at an internal temperature of 50° C. for 20 min. After cooling to room temperature chlorotrimethylsilane (8.86 mg, 10.36 µL, 0.082 mmol) was added and the mixture was heated to an internal temp of 50° C. for 20 min. After cooling to room temperature diiodine (8.28 mg, 0.033 mmol) was added as a solution in THF 0.1 mL and the mixture was heated to an internal temp of 50° C. for 20 min. While still hot, 4-bromotetrahydro-2H-pyran-2-yl)-1-methyl-1H-pyrazole (0.4 g, 1.632 mmol, 3.3:1 mixture of cis/trans isomers) was added as a THF solution (1.5 mL). The resulting mixture was stirred at 50° C. for 18 h and the reaction solution was cooled to room temperature and allowed to stand for 3 h (zinc powder to settles) to provide a light-yellow solution, which was used in the next step without further treatment.

Step 3: 5-(4-chloro-2-fluorophenyl)-2,3-dimethyl-7-(2-(1-methyl-1H-pyrazol-4-yl)tetrahydro-2H-pyran-4-yl)pyrido[4,3-d]pyrimidin-4(3H)-one. To a 1-dram vial was added palladium(II) acetate (1.992 mg, 8.87 µmol.), 2-dicyclohexylphosphino-2',6'-dimethylamino-1,1'-biphenyl (7.75 mg, 0.018 mmol) and 7-chloro-5-(4-chloro-2-fluorophenyl)-2,3-dimethylpyrido[4,3-d]pyrimidin-4(3H)-one (60 mg, 0.177 mmol). The vial was purged with nitrogen then 2-(1-methyl-1H-pyrazol-4-yl)tetrahydro-2H-pyran-4-yl)zinc(II) bromide (~0.3 M in THF, 0.47 mL, 0.141 mmol) was added and the vial was stirred at room temperature. After 3 h, the reaction was quenched with saturated sodium bicarbonate solution and extracted four times with EtOAc. The combined organic layer was dried over sodium sulfate, filtered, and concentrated. The crude material was absorbed onto a plug of silica gel and purified by chromatography through a 24 g silica gel column, eluting with 0-100% EtOAc/EtOH 3:1 in heptane to provide the crude products as a 2.7:1 dr mixture (50 mg, 0.11 mmol, 60% yield). Single stereoisomers were obtained by SFC, Chiralpak AD-H 2×25 cm, 5 um column, (45% isopropanol using a F=80 mL/min) to generate 3 mg of peak 1 with a purity of >99%, 9.3 mg of peak 2 with an ee of >99% and 8.0 mg of peak 3 with an ee of >99%.

Peak 1 (Example 161): Mixture of trans isomers 2R,4R and 2S,4S: 5-(4-chloro-2-fluorophenyl)-2,3-dimethyl-7-((2R,4R)-2-(1-methyl-1H-pyrazol-4-yl)tetrahydro-2H-pyran-4-yl)pyrido[4,3-d]pyrimidin-4(3H)-one and 5-(4-chloro-2-fluorophenyl)-2,3-dimethyl-7-((2S,4S)-2-(1-methyl-1H-pyrazol-4-yl)tetrahydro-2H-pyran-4-yl)pyrido[4,3-d]pyrimidin-4(3H)-one, yellow oil. LC/MS $^1$H NMR (500 MHz, CDCl$_3$) δ ppm 7.47 (s, 1H), 7.39-7.44 (m, 2H), 7.26 (s, 1H), 7.17 (dd, J=1.95, 9.73 Hz, 1H), 4.98 (br t, J=4.80 Hz, 1H), 3.89 (s, 3H), 3.82-3.88 (m, 2H), 3.53-3.55 (m, 3H), 3.39-3.45 (m, 1H), 2.65 (s, 3H), 2.44 (dt, J=4.02, 8.82 Hz, 1H), 2.30 (ddd, J=5.06, 5.19, 13.62 Hz, 1H), 2.03-2.15 (m, 2H). (ESI+)=468.0 (M+H)$^+$.

Peak 2 (Example 162): 5-(4-chloro-2-fluorophenyl)-2,3-dimethyl-7-((2R,4S)-2-(1-methyl-1H-pyrazol-4-yl)tetrahydro-2H-pyran-4-yl)pyrido[4,3-d]pyrimidin-4(3H)-one (9.3 mg, 0.020 mmol, 4.2% yield), yellow oil. $^1$H NMR (500 MHz, CDCl$_3$) δ 7.48 (s, 1H), 7.40 (t, J=7.91 Hz, 1H), 7.37 (s, 2H), 7.26 (s, 1H), 7.17 (dd, J=1.88, 9.67 Hz, 1H), 4.54 (dd, J=1.88, 11.22 Hz, 1H), 4.21-4.27 (m, 1H), 3.87 (s, 3H), 3.67-3.83 (m, 1H), 3.53 (s, 3H), 3.16-3.30 (m, 1H), 2.64 (s, 3H), 2.31 (br d, J=12.98 Hz, 1H), 2.02 (br s, 1H), 1.80-2.00 (m, 3H). m/z (ESI, +ive ion): 468.0 (M+H)$^+$.

Peak 3 (Example 163): 5-(4-chloro-2-fluorophenyl)-2,3-dimethyl-7-((2S,4R)-2-(1-methyl-1H-pyrazol-4-yl)tetrahydro-2H-pyran-4-yl)pyrido[4,3-d]pyrimidin-4(3H)-one (8.0 mg, 0.017 mmol, 3.6% yield), yellow oil. $^1$H NMR (500 MHz, CDCl$_3$) δ ppm 7.49 (s, 1H), 7.39-7.43 (m, 1H), 7.38 (s, 2H), 7.26-7.28 (m, 1H), 7.18 (dd, J=9.6, 1.9 Hz, 1H), 4.55 (dd, J=11.3, 1.9 Hz, 1H), 4.22-4.28 (m, 1H), 3.88 (s, 3H), 3.78 (td, J=11.7, 2.5 Hz, 1H), 3.54 (s, 3H), 3.27 (tt, J=12.0, 3.8 Hz, 1H), 2.65 (s, 3H), 2.33 (br d, J=13.0 Hz, 1H), 1.88-2.07 (m, 3H). m/z (ESI, +ive ion): 468.0 (M+H)$^+$.

The absolute stereochemistry was assigned arbitrarily. Relative stereochemistry (cis/trans) determined by NMR.

Method 12

Example 164: 5-(4-chloro-2-fluorophenyl)-2,3-dimethyl-7-(6-(1-methyl-1H-pyrazol-4-yl)-3,6-dihydro-2H-pyran-4-yl)pyrido[4,3-d]pyrimidin-4(3H)-one

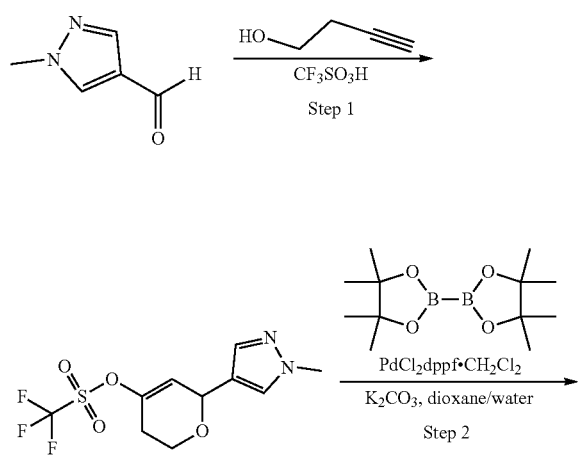

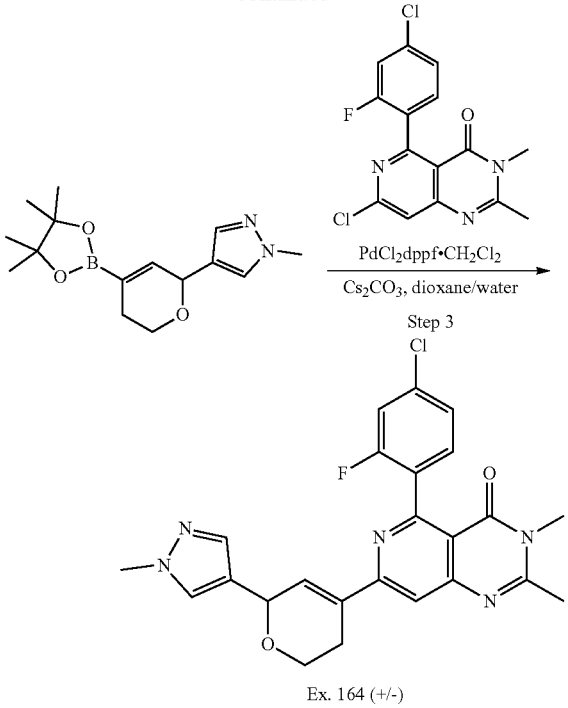

Ex. 164 (+/-)

Step 1: 6-(1-methyl-1H-pyrazol-4-yl)-3,6-dihydro-2H-pyran-4-yl. To a 20 mL scintillation vial was added 1-methyl-1H-pyrazole-4-carbaldehyde (200 mg, 1.816 mmol), (2-hydroxyethyl)-acetylene (191 mg, 206 μl, 2.72 mmol) and DCM (3633 μl). Trifluoromethane-sulfonic acid (327 mg, 194 μl, 2.180 mmol) was added slowly at 0° C. and the mixture was warmed to room temperature. After 30 min, additional trifluoromethanesulfonic acid (327 mg, 194 μl, 2.180 mmol) was added and the mixture was stirred at room temperature for 2 h. The reaction was quenched with saturated sodium bicarbonate solution and washed with DCM. The combined organic layers were dried over sodium sulfate, filtered and concentrated. The resulting material was purified by silica gel chromatography eluting with 0-70% EtOAc in heptane, to provide 6-(1-methyl-1H-pyrazol-4-yl)-3,6-dihydro-2H-pyran-4-yl trifluoromethane-sulfonate (227 mg, 0.727 mmol, 40.0% yield) as a yellow oil. $^1$H NMR (500 MHz, CDCl$_3$) δ ppm 2.45-2.60 (m, 2H) 3.82-3.88 (m, 1H) 3.91-3.94 (m, 3H) 3.98-4.04 (m, 1H) 5.20-5.23 (m, 1H) 5.30-5.33 (m, 1H) 5.33-5.37 (m, 1H) 5.94-5.98 (m, 1H) 7.34-7.38 (m, 1H) 7.48-7.50 (m, 1H).

Step 2: 1-methyl-4-(4-(4,4,5,5-tetramethyl-1,3,2-dioxaborolan-2-yl)-5,6-dihydro-2H-pyran-2-yl)-1H-pyrazole. To a 20 mL scintillation vial was charged with 6-(1-methyl-1H-pyrazol-4-yl)-3,6-dihydro-2H-pyran-4-yl trifluoromethanesulfonate (227 mg, 0.727 mmol), [1,1'-bis(diphenylphosphino)ferrocene]-dichloropalladium (II), complex with DCM (59.4 mg, 0.073 mmol), [1,1'-bis(diphenylphosphino)ferrocene]-dichloropalladium(ii), complex with DCM (59.4 mg, 0.073 mmol) and potassium acetate (285 mg, 2.91 mmol), which was purged with N$_2$. Then 1,4-dioxane (2908 μl) was added and the reaction was heated to 90° C. for 2 h, the reaction was cooled to rt. The reaction mixture was diluted with EtOAc and filtered through a plug of silica gel, and the crude material purified by chromatography through silica gel column eluting with 0-100% EtOAc in heptane, to provide 1-methyl-4-(4-(4,4,5,5-tetramethyl-1,3,2-dioxaborolan-2-yl)-5,6-dihydro-2H-pyran-2-yl)-1H-pyrazole (87 mg, 0.300 mmol, 41.2% yield) as a red oil. $^1$H NMR (CDCl$_3$, 500 MHz) δ 7.48 (s, 1H), 7.36 (s, 1H), 6.61 (q, 1H, J=1.9 Hz), 5.20 (q, 1H, J=2.6 Hz), 3.9-3.9 (m, 4H), 3.74 (ddd, 1H, J=4.5, 7.2, 11.4 Hz), 2.30 (dt, 1H, J=2.5, 4.9 Hz), 2.2-2.3 (m, 1H), 1.30 (s, 12H).

Step 3: 5-(4-chloro-2-fluorophenyl)-2,3-dimethyl-7-(6-(1-methyl-1H-pyrazol-4-yl)-3,6-dihydro-2H-pyran-4-yl) pyrido[4,3-d]pyrimidin-4(3H)-one. In a 20 mL scintillation vial equipped with a condenser was added 1-methyl-4-(4-(4,4,5,5-tetramethyl-1,3,2-dioxaborolan-2-yl)-5,6-dihydro-2H-pyran-2-yl)-1H-pyrazole (87 mg, 0.300 mmol, 125536-50-10), [1,1'-bis(diphenylphosphino)ferrocene]-dichloropalladium (II), complex with DCM (24.48 mg, 0.030 mmol) and cesium carbonate (293 mg, 0.899 mmol). The vial was sealed and purged with N$_2$ for 20 min, 1,4-dioxane (1124 μl) and water (375 μl) (degassed) was added. The flask was heated to 70° C. for 2 h, cooled to room temperature and diluted with EtOAc and saturated sodium bicarbonate solution. The layers were separated, and the aqueous layer was extracted with EtOAc. The organic extract was dried over Na$_2$SO$_4$ and concentrated in vacuo to give the crude material as a brown oil. Purification by silica gel chromatography, eluting with 0-100% EtOAc/EtOH 3:1 in heptane, provided crude product as a brown oil. The material was further purified by reverse-phase preparative HPLC using 0.1% TFA in CH$_3$CN/H$_2$O, gradient 25-70% over 14 min to provide racemic 5-(4-chloro-2-fluorophenyl)-2,3-dimethyl-7-(6-(1-methyl-1H-pyrazol-4-yl)-3,6-dihydro-2H-pyran-4-yl)pyrido[4,3-d]pyrimidin-4(3H)-one (58.6 mg, 0.126 mmol, 41.9% yield). $^1$H NMR (CDCl$_3$, 500 MHz) δ 7.52 (s, 1H), 7.50 (s, 1H), 7.4-7.5 (m, 1H), 7.38 (s, 1H), 7.2-7.3 (m, 1H), 7.16 (dd, 1H, J=1.9, 9.7 Hz), 7.13 (s, 1H), 5.4-5.4 (m, 1H), 4.1-4.1 (m, 1H), 3.92 (ddd, 1H, J=4.6, 7.2, 11.6 Hz), 3.88 (s, 3H), 3.54 (s, 3H), 2.74 (br s, 1H), 2.65 (s, 4H). (ESI, +ive ion): 466.0 (M+H)$^+$.

Method 13

Example 165: 5-(4-chloro-2-fluorophenyl)-7-((2R,4S)-2-(1-cyclopropyl-1H-pyrazol-4-yl)tetrahydro-2H-pyran-4-yl)-2,3-dimethylpyrido[4,3-d]pyrimidin-4(3H)-one Example 166: 5-(4-chloro-2-fluorophenyl)-7-((2S,4R)-2-(1-cyclopropyl-1H-pyrazol-4-yl)tetrahydro-2H-pyran-4-yl)-2,3-dimethylpyrido[4,3-d]pyrimidin-4(3H)-one

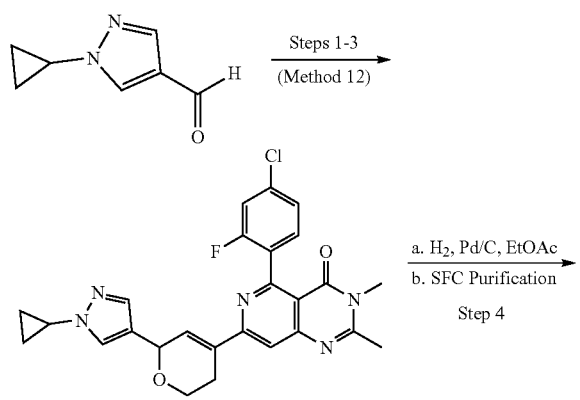

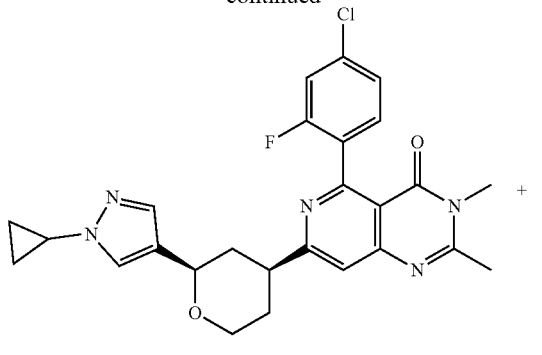

Ex. 165

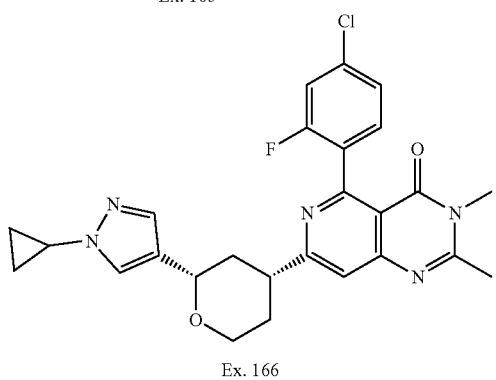

Ex. 166

Steps 1-3: 5-(4-chloro-2-fluorophenyl)-7-(6-(1-cyclopropyl-1H-pyrazol-4-yl)-3,6-dihydro-2H-pyran-4-yl)-2,3-dimethylpyrido[4,3-d]pyrimidin-4(3H)-one. Steps 1-3 from Method 12 were followed using 1-cyclopropyl-1H-pyrazole-4-carbaldehyde as starting material to provide 5-(4-chloro-2-fluorophenyl)-7-(6-(1-cyclopropyl-1H-pyrazol-4-yl)-3,6-dihydro-2H-pyran-4-yl)-2,3-diethylpyrido[4,3-d]pyrimidin-4(3H)-one, as a light brown solid. m/z (ESI, +ive ion): 492.1 (M+H)$^+$.

Step 4: (2R,4S)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate. To a 50 mL round-bottom flask was added 5-(4-chloro-2-fluorophenyl)-7-(6-(1-cyclopropyl-1H-pyrazol-4-yl)-3,6-dihydro-2H-pyran-4-yl)-2,3-dimethylpyrido[4,3-d]pyrimidin-4(3H)-one (300 mg, 0.610 mmol) and Pd/C (10%) (300 mg, 0.610 mmol), in EtOAc (30 mL). The reaction mixture was stirred at 42 PSI under H$_2$ gas at room temperature for over 16 h. After completion of the reaction was filtered through celite and washed with EtOAc (50 mL) and the filtrate was concentrated under reduced pressure and purified by silica gel chromatography, eluting with a gradient of 0-5% MeOH in EtOAc, to provide a brown gummy solid (300 mg). The crude products were purified by SFC, Chiralpak AS-H 250×30 mm, 5 um column, (10% methanol, F=80 mL/min) to generate 55.7 mg of peak 1 (>99% ee), 52.1 mg of peak 2 with (>99% ee) as off-white solids (35.5% total yield).

Peak 1: Example 165 5-(4-chloro-2-fluorophenyl)-7-((2R,4S)-2-(1-cyclopropyl-1H-pyrazol-4-yl)tetrahydro-2H-pyran-4-yl)-2,3-dimethylpyrido[4,3-d]pyrimidin-4(3H)-one. $^1$H NMR (400 MHz, Methanol-d4) δ ppm 7.70 (s, 1H), 7.56 (s, 1H), 6.52 (s, 1H), 5.61 (dt, J=4.0, 2.2 Hz, 1H), 4.62 (dd, J=10.3, 2.8 Hz, 1H), 4.45 (d, J=12.9 Hz, 1H), 4.24 (d, J=13.1 Hz, 1H), 4.08 (ddd, J=11.5, 3.6, 1.8 Hz, 1H), 3.91 (s, 3H), 3.80 (td, J=11.5, 2.8 Hz, 1H), 3.52 (s, 3H), 3.06-3.21

(m, 2H), 2.59 (s, 3H), 2.16-2.31 (m, 4H), 1.70-1.91 (m, 4H). m/z (ESI, +ive ion): 494.1 (M+H)+.

Peak 2: Example 166 5-(4-chloro-2-fluorophenyl)-7-((2S,4R)-2-(1-cyclopropyl-1H-pyrazol-4-yl)tetrahydro-2H-pyran-4-yl)-2,3-dimethylpyrido[4,3-d]pyrimidin-4(3H)-one. $^1$H NMR (400 MHz, Methanol-d4) δ ppm 7.71 (s, 1H), 7.57 (s, 1H), 6.48 (s, 1H), 4.63 (d, J=9.3 Hz, 1H), 4.40-4.53 (m, 2H), 4.30 (d, J=13.1 Hz, 1H), 4.08 (t, J=12.4 Hz, 3H), 3.91 (s, 3H), 3.81 (t, J=11.4 Hz, 1H), 3.64 (t, J=11.8 Hz, 2H), 3.54 (s, 3H), 3.18 (dd, J=18.3, 12.0 Hz, 2H), 2.58 (s, 3H), 1.97 (qd, J=12.7, 4.3 Hz, 4H). m/z (ESI, +ive ion): 494.1 (M+H)+.

The absolute stereochemistry was arbitrarily assigned.

Method 14

Example 167: ethyl (2R,4S)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate and ethyl (2S,4R)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate (mixture of cis isomers)

Example 168: ethyl (2S,4S)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate and ethyl (2R,4R)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate (mixture of trans isomers)

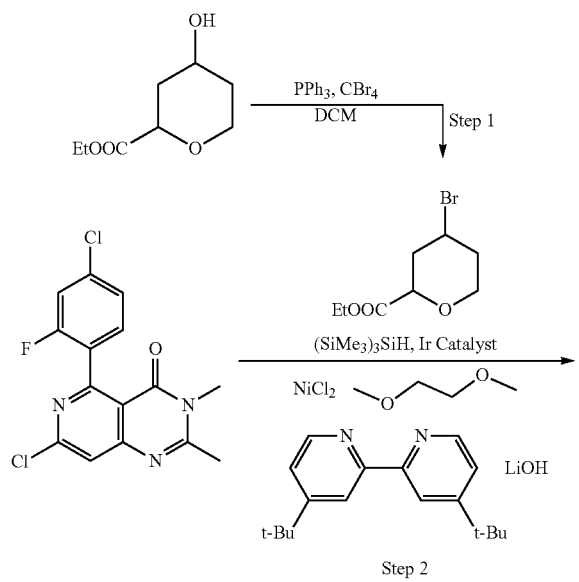

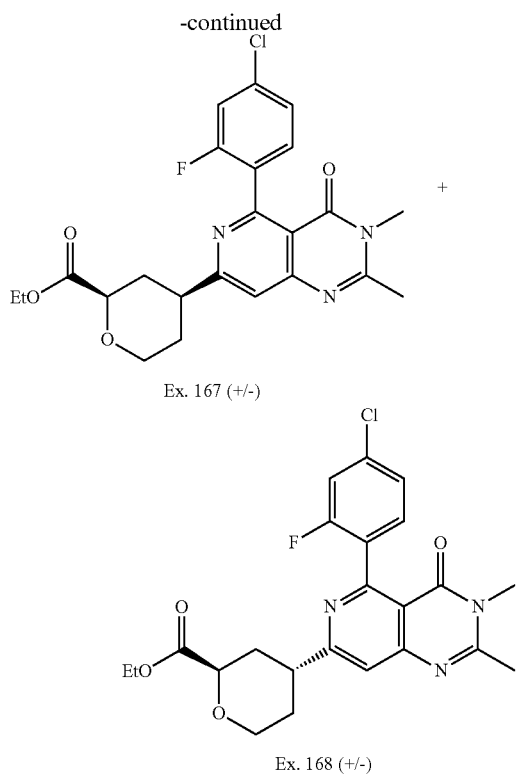

Ex. 167 (+/-)

Ex. 168 (+/-)

Step 1: Ethyl 4-bromotetrahydro-2H-pyran-2-carboxylate. To a 20-mL vial was added ethyl 4-hydroxyoxane-2-carboxylate (675 mg, 3.87 mmol, Aurum Pharmatech LLC) and DCM (7750 μl) and the vial was cooled to 0° C. It was followed by the addition of triphenylphosphine (1118 mg, 4.26 mmol) and carbon tetrabromide (1285 mg, 3.87 mmol). The reaction was warmed to room temperature stirred for 16 h, then quenched with saturated sodium bicarbonate and extracted with DCM. The combined organic layers were dried over Na$_2$SO$_4$ and concentrated. The crude product was purified via silica gel chromatography, eluting with 0-25% EtOAc in heptane to provide ethyl 4-bromotetrahydro-2H-pyran-2-carboxylate (0.49 g, 2.067 mmol, 53.3% yield) as a colorless oil. $^1$H NMR (500 MHz, CDCl$_3$) δ ppm 1.30 (t, J=7.14 Hz, 3H) 1.89-1.96 (m, 1H) 2.13-2.23 (m, 2H) 2.25-2.37 (m, 1H) 4.00 (dd, J=7.79, 2.72 Hz, 2H) 4.24 (q, J=7.14 Hz, 2H) 4.50 (dd, J=10.12, 2.85 Hz, 1H) 4.68 (quin, J=3.76 Hz, 1H).

Step 2: Ethyl 4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate. To a 2-dram vial were added 7-chloro-5-(4-chloro-2-fluorophenyl)-2,3-dimethylpyrido[4,3-d]pyrimidin-4(3H)-one (50 mg, 0.148 mmol), nickel (II) chloride ethylene glycol dimethyl ether complex (3.25 mg, 0.015 mmol), 4,4'-di-tert-butyl-2,2'-dipyridyl (3.97 mg, 0.015 mmol) lithium hydroxide (7.08 mg, 0.296 mmol) and (4,4'-Di-t-butyl-2,2'-bipyridine)bis[3,5-difluoro-2-[5-trifluoromethyl-2-pyridinyl-N)phenyl-C]iridium(III) hexafluorophosphate (Ir catalyst, 1.66 mg, 1.479 μmol). The vial was flushed with N$_2$ and 1,2-dimethoxyethane (1680 μl), tris(trimethylsilyl)silane (36.8 mg, 46.0 μl, 0.148 mmol) and tris(trimethylsilyl)silane (36.8 mg, 46.0 μl, 0.148 mmol) and ethyl 4-bromotetrahydro-2H-pyran-2-carboxylate (52.6 mg, 0.222 mmol) were added. After stirring and irradiation (Kessil lamps, full intensity, 800 rpm, fan on) for 3 h the reaction was filtered and concentrated. The crude material was subjected to reverse-phase preparative HPLC using 0.1% TFA in CH$_3$CN/H$_2$O, gradient 25% to 70% over 12 min to provide two peaks:

Peak 1: Example 167, ethyl (2R,4S)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate and ethyl (2S,4R)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate (mixture of cis isomers) (5.7 mg, 0.012 mmol, 8.38% yield) as a white solid. $^1$H NMR (500 MHz, DMSO-d6) δ 7.40-7.46 (m, 3H), 7.32-7.39 (m, 1H), 4.04-4.17 (m, 4H), 3.58 (dt, J=2.72, 11.68 Hz, 1H), 3.42 (s, 3H), 3.17-3.26 (m, 1H), 2.60 (s, 3H), 2.10-2.18 (m, 1H), 1.76-1.87 (m, 2H), 1.72 (q, J=12.02 Hz, 1H), 1.18 (t, J=7.07 Hz, 3H). m/z (ESI, +ive ion): 460.0 (M+H)$^+$.

Peak 2: Example 168, ethyl (2S,4S)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate and ethyl (2R,4R)-4-(5-(4-chloro-2-fluorophenyl)-2,3-dimethyl-4-oxo-3,4-dihydropyrido[4,3-d]pyrimidin-7-yl)tetrahydro-2H-pyran-2-carboxylate (mixture of trans enantiomers) (7 mg, 0.014 mmol, 10.3% yield) as a white solid. $^1$H NMR (500 MHz, DMSO-d6) δ 7.41-7.48 (m, 3H), 7.34-7.39 (m, 1H), 4.52-4.62 (m, 1H), 4.13-4.23 (m, 2H), 3.79-3.88 (m, 2H), 3.42-3.44 (m, 3H), 3.02-3.09 (m, 1H), 2.59-2.62 (m, 3H), 2.21-2.29 (m, 1H), 2.07-2.17 (m, 1H), 1.80-1.91 (m, 2H), 1.20-1.28 (m, 3H). m/z (ESI, +ive ion): 460.0 (M+H)$^+$.

The absolute stereochemistry was arbitrarily assigned. The relative stereochemistry (cis/trans) was confirmed by NMR.

TABLE 6

Examples 169 to 178 were prepared following the procedure described in Method 14, steps 1-4, as follows:

| Ex. # | Structure | Name | Reagents/Conditions |
|---|---|---|---|
| 169 | (structure) | 5-(4-chloro-2-fluorophenyl)-2,3-dimethyl-7-((2R,4S)-2-(2-methyl-4-pyridinyl)tetrahydro-2H-pyran-4-yl)pyrido[4,3-d]pyrimidin-4(3H)-one. Absolute stereochemistry was arbitrarily assigned. Relative stereochemistry (cis/trans) was confirmed by NMR. | Step 1: Skip Step 2: 4-(4-bromotetrahydro-2H-pyran-2-yl)-2-methylpyridine (Intermediate 18). Purification by chiral SFC, Chiralpak AD-H 2 × 15 cm, 5 um column, 40% isopropanol, F = 70 mL/min |
| 170 | (structure) | 5-(4-chloro-2-fluorophenyl)-2,3-dimethyl-7-((2S,4R)-2-(2-methyl-4-pyridinyl)tetrahydro-2H-pyran-4-yl)pyrido[4,3-d]pyrimidin-4(3H)-one. Absolute stereochemistry was arbitrarily assigned. Relative stereochemistry (cis/trans) was confirmed by NMR. | Step 1: Skip Step 2: 4-(4-bromo-tetrahydro-2H-pyran-2-yl)-2-methylpyridine (Intermediate 18). Purification by chiral SFC, Chiralpak AD-H 2 × 15 cm, 5 um column, 40% isopropanol, F = 70 mL/min |
| 171 | (structure) | 5-(4-chloro-2-fluorophenyl)-2,3-dimethyl-7-(2-(6-methylpyridin-3-yl)tetrahydro-2H-pyran-4-yl)pyrido[4,3-d]pyrimidin-4(3H)-one | Step 1: Skip Step 2: 5-(4-bromotetrahydro-2H-pyran-2-yl)-2-methylpyridine (Intermediate 20). |

TABLE 6-continued

Examples 169 to 178 were prepared following the procedure described in Method 14, steps 1-4, as follows:

| Ex. # | Structure | Name | Reagents/Conditions |
|---|---|---|---|
| 172 | 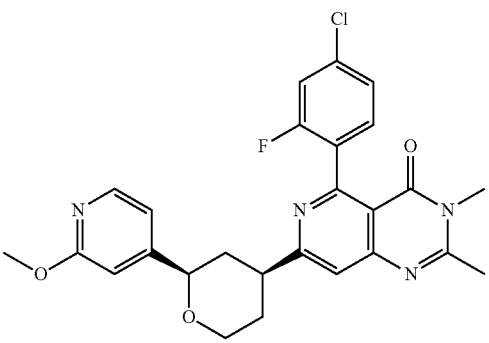 | 5-(4-chloro-2-fluorophenyl)-7-((2R,4S)-2-(2-methoxy-4-pyridinyl)tetrahydro-2H-pyran-4-yl)-2,3-dimethylpyrido[4,3-d]pyrimidin-4(3H)-one. Absolute stereochemistry was arbitrarily assigned. Relative stereochemistry assigned by NMR. | Step 1: Skip Step 2: 4-(4-bromotetrahydro-2H-pyran-2-yl)-2-methoxypyridine (Intermediate 19); Purification by SFC. Chiralpak AS-H 2 × 15 cm, 5 um column, 20% methanol, F = 80 mL/min. Peak 1. |
| 173 | 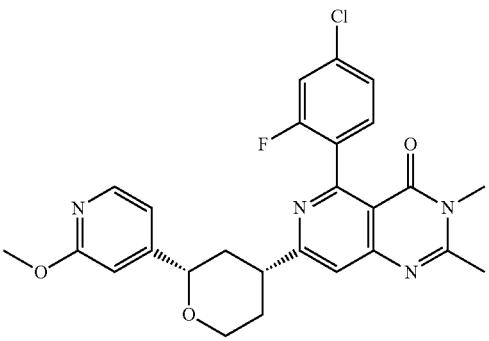 | 5-(4-chloro-2-fluorophenyl)-7-((2S,4R)-2-(2-methoxy-4-pyridinyl)tetrahydro-2H-pyran-4-yl)-2,3-dimethylpyrido[4,3-d]pyrimidin-4(3H)-one. Absolute stereochemistry was arbitrarily assigned. Relative stereochemistry assigned by NMR. | Step 1: Skip Step 2: 4-(4-bromotetrahydro-2H-pyran-2-yl)-2-methoxypyridine (Intermediate 19); Purification by SFC. Chiralpak AS-H 2 × 15 cm, 5 um column, 20% methanol, F = 80 mL/min. Peak 2. |
| 174 | 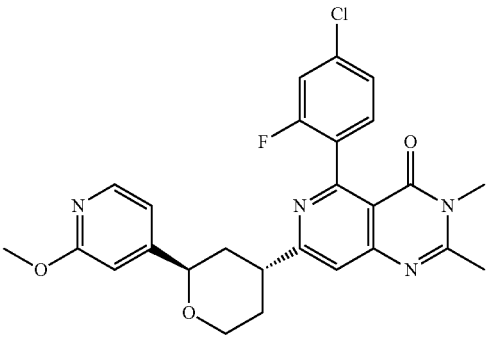 | 5-(4-chloro-2-fluorophenyl)-7-((2R,4R)-2-(2-methoxy-4-pyridinyl)tetrahydro-2H-pyran-4-yl)-2,3-dimethylpyrido[4,3-d]pyrimidin-4(3H)-one. Absolute stereochemistry was arbitrarily assigned. Relative stereochemistry assigned by NMR. | Step 1: Skip Step 2: 4-(4-bromotetrahydro-2H-pyran-2-yl)-2-methoxypyridine (Intermediate 19); Purification by SFC. Chiralpak AS-H 2 × 15 cm, 5 um column, 20% methanol, F = 80 mL/min. Peak 3. |
| 175 | 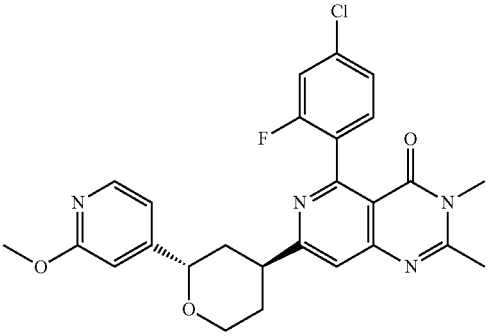 | 5-(4-chloro-2-fluorophenyl)-7-((2S,4S)-2-(2-methoxy-4-pyridinyl)tetrahydro-2H-pyran-4-yl)-2,3-dimethylpyrido[4,3-d]pyrimidin-4(3H)-one. Absolute stereochemistry was arbitrarily assigned. Relative stereochemistry assigned by NMR. | Step 1: Skip Step 2: 4-(4-bromotetrahydro-2H-pyran-2-yl)-2-methoxypyridine (Intermediate 19); Purification by SFC. Chiralpak AS-H 2 × 15 cm, 5 um column, 20% methanol, F = 80 mL/min. Peak 4. |

TABLE 6-continued

Examples 169 to 178 were prepared following the procedure described in Method 14, steps 1-4, as follows:

| Ex. # | Structure | Name | Reagents/Conditions |
|---|---|---|---|
| 176 | 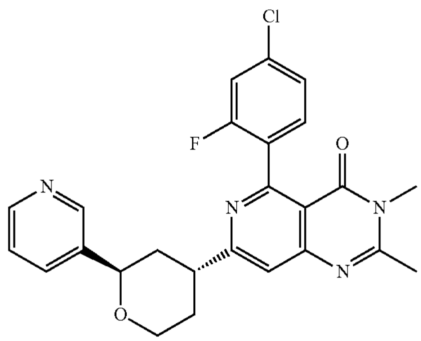 | 5-(4-chloro-2-fluorophenyl)-2,3-dimethyl-7-((2R,4R)-2-(3-pyridinyl)tetrahydro-2H-pyran-4-yl)pyrido[4,3-d]pyrimidin-4(3H)-one and 5-(4-chloro-2-fluorophenyl)-2,3-dimethyl-7-((2S,4S)-2-(3-pyridinyl)tetrahydro-2H-pyran-4-yl)pyrido[4,3-d]pyrimidin-4(3H)-one (Mixture of trans isomers). Relative stereochemistry assigned by NMR. | Step 1: Skip Step 2: 3-(4-bromotetrahydro-2H-pyran-2-yl)pyridine (Intermediate 21); Purification by SFC, Chiralpak AD-H 2 × 15 cm, 5 um column, 35% methanol w/ 0.2% DEA, F = 80 mL/min. Peak 1. |
| 177 | 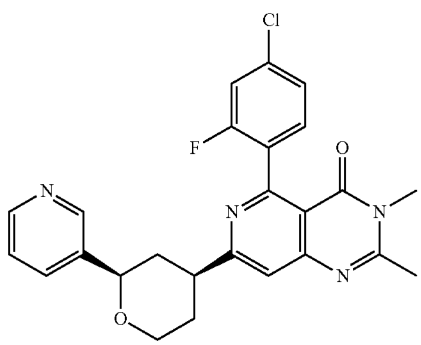 [SMILES: Cc1nc2cc([C@H]3CCO[C@@H](c4cccnc4)C3)nc(-c3ccc(Cl)cc3F)c2c(=O)n1C] | 5-(4-chloro-2-fluorophenyl)-2,3-dimethyl-7-((2R,4S)-2-(3-pyridinyl)tetrahydro-2H-pyran-4-yl)pyrido[4,3-d]pyrimidin-4(3H)-one. Absolute stereochemistry was arbitrarily assigned Relative stereochemistry assigned by NMR. | Step 1: Skip Step 2: 3-(4-bromotetrahydro-2H-pyran-2-yl)pyridine (Intermediate 21); Purification by SFC, Chiralpak AD-H 2 × 15 cm, 5 um column, 35% methanol w/ 0.2% DEA, F = 80 mL/min. Peak 2. |
| 178 | 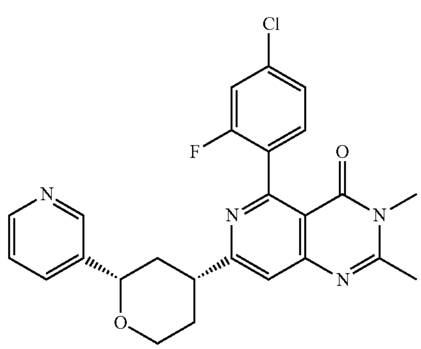 | 5-(4-chloro-2-fluorophenyl)-2,3-dimethyl-7-((2S,4R)-2-(3-pyridinyl)tetrahydro-2H-pyran-4-yl)pyrido[4,3-d]pyrimidin-4(3H)-one. Absolute stereochemistry was arbitrarily assigned. Relative stereochemistry assigned by NMR. | Step 1: Skip Step 2: 3-(4-bromotetrahydro-2H-pyran-2-yl)pyridine (Intermediate 21); Purification by SFC, Chiralpak AD-H 2 × 15 cm, 5 um column, 35% methanol w/ 0.2% DEA, F = 80 mL/min. Peak 3. |

TABLE B

| Ex # | Structure | Name | M + H |
|---|---|---|---|
| 179 | 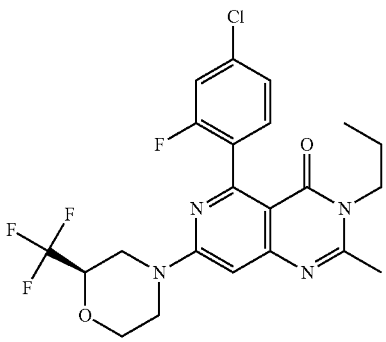 [SMILES: CCCn1c(C)nc2cc(N3CCO[C@@H](C(F)(F)F)C3)nc(-c3ccc(Cl)cc3F)c2c1=O] | (R)-5-(4-chloro-2-fluorophenyl)-2-methyl-3-propyl-7-(2-(trifluoromethyl)morpholino)pyrido[4,3-d]pyrimidin-4(3H)-one | 485.2 |
| 180 | 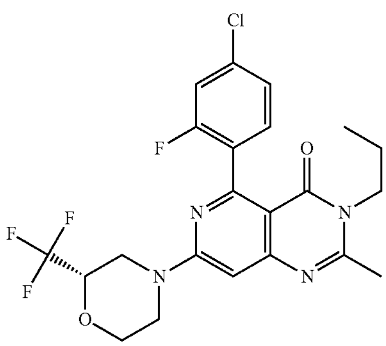 | (S)-5-(4-chloro-2-fluorophenyl)-2-methyl-3-propyl-7-(2-(trifluoromethyl)morpholino)pyrido[4,3-d]pyrimidin-4(3H)-one | 485.2 |
| 181 | 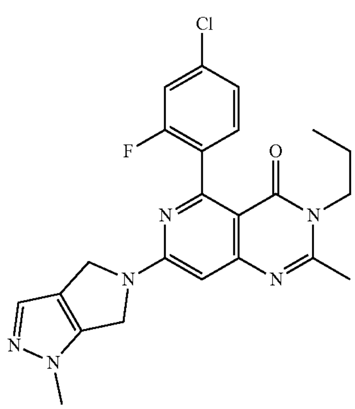 [SMILES: CCCn1c(C)nc2cc(N3Cc4cnn(C)c4C3)nc(-c3ccc(Cl)cc3F)c2c1=O] | 5-(4-chloro-2-fluorophenyl)-2-methyl-7-(1-methyl-4,6-dihydropyrrolo[3,4-c]pyrazol-5(1H)-yl)-3-propylpyrido[4,3-d]pyrimidin-4(3H)-one | 453.0 |
| 182 | 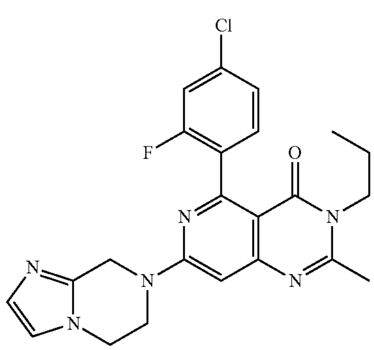 [SMILES: CCCn1c(C)nc2cc(N3CCn4ccnc4C3)nc(-c3ccc(Cl)cc3F)c2c1=O] | 5-(4-chloro-2-fluorophenyl)-7-(5,6-dihydroimidazo[1,2-a]pyrazin-7(8H)-yl)-2-methyl-3-propylpyrido[4,3-d]pyrimidin-4(3H)-one | 453.0 |

TABLE B-continued

Additonal Compounds

| Ex # | Structure | Name | M + H |
|---|---|---|---|
| 183 | 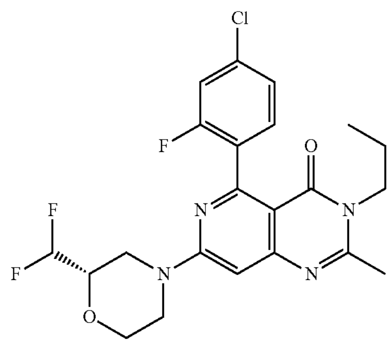 | (S)-5-(4-chloro-2-fluorophenyl)-7-(2-(difluoromethyl)morpholino)-2-methyl-3-propylpyrido[4,3-d]pyrimidin-4(3H)-one | 467.0 |
| 184 | 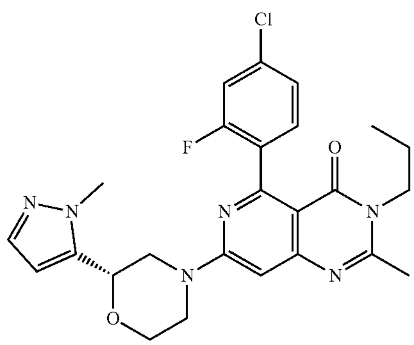 [SMILES: CCCn1c(C)nc2cc(N3CCO[C@H](c4ccnn4C)C3)nc(-c3ccc(Cl)cc3F)c2c1=O] | (S)-5-(4-chloro-2-fluorophenyl)-2-methyl-7-(2-(1-methyl-1H-pyrazol-5-yl)morpholino)-3-propylpyrido[4,3-d]pyrimidin-4(3H)-one | 497.0 |
| 185 | 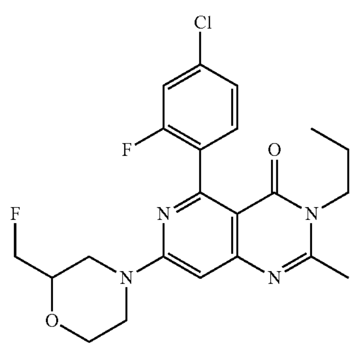 [SMILES: CCCn1c(C)nc2cc(N3CCOC(CF)C3)nc(-c3ccc(Cl)cc3F)c2c1=O] | 5-(4-chloro-2-fluorophenyl)-7-(2-(fluoromethyl)morpholino)-2-methyl-3-propylpyrido[4,3-d]pyrimidin-4(3H)-one | 449.0 |
| 186 | 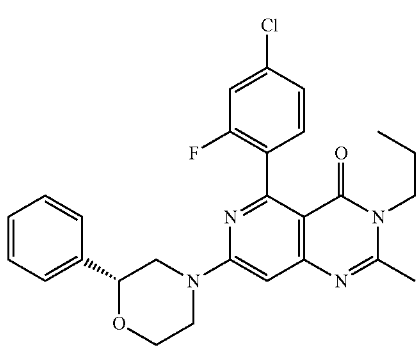 [SMILES: CCCn1c(C)nc2cc(N3CCO[C@H](c4ccccc4)C3)nc(-c3ccc(Cl)cc3F)c2c1=O] | (R)-5-(4-chloro-2-fluorophenyl)-2-methyl-7-(2-phenylmorpholino)-3-propylpyrido[4,3-d]pyrimidin-4(3H)-one | 493.2 |

TABLE B-continued

Additonal Compounds

| Ex # | Structure | Name | M + H |
|---|---|---|---|
| 187 | 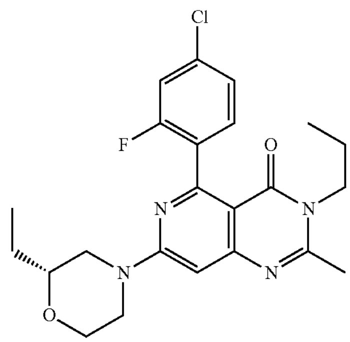 | (R)-5-(4-chloro-2-fluorophenyl)-7-(2-ethylmorpholino)-2-methyl-3-propylpyrido[4,3-d]pyrimidin-4(3H)-one | 445.2 |
| 188 | 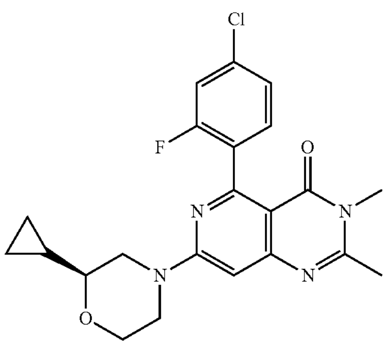 [SMILES: Cc1nc2cc(N3CCO[C@@H](C4CC4)C3)nc(-c3ccc(Cl)cc3F)c2c(=O)n1C] | (S)-5-(4-chloro-2-fluorophenyl)-7-(2-cyclopropylmorpholino)-2,3-dimethylpyrido[4,3-d]pyrimidin-4(3H)-one | 429.2 |
| 189 | 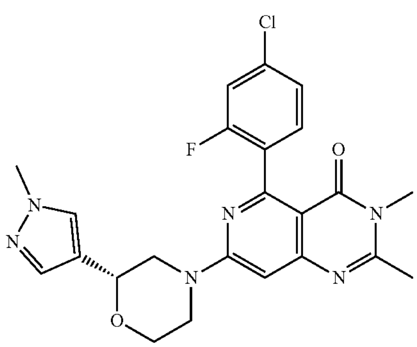 [SMILES: Cc1nc2cc(N3CCO[C@H](c4cnn(C)c4)C3)nc(-c3ccc(Cl)cc3F)c2c(=O)n1C] | (R)-5-(4-chloro-2-fluorophenyl)-2,3-dimethyl-7-(2-(1-methyl-1H-pyrazol-4-yl)morpholino)pyrido[4,3-d]pyrimidin-4(3H)-one | 469.2 |
| 190 | 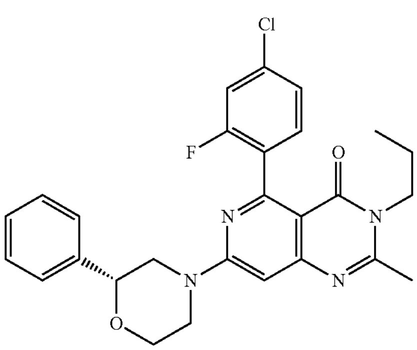 [SMILES: CCCn1c(C)nc2cc(N3CCO[C@H](c4ccccc4)C3)nc(-c3ccc(Cl)cc3F)c2c1=O] | (R)-5-(4-chloro-2-fluorophenyl)-2-methyl-7-(2-phenylmorpholino)-3-propylpyrido[4,3-d]pyrimidin-4(3H)-one | — |

TABLE B-continued

Additonal Compounds

| Ex # | Structure | Name | M + H |
|---|---|---|---|
| 191 | 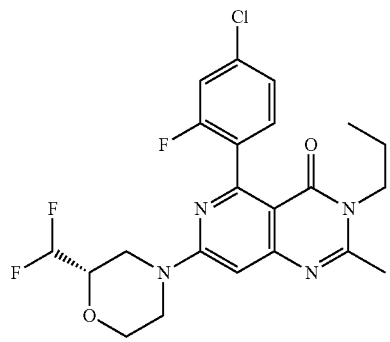 [SMILES: CCCn1c(C)nc2cc(N3CCO[C@H](C(F)F)C3)nc(-c3ccc(Cl)cc3F)c2c1=O] | (S)-5-(4-chloro-2-fluorophenyl)-7-(2-(difluoromethyl)morpholino)-2-methyl-3-propylpyrido[4,3-d]pyrimidin-4(3H)-one | — |
| 192 | 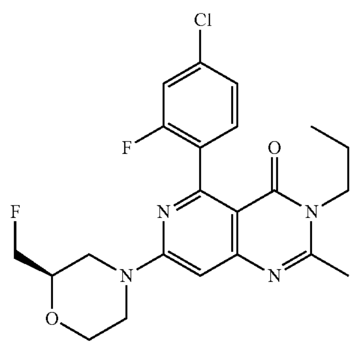 [SMILES: CCCn1c(C)nc2cc(N3CCO[C@@H](CF)C3)nc(-c3ccc(Cl)cc3F)c2c1=O] | (R)-5-(4-chloro-2-fluorophenyl)-7-(2-(fluoromethyl)morpholino)-2-methyl-3-propylpyrido[4,3-d]pyrimidin-4(3H)-one | — |
| 193 | 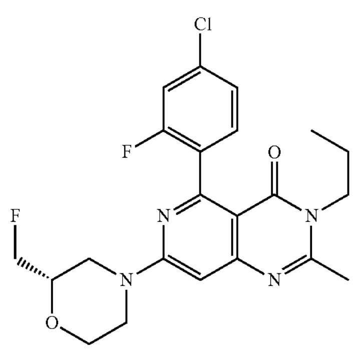 | (S)-5-(4-chloro-2-fluorophenyl)-7-(2-(fluoromethyl)morpholino)-2-methyl-3-propylpyrido[4,3-d]pyrimidin-4(3H)-one | — |
| 194 | 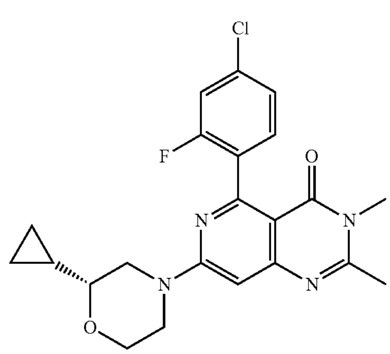 [SMILES: Cc1nc2cc(N3CCO[C@H](C4CC4)C3)nc(-c3ccc(Cl)cc3F)c2c(=O)n1C] | (R)-5-(4-chloro-2-fluorophenyl)-7-(2-cyclopropylmorpholino)-2,3-dimethylpyrido[4,3-d]pyrimidin-4(3H)-one | — |

TABLE B-continued

Additonal Compounds

| Ex # | Structure | Name | M + H |
|---|---|---|---|
| 195 | 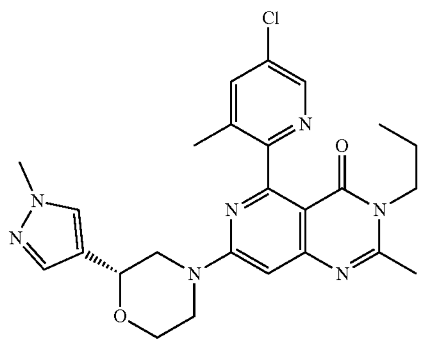 | (R)-5-(5-chloro-3-methylpyridin-2-yl)-2-methyl-7-(2-(1-methyl-1H-pyrazol-4-yl)morpholino)-3-propylpyrido[4,3-d]pyrimidin-4(3H)-one | 494.2 |
| 196 | 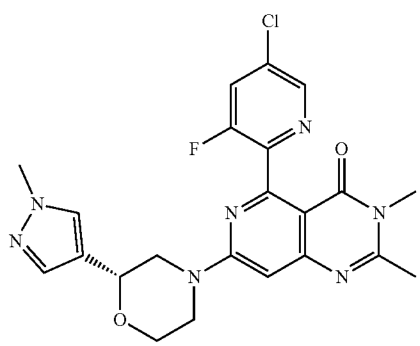 | (R)-5-(5-chloro-3-fluoropyridin-2-yl)-2,3-dimethyl-7-(2-(1-methyl-1H-pyrazol-4-yl)morpholino)pyrido[4,3-d]pyrimidin-4(3H)-one | 469.8 |
| 197 | 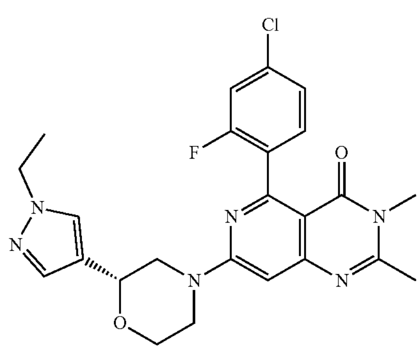 [SMILES: CCn1cc([C@@H]2CN(c3cc4nc(C)n(C)c(=O)c4c(-c4ccc(Cl)cc4F)n3)CCO2)cn1] | (R)-5-(4-chloro-2-fluorophenyl)-7-(2-(1-ethyl-1H-pyrazol-4-yl)morpholino)-2,3-dimethylpyrido[4,3-d]pyrimidin-4(3H)-one | 483.2 |
| 198 | 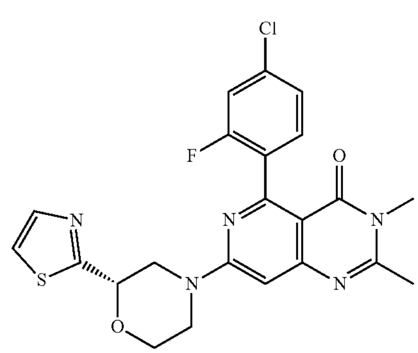 [SMILES: Cc1nc2cc(N3CCO[C@H](c4nccs4)C3)nc(-c3ccc(Cl)cc3F)c2c(=O)n1C] | (S)-5-(4-chloro-2-fluorophenyl)-2,3-dimethyl-7-(2-(thiazol-2-yl)morpholino)pyrido[4,3-d]pyrimidin-4(3H)-one | 472.0 |

TABLE B-continued

Additonal Compounds

| Ex # | Structure | Name | M + H |
|---|---|---|---|
| 199 | 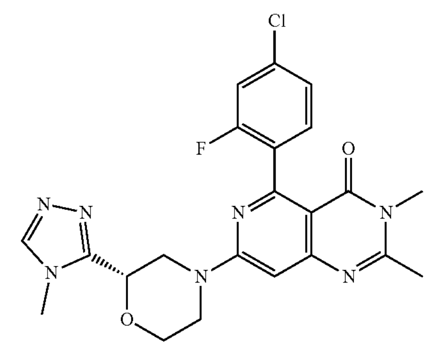 [SMILES: Cc1nc2cc(N3CCO[C@H](c4nncn4C)C3)nc(-c3ccc(Cl)cc3F)c2c(=O)n1C] | (R)-5-(4-chloro-2-fluorophenyl)-7-(2-(1-ethyl-1H-pyrazol-4-yl)morpholino)-2,3-dimethylpyrido[4,3-d]pyrimidin-4(3H)-one | 470.0 |
| 200 | 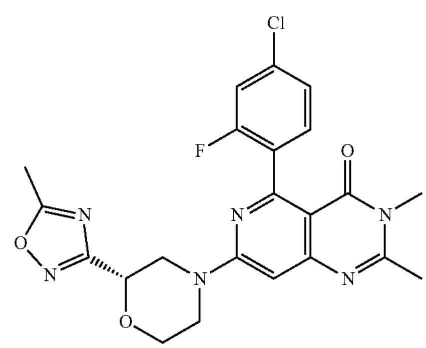 | (S)-5-(4-chloro-2-fluorophenyl)-2,3-dimethyl-7-(2-(5-methyl-1,2,4-oxadiazol-3-yl)morpholino)pyrido[4,3-d]pyrimidin-4(3H)-one | 471.0 |
| 201 | 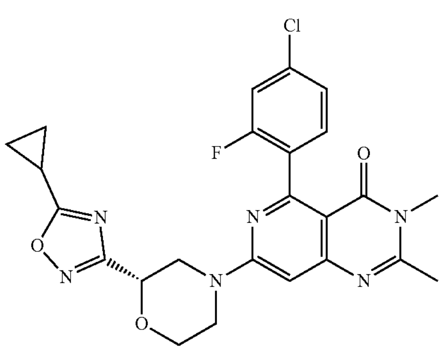 | (S)-5-(4-chloro-2-fluorophenyl)-7-(2-(5-cyclopropyl-1,2,4-oxadiazol-3-yl)morpholino)-2,3-dimethylpyrido[4,3-d]pyrimidin-4(3H)-one | 497.2 |
| 202 | 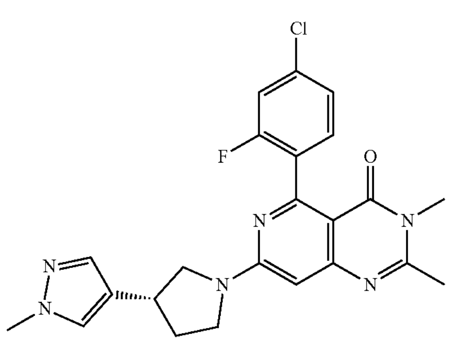 | (R)-5-(4-chloro-2-fluorophenyl)-2,3-dimethyl-7-(3-(1-methyl-1H-pyrazol-4-yl)pyrrolidin-1-yl)pyrido[4,3-d]pyrimidin-4(3H)-one | 453.2 |

TABLE B-continued

Additonal Compounds

| Ex # | Structure | Name | M + H |
|---|---|---|---|
| 203 | 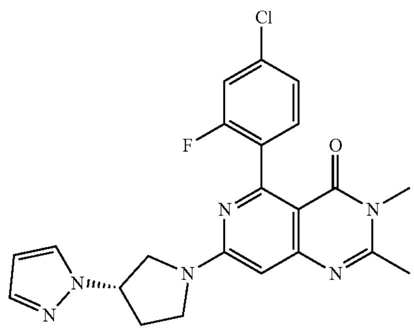 | (S)-7-(3-(1H-pyrazol-1-yl)pyrrolidin-1-yl)-5-(4-chloro-2-fluorophenyl)-2,3-dimethylpyrido[4,3-d]pyrimidin-4(3H)-one | 439.0 |
| 204 | 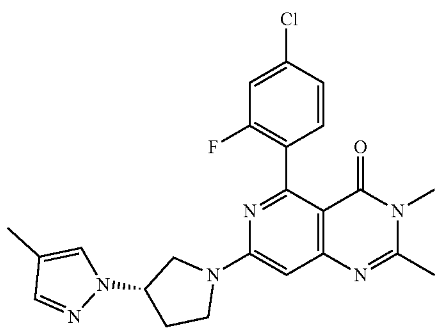 | (S)-5-(4-chloro-2-fluorophenyl)-2,3-dimethyl-7-(3-(4-methyl-1H-pyrazol-1-yl)pyrrolidin-1-yl)pyrido[4,3-d]pyrimidin-4(3H)-one | 453.2 |
| 205 | 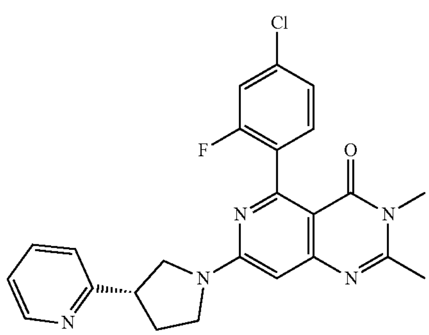 [SMILES: Cc1nc2cc(N3CC[C@H](c4ccccn4)C3)nc(-c3ccc(Cl)cc3F)c2c(=O)n1C] | (S)-5-(4-chloro-2-fluorophenyl)-2,3-dimethyl-7-(3-(pyridin-2-yl)pyrrolidin-1-yl)pyrido[4,3-d]pyrimidin-4(3H)-one | 450.0 |
| 206 | 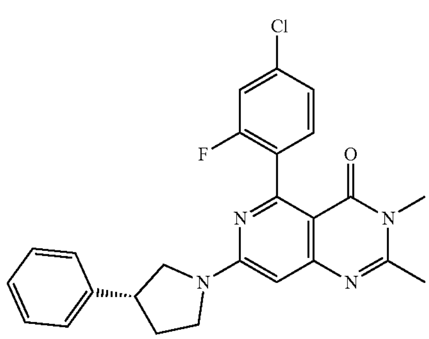 | (R)-5-(4-chloro-2-fluorophenyl)-2,3-dimethyl-7-(3-phenylpyrrolidin-1-yl)pyrido[4,3-d]pyrimidin-4(3H)-one | 449.2 |

TABLE B-continued

Additonal Compounds

| Ex # | Structure | Name | M + H |
|---|---|---|---|
| 207 | 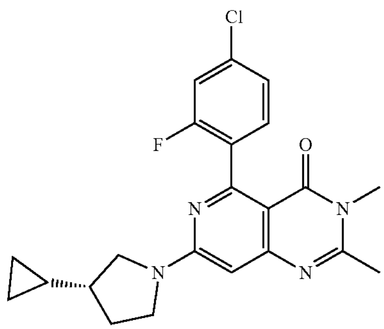 [SMILES: Cc1nc2cc(N3CC[C@H](C4CC4)C3)nc(-c3ccc(Cl)cc3F)c2c(=O)n1C] | (R)-5-(4-chloro-2-fluorophenyl)-7-(3-cyclopropylpyrrolidin-1-yl)-2,3-dimethylpyrido[4,3-d]pyrimidin-4(3H)-one | 413.0 |
| 208 | 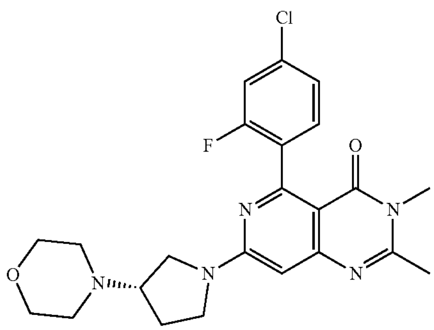 [SMILES: Cc1nc2cc(N3CC[C@H](N4CCOCC4)C3)nc(-c3ccc(Cl)cc3F)c2c(=O)n1C] | (S)-5-(4-chloro-2-fluorophenyl)-2,3-dimethyl-7-(3-morpholinopyrrolidin-1-yl)pyrido[4,3-d]pyrimidin-4(3H)-one | 458.2 |
| 209 | 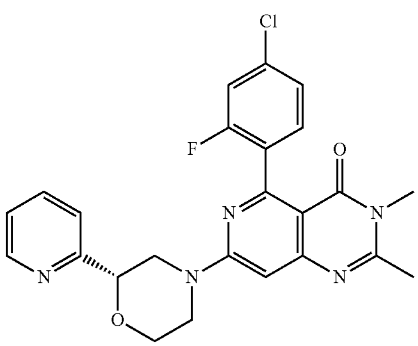 [SMILES: Cc1nc2cc(N3CCO[C@H](c4ccccn4)C3)nc(-c3ccc(Cl)cc3F)c2c(=O)n1C] | (S)-5-(4-chloro-2-fluorophenyl)-2,3-dimethyl-7-(2-(pyridin-2-yl)morpholino)pyrido[4,3-d]pyrimidin-4(3H)-one | 466.2 |
| 210 | 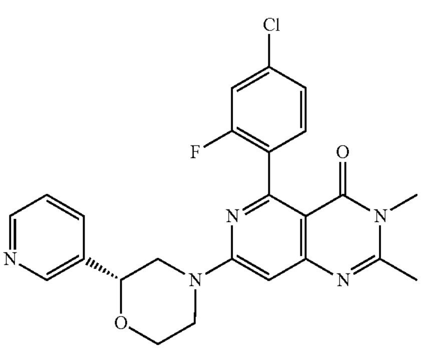 | (R)-5-(4-chloro-2-fluorophenyl)-2,3-dimethyl-7-(2-(pyridin-3-yl)morpholino)pyrido[4,3-d]pyrimidin-4(3H)-one | 466.2 |

TABLE B-continued

Additonal Compounds

| Ex # | Structure | Name | M + H |
|---|---|---|---|
| 211 | 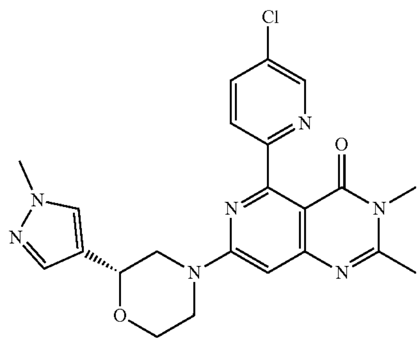 [SMILES: Cc1nc2cc(N3CCO[C@H](c4cnn(C)c4)C3)nc(-c3ccc(Cl)cn3)c2c(=O)n1C] | (R)-5-(5-chloropyridin-2-yl)-2,3-dimethyl-7-(2-(1-methyl-1H-pyrazol-4-yl)morpholino)pyrido[4,3-d]pyrimidin-4(3H)-one | 452.0 |
| 212 | 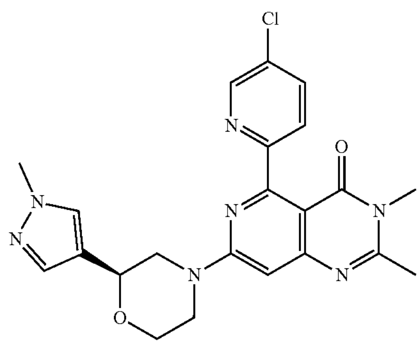 | (S)-5-(5-chloropyridin-2-yl)-2,3-dimethyl-7-(2-(1-methyl-1H-pyrazol-4-yl)morpholino)pyrido[4,3-d]pyrimidin-4(3H)-one | — |
| 213 | 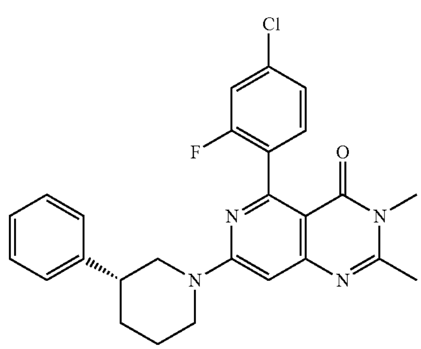 | (R)-5-(4-chloro-2-fluorophenyl)-2,3-dimethyl-7-(3-phenylpiperidin-1-yl)pyrido[4,3-d]pyrimidin-4(3H)-one | 463.2 |
| 214 | 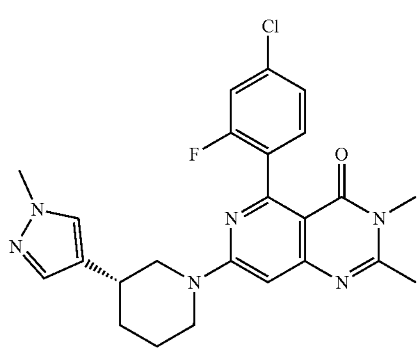 | (R)-5-(4-chloro-2-fluorophenyl)-2,3-dimethyl-7-(3-(1-methyl-1H-pyrazol-4-yl)piperidin-1-yl)pyrido[4,3-d]pyrimidin-4(3H)-one | 467.2 |

TABLE B-continued

Additional Compounds

| Ex # | Structure | Name | M + H |
|---|---|---|---|
| 215 | 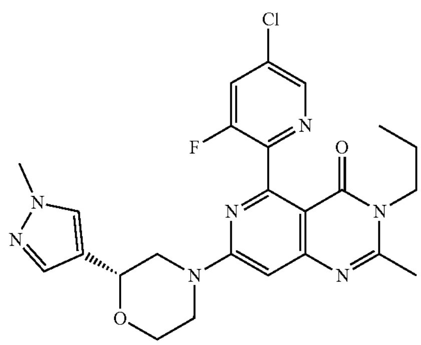 | (R)-5-(5-chloro-3-fluoropyridin-2-yl)-2-methyl-7-(2-(1-methyl-1H-pyrazol-4-yl)morpholino)-3-propylpyrido[4,3-d]pyrimidin-4(3H)-one | 498.0 |
| 216 | 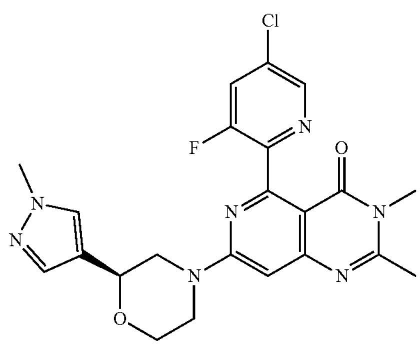 [SMILES: Cc1nc2cc(N3CCO[C@@H](c4cnn(C)c4)C3)nc(-c3ncc(Cl)cc3F)c2c(=O)n1C] | (S)-5-(5-chloro-3-fluoropyridin-2-yl)-2,3-dimethyl-7-(2-(1-methyl-1H-pyrazol-4-yl)morpholino)pyrido[4,3-d]pyrimidin-4(3H)-one | 470.0 |
| 217 | 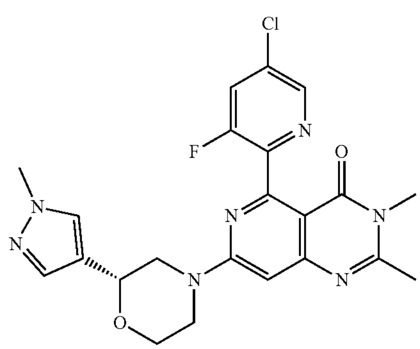 | (R)-5-(5-chloro-3-fluoropyridin-2-yl)-2,3-dimethyl-7-(2-(1-methyl-1H-pyrazol-4-yl)morpholino)pyrido[4,3-d]pyrimidin-4(3H)-one | 470.0 |
| 218 | 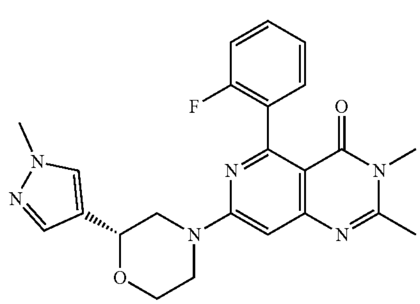 [SMILES: Cc1nc2cc(N3CCO[C@H](c4cnn(C)c4)C3)nc(-c3ccccc3F)c2c(=O)n1C] | (R)-5-(2-fluorophenyl)-2,3-dimethyl-7-(2-(1-methyl-1H-pyrazol-4-yl)morpholino)pyrido[4,3-d]pyrimidin-4(3H)-one | 434.8 |

TABLE B-continued

Additonal Compounds

| Ex # | Structure | Name | M + H |
|---|---|---|---|
| 219 | 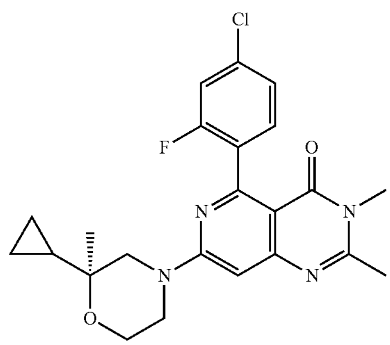 | (S)-5-(4-chloro-2-fluorophenyl)-7-(2-cyclopropyl-2-methylmorpholino)-2,3-dimethylpyrido[4,3-d]pyrimidin-4(3H)-one | 442.8 |
| 220 | 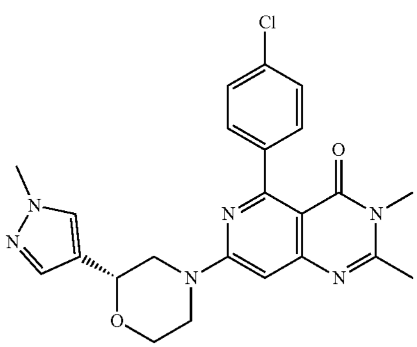 [SMILES: Cc1nc2cc(N3CCO[C@H](c4cnn(C)c4)C3)nc(-c3ccc(Cl)cc3)c2c(=O)n1C] | (R)-5-(4-chlorophenyl)-2,3-dimethyl-7-(2-1-methyl-1H-pyrazol-4-yl)morpholino)pyrido[4,3-d]pyrimidin-4(3H)-one | 450.8 |
| 221 | 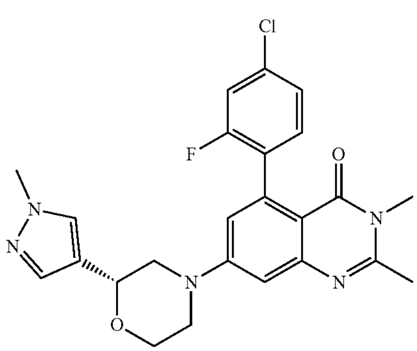 [SMILES: Cc1nc2cc(N3CCO[C@H](c4cnn(C)c4)C3)cc(-c3ccc(Cl)cc3F)c2c(=O)n1C] | (R)-5-(4-chloro-2-fluorophenyl)-2,3-dimethyl-7-(2-(1-methyl-1H-pyrazol-4-yl)morpholino)quinazolin-4(3H)-one | 468.0 |
| 222 | 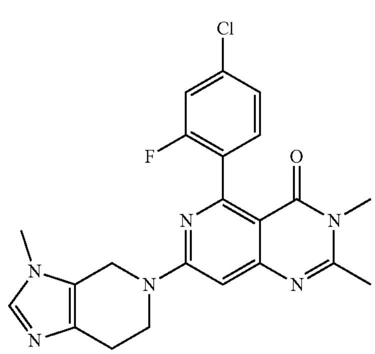 [SMILES: Cc1nc2cc(N3CCc4ncn(C)c4C3)nc(-c3ccc(Cl)cc3F)c2c(=O)n1C] | 5-(4-chloro-2-fluorophenyl)-2,3-dimethyl-7-(3-methyl-3,4,6,7-tetrahydro-5H-imidazo[4,5-c]pyridin-5-yl)pyrido[4,3-d]pyrimidin-4(3H)-one | 439.0 |

TABLE B-continued

Additonal Compounds

| Ex # | Structure | Name | M + H |
|---|---|---|---|
| 223 | 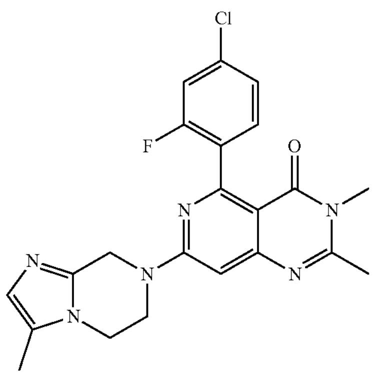 [SMILES: Cc1cnc2n1CCN(c1cc3nc(C)n(C)c(=O)c3c(-c3ccc(Cl)cc3F)n1)C2] | 5-(4-chloro-2-fluorophenyl)-2,3-dimethyl-7-(3-methyl-5,6-dihydroimidazo[1,2-a]pyrazin-7(8H)-yl)pyrido[4,3-d]pyrimidin-4(3H)-one | 439.0 |
| 224 | 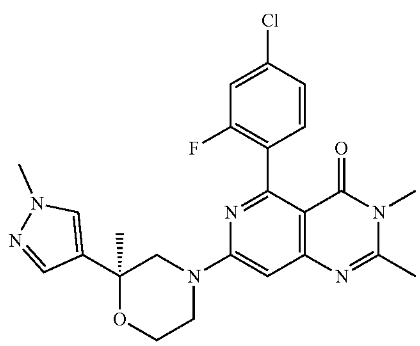 | (S)-5-(4-chloro-2-fluorophenyl)-2,3-dimethyl-7-(2-methyl-2-(1-methyl-1H-pyrazol-4-yl)morpholino)pyrido[4,3-d]pyrimidin-4(3H)-one | 483.0 |
| 225 | 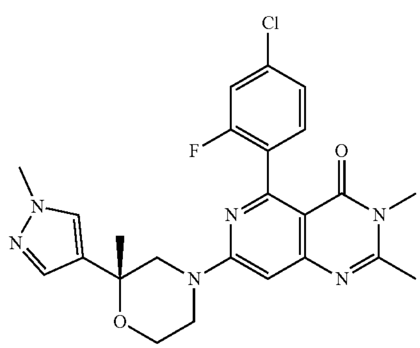 [SMILES: Cc1nc2cc(N3CCO[C@](C)(c4cnn(C)c4)C3)nc(-c3ccc(Cl)cc3F)c2c(=O)n1C] | (R)-5-(4-chloro-2-fluorophenyl)-2,3-dimethyl-7-(2-methyl-2-(1-methyl-1H-pyrazol-4-yl)morpholino)pyrido[4,3-d]pyrimidin-4(3H)-one | 483.0 |
| 226 | 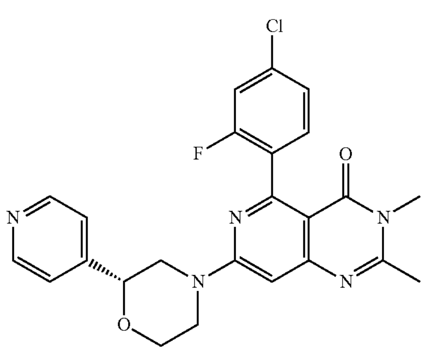 | (R)-5-(4-chloro-2-fluorophenyl)-2,3-dimethyl-7-(2-(pyridin-4-yl)morpholino)pyrido[4,3-d]pyrimidin-4(3H)-one | 465.8 |

TABLE B-continued

Additonal Compounds

| Ex # | Structure | Name | M + H |
|---|---|---|---|
| 227 | 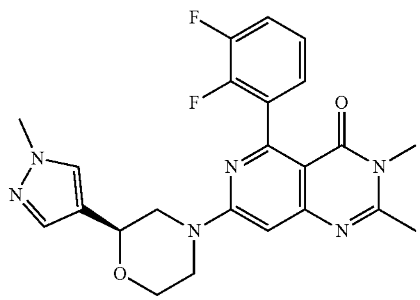 [SMILES: Cc1nc2cc(N3CCO[C@@H](c4cnn(C)c4)C3)nc(-c3cccc(F)c3F)c2c(=O)n1C] | (S)-5-(2,3-difluorophenyl)-2,3-dimethyl-7-(2-(1-methyl-1H-pyrazol-4-yl)morpholino)pyrido[4,3-d]pyrimidin-4(3H)-one | 453.0 |
| 228 | 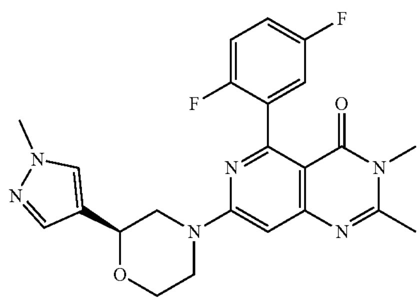 [SMILES: Cc1nc2cc(N3CCO[C@@H](c4cnn(C)c4)C3)nc(-c3cc(F)ccc3F)c2c(=O)n1C] | (S)-5-(2,5-difluorophenyl)-2,3-dimethyl-7-(2-(1-methyl-1H-pyrazol-4-yl)morpholino)pyrido[4,3-d]pyrimidin-4(3H)-one | 453.0 |
| 229 | 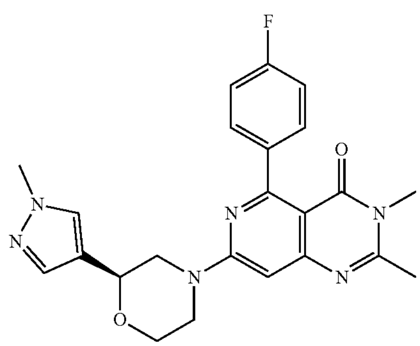 [SMILES: Cc1nc2cc(N3CCO[C@@H](c4cnn(C)c4)C3)nc(-c3ccc(F)cc3)c2c(=O)n1C] | (S)-5-(4-fluorophenyl)-2,3-dimethyl-7-(2-(1-methyl-1H-pyrazol-4-yl)morpholino)pyrido[4,3-d]pyrimidin-4(3H)-one | 435.0 |
| 230 | 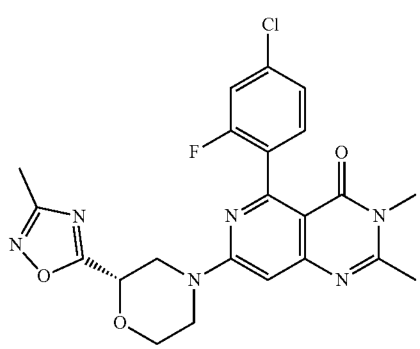 [SMILES: Cc1noc([C@@H]2CN(c3cc4nc(C)n(C)c(=O)c4c(-c4ccc(Cl)cc4F)n3)CCO2)n1] | (S)-5-(4-chloro-2-fluorophenyl)-2,3-dimethyl-7-(3-(3-methyl-1,2,4-oxadiazol-5-yl)piperidin-1-yl)pyrido[4,3-d]pyrimidin-4(3H)-one | 468.8 |

TABLE B-continued

Additional Compounds

| Ex # | Structure | Name | M + H |
|---|---|---|---|
| 231 | 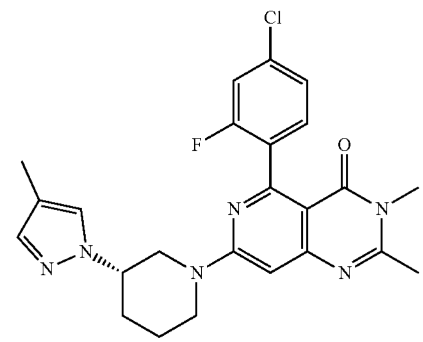 [SMILES: Cc1cnn([C@H]2CCCN(c3cc4nc(C)n(C)c(=O)c4c(-c4ccc(Cl)cc4F)n3)C2)c1] | (S)-5-(4-chloro-2-fluorophenyl)-2,3-dimethyl-7-(3-(4-methyl-1H-pyrazol-1-yl)piperidin-1-yl)pyrido[4,3-d]pyrimidin-4(3H)-one | 467.0 |
| 232 | 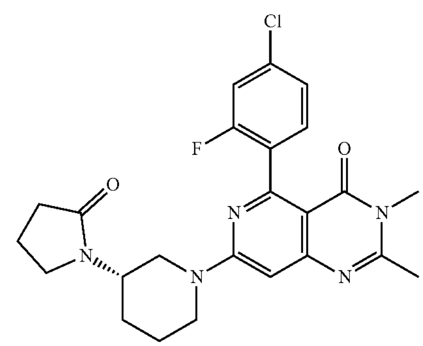 [SMILES: Cc1nc2cc(N3CCC[C@H](N4CCCC4=O)C3)nc(-c3ccc(Cl)cc3F)c2c(=O)n1C] | (S)-5-(4-chloro-2-fluorophenyl)-2,3-dimethyl-7-(3-(2-oxopyrrolidin-1-yl)piperidin-1-yl)pyrido[4,3-d]pyrimidin-4(3H)-one | 469.8 |
| 233 | 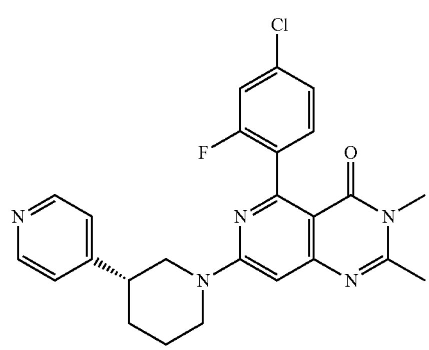 | (R)-5-(4-chloro-2-fluorophenyl)-2,3-dimethyl-7-(3-(pyridin-4-yl)piperidin-1-yl)pyrido[4,3-d]pyrimidin-4(3H)-one | 463.8 |
| 234 | 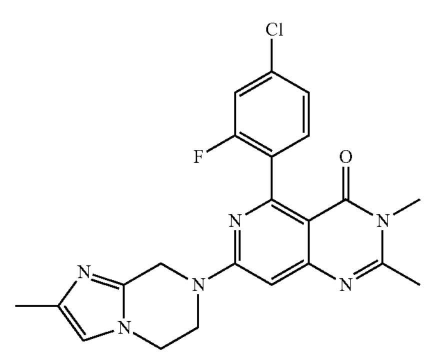 | 5-(4-chloro-2-fluorophenyl)-2,3-dimethyl-7-(2-methyl-5,6-dihydroimidazo[1,2-a]pyrazin-7(8H)-yl)pyrido[4,3-d]pyrimidin-4(3H)-one | 438.8 |

TABLE B-continued

Additonal Compounds

| Ex # | Structure | Name | M + H |
|---|---|---|---|
| 235 | 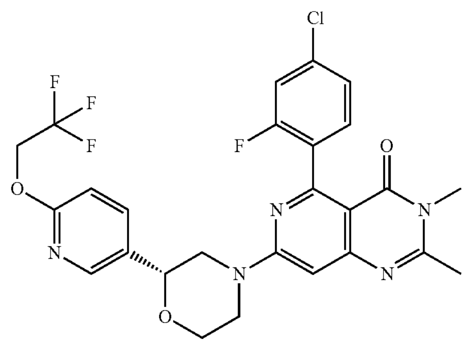 | (R)-5-(4-chloro-2-fluorophenyl)-2,3-dimethyl-7-(2-(6-(2,2,2-trifluoroethoxy)pyridin-3-yl)morpholino)pyrido[4,3-d]pyrimidin-4(3H)-one | 563.8 |
| 236 | 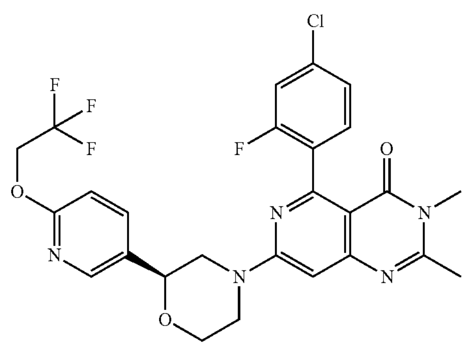 [SMILES: Cc1nc2cc(N3CCO[C@@H](c4ccc(OCC(F)(F)F)nc4)C3)nc(-c3ccc(Cl)cc3F)c2c(=O)n1C] | (S)-5-(4-chloro-2-fluorophenyl)-2,3-dimethyl-7-(2-(6-(2,2,2-trifluoroethoxy)pyridin-3-yl)morpholino)pyrido[4,3-d]pyrimidin-4(3H)-one | 563.8 |
| 237 | 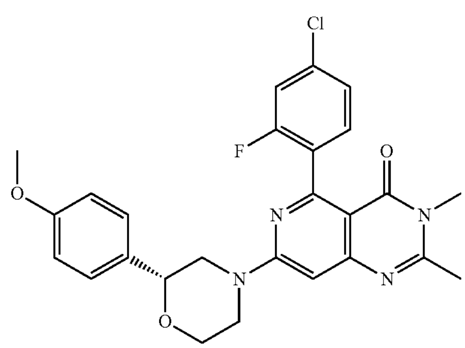 | (R)-5-(4-chloro-2-fluorophenyl)-7-(2-(4-methoxyphenyl)morpholino)-2,3-dimethylpyrido[4,3-d]pyrimidin-4(3H)-one | 494.8 |
| 238 | 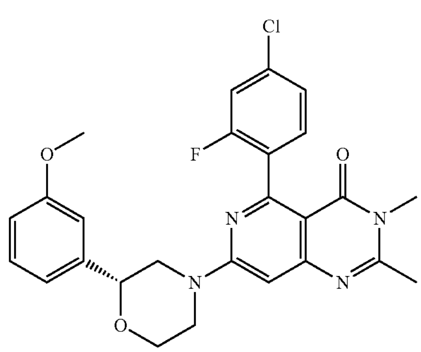 [SMILES: COc1cccc([C@@H]2CN(c3cc4nc(C)n(C)c(=O)c4c(-c4ccc(Cl)cc4F)n3)CCO2)c1] | (R)-5-(4-chloro-2-fluorophenyl)-7-(2-(3-methoxyphenyl)morpholino)-2,3-dimethylpyrido[4,3-d]pyrimidin-4(3H)-one | 494.8 |

TABLE B-continued

Additonal Compounds

| Ex # | Structure | Name | M + H |
|---|---|---|---|
| 239 | 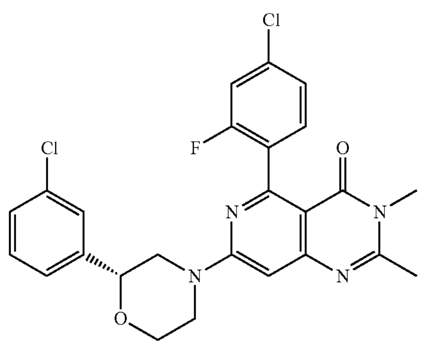 [SMILES: Cc1nc2cc(N3CCO[C@H](c4cccc(Cl)c4)C3)nc(-c3ccc(Cl)cc3F)c2c(=O)n1C] | (R)-5-(4-chloro-2-fluorophenyl)-7-(2-(3-chlorophenyl)morpholino)-2,3-dimethylpyrido[4,3-d]pyrimidin-4(3H)-one | 498.8 |
| 240 | 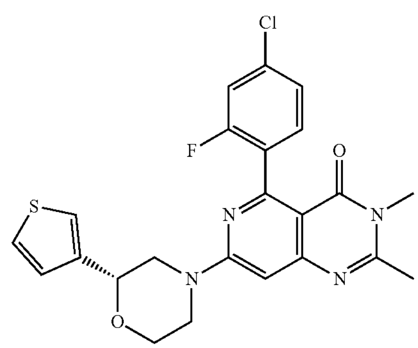 [SMILES: Cc1nc2cc(N3CCO[C@H](c4ccsc4)C3)nc(-c3ccc(Cl)cc3F)c2c(=O)n1C] | (R)-5-(4-chloro-2-fluorophenyl)-2,3-dimethyl-7-(2-(thiophen-3-yl)morpholino)pyrido[4,3-d]pyrimidin-4(3H)-one | 471.0 |
| 241 | 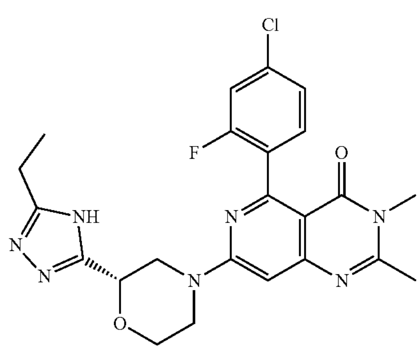 | (S)-5-(4-chloro-2-fluorophenyl)-7-(2-(5-ethyl-4H-1,2,4-triazol-3-yl)morpholino)-2,3-dimethylpyrido[4,3-d]pyrimidin-4(3H)-one | 483.8 |
| 242 | 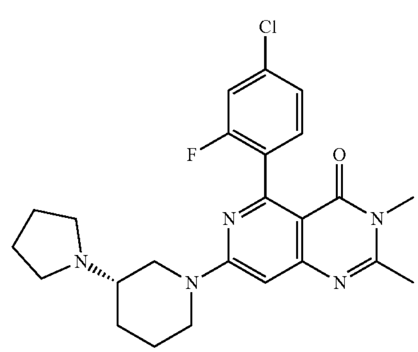 [SMILES: Cc1nc2cc(N3CCC[C@H](N4CCCC4)C3)nc(-c3ccc(Cl)cc3F)c2c(=O)n1C] | (S)-5-(4-chloro-2-fluorophenyl)-2,3-dimethyl-7-(3-(pyrrolidin-1-yl)piperidin-1-yl)pyrido[4,3-d]pyrimidin-4(3H)-one | 456.2 |

TABLE B-continued

Additonal Compounds

| Ex # | Structure | Name | M + H |
|---|---|---|---|
| 243 | 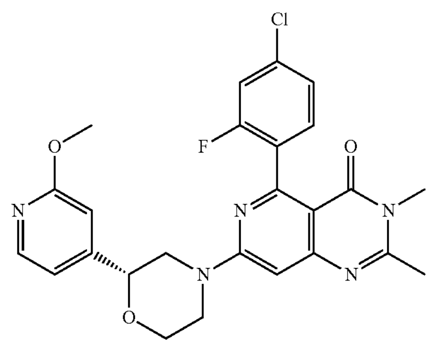 | (R)-5-(4-chloro-2-fluorophenyl)-7-(2-(2-methoxypyridin-4-yl)morpholino)-2,3-dimethylpyrido[4,3-d]pyrimidin-4(3H)-one | 496.0 |
| 244 | 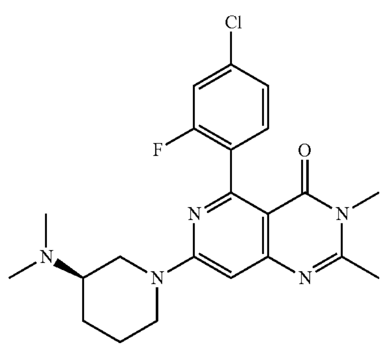 | (R)-5-(4-chloro-2-fluorophenyl)-7-(3-(dimethylamino)piperidin-1-yl)-2,3-dimethylpyrido[4,3-d]pyrimidin-4(3H)-one | 430.0 |
| 245 | 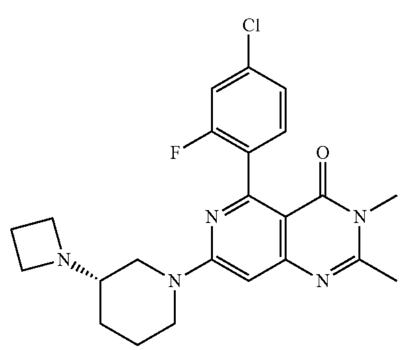 | (S)-7-(3-(azetidin-1-yl)piperidin-1-yl)-5-(4-chloro-2-fluorophenyl)-2,3-dimethylpyrido[4,3-d]pyrimidin-4(3H)-one | 442.0 |
| 246 | 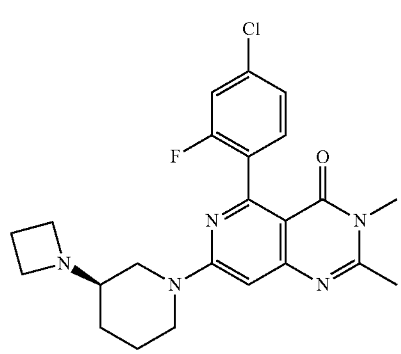 [SMILES: Cc1nc2cc(N3CCC[C@@H](N4CCC4)C3)nc(-c3ccc(Cl)cc3F)c2c(=O)n1C] | (R)-7-(3-(azetidin-1-yl)piperidin-1-yl)-5-(4-chloro-2-fluorophenyl)-2,3-dimethylpyrido[4,3-d]pyrimidin-4(3H)-one | 442.0 |

TABLE B-continued

Additonal Compounds

| Ex # | Structure | Name | M + H |
|---|---|---|---|
| 247 | 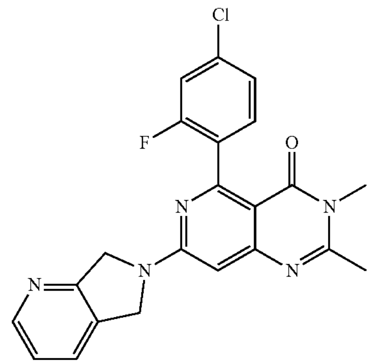 [SMILES: Cc1nc2cc(N3Cc4cccnc4C3)nc(-c3ccc(Cl)cc3F)c2c(=O)n1C] | 5-(4-chloro-2-fluorophenyl)-7-(5,7-dihydro-6H-pyrrolo[3,4-b]pyridin-6-yl)-2,3-dimethylpyrido[4,3-d]pyrimidin-4(3H)-one | 422.0 |
| 248 | 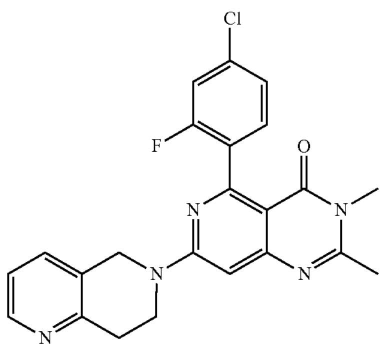 [SMILES: Cc1nc2cc(N3CCc4ncccc4C3)nc(-c3ccc(Cl)cc3F)c2c(=O)n1C] | 5-(4-chloro-2-fluorophenyl)-7-(7,8-dihydro-1,6-naphthyridin-6(5H)-yl)-2,3-dimethylpyrido[4,3-d]pyrimidin-4(3H)-one | 436.0 |
| 249 | 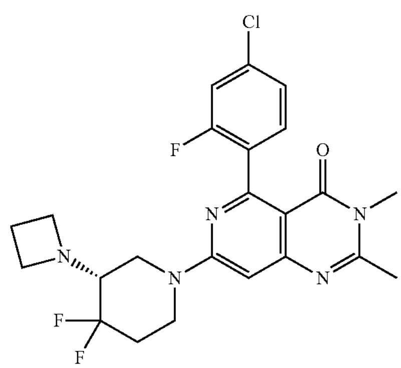 [SMILES: Cc1nc2cc(N3CCC(F)(F)[C@H](N4CCC4)C3)nc(-c3ccc(Cl)cc3F)c2c(=O)n1C] | (R)-7-(3-(azetidin-1-yl)-4,4-difluoropiperidin-1-yl)-5-(4-chloro-2-fluorophenyl)-2,3-dimethylpyrido[4,3-d]pyrimidin-4(3H)-one | 478.0 |
| 250 | 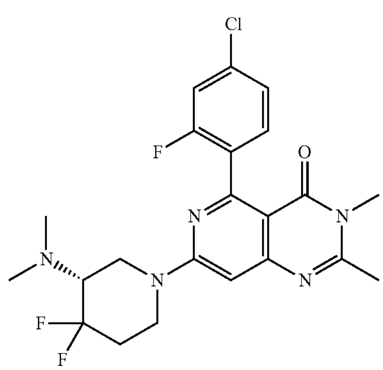 | (R)-5-(4-chloro-2-fluorophenyl)-7-(3-(dimethylamino)-4,4-difluoropiperidin-1-yl)-2,3-dimethylpyrido[4,3-d]pyrimidin-4(3H)-one | 466.0 |

TABLE B-continued

Additonal Compounds

| Ex # | Structure | Name | M + H |
|---|---|---|---|
| 251 | 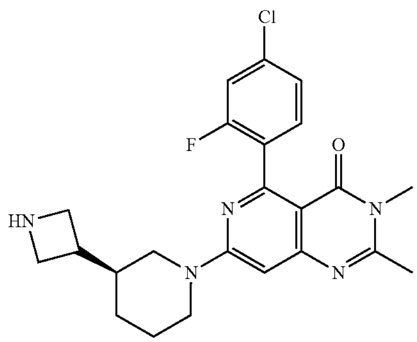 [SMILES: Cc1nc2cc(N3CCC[C@@H](C4CNC4)C3)nc(-c3ccc(Cl)cc3F)c2c(=O)n1C] | (S)-7-(3-(azetidin-3-yl)piperidin-1-yl)-5-(4-chloro-2-fluorophenyl)-2,3-dimethylpyrido[4,3-d]pyrimidin-4(3H)-one | 442.0 |
| 252 | 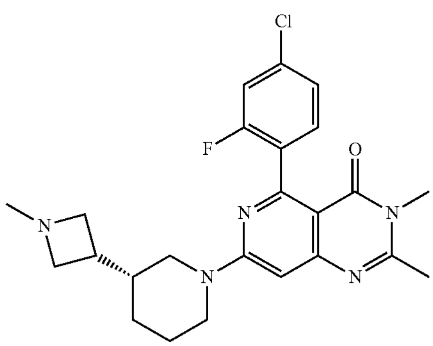 | (R)-5-(4-chloro-2-fluorophenyl)-2,3-dimethyl-7-(3-(1-methylazetidin-3-yl)piperidin-1-yl)pyrido[4,3-d]pyrimidin-4(3H)-one | 456.0 |
| 253 | 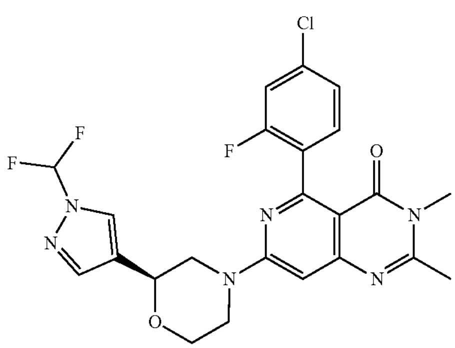 [SMILES: Cc1nc2cc(N3CCO[C@@H](c4cnn(C(F)F)c4)C3)nc(-c3ccc(Cl)cc3F)c2c(=O)n1C] | (S)-5-(4-chloro-2-fluorophenyl)-7-(2-(1-(difluoromethyl)-1H-pyrazol-4-yl)morpholino)-2,3-dimethylpyrido[4,3-d]pyrimidin-4(3H)-one | 505.0 |
| 254 | 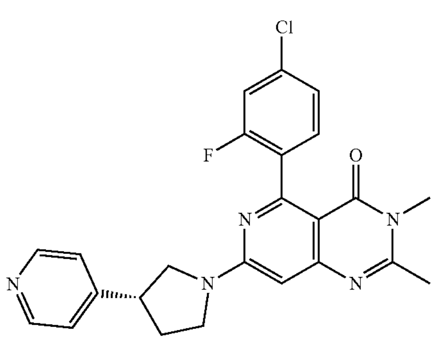 [SMILES: Cc1nc2cc(N3CC[C@H](c4ccncc4)C3)nc(-c3ccc(Cl)cc3F)c2c(=O)n1C] | (R)-5-(4-chloro-2-fluorophenyl)-2,3-dimethyl-7-(3-(pyridin-4-yl)pyrrolidin-1-yl)pyrido[4,3-d]pyrimidin-4(3H)-one | 450.0 |

TABLE B-continued

Additonal Compounds

| Ex # | Structure | Name | M + H |
|---|---|---|---|
| 255 | 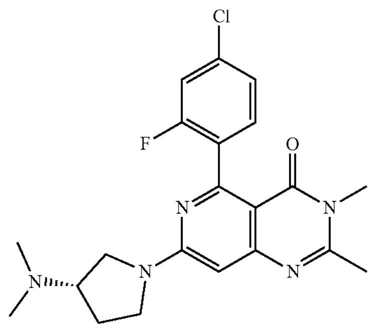 | (S)-5-(4-chloro-2-fluorophenyl)-7-(3-(dimethylamino)pyrrolidin-1-yl)-2,3-dimethylpyrido[4,3-d]pyrimidin-4(3H)-one | 416.0 |
| 256 | 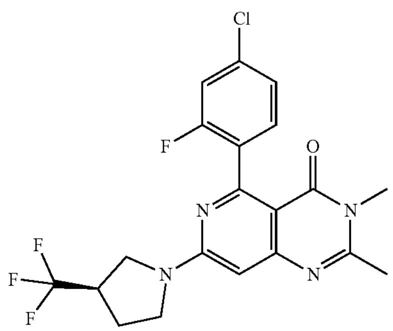 [SMILES: Cc1nc2cc(N3CC[C@@H](C(F)(F)F)C3)nc(-c3ccc(Cl)cc3F)c2c(=O)n1C] | (R)-5-(4-chloro-2-fluorophenyl)-2,3-dimethyl-7-(3-(trifluoromethyl)pyrrolidin-1-yl)pyrido[4,3-d]pyrimidin-4(3H)-one | — |
| 257 | 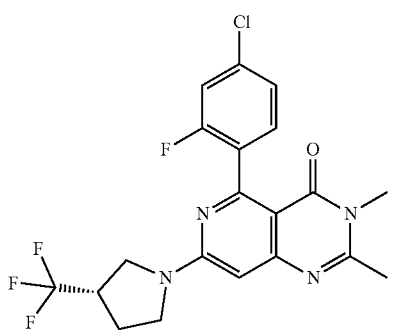 | (S)-5-(4-chloro-2-fluorophenyl)-2,3-dimethyl-7-(3-(trifluoromethyl)pyrrolidin-1-yl)pyrido[4,3-d]pyrimidin-4(3H)-one | — |
| 258 | 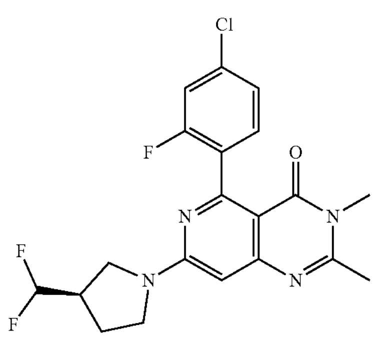 [SMILES: Cc1nc2cc(N3CC[C@@H](C(F)F)C3)nc(-c3ccc(Cl)cc3F)c2c(=O)n1C] | (R)-5-(4-chloro-2-fluorophenyl)-7-(3-(difluoromethyl)pyrrolidin-1-yl)-2,3-dimethylpyrido[4,3-d]pyrimidin-4(3H)-one | — |

TABLE B-continued

Additonal Compounds

| Ex # | Structure | Name | M + H |
|---|---|---|---|
| 259 | 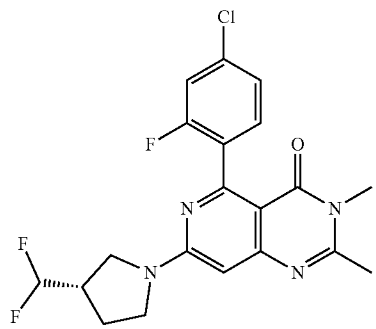 | (S)-5-(4-chloro-2-fluorophenyl)-7-(3-(difluoromethyl)pyrrolidin-1-yl)-2,3-dimethylpyrido[4,3-d]pyrimidin-4(3H)-one | — |
| 260 | 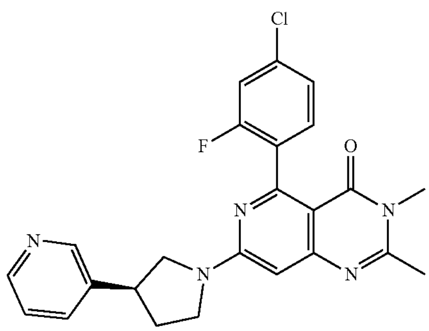 [SMILES: Cc1nc2cc(N3CC[C@@H](c4cccnc4)C3)nc(-c3ccc(Cl)cc3F)c2c(=O)n1C] | (S)-5-(4-chloro-2-fluorophenyl)-2,3-dimethyl-7-(3-(pyridin-3-yl)pyrrolidin-1-yl)pyrido[4,3-d]pyrimidin-4(3H)-one | — |
| 261 | 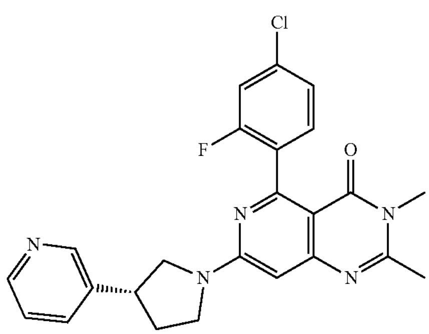 | (R)-5-(4-chloro-2-fluorophenyl)-2,3-dimethyl-7-(3-(pyridin-3-yl)pyrrolidin-1-yl)pyrido[4,3-d]pyrimidin-4(3H)-one | — |
| 262 | 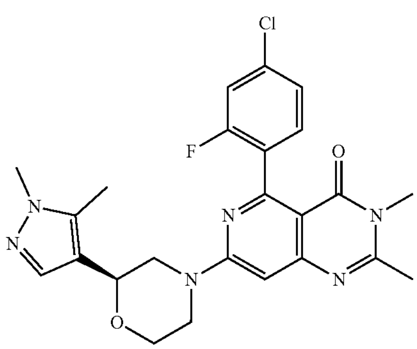 [SMILES: Cc1c([C@H]2CN(c3cc4nc(C)n(C)c(=O)c4c(-c4ccc(Cl)cc4F)n3)CCO2)cnn1C] | (S)-5-(4-chloro-2-fluorophenyl)-7-(2-(1,5-dimethyl-1H-pyrazol-4-yl)morpholino)-2,3-dimethylpyrido[4,3-d]pyrimidin-4(3H)-one | 483.0 |

TABLE B-continued

Additonal Compounds

| Ex # | Structure | Name | M + H |
|---|---|---|---|
| 263 | 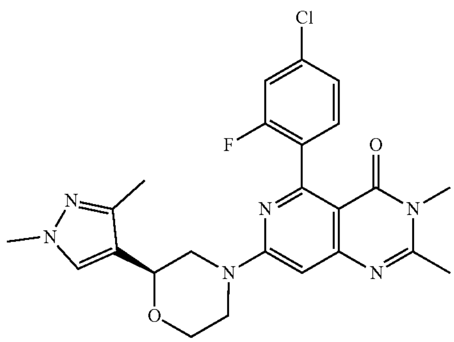 | (S)-5-(4-chloro-2-fluorophenyl)-7-(2-(1,3-dimethyl-1H-pyrazol-4-yl)morpholino)-2,3-dimethylpyrido[4,3-d]pyrimidin-4(3H)-one | 483.0 |
| 264 | 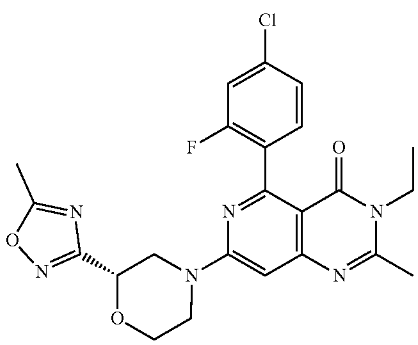 | (S)-5-(4-chloro-2-fluorophenyl)-3-ethyl-2-methyl-7-(2-(5-methyl-1,2,4-oxadiazol-3-yl)morpholino)pyrido[4,3-d]pyrimidin-4(3H)-one | 485.0 |
| 265 | 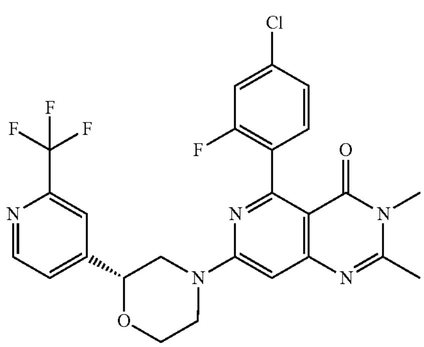 | (R)-5-(4-chloro-2-fluorophenyl)-2,3-dimethyl-7-(2-(2-(trifluoromethyl)pyridin-4-yl)morpholino)pyrido[4,3-d]pyrimidin-4(3H)-one | — |
| 266 | 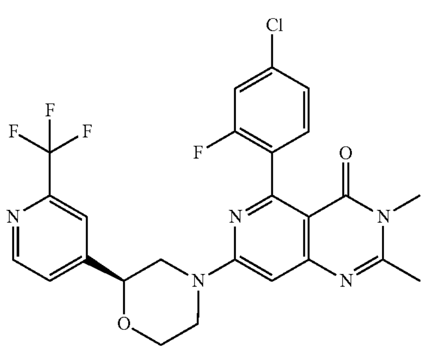 [SMILES: Cc1nc2cc(N3CCO[C@@H](c4ccnc(C(F)(F)F)c4)C3)nc(-c3ccc(Cl)cc3F)c2c(=O)n1C] | (S)-5-(4-chloro-2-fluorophenyl)-2,3-dimethyl-7-(2-(2-(trifluoromethyl)pyridin-4-yl)morpholino)pyrido[4,3-d]pyrimidin-4(3H)-one | — |

TABLE B-continued

Additonal Compounds

| Ex # | Structure | Name | M + H |
|---|---|---|---|
| 267 | 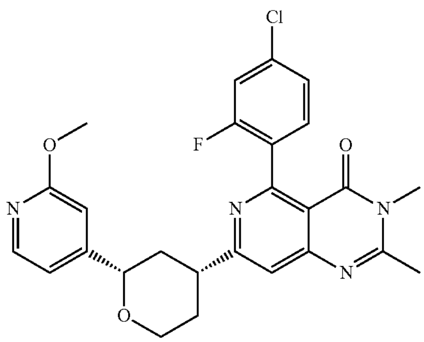 | 5-(4-chloro-2-fluorophenyl)-7-((2S,4R)-2-(2-methoxypyridin-4-yl)tetrahydro-2H-pyran-4-yl)-2,3-dimethylpyrido[4,3-d]pyrimidin-4(3H)-one | 495.0 |
| 268 | 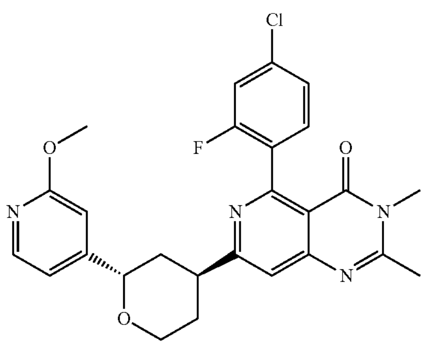 [SMILES: COc1cc([C@@H]2C[C@@H](c3cc4nc(C)n(C)c(=O)c4c(-c4ccc(Cl)cc4F)n3)CCO2)ccn1] | 5-(4-chloro-2-fluorophenyl)-7-((2S,4S)-2-(2-methoxypyridin-4-yl)tetrahydro-2H-pyran-4-yl)-2,3-dimethylpyrido[4,3-d]pyrimidin-4(3H)-one | 495.0 |
| 269 | 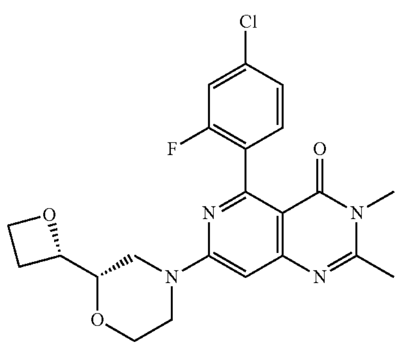 | 5-(4-chloro-2-fluorophenyl)-2,3-dimethyl-7-((S)-2-((S)-oxetan-2-yl)morpholino)pyrido[4,3-d]pyrimidin-4(3H)-one | 445.0 |
| 270 | 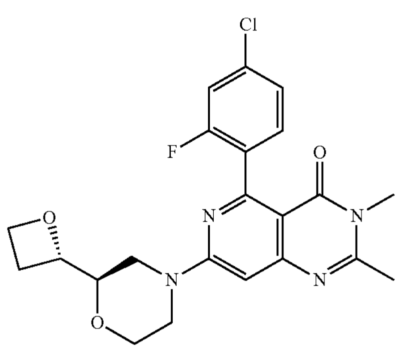 [SMILES: Cc1nc2cc(N3CCO[C@@H]([C@@H]4CCO4)C3)nc(-c3ccc(Cl)cc3F)c2c(=O)n1C] | 5-(4-chloro-2-fluorophenyl)-2,3-dimethyl-7-((R)-2-((S)-oxetan-2-yl)morpholino)pyrido[4,3-d]pyrimidin-4(3H)-one | 445.0 |

TABLE B-continued

Additional Compounds

| Ex # | Structure | Name | M + H |
|---|---|---|---|
| 271 | 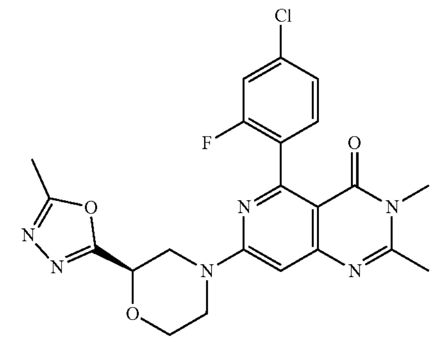 [SMILES: Cc1nnc([C@H]2CN(c3cc4nc(C)n(C)c(=O)c4c(-c4ccc(Cl)cc4F)n3)CCO2)o1] | (R)-5-(4-chloro-2-fluorophenyl)-2,3-dimethyl-7-(2-(5-methyl-1,3,4-oxadiazol-2-yl)morpholino)pyrido[4,3-d]pyrimidin-4(3H)-one | 471.0 |
| 272 | 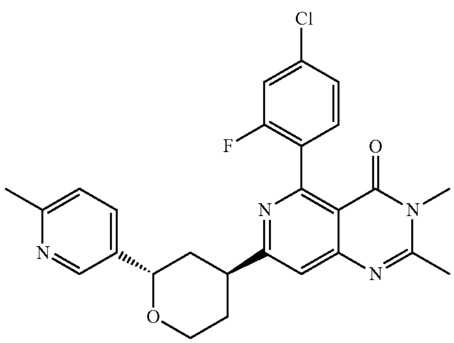 | 5-(4-chloro-2-fluorophenyl)-2,3-dimethyl-7-((2S,4S)-2-(6-methylpyridin-3-yl)tetrahydro-2H-pyran-4-yl)pyrido[4,3-d]pyrimidin-4(3H)-one | 479.0 |
| 273 | 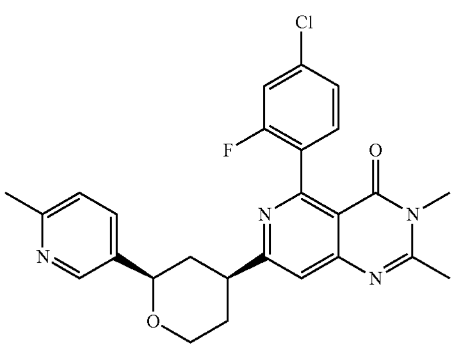 | 5-(4-chloro-2-fluorophenyl)-2,3-dimethyl-7-((2R,4S)-2-(6-methylpyridin-3-yl)tetrahydro-2H-pyran-4-yl)pyrido[4,3-d]pyrimidin-4(3H)-one | 479.0 |
| 274 | 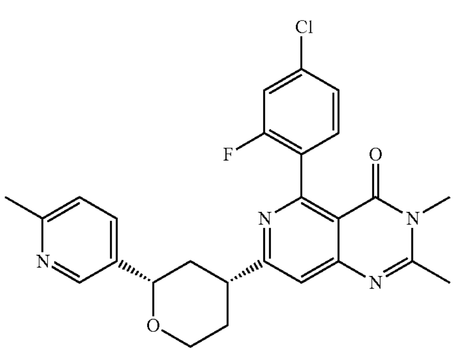 | 5-(4-chloro-2-fluorophenyl)-2,3-dimethyl-7-((2S,4R)-2-(6-methylpyridin-3-yl)tetrahydro-2H-pyran-4-yl)pyrido[4,3-d]pyrimidin-4(3H)-one | 479.0 |

TABLE B-continued

Additional Compounds

| Ex # | Structure | Name | M + H |
|---|---|---|---|
| 275 | 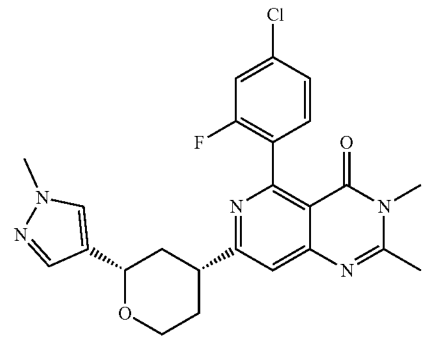 | 5-(4-chloro-2-fluorophenyl)-2,3-dimethyl-7-((2S,4R)-2-(1-methyl-1H-pyrazol-4-yl)tetrahydro-2H-pyran-4-yl)pyrido[4,3-d]pyrimidin-4(3H)-one | 468.2 |

The compounds disclosed below in Table B were made by a method of the present disclosure or a similar method. The appropriate reagents, starting materials and conditions necessary for synthesizing the compounds of Table B would be apparent to a person of ordinary skill in the art.

TABLE C

Additional Compounds

| Ex # | Structure | Name | M + H |
|---|---|---|---|
| 276 | (rac) | 5-(2,4-difluorophenyl)-2,3-dimethyl-7-(2-(2-methylpyridin-4-yl)morpholino)pyrido[4,3-d]pyrimidin-4(3H)-one | 463.8 |
| 277 | (+/−) | 2,3-dimethyl-7-(2-(2-methylpyridin-4-yl)tetrahydro-2H-pyran-4-yl)-5-(6-(trifluoromethyl)pyridin-3-yl)pyrido[4,3-d]pyrimidin-4(3H)-one | 496.2 |

TABLE C-continued

Additional Compounds

| Ex # | Structure | Name | M + H |
|---|---|---|---|
| 278 | 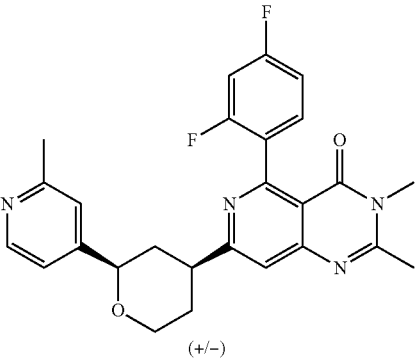 (+/−) | 5-(2,4-difluorophenyl)-2,3-dimethyl-7-(2-(2-methylpyridin-4-yl)tetrahydro-2H-pyran-4-yl)pyrido[4,3-d]pyrimidin-4(3H)-one | 463.2 |
| 279 | 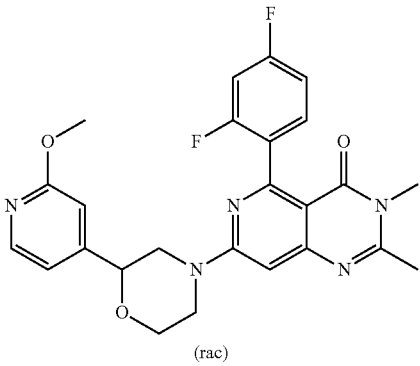 (rac) | 5-(2,4-difluorophenyl)-7-(2-(2-methoxypyridin-4-yl)morpholino)-2,3-dimethylpyrido[4,3-d]pyrimidin-4(3H)-one | 480.1 |
| 280 | 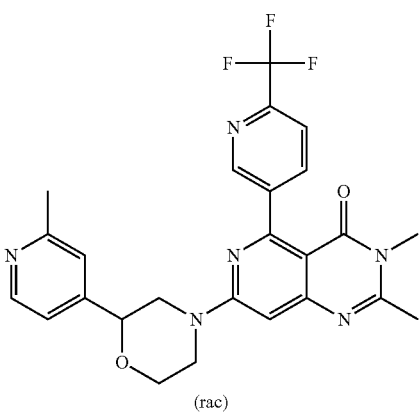 (rac) | 2,3-dimethyl-7-(2-(2-methylpyridin-4-yl)morpholino)-5-(6-(trifluoromethyl)pyridin-3-yl)pyrido[4,3-d]pyrimidin-4(3H)-one | 497.2 |
| 281 | 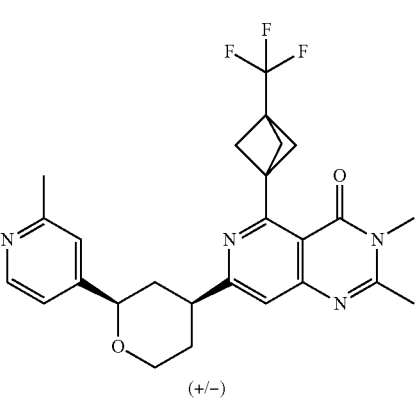 (+/−) | 2,3-dimethyl-7-(2-(2-methylpyridin-4-yl)tetrahydro-2H-pyran-4-yl)-5-(3-(trifluoromethyl)bicyclo[1.1.1]pentan-1-yl)pyrido[4,3-d]pyrimidin-4(3H)-one | 585.2 |

TABLE C-continued

Additional Compounds

| Ex # | Structure | Name | M + H |
|---|---|---|---|
| 282 | (structure shown) (rac) | 2,3-dimethyl-7-(2-(2-methylpyridin-4-yl)morpholino)-5-(3-(trifluoromethyl)bicyclo[1.1.1]pentan-1-yl)pyrido[4,3-d]pyrimidin-4(3H)-one | 486.2 |
| 283 | (structure shown) (rac) | 7-(2-(2-methoxypyridin-4-yl)morpholino)-2,3-dimethyl-5-(3-(trifluoromethyl)bicyclo[1.1.1]pentan-1-yl)pyrido[4,3-d]pyrimidin-4(3H)-one | 502.2 |

The compounds disclosed below in Table C were made by a method of the present disclosure or a similar method. The appropriate reagents, starting materials and conditions necessary for synthesizing the compounds of Table C would be apparent to a person of ordinary skill in the art. Compounds designated with "(+/−)" were isolated as a mixture of diastereomers sharing the same relative stereochemistry (ie. cis or trans). Compounds designated with "(rac)" were isolated as a mixture of all possible stereoisomers of the shown compound.

TABLE 7

| Analytical Data | | |
|---|---|---|
| Ex. # | NMR | M + H |
| 1 | $^1$H NMR (500 MHz, DMSO-d6) δ ppm 7.70-7.73 (m, 1 H), 7.44-7.46 (m, 1 H), 7.36-7.41 (m, 2 H), 7.30-7.34 (m, 1 H), 6.81-6.83 (m, 1 H), 4.50-4.54 (m, 1 H), 4.36-4.40 (m, 1 H), 4.19-4.24 (m, 1 H), 3.96-4.02 (m, 1 H), 3.78-3.82 (m, 3 H), 3.63-3.70 (m, 1 H), 3.34-3.37 (m, 3 H), 3.04-3.11 (m, 1 H), 2.97-3.02 (m, 1 H), 2.52-2.55 (m, 3 H) | 469.0 |
| 2 | $^1$H NMR (500 MHz, DMSO-d6) δ ppm 7.70-7.73 (m, 1 H), 7.44-7.46 (m, 1 H), 7.36-7.41 (m, 2 H), 7.30-7.34 (m, 1 H), 6.81-6.83 (m, 1 H), 4.50-4.54 (m, 1 H), 4.36-4.40 (m, 1 H), 4.19-4.24 (m, 1 H), 3.96-4.02 (m, 1 H), 3.78-3.82 (m, 3 H), 3.63-3.70 (m, 1 H), 3.34-3.37 (m, 3 H), 3.04-3.11 (m, 1 H), 2.97-3.02 (m, 1 H), 2.52-2.55 (m, 3 H) | 469.0 |
| 3 | $^1$H NMR (500 MHz, DMSO-d6) δ ppm 7.74 (s, 1 H), 7.47 (s, 1 H), 7.35 (d, J = 9.9 Hz, 1 H), 7.25-7.33 (m, 2 H), 7.00 (d, J = 2.7 Hz, 1 H), 6.95 (t, J = 2.9 Hz, 1 H), 4.54-4.59 (m, 1 H), 3.98-4.03 (m, 2 H), 3.81-3.84 (m, 1 H), 3.81 (d, J = 2.7 Hz, 3 H), 3.70-3.78 (m, 1 H), 3.35 (s, 3 H), 2.90-2.98 (m, 1 H), 2.85 (dd, J = 12.4, 10.4 Hz, 1 H), 2.52 (br s, 3 H) | 468.0 |
| 4 | $^1$H NMR (500 MHz, DMSO-d6) δ ppm 7.74 (s, 1 H), 7.47 (s, 1 H), 7.32-7.36 (m, 1 H), 7.25-7.32 (m, 2 H), 7.00 (d, J = 2.6 Hz, 1 H), 6.95 (t, J = 3.0 Hz, 1 H), 4.55-4.59 (m, 1 H), 3.96-4.05 (m, 2 H), 3.82 (br s, 1 H), 3.81 (d, J = 2.7 Hz, 3 H), 3.74 (td, J = 11.5, 2.1 Hz, 1 H), 3.35 (s, 3 H), 2.91-2.98 (m, 1 H), 2.85 (dd, J = 12.4, 10.6 Hz, 1 H), 2.52 (br s, 3 H) | 468.0 |

TABLE 7-continued

Analytical Data

| Ex. # | NMR | M + H |
|---|---|---|
| 5 | ¹H NMR (600 MHz, DMSO-d6) δ ppm 7.71-7.74 (m, 1 H), 7.44-7.46 (m, 1 H), 7.38-7.44 (m, 4 H), 6.75-6.78 (m, 1 H), 4.49-4.52 (m, 1 H), 4.38-4.44 (m, 1 H), 4.20-4.27 (m, 1 H), 3.95-4.01 (m, 1 H), 3.79-3.81 (m, 3 H), 3.64-3.69 (m, 1 H), 3.34 (s, 3 H), 3.01-3.07 (m, 1 H), 2.94-3.01 (m, 1 H), 2.52-2.53 (m, 3 H) | 450.8 |
| 6 | ¹H NMR (600 MHz, DMSO-d6) δ ppm 7.71-7.74 (m, 1 H), 7.44-7.46 (m, 1 H), 7.38-7.44 (m, 4 H), 6.75-6.78 (m, 1 H), 4.49-4.52 (m, 1 H), 4.38-4.44 (m, 1 H), 4.20-4.27 (m, 1 H), 3.95-4.01 (m, 1 H), 3.79-3.81 (m, 3 H), 3.64-3.69 (m, 1 H), 3.34 (s, 3 H), 3.01-3.07 (m, 1 H), 2.94-3.01 (m, 1 H), 2.52-2.53 (m, 3 H) | 450.8 |
| 7 | ¹H NMR (500 MHz, DMSO-d6) δ 7.72 (s, 1H), 7.56 (t, J = 8.04 Hz, 1H), 7.43-7.46 (m, 2H), 7.27 (td, J = 1.01, 8.24 Hz, 1H), 6.80 (s, 1H), 4.50 (dd, J = 2.59, 10.38 Hz, 1H), 4.39 (br d, J = 12.98 Hz, 1H), 4.24 (br d, J = 14.01 Hz, 1H), 3.95-4.02 (m, 1H), 3.80 (s, 3H), 3.66 (dt, J = 2.85, 11.55 Hz, 1H), 3.35 (s, 3H), 3.02-3.08 (m, 1H), 2.98 (dd, J = 10.51, 12.98 Hz, 1H), 2.52 (s, 3H) | 469.0 |
| 8 | ¹H NMR (500 MHz, DMSO-d6) δ 7.72 (s, 1H), 7.45 (dt, J = 6.81, 8.40 Hz, 1H), 7.19 (dt, J = 2.47, 9.86 Hz, 1H), 7.09 (dt, J = 2.34, 8.50 Hz, 1H), 6.81 (s, 1H), 4.51 (dd, J = 2.53, 10.44 Hz, 1H), 4.38 (br d, J = 12.72 Hz, 1H), 4.22 (br d, J = 12.85 Hz, 1H), 3.94-4.00 (m, 1H), 3.80 (s, 3H), 3.66 (dt, J = 2.60, 11.55 Hz, 1H), 3.34 (s, 3H), 3.02-3.08 (m, 1H), 2.98 (dd, J = 10.51, 12.98 Hz, 1H), 2.52 (s, 3H) | 453.0 |
| 9 | ¹H NMR (500 MHz, CDCl₃) δ 7.52 (s, 1H), 7.42 (s, 1H), 7.09-7.16 (m, 1H), 7.00-7.08 (m, 1H), 6.58-6.71 (m, 1H), 4.61 (dd, J = 2.60, 10.25 Hz, 1H), 4.38-4.45 (m, 1H), 4.16-4.25 (m, 1H), 4.07-4.13 (m, 1H), 3.91 (s, 3H), 3.82 (dt, J = 2.92, 11.52 Hz, 1H), 3.48 (s, 3H), 3.19-3.27 (m, 1H), 3.15 (br dd, J = 11.03, 12.33 Hz, 1H), 2.55-2.64 (m, 3H) | 471.0 |
| 10 | ¹H NMR (500 MHz, CDCl₃) δ 7.53 (s, 1H), 7.42 (s, 1H), 7.21-7.27 (m, 1H), 6.98 (ddd, J = 6.42, 9.24, 10.02 Hz, 1H), 6.64 (br s, 1H), 4.61 (dd, J = 2.72, 10.25 Hz, 1H), 4.41 (br d, J = 13.23 Hz, 1H), 4.21 (br d, J = 13.10 Hz, 1H), 4.07-4.13 (m, 1H), 3.91 (s, 3H), 3.82 (dt, J = 2.92, 11.52 Hz, 1H), 3.48 (s, 3H), 3.23 (ddd, J = 3.50, 11.55, 12.85 Hz, 1H), 3.14 (br dd, J = 10.51, 12.85 Hz, 1H), 2.59 (br s, 3H) | 471.0 |
| 11 | ¹H NMR (500 MHz, CDCl₃) δ 7.53 (s, 1H), 7.42 (s, 1H), 7.16-7.24 (m, 2H), 6.64 (br d, J = 0.78 Hz, 1H), 4.61 (dd, J = 2.79, 10.32 Hz, 1H), 4.37-4.44 (m, 1H), 4.21 (br d, J = 12.98 Hz, 1H), 4.07-4.14 (m, 1H), 3.91 (s, 3H), 3.82 (dt, J = 2.85, 11.55 Hz, 1H), 3.48 (s, 3H), 3.19-3.27 (m, 1H), 3.10-3.18 (m, 1H), 2.59 (br s, 3H) | 487.0 |
| 12 | ¹H NMR (500 MHz, DMSO-d6) δ 8.98 (s, 1H), 8.64 (s, 1H), 7.39-7.44 (m, 2H), 7.34 (dd, J = 1.95, 8.17 Hz, 1H), 6.87 (s, 1H), 4.83 (s, 2H), 4.01 (t, J = 5.71 Hz, 2H), 3.34 (s, 3H), 2.93 (br t, J = 5.51 Hz, 2H), 2.53 (s, 3H) | 437.0 |
| 13 | ¹H NMR (500 MHz, DMSO-d6) δ 7.72 (s, 1H), 7.54-7.67 (m, 3H), 7.45 (s, 1H), 6.86 (s, 1H), 4.51 (dd, J = 2.14, 10.32 Hz, 1H), 4.38 (br d, J = 12.33 Hz, 1H), 4.22 (br d, J = 12.59 Hz, 1H), 3.97 (br dd, J = 1.49, 11.35 Hz, 1H), 3.80 (s, 3H), 3.66 (br t, J = 10.64 Hz, 1H), 3.34 (s, 3H), 3.06 (br t, J = 11.35 Hz, 1H), 2.99 (dd, J = 10.51, 12.98 Hz, 1H), 2.53 (s, 3H) | 503.0 |
| 14 | ¹H NMR (500 MHz, CDCl₃) δ 7.52 (s, 1H), 7.42 (s, 1H), 7.24 (ddd, J = 1.69, 6.42, 8.37 Hz, 1H), 7.12 (ddd, J = 1.95, 6.62, 8.43 Hz, 1H), 6.64 (br s, 1H), 4.61 (dd, J = 2.79, 10.32 Hz, 1H), 4.41 (br d, J = 12.72 Hz, 1H), 4.17-4.23 (m, 1H), 4.07-4.12 (m, 1H), 3.91 (s, 3H), 3.82 (dt, J = 2.85, 11.48 Hz, 1H), 3.48 (s, 3H), 3.19-3.26 (m, 1H), 3.14 (br t, J = 11.74 Hz, 1H), 2.59 (s, 3H) | 487.0 |
| 15 | ¹H NMR (500 MHz, DMSO-d6) δ ppm 8.49 (dt, J = 2.0, 1.1 Hz, 1 H), 8.02 (dt, J = 9.2, 1.8 Hz, 1 H), 7.74 (s, 1 H), 7.47 (s, 1 H), 7.03-7.09 (m, 2 H), 4.57 (ddd, J = 10.4, 4.8, 2.6 Hz, 1 H), 3.96-4.06 (m, 2 H), 3.82-3.84 (m, 1 H), 3.81 (d, J = 2.3 Hz, 3 H), 3.69-3.78 (m, 1 H), 3.36 (s, 3 H), 2.96 (td, J = 11.8, 3.1 Hz, 1 H), 2.87 (dd, J = 12.3, 10.5 Hz, 1 H), 2.53 (s, 3 H) | 469.0 |
| 16 | ¹H NMR (500 MHz, DMSO-d6) δ ppm 8.35 (d, J = 2.34 Hz, 1H), 7.82 (s, 1H), 7.71 (d, J = 4.54 Hz, 1H), 7.44 (d, J = 2.34 Hz, 1H), 6.83 (d, J = 1.30 Hz, 1H), 4.47-4.53 (m, 1H), 4.34 (br d, J = 12.98 Hz, 1H), 4.19 (br t, J = 14.21 Hz, 1H), 3.93-3.99 (m, 1H), 3.78-3.81 (m, 3H), 3.65 (dt, J = 2.79, 11.58 Hz, 1H), 3.30 (s, 3H), 2.95-3.09 (m, 2H), 2.51 (s, 3H), 2.01 (d, J = 4.93 Hz, 3H) | 465.8 |
| 17 | ¹H NMR (600 MHz, DMSO-d6) δ ppm 8.75-8.80 (m, 1 H), 8.09-8.15 (m, 1 H), 7.91-7.94 (m, 1 H), 7.71-7.73 (m, 1 H), 7.44-7.47 (m, 1 H), 6.85-6.89 (m, 1 H), 4.48-4.53 (m, 1 H), 4.39-4.45 (m, 1 H), 4.22-4.29 (m, 1 H), 3.96-4.02 (m, 1 H), 3.80-3.81 (m, 3 H), 3.64-3.69 (m, 1 H), 3.34-3.37 (m, 3 H), 3.06-3.12 (m, 1 H), 2.99-3.04 (m, 1 H), 2.52-2.57 (m, 3 H) | 486.2 |
| 18 | ¹H NMR (600 MHz, DMSO-d6) δ ppm 7.72 (s, 1 H), 7.39-7.47 (m, 3 H), 7.33 (dd, J = 8.25, 1.87 Hz, 1 H), 6.79 (s, 1 H), 5.76 (s, 1 H), 4.46-4.53 (m, 1 H), 4.37 (br d, J = 12.69 Hz, 1 H), 4.21 (br d, | 537.0 |

TABLE 7-continued

| Ex. # | NMR | M + H |
|---|---|---|
|  | J = 12.48 Hz, 1 H), 3.97 (br d, J = 11.51 Hz, 1 H), 3.79-3.82 (m, 3 H), 3.66 (br t, J = 11.37 Hz, 1 H), 2.96-3.08 (m, 2 H), 2.59 (s, 3 H), 1.74 (br s, 2H), 1.67 (br d, J = 11.31 Hz, 2 H), 1.59 (br d, J = 12.83 Hz, 1 H), 1.23-1.36 (m, 2 H), 1.05-1.15 (m, 1 H) |  |
| 19 | $^1$H NMR (600 MHz, DMSO-d6) δ ppm 7.72 (s, 1 H), 7.40-7.46 (m, 3 H), 7.34 (dd, J = 8.17, 1.91 Hz, 1 H), 6.88 (s, 1 H), 4.85-4.89 (m, 2 H), 4.52 (dd, J = 10.35, 2.27 Hz, 1 H), 4.39-4.47 (m, 1 H), 4.23-4.33 (m, 1 H), 3.98 (br d, J = 12.08 Hz, 1 H), 3.81 (s, 3 H), 3.63-3.71 (m, 1 H), 3.07-3.15 (m, 1 H), 3.04 (dd, J = 12.99, 10.54 Hz, 1 H), 2.57 (s, 3 H) | 537.0 |
| 20 | $^1$H NMR (600 MHz, DMSO-d6) δ ppm 7.72 (s, 1 H), 7.38-7.46 (m, 3 H), 7.33 (dd, J = 8.18, 1.73 Hz, 1 H), 6.80 (s, 1 H), 4.51 (br d, J = 10.54 Hz, 1 H), 4.37 (br d, J = 12.76 Hz, 1 H), 4.21 (br d, J = 13.39 Hz, 1H), 3.98 (brd, J = 11.58 Hz, 1H), 3.81 (s, 3 H), 3.63-3.71 (m, 1 H), 3.03-3.08 (m, 1 H), 2.99 (dd, J = 12.94, 10.51 Hz, 1 H), 2.83-2.87 (m, 1 H), 2.60 (s, 3 H), 1.07 (br d, J = 6.45 Hz, 2 H), 0.76 (br s, 2H) | 495.0 |
| 21 | $^1$H NMR (500 MHz, DMSO-d6) δ ppm 8.52 (s, 1 H), 8.11 (dd, J = 9.2, 1.9 Hz, 1 H), 7.72 (s, 1 H), 7.45 (s, 1 H), 6.89 (s, 1 H), 4.51 (dd, J = 10.4, 2.6 Hz, 1 H), 4.37 (br d, J = 12.7 Hz, 1 H), 4.21 (br d, J = 13.0 Hz, 1 H), 3.98 (dt, J = 10.1, 1.7 Hz, 1 H), 3.80 (s, 3 H), 3.75-3.80 (m, 2 H), 3.67 (td, J = 11.5, 2.7 Hz, 1 H), 3.04-3.14 (m, 1 H), 3.02 (dd, J = 13.0, 10.4 Hz, 1 H), 2.57 (s, 3 H), 1.50-1.58 (m, 2 H), 0.86 (t, J = 7.4 Hz, 3 H) | 498.2 |
| 22 | $^1$H NMR (500 MHz, DMSO-d6) δ ppm 12.76 (br d, J = 1.82 Hz, 1H), 7.77 (br s, 1H), 7.54 (br s, 1H), 7.37-7.42 (m, 2H), 7.31 (dd, J = 2.08, 8.17 Hz, 1H), 6.83 (s, 1H), 4.56 (dd, J = 2.66, 10.44 Hz, 1H), 4.38 (br d, J = 12.59 Hz, 1H), 4.24 (br d, J = 12.20 Hz, 1H), 3.96-4.02 (m, 1H), 3.68 (dt, J = 2.60, 11.55 Hz, 1H), 3.35 (s, 3H), 3.01-3.11 (m, 2H), 2.53 (s, 3H) | 455.0 |
| 23 | $^1$H NMR (500 MHz, DMSO-d6) δ ppm 7.76-7.79 (m, 1 H), 7.44-7.48 (m, 1 H), 7.36-7.41 (m, 2 H), 7.29-7.33 (m, 1 H), 6.82-6.85 (m, 1 H), 4.50-4.55 (m, 1 H), 4.38-4.43 (m, 1 H), 4.22-4.28 (m, 1 H), 4.08-4.13 (m, 2 H), 3.96-4.02 (m, 1 H), 3.64-3.72 (m, 1 H), 3.34-3.37 (m, 3 H), 2.97-3.07 (m, 2 H), 2.52-2.55 (m, 3 H), 1.32-1.38 (m, 3 H) | 483.0 |
| 24 | $^1$H NMR (500 MHz, DMSO-d6) δ ppm 7.76-7.79 (m, 1 H), 7.44-7.48 (m, 1 H), 7.36-7.41 (m, 2 H), 7.29-7.33 (m, 1 H), 6.82-6.85 (m, 1 H), 4.50-4.55 (m, 1 H), 4.38-4.43 (m, 1 H), 4.22-4.28 (m, 1 H), 4.08-4.13 (m, 2 H), 3.96-4.02 (m, 1 H), 3.64-3.72 (m, 1 H), 3.34-3.37 (m, 3 H), 2.97-3.07 (m, 2 H), 2.52-2.55 (m, 3 H), 1.32-1.38 (m, 3 H) | 483.0 |
| 25 | $^1$H NMR (500 MHz, DMSO-d6) δ ppm 7.77 (s, 1 H), 7.49 (s, 1 H), 7.35-7.42 (m, 2 H), 7.29-7.34 (m, 1 H), 6.76 (s, 1 H), 4.48 (br dd, J = 11.09, 2.79 Hz, 2 H), 4.27 (br s, 1 H), 3.82 (s, 5 H), 3.32-3.38 (m, 3 H), 3.07 (br t, J = 12.20 Hz, 1 H), 2.52-2.54 (m, 3 H), 1.22 (br d, J = 6.49 Hz, 3 H) | 483.0 |
| 26 | $^1$H NMR (600 MHz, DMSO-d6) δ ppm 7.77 (s, 1 H), 7.49 (s, 1 H), 7.35-7.42 (m, 2 H), 7.31 (br d, J = 8.08 Hz, 1 H), 6.76 (s, 1 H), 4.48 (br dd, J = 11.04, 2.50 Hz, 2 H), 4.26 (br s, 1 H), 3.82 (s, 5 H), 3.35 (s, 3 H), 3.17-3.29 (m, 1 H), 3.07 (br t, J = 12.13 Hz, 1 H), 2.52-2.53 (m, 3 H), 1.22 (br d, J = 6.27 Hz, 3 H) | 483.0 |
| 27 | $^1$H NMR (600 MHz, DMSO-d6) δ ppm 7.58 (s, 1 H), 7.36-7.45 (m, 2 H), 7.28-7.35 (m, 2 H), 6.79 (s, 1 H), 4.97 (t, J = 3.9 Hz, 1 H), 4.12-4.20 (m, 1 H), 3.97 (br d, J = 12.4 Hz, 1 H), 3.85-3.92 (m, 1 H), 3.76 (s, 3 H), 3.62 (dd, J = 13.3, 3.8 Hz, 1 H), 3.34 (s, 3 H), 3.10 (br dd, J = 12.8, 8.2 Hz, 1 H), 2.52 (s, 3 H), 1.15 (d, J = 6.4 Hz, 3 H) | 483.0 |
| 28 | $^1$H NMR (600 MHz, DMSO-d6) δ ppm 7.73 (s, 1 H), 7.46 (s, 1 H), 7.36-7.42 (m, 2 H), 7.32 (dd, J = 8.1, 1.9 Hz, 1 H), 6.84 (s, 1 H), 4.54 (dd, J = 10.8, 2.3 Hz, 1 H), 4.39-4.47 (m, 1 H), 4.29-4.38 (m, 1 H), 3.81 (s, 3 H), 3.71-3.78 (m, 1 H), 3.35 (s, 3 H), 2.87 (dd, J = 12.7, 11.0 Hz, 1H), 2.59-2.68 (m, 1 H), 2.52 (s, 3 H), 1.20 (d, J = 6.2 Hz, 3 H) | 483.0 |
| 29 | $^1$H NMR (600 MHz, DMSO-d6) δ ppm 7.73 (s, 1 H), 7.46 (s, 1 H), 7.36-7.41 (m, 2 H), 7.30-7.33 (m, 1 H), 6.84 (s, 1 H), 4.54 (dd, J = 10.9, 1.8 Hz, 1 H), 4.39-4.46 (m, 1 H), 4.32-4.38 (m, 1 H), 3.81 (s, 3 H), 3.71-3.78 (m, 1 H), 3.35 (s, 3 H), 2.87 (dd, J = 12.3, 11.5 Hz, 1 H), 2.63 (br t, J = 11.8 Hz, 1 H), 2.52 (s, 3 H), 1.20 (d, J = 6.0 Hz, 3H) | 483.0 |
| 30 | $^1$H NMR (600 MHz, DMSO-d6) δ ppm 7.58 (s, 1 H), 7.36-7.43 (m, 2 H), 7.30-7.35 (m, 2 H), 6.79 (s, 1 H), 4.97 (t, J = 3.9 Hz, 1 H), 4.07-4.22 (m, 1 H), 3.93-4.01 (m, 1 H), 3.84-3.93 (m, 1 H), 3.76 (s, 3 H), 3.62 (dd, J = 13.2, 3.9 Hz, 1 H), 3.34 (s, 3 H), 3.10 (br dd, J = 12.6, 8.5 Hz, 1 H), 2.52 (s, 3 H), 1.15 (d, J = 6.3 Hz, 3 H) | 483.0 |
| 31 | $^1$H NMR (500 MHz, DMSO-d6) δ ppm 7.54 (s, 1 H), 7.37-7.47 (m, 2 H), 7.30-7.36 (m, 2 H), 6.80 (s, 1 H), 4.35 (br d, J = 13.0 Hz, 1 H), | 483.0 |

TABLE 7-continued

Analytical Data

| Ex. # | NMR | M + H |
|---|---|---|
|  | 3.82 (br d, J = 12.5 Hz, 1 H), 3.75 (s, 3 H), 3.71 (dt, J = 11.7, 3.7 Hz, 1 H), 3.53-3.62 (m, 1 H), 3.35-3.38 (m, 1 H), 3.34 (s, 3 H), 2.52 (br s, 3H) | |
| 32 | $^1$H NMR (500 MHz, CDCl$_3$) δ ppm 7.35-7.40 (m, 1 H), 7.23-7.27 (m, 1 H), 7.15-7.19 (m, 1 H), 6.60-6.81 (m, 1 H), 4.22-4.40 (m, 2 H), 4.02-4.07 (m, 1 H), 3.60-3.67 (m, 1 H), 3.45-3.51 (m, 3 H), 3.08-3.15 (m, 1 H), 2.93-3.00 (m, 1 H), 2.81-2.86 (m, 1 H), 0.92-1.00 (m, 1 H), 0.55-0.66 (m, 2 H), 0.43-0.49 (m, 1 H), 0.29-0.35 (m, 1 H) | 429.2 |
| 33 | $^1$H NMR (600 MHz, DMSO-d6) δ ppm 7.36-7.41 (m, 2 H), 7.30-7.33 (m, 1 H), 6.73-6.75 (m, 1 H), 4.09-4.23 (m, 2 H), 3.92-3.97 (m, 1 H), 3.50-3.55 (m, 1 H), 3.36-3.40 (m, 1 H), 3.33-3.34 (m, 3 H), 2.90-2.96 (m, 1 H), 2.53-2.58 (m, 1 H), 2.51-2.52 (m, 3 H), 2.37-2.43 (m, 1 H), 1.82-1.96 (m, 5 H), 1.71-1.80 (m, 1 H) | 443.2 |
| 34 | $^1$H NMR (500 MHz, DMSO-d6) δ ppm 7.32-7.42 (m, 3 H), 6.77 (s, 1 H), 4.22-4.35 (m, 2 H), 3.49-3.56 (m, 1 H), 3.33 (s, 3 H), 2.86 (ddd, J = 10.5, 8.0, 2.5 Hz, 1 H), 2.67-2.73 (m, 1 H), 2.51 (br s, 3 H), 1.15 (d, J = 6.2 Hz, 3 H), 0.84-0.91 (m, 1 H), 0.43-0.49 (m, 2 H), 0.28-0.35 (m, 2 H) | 443.2 |
| 35 | $^1$H NMR (500 MHz, DMSO-d6) δ ppm 7.35-7.41 (m, 2 H), 7.31-7.35 (m, 1 H), 6.73 (s, 1 H), 4.05-4.12 (m, 1 H), 3.85-3.93 (m, 1 H), 3.66-3.76 (m, 1 H), 3.59-3.66 (m, 1 H), 3.33 (s, 3 H), 3.19 (dd, J = 12.9, 7.7 Hz, 1 H), 3.05-3.11 (m, 1 H), 2.51 (br s, 3 H), 1.12 (d, J = 6.4 Hz, 3 H), 1.03-1.10 (m, 1 H), 0.41-0.49 (m, 2 H), 0.24-0.31 (m, 2H) | 443.2 |
| 36 | $^1$H NMR (500 MHz, DMSO-d6) δ ppm 7.35-7.41 (m, 2 H), 7.31-7.35 (m, 1 H), 6.73 (s, 1 H), 4.08 (td, J = 6.8, 2.9 Hz, 1 H), 3.89 (br dd, J = 12.8, 2.5 Hz, 1 H), 3.66-3.78 (m, 1 H), 3.58-3.66 (m, 1 H), 3.33 (s, 3 H), 3.19 (dd, J = 12.9, 7.6 Hz, 1 H), 3.08 (dt, J = 8.7, 4.5 Hz, 1 H), 2.51 (br s, 3 H), 1.12 (d, J = 6.2 Hz, 3 H), 1.05-1.10 (m, 1 H), 0.40-0.49 (m, 2 H), 0.27 (br d, J = 3.9 Hz, 2 H) | 443.2 |
| 37 | $^1$H NMR (500 MHz, DMSO-d6) δ ppm 7.35-7.43 (m, 2 H), 7.30-7.35 (m, 1 H), 6.77 (s, 1 H), 4.15-4.40 (m, 2 H), 3.44-3.63 (m, 1 H), 3.33 (s, 3 H), 2.86 (ddd, J = 10.5, 8.0, 2.5 Hz, 1 H), 2.65-2.74 (m, 1 H), 2.51 (br s, 3 H), 1.15 (d, J = 6.1 Hz, 3 H), 0.82-0.95 (m, 1 H), 0.46 (d, J = 8.2 Hz, 2 H), 0.25-0.37 (m, 2 H) | 443.0 |
| 38 | $^1$H NMR (500 MHz, DMSO-d6) δ ppm 7.37-7.42 (m, 2 H), 7.31-7.34 (m, 1 H), 6.78 (s, 1 H), 4.75 (td, J = 7.4, 4.5 Hz, 1 H), 4.51 (ddd, J = 8.2, 7.2, 5.6 Hz, 1 H), 4.41 (dt, J = 8.9, 6.0 Hz, 1 H), 4.23 (br d, J = 12.7 Hz, 1 H), 4.16 (br d, J = 12.3 Hz, 1 H), 4.03 (dd, J = 11.5, 2.3 Hz, 1 H), 3.55-3.63 (m, 2 H), 3.35 (s, 3 H), 2.95-3.02 (m, 1 H), 2.78 (t, J = 11.8 Hz, 1 H), 2.55-2.67 (m, 2 H), 2.52 (s, 3 H) | 445.0 |
| 39 | $^1$H NMR (500 MHz, DMSO-d6) δ ppm 7.36-7.43 (m, 2 H), 7.31-7.36 (m, 1 H), 6.76 (s, 1 H), 4.64-4.73 (m, 1 H), 4.50-4.57 (m, 1 H), 4.46 (dt, J = 8.5, 6.2 Hz, 1 H), 4.32 (br d, J = 12.5 Hz, 1 H), 4.19 (br d, J = 12.7 Hz, 1 H), 4.01 (dd, J = 11.4, 2.4 Hz, 1 H), 3.57-3.70 (m, 2 H), 3.35 (s, 3 H), 2.99 (td, J = 12.4, 3.2 Hz, 1 H), 2.55-2.68 (m, 3 H), 2.52 (s, 3 H) | 445.0 |
| 40 | $^1$H NMR (500 MHz, DMSO-d6) δ ppm 7.37-7.42 (m, 2 H), 7.31-7.34 (m, 1 H), 6.78 (s, 1 H), 4.75 (td, J = 7.4, 4.4 Hz, 1 H), 4.48-4.54 (m, 1 H), 4.41 (dt, J = 8.9, 6.0 Hz, 1 H), 4.23 (br d, J = 13.9 Hz, 1 H), 4.16 (br d, J = 12.8 Hz, 1 H), 4.03 (dd, J = 11.5, 2.3 Hz, 1 H), 3.54-3.63 (m, 2 H), 3.35 (s, 3 H), 2.98 (td, J = 12.3, 3.4 Hz, 1 H), 2.78 (dd, J = 12.3, 11.4 Hz, 1 H), 2.54-2.66 (m, 2 H), 2.52 (s, 3 H) | 445.0 |
| 41 | $^1$H NMR (500 MHz, DMSO-d6) δ ppm 7.37-7.41 (m, 2 H), 7.31-7.34 (m, 1 H), 6.76 (s, 1 H), 4.69 (td, J = 7.1, 5.0 Hz, 1 H), 4.44-4.55 (m, 2 H), 4.32 (br d, J = 12.8 Hz, 1 H), 4.15-4.23 (m, 1 H), 4.01 (dd, J = 11.6, 2.4 Hz, 1 H), 3.58-3.69 (m, 2 H), 3.35 (s, 3 H), 2.99 (td, J = 12.4, 3.5 Hz, 1 H), 2.57-2.67 (m, 3 H), 2.53 (s, 3 H) | 445.0 |
| 42 | $^1$H NMR (500 MHz, CDCl$_3$) δ ppm 7.36 (t, J = 7.8 Hz, 1 H), 7.24 (d, J = 8.2 Hz, 1 H), 7.16 (dd, J = 9.6, 1.8 Hz, 1 H), 6.63 (br s, 1 H), 4.16-4.37 (m, 2 H), 4.02 (br dd, J = 11.5, 2.7 Hz, 1 H), 3.86-3.98 (m, 2 H), 3.72-3.81 (m, 2 H), 3.61-3.72 (m, 1 H), 3.48 (s, 3 H), 3.36-3.45 (m, 1 H), 3.05-3.16 (m, 1 H), 2.80 (dd, J = 12.5, 10.7 Hz, 1 H), 2.60 (br s, 3 H), 2.32-2.49 (m, 1 H), 1.92-2.10 (m, 1 H), 1.64-1.73 (m, 1 H) | 459.0 |
| 43 | $^1$H NMR (500 MHz, CDCl$_3$) δ ppm 7.35 (t, J = 7.9 Hz, 1 H), 7.23 (dd, J = 8.2, 1.8 Hz, 1 H), 7.16 (dd, J = 9.6, 1.8 Hz, 1 H), 6.57 (s, 1 H), 4.12-4.28 (m, 2 H), 4.05 (dd, J = 11.6, 2.3 Hz, 1 H), 3.84-3.93 (m, 2 H), 3.78 (q, J = 7.6 Hz, 1 H), 3.68 (td, J = 11.6, 2.7 Hz, 1 H), 3.61 (dd, J = 8.4, 7.1 Hz, 1 H), 3.47 (s, 3 H), 3.43 (ddd, J = 10.2, 7.7, 2.4 Hz, 1 H), 3.05-3.15 (m, 1 H), 2.83 (dd, J = 12.7, 10.5 Hz, 1 H), 2.57 (s, 3 H), 2.33-2.46 (m, 1 H), 2.01-2.13 (m, 1 H), 1.89-2.00 (m, 1 H) | 459.0 |
| 44 | $^1$H NMR (500 MHz, CDCl$_3$) δ ppm 7.33-7.38 (m, 1 H), 7.24 (dd, J = 8.2, 1.7 Hz, 1H), 7.16 (dd, J = 9.6, 1.9 Hz, 1 H), 6.57 (s, 1H), | 459.0 |

TABLE 7-continued

Analytical Data

| Ex. # | NMR | M + H |
|---|---|---|
|  | 4.14-4.26 (m, 2 H), 4.00-4.08 (m, 1 H), 3.85-3.91 (m, 2 H), 3.78 (q, J = 7.5 Hz, 1 H), 3.69 (td, J = 11.6, 2.8 Hz, 1 H), 3.61 (dd, J = 8.6, 7.0 Hz, 1 H), 3.47 (s, 3 H), 3.43 (ddd, J = 10.3, 7.7, 2.6 Hz, 1 H), 3.10 (ddd, J = 12.9, 11.8, 3.6 Hz, 1 H), 2.83 (dd, J = 12.8, 10.3 Hz, 1 H), 2.57 (s, 3H), 2.36-2.43 (m, 1 H), 2.04-2.10 (m, 1 H), 1.91-1.98 (m, 1 H) |  |
| 45 | $^1$H NMR (500 MHz, CDCl$_3$) δ ppm 7.30-7.40 (m, 2 H), 7.21-7.26 (m, 1 H), 7.14-7.19 (m, 1 H), 6.59 (s, 1 H), 4.18-4.36 (m, 2 H), 4.01 (dd, J = 11.6, 2.3 Hz, 1 H), 3.86-3.99 (m, 2 H), 3.73-3.82 (m, 2H), 3.67 (td, J = 11.6, 2.8 Hz, 1 H), 3.47 (s, 3 H), 3.35-3.45 (m, 1 H), 3.03-3.16 (m, 1 H), 2.80 (dd, J = 12.8, 10.4 Hz, 1 H), 2.58 (s, 3 H), 2.32-2.45 (m, 1 H), 1.95-2.10 (m, 1 H), 1.62-1.73 (m, 1 H) | 460.0 |
| 46 | $^1$H NMR (600 MHz, DMSO-d6) δ ppm 8.64-8.68 (m, 1 H), 8.52-8.55 (m, 1 H), 7.84-7.87 (m, 1 H), 7.37-7.42 (m, 3 H), 7.29-7.33 (m, 1 H), 6.86-6.89 (m, 1 H), 4.64-4.68 (m, 1 H), 4.43-4.48 (m, 1 H), 4.29-4.36 (m, 1 H), 4.07-4.12 (m, 1 H), 3.75-3.77 (m, 1 H), 3.41-3.42 (m, 3 H), 3.10-3.13 (m, 1 H), 2.93-2.99 (m, 1 H), 2.52-2.54 (m, 3 H) | 466.0 |
| 47 | $^1$H NMR (600 MHz, DMSO-d6) δ ppm 8.64-8.68 (m, 1 H), 8.52-8.55 (m, 1 H), 7.84-7.87 (m, 1 H), 7.37-7.42 (m, 3 H), 7.29-7.33 (m, 1 H), 6.86-6.89 (m, 1 H), 4.64-4.68 (m, 1 H), 4.43-4.48 (m, 1 H), 4.29-4.36 (m, 1 H), 4.07-4.12 (m, 1 H), 3.75-3.77 (m, 1 H), 3.41-3.42 (m, 3 H), 3.10-3.13 (m, 1 H), 2.93-2.99 (m, 1 H), 2.52-2.54 (m, 3 H) | 466 |
| 48 | $^1$H NMR (500 MHz, DMSO-d6) δ ppm 8.58 (d, J = 5.0 Hz, 2 H), 7.48 (d, J = 6.0 Hz, 2 H), 7.37-7.43 (m, 2 H), 7.33 (dd, J = 8.2, 1.9 Hz, 1 H), 6.90 (s, 1 H), 4.66 (dd, J = 10.4, 2.6 Hz, 1 H), 4.50 (br d, J = 12.5 Hz, 1 H), 4.33 (br d, J = 13.0 Hz, 1H), 4.12 (dd, J = 11.7, 2.3 Hz, 1 H), 3.76 (td, J = 11.6, 2.6 Hz, 1 H), 3.35 (s, 3 H), 3.05-3.16 (m, 1 H), 2.88 (dd, J = 13.0, 10.5 Hz, 1 H), 2.53 (s, 3 H) | 466.0 |
| 49 | $^1$H NMR (500 MHz, DMSO-d6) δ ppm 8.56-8.60 (m, 2 H), 7.46-7.50 (m, 2 H), 7.37-7.43 (m, 2 H), 7.33 (dd, J = 8.2, 1.8 Hz, 1 H), 6.90 (s, 1 H), 4.66 (dd, J = 10.5, 2.6 Hz, 1 H), 4.51 (br d, J = 13.2 Hz, 1 H), 4.33 (br d, J = 13.1 Hz, 1 H), 4.12 (dd, J = 11.6, 2.1 Hz, 1 H), 3.76 (td, J = 11.7, 2.7 Hz, 1 H), 3.35 (s, 3 H), 3.05-3.15 (m, 1 H), 2.88 (dd, J = 13.0, 10.5 Hz, 1 H), 2.53 (s, 3 H) | 466.0 |
| 50 | $^1$H NMR (600 MHz, DMSO-d6) δ ppm 9.34-9.38 (m, 1 H), 9.22-9.27 (m, 1 H), 7.74-7.78 (m, 1 H), 7.38-7.44 (m, 2 H), 7.30-7.34 (m, 1 H), 6.94-6.97 (m, 1 H), 4.73-4.78 (m, 1 H), 4.51-4.58 (m, 1 H), 4.33-4.41 (m, 1 H), 4.10-4.16 (m, 1 H), 3.73-3.79 (m, 1 H), 3.34-3.36 (m, 3 H), 3.06-3.13 (m, 1 H), 2.92-2.97 (m, 1 H), 2.53-2.55 (m, 3 H) | 467.2 |
| 51 | $^1$H NMR (500 MHz, CDCl$_3$) δ ppm 9.20-9.22 (m, 1 H), 8.78-8.81 (m, 1 H), 7.58-7.62 (m, 1 H), 7.35-7.42 (m, 1 H), 7.23-7.26 (m, 1 H), 7.14-7.18 (m, 1 H), 6.72-6.75 (m, 1 H), 4.72-4.79 (m, 1 H), 4.66-4.71 (m, 1 H), 4.42-4.48 (m, 1 H), 4.20-4.26 (m, 1 H), 3.87-3.91 (m, 1 H), 3.46-3.49 (m, 3 H), 3.15-3.24 (m, 1 H), 2.95-3.02 (m, 1 H), 2.57-2.60 (m, 3 H) | 467.0 |
| 52 | $^1$H NMR (600 MHz, DMSO-d6) δ ppm 7.38-7.43 (m, 2 H), 7.35-7.37 (m, 1 H), 7.30-7.33 (m, 1 H), 6.85-6.87 (m, 1 H), 6.31-6.34 (m, 1 H), 4.75-4.79 (m, 1 H), 4.39-4.49 (m, 1 H), 4.19-4.26 (m, 1 H), 3.93-3.99 (m, 1 H), 3.81-3.85 (m, 3 H), 3.73-3.79 (m, 1 H), 3.35-3.36 (m, 3 H), 3.29-3.32 (m, 1 H), 3.15-3.22 (m, 1 H), 2.52 (s, 3 H) | 469.2 |
| 53 | $^1$H NMR (600 MHz, DMSO-d6) δ ppm 7.37-7.41 (m, 2 H), 7.31-7.34 (m, 1 H), 6.75-6.78 (m, 1 H), 4.30-4.39 (m, 1 H), 4.14-4.23 (m, 1 H), 3.92-3.98 (m, 1 H), 3.75-3.83 (m, 1 H), 3.55-3.63 (m, 1 H), 3.34-3.36 (m, 3 H), 2.96-3.05 (m, 1 H), 2.75-2.82 (m, 1 H), 2.59-2.68 (m, 1 H), 2.52-2.54 (m, 3 H), 2.46-2.50 (m, 1 H) | 471.0 |
| 54 | $^1$H NMR (600 MHz, DMSO-d6) δ ppm 7.50-7.56 (m, 2 H), 7.36-7.44 (m, 2 H), 7.32 (dd, J = 8.1, 1.9 Hz, 1 H), 7.21 (dd, J = 4.7, 1.3 Hz, 1 H), 6.87 (s, 1 H), 4.64 (dd, J = 10.3, 2.3 Hz, 1 H), 4.47 (br d, J = 13.0 Hz, 1 H), 4.20-4.34 (m, 1 H), 4.04 (br dd, J = 11.6, 1.8 Hz, 1 H), 3.64-3.79 (m, 1 H), 3.34 (s, 3 H), 3.04-3.11 (m, 1 H), 2.99 (dd, J = 12.8, 10.6 Hz, 1 H), 2.52 (s, 3 H) | 470.8 |
| 55 | $^1$H NMR (500 MHz, DMSO-d6) δ ppm 7.51-7.54 (m, 2 H), 7.37-7.42 (m, 2 H), 7.32 (dd, J = 8.2, 2.1 Hz, 1 H), 7.21 (dd, J = 4.6, 1.6 Hz, 1 H), 6.86 (s, 1 H), 4.65 (dd, J = 10.4, 2.6 Hz, 1 H), 4.47 (br d, J = 12.6 Hz, 1 H), 4.27 (br d, J = 12.3 Hz, 1 H), 4.05 (dt, J = 10.0, 1.8 Hz, 1 H), 3.72 (td, J = 11.6, 2.7 Hz, 1 H), 3.35 (s, 3 H), 3.05-3.13 (m, 1 H), 3.01 (dd, J = 13.0, 10.5 Hz, 1 H), 2.53 (s, 3 H) | 471.0 |
| 56 | $^1$H NMR (500 MHz, CDCl$_3$) δ ppm 7.37 (t, J = 7.91 Hz, 1 H), 7.23 (dd, J = 8.17, 1.82 Hz, 1 H), 7.16 (dd, J = 9.60, 1.95 Hz, 1 H), 6.67 (s, 1 H), 4.84 (dd, J = 10.25, 2.85 Hz, 1 H), 4.63 (br d, J = 13.23 Hz, 1 H), 4.16-4.28 (m, 2 H), 3.85-3.93 (m, 1 H), 3.46-3.49 (m, 3 H), 3.30-3.44 (m, 2 H), 2.64 (s, 3 H), 2.58 (s, 3 H) | 471.0 |

TABLE 7-continued

Analytical Data

| Ex. # | NMR | M + H |
|---|---|---|
| 57 | $^1$H NMR (500 MHz, CDCl$_3$) δ ppm 7.37 (t, J = 7.91 Hz, 1 H), 7.23 (dd, J = 8.17, 1.82 Hz, 1 H), 7.16 (dd, J = 9.60, 1.95 Hz, 1 H), 6.67 (s, 1 H), 4.84 (dd, J = 10.25, 2.85 Hz, 1 H), 4.63 (br d, J = 13.23 Hz, 1 H), 4.16-4.28 (m, 2 H), 3.85-3.93 (m, 1 H), 3.46-3.49 (m, 3 H), 3.30-3.44 (m, 2 H), 2.64 (s, 3 H), 2.58 (s, 3 H) | 471.0 |
| 58 | $^1$H NMR (600 MHz, DMSO-d6) δ 7.37-7.42 (m, 2H), 7.33 (dd, J = 1.86, 8.22 Hz, 1H), 6.83 (s, 1H), 4.96 (dd, J = 2.91, 9.45 Hz, 1H), 4.50-4.56 (m, 1H), 4.09 (br d, J = 13.17 Hz, 1H), 4.00 (td, J = 2.95, 11.44 Hz, 1H), 3.76-3.83 (m, 1H), 3.50 (br dd, J = 10.49, 12.85 Hz, 1H), 3.35 (s, 3H), 3.28 (s, 1H), 2.53 (s, 3H) | 471 |
| 59 | $^1$H NMR (600 MHz, DMSO-d6) δ 7.38-7.41 (m, 2H), 7.33 (dd, J = 1.91, 8.17 Hz, 1H), 6.83 (s, 1H), 4.96 (dd, J = 3.00, 9.45 Hz, 1H), 4.53 (br d, J = 13.08 Hz, 1H), 4.09 (br d, J = 12.99 Hz, 1H), 4.00 (td, J = 3.12, 11.56 Hz, 1H), 3.76-3.82 (m, 1H), 3.50 (br dd, J = 10.04, 12.67 Hz, 1H), 3.35 (s, 3H), 3.29 (br s, 1H), 2.55 (s, 3H), 2.53 (s, 3H) | 471.0 |
| 60 | $^1$H NMR (500 MHz, CDCl$_3$) δ ppm 8.54-8.57 (m, 1 H), 7.64-7.69 (m, 1 H), 7.33-7.38 (m, 1 H), 7.22-7.26 (m, 1 H), 7.18-7.21 (m, 1 H), 7.14-7.18 (m, 1 H), 6.62-6.66 (m, 1 H), 4.62 (dd, J = 10.5, 2.7 Hz, 1 H), 4.46-4.54 (m, 1 H), 4.23-4.30 (m, 1 H), 4.17-4.22 (m, 1 H), 3.83-3.91 (m, 1 H), 3.47-3.49 (m, 3 H), 3.20-3.27 (m, 1 H), 2.96-3.04 (m, 1 H), 2.59-2.60 (m, 3 H), 2.56-2.58 (m, 3 H) | 480.0 |
| 61 | $^1$H NMR (400 MHz, CDCl$_3$) δ ppm 8.49-8.56 (m, 1 H), 7.32-7.39 (m, 1 H), 7.21-7.25 (m, 2 H), 7.13-7.19 (m, 2 H), 6.62-6.65 (m, 1 H), 4.53-4.60 (m, 1 H), 4.43-4.51 (m, 1 H), 4.25-4.34 (m, 1 H), 4.16-4.23 (m, 1 H), 3.82-3.90 (m, 1 H), 3.46-3.51 (m, 3 H), 3.16-3.25 (m, 1 H), 2.89-2.97 (m, 1 H), 2.59-2.61 (m, 3 H), 2.57-2.59 (m, 3H) | 480.0 |
| 62 | $^1$H NMR (400 MHz, CDCl$_3$) δ ppm 8.49-8.56 (m, 1 H), 7.32-7.39 (m, 1 H), 7.21-7.25 (m, 2 H), 7.13-7.19 (m, 2 H), 6.62-6.65 (m, 1 H), 4.53-4.60 (m, 1 H), 4.43-4.51 (m, 1 H), 4.25-4.34 (m, 1 H), 4.16-4.23 (m, 1 H), 3.82-3.90 (m, 1 H), 3.46-3.51 (m, 3 H), 3.16-3.25 (m, 1 H), 2.89-2.97 (m, 1 H), 2.59-2.61 (m, 3 H), 2.57-2.59 (m, 3H) | 480.0 |
| 63 | $^1$H NMR (600 MHz, DMSO-d6) δ ppm 8.69-8.76 (m, 1 H), 7.38-7.45 (m, 3 H), 7.30-7.34 (m, 1 H), 6.77-6.82 (m, 1 H), 4.63-4.70 (m, 1 H), 4.57-4.62 (m, 1 H), 4.20-4.28 (m, 1 H), 4.10-4.17 (m, 1 H), 3.72-3.83 (m, 1 H), 3.34 (s, 3 H), 3.09-3.15 (m, 1 H), 2.91-2.98 (m, 1 H), 2.62 (s, 3 H), 2.53 (s, 3 H) | 480.8 |
| 64 | $^1$H NMR (400 MHz, DMSO-d6) δ ppm 8.78 (s, 2H), 7.39-7.42 (m, 2H), 7.31-7.43 (m, 1H), 6.92 (s, 1H), 4.67-4.69 (m, 1H), 4.46-4.49 (m, 1H), 4.34-4.38 (m, 1H), 4.09-4.12 (m, 1H), 3.71-3.76 (m, 1H), 3.35 (s, 3 H), 3.04-3.10 (m, 1H), 3.98-3.02 (m, 1H), 2.63 (s, 3H), 2.53 (s, 3H) | 481.1 |
| 65 | $^1$H NMR (400 MHz, DMSO-d6) δ ppm 8.78 (s, 2H), 7.39-7.42 (m, 2H), 7.31-7.43 (m, 1H), 6.92 (s, 1H), 4.67-4.69 (m, 1H), 4.46-4.49 (m, 1H), 4.34-4.38 (m, 1H), 4.09-4.12 (m, 1H), 3.71-3.76 (m, 1H), 3.35 (s, 3 H), 3.04-3.10 (m, 1H), 3.98-3.02 (m, 1H), 2.63 (s, 3H), 2.53 (s, 3H) | 481.1 |
| 66 | $^1$H NMR (500 MHz, DMSO-d6) δ ppm 7.36-7.40 (m, 2H), 7.35 (s, 1H), 7.30 (dd, J = 2.01, 8.24 Hz, 1H), 6.78 (s, 1H), 4.44 (dd, J = 2.60, 10.51 Hz, 1H), 4.26-4.32 (m, 1H), 4.20 (br d, J = 13.36 Hz, 1H), 3.96 (dd, J = 1.95, 11.55 Hz, 1H), 3.69 (s, 3H), 3.63-3.68 (m, 1H), 3.34 (s, 3H), 3.04-3.13 (m, 2H), 2.51 (s, 3H), 2.23 (s, 3H) | 483.0 |
| 67 | $^1$H NMR (500 MHz, DMSO-d6) δ ppm 7.36-7.40 (m, 2H), 7.35 (s, 1H), 7.30 (dd, J = 2.01, 8.24 Hz, 1H), 6.78 (s, 1H), 4.44 (dd, J = 2.60, 10.51 Hz, 1H), 4.26-4.32 (m, 1H), 4.20 (br d, J = 13.36 Hz, 1H), 3.96 (dd, J = 1.95, 11.55 Hz, 1H), 3.69 (s, 3H), 3.63-3.68 (m, 1H), 3.34 (s, 3H), 3.04-3.13 (m, 2H), 2.51 (s, 3H), 2.23 (s, 3H) | 483.0 |
| 68 | $^1$H NMR (500 MHz, DMSO-d6) δ ppm 7.59-7.62 (m, 1 H), 7.37-7.41 (m, 2H), 7.31 (dd, J = 8.3, 2.1 Hz, 1 H), 6.78-6.81 (m, 1 H), 4.44 (dd, J = 10.6, 2.6 Hz, 1 H), 4.30-4.38 (m, 1 H), 4.16-4.25 (m, 1 H), 3.95-3.99 (m, 1 H), 3.72 (s, 3 H), 3.64-3.70 (m, 1 H), 3.35 (s, 3 H), 3.06-3.12 (m, 1 H), 2.99-3.04 (m, 1 H), 2.52-2.54 (m, 3 H), 2.12-2.17 (m, 3 H) | 483.0 |
| 69 | $^1$H NMR (500 MHz, CDCl$_3$) δ ppm 8.44-8.52 (m, 2 H), 7.51-7.56 (m, 1 H), 7.34-7.38 (m, 1 H), 7.23-7.26 (m, 1 H), 7.14-7.19 (m, 1 H), 6.64-6.70 (m, 1 H), 4.66-4.72 (m, 1 H), 4.53-4.61 (m, 1 H), 4.18-4.27 (m, 2 H), 3.85-3.92 (m, 1 H), 3.46-3.49 (m, 3 H), 3.22-3.28 (m, 1 H), 2.94-3.03 (m, 1 H), 2.57-2.59 (m, 3 H) | 483.8 |
| 70 | $^1$H NMR (600 MHz, DMSO-d6) δ ppm 7.37-7.43 (m, 2 H), 7.30-7.34 (m, 1H), 6.81-6.84 (m, 1 H), 4.94-4.99 (m, 1 H), 4.51-4.56 (m, 1 H), 4.07-4.11 (m, 1 H), 3.97-4.02 (m, 1 H), 3.76-3.82 (m, 1 H), 3.47-3.54 (m, 1 H), 3.34-3.36 (m, 3 H), 3.29-3.31 (m, 1 H), 2.84-2.89 (m, 2 H), 2.52-2.54 (m, 3 H), 1.24-1.27 (m, 3 H) | 485.2 |

TABLE 7-continued

| | Analytical Data | |
|---|---|---|
| Ex. # | NMR | M + H |
| 71 | $^1$H NMR (500 MHz, DMSO-d6) δ ppm 7.51-7.55 (m, 2 H), 7.37-7.42 (m, 2 H), 7.30-7.35 (m, 1 H), 7.21 (dd, J = 4 1, 2.1 Hz, 1 H), 6.88 (s, 1 H), 4.68 (dd, J = 10.8, 2.5 Hz, 1 H), 4.51 (br d, J = 12.5 Hz, 1 H), 4.39 (br d, J = 12.5 Hz, 1 H), 3.74-3.83 (m, 1 H), 3.35 (s, 3 H), 2.88 (dd, J = 12.8, 10.9 Hz, 1 H), 2.63-2.70 (m, 1 H), 2.52-2.55 (m, 3H), 1.23 (d, J = 6.2 Hz, 3 H) | 485.0 |
| 72 | $^1$H NMR (500 MHz, DMSO-d6) δ ppm 7.51 (dd, J = 4.9, 2.9 Hz, 1 H), 7.37-7.43 (m, 3 H), 7.31-7.37 (m, 1 H), 7.14 (d, J = 4.0 Hz, 1 H), 6.83 (s, 1 H), 5.04 (t, J = 4.0 Hz, 1 H), 4.22 (br dd, J = 13.8, 4.7 Hz, 1 H), 3.85-3.95 (m, 2 H), 3.75 (dd, J = 13.3, 3.8 Hz, 1 H), 3.33-3.36 (m, 3 H), 3.22 (br dd, J = 12.8, 7.7 Hz, 1 H), 2.52 (s, 3 H), 1.19 (d, J = 6.4 Hz, 3 H) | 485 |
| 73 | $^1$H NMR (500 MHz, DMSO-d6) δ ppm 7.51 (dd, J = 4.7, 2.9 Hz, 1 H), 7.37-7.43 (m, 3 H), 7.33 (br d, J = 7.5 Hz, 1 H), 7.14 (d, J = 4.2 Hz, 1 H), 6.83 (s, 1 H), 5.04 (t, J = 4.2 Hz, 1 H), 4.19-4.25 (m, 1 H), 3.86-3.94 (m, 2 H), 3.73-3.79 (m, 1 H), 3.34 (s, 3 H), 3.22 (br dd, J = 12.8, 7.8 Hz, 1 H), 2.52 (s, 3 H), 1.19 (d, J = 6.4 Hz, 3 H) | 485 |
| 74 | $^1$H NMR (600 MHz, DMSO-d6) δ ppm 7.50-7.56 (m, 2 H), 7.36-7.44 (m, 2 H), 7.31 (dd, J = 8.2, 1.6 Hz, 1 H), 7.20 (dd, J = 4.0, 2.1 Hz, 1 H), 6.87 (s, 1 H), 4.67 (dd, J = 10.7, 2.2 Hz, 1 H), 4.50 (br d, J = 12.3 Hz, 1 H), 4.38 (br d, J = 12.5 Hz, 1 H), 3.73-3.83 (m, 1 H), 3.34 (s, 3 H), 2.88 (dd, J = 12.6, 11.2 Hz, 1 H), 2.66 (br t, J = 11.8 Hz, 1 H), 2.52 (s, 3 H), 1.23 (d, J = 6.2 Hz, 3 H) | 485 |
| 75 | $^1$H NMR (600 MHz, DMSO-d6) δ ppm 7.37-7.43 (m, 2 H), 7.32-7.35 (m, 1 H), 7.25-7.29 (m, 1 H), 6.79-6.82 (m, 1 H), 4.83-4.89 (m, 1 H), 4.74-4.81 (m, 1 H), 4.15-4.23 (m, 1 H), 4.08-4.14 (m, 1 H), 3.79-3.86 (m, 1 H), 3.34-3.34 (m, 3 H), 3.14-3.21 (m, 1 H), 2.96-3.06 (m, 1 H), 2.52-2.54 (m, 3 H), 2.35-2.37 (m, 3 H) | 486.0 |
| 76 | $^1$H NMR (600 MHz, DMSO-d6) δ ppm 7.37-7.43 (m, 2 H), 7.30-7.34 (m, 1 H), 7.13-7.17 (m, 2 H), 6.87-6.91 (m, 1 H), 4.53-4.59 (m, 1 H), 4.41-4.47 (m, 1 H), 4.32-4.39 (m, 1 H), 4.07-4.13 (m, 1 H), 3.68-3.77 (m, 1 H), 3.34-3.37 (m, 3 H), 3.03-3.09 (m, 1 H), 2.82-2.88 (m, 1 H), 2.52-2.53 (m, 3 H), 2.43-2.45 (m, 6 H) | 494.2 |
| 77 | $^1$H NMR (600 MHz, DMSO-d6) δ ppm 7.37-7.43 (m, 2 H), 7.30-7.34 (m, 1 H), 7.13-7.17 (m, 2 H), 6.87-6.91 (m, 1 H), 4.53-4.59 (m, 1 H), 4.41-4.47 (m, 1 H), 4.32-4.39 (m, 1 H), 4.07-4.13 (m, 1 H), 3.68-3.77 (m, 1 H), 3.34-3.37 (m, 3 H), 3.03-3.09 (m, 1 H), 2.82-2.88 (m, 1 H), 2.52-2.53 (m, 3 H), 2.43-2.45 (m, 6 H) | 494.2 |
| 78 | $^1$H NMR (600 MHz, DMSO-d6) δ ppm 7.33-7.42 (m, 4 H), 7.27-7.32 (m, 1 H), 6.90-6.93 (m, 2 H), 6.80-6.83 (m, 1 H), 4.48-4.52 (m, 1 H), 4.34-4.41 (m, 1 H), 4.23-4.31 (m, 1 H), 4.04-4.10 (m, 1 H), 3.73-3.76 (m, 3 H), 3.67-3.72 (m, 1 H), 3.34-3.34 (m, 3 H), 3.03-3.12 (m, 1 H), 2.82-2.91 (m, 1 H), 2.51-2.52 (m, 3 H) | 494.8 |
| 79 | $^1$H NMR (600 MHz, DMSO-d6) δ ppm 7.33-7.42 (m, 4 H), 7.27-7.32 (m, 1 H), 6.90-6.93 (m, 2 H), 6.80-6.83 (m, 1 H), 4.48-4.52 (m, 1 H), 4.34-4.41 (m, 1 H), 4.23-4.31 (m, 1 H), 4.04-4.10 (m, 1 H), 3.73-3.76 (m, 3 H), 3.67-3.72 (m, 1 H), 3.34-3.34 (m, 3 H), 3.03-3.12 (m, 1 H), 2.82-2.91 (m, 1 H), 2.51-2.52 (m, 3 H) | 494.8 |
| 80 | $^1$H NMR (600 MHz, DMSO-d6) δ ppm 7.36-7.43 (m, 2 H), 7.25-7.33 (m, 2 H), 6.99-7.02 (m, 2 H), 6.86-6.89 (m, 1 H), 6.83-6.85 (m, 1H), 4.51-4.56 (m, 1 H), 4.38-4.44 (m, 1 H), 4.24-4.31 (m, 1 H), 4.05-4.12 (m, 1 H), 3.75-3.78 (m, 3 H), 3.68-3.74 (m, 1 H), 3.34-3.35 (m, 3 H), 3.05-3.12 (m, 1 H), 2.85-2.91 (m, 1 H), 2.51-2.53 (m, 3 H) | 494.8 |
| 81 | $^1$H NMR (600 MHz, DMSO-d6) δ ppm 7.36-7.43 (m, 2 H), 7.25-7.33 (m, 2 H), 6.99-7.02 (m, 2 H), 6.86-6.89 (m, 1 H), 6.83-6.85 (m, 1H), 4.51-4.56 (m, 1 H), 4.38-4.44 (m, 1 H), 4.24-4.31 (m, 1 H), 4.05-4.12 (m, 1 H), 3.75-3.78 (m, 3 H), 3.68-3.74 (m, 1 H), 3.34-3.35 (m, 3 H), 3.05-3.12 (m, 1 H), 2.84-2.91 (m, 1 H), 2.51-2.53 (m, 3 H) | 494.8 |
| 82 | $^1$H NMR (500 MHz, CDCl$_3$) δ ppm 8.16-8.19 (m, 1 H), 7.33-7.38 (m, 1 H), 7.23-7.26 (m, 1 H), 7.14-7.19 (m, 1 H), 6.90-6.96 (m, 1 H), 6.80-6.84 (m, 1 H), 6.61-6.65 (m, 1 H), 4.55-4.59 (m, 1 H), 4.48-4.54 (m, 1 H), 4.24-4.31 (m, 1 H), 4.17-4.23 (m, 1 H), 3.94-3.98 (m, 3 H), 3.81-3.88 (m, 1 H), 3.46-3.51 (m, 3 H), 3.18-3.26 (m, 1 H), 2.91-2.98 (m, 1 H), 2.56-2.60 (m, 3 H) | 496.0 |
| 83 | $^1$H NMR (500 MHz, CDCl$_3$) δ ppm 8.16-8.19 (m, 1 H), 7.33-7.38 (m, 1 H), 7.23-7.26 (m, 1 H), 7.14-7.19 (m, 1 H), 6.90-6.96 (m, 1 H), 6.80-6.84 (m, 1 H), 6.61-6.65 (m, 1 H), 4.55-4.59 (m, 1 H), 4.48-4.54 (m, 1 H), 4.24-4.31 (m, 1 H), 4.17-4.23 (m, 1 H), 3.94-3.98 (m, 3 H), 3.81-3.88 (m, 1 H), 3.46-3.51 (m, 3 H), 3.18-3.26 (m, 1 H), 2.91-2.98 (m, 1 H), 2.56-2.60 (m, 3 H) | 496.0 |
| 84 | $^1$H NMR (500 MHz, CDCl$_3$) δ ppm 7.34-7.38 (m, 1 H), 7.21-7.25 (m, 1 H), 7.14-7.17 (m, 1 H), 6.67-6.73 (m, 1 H), 4.78-4.83 (m, 1 H), 4.56-4.63 (m, 1 H), 4.22-4.28 (m, 1 H), 4.16-4.21 (m, 1 H), 3.83-3.91 (m, 1 H), 3.46-3.51 (m, 3 H), 3.37-3.43 (m, 1 H), | 497.2 |

TABLE 7-continued

Analytical Data

| Ex. # | NMR | M + H |
|---|---|---|
| | 3.29-3.35 (m, 1 H), 2.55-2.62 (m, 3 H), 2.21-2.28 (m, 1 H), 1.28-1.32 (m, 2 H), 1.24-1.27 (m, 2 H) | |
| 85 | $^1$H NMR (500 MHz, CDCl$_3$) δ ppm 7.34-7.38 (m, 1 H), 7.21-7.25 (m, 1 H), 7.14-7.17 (m, 1 H), 6.67-6.73 (m, 1 H), 4.78-4.83 (m, 1 H), 4.56-4.63 (m, 1 H), 4.22-4.28 (m, 1 H), 4.16-4.21 (m, 1 H), 3.83-3.91 (m, 1 H), 3.46-3.51 (m, 3 H), 3.37-3.43 (m, 1 H), 3.29-3.35 (m, 1 H), 2.55-2.62 (m, 3 H), 2.21-2.28 (m, 1 H), 1.28-1.32 (m, 2 H), 1.24-1.27 (m, 2 H) | 497.2 |
| 86 | $^1$H NMR (600 MHz, DMSO-d6) δ ppm 7.52-7.54 (m, 1 H), 7.38-7.45 (m, 5 H), 7.29-7.33 (m, 1 H), 6.87-6.89 (m, 1 H), 4.59-4.63 (m, 1 H), 4.42-4.47 (m, 1 H), 4.29-4.37 (m, 1 H), 4.06-4.13 (m, 1 H), 3.69-3.76 (m, 1 H), 3.32-3.33 (m, 3 H), 3.04-3.11 (m, 1 H), 2.86-2.91 (m, 1 H), 2.52-2.54 (m, 3 H) | 497.2 |
| 87 | $^1$H NMR (600 MHz, DMSO-d6) δ ppm 7.52-7.54 (m, 1 H), 7.38-7.45 (m, 5 H), 7.29-7.33 (m, 1 H), 6.87-6.89 (m, 1 H), 4.59-4.63 (m, 1 H), 4.42-4.47 (m, 1 H), 4.29-4.37 (m, 1 H), 4.06-4.13 (m, 1 H), 3.69-3.76 (m, 1 H), 3.32-3.33 (m, 3 H), 3.04-3.11 (m, 1 H), 2.86-2.91 (m, 1 H), 2.52-2.54 (m, 3 H) | 498.8 |
| 88 | $^1$H NMR (500 MHz, CDCl$_3$) δ ppm 8.39-8.42 (m, 1 H), 7.42-7.45 (m, 1 H), 7.32-7.37 (m, 1 H), 7.24-7.28 (m, 2 H), 7.15-7.19 (m, 1 H), 6.65-6.72 (m, 1 H), 4.60-4.64 (m, 1 H), 4.53-4.58 (m, 1 H), 4.23-4.28 (m, 1 H), 4.17-4.22 (m, 1 H), 3.82-3.88 (m, 1 H), 3.46-3.50 (m, 3 H), 3.19-3.26 (m, 1 H), 2.91-2.98 (m, 1 H), 2.58-2.63 (m, 3 H) | 499.8 |
| 89 | $^1$H NMR (500 MHz, CDCl$_3$) δ ppm 8.39-8.42 (m, 1 H), 7.42-7.45 (m, 1 H), 7.32-7.37 (m, 1 H), 7.24-7.28 (m, 2 H), 7.15-7.19 (m, 1 H), 6.65-6.72 (m, 1 H), 4.60-4.64 (m, 1 H), 4.53-4.58 (m, 1 H), 4.23-4.28 (m, 1 H), 4.17-4.22 (m, 1 H), 3.82-3.88 (m, 1 H), 3.46-3.50 (m, 3 H), 3.19-3.26 (m, 1 H), 2.91-2.98 (m, 1 H), 2.58-2.63 (m, 3 H) | 499.8 |
| 90 | $^1$H NMR (600 MHz, DMSO-d6) δ ppm 7.84-7.87 (m, 2 H), 7.65-7.68 (m, 2 H), 7.36-7.41 (m, 2 H), 7.30-7.33 (m, 1 H), 6.87-6.90 (m, 1 H), 4.67-4.73 (m, 1 H), 4.44-4.53 (m, 1 H), 4.30-4.37 (m, 1 H), 4.10-4.14 (m, 1 H), 3.70-3.78 (m, 1 H), 3.34 (s, 3 H), 3.05-3.12 (m, 1 H), 2.83-2.89 (m, 1 H), 2.52-2.54 (m, 3 H) | 489.8 |
| 91 | $^1$H NMR (600 MHz, DMSO-d6) δ ppm 7.81-7.84 (m, 1 H), 7.76-7.79 (m, 1 H), 7.68-7.72 (m, 1 H), 7.60-7.64 (m, 1 H), 7.36-7.42 (m, 2 H), 7.29-7.34 (m, 1 H), 6.89-6.94 (m, 1 H), 4.69-4.73 (m, 1 H), 4.46-4.51 (m, 1 H), 4.33-4.39 (m, 1 H), 4.11-4.16 (m, 1 H), 3.72-3.79 (m, 1 H), 3.34-3.35 (m, 3 H), 3.06-3.13 (m, 1 H), 2.88-2.93 (m, 1 H), 2.52-2.53 (m, 3 H) | 532.8 |
| 92 | $^1$H NMR (600 MHz, DMSO-d6) δ ppm 7.81-7.84 (m, 1 H), 7.76-7.79 (m, 1 H), 7.68-7.72 (m, 1 H), 7.60-7.64 (m, 1 H), 7.36-7.42 (m, 2 H), 7.29-7.34 (m, 1 H), 6.89-6.94 (m, 1 H), 4.69-4.73 (m, 1 H), 4.46-4.51 (m, 1 H), 4.33-4.39 (m, 1 H), 4.11-4.16 (m, 1 H), 3.72-3.79 (m, 1 H), 3.34-3.35 (m, 3 H), 3.06-3.13 (m, 1 H), 2.88-2.93 (m, 1 H), 2.52-2.53 (m, 3 H) | 532.8 |
| 93 | $^1$H NMR (600 MHz, DMSO-d6) δ ppm 8.10-8.12 (m, 2 H), 7.70-7.74 (m, 1 H), 7.62-7.65 (m, 2 H), 7.35-7.41 (m, 2 H), 7.29-7.33 (m, 1 H), 6.81-6.87 (m, 1 H), 4.93-4.97 (m, 1 H), 4.53-4.60 (m, 1H), 4.13-4.17 (m, 1 H), 4.05-4.08 (m, 1 H), 3.79-3.87 (m, 1 H), 3.47-3.52 (m, 1 H), 3.34-3.34 (m, 3 H), 3.18-3.22 (m, 3 H), 2.52-2.53 (m, 3 H) | 532.8 |
| 94 | $^1$H NMR (600 MHz, DMSO-d6) δ ppm 8.76-8.82 (m, 1 H), 7.98-8.03 (m, 1 H), 7.81-7.85 (m, 1 H), 7.37-7.44 (m, 2 H), 7.30-7.34 (m, 1 H), 6.93-7.02 (m, 1 H), 4.75-4.87 (m, 1 H), 4.54-4.63 (m, 1H), 4.38-4.47 (m, 1 H), 4.10-4.19 (m, 1 H), 3.73-3.80 (m, 1 H), 3.35-3.39 (m, 3 H), 3.07-3.14 (m, 1 H), 2.90-2.97 (m, 1 H), 2.53-2.57 (m, 3 H) | 534.0 |
| 95 | $^1$H NMR (600 MHz, DMSO-d6) δ ppm 8.18-8.21 (m, 1 H), 7.38-7.44 (m, 2 H), 7.29-7.34 (m, 1 H), 7.20-7.23 (m, 1 H), 7.08 (s, 1 H), 6.92-6.96 (m, 1 H), 4.96-5.04 (m, 2 H), 4.62-4.67 (m, 1 H), 4.45-4.52 (m, 1 H), 4.30-4.40 (m, 1 H), 4.04-4.13 (m, 1 H), 3.68-3.76 (m, 1 H), 3.34 (s, 3 H), 3.04-3.10 (m, 1 H), 2.83-2.92 (m, 1 H), 2.52-2.54 (m, 3 H) | 563.8 |
| 96 | $^1$H NMR (600 MHz, DMSO-d6) δ ppm 8.18-8.21 (m, 1 H), 7.38-7.44 (m, 2 H), 7.29-7.34 (m, 1 H), 7.20-7.23 (m, 1 H), 7.08 (s, 1 H), 6.92-6.96 (m, 1 H), 4.96-5.04 (m, 2 H), 4.62-4.67 (m, 1 H), 4.45-4.52 (m, 1 H), 4.30-4.40 (m, 1 H), 4.04-4.13 (m, 1 H), 3.68-3.76 (m, 1 H), 3.34 (s, 3 H), 3.04-3.10 (m, 1 H), 2.83-2.92 (m, 1 H), 2.52-2.54 (m, 3 H) | 563.8 |
| 97 | $^1$H NMR (600 MHz, DMSO-d6) δ ppm 7.49-7.55 (m, 2 H), 7.43-7.46 (m, 1 H), 7.36-7.41 (m, 2 H), 7.29-7.33 (m, 2 H), 6.87-6.90 (m, 1 H), 4.63-4.68 (m, 1 H), 4.44-4.50 (m, 1 H), 4.29-4.36 (m, 1 H), 4.08-4.14 (m, 1 H), 3.69-3.76 (m, 1 H), 3.34-3.35 (m, 3 H), 3.05-3.13 (m, 1 H), 2.86-2.91 (m, 1 H), 2.52-2.53 (m, 3 H) | 548.8 |

TABLE 7-continued

| Ex. # | NMR | M + H |
|---|---|---|
| 98 | ¹H NMR (600 MHz, DMSO-d6) δ ppm 7.49-7.55 (m, 2 H), 7.43-7.46 (m, 1 H), 7.36-7.41 (m, 2 H), 7.29-7.33 (m, 2 H), 6.87-6.90 (m, 1 H), 4.63-4.68 (m, 1 H), 4.44-4.50 (m, 1 H), 4.29-4.36 (m, 1 H), 4.08-4.14 (m, 1 H), 3.69-3.76 (m, 1 H), 3.34-3.35 (m, 3 H), 3.05-3.13 (m, 1 H), 2.86-2.91 (m, 1 H), 2.52-2.53 (m, 3 H) | 548.8 |
| 99 | ¹H NMR (600 MHz, DMSO-d6) δ ppm 7.54-7.58 (m, 1 H), 7.35-7.40 (m, 2 H), 7.33-7.35 (m, 1 H), 7.29-7.32 (m, 1 H), 6.72-6.76 (m, 1 H), 5.72-5.77 (m, 1 H), 4.41-4.46 (m, 1 H), 4.33-4.39 (m, 1 H), 3.77 (s, 3 H), 3.33-3.35 (m, 3 H), 2.95-3.01 (m, 1 H), 2.89-2.95 (m, 1 H), 2.63-2.70 (m, 1 H), 2.51-2.51 (m, 3 H), 1.99-2.03 (m, 1 H), 1.71-1.77 (m, 1 H), 1.48-1.61 (m, 2 H) | 467.2 |
| 100 | ¹H NMR (600 MHz, DMSO-d6) δ ppm 7.54-7.58 (m, 1 H), 7.35-7.40 (m, 2 H), 7.33-7.35 (m, 1 H), 7.29-7.32 (m, 1 H), 6.72-6.76 (m, 1 H), 5.72-5.77 (m, 1 H), 4.41-4.46 (m, 1 H), 4.33-4.39 (m, 1 H), 3.77 (s, 3 H), 3.33-3.35 (m, 3 H), 2.95-3.01 (m, 1 H), 2.89-2.95 (m, 1 H), 2.63-2.70 (m, 1 H), 2.51-2.51 (m, 3 H), 1.99-2.03 (m, 1 H), 1.71-1.77 (m, 1 H), 1.48-1.61 (m, 2 H) | 467.2 |
| 101 | ¹H NMR (500 MHz, DMSO-d6) δ 8.42 (s, 1H), 8.36 (d, J = 5.06 Hz, 1H), 7.39-7.45 (m, 2H), 7.35 (dd, J = 2.01, 8.11 Hz, 1H), 7.29 (d, J = 5.06 Hz, 1H), 4.81 (s, 2H), 3.97 (t, J = 5.84 Hz, 2H), 3.35 (s, 3H), 2.92 (br t, J = 5.71 Hz, 2H), 2.55 (s, 1H), 2.53 (s, 3H) | 436.0 |
| 102 | ¹H NMR (500 MHz, DMSO-d6) δ 8.48 (s, 1H), 8.35 (d, J = 4.93 Hz, 1H), 7.39-7.45 (m, 2H), 7.33-7.37 (m, 1H), 7.23 (d, J = 5.06 Hz, 1H), 6.82 (s, 1H), 4.83 (br s, 2H), 3.94 (t, J = 5.84 Hz, 2H), 3.35 (s, 3H), 2.93 (br t, J = 5.77 Hz, 2H), 2.53 (s, 3H) | 436.0 |
| 103 | ¹H NMR (600 MHz, DMSO-d6) δ ppm 7.43-7.49 (m, 2 H), 7.38-7.43 (m, 2 H), 7.32-7.37 (m, 1 H), 7.24-7.31 (m, 2 H), 7.14-7.18 (m, 1 H), 6.71-6.79 (m, 1 H), 4.09-4.42 (m, 1 H), 3.47-3.73 (m, 3 H), 3.31-3.32 (m, 3 H), 2.50-2.50 (m, 3 H), 2.13-2.20 (m, 1 H), 1.63-1.77 (m, 2 H), 1.40-1.51 (m, 1 H), 1.14-1.19 (m, 3 H) | 476.8 |
| 104 | ¹H NMR (500 MHz, CDCl₃) δ ppm 2.58 (s, 13 H) 2.73 (t, J = 5.64 Hz, 8 H) 3.47 (s, 12 H) 3.80 (s, 12 H) 3.95 (t, J = 5.58 Hz, 9 H) 4.80 (br s, 8 H) 5.32 (s, 1 H) 6.70 (s, 4 H) 7.17 (dd, 1 = 9.60, 1.95 Hz, 4 H) 7.23-7.27 (m, 7 H) 7.28-7.32 (m, 6 H) 7.33-7.40 (m, 5 H) | 439.0 |
| 105 | ¹H NMR (600 MHz, DMSO-d6) δ ppm 8.21-8.27 (m, 1 H), 7.37-7.40 (m, 2 H), 7.31-7.34 (m, 1 H), 6.94-6.98 (m, 1 H), 6.74-6.77 (m, 1 H), 4.47-4.57 (m, 1 H), 4.15-4.26 (m, 1 H), 3.32-3.33 (m, 3 H), 3.20-3.26 (m, 1 H), 3.12-3.17 (m, 1 H), 2.93-3.00 (m, 1 H), 2.51-2.51 (m, 3 H), 2.06-2.12 (m, 1 H), 1.70-1.80 (m, 2 H), 1.52-1.65 (m, 1 H) | 453.8 |
| 106 | ¹H NMR (600 MHz, DMSO-d6) δ ppm 7.49-7.55 (m, 1 H), 7.34-7.41 (m, 2 H), 7.30-7.33 (m, 1 H), 6.68-6.72 (m, 1 H), 4.09-4.37 (m, 2 H), 3.32-3.32 (m, 3 H), 3.26-3.30 (m, 1 H), 2.95-3.08 (m, 2 H), 2.77-2.90 (m, 1 H), 2.51-2.51 (m, 3 H), 2.09-2.25 (m, 2 H), 1.92-2.04 (m, 1 H), 1.72-1.82 (m, 1 H), 1.65-1.72 (m, 1 H), 1.46-1.55 (m, 1 H), 1.36-1.45 (m, 1 H), 1.21-1.31 (m, 1 H) | 469.8 |
| 107 | ¹H NMR (600 MHz, DMSO-d6) δ ppm 7.44-7.80 (m, 1 H), 7.35-7.40 (m, 2 H), 7.29-7.33 (m, 1 H), 6.74-6.78 (m, 1 H), 4.34-4.48 (m, 2 H), 3.28-3.32 (m, 3 H), 2.91-3.01 (m, 2 H), 2.66-2.72 (m, 1 H), 2.50-2.51 (m, 3 H), 2.00-2.06 (m, 1 H), 1.70-1.76 (m, 1 H), 1.49-1.63 (m, 2H) | 453.2 |
| 108 | ¹H NMR (600 MHz, DMSO-d6) δ ppm 7.44-7.80 (m, 1 H), 7.35-7.40 (m, 2 H), 7.29-7.33 (m, 1 H), 6.74-6.78 (m, 1 H), 4.34-4.48 (m, 2 H), 3.28-3.32 (m, 3 H), 2.91-3.01 (m, 2 H), 2.66-2.72 (m, 1 H), 2.50-2.51 (m, 3 H), 2.00-2.06 (m, 1 H), 1.70-1.76 (m, 1 H), 1.49-1.63 (m, 2H) | 453.2 |
| 109 | ¹H NMR (600 MHz, DMSO-d6) δ ppm 7.34-7.42 (m, 2 H), 7.29-7.33 (m, 1 H), 6.64-6.68 (m, 1 H), 4.29-4.45 (m, 1 H), 4.17-4.22 (m, 1 H), 3.31-3.32 (m, 3 H), 2.92-2.98 (m, 2 H), 2.50-2.50 (m, 3H), 2.20-2.24 (m, 6 H), 2.13-2.19 (m, 1 H), 1.83-1.92 (m, 1 H), 1.69-1.77 (m, 1 H), 1.45-1.53 (m, 1 H), 1.35-1.44 (m, 1 H) | 430.2 |
| 110 | ¹H NMR (600 MHz, DMSO-d6) δ ppm 7.35-7.40 (m, 2 H), 7.30-7.33 (m, 1 H), 6.61-6.65 (m, 1 H), 3.80-3.94 (m, 2 H), 3.32-3.32 (m, 3 H), 3.05-3.13 (m, 6 H), 2.50-2.50 (m, 3 H), 2.09-2.16 (m, 1 H), 1.85-1.92 (m, 2 H), 1.65-1.74 (m, 2 H), 1.33-1.42 (m, 1 H), 1.21-1.30 (m, 1 H) | 442.2 |
| 111 | ¹H NMR (600 MHz, DMSO-d6) δ ppm 7.34-7.41 (m, 2 H), 7.30-7.33 (m, 1 H), 6.75-6.82 (m, 1 H), 4.53-4.63 (m, 1 H), 4.09-4.18 (m, 1 H), 3.41-3.52 (m, 1 H), 3.30-3.32 (m, 3 H), 3.20-3.25 (m, 2 H), 2.51-2.52 (m, 3 H), 2.29-2.31 (m, 3 H), 2.13-2.19 (m, 1 H), 1.83-1.90 (m, 1 H), 1.75-1.81 (m, 1 H), 1.54-1.65 (m, 1 H) | 468.8 |
| 112 | ¹H NMR (600 MHz, DMSO-d6) δ ppm 7.34-7.41 (m, 2 H), 7.30-7.33 (m, 1 H), 6.75-6.82 (m, 1 H), 4.53-4.63 (m, 1 H), 4.09-4.18 (m, 1 H), 3.41-3.52 (m, 1 H), 3.30-3.32 (m, 3 H), 3.20-3.25 (m, 2 H), 2.51-2.52 (m, 3H), 2.29-2.31 (m, 3 H), 2.13-2.19 (m, 1 H), 1.83-1.90 (m, 1 H), 1.75-1.81 (m, 1 H), 1.54-1.65 (m, 1 H) | 468.8 |

TABLE 7-continued

| Ex. # | NMR | M + H |
|---|---|---|
| 113 | ¹H NMR (600 MHz, DMSO-d6) δ ppm 8.46-8.50 (m, 2 H), 7.36-7.40 (m, 2 H), 7.32-7.35 (m, 2 H), 7.28-7.32 (m, 1 H), 6.74-6.79 (m, 1 H), 4.38-4.52 (m, 2 H), 3.34-3.35 (m, 3 H), 3.06-3.12 (m, 1 H), 2.98-3.05 (m, 1 H), 2.74-2.80 (m, 1 H), 2.50-2.51 (m, 3 H), 1.92-1.99 (m, 1 H), 1.74-1.83 (m, 2 H), 1.55-1.64 (m, 1 H) | 463.8 |
| 114 | ¹H NMR (600 MHz, DMSO-d6) δ ppm 8.46-8.50 (m, 2 H), 7.36-7.40 (m, 2 H), 7.32-7.35 (m, 2 H), 7.28-7.32 (m, 1 H), 6.74-6.79 (m, 1 H), 4.38-4.52 (m, 2 H), 3.34-3.35 (m, 3 H), 3.06-3.12 (m, 1 H), 2.98-3.05 (m, 1 H), 2.74-2.80 (m, 1 H), 2.50-2.51 (m, 3 H), 1.92-1.99 (m, 1 H), 1.74-1.83 (m, 2 H), 1.55-1.64 (m, 1 H) | 463.8 |
| 115 | ¹H NMR (500 MHz, DMSO-d6) δ 8.21 (d, J = 4.93 Hz, 1H), 7.39-7.44 (m, 2H), 7.34-7.37 (m, 1H), 7.30 (d, J = 4.93 Hz, 1H), 6.84 (s, 1H), 4.68-4.82 (m, 2H), 3.96 (t, J = 5.77 Hz, 2H), 3.34 (s, 3H), 2.96 (br t, J = 5.71 Hz, 2H), 2.53 (s, 3H) | 470.0 |
| 116 | ¹H NMR (500 MHz, DMSO-d6) δ 7.72 (s, 1H), 7.57-7.67 (m, 3H), 7.45 (s, 1H), 6.86 (s, 1H), 4.51 (dd, J = 2.14, 10.32 Hz, 1H), 4.38 (br d, J = 12.33 Hz, 1H), 4.22 (br d, J = 12.59 Hz, 1H), 3.97 (br dd, J = 1.49, 11.35 Hz, 1H), 3.80 (s, 3H), 3.66 (br t, J = 10.64 Hz, 1H), 3.34 (s, 3H), 2.53 (s, 3H) | 467.0 |
| 117 | ¹H NMR (400 MHz, CDCl₃) δ ppm 7.48 (s, 1H), 7.37 (s, 1H), 7.33-7.35 (m, 1H), 7.22-7.25 (m, 1H), 7.16-7.19 (m, 1H), 6.70 (s, 1H), 4.45.4.47 (m, 2H), 3.91 (s, 3H), 3.41-3.52 (m, 5H), 3.14-3.21 (m, 1H), 3.58 (s, 3H), 2.20-2.29 (m, 1H), 1.97-2.10 (m, 1H) | 503.2 |
| 118 | ¹H NMR (400 MHz, CDCl3) δ ppm 7.48 (s, 1H), 7.37 (s, 1H), 7.33-7.35 (m, 1H), 7.22-7.25 (m, 1H), 7.16-7.19 (m, 1H), 6.70 (s, 1H), 4.45.4.47 (m, 2H), 3.91 (s, 3H), 3.41-3.52 (m, 5H), 3.14-3.21 (m, 1H), 3.58 (s, 3H), 2.20-2.29 (m, 1H), 1.97-2.10 (m, 1H) | 503.2 |
| 119 | ¹H NMR (600 MHz, DMSO-d6) δ ppm 7.36-7.42 (m, 2 H), 7.30-7.34 (m, 1 H), 6.42-6.47 (m, 1 H), 3.77-3.84 (m, 1 H), 3.60-3.68 (m, 1 H), 3.48-3.58 (m, 2 H), 3.37-3.44 (m, 1 H), 3.33-3.35 (m, 3 H), 2.51-2.53 (m, 3 H), 2.26-2.36 (m, 1 H), 2.08-2.17 (m, 1 H) | 441.0 |
| 120 | ¹H NMR (600 MHz, DMSO-d6) δ ppm 7.36-7.41 (m, 2 H), 7.30-7.35 (m, 1 H), 6.37-6.41 (m, 1 H), 6.07-6.29 (m, 1 H), 3.55-3.70 (m, 2 H), 3.42-3.52 (m, 2 H), 3.33-3.35 (m, 3 H), 2.82-2.91 (m, 1 H), 2.51-2.53 (m, 3 H), 2.12-2.20 (m, 1 H), 1.97-2.05 (m, 1 H) | 422.8 |
| 121 | ¹H NMR (600 MHz, DMSO-d6) δ ppm 8.56-8.62 (m, 1 H), 8.43-8.50 (m, 1 H), 7.76-7.82 (m, 1 H), 7.36-7.42 (m, 3 H), 7.28-7.33 (m, 1 H), 6.40-6.44 (m, 1 H), 3.93-4.15 (m, 1 H), 3.67-3.86 (m, 1H), 3.51-3.64 (m, 2H), 3.41-3.50 (m, 1 H), 3.30-3.31 (m, 3 H), 2.50-2.50 (m, 3 H), 2.37-2.43 (m, 1 H), 2.09-2.20 (m, 1 H) | 450.0 |
| 122 | ¹H NMR (600 MHz, DMSO-d6) δ ppm 7.35-7.42 (m, 2 H), 7.28-7.33 (m, 1 H), 7.03-7.08 (m, 1 H), 6.73-6.77 (m, 1 H), 6.36-6.40 (m, 1 H), 4.07-4.13 (m, 1 H), 3.83-3.99 (m, 1 H), 3.70-3.76 (m, 1 H), 3.60-3.67 (m, 4 H), 3.48-3.57 (m, 1 H), 3.32-3.33 (m, 3 H), 2.50-2.51 (m, 3 H), 2.30-2.43 (m, 1 H), 2.10-2.26 (m, 1 H) | 453.2 |
| 123 | ¹H NMR (500 MHz, DMSO-d6) δ 7.80 (s, 1H), 7.46 (s, 1H), 7.36-7.41 (m, 2H), 7.31 (dd, J = 2.01, 8.24 Hz, 1H), 6.84 (s, 1H), 4.50 (dd, J = 2.53, 10.44 Hz, 1H), 4.45 (td, J = 6.63, 13.33 Hz, 1H), 4.39 (br d, J = 12.20 Hz, 1H), 4.25 (br d, J = 12.07 Hz, 1H), 3.97 (dd, J = 2.01, 11.61 Hz, 1H), 3.66 (dt, J = 2.47, 11.55 Hz, 1H), 3.34 (s, 3H), 2.97-3.08 (m, 2H), 2.52 (s, 3H), 1.40 (s, 3H), 1.38 (s, 3H) | 497.0 |
| 124 | ¹H NMR (500 MHz, DMSO-d6) δ 7.86 (s, 1H), 7.50 (s, 1H), 7.36-7.41 (m, 2H), 7.31 (dd, J = 1.95, 8.17 Hz, 1H), 6.84 (s, 1H), 4.78 (quin, J = 8.47 Hz, 1H), 4.51 (dd, J = 2.53, 10.44 Hz, 1H), 4.38 (br d, J = 12.33 Hz, 1H), 4.24 (br d, J = 12.98 Hz, 1H), 3.97 (dd, J = 1.95, 11.68 Hz, 1H), 3.66 (dt, J = 2.72, 11.61 Hz, 1H), 3.34 (s, 3H), 2.95-3.09 (m, 2H), 2.52 (s, 3H), 2.29-2.47 (m, 4H), 1.71-1.81 (m, 2H) | 509.0 |
| 125 | ¹H NMR (500 MHz, DMSO-d6) δ 7.94 (s, 1H), 7.63 (s, 1H), 7.36-7.41 (m, 2H), 7.31 (dd, J = 2.01, 8.24 Hz, 1H), 6.84 (s, 1H), 5.49-5.58 (m, 1H), 4.83-4.92 (m, 4H), 4.54 (dd, J = 2.53, 10.45 Hz, 1H), 4.37-4.46 (m, 1H), 4.24 (br d, J = 13.36 Hz, 1H), 3.94-4.01 (m, 1H), 3.63-3.71 (m, 1H), 3.34 (s, 3H), 2.96-3.10 (m, 2H), 2.52 (s, 3H) | 511.0 |
| 126 | ¹H NMR (500 MHz, DMSO-d6) δ ppm 7.88 (s, 1 H), 7.64 (s, 1 H), 7.36-7.41 (m, 2 H), 7.29-7.33 (m, 1 H), 6.84-6.88 (m, 1 H), 5.06-5.14 (m, 2 H), 4.53-4.59 (m, 1 H), 4.38-4.45 (m, 1 H), 4.21-4.29 (m, 1 H), 3.96-4.03 (m, 1 H), 3.66-3.72 (m, 1 H), 3.33-3.36 (m, 3 H), 3.03-3.09 (m, 1 H), 2.96-3.02 (m, 1 H), 2.52-2.53 (m, 3 H) | 537.0 |
| 127 | ¹H NMR (600 MHz, DMSO-d6) δ 7.74 (s, 1H), 7.48 (s, 1H), 7.37-7.41 (m, 2H), 7.31 (dd, J = 1.87, 8.17 Hz, 1H), 6.81-6.85 (m, 1H), 4.51 (dd, J = 2.37, 10.47 Hz, 1H), 4.36-4.42 (m, 1H), 4.19-4.26 (m, 3H), 3.98 (br dd, J = 1.56, 11.68 Hz, 1H), 3.63-3.70 (m, 3H), 3.34 (s, 1H), 3.22 (s, 3H), 3.03-3.08 (m, 1H), 3.00 (dd, J = 10.63, 12.88 Hz, 1H), 2.52 (s, 3H) | 513.2 |
| 128 | ¹H NMR (500 MHz, DMSO-d6) δ 7.81 (s, 1H), 7.53 (s, 1H), 7.36-7.41 (m, 2H), 7.28-7.33 (m, 1H), 6.84 (s, 1H), 4.79 (t, J = 4.80 Hz, | 501.0 |

TABLE 7-continued

Analytical Data

| Ex. # | NMR | M + H |
|---|---|---|
| | 1H), 4.70 (t, J = 4.74 Hz, 1H), 4.53 (dd, J = 2.66, 10.57 Hz, 1H), 4.42 (t, J = 4.67 Hz, 1H), 4.36 (t, J = 4.74 Hz, 1H), 4.21-4.26 (m, 1H), 3.96-4.00 (m, 1H), 3.67 (dt, J = 2.59, 11.55 Hz, 1H), 3.34 (s, 3H), 3.03-3.09 (m, 1H), 3.00 (dd, J = 10.51, 12.98 Hz, 1H), 2.52 (s, 4H) | |
| 129 | $^1$H NMR (500 MHz, DMSO-d6) δ ppm 8.15 (s, 1 H), 7.69-7.72 (m, 1 H), 7.37-7.43 (m, 2 H), 7.28-7.34 (m, 1 H), 6.86-6.90 (m, 1 H), 6.42-6.56 (m, 1 H), 4.54-4.60 (m, 1 H), 4.40-4.46 (m, 1 H), 4.24-4.31 (m, 1 H), 3.97-4.04 (m, 1 H), 3.65-3.72 (m, 1H), 3.31-3.38 (m, 3 H), 3.05-3.12 (m, 1 H), 2.98-3.04 (m, 1 H), 2.52-2.55 (m, 3 H), 1.81-1.90 (m, 3 H) | 501.0 |
| 130 | $^1$H NMR (500 MHz, DMSO-d6) δ ppm 8.16 (s, 1 H), 7.78-7.81 (m, 1 H), 7.37-7.41 (m, 2 H), 7.30-7.33 (m, 1 H), 6.85-6.87 (m, 1 H), 6.79-6.83 (m, 1 H), 4.86-4.92 (m, 2 H), 4.55-4.59 (m, 1 H), 4.41-4.46 (m, 1 H), 4.22-4.27 (m, 1 H), 3.97-4.02 (m, 1 H), 3.66-3.72 (m, 1 H), 3.33-3.35 (m, 3 H), 3.03-3.09 (m, 1 H), 2.97-3.02 (m, 1 H), 2.51-2.53 (m, 3 H) | 541.0 |
| 131 | $^1$H NMR (500 MHz, DMSO-d6) δ ppm 7.89-7.94 (m, 1 H), 7.59-7.63 (m, 1 H), 7.36-7.42 (m, 2 H), 7.29-7.34 (m, 1 H), 6.83-6.87 (m, 1 H), 4.86-4.93 (m, 1 H), 4.52-4.57 (m, 1 H), 4.38-4.46 (m, 1 H), 4.21-4.28 (m, 1 H), 3.97-4.02 (m, 1 H), 3.66-3.73 (m, 1 H), 3.33-3.36 (m, 3 H), 3.04-3.20 (m, 5 H), 2.97-3.03 (m, 1 H), 2.52-2.55 (m, 3 H) | 545.0 |
| 132 | $^1$H NMR (500 MHz, CDCl$_3$) δ ppm 7.59-7.63 (m, 2 H), 7.34-7.38 (m, 1 H), 7.22-7.25 (m, 1 H), 7.14-7.18 (m, 1 H), 6.62-6.64 (m, 1 H), 4.90-4.97 (m, 1 H), 4.60-4.65 (m, 1 H), 4.40-4.49 (m, 1 H), 4.18-4.25 (m, 1 H), 4.07-4.13 (m, 1 H), 3.77-3.93 (m, 3 H), 3.52-3.59 (m, 2 H), 3.46-3.49 (m, 3 H), 3.19-3.26 (m, 1 H), 3.11-3.19 (m, 1 H), 2.56-2.60 (m, 3 H), 2.46-2.53 (m, 3 H) | 524.0 |
| 133 | $^1$H NMR (500 MHz, DMSO-d6) δ ppm 7.93 (s, 1 H), 7.60 (s, 1 H), 7.36-7.41 (m, 2 H), 7.31 (dd, J = 8.2, 1.9 Hz, 1 H), 6.83-6.89 (m, 1 H), 4.93-5.01 (m, 1 H), 4.81-4.90 (m, 2 H), 4.72-4.80 (m, 2 H), 4.55 (dd, J = 10.5, 2.5 Hz, 1 H), 4.39-4.46 (m, 1 H), 4.22-4.28 (m, 1 H), 3.96-4.01 (m, 1 H), 3.68 (td, J = 11.5, 2.6 Hz, 1 H), 3.31-3.37 (m, 3 H), 3.07 (br dd, J = 12.6, 2.7 Hz, 1 H), 2.98-3.03 (m, 1 H), 2.51-2.53 (m, 3 H) | 533.0 |
| 134 | $^1$H NMR (500 MHz, DMSO-d6) δ ppm 7.93 (s, 1 H), 7.62 (s, 1 H), 7.35-7.45 (m, 2 H), 7.31 (dd, J = 8.2, 1.9 Hz, 1 H), 6.84 (s, 1 H), 5.17 (tt, J = 8.0, 5.4 Hz, 1 H), 4.53 (dd, J = 10.4, 2.5 Hz, 1 H), 4.40 (br dd, J = 13.2, 0.9 Hz, 1 H), 4.19-4.33 (m, 3 H), 4.10 (br d, J = 1.8 Hz, 2 H), 3.98 (br dd, J = 11.5, 1.8 Hz, 1 H), 3.67 (td, J = 11.5, 2.5 Hz, 1 H), 3.34 (s, 3 H), 2.96-3.10 (m, 2 H), 2.52 (s, 3 H), 1.40 (s, 9 H) | 610.2 |
| 135 | $^1$H NMR (500 MHz, DMSO-d6) δ ppm 8.15-8.18 (m, 1 H), 7.78-7.81 (m, 1 H), 7.37-7.41 (m, 2 H), 7.29-7.33 (m, 1 H), 6.86-6.88 (m, 1 H), 6.80-6.84 (m, 1 H), 4.86-4.93 (m, 2 H), 4.56-4.59 (m, 1 H), 4.41-4.45 (m, 1 H), 4.22-4.27 (m, 1 H), 3.98-4.02 (m, 1 H), 3.66-3.71 (m, 1 H), 3.33-3.35 (m, 3 H), 3.03-3.09 (m, 1 H), 2.96-3.02 (m, 1 H), 2.51-2.53 (m, 3 H) | 541 M + H + Na |
| 136 | $^1$H NMR (500 MHz, DMSO-d6) δ 7.81 (s, 1H), 7.45 (s, 1H), 7.36-7.41 (m, 2H), 7.29-7.33 (m, 1H), 6.83 (s, 1H), 4.46-4.52 (m, 1H), 4.37 (br d, J = 12.85 Hz, 1H), 4.24 (br d, J = 12.98 Hz, 1H), 3.95-3.99 (m, 1H), 3.61-3.70 (m, 2H), 3.34 (s, 3H), 2.96-3.08 (m, 2H), 2.52 (s, 3H), 1.00 (sxt, J = 4 18 Hz, 2H), 0.90-0.96 (m, 2H) | 495.0 |
| 137 | $^1$H NMR (500 MHz, DMSO-d6) δ 8.13 (s, 1H), 7.69 (s, 1H), 7.37-7.44 (m, 2H), 7.32 (dd, J = 2.01, 8.11 Hz, 1H), 7.20 (dd, J = 8.89, 15.64 Hz, 1H), 6.86 (s, 1H), 5.55 (d, J = 15.57 Hz, 1H), 4.84 (d, J = 8.43 Hz, 1H), 4.58 (dd, J = 2.66, 10.32 Hz, 1H), 4.43 (br d, J = 12.20 Hz, 1H), 4.27 (br d, J = 12.46 Hz, 1H), 3.98-4.04 (m, 1H), 3.70 (dt, J = 2.59, 11.55 Hz, 1H), 3.35 (s, 3H), 2.99-3.11 (m, 2H), 2.53 (s, 3H) | 481.0 |
| 138 | $^1$H NMR (500 MHz, CDCl$_3$) δ ppm 7.59-7.63 (m, 2 H), 7.34-7.38 (m, 1 H), 7.22-7.25 (m, 1 H), 7.14-7.18 (m, 1 H), 6.62-6.64 (m, 1 H), 4.90-4.97 (m, 1 H), 4.60-4.65 (m, 1 H), 4.40-4.49 (m, 1 H), 4.18-4.25 (m, 1 H), 4.07-4.13 (m, 1 H), 3.77-3.93 (m, 3 H), 3.52-3.59 (m, 2 H), 3.46-3.49 (m, 3 H), 3.19-3.26 (m, 1 H), 3.11-3.19 (m, 1 H), 2.56-2.60 (m, 3 H), 2.46-2.53 (m, 3 H) | 524.0 |
| 139 | $^1$H NMR (500 MHz, CDCl$_3$) δ ppm 8.56-8.58 (m, 1 H), 7.64-7.69 (m, 1 H), 7.34-7.39 (m, 1 H), 7.22-7.25 (m, 1 H), 7.18-7.21 (m, 1 H), 7.14-7.17 (m, 1 H), 6.62-6.64 (m, 1 H), 4.60-4.65 (m, 1 H), 4.46-4.52 (m, 1 H), 4.24-4.31 (m, 1 H), 4.16-4.21 (m, 1 H), 3.85-3.91 (m, 1 H), 3.48 (s, 3 H), 3.21-3.27 (m, 1 H), 2.97-3.03 (m, 1 H), 2.60 (s, 3 H), 2.57-2.58 (m, 3 H) | 480.0 |

TABLE 7-continued

| | Analytical Data | |
|---|---|---|
| Ex. # | NMR | M + H |
| 140 | ¹H NMR (500 MHz, CDCl₃) δ ppm 8.56-8.58 (m, 1 H), 7.64-7.69 (m, 1 H), 7.34-7.39 (m, 1 H), 7.22-7.25 (m, 1 H), 7.18-7.21 (m, 1 H), 7.14-7.17 (m, 1 H), 6.62-6.64 (m, 1 H), 4.60-4.65 (m, 1 H), 4.46-4.52 (m, 1 H), 4.24-4.31 (m, 1 H), 4.16-4.21 (m, 1 H), 3.85-3.91 (m, 1 H), 3.48 (s, 3 H), 3.21-3.27 (m, 1 H), 2.97-3.03 (m, 1 H), 2.60 (s, 3 H), 2.57-2.58 (m, 3 H) | 480.0 |
| 141 | ¹H NMR (500 MHz, DMSO-d6) δ 8.55 (s, 1H), 8.04 (s, 1H), 7.36-7.43 (m, 2H), 7.29-7.34 (m, 1H), 6.91 (s, 1H), 4.61-4.65 (m, 1H), 4.46 (br d, J = 12.20 Hz, 1H), 4.32 (br d, J = 13.10 Hz, 1H), 3.99-4.06 (m, 1H), 3.67-3.75 (m, 1H), 3.34 (s, 3H), 3.00-3.09 (m, 2H), 2.52 (s, 3H) | 523.0 |
| 142 | ¹H NMR (500 MHz, DMSO-d6) δ ppm 7.72 (s, 1 H), 7.45 (s, 1 H), 7.36-7.41 (m, 2 H), 7.29-7.33 (m, 1 H), 6.72 (s, 1 H), 4.50 (dd, J = 10.32, 2.53 Hz, 1 H), 4.36 (br d, J = 12.07 Hz, 1 H), 4.22 (br d, J = 12.07 Hz, 1 H), 3.94-4.00 (m, 1 H), 3.81 (s, 3 H), 3.62-3.70 (m, 1 H), 3.52 (s, 3 H), 2.95-3.08 (m, 2H), 2.21-2.26 (m, 1 H), 1.15 (br s, 2 H), 1.08 (br dd, J = 8.04, 3.24 Hz, 2 H) | 495.0 |
| 143 | ¹H NMR (600 MHz, DMSO-d6) δ ppm 7.73 (s, 1 H), 7.41-7.48 (m, 3H), 7.35 (dd, J = 8.17, 1.91 Hz, 1H), 7.12 (s, 1 H), 4.49-4.54 (m, 1 H), 4.46 (br d, J = 12.26 Hz, 1 H), 4.32 (br s, 1 H), 3.99 (br d, J = 11.72 Hz, 1 H), 3.81 (s, 3 H), 3.64-3.70 (m, 1 H), 3.39-3.43 (m, 3H), 3.05-3.17 (m, 2 H) | 523.0 |
| 144 | ¹H NMR (600 MHz, DMSO-d6) δ ppm 7.73 (s, 1 H), 7.43-7.48 (m, 3 H), 7.36 (dd, J = 8.22, 1.95 Hz, 1 H), 7.12 (s, 1 H), 4.52 (br d, J = 10.35 Hz, 1 H), 4.47 (br d, J = 12.08 Hz, 1 H), 4.35 (br s, 1 H), 3.99 (br d, J = 11.35 Hz, 1 H), 3.93 (br d, J = 6.81 Hz, 2 H), 3.81 (s, 3 H), 3.64-3.70 (m, 1 H), 3.05-3.21 (m, 2 H), 1.19 (t, J = 6.86 Hz, 3 H) | 537.0 |
| 145 | ¹H NMR (600 MHz, DMSO-d6) δ ppm 11.76 (br s, 1 H), 7.72 (s, 1 H), 7.36-7.47 (m, 3 H), 7.31 (dd, J = 8.17, 1.91 Hz, 1 H), 6.83 (s, 1 H), 4.51 (dd, J = 10.31, 2.50 Hz, 1 H), 4.38 (br d, J = 13.17 Hz, 1 H), 4.22 (brd, J = 12.17 Hz, 1 H), 3.98 (br d, J = 10.17 Hz, 1 H), 3.81 (s, 3 H), 3.63-3.75 (m, 1 H), 2.97-3.10 (m, 2 H), 2.29 (s, 3 H) | 455.0 |
| 146 | ¹H NMR (600 MHz, DMSO-d6) δ ppm 7.72 (s, 1 H), 7.38-7.46 (m, 3 H), 7.32 (dd, J = 8.22, 1.91 Hz, 1 H), 6.82 (s, 1 H), 4.52 (dd, J = 10.40, 2.43 Hz, 1 H), 4.38 (br d, J = 12.76 Hz, 1 H), 4.22 (br d, J = 12.48 Hz, 1 H), 3.98 (br d, J = 9.71 Hz, 1 H), 3.91 (q, J = 7.01 Hz, 2 H), 3.81 (s, 3 H), 3.64-3.71 (m, 1 H), 2.98-3.10 (m, 2 H), 2.53-2.59 (m, 3 H), 1.15 (t, J = 7.07 Hz, 3 H) | 483.0 |
| 147 | ¹H NMR (600 MHz, DMSO-d6) δ ppm 7.37-7.46 (m, 2 H), 7.29-7.35 (m, 1 H), 6.79-6.81 (m, 1 H), 4.81-4.85 (m, 1 H), 4.51-4.57 (m, 1H), 4.10-4.16 (m, 1 H), 4.02-4.06 (m, 1 H), 3.87-3.94 (m, 2 H), 3.73-3.80 (m, 1 H), 3.32-3.38 (m, 1 H), 3.21-3.28 (m, 1 H), 2.60-2.62 (m, 3 H), 2.57-2.59 (m, 3 H), 1.11-1.16 (m, 3 H) | 485.0 |
| 148 | ¹H NMR (600 MHz, DMSO-d6) δ ppm 7.37-7.46 (m, 2 H), 7.29-7.35 (m, 1 H), 6.79-6.81 (m, 1 H), 4.81-4.85 (m, 1 H), 4.51-4.57 (m, 1H), 4.10-4.16 (m, 1 H), 4.02-4.06 (m, 1 H), 3.87-3.94 (m, 2 H), 3.73-3.80 (m, 1 H), 3.32-3.38 (m, 1 H), 3.21-3.28 (m, 1 H), 2.60-2.62 (m, 3 H), 2.57-2.59 (m, 3 H), 1.11-1.16 (m, 3 H) | 485.0 |
| 149 | ¹H NMR (600 MHz, DMSO-d6) δ ppm 8.44-8.50 (m, 1 H), 7.38-7.47 (m, 3 H), 7.31-7.36 (m, 2 H), 6.88-6.94 (m, 1 H), 4.62-4.67 (m, 1 H), 4.45-4.53 (m, 1 H), 4.33-4.39 (m, 1 H), 4.09-4.15 (m, 1H), 3.87-3.96 (m, 2 H), 3.72-3.79 (m, 1 H), 3.03-3.11 (m, 1 H), 2.84-2.89 (m, 1 H), 2.57-2.59 (m, 3 H), 2.54-2.55 (m, 3 H), 1.13-1.17 (m, 3 H) | 494.0 |
| 150 | ¹H NMR (600 MHz, DMSO-d6) δ ppm 8.41-8.45 (m, 1 H), 7.43-7.49 (m, 1 H), 7.35-7.37 (m, 1 H), 7.25-7.28 (m, 1 H), 7.17-7.22 (m, 1 H), 7.09-7.14 (m, 1 H), 6.88-6.90 (m, 1 H), 4.58-4.63 (m, 1 H), 4.44-4.49 (m, 1 H), 4.31-4.38 (m, 1 H), 4.09-4.12 (m, 1 H), 3.87-3.93 (m, 2 H), 3.70-3.76 (m, 1 H), 3.05-3.10 (m, 1 H), 2.84-2.89 (m, 1 H), 2.55-2.58 (m, 3 H), 2.48-2.49 (m, 3 H), 1.12-1.17 (m, 3 H) | 478.0 |
| 151 | ¹H NMR (600 MHz, DMSO-d6) δ ppm 7.81-7.84 (m, 1 H), 7.39-7.46 (m, 3 H), 7.16-7.22 (m, 1 H), 7.06-7.13 (m, 1 H), 6.79-6.85 (m, 1 H), 4.47-4.55 (m, 1 H), 4.33-4.40 (m, 1 H), 4.22-4.29 (m, 1 H), 3.96-4.00 (m, 1 H), 3.88-3.93 (m, 2 H), 3.64-3.71 (m, 2 H), 2.97-3.08 (m, 2 H), 2.56-2.58 (m, 3 H), 1.12-1.17 (m, 3 H), 0.98-1.03 (m, 2 H), 0.90-0.95 (m, 2 H) | 492.8 |
| 152 | ¹H NMR (400 MHz, DMSO-d6) δ ppm 7.72 (s, 1 H), 7.37-7.47 (m, 3 H), 7.30-7.34 (m, 1 H), 6.82 (s, 1 H), 4.50 (dd, J = 10.37, 2.49 Hz, 1 H), 4.38 (br d, J = 11.82 Hz, 1 H), 4.22 (br d, J = 13.27 Hz, 1 H), 3.97 (br d, J = 10.26 Hz, 1 H), 3.76-3.84 (m, 4 H), 3.62-3.70 (m, 1 H), 2.94-3.09 (m, 2 H), 2.55 (s, 3 H), 2.39-2.48 (m, 1 H), 1.49-1.59 (m, 2 H), 0.82-0.95 (m, 4 H) | 497.0 |
| 153 | ¹H NMR (500 MHz, CDCl₃) δ ppm 8.48 (d, J = 1.4 Hz, 1 H), 7.53 (dd, J = 8.6, 1.9 Hz, 1 H), 7.51 (s, 1 H), 7.42 (s, 1 H), 6.66 (s, 1 H), 4.61 (brd, J = 9.1 Hz, 1 H), 4.43 (br d, J = 13.1 Hz, 1 H), 4.12-4.27 | 498.0 |

TABLE 7-continued

Analytical Data

| Ex. # | NMR | M + H |
|---|---|---|
| | (m, 1 H), 4.05-4.11 (m, 1 H), 3.90 (s, 3 H), 3.85-3.89 (m, 2 H), 3.77-3.85 (m, 1 H), 3.19-3.31 (m, 1 H), 3.16 (dd, J = 13.1, 10.3 Hz, 1 H), 2.60 (s, 3 H), 1.63-1.76 (m, 2 H), 0.96 (t, J = 7.5 Hz, 3 H) | |
| 154 | $^1$H NMR (500 MHz, DMSO-d6) δ ppm 7.39-7.44 (m, 2 H), 7.35-7.38 (m, 1 H), 7.30-7.34 (m, 1 H), 6.84-6.86 (m, 1 H), 6.31-6.33 (m, 1 H), 4.75-4.80 (m, 1 H), 4.41-4.49 (m, 1 H), 4.19-4.25 (m, 1 H), 3.93-3.99 (m, 1 H), 3.83 (s, 3 H), 3.78-3.82 (m, 2 H), 3.73-3.77 (m, 1 H), 3.32-3.37 (m, 1 H), 3.15-3.23 (m, 1 H), 2.55-2.58 (m, 3 H), 1.52-1.59 (m, 2 H), 0.84-0.89 (m, 3 H) | 497.0 |
| 155 | $^1$H NMR (500 MHz, DMSO-d6) δ ppm 7.39-7.44 (m, 2 H), 7.35-7.38 (m, 1 H), 7.30-7.34 (m, 1 H), 6.84-6.86 (m, 1 H), 6.31-6.33 (m, 1 H), 4.75-4.80 (m, 1 H), 4.41-4.49 (m, 1 H), 4.19-4.25 (m, 1 H), 3.93-3.99 (m, 1 H), 3.83 (s, 3 H), 3.78-3.82 (m, 2 H), 3.73-3.77 (m, 1 H), 3.32-3.37 (m, 1 H), 3.15-3.23 (m, 1 H), 2.55-2.58 (m, 3 H), 1.52-1.59 (m, 2 H), 0.84-0.89 (m, 3 H) | 497.0 |
| 156 | $^1$H NMR (500 MHz, DMSO-d6) δ ppm 7.39-7.44 (m, 2 H), 7.33-7.37 (m, 1 H), 6.78-6.81 (m, 1 H), 6.00-6.24 (m, 1 H), 4.38-4.43 (m, 1H), 4.14-4.19 (m, 1 H), 4.00-4.06 (m, 1 H), 3.78-3.89 (m, 3 H), 3.60-3.67 (m, 1 H), 3.04-3.10 (m, 1 H), 2.92-2.98 (m, 1 H), 2.56-2.57 (m, 3 H), 1.51-1.60 (m, 2H), 0.85-0.90 (m, 3 H) | 467.0 |
| 157 | $^1$H NMR (500 MHz, DMSO-d6) δ ppm 7.44-7.48 (m, 2 H), 7.35-7.43 (m, 4 H), 7.29-7.34 (m, 2 H), 6.82-6.85 (m, 1 H), 4.55-4.59 (m, 1 H), 4.42-4.48 (m, 1 H), 4.26-4.32 (m, 1 H), 4.07-4.13 (m, 1 H), 3.78-3.83 (m, 2 H), 3.71-3.77 (m, 1 H), 3.07-3.15 (m, 1 H), 2.86-2.93 (m, 1 H), 2.55-2.58 (m, 3 H), 1.51-1.60 (m, 2 H), 0.84-0.89 (m, 3 H) | 493.2 |
| 158 | $^1$H NMR (600 MHz, DMSO-d6) δ ppm 8.31-8.35 (m, 1 H), 7.69-7.74 (m, 1 H), 7.42-7.47 (m, 1 H), 7.38-7.41 (m, 2 H), 7.29-7.35 (m, 1 H), 6.88-6.94 (m, 1 H), 4.49-4.54 (m, 1 H), 4.34-4.40 (m, 1 H), 4.20-4.26 (m, 1 H), 3.95-4.00 (m, 1 H), 3.79-3.81 (m, 3 H), 3.63-3.69 (m, 1 H), 3.28-3.30 (m, 3 H), 2.97-3.13 (m, 2 H) | 455.0 |
| 159 | $^1$H NMR (400 MHz, Chloroform-d) δ ppm 7.53 (s, 1 H), 7.44 (s, 1 H), 4.59 (dd, J = 11.4, 2.1 Hz, 1 H), 4.28 (dt, J = 11.2, 3.2 Hz, 1 H), 4.18 (t, J = 11.7 Hz, 1 H), 3.90 (s, 3 H), 3.83 (ddd, J = 11.5, 8.2, 5.3 Hz, 1 H), 3.41-3.52 (m, 1 H), 2.84 (s, 3 H), 2.80 (s, 3 H), 2.42 (d, J = 13.5 Hz, 1 H), 2.32 (d, J = 8.2 Hz, 2 H), 2.12-2.23 (m, 5 H), 1.96-2.12 (m, 4H) | 443.2 |
| 160 | $^1$H NMR (600 MHz, DMSO-d6) δ ppm 7.73 (s, 1 H), 7.46 (s, 1 H), 6.55 (s, 1H), 4.49-4.59 (m, 2 H), 4.39 (br d, J = 12.17 Hz, 1 H), 4.25 (br d, J = 12.26 Hz, 1 H), 3.96-4.04 (m, 1 H), 3.83 (s, 3 H), 3.63-3.71 (m, 1 H), 3.43 (s, 3 H), 2.97-3.08 (m, 2 H), 2.48-2.50 (m, 3 H), 1.90-1.97 (m, 2 H), 1.69-1.83 (m, 4 H), 1.62 (br dd, J = 6.90, 4.36 Hz, 2 H) | 409.0 |
| 161 | $^1$H NMR (500 MHz, CDCl$_3$) δ ppm 7.47 (s, 1H), 7.39-7.44 (m, 2H), 7.26 (s, 1H), 7.17 (dd, J = 1.95, 9.73 Hz, 1H), 4.98 (br t, J = 4.80 Hz, 1H), 3.89 (s, 3H), 3.82-3.88 (m, 2H), 3.53-3.55 (m, 3H), 3.39-3.45 (m, 1H), 2.65 (s, 3H), 2.44 (dt, J = 4.02, 8.82 Hz, 1H), 2.30 (ddd, J = 5.06, 5.19, 13.62 Hz, 1H), 2.03-2.15 (m, 2H) | 468.0 |
| 162 | $^1$H NMR (500 MHz, CDCl$_3$) δ ppm 7.49 (s, 1 H), 7.39-7.43 (m, 1 H), 7.38 (s, 2 H), 7.26-7.28 (m, 1 H), 7.18 (dd, J = 9.6, 1.9 Hz, 1 H), 4.55 (dd, J = 11.3, 1.9 Hz, 1 H), 4.22-4.28 (m, 1 H), 3.88 (s, 3 H), 3.78 (td, J = 11.7, 2.5 Hz, 1 H), 3.54 (s, 3 H), 3.27 (tt, J = 12.0, 3.8 Hz, 1 H), 2.65 (s, 3 H), 2.33 (br d, J = 13.0 Hz, 1 H), 1.88-2.07 (m, 3 H) | 468.0 |
| 163 | $^1$H NMR (500 MHz, CDCl$_3$) δ ppm 7.49 (s, 1 H), 7.39-7.43 (m, 1 H), 7.38 (s, 2 H), 7.26-7.28 (m, 1 H), 7.18 (dd, J = 9.6, 1.9 Hz, 1 H), 4.55 (dd, J = 11.3, 1.9 Hz, 1 H), 4.22-4.28 (m, 1 H), 3.88 (s, 3 H), 3.78 (td, J = 11.7, 2.5 Hz, 1 H), 3.54 (s, 3 H), 3.27 (tt, J = 12.0, 3.8 Hz, 1 H), 2.65 (s, 3 H), 2.33 (br d, J = 13.0 Hz, 1 H), 1.88-2.07 (m, 3 H) | 468.0 |
| 164 | $^1$H NMR (500 MHz, CDCl$_3$) δ ppm 7.53 (s, 1 H), 7.51 (s, 1 H), 7.45 (t, J = 8.0 Hz, 1 H), 7.40 (s, 1 H), 7.26-7.28 (m, 1 H), 7.17 (dd, J = 9.7, 1.9 Hz, 1 H), 7.14-7.16 (m, 1 H), 5.43 (q, J = 2.5 Hz, 1 H), 4.08-4.18 (m, 1 H), 3.94 (ddd, J = 11.6, 7.2, 4.6 Hz, 1 H), 3.90 (s, 3 H), 3.55 (s, 3 H), 2.71-2.83 (m, 1 H), 2.64-2.71 (m, 4 H) | 466.0 |
| 165 | $^1$H NMR (400 MHz, Methanol-d4) δ ppm 7.70 (s, 1 H), 7.56 (s, 1 H), 6.52 (s, 1 H), 5.61 (dt, J = 4.0, 2.2 Hz, 1 H), 4.62 (dd, J = 10.3, 2.8 Hz, 1 H), 4.45 (d, J = 12.9 Hz, 1 H), 4.24 (d, J = 13.1 Hz, 1 H), 4.08 (ddd, J = 11.5, 3.6, 1.8 Hz, 1 H), 3.91 (s, 3 H), 3.80 (td, J = 11.5, 2.8 Hz, 1 H), 3.52 (s, 3 H), 3.06-3.21 (m, 2 H), 2.59 (s, 3 H), 2.16-2.31 (m, 4 H), 1.70-1.91 (m, 4 H) | 494.1 |
| 166 | $^1$H NMR (400 MHz, Methanol-d4) δ ppm 7.71 (s, 1 H), 7.57 (s, 1 H), 6.48 (s, 1 H), 4.63 (d, J = 9.3 Hz, 1 H), 4.40-4.53 (m, 2 H), 4.30 (d, J = 13.1 Hz, 1 H), 4.08 (t, J = 12.4 Hz, 3 H), 3.91 (s, 3 H), 3.81 (t, J = 11.4 Hz, 1 H), 3.64 (t, J = 11.8 Hz, 2 H), 3.54 (s, 3 H), 3.18 (dd, J = 18.3, 12.0 Hz, 2 H), 2.58 (s, 3 H), 1.97 (qd, J = 12.7, 4.3 Hz, 4 H) | 494.1 |
| 167 | $^1$H NMR (500 MHz, DMSO-d6) δ ppm 7.40-7.46 (m, 3H), 7.32-7.39 (m, 1H), 4.04-4.17 (m, 4H), 3.58 (dt, J = 2.72, 11.68 Hz, 1H), | 460.0 |

TABLE 7-continued

Analytical Data

| Ex. # | NMR | M + H |
|---|---|---|
| | 3.42 (s, 3H), 3.17-3.26 (m, 1H), 2.60 (s, 3H), 2.10-2.18 (m, 1H), 1.76-1.87 (m, 2H), 1.72 (q, J = 12.02 Hz, 1H), 1.18 (t, J = 7.07 Hz, 3H) | |
| 168 | $^1$H NMR (500 MHz, DMSO-d6) δ ppm 7.40-7.48 (m, 3 H), 7.35-7.40 (m, 1 H), 4.57 (dd, J = 5.3, 3.1 Hz, 1 H), 4.19 (d, J = 7.1 Hz, 2 H), 3.78-3.89 (m, 2 H), 3.43 (s, 3 H), 3.01-3.09 (m, 1 H), 2.61 (s, 3 H), 2.25 (br d, J = 12.8 Hz, 1 H), 2.07-2.17 (m, 1 H), 1.79-1.91 (m, 2H), 1.24 (t, J = 7.1 Hz, 3H) | 460.0 |
| 169 | $^1$H NMR (CDCl$_3$, 500 MHz) δ 8.53 (d, 1H, J = 5.2 Hz), 7.4-7.5 (m, 1H), 7.42 (s, 1H), 7.33 (d, 1H, J = 1.9 Hz), 7.3-7.3 (m, 1H), 7.24 (d, 1H, J = 9.3 Hz), 7.17 (d, 1H, J = 4.8 Hz), 4.57 (dd, 1H, J = 1.6, 11.2 Hz), 4.4-4.5 (m, 1H), 3.87 (dt, 1H, J = 2.7, 11.7 Hz), 3.60 (s, 3H), 3.3-3.5 (m, 1H), 2.71 (s, 3H), 2.63 (s, 3H), 2.39 (br d, 1H, J = 12.3 Hz), 2.0-2.2 (m, 2H), 1.7-1.9 (m, 2H) | 479.0 |
| 170 | $^1$H NMR (CDCl$_3$, 500 MHz) δ 8.53 (d, 1H, J = 5.1 Hz), 7.45 (t, 1H, J = 7.8 Hz), 7.42 (s, 1H), 7.33 (s, 1H), 7.27 (s, 1H), 7.24 (dd, 1H, J = 1.9, 9.6 Hz), 7.17 (d, 1H, J = 4.9 Hz), 4.57 (dd, 1H, J = 1.7, 11.2 Hz), 4.4-4.5 (m, 1H), 3.86 (dt, 1H, J = 2.8, 11.6 Hz), 3.60 (s, 3H), 3.3-3.5 (m, 1H), 2.71 (s, 3H), 2.63 (s, 3H), 2.39 (br d, 1H, J = 12.3 Hz), 2.0-2.2 (m, 2H), 1.7-1.9 (m, 2H) | 479.0 |
| 171 | $^1$H NMR (500 MHz, DMSO-d6) δ ppm 8.45 (d, J = 2.1 Hz, 2 H), 8.39 (d, J = 1.6 Hz, 1 H), 7.61-7.68 (m, 3 H), 7.60 (s, 1 H), 7.52 (t, J = 8.0 Hz, 1 H), 7.32-7.45 (m, 6 H), 7.18-7.27 (m, 3 H), 4.77 (br d, J = 7.4 Hz, 1 H), 4.51-4.60 (m, 2 H), 4.32 (t, J = 5 1 Hz, 1 H), 4.18 (br dd, J = 11.0, 3.2 Hz, 2 H), 3.65-3.87 (m, 4 H), 3.44 (s, 3 H), 3.42 (s, 5 H), 3.38-3.41 (m, 1 H), 2.62 (s, 2 H), 2.60 (s, 4 H), 2.43-2.46 (m, 9 H), 2.12-2.23 (m, 4 H), 2.01-2.10 (m, 1 H), 1.83-1.99 (m, 4 H), 1.68-1.81 (m, 2 H) (This is a mixture of two diastereomers with a ratio of 1.7:1) | 479.0 |
| 172 | $^1$H NMR (500 MHz, DMSO-d6) δ ppm 8.10 (d, J = 5.3 Hz, 1 H), 7.45 (s, 1 H), 7.42 (br dd, J = 9.7, 1.9 Hz, 2 H), 7.33-7.37 (m, 1 H), 6.99 (dd, J = 5.3, 1.3 Hz, 1 H), 6.78 (s, 1 H), 4.54 (dd, J = 11.0, 1.5 Hz, 1 H), 4.20 (dd, J = 11.4, 3.2 Hz, 1 H), 3.83 (s, 3 H), 3.72 (td, J = 11.7, 2.5 Hz, 1 H), 3.42 (s, 3 H), 3.31-3.36 (m, 1 H), 2.60 (s, 3 H), 2.14-2.24 (m, 1 H), 1.80-1.99 (m, 2 H), 1.57-1.69 (m, 1 H) | 495.0 |
| 173 | $^1$H NMR (500 MHz, DMSO-d6) δ ppm 8.10 (d, J = 5.3 Hz, 1 H), 7.45 (s, 1 H), 7.39-7.44 (m, 2 H), 7.33-7.37 (m, 1 H), 6.99 (dd, J = 5.3, 1.2 Hz, 1H), 6.78 (s, 1 H), 4.54 (dd, J = 11.1, 1.6 Hz, 1 H), 4.20 (dd, J = 11.5, 3.2 Hz, 1 H), 3.83 (s, 3 H), 3.66-3.77 (m, 1 H), 3.42 (s, 3 H), 3.31-3.35 (m, 1 H), 2.60 (s, 3 H), 2.15-2.25 (m, 1 H), 1.80-1.97 (m, 2 H), 1.64 (q, J = 11.6 Hz, 1 H) | 495.0 |
| 174 | $^1$H NMR (600 MHz, DMSO-d6) δ ppm 8.13 (d, J = 5.4 Hz, 1 H), 7.59 (s, 1 H), 7.52 (br t, J = 8.0 Hz, 1 H), 7.43-7.47 (m, 1 H), 7.39 (dd, J = 8.1, 1.9 Hz, 1 H), 6.92-6.96 (m, 1 H), 6.74 (s, 1 H), 4.76 (br d, J = 5.3 Hz, 1 H), 3.85 (s, 3 H), 3.79 (br t, J = 4.7 Hz, 2 H), 3.44 (s, 3 H), 3.32-3.36 (m, 1 H), 2.62 (s, 3 H), 2.41-2.49 (m, 1 H), 2.07-2.19 (m, 2 H), 1.98-2.06 (m, 1 H) | 495.0 |
| 175 | $^1$H NMR (600 MHz, DMSO-d6) δ ppm 8.13 (d, J = 5.3 Hz, 1 H), 7.59 (s, 1 H), 7.51 (br t, J = 7.9 Hz, 1 H), 7.45 (dd, J = 9.8, 1.9 Hz, 1 H), 7.39 (dd, J = 8.2, 1.8 Hz, 1 H), 6.94 (d, J = 5.3 Hz, 1 H), 6.74 (s, 1 H), 4.76 (br d, J = 5.6 Hz, 1 H), 3.85 (s, 3 H), 3.70-3.82 (m, 2 H), 3.44 (s, 3 H), 3.32-3.37 (m, 1 H), 2.62 (s, 3 H), 2.41-2.48 (m, 1 H), 2.08-2.20 (m, 2 H), 1.93-2.07 (m, 1 H) | 495.0 |
| 176 | $^1$H NMR (500 MHz, DMSO-d6) δ ppm 8.53 (s, 1 H), 8.48 (dd, J = 4.7, 1.2 Hz, 1 H), 7.74 (br d, J = 7.9 Hz, 1 H), 7.61 (s, 1 H), 7.52 (br t, J = 8.0 Hz, 1 H), 7.45 (dd, J = 9.9, 1.8 Hz, 1 H), 7.35-7.41 (m, 2 H), 4.80 (br d, J = 7.3 Hz, 1 H), 3.65-3.88 (m, 2 H), 3.44 (s, 3 H), 3.39-3.43 (m, 1 H), 2.61 (s, 3 H), 2.41-2.47 (m, 1 H), 2.13-2.23 (m, 2H), 1.98-2.12 (m, 1 H) | 465.0 |
| 177 | $^1$H NMR (500 MHz, DMSO-d6) δ ppm 8.60 (s, 1 H), 8.48 (br d, J = 3.5 Hz, 1 H), 7.76-7.85 (m, 1 H), 7.46 (s, 1 H), 7.39-7.45 (m, 2 H), 7.32-7.39 (m, 2 H), 4.61 (dd, J = 11.2, 1.8 Hz, 1 H), 4.14-4.26 (m, 1 H), 3.74 (td, J = 11.7, 2.7 Hz, 1H), 3.41 (s, 3 H), 2.59 (s, 3 H), 2.51-2.53 (m, 1 H), 2.19 (br d, J = 11.0 Hz, 1 H), 1.83-2.00 (m, 2 H), 1.68-1.81 (m, 1 H) | 465.0 |

TABLE 7-continued

Analytical Data

| Ex. # | NMR | M + H |
|---|---|---|
| 178 | ¹H NMR (500 MHz, DMSO-d6) δ ppm 8.60 (s, 1 H), 8.48 (br d, J = 3.5 Hz, 1 H), 7.76-7.85 (m, 1 H), 7.46 (s, 1 H), 7.39-7.45 (m, 2 H), 7.32-7.39 (m, 2 H), 4.61 (dd, J = 11.2, 1.8 Hz, 1 H), 4.14-4.26 (m, 1 H), 3.74 (td, J = 11.7, 2.7 Hz, 1H), 3.41 (s, 3 H), 2.59 (s, 3 H), 2.51-2.53 (m, 1 H), 2.19 (br d, J = 11.0 Hz, 1 H), 1.83-2.00 (m, 2 H), 1.68-1.81 (m, 1 H) | 465.0 |
| 276 | ¹H NMR (400 MHz, DMSO-d6) δ ppm 8.43 (d, J = 5.1 Hz, 1H), 7.42 (q, J = 7.9 Hz, 1H), 7.35 (s, 1H), 7.26 (d, J = 5.1 Hz, 1H), 7.20 (t, J = 10.2 Hz, 1H), 7.11 (t, J = 8.5 Hz, 1H), 4.60 (d, J = 8.7 Hz, 1H), 4.46 (d, J = 13.0 Hz, 1H), 4.34 (d, J = 13.1 Hz, 1H), 4.10 (d, J = 11.0 Hz, 1H), 3.73 (dd, J = 12.9, 10.1 Hz, 1H), 3.31 (s, 3H), 3.07 (td, J = 12.3, 3.1 Hz, 1H), 2.85 (dd, J = 12.9, 10.6 Hz, 1H), 2.52 (s, 3H), 2.48 (s, 3H). | 463.8 |
| 277 | ¹H NMR (400 MHz, Chloroform-d): δ ppm 8.82 (1H, s), 8.63-8.39 (1H, m), 8.01 (1H, d, J = 8.1 Hz), 7.76 (1H, m), 7.38 (1H, s), 7.22 (1H, br s), 7.14 (1H, br s), 4.52 (1H, d, J = 11.2 Hz), 4.34 (1H, d, J = 11.7 Hz), 3.82-3.76 (1H, m), 3.52 (3H, s), 3.33-3.26 (1H, m), 2.65 (3H, s), 2.57 (3H, s), 2.29 (1H, d, J = 12.7 Hz), 2.08-1.96 (2H, m), 1.82-1.73 (3H, m). | 496.2 |
| 278 | ¹H NMR (400 MHz, Chloroform-d) δ ppm 9.49 (s, 1H), 8.69 (d, J = 7.7 Hz, 1H), 8.53 (d, J = 5.0 Hz, 1H), 8.50 (s, 1H), 7.83 (d, J = 8.2 Hz, 1H), 7.18 (d, J = 4.3 Hz, 1H), 7.02 (s, 1H), 4.65 (d, J = 11.9 Hz, 1H), 4.56 (d, J = 12.5 Hz, 1H), 4.36-4.23 (m, 2H), 3.95 (dd, J = 16.5, 6.3 Hz, 1H), 3.27 (dd, J = 13.3, 10.2 Hz, 1H), 2.98 (dd, J = 12.1, 10.8 Hz, 1H), 2.74 (s, 3H), 2.61 (s, 3H). Note: One aromatic proton is obscured by solvent signal. 19F NMR (376 MHz, Chloroform-d) δ ppm −67.94 (s). | 463.2 |
| 279 | 1HNMR (400 MHz, DMSO-d6) δ ppm 8.15 (d, J = 5.2 Hz, 1H), 7.42 (q, J = 7.9 Hz, 1H), 7.19 (td, J = 9.9, 2.5 Hz, 1H), 7.14-7.03 (m, 2H), 6.89 (s, 2H), 4.60 (dd, J = 10.6, 2.7 Hz, 1H), 4.46 (d, J = 13.0 Hz, 1H), 4.32 (d, J = 13.2 Hz, 1H), 4.10 (dd, J = 11.9, 2.4 Hz, 1H), 3.85 (s, 3H), 3.72 (td, J = 11.4, 1.8 Hz, 1H), 3.34 (s, 3H), 3.07 (td, J = 12.9, 3.3 Hz, 1H), 2.85 (dd, J = 12.9, 10.4 Hz, 1H), 2.52 (s, 3H). | 480.1 |
| 280 | ¹H NMR (400 MHz, DMSO-d6) δ ppm 8.79 (d, J = 2.1 Hz, 1H), 8.43 (d, J = 5.1 Hz, 1H), 8.13 (dd, J = 8.0, 2.1 Hz, 1H), 7.93 (d, J = 8.1 Hz, 1H), 7.35 (s, 1H), 7.27 (d, J = 4.9 Hz, 1H), 6.95 (s, 1H), 4.60 (dd, J = 10.3, 2.7 Hz, 1H), 4.51 (d, J = 13.1 Hz, 1H), 4.38 (d, J = 13.4 Hz, 1H), 4.11 (dd, J = 11.3, 2.6 Hz, 1H), 3.74 (td, J = 11.8, 2.7 Hz, 1H), 3.36 (s, 3H), 3.09 (td, J = 13.0, 12.5, 3.3 Hz, 1H), 2.87 (dd, J = 13.0, 10.5 Hz, 1H), 2.55 (s, 3H), 2.48 (s, 3H). | 497.2 |
| 281 | ¹H NMR (400 MHz, Chloroform-d) δ ppm 9.57 (1H, s), 8.87-8.90 (1H, m), 8.18 (1H, d, J = 5.1 Hz), 8.13 (1H, d, J = 8.3 Hz), 7.07-7.08 (1H, m), 6.89 (1H, s), 4.82 (2H, bd, J = 64.4 Hz), 4.64 (1H, d, J = 10.1 Hz), 4.13-4.18 (1H, m), 3.85 (3H, s), 3.71-3.79 (1H, m), 3.00-3.12 (1H, m), 2.71-2.77 (1H, m), 2.65-2.67 (3H, s), 2.61-2.61 (3H, s). | 585.2 |
| 282 | ¹H NMR (400 MHz, Chloroform-d) δ ppm 8.47 (s, 1H), 7.55 (dd, J = 8.9, 5.9 Hz, 1H), 7.34 (dd, J = 8.8, 6.0 Hz, 1H), 7.29 (s, 1H), 7.21 (s, 1H), 5.02 (d, J = 13.2 Hz, 1H), 4.85 (d, J = 13.6 Hz, 1H), 4.57 (d, J = 9.7 Hz, 1H), 4.19 (dd, J = 11.6, 2.7 Hz, 1H), 3.88-3.78 (m, 1H), 3.36-3.26 (m, 1H), 3.03 (dd, J = 13.3, 10.6 Hz, 1H), 2.68 (s, 3H), 2.57 (s, 3H), 2.56 (s, 3H). 19F NMR (376 MHz, Methylene Chloride-d2) δ ppm −115.09 (s), −122.08 (s) | 486.2 |
| 283 | ¹H NMR (400 MHz, DMSO-d6) δ ppm 8.18 (d, J = 5.3 Hz, 1H), 7.09 (dd, J = 5.4, 1.4 Hz, 1H), 6.89 (s, 1H), 6.75 (s, 1H), 4.63-4.51 (m, 2H), 4.34 (d, J = 13.1 Hz, 1H), 4.10 (dd, J = 11.3, 2.7 Hz, 1H), 3.86 (s, 3H), 3.71 (td, J = 11.5, 2.5 Hz, 1H), 3.44 (s, 3H), 3.31 (s, 6H), 3.08 (td, J = 12.9, 3.2 Hz, 1H), 2.85 (dd, J = 13.4, 10.8 Hz, 1H), 2.47 (s, 3H). | 502.2 |

SYNTHESIS OF INTERMEDIATES

Method 15

Intermediate 1: (S)-2-(1H-pyrazol-4-yl)morpholine

Intermediate 2: (R)-2-(1H-pyrazol-4-yl)morpholine

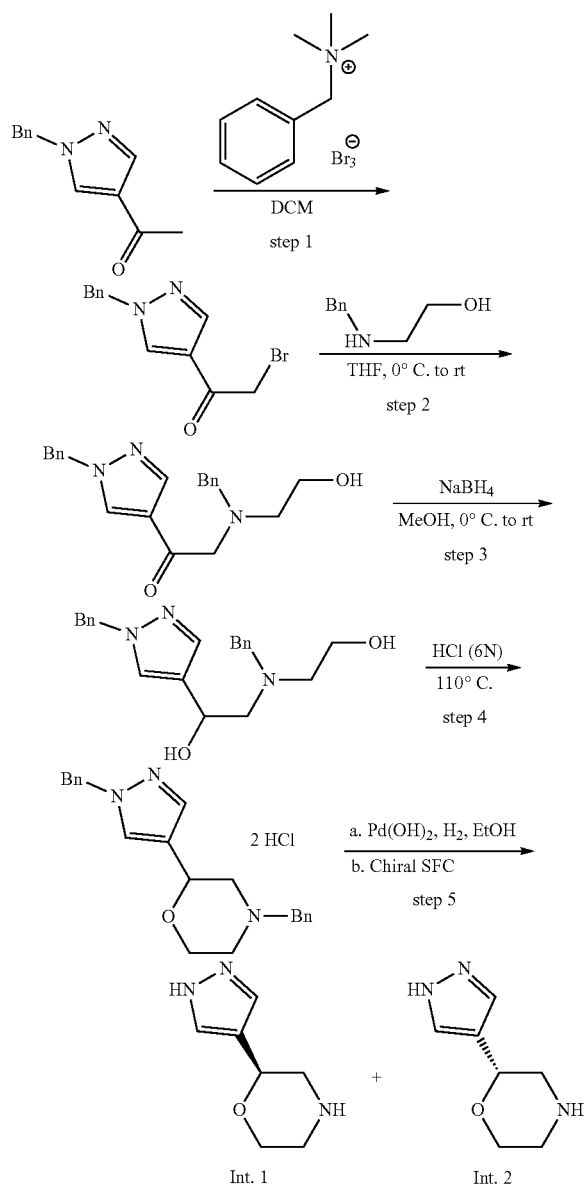

Step 1: 1-(1-benzyl-1H-pyrazol-4-yl)-2-bromoethan-1-one. To a solution of 1-(1-benzyl-1H-pyrazol-4-yl)ethan-1-one (4.5 g, 22.47 mmol) in DCM (204 mL) was added portion wise mono(N,N,N-trimethylbenzenaminium) tribromide (9.15 g, 23.60 mmol) at room temperature. The reaction mixture was stirred overnight at room temperature. The reaction mixture was diluted with water and the aqueous phase was extracted with DCM. The combined organic phases were dried over MgSO$_4$, filtered and solvents were evaporated. The reaction was repeated on the same scale (4.5 g). The combined crude was purified by column chromatography eluting with a gradient of 0 to 30% heptane/EtOAc-EtOH (3/1) to provide 1-(1-benzyl-1H-pyrazol-4-yl)-2-bromoethan-1-one (9.9 g, 35.47 mmol, 79%) as a white solid. $^1$H NMR (400 MHz, DMSO-d6) δ ppm 8.65 (s, 1H), 8.05 (s, 1H), 7.27-7.40 (m, 5H), 5.39 (s, 2H), 4.60 (s, 2H). m/z (ESI, +ive ion): 279.0 (M+H)$^+$.

Step 2: 2-(benzyl(2-hydroxyethyl)amino)-1-(1-benzyl-1H-pyrazol-4-yl)ethan-1-one. To a solution of 1-(1-benzyl-1H-pyrazol-4-yl)-2-bromoethan-1-one (4.45 g, 15.94 mmol) in THF (46 mL) at 0° C. was slowly added 2-(benzylamino)ethan-1-ol (2.84 g, 18.81 mmol). The reaction mixture was stirred at 0° C. for 1 hour and then at room temperature for 6 h. Water was then added to the reaction mixture and the aqueous phase was extracted with EtOAc (x3). The combined organic phases were dried over MgSO$_4$, filtered, and concentrated. The reaction was repeated on the same scale. The combined crude material was absorbed onto a plug of silica gel and purified by chromatography through a silica gel column eluting with a gradient of 0% to 10% DCM/MeOH, to provide 2-(benzyl(2-hydroxyethyl)amino)-1-(1-benzyl-1H-pyrazol-4-yl)ethan-1-one (8.3 g, 23.75 mmol, 75% yield). $^1$H NMR (400 MHz, DMSO-d6) δ ppm 8.57 (s, 1H), 7.96 (s, 1H), 7.20-7.31 (m, 10H), 5.36 (s, 2H), 4.44 (t, J=5.2 Hz, 1H), 3.68 (d, J=3.1 Hz, 2H), 3.43-3.53 (m, 4H), 2.60 (d, J=6.2 Hz, 2H). m/z (ESI, +ive ion): 350.0 (M+H)$^+$.

Step 3: 2-(benzyl(2-hydroxyethyl)amino)-1-(1-benzyl-1H-pyrazol-4-yl)ethan-1-ol. To a solution of 2-(benzyl(2-hydroxyethyl)amino)-1-(1-benzyl-1H-pyrazol-4-yl)ethan-1-one (8.30 g, 23.75 mmol) in methanol (79 mL) at 0° C. was added sodium tetrahydroborate (1.797 g, 47.5 mmol) portion wise. The reaction mixture was stirred at 0° C. for 30 min and then at room temperature for 2 h. 90% of the solvent was concentrated under vacuo. Ice-cooled water was added dropwise to quench the reaction. The reaction mixture was extracted with EtOAc (x3). The combined organic layer was dried over anhydrous MgSO$_4$, filtered and concentrated under reduced pressure. The crude 2-(benzyl(2-hydroxyethyl)amino)-1-(1-benzyl-1H-pyrazol-4-yl)ethan-1-ol (8.35 g, 23.76 mmol, 100% yield) was used as such in the next step. $^1$H NMR (400 MHz, DMSO-d6) δ ppm 7.63 (s, 1H), 7.25-7.35 (m, 8H), 7.18-7.24 (m, 3H), 5.26 (s, 2H), 4.82 (d, J=3.8 Hz, 1H), 4.37 (t, J=5.4 Hz, 2H), 3.68 (d, J=3.5 Hz, 2H), 3.40-3.47 (m, 2H), 3.17 (d, J=5.3 Hz, 1H), 2.64 (dd, J=6.4, 4.2 Hz, 4H). m/z (ESI, +ive ion): 352.2 (M+H)$^+$.

Step 4: 4-benzyl-2-(1-benzyl-1H-pyrazol-4-yl)morpholine, hydrochloric acid salt. A solution of 2-(benzyl(2-hydroxyethyl)amino)-1-(1-benzyl-1H-pyrazol-4-yl)ethan-1-ol (8.35 g) in 6N HCl (61 mL) was heated at 110° C. for 2 h. The reaction mixture was evaporated to dryness under reduced pressure. The resulting solid was triturated with Et$_2$O which afforded 4-benzyl-2-(1-benzyl-1H-pyrazol-4-yl)morpholine as HCl salt. The crude was used in the next step without any further purification. $^1$H NMR (400 MHz, DMSO-d6) δ ppm 11.97 (s, 1H), 7.87 (s, 1H), 7.65 (dt, J=7.5, 3.6 Hz, 2H), 7.42-7.51 (m, 4H), 7.31 (dt, J=13.8, 6.7 Hz, 3H), 7.19-7.24 (m, 2H), 5.29 (s, 2H), 4.97 (dd, J=11.1, 2.3 Hz, 1H), 4.27-4.39 (m, 2H), 3.96-4.06 (m, 2H), 3.37 (d, J=12.1 Hz, 1H), 3.14 (dt, J=31.1, 11.0 Hz, 3H). m/z (ESI, +ive ion): 334.2 (M+H)$^+$.

Step 5: 2-(1H-pyrazol-4-yl)morpholine. A suspension of 4-benzyl-2-(1-benzyl-1H-pyrazol-4-yl)morpholine as HCl salt (23.75 mmol) and dihydroxypalladium (3.34 g, 4.75 mmol) in ethanol (120 mL) was put under vacuum and flushed with nitrogen. The reaction mixture was flushed with hydrogen and was stirred under hydrogen atm (25 psi) at room temperature for 18 h. The catalyst was removed by filtration over celite and washed with ethanol several times.

The solvent was concentrated under vacuum. The crude 2-(1H-pyrazol-4-yl)morpholine was purified by chiral SFC using an AD 30×250 mm, 5 micron column (mobile phase 20% ethanol, 0.2% diethylamine), F=180 mL/min. to provide two isomers as light brown solids. Absolute stereochemistry of Intermediates 1-4 was assigned based on independent synthesis of both stereoisomers of example 1 (pyrazole methylation followed by SnAr coupling) and subsequent x-ray crystallography. The stereochemical indicators for intermediates 5-15 of Table 8 below have been assigned arbitrarily.

Peak 1 (Intermediate 1): (S)-2-(1H-pyrazol-4-yl)morpholine (1.67 g, 10.9 mmol, 46% yield, ee>97%). $^1$H NMR (400 MHz, CDCl$_3$) δ ppm 7.58 (s, 2H), 4.62 (dd, J=10.3, 2.3 Hz, 1H), 3.95-4.03 (m, 1H), 3.78-3.87 (m, 1H), 3.14 (dd, J=12.4, 1.8 Hz, 1H), 2.89-3.01 (m, 3H). m/z (ESI, +ive ion): 154.2 (M+H)$^+$.

Peak 2 (Intermediate 2): (R)-2-(1H-pyrazol-4-yl)morpholine (1.59 g, 10.4 mmol, 44% yield, ee>89%). $^1$H NMR (400 MHz, CDCl$_3$) δ ppm 7.58 (s, 2H), 4.62 (dd, J=10.3, 2.3 Hz, 1H), 3.93-4.03 (m, 1H), 3.78-3.87 (m, 1H), 3.16 (dd, J=12.4, 1.8 Hz, 1H), 2.89-3.01 (m, 3H). m/z (ESI, +ive ion): 154.2 (M+H)$^+$.

TABLE 8

Intermediates prepared using Method 15

| Int. # | Structure | Name | Starting Material |
| --- | --- | --- | --- |
| 3 | 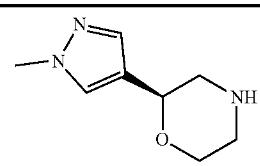 | (S)-2-(1-methyl-1H-pyrazol-4-yl)morpholine | 1-(1-methyl-1H-pyrazol-4-yl)ethan-1-one |
| 4 | 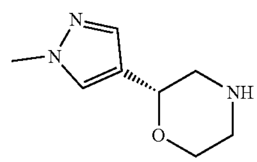 | (R)-2-(1-methyl-1H-pyrazol-4-yl)morpholine | 1-(1-methyl-1H-pyrazol-4-yl)ethan-1-one |
| 5 | 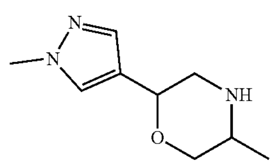 | 5-methyl-2-(1-methyl-1H-pyrazol-4-yl)morpholine | 1-(1-methyl-1H-pyrazol-4-yl)ethan-1-one |
| 6 | 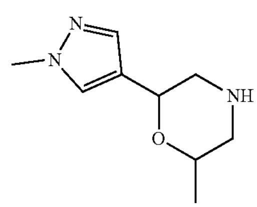 | 2-methyl-6-(1-methyl-1H-pyrazol-4-yl)morpholine | 1-(1-methyl-1H-pyrazol-4-yl)ethan-1-one |
| 7 | 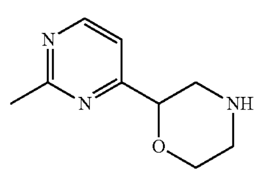 | 2-(2-methylpyrimidin-4-yl)morpholine | 1-(2-methylpyrimidin-4-yl)ethan-1-one |
| 8 | 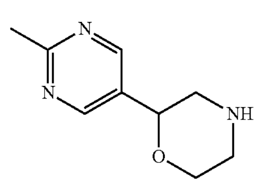 | 2-(2-methylpyrimidin-5-yl)morpholine | 1-(2-methylpyrimidin-5-yl)ethan-1-one |
| 9 | 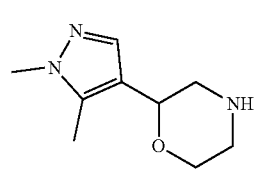 | 2-(1,5-dimethyl-1H-pyrazol-4-yl)morpholine | 1-(1,5-dimethyl-1H-pyrazol-4-yl)ethan-1-one |

TABLE 8-continued

Intermediates prepared using Method 15

| Int. # | Structure | Name | Starting Material |
|---|---|---|---|
| 10 | 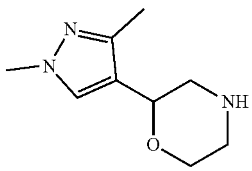 | 2-(1,3-dimethyl-1H-pyrazol-4-yl)morpholine | 1-(1,3-dimethyl-1H-pyrazol-4-yl)ethan-1-one |
| 11 | 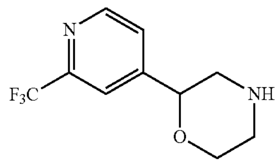 [SMILES: FC(F)(F)c1cc(C2CNCCO2)ccn1] | 2-(2-(trifluoromethyl)pyridin-4-yl)morpholine | 1-2-(trifluoromethyl)pyridin-4-yl)ethan-1-one |
| 12 | 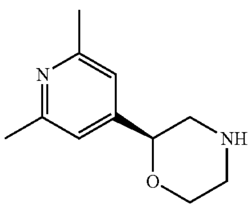 | (S)-2-(2,6-dimethylpyridin-4-yl)morpholine | 1-(2,6-dimethylpyridin-4-yl)ethan-1-one |
| 13 | 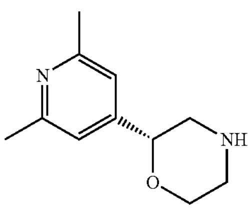 | (R)-2-(2,6-dimethylpyridin-4-yl)morpholine | 1-(2,6-dimethylpyridin-4-yl)ethan-1-one |
| 14 | 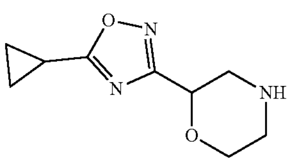 [SMILES: C1COC(c2noc(C3CC3)n2)CN1] | 2-(5-cyclopropyl-1,2,4-oxadiazol-3-yl)morpholine | 1-(5-cyclopropyl-1,2,4-oxadiazol-3-yl)ethan-1-one |
| 15 | 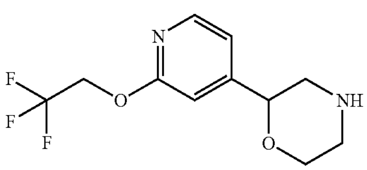 [SMILES: FC(F)(F)COc1cc(C2CNCCO2)ccn1] | 2-(2-(2,2,2-trifluoroethoxy)pyridin-4-yl)morpholine | 1-(2-(2,2,2-trifluoroethoxy)pyridin-4-yl)ethan-1-one |

Method 16

Intermediate 17: 4,4-difluoro-3-(1-methyl-1H-pyrazol-4-yl)piperidine

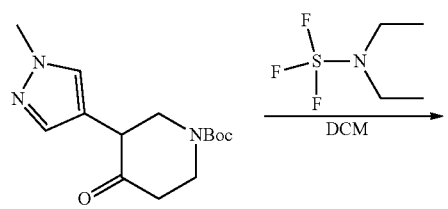

-continued

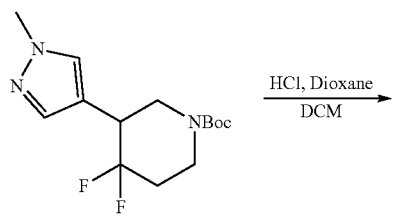

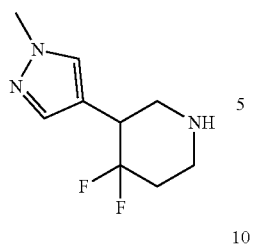

Step 1: Tert-butyl 4,4-difluoro-3-(1-methyl-1H-pyrazol-4-yl)piperidine-1-carboxylate. To a 100-mL round-bottomed flask was added tert-butyl 3-(1-methyl-1H-pyrazol-4-yl)-4-oxopiperidine-1-carboxylate (1 g, 1.647 mmol)) in DCM (40 mL) and DAST (2.2 mL, 16.47 mmol) at 0° C. The reaction mixture was warmed to room temperature, stirred for 48 h. then quenched with 10% sodium bicarbonate (50 mL) and extracted with DCM (30 mL). The organic extract was dried over Na$_2$SO$_4$. The solution was filtered and concentrated in vacuo to give the crude material as an orange oil. The crude material was purified by silica gel chromatography eluting with 50% EtOAc in hexane, to provide tert-butyl 4,4-difluoro-3-(1-methyl-1H-pyrazol-4-yl)piperidine-1-carboxylate (500 mg, 1.1 mmol, 64.5% yield) as yellow oil.

Step 2: 4,4-difluoro-3-(1-methyl-1H-pyrazol-4-yl)piperidine hydrochloride. To a 10-mL round-bottomed flask was added tert-butyl 4,4-difluoro-3-(1-methyl-1H-pyrazol-4-yl)piperidine-1-carboxylate (60 mg, 0.199 mmol)) in DCM (4 mL). The mixture was cooled to 0° C. and HCl in dioxane (0.5 mL, 2.000 mmol) was added. The reaction mixture was warmed to room temperature, stirred for 2 h, then concentrated in vacuo to give the crude product which was washed with diethyl ether to provide 4,4-difluoro-3-(1-methyl-1H-pyrazol-4-yl)piperidine hydrochloride (25 mg, 0.124 mmol, 62.4% yield) as white solid (hygroscopic). $^1$H NMR (400 MHz, DMSO-d6): δ ppm 9.36 (d, J=25.1 Hz, 2H), 7.73 (s, 1H), 7.41 (s, 1H), 3.82 (s, 4H), 3.57 (s, 2H), 3.18 (d, J=5.1 Hz, 1H), 2.39 (d, J=11.9 Hz, 2H).

Method 17

Intermediate 18: 4-(4-bromotetrahydro-2H-pyran-2-yl)-2-methylpyridine

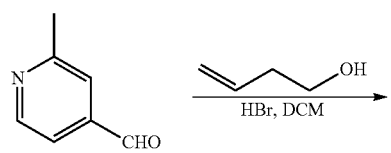

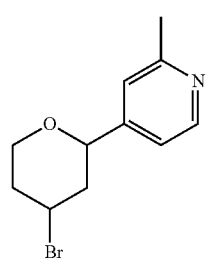

To a 500 mL flask was added 2-methylisonicotinaldehyde (5 g, 41.3 mmol), 3-buten-1-ol (3.13 g, 3.72 mL, 43.3 mmol) and DCM (83 mL). The mixture was stirred at 0° C. and hydrogen bromide-acetic acid (30.4 g, 22.42 mL, 124 mmol) was added slowly in one portion. The reaction mixture was warmed to rt after 5 min and stirred for 4 h. The mixture was quenched with saturated sodium bicarbonate solution and extracted with DCM. The combined organic layers were dried over sodium sulfate, filtered and concentrated. The resulting crude material was purified by silica gel chromatography eluting with 0-30% EtOAc/EtOH (3:1) in heptane, to provide 4-(4-bromotetrahydro-2H-pyran-2-yl)-2-methylpyridine as a mixture of 4 diastereomers (52% overall yield). A second silica gel column may be used to separate cis and trans isomers of the product.

Product 1: 4-((2R,4S)-4-bromotetrahydro-2H-pyran-2-yl)-2-methylpyridine and 4-((2S,4R)-4-bromotetrahydro-2H-pyran-2-yl)-2-methylpyridine (mixture of cis isomers): 3.83 g $^1$H NMR (500 MHz, CDCl$_3$) δ ppm 3.56-3.65 (m, 1H) 4.01-4.10 (m, 1H) 4.11-4.19 (m, 1H) 4.37-4.42 (m, 1H) 4.52-4.58 (m, 1H) 4.76-4.83 (m, 1H) 4.84-4.95 (m, 1H) 7.00-7.09 (m, 1H) 7.09-7.19 (m, 1H) 8.43-8.49 (m, 1H).

Product 2: 4-((2S,4S)-4-bromotetrahydro-2H-pyran-2-yl)-2-methylpyridine and 4-((2R,4R)-4-bromotetrahydro-2H-pyran-2-yl)-2-methylpyridine (mixture of trans isomers): 1.69 g. $^1$H NMR (500 MHz, CDCl$_3$) δ ppm 1.92-2.06 (m, 1H) 2.12-2.24 (m, 1H) 2.25-2.35 (m, 1H) 2.47-2.55 (m, 1H) 2.56-2.62 (m, 3H) 3.56-3.71 (m, 1H) 4.16-4.22 (m, 1H) 4.23-4.39 (m, 2H) 7.00-7.09 (m, 1H) 7.11-7.18 (m, 1H) 8.45-8.50 (m, 1H).

The absolute stereochemistry was assigned arbitrarily. The relative stereochemistry (cis/trans) was confirmed by NMR.

TABLE 9

Intermediates Prepared Using Method 17

| Intermediate # | Structure | Name | Starting Material |
|---|---|---|---|
| 19 | 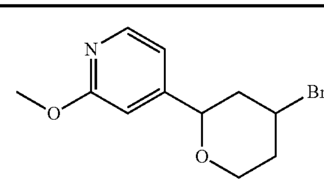 | 4-(4-bromotetrahydro-2H-pyran-2-yl)-2-methoxypyridine | 2-methoxyisonicotinaldehyde |

TABLE 9-continued

Intermediates Prepared Using Method 17

| Intermediate # | Structure | Name | Starting Material |
|---|---|---|---|
| 20 | 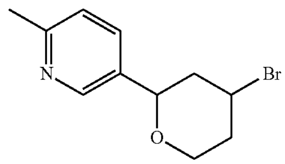 | 5-(4-bromotetrahydro-2H-pyran-2-yl)-2-methylpyridine | 6-methylnicotinaldehyde |
| 21 | 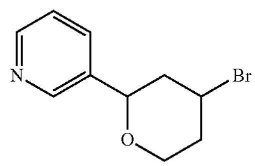 [SMILES: BrC1CCOC(c2cccnc2)C1] | 3-(4-bromotetrahydro-2H-pyran-2-yl)pyridine | nicotinaldehyde |

Biological Evaluation

Provided in this section is the biological evaluation of the specific examples provided herein. See Examples A1 and A2 and Tables 10 and 11.

Example A1

In Vitro Measurement of Triggering Receptor Expressed on Myeloid Cells 2 Activity Using Cellular Phosphorylation of Spleen Tyrosine Kinase ("Syk") Assays Pharmacological measurements of TREM2 signaling through DAP12 were made with TREM2 and DAP12 overexpressing HEK293 cells stable cell lines that had been single-cell cloned ("TREM2/DAP12-HEK"). The readout of the TREM2 signaling utilized Perkin Elmer AlphaScreen/AlphaLISA technology monitoring the phosphorylation levels of the Syk kinase. TREM2/DAP12-HEK cell lines were cultured in DMEM-F12 (Corning 10-092-CM) supplemented with 1× Penicillin/Streptomycin (Corning 30-002-CI), 1× GlutaMAX (Gibco 35050-061), and 10% Fetal Bovine Serum (Life Technologies 10099) referred to as "HEK Culture Medium". Suspensions of TREM2/DAP12-HEK cells were prepared in HEK Culture Medium and dispensed into 384-well poly-D-lysine coated microplates (Corning 354661) at a density of 20,000 cells/well using a Multidrop Combi peristaltic microplate dispenser (Thermo), 25 uL volume of cell suspension/well. Plates containing cells were then incubated for 20 hours in a humidified cell culture incubator at 37° C. with 5% $CO_2$ (Thermo). After incubation, removed culture medium from all wells of each microplate and replaced medium with 20 uL of "Assay Buffer" comprised of DMEM-F12 (Corning 10-092-CM) supplemented with 1× Penicillin/Streptomycin (Corning 30-002-CI) and 0.1% Pluronic F-68 Polyol (MP Biomedical 092750049) using a Bravo 384-well pipette-based liquid handling system (Agilent). Assay Buffer contained diluted test articles (in 1% final DMSO concentration for compounds) or 100 nM anti-human/mouse TREM2 antibody (R&D Systems MAB17291) as a positive control, 100 nM or rat IgG2B isotype Ab as a negative control (R&D Systems MAB0061). Incubated the plates with test articles and controls for 45 minutes at room temperature and then aspirated/removed the medium from each well of the plates. Used a Multidrop Combi peristaltic liquid handler (Thermo) to dispense 15 uL/well of "Cell Lysis Immunoassay Buffer". The Cell Lysis Immunoassay Buffer contained M-PER Mammalian Protein Extraction Reagent (Pierce/ThermoFisher 78505), 1× Halt Phosphatase Inhibitor Cocktail (ThermoFisher #78427), 0.1875 nM anti-phospho-Syk (Tyr525/526) (C87C1) rabbit mAb (Cell Signaling Technologies catalog #2710), and 1.5 nM biotinylated Mouse anti-human Syk (4D10) antibody (BD Biosciences, catalog #624008). Incubated plates for 1 hour at room temperature after the addition of the Cell Lysis Immunoassay Buffer. Used the Multidrop Combi liquid handler to dispense 15 uL of AlphaScreen Acceptor Bead Solution containing 7.5 µg/mL anti-rabbit IgG (Fc specific) AlphaLISA Acceptor Beads (Perkin Elmer AL104R) in 1× Immunoassay buffer (Perkin Elmer AL000F) to each well of the microplates. Incubated plates for 2 hours at room temperature. Following the incubation with the AlphaLISA Acceptor Bead Solution, used a Multidrop Combi liquid handler (Thermo) to dispense 15 uL of AlphaScreen Donor Bead Solution containing 30 µg/mL of AlphaScreen Streptavidin Donor beads (Perkin Elmer 6760002B) in 1× Immunoassay buffer (Perkin Elmer AL000F) to each well of the microplates. Incubated microplates for 2 hours protected from light sources as the AlphaScreen reagents are light sensitive. Once the final incubation was completed, acquired AlphaScreen signal from the donor and acceptor beads using an Envision high throughput multi-modal microplate reader (Perkin Elmer) calibrated to the plate type with the AlphaScreen mirror and filter-set in 384-well mode, 680 nanometer excitation wavelength. The total measurement time per well was 550 milliseconds with a 180 millisecond excitation time.

After reading the AlphaScreen signal for each well of the microplates, on a plate-by-plate basis, each raw test article well value (x) was normalized to a Percent of Control ("POC") value using the following formula: POC=$((x-\mu_a)/(\mu_p-\mu_n))*100$ where ($\mu_a$) is the mean negative control well signal for the given plate and ($\mu_p$) is the mean positive control TREM2 antibody signal for the given plate. Each plate contained 12 of each type of control wells that were used to generate the mean values. For concentration response curve analysis with test articles tested at various concentrations, the % of activation values were analyzed with 4 Parameter Logistic or Sigmoidal Dose-Response Models using GeneData Screener (GeneData, AG) or GraphPad Prism 7 (Graphpad Software, Inc.). The potency of the test item was expressed as EC50 corresponding to the test item concentration able to activate the phospho-Syk AlphaScreen signal to 50% of the maximal response.

For pharmacological assessment of TREM2 signaling in cellular systems natively expressing TREM2, human monocyte-derived macrophages were utilized. CD14+ monocytes positively selected from large-scale apheresis on healthy human donors (Lonza) were differentiated into macrophages in low-attachment bioprocess bags (Saint-Gobain Performance Plastics) for 9 days in RPMI-1640 medium (Gibco 11875093) supplemented with 10% Fetal Bovine Serum (Gibco 10082139), 10 mM HEPES (Gibco 15630080), 1× Penicillin-Streptomycin (Gibco 15140122), 1× Non-essential amino acids (Gibco 11140050), 1 mM Sodium Pyruvate (Gibco 11360070), 1× GlutaMAX (Gibco 35050-061), and 50 ng/mL M-CSF (Promocell C-60442A). After differentiation, macrophages were harvested and cryopreserved in BamBanker (Wako/GC LYMPHOTEC 302-14681/CS-02-001) in addition to undergoing quality control for expression of cell surface markers including TREM2 using flow cytometry. Batches utilized for phospho-Syk assays were approximately 80-90% TREM2+ by flow cytometry.

After cryorecovering macrophages, prepared live cell suspensions of 100,000 cells/mL in "Macrophage pSyk Assay Medium" composed of RPMI-1640 with GlutaMAX medium (Gibco 61870036) supplemented with 10% Fetal Bovine Serum (Gibco 10082139), 10 mM HEPES (Gibco 15630080), 1× Penicillin-Streptomycin (Gibco 15140122), 1× Non-essential amino acids (Gibco 11140050), 1 mM Sodium Pyruvate (Gibco 11360070), and 10 ng/mL M-CSF (Promocell C-60442A). Used a Multidrop Combi peristatic liquid handling instrument (Thermo) to dispense 50 uL/well of cell suspension (5,000 cells/well) into poly-d-lysine coated 384-well plates (Corning 354661). After a 30 minute incubation at room temperature, incubated plates in a humidified cell culture incubator at 37° C. with 5% $CO_2$ (Thermo) for 16 hours. To initiate assay with test articles, medium in each well of the assay plates was aspirated and replaced with 20 uL Assay Buffer containing diluted test articles (in 1% final DMSO concentration for compounds) or Assay Buffer containing 1% DMSO for as a negative control. The remainder of the macrophage AlphaScreen phospho-Syk assay followed the procedure detailed above for the HEK cell lines.

After reading the AlphaScreen signal for each well of the microplates containing macrophages, on a plate-by-plate basis, each raw test article well value (x) was background subtracted from the mean negative control well signal for the given plate. Each plate contained 12-24 negative control wells that were used to generate the mean value for background subtraction. For concentration response curve analysis with the test articles tested at various concentrations, the values were analyzed with a 4 Parameter Logistic curve fit using GraphPad Prism 7 (Graphpad Software, Inc.). The potency of each test item was expressed as EC50 corresponding to the test item concentration able to activate the background subtracted phospho-Syk AlphaScreen signal to 50% of the maximal response.

The results presented in Table 10 have been generated with the in vitro assay described above for Examples 1-275. This assay may be used to test any of the compounds described herein to assess and characterize a compound's ability to act as an agonist of TREM2.

Compounds designated as "A" demonstrated an EC50 of ≤0.05 μM. Compounds designated as "B" demonstrated an EC50>0.05 μM and ≤0.5 μM. Compounds designated as "C" demonstrated an EC50>0.5 μM and ≤3.0 μM. Compounds designated as "D" demonstrated an EC50>3.0 μM and ≤100 μM.

Compounds designated as "++++" demonstrated an Emax>300. Compounds designated as "+++" demonstrated an Emax>200 and ≤300. Compounds designated as "++" demonstrated an Emax>100 and ≤200. Compounds designated as "+" demonstrated an Emax>45 and ≤100.

TABLE 10 hTREM2 EC50 Data (HEK293 Cells) for Examples provided herein.

| Example | hTREM2 EC50 μM | Emax |
|---|---|---|
| 1 | B | +++ |
| 2 | C | +++ |
| 3 | A | +++ |
| 4 | C | +++ |
| 5 | B | ++++ |
| 6 | C | ++ |
| 7 | B | ++++ |
| 8 | B | ++++ |
| 9 | B | +++ |
| 10 | B | ++++ |
| 11 | B | ++++ |
| 12 | B | +++ |
| 13 | B | ++++ |
| 14 | B | ++++ |
| 15 | C | ++++ |
| 16 | D | + |
| 17 | C | ++++ |
| 18 | C | ++ |
| 19 | A | ++++ |
| 20 | B | ++++ |
| 21 | B | ++++ |
| 22 | A | ++++ |
| 23 | A | ++++ |
| 24 | B | ++++ |
| 25 | C | +++ |
| 26 | C | +++ |
| 27 | B | ++++ |
| 28 | A | +++ |
| 29 | C | +++ |
| 30 | C | +++ |
| 31 | D | ++++ |
| 32 | C | ++++ |
| 33 | C | ++++ |
| 34 | C | ++++ |
| 35 | C | +++ |
| 36 | D | +++ |
| 37 | B | ++++ |
| 38 | C | +++ |
| 39 | C | +++ |
| 40 | C | +++ |
| 41 | C | +++ |
| 42 | B | ++++ |
| 43 | B | +++ |
| 44 | B | +++ |
| 45 | C | +++ |
| 46 | B | ++++ |
| 47 | D | ++++ |
| 48 | C | +++ |
| 49 | A | ++++ |
| 50 | B | ++++ |
| 51 | B | +++ |
| 52 | C | ++++ |
| 53 | C | ++++ |
| 54 | B | ++++ |
| 55 | C | ++++ |
| 56 | D | +++ |
| 57 | C | +++ |
| 58 | C | +++ |
| 59 | B | +++ |
| 60 | B | ++++ |
| 61 | A | +++ |
| 62 | B | +++ |
| 63 | C | ++++ |
| 64 | B | ++++ |
| 65 | D | ++ |
| 66 | B | +++ |
| 67 | D | ++ |
| 68 | B | +++ |

TABLE 10-continued hTREM2 EC50 Data (HEK293 Cells) for Examples provided herein.

| Example | hTREM2 EC50 μM | Emax |
|---|---|---|
| 69 | B | ++++ |
| 70 | B | ++++ |
| 71 | B | ++++ |
| 72 | C | ++++ |
| 73 | D | +++ |
| 74 | C | + |
| 75 | B | ++++ |
| 76 | B | ++++ |
| 77 | A | ++++ |
| 78 | B | ++++ |
| 79 | C | +++ |
| 80 | B | ++++ |
| 81 | D | +++ |
| 82 | A | ++++ |
| 83 | B | ++++ |
| 84 | C | ++++ |
| 85 | D | ++++ |
| 86 | C | ++++ |
| 87 | C | ++++ |
| 88 | C | +++ |
| 89 | B | ++++ |
| 90 | B | ++++ |
| 91 | C | ++ |
| 92 | B | ++++ |
| 93 | C | +++ |
| 94 | A | +++ |
| 95 | B | ++++ |
| 96 | C | ++++ |
| 97 | C | ++++ |
| 98 | D | +++ |
| 99 | B | ++++ |
| 100 | B | +++ |
| 101 | C | +++ |
| 102 | B | +++ |
| 103 | D | + |
| 104 | B | ++++ |
| 105 | B | ++++ |
| 106 | B | +++ |
| 107 | A | ++++ |
| 108 | B | ++++ |
| 109 | C | ++++ |
| 110 | C | ++++ |
| 111 | B | ++++ |
| 112 | D | +++ |
| 113 | B | ++++ |
| 114 | B | +++ |
| 115 | B | +++ |
| 116 | B | ++ |
| 117 | A | +++ |
| 118 | B | +++ |
| 119 | B | +++ |
| 120 | B | +++ |
| 121 | B | ++++ |
| 122 | D | + |
| 123 | A | ++++ |
| 124 | A | ++++ |
| 125 | A | ++++ |
| 126 | A | +++ |
| 127 | B | ++++ |
| 128 | A | +++ |
| 129 | A | +++ |
| 130 | B | +++ |
| 131 | A | +++ |
| 132 | B | ++++ |
| 133 | A | +++ |
| 134 | B | ++++ |
| 135 | B | ++++ |
| 136 | A | ++++ |
| 137 | A | ++++ |
| 138 | B | +++ |
| 139 | B | ++++ |
| 140 | B | ++++ |
| 141 | B | ++++ |
| 142 | B | ++++ |
| 143 | B | ++++ |
| 144 | B | ++++ |
| 145 | C | ++ |
| 146 | A | ++++ |
| 147 | B | ++++ |
| 148 | D | ++++ |
| 149 | A | +++ |
| 150 | A | +++ |
| 151 | A | +++ |
| 152 | A | +++ |
| 153 | B | ++++ |
| 154 | D | ++++ |
| 155 | B | ++++ |
| 156 | C | ++++ |
| 157 | C | ++++ |
| 158 | C | +++ |
| 159 | C | +++ |
| 160 | C | +++ |
| 161 | C | +++ |
| 162 | A | +++ |
| 163 | D | +++ |
| 164 | B | +++ |
| 165 | A | +++ |
| 166 | C | +++ |
| 167 | B | ++++ |
| 168 | D | +++ |
| 169 | A | +++ |
| 170 | C | +++ |
| 171 | B | +++ |
| 172 | A | ++++ |
| 173 | C | +++ |
| 174 | B | ++++ |
| 175 | B | +++ |
| 176 | C | ++++ |
| 177 | B | ++++ |
| 178 | C | ++++ |
| 179 | C | ++++ |
| 180 | C | ++++ |
| 181 | D | ++++ |
| 182 | D | +++ |
| 183 | C | +++ |
| 184 | B | ++++ |
| 185 | C | +++ |
| 186 | C | ++++ |
| 187 | C | ++++ |
| 188 | C | ++++ |
| 189 | B | ++++ |
| 190 | C | +++ |
| 191 | C | ++++ |
| 192 | C | ++++ |
| 193 | C | +++ |
| 194 | D | +++ |
| 195 | D | + |
| 196 | C | ++++ |
| 197 | B | ++++ |
| 198 | C | ++++ |
| 199 | D | +++ |
| 200 | B | ++++ |
| 201 | B | ++++ |
| 202 | D | +++ |
| 203 | D | + |
| 204 | D | + |
| 205 | D | +++ |
| 206 | D | ++ |
| 207 | D | ++ |
| 208 | D | ++ |
| 209 | C | +++ |
| 210 | B | ++++ |
| 211 | D | +++ |
| 212 | D | ++++ |
| 213 | D | ++++ |
| 214 | B | ++++ |
| 215 | D | ++++ |
| 216 | C | ++++ |
| 217 | D | +++ |
| 218 | D | +++ |

TABLE 10-continued hTREM2 EC50 Data (HEK293 Cells) for Examples provided herein.

| Example | hTREM2 EC50 μM | Emax |
|---|---|---|
| 219 | C | ++ |
| 220 | B | ++++ |
| 221 | B | ++++ |
| 222 | C | ++ |
| 223 | D | ++ |
| 224 | C | +++ |
| 225 | C | ++++ |
| 226 | B | ++++ |
| 227 | D | +++ |
| 228 | C | +++ |
| 229 | C | ++++ |
| 230 | C | ++++ |
| 231 | C | +++ |
| 232 | C | ++++ |
| 233 | B | ++++ |
| 234 | D | ++ |
| 235 | C | ++++ |
| 236 | D | ++ |
| 237 | B | ++ |
| 238 | B | ++++ |
| 239 | D | +++ |
| 240 | D | ++++ |
| 241 | D | +++ |
| 242 | D | +++ |
| 243 | A | ++++ |
| 244 | D | +++ |
| 245 | D | ++ |
| 246 | D | +++ |
| 247 | D | ++ |
| 248 | D | +++ |
| 249 | C | ++++ |
| 250 | D | ++++ |
| 251 | D | ++ |
| 252 | D | +++ |
| 253 | A | ++++ |
| 254 | D | ++++ |
| 255 | D | +++ |
| 256 | D | ++++ |
| 257 | C | ++ |
| 258 | D | +++ |
| 259 | D | ++ |
| 260 | D | ++++ |
| 261 | D | ++++ |
| 262 | C | +++ |
| 263 | B | +++ |
| 264 | B | +++ |
| 265 | C | +++ |
| 266 | A | +++ |
| 267 | A | +++ |
| 268 | B | ++++ |
| 269 | C | ++++ |
| 270 | C | +++ |
| 271 | B | +++ |
| 272 | B | ++++ |
| 273 | B | ++++ |
| 274 | B | ++++ |
| 275 | A | ++ |

Example A2

In Vitro Measurement of Triggering Receptor Expressed on Myeloid Cells 2 Activity Using Cellular Phosphorylation of Spleen Tyrosine Kinase ("Syk") Assays Used for Examples 276-283

Measurement of TREM2 agonist potency was done using a HEK cell line expressing human TREM2 and DAP12 (HEK293T-hTREM2 cells). Binding of small molecules to, and activation of, TREM2 increases the phosphorylation of Syk. The resultant levels of Syk phosphorylation were measured using a commercial AlphaLisa reagent kit. To perform the assay, HEK-hTREM2 cells were plated at 14,000 cells per well in a 384 well plate, in 25 μL of complete growth media and incubated at 37° C., 5% $CO_2$ for 20-24 hours. Prior to the assay, test compounds were diluted in the 384 well plates in assay buffer and allowed to equilibrate for 30 minutes. Growth media was removed from cell plates by inversion on blotting paper, and 25 μL of test compounds in assay buffer was added to cells. Cells were incubated for 45 minutes at room temperature. After 45 minutes, assay buffer was removed and 10 μL of lysis buffer was added. Plates were shaken for 20 minutes at 350 RPM at room temperature. After complete lysis, AlphaLisa reagents were added to the lysate, and fluorescence intensity was measured using a Perkin Elmer Envision plate reader. Intensities were used to generate a standard curve, and % activation was calculated. Curve fitting was performed using Prism v9 software, log(agonist) vs response-variable slope (four parameters), and EC50s were calculated from the curve fit.

The results presented in Table 11 have been generated with the in vitro assay described above for Examples 276-283. This assay may be used to test any of the compounds described herein to assess and characterize a compound's ability to act as an agonist of TREM2.

Compounds designated as "A" demonstrated an EC50 of ≤0.05 μM. Compounds designated as "B" demonstrated an EC50>0.05 μM and ≤0.5 μM. Compounds designated as "C" demonstrated an EC50>0.5 μM and ≤3.0 μM. Compounds designated as "D" demonstrated an EC50>3.0 μM and ≤100 μM.

TABLE 11 hTREM2 EC50 Data (HEK293 Cells) for Examples 276-283 provided herein.

| Ex # | hTREM2 EC50 μM |
|---|---|
| 276 | A |
| 277 | B |
| 278 | B |
| 279 | A |
| 280 | A |
| 281 | A |
| 282 | A |
| 283 | B |

REFERENCES

Bianchin, M. M., H. M. Capella, D. L. Chaves, M. Steindel, E. C. Grisard, G. G. Ganev, J. P. da Silva Junior, S. Neto Evaldo, M. A. Poffo, R. Walz, C. G. Carlotti Junior and A. C. Sakamoto (2004). "Nasu-Hakola disease (polycystic lipomembranous osteodysplasia with sclerosing leukoencephalopathy—PLOSL): a dementia associated with bone cystic lesions. From clinical to genetic and molecular aspects." Cell Mol Neurobiol 24(1): 1-24.

Bianchin, M. M., K. C. Martin, A. C. de Souza, M. A. de Oliveira and C. R. Rieder (2010). "Nasu-Hakola disease and primary microglial dysfunction." Nat Rev Neurol 6(9): 2 p following 523.

Cantoni, C., B. Bollman, D. Licastro, M. Xie, R. Mikesell, R. Schmidt, C. M. Yuede, D. Galimberti, G. Olivecrona, R. S. Klein, A. H. Cross, K. Otero and L. Piccio (2015). "TREM2 regulates microglial cell activation in response to demyelination in vivo." Acta Neuropathol 129(3): 429-447.

Colonna, M. and O. Butovsky (2017). "Microglia Function in the Central Nervous System During Health and Neurodegeneration." Annu Rev Immunol 35: 441-468.

Cserep, C., B. Posfai, N. Lenart, R. Fekete, Z. I. Laszlo, Z. Lele, B. Orsolits, G. Molnar, S. Heindl, A. D. Schwarcz, K. Ujvari, Z. Kornyei, K. Toth, E. Szabadits, B. Sperlagh, M. Baranyi, L. Csiba, T. Hortobagyi, Z. Magloczky, B. Martinecz, G. Szabo, F. Erdelyi, R. Szipocs, M. M. Tamkun, B. Gesierich, M. Duering, I. Katona, A. Liesz, G. Tamas and A. Denes (2019). "Microglia monitor and protect neuronal function via specialized somatic purinergic junctions." Science 10.1126/science.aax6752: pp. 1-18.

Dardiotis, E., V. Siokas, E. Pantazi, M. Dardioti, D. Rikos, G. Xiromerisiou, A. Markou, D. Papadimitriou, M. Speletas and G. M. Hadjigeorgiou (2017). "A novel mutation in TREM2 gene causing Nasu-Hakola disease and review of the literature." Neurobiol Aging 53: 194.e13-194.e22.

Deming, Y., F. Filipello, F. Cignarella, C. Cantoni, S. Hsu, R. Mikesell, Z. Li, J. L. Del-Aguila, U. Dube, F. G. Farias, J. Bradley, J. Budde, L. Ibanez, M. V. Fernandez, K. Blennow, H. Zetterberg, A. Heslegrave, P. M. Johansson, J. Svensson, B. Nellgard, A. Lleo, D. Alcolea, J. Clarimon, L. Rami, J. L. Molinuevo, M. Suarez-Calvet, E. Morenas-Rodriguez, G. Kleinberger, M. Ewers, O. Harari, C. Haass, T. J. Brett, B. A. Benitez, C. M. Karch, L. Piccio and C. Cruchaga (2019). "The MS4A gene cluster is a key modulator of soluble TREM2 and Alzheimer's disease risk." Sci Transl Med 11(505) eaau2291: pp. 1-19.

Doens, D. and P. L. Fernandez (2014). "Microglia receptors and their implications in the response to amyloid beta for Alzheimer's disease pathogenesis." J Neuroinflammation 11: 48 (pp. 1-14).

Domingues, H. S., C. C. Portugal, R. Socodato and J. B. Relvas (2016). "Oligodendrocyte, Astrocyte, and Microglia Crosstalk in Myelin Development, Damage, and Repair." Front Cell Dev Biol 4: 71 (pp. 1-16).

Ewers, M., N. Franzmeier, M. Suarez-Calvet, E. Morenas-Rodriguez, M. A. A. Caballero, G. Kleinberger, L. Piccio, C. Cruchaga, Y. Deming, M. Dichgans, J. Q. Trojanowski, L. M. Shaw, M. W. Weiner, C. Haass and I. Alzheimer's Disease Neuroimaging (2019). "Increased soluble TREM2 in cerebrospinal fluid is associated with reduced cognitive and clinical decline in Alzheimer's disease." Sci Transl Med 11(507): eaav6221 (pp. 1-13).

Golde, T. E., W. J. Streit and P. Chakrabarty (2013). "Alzheimer's disease risk alleles in TREM2 illuminate innate immunity in Alzheimer's disease." Alzheimers Res Ther 5(3): 24 (pp. 1-6).

Guerreiro, R., A. Wojtas, J. Bras, M. Carrasquillo, E. Rogaeva, E. Majounie, C. Cruchaga, C. Sassi, J. S. Kauwe, S. Younkin, L. Hazrati, J. Collinge, J. Pocock, T. Lashley, J. Williams, J. C. Lambert, P. Amouyel, A. Goate, R. Rademakers, K. Morgan, J. Powell, P. St George-Hyslop, A. Singleton and J. Hardy (2013). "TREM2 variants in Alzheimer's disease." N Engl J Med 10(368): 117-127.

Guerreiro R., E. Lohmann, J. M. Bris, J. R. Gibbs, J. D. Rohrer, N. Gurunlian, B. Dursun, B. Bilgic, H. Hanagasi, H. Gurvit, M. Emre, A. Singleton and J. Hardy (2013). "Using exome sequencing to reveal mutations in TREM2 presenting as a frontotemporal dementia-like syndrome without bone involvement." JAMA Neurol 70(1): 78-84.

Guo, Y., X. Wei, H. Yan, Y. Qin, S. Yan, J. Liu, Y. Zhao, F. Jiang, H. Lou (2019). "TREM2 deficiency aggravates α-synuclein-induced neurodegeneration and neuroinflammation in Parkinson's disease models." FASEB J 33(11): 12164-12174.

Hickman, S., S. Izzy, P. Sen, L. Morsett and J. El Khoury (2018). "Microglia in neurodegeneration." Nat Neurosci 21(10): 1359-1369.

Hickman, S. E. and J. El Khoury (2019). "Analysis of the Microglial Sensome." Methods Mol Biol 2034: 305-323.

Hickman, S. E., N. D. Kingery, T. K. Ohsumi, M. L. Borowsky, L. C. Wang, T. K. Means and J. El Khoury (2013). "The microglial sensome revealed by direct RNA sequencing." Nat Neurosci 16(12): 1896-1905.

Hollingworth, P., D. Harold, R. Sims, A. Gerrish, J. C. Lambert, M. M. Carrasquillo, R. Abraham, M. L. Hamshere, J. S. Pahwa, V. Moskvina, K. Dowzell, N. Jones, A. Stretton, C. Thomas, A. Richards, D. Ivanov, C. Widdowson, J. Chapman, S. Lovestone, J. Powell, P. Proitsi, M. K. Lupton, C. Brayne, D. C. Rubinsztein, M. Gill, B. Lawlor, A. Lynch, K. S. Brown, P. A. Passmore, D. Craig, B. McGuinness, S. Todd, C. Holmes, D. Mann, A. D. Smith, H. Beaumont, D. Warden, G. Wilcock, S. Love, P. G. Kehoe, N. M. Hooper, E. R. Vardy, J. Hardy, S. Mead, N. C. Fox, M. Rossor, J. Collinge, W. Maier, F. Jessen, E. Ruther, B. Schurmann, R. Heun, H. Kolsch, H. van den Bussche, I. Heuser, J. Kornhuber, J. Wiltfang, M. Dichgans, L. Frolich, H. Hampel, J. Gallacher, M. Hull, D. Rujescu, I. Giegling, A. M. Goate, J. S. Kauwe, C. Cruchaga, P. Nowotny, J. C. Morris, K. Mayo, K. Sleegers, K. Bettens, S. Engelborghs, P. P. De Deyn, C. Van Broeckhoven, G. Livingston, N. J. Bass, H. Gurling, A. McQuillin, R. Gwilliam, P. Deloukas, A. Al-Chalabi, C. E. Shaw, M. Tsolaki, A. B. Singleton, R. Guerreiro, T. W. Muhleisen, M. M. Nothen, S. Moebus, K. H. Jockel, N. Klopp, H. E. Wichmann, V. S. Pankratz, S. B. Sando, J. O. Aasly, M. Barcikowska, Z. K. Wszolek, D. W. Dickson, N. R. Graff-Radford, R. C. Petersen, I. Alzheimer's Disease Neuroimaging, C. M. van Duijn, M. M. Breteler, M. A. Ikram, A. L. DeStefano, A. L. Fitzpatrick, O. Lopez, L. J. Launer, S. Seshadri, C. consortium, C. Berr, D. Campion, J. Epelbaum, J. F. Dartigues, C. Tzourio, A. Alperovitch, M. Lathrop, E. consortium, T. M. Feulner, P. Friedrich, C. Riehle, M. Krawczak, S. Schreiber, M. Mayhaus, S. Nicolhaus, S. Wagenpfeil, S. Steinberg, H. Stefansson, K. Stefansson, J. Snaedal, S. Bjornsson, P. V. Jonsson, V. Chouraki, B. Genier-Boley, M. Hiltunen, H. Soininen, O. Combarros, D. Zelenika, M. Delepine, M. J. Bullido, F. Pasquier, I. Mateo, A. Frank-Garcia, E. Porcellini, O. Hanon, E. Coto, V. Alvarez, P. Bosco, G. Siciliano, M. Mancuso, F. Panza, V. Solfrizzi, B. Nacmias, S. Sorbi, P. Bossu, P. Piccardi, B. Arosio, G. Annoni, D. Seripa, A. Pilotto, E. Scarpini, D. Galimberti, A. Brice, D. Hannequin, F. Licastro, L. Jones, P. A. Holmans, T. Jonsson, M. Riemenschneider, K. Morgan, S. G. Younkin, M. J. Owen, M. O'Donovan, P. Amouyel and J. Williams (2011). "Common variants at ABCA7, MS4A6A/MS4A4E, EPHA1, CD33 and CD2AP are associated with Alzheimer's disease." Nat Genet 43(5): 429-435.

Hong, S., L. Dissing-Olesen and B. Stevens (2016). "New insights on the role of microglia in synaptic pruning in health and disease." Curr Opin Neurobiol 36: 128-134.

Huang, Q. Q. and R. M. Pope (2009). "The role of toll-like receptors in rheumatoid arthritis." Curr Rheumatol Rep 11(5): 357-364.

Ikegami, A., K. Haruwaka and H. Wake (2019). "Microglia: Lifelong modulator of neural circuits." Neuropathology 39(3): 173-180.

Jaitin, D. A., L. Adlung, C. A. Thaiss, A. Weiner, B. Li, H. Descamps, P. Lundgren, C. Bleriot, Z. Liu, A. Deczkowska, H. Keren-Shaul, E. David, N. Zmora, S. M.

Eldar, N. Lubezky, O. Shibolet, D. A. Hill, M. A. Lazar, M. Colonna, F. Ginhoux, H. Shapiro, E. Elinav and I. Amit (2019). "Lipid-Associated Macrophages Control Metabolic Homeostasis in a Trem2-Dependent Manner." Cell 178(3): 686-698.e14.

Jay, T. R., V. E. von Saucken and G. E. Landreth (2017). "TREM2 in Neurodegenerative Diseases." Mol Neurodegener 12(1): 56 (pp. 1-33).

Jay, T. R., C. M. Miller, P. J. Cheng, L. C. Graham, S. Bemiller, M. L. Broihier, G. Xu, D. Margevicius, J. C. Karlo, G. L. Sousa, A. C. Cotleur, O. Butovsky, L. Bekris, S. M. Staugaitis, J. B. Leverenz, S. W. Pimplikar, G. E. Landreth, G. R. Howell, R. M. Ransohoff, B. T. Lamb (2015). "TREM2 deficiency eliminates TREM2+ inflammatory macrophages and ameliorates pathology in Alzheimer's disease mouse models." J Exp Med 212(3): 287-295.

Jonsson, T., H. Stefansson, S. Steinberg, I. Jonsdottir, P. V. Jonsson, J. Snaedal, S. Bjornsson, J. Huttenlocher, A. I. Levey, J. J. Lah, D. Rujescu, H. Hampel, I. Giegling, O. A. Andreassen, K. Engedal, I. Ulstein, S. Djurovic, C. Ibrahim-Verbaas, A. Hofman, M. A. Ikram, C. M. van Duijn, U. Thorsteinsdottir, A. Kong and K. Stefansson (2013). "Variant of TREM2 associated with the risk of Alzheimer's disease." N Engl J Med 368(2): 107-116.

Kang, S. S., A. Kurti, K. E. Baker, C. C. Liu, M. Colonna, J. D. Ulrich, D. M. Holtzman, G. Bu and J. D. Fryer (2018). "Behavioral and transcriptomic analysis of Trem2-null mice: not all knockout mice are created equal." Hum Mol Genet 27(2): 211-223.

Keren-Shaul, H., A. Spinrad, A. Weiner, O. Matcovitch-Natan, R. Dvir-Szternfeld, T. K. Ulland, E. David, K. Baruch, D. Lara-Astaiso, B. Toth, S. Itzkovitz, M. Colonna, M. Schwartz and I. Amit (2017). "A Unique Microglia Type Associated with Restricting Development of Alzheimer's Disease." Cell 169(7): 1276-1290.e17.

Kleinberger, G., Y. Yamanishi, M. Suarez-Calvet, E. Czirr, E. Lohmann, E. Cuyvers, H. Struyfs, N. Pettkus, A. Wenninger-Weinzierl, F. Mazaheri, S. Tahirovic, A. Lleo, D. Alcolea, J. Fortea, M. Willem, S. Lammich, J. L. Molinuevo, R. Sanchez-Valle, A. Antonell, A. Ramirez, M. T. Heneka, K. Sleegers, J. van der Zee, J. J. Martin, S. Engelborghs, A. Demirtas-Tatlidede, H. Zetterberg, C. Van Broeckhoven, H. Gurvit, T. Wyss-Coray, J. Hardy, M. Colonna and C. Haass (2014). "TREM2 mutations implicated in neurodegeneration impair cell surface transport and phagocytosis." Sci Transl Med 6(243): 243ra286 (pp. 1-13).

Kobayashi, M., H. Konishi, A. Sayo, T. Takai and H. Kiyama (2016). "TREM2/DAP12 Signal Elicits Proinflammatory Response in Microglia and Exacerbates Neuropathic Pain." J Neurosci 36(43): 11138-11150.

Kober, D. L. and T. J. Brett (2017). "TREM2-Ligand Interactions in Health and Disease." J Mol Biol 429(11): 1607-1629.

Lee, C. Y. D., A. Daggett, X. Gu, L. L. Jiang, P. Langfelder, X. Li, N. Wang, Y. Zhao, C. S. Park, Y. Cooper, I. Ferando, I. Mody, G. Coppola, H. Xu and X. W. Yang (2018). "Elevated TREM2 Gene Dosage Reprograms Microglia Responsivity and Ameliorates Pathological Phenotypes in Alzheimer's Disease Models." Neuron 97(5): 1032-1048.e5.

Leyns, C. E. G., M. Gratuze, S. Narasimhan, N. Jain, L. J. Koscal, H. Jiang, M. Manis, M. Colonna, V. M. Y. Lee, J. D. Ulrich and D. M. Holtzman (2019). "TREM2 function impedes tau seeding in neuritic plaques." Nat Neurosci 22(8): 1217-1222.

Li, Q. and B. A. Barres (2018). "Microglia and macrophages in brain homeostasis and disease." Nat Rev Immunol 18(4): 225-242.

Liddelow, S. A., K. A. Guttenplan, L. E. Clarke, F. C. Bennett, C. J. Bohlen, L. Schirmer, M. L. Bennett, A. E. Munch, W. S. Chung, T. C. Peterson, D. K. Wilton, A. Frouin, B. A. Napier, N. Panicker, M. Kumar, M. S. Buckwalter, D. H. Rowitch, V. L. Dawson, T. M. Dawson, B. Stevens and B. A. Barres (2017). "Neurotoxic reactive astrocytes are induced by activated microglia." Nature 541(7638): 481-487.

Madry, C. and D. Attwell (2015). "Receptors, ion channels, and signaling mechanisms underlying microglial dynamics." J Biol Chem 290(20): 12443-12450.

Madry, H., J. Prudlo, A. Grgic and J. Freyschmidt (2007). "Nasu-Hakola disease (PLOSL): report of five cases and review of the literature." Clin Orthop Relat Res 454: 262-269.

Otero, K., M. Shinohara, H. Zhao, M. Cella, S. Gilfillan, A. Colucci, R. Faccio, F. P. Ross, S. L. Teitelbaum, H. Takayanagi and M. Colonna (2012). "TREM2 and beta-catenin regulate bone homeostasis by controlling the rate of osteoclastogenesis." J Immunol 188(6): 2612-2621.

Paloneva, J., J. Mandelin, A. Kiialainen, T. Bohling, J. Prudlo, P. Hakola, M. Haltia, Y. T. Konttinen and L. Peltonen (2003). "DAP12/TREM2 deficiency results in impaired osteoclast differentiation and osteoporotic features." J Exp Med 198(4): 669-675.

Paolicelli, R. C., G. Bolasco, F. Pagani, L. Maggi, M. Scianni, P. Panzanelli, M. Giustetto, T. A. Ferreira, E. Guiducci, L. Dumas, D. Ragozzino and C. T. Gross (2011). "Synaptic pruning by microglia is necessary for normal brain development." Science 333(6048): 1456-1458.

Parhizkar, S., T. Arzberger, M. Brendel, G. Kleinberger, M. Deussing, C. Focke, B. Nuscher, M. Xiong, A. Ghasemigharagoz, N. Katzmarski, S. Krasemann, S. F. Lichtenthaler, S. A. Muller, A. Colombo, L. S. Monasor, S. Tahirovic, J. Herms, M. Willem, N. Pettkus, O. Butovsky, P. Bartenstein, D. Edbauer, A. Rominger, A. Erturk, S. A. Grathwohl, J. J. Neher, D. M. Holtzman, M. Meyer-Luehmann and C. Haass (2019). "Loss of TREM2 function increases amyloid seeding but reduces plaque-associated ApoE." Nat Neurosci 22(2): 191-204.

Peng, Q., S. Malhotra, J. A. Torchia, W. G. Kerr, K. M. Coggeshall and M. B. Humphrey (2010). "TREM2- and DAP12-dependent activation of PI3K requires DAP10 and is inhibited by SHIP1." Sci Signal 3(122): ra38 (pp. 1-18).

Sellgren, C. M., J. Gracias, B. Watmuff, J. D. Biag, J. M. Thanos, P. B. Whittredge, T. Fu, K. Worringer, H. E. Brown, J. Wang, A. Kaykas, R. Karmacharya, C. P. Goold, S. D. Sheridan and R. H. Perlis (2019). "Increased synapse elimination by microglia in schizophrenia patient-derived models of synaptic pruning." Nat Neurosci 22(3): 374-385.

Shinozaki, Y., K. Shibata, K. Yoshida, E. Shigetomi, C. Gachet, K. Ikenaka, K. F. Tanaka and S. Koizumi (2017). "Transformation of Astrocytes to a Neuroprotective Phenotype by Microglia via P2Y1 Receptor Downregulation." Cell Rep 19(6): 1151-1164.

Shirotani, K., Y. Hori, R. Yoshizaki, E. Higuchi, M. Colonna, T. Saito, S. Hashimoto, T. Saito, T. C. Saido and N. Iwata (2019). "Aminophospholipids are signal-transducing TREM2 ligands on apoptotic cells." Sci Rep 9(1): 7508 (pp. 1-9).

Sims, R., S. J. van der Lee, A. C. Naj, C. Bellenguez, N. Badarinarayan, J. Jakobsdottir, B. W. Kunkle, A. Boland, R. Raybould, J. C. Bis, E. R. Martin, B. Grenier-Boley, S. Heilmann-Heimbach, V. Chouraki, A. B. Kuzma, K. Sleegers, M. Vronskaya, A. Ruiz, R. R. Graham, R. Olaso, P. Hoffmann, M. L. Grove, B. N. Vardarajan, M. Hiltunen, M. M. Nothen, C. C. White, K. L. Hamilton-Nelson, J. Epelbaum, W. Maier, S. H. Choi, G. W. Beecham, C. Dulary, S. Herms, A. V. Smith, C. C. Funk, C. Derbois, A. J. Forstner, S. Ahmad, H. Li, D. Bacq, D. Harold, C. L. Satizabal, O. Valladares, A. Squassina, R. Thomas, J. A. Brody, L. Qu, P. Sanchez-Juan, T. Morgan, F. J. Wolters, Y. Zhao, F. S. Garcia, N. Denning, M. Fornage, J. Malamon, M. C. D. Naranjo, E. Majounie, T. H. Mosley, B. Dombroski, D. Wallon, M. K. Lupton, J. Dupuis, P. Whitehead, L. Fratiglioni, C. Medway, X. Jian, S. Mukherjee, L. Keller, K. Brown, H. Lin, L. B. Cantwell, F. Panza, B. McGuinness, S. Moreno-Grau, J. D. Burgess, V. Solfrizzi, P. Proitsi, H. H. Adams, M. Allen, D. Seripa, P. Pastor, L. A. Cupples, N. D. Price, D. Hannequin, A. Frank-Garcia, D. Levy, P. Chakrabarty, P. Caffarra, I. Giegling, A. S. Beiser, V. Giedraitis, H. Hampel, M. E. Garcia, X. Wang, L. Lannfelt, P. Mecocci, G. Eiriksdottir, P. K. Crane, F. Pasquier, V. Boccardi, J. Henandez, R. C. Barber, M. Scherer, L. Tarraga, P. M. Adams, M. Leber, Y. Chen, M. S. Albert, S. Riedel-Heller, V. Emilsson, D. Beekly, A. Braae, R. Schmidt, D. Blacker, C. Masullo, H. Schmidt, R. S. Doody, G. Spalletta, W. T. Longstreth, Jr., T. J. Fairchild, P. Bossu, O. L. Lopez, M. P. Frosch, E. Sacchinelli, B. Ghetti, Q. Yang, R. M. Huebinger, F. Jessen, S. Li, M. I. Kamboh, J. Morris, O. Sotolongo-Grau, M. J. Katz, C. Corcoran, M. Dunstan, A. Braddel, C. Thomas, A. Meggy, R. Marshall, A. Gerrish, J. Chapman, M. Aguilar, S. Taylor, M. Hill, M. D. Fairen, A. Hodges, B. Vellas, H. Soininen, I. Kloszewska, M. Daniilidou, J. Uphill, Y. Patel, J. T. Hughes, J. Lord, J. Turton, A. M. Hartmann, R. Cecchetti, C. Fenoglio, M. Serpente, M. Arcaro, C. Caltagirone, M. D. Orfei, A. Ciaramella, S. Pichler, M. Mayhaus, W. Gu, A. Lleo, J. Fortea, R. Blesa, I. S. Barber, K. Brookes, C. Cupidi, R. G. Maletta, D. Carrell, S. Sorbi, S. Moebus, M. Urbano, A. Pilotto, J. Kornhuber, P. Bosco, S. Todd, D. Craig, J. Johnston, M. Gill, B. Lawlor, A. Lynch, N. C. Fox, J. Hardy, A. Consortium, R. L. Albin, L. G. Apostolova, S. E. Arnold, S. Asthana, C. S. Atwood, C. T. Baldwin, L. L. Barnes, S. Barral, T. G. Beach, J. T. Becker, E. H. Bigio, T. D. Bird, B. F. Boeve, J. D. Bowen, A. Boxer, J. R. Burke, J. M. Burns, J. D. Buxbaum, N. J. Cairns, C. Cao, C. S. Carlson, C. M. Carlsson, R. M. Carney, M. M. Carrasquillo, S. L. Carroll, C. C. Diaz, H. C. Chui, D. G. Clark, D. H. Cribbs, E. A. Crocco, C. DeCarli, M. Dick, R. Duara, D. A. Evans, K. M. Faber, K. B. Fallon, D. W. Fardo, M. R. Farlow, S. Ferris, T. M. Foroud, D. R. Galasko, M. Gearing, D. H. Geschwind, J. R. Gilbert, N. R. Graff-Radford, R. C. Green, J. H. Growdon, R. L. Hamilton, L. E. Harrell, L. S. Honig, M. J. Huentelman, C. M. Hulette, B. T. Hyman, G. P. Jarvik, E. Abner, L. W. Jin, G. Jun, A. Karydas, J. A. Kaye, R. Kim, N. W. Kowall, J. H. Kramer, F. M. LaFerla, J. J. Lah, J. B. Leverenz, A. I. Levey, G. Li, A. P. Lieberman, K. L. Lunetta, C. G. Lyketsos, D. C. Marson, F. Martiniuk, D. C. Mash, E. Masliah, W. C. McCormick, S. M. McCurry, A. N. McDavid, A. C. McKee, M. Mesulam, B. L. Miller, C. A. Miller, J. W. Miller, J. C. Morris, J. R. Murrell, A. J. Myers, S. O'Bryant, J. M. Olichney, V. S. Pankratz, J. E. Parisi, H. L. Paulson, W. Perry, E. Peskind, A. Pierce, W. W. Poon, H. Potter, J. F. Quinn, A. Raj, M. Raskind, B. Reisberg, C. Reitz, J. M. Ringman, E. D. Roberson, E. Rogaeva, H. J. Rosen, R. N. Rosenberg, M. A. Sager, A. J. Saykin, J. A. Schneider, L. S. Schneider, W. W. Seeley, A. G. Smith, J. A. Sonnen, S. Spina, R. A. Stem, R. H. Swerdlow, R. E. Tanzi, T. A. Thornton-Wells, J. Q. Trojanowski, J. C. Troncoso, V. M. Van Deerlin, L. J. Van Eldik, H. V. Vinters, J. P. Vonsattel, S. Weintraub, K. A. Welsh-Bohmer, K. C. Wilhelmsen, J. Williamson, T. S. Wingo, R. L. Woltjer, C. B. Wright, C. E. Yu, L. Yu, F. Garzia, F. Golamaully, G. Septier, S. Engelborghs, R. Vandenberghe, P. P. De Deyn, C. M. Fernadez, Y. A. Benito, H. Thonberg, C. Forsell, L. Lilius, A. Kinhult-Stahlbom, L. Kilander, R. Brundin, L. Concari, S. Helisalmi, A. M. Koivisto, A. Haapasalo, V. Dermecourt, N. Fievet, O. Hanon, C. Dufouil, A. Brice, K. Ritchie, B. Dubois, J. J. Himali, C. D. Keene, J. Tschanz, A. L. Fitzpatrick, W. A. Kukull, M. Norton, T. Aspelund, E. B. Larson, R. Munger, J. I. Rotter, R. B. Lipton, M. J. Bullido, A. Hofman, T. J. Montine, E. Coto, E. Boerwinkle, R. C. Petersen, V. Alvarez, F. Rivadeneira, E. M. Reiman, M. Gallo, C. J. O'Donnell, J. S. Reisch, A. C. Bruni, D. R. Royall, M. Dichgans, M. Sano, D. Galimberti, P. St George-Hyslop, E. Scarpini, D. W. Tsuang, M. Mancuso, U. Bonuccelli, A. R. Winslow, A. Daniele, C. K. Wu, C. A. E. Gerad/Perades, O. Peters, B. Nacmias, M. Riemenschneider, R. Heun, C. Brayne, D. C. Rubinsztein, J. Bras, R. Guerreiro, A. Al-Chalabi, C. E. Shaw, J. Collinge, D. Mann, M. Tsolaki, J. Clarimon, R. Sussams, S. Lovestone, M. C. O'Donovan, M. J. Owen, T. W. Behrens, S. Mead, A. M. Goate, A. G. Uitterlinden, C. Holmes, C. Cruchaga, M. Ingelsson, D. A. Bennett, J. Powell, T. E. Golde, C. Graff, P. L. De Jager, K. Morgan, N. Ertekin-Taner, O. Combarros, B. M. Psaty, P. Passmore, S. G. Younkin, C. Berr, V. Gudnason, D. Rujescu, D. W. Dickson, J. F. Dartigues, A. L. DeStefano, S. Ortega-Cubero, H. Hakonarson, D. Campion, M. Boada, J. K. Kauwe, L. A. Farrer, C. Van Broeckhoven, M. A. Ikram, L. Jones, J. L. Haines, C. Tzourio, L. J. Launer, V. Escott-Price, R. Mayeux, J. F. Deleuze, N. Amin, P. A. Holmans, M. A. Pericak-Vance, P. Amouyel, C. M. van Duijn, A. Ramirez, L. S. Wang, J. C. Lambert, S. Seshadri, J. Williams and G. D. Schellenberg (2017). "Rare coding variants in PLCG2, ABI3, and TREM2 implicate microglial-mediated innate immunity in Alzheimer's disease." Nat Genet 49(9): 1373-1384.

Suarez-Calvet, M., E. Morenas-Rodriguez, G. Kleinberger, K. Schlepckow, M. A. Araque Caballero, N. Franzmeier, A. Capell, K. Fellerer, B. Nuscher, E. Eren, J. Levin, Y. Deming, L. Piccio, C. M. Karch, C. Cruchaga, L. M. Shaw, J. Q. Trojanowski, M. Weiner, M. Ewers, C. Haass and I. Alzheimer's Disease Neuroimaging (2019). "Early increase of CSF sTREM2 in Alzheimer's disease is associated with tau related-neurodegeneration but not with amyloid-beta pathology." Mol Neurodegener 14(1): 1 (pp. 1-14).

Ulland, T. K., W. M. Song, S. C. Huang, J. D. Ulrich, A. Sergushichev, W. L. Beatty, A. A. Loboda, Y. Zhou, N. J. Cairns, A. Kambal, E. Loginicheva, S. Gilfillan, M. Cella, H. W. Virgin, E. R. Unanue, Y. Wang, M. N. Artyomov, D. M. Holtzman and M. Colonna (2017). "TREM2 Maintains Microglial Metabolic Fitness in Alzheimer's Disease." Cell 170(4): 649-663.e13.

Ulrich, J. D., D. M. Holtzman (2016). "TREM2 Function in Alzheimer's Disease and Neurodegeneration." ACS Chem Neurosci 20(7): 420-427.

Ulrich, J. D., T. K. Ulland, M. Colonna and D. M. Holtzman (2017). "Elucidating the Role of TREM2 in Alzheimer's Disease." Neuron 94(2): 237-248.

Wang, Y., M. Cella, K. Mallinson, J. D. Ulrich, K. L. Young, M. L. Robinette, S. Gilfillan, G. M. Krishnan, S. Sudhakar, B. H. Zinselmeyer, D. M. Holtzman, J. R. Cirrito and M. Colonna (2015). "TREM2 lipid sensing sustains the microglial response in an Alzheimer's disease model." Cell 160(6): 1061-1071.

Wu, R., X. Li, P. Xu, L. Huang, J. Cheng, X. Huang, J. Jiang, L. J. Wu and Y. Tang (2017). "TREM2 protects against cerebral ischemia/reperfusion injury." Mol Brain 10(1): 20 (pp. 1-13).

Yeh, F. L., Y. Wang, I. Tom, L. C. Gonzalez, M. Sheng (2016). "TREM2 Binds to Apolipoproteins, Including APOE and CLU/APOJ, and Thereby Facilitates Uptake of Amyloid-Beta by Microglia." Neuron 91(2): 328-340.

Yuan, P., C. Condello, C. D. Keene, Y. Wang, T. D. Bird, S. M. Paul, W. Luo, M. Colonna, D. Baddeley and J. Grutzendler (2016). "TREM2 Haplodeficiency in Mice and Humans Impairs the Microglia Barrier Function Leading to Decreased Amyloid Compaction and Severe Axonal Dystrophy." Neuron 90(4): 724-739.

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:

1. A method of treating Parkinson's disease, rheumatoid arthritis, Alzheimer's disease, Nasu-Hakola disease, frontotemporal dementia, multiple sclerosis, prion disease, or stroke in a subject in need thereof, the method comprising administering to the subject a therapeutically effective amount of a compound selected from:

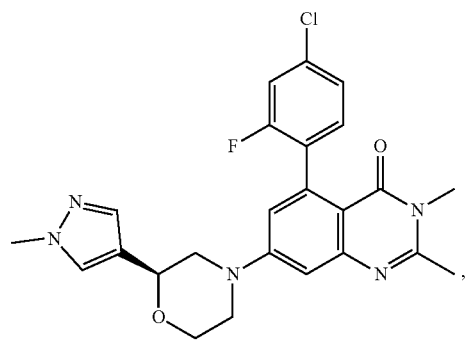

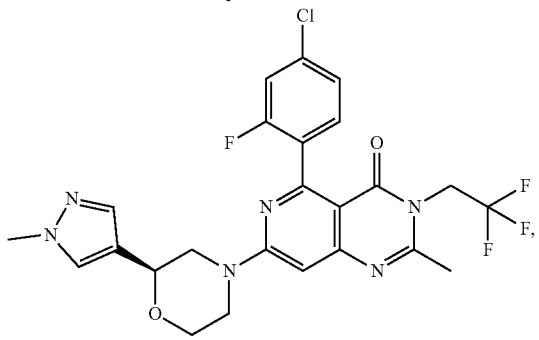

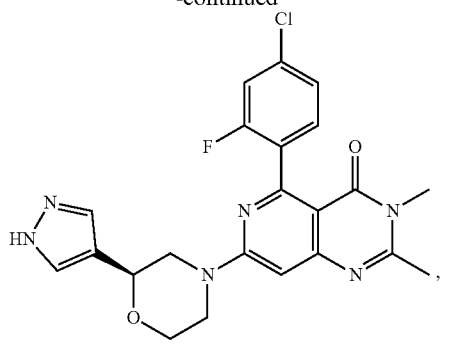

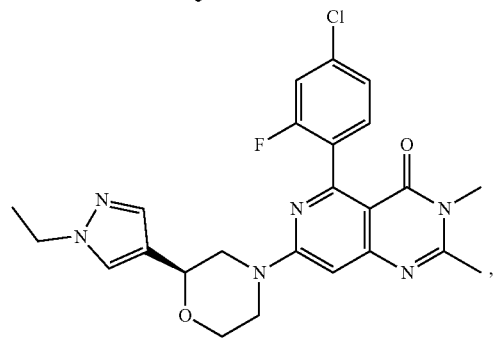

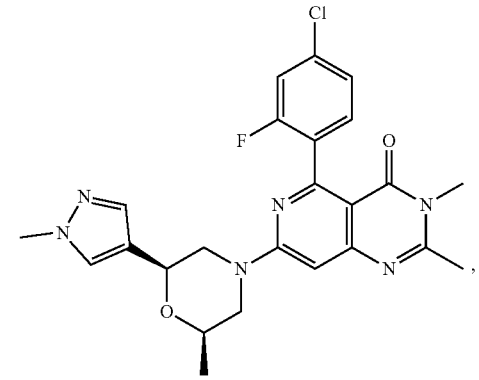

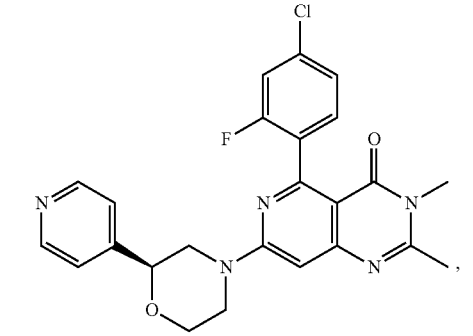

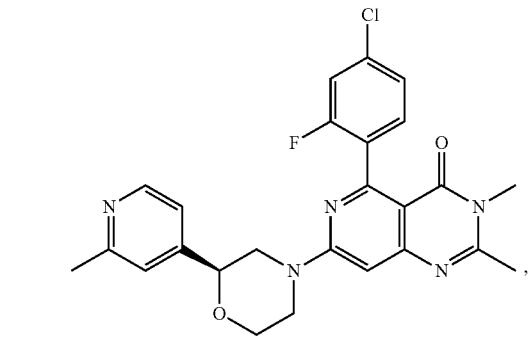

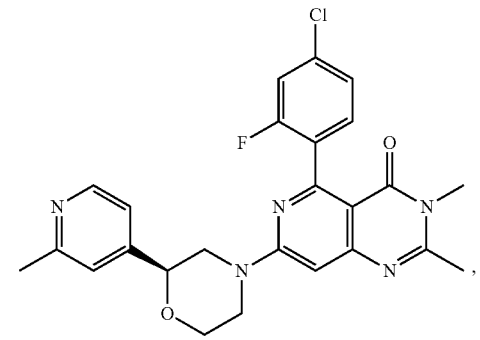

393
-continued
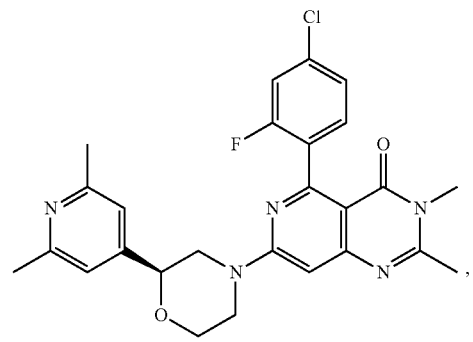
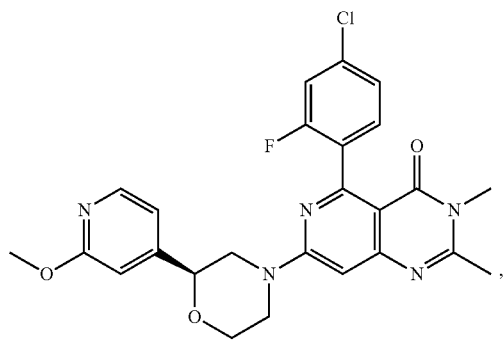
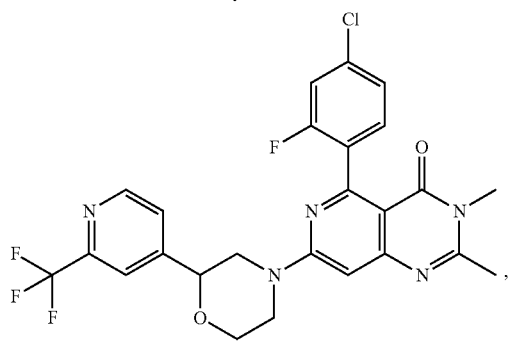
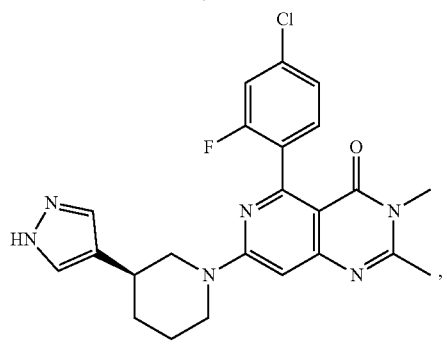
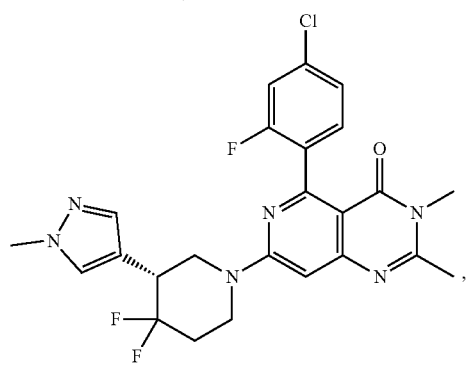
394
-continued
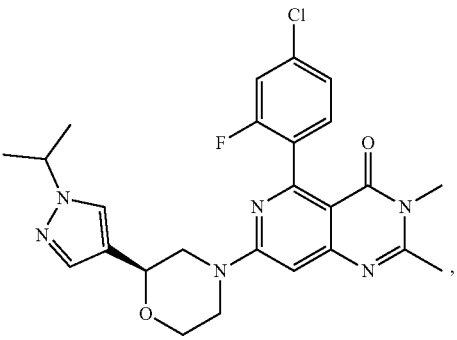
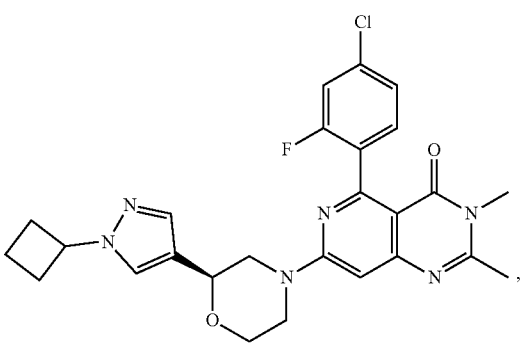
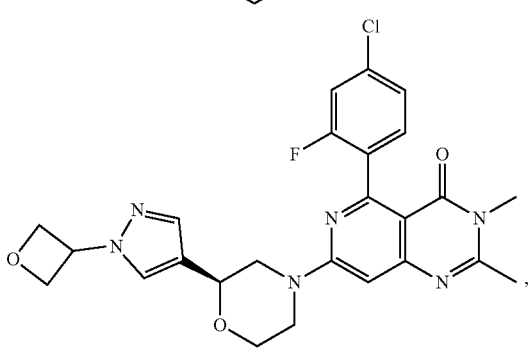
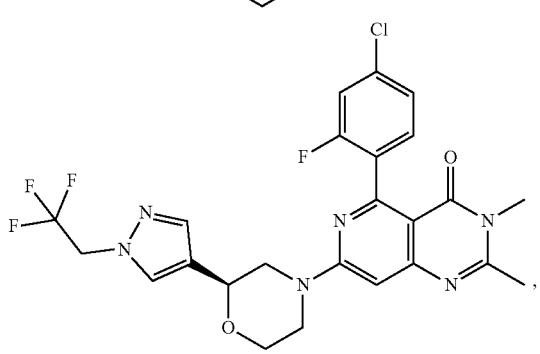
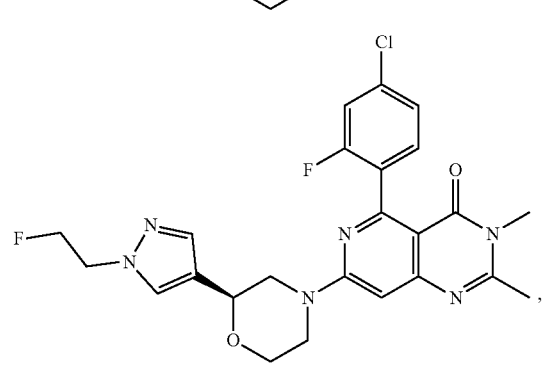

395
-continued
396
-continued
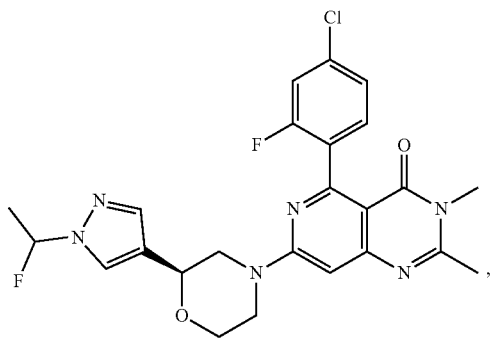
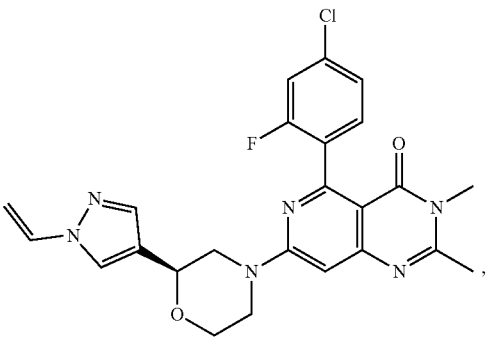

397
-continued
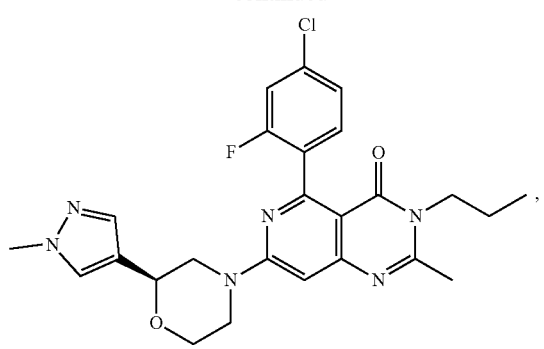
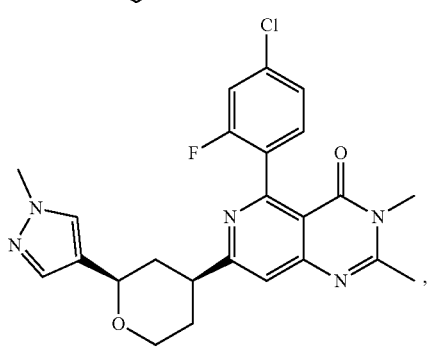
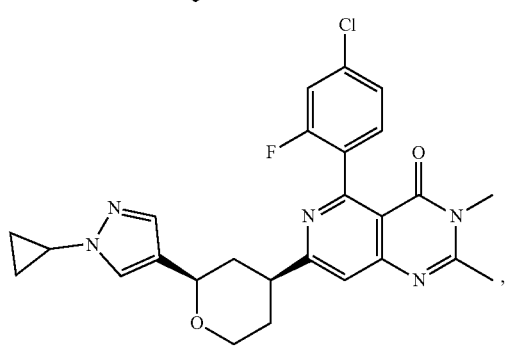
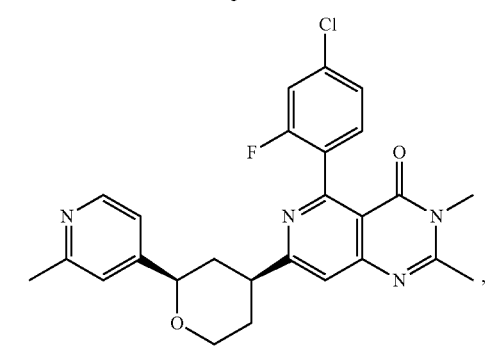
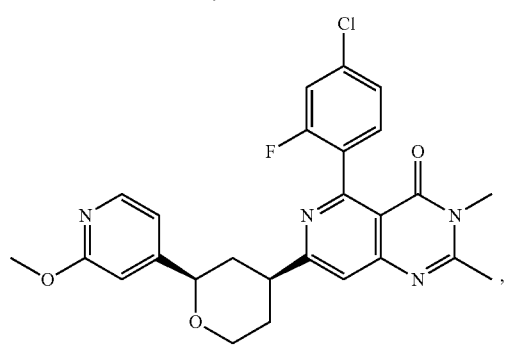
398
-continued
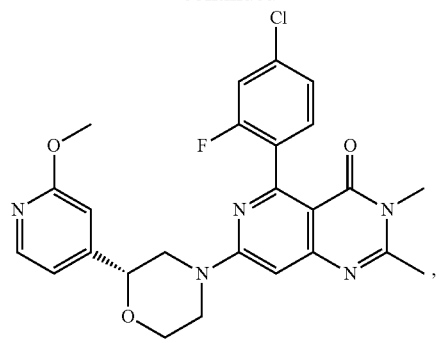
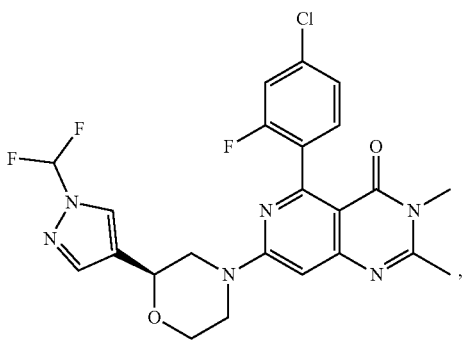
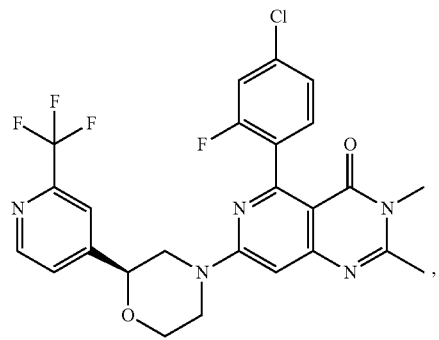
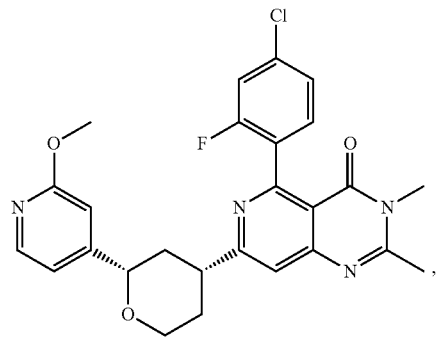
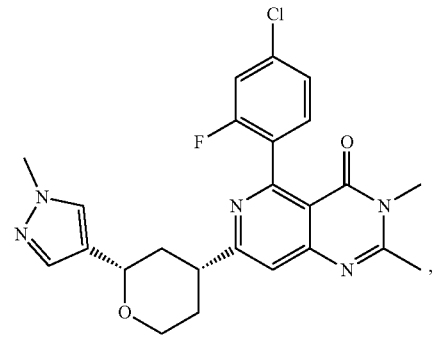

-continued

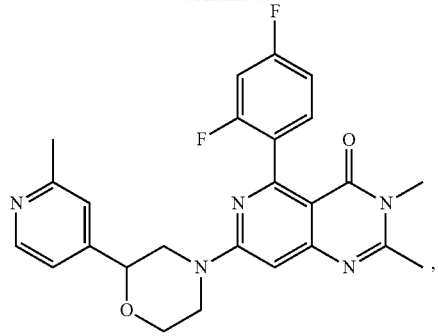

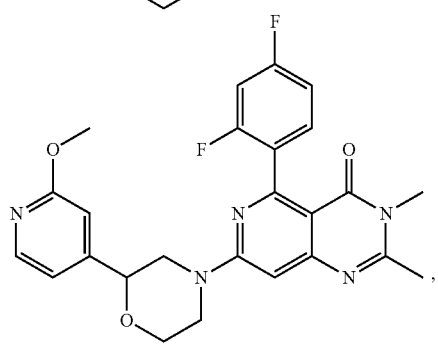

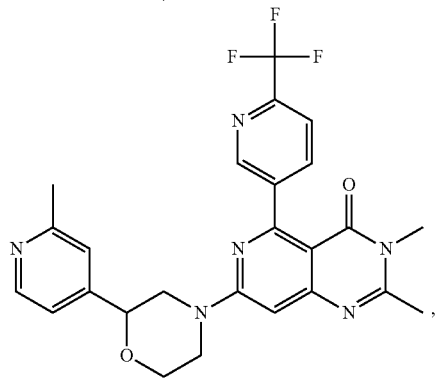

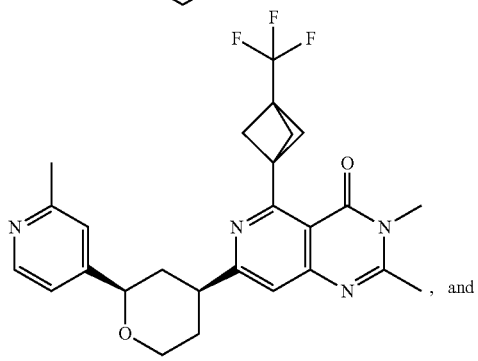,  and

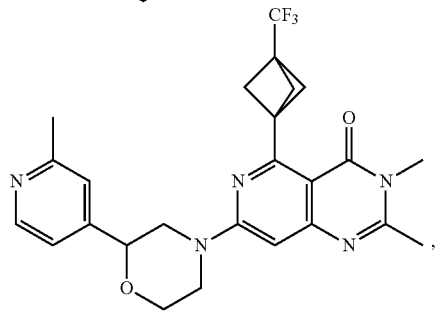, or a tautomer thereof, or a pharmaceutically acceptable salt of said compound or said tautomer.

2. The method of claim 1, wherein the compound is:

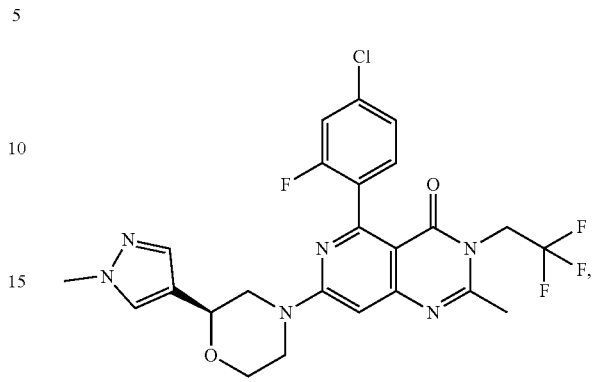

or a tautomer thereof, or a pharmaceutically acceptable salt of said compound or said tautomer.

3. The method of claim 1, wherein the compound is:

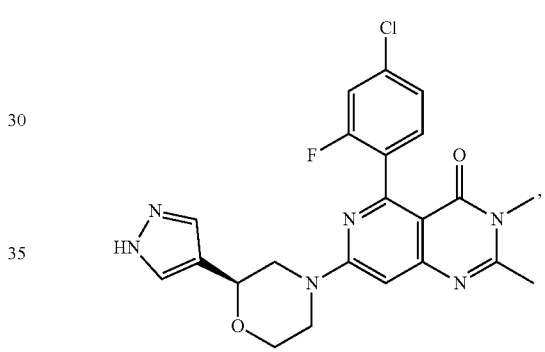

or a tautomer thereof, or a pharmaceutically acceptable salt of said compound or said tautomer.

4. The method of claim 1, wherein the compound is:

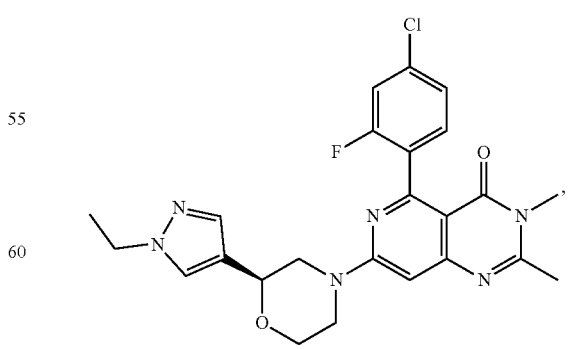

or a tautomer thereof, or a pharmaceutically acceptable salt of said compound or said tautomer.

5. The method of claim 1, wherein the compound is:

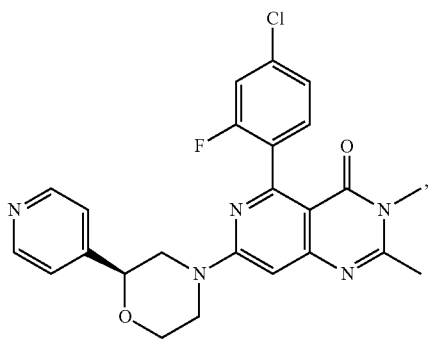 [SMILES: Cc1nc2cc(N3CCO[C@@H](c4ccncc4)C3)nc(-c3ccc(Cl)cc3F)c2c(=O)n1C]

or a tautomer thereof, or a pharmaceutically acceptable salt of said compound or said tautomer.

6. The method of claim 1, wherein the compound is:

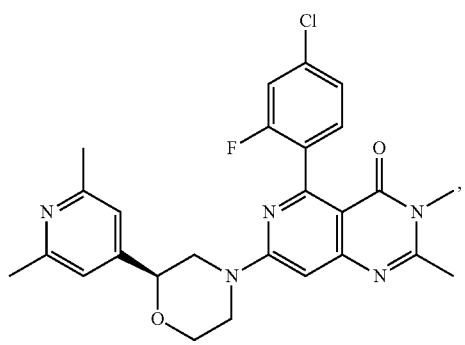

or a tautomer thereof, or a pharmaceutically acceptable salt of said compound or said tautomer.

7. The method of claim 1, wherein the compound is:

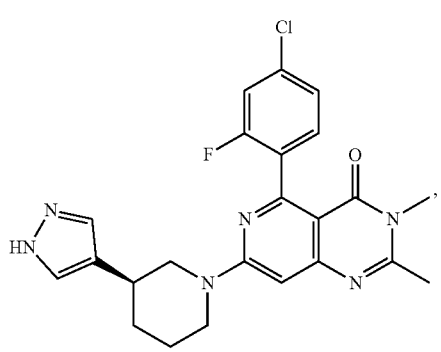 [SMILES: Cc1nc2cc(N3CCC[C@@H](c4cn[nH]c4)C3)nc(-c3ccc(Cl)cc3F)c2c(=O)n1C]

or a tautomer thereof, or a pharmaceutically acceptable salt of said compound or said tautomer.

8. The method of claim 1, wherein the compound is:

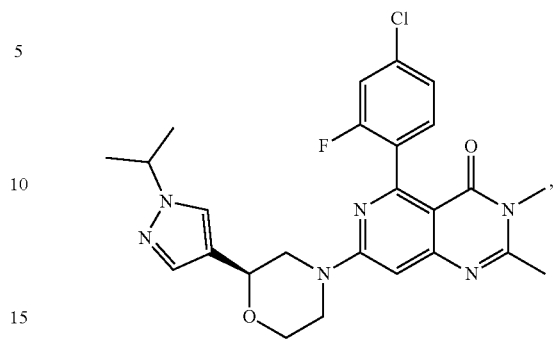

or a tautomer thereof, or a pharmaceutically acceptable salt of said compound or said tautomer.

9. The method of claim 1, wherein the compound is:

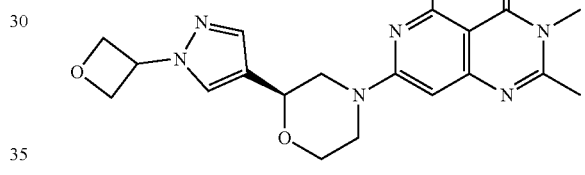

or a tautomer thereof, or a pharmaceutically acceptable salt of said compound or said tautomer.

10. The method of claim 1, wherein the compound is:

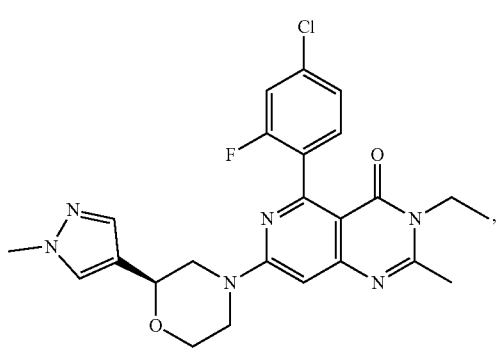 [SMILES: CCn1c(C)nc2cc(N3CCO[C@@H](c4cnn(C)c4)C3)nc(-c3ccc(Cl)cc3F)c2c1=O]

or a tautomer thereof, or a pharmaceutically acceptable salt of said compound or said tautomer.

11. The method of claim 1, wherein the compound is:

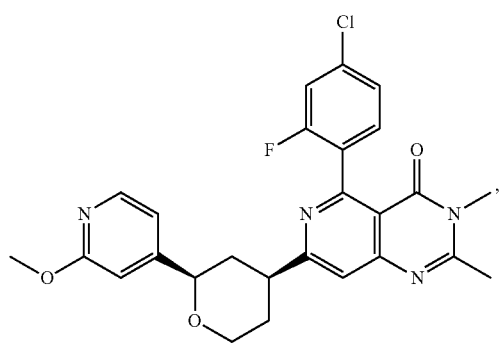

or a tautomer thereof, or a pharmaceutically acceptable salt of said compound or said tautomer.

12. The method of claim 1, wherein the compound is:

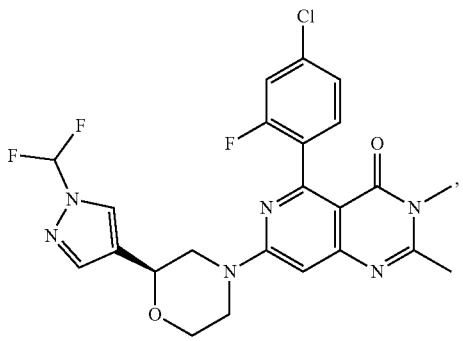 [SMILES: Cc1nc2cc(N3CCO[C@@H](c4cnn(C(F)F)c4)C3)nc(-c3ccc(Cl)cc3F)c2c(=O)n1C]

or a tautomer thereof, or a pharmaceutically acceptable salt of said compound or said tautomer.

13. The method of claim 1, wherein the compound is:

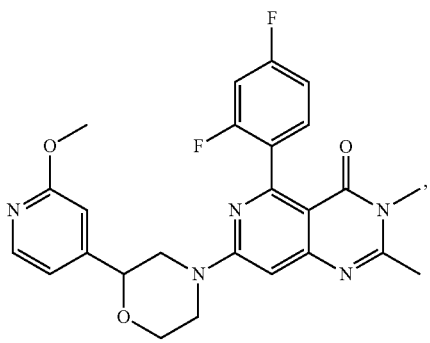 [SMILES: COc1cc(C2CN(c3cc4nc(C)n(C)c(=O)c4c(-c4ccc(F)cc4F)n3)CCO2)ccn1]

or a tautomer thereof, or a pharmaceutically acceptable salt of said compound or said tautomer.

14. The method of claim 1, wherein the compound is:

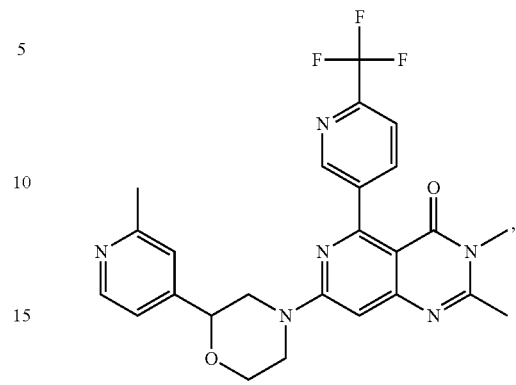

or a tautomer thereof, or a pharmaceutically acceptable salt of said compound or said tautomer.

15. The method of claim 1, wherein the compound is:

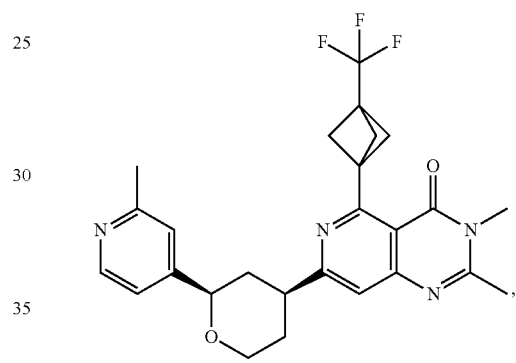

or a tautomer thereof, or a pharmaceutically acceptable salt of said compound or said tautomer.

16. The method of claim 1, wherein the disease or condition is Alzheimer's disease.

17. The method of claim 1, wherein the disease or condition is Nasu-Hakola disease.

18. The method of claim 1, wherein the compound or tautomer thereof, or pharmaceutically acceptable salt of said compound or said tautomer is administered as a pharmaceutical composition comprising a pharmaceutically acceptable excipient and the compound or tautomer thereof, or pharmaceutically acceptable salt of said compound or said tautomer.

19. The method of claim 1, wherein the pharmaceutical composition is administered orally, mucosally, topically, transdermally, rectally, pulmonarily, parentally, intranasally, intravascularly, intravenously, intraarterial, intraperitoneally, intrathecally, subcutaneously, sublingually, intramuscularly, intrasternally, vaginally, or by infusion techniques.

20. The method of claim 19, wherein the pharmaceutical composition is orally administered.

* * * * *